US009982249B2

(12) United States Patent
Nunn et al.

(10) Patent No.: US 9,982,249 B2
(45) **Date of Patent: *May 29, 2018**

(54) XYLOSE ISOMERASES AND THEIR USES

(71) Applicant: BP Corporation North America Inc., Houston, TX (US)

(72) Inventors: David Neal Nunn, Carlsbad, CA (US); Peter Luginbuhl, San Diego, CA (US); Ling Lee, San Diego, CA (US); Adam Martin Burja, San Diego, CA (US); Jon Peter Flash Bartnek, San Diego, CA (US)

(73) Assignee: BP Corporation North America Inc., Houston, TX (US)

( * ) Notice: Subject to any disclaimer, the term of this patent is extended or adjusted under 35 U.S.C. 154(b) by 120 days.

This patent is subject to a terminal disclaimer.

(21) Appl. No.: 14/417,080

(22) PCT Filed: Jul. 23, 2013

(86) PCT No.: PCT/US2013/051718

§ 371 (c)(1),
(2) Date: Jan. 23, 2015

(87) PCT Pub. No.: WO2014/018552

PCT Pub. Date: Jan. 30, 2014

(65) Prior Publication Data

US 2015/0203835 A1 Jul. 23, 2015

Related U.S. Application Data

(60) Provisional application No. 61/675,241, filed on Jul. 24, 2012.

(51) Int. Cl.

| | |
|---|---|
| ***C12N 9/92*** | (2006.01) |
| ***C12P 7/10*** | (2006.01) |
| ***C12N 9/90*** | (2006.01) |
| ***C12P 17/18*** | (2006.01) |
| ***C12P 35/06*** | (2006.01) |
| ***C12P 7/06*** | (2006.01) |
| ***C12P 7/16*** | (2006.01) |
| ***C12P 7/18*** | (2006.01) |
| ***C12P 7/20*** | (2006.01) |
| ***C12P 7/40*** | (2006.01) |
| ***C12P 7/64*** | (2006.01) |
| ***C12P 13/04*** | (2006.01) |
| ***C12P 5/02*** | (2006.01) |
| ***C12P 7/42*** | (2006.01) |
| ***C12P 7/46*** | (2006.01) |
| ***C12P 7/48*** | (2006.01) |
| ***C12P 7/54*** | (2006.01) |
| ***C12P 7/56*** | (2006.01) |
| ***C12P 13/02*** | (2006.01) |

(52) U.S. Cl.
CPC ................ *C12N 9/92* (2013.01); *C12N 9/90* (2013.01); *C12P 5/026* (2013.01); *C12P 7/06* (2013.01); *C12P 7/10* (2013.01); *C12P 7/16* (2013.01); *C12P 7/18* (2013.01); *C12P 7/20* (2013.01); *C12P 7/40* (2013.01); *C12P 7/42* (2013.01); *C12P 7/46* (2013.01); *C12P 7/48* (2013.01); *C12P 7/54* (2013.01); *C12P 7/56* (2013.01); *C12P 7/649* (2013.01); *C12P 13/02* (2013.01); *C12P 13/04* (2013.01); *C12P 17/184* (2013.01); *C12P 35/06* (2013.01); *C12Y 503/01005* (2013.01); *C12P 2203/00* (2013.01); *Y02E 50/10* (2013.01); *Y02E 50/13* (2013.01); *Y02E 50/16* (2013.01); *Y02E 50/17* (2013.01); *Y02E 50/343* (2013.01)

(58) Field of Classification Search
None
See application file for complete search history.

(56) References Cited

U.S. PATENT DOCUMENTS

| | | | |
|---|---|---|---|
| 2012/0142067 | A1 | 6/2012 | Desfougeres et al. |
| 2012/0225452 | A1 | 9/2012 | Bao et al. |

FOREIGN PATENT DOCUMENTS

| | | | |
|---|---|---|---|
| CN | 102 174 549 | A | 9/2011 |
| DE | 10 2008 031350 | A1 | 1/2010 |
| WO | WO 2003/062430 | A1 | 7/2003 |
| WO | WO2008000632 | * | 1/2008 |
| WO | WO 2009/109634 | A1 | 9/2009 |
| WO | WO2010039692 | * | 4/2010 |
| WO | WO 2010/074577 | A1 | 7/2010 |
| WO | WO 2011/090731 | A1 | 7/2011 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Accession AJ249909. Apr. 15, 2005.*
Accession D3I1K1. Mar. 23, 2010.*
Database EMBL HD069893, Database accession No. HD069893 sequence. Sequence 18 from Patent WO2010074577, XP002714607. Aug. 3, 2010.
Database EMBL HD069894, Database accession No. HD069894 sequence. Sequence 19 from Patent WO2010074577, XP002714608. Aug. 3, 2010.
Database EMBL HD069895, Database accession No. HD069895 sequence. Sequence 20 from Patent WO2010074577, XP002714609. Aug. 3, 2010.
Database UniProt XP002714610, retrieved from EBI accession No. UNIPROT: D3I1K1. "RecName: Full=Xylose isomerase; EC=5.3.1.5" Mar. 23, 2010.
Database UniProt XP002714611, retrieved from EBI accession No. UNIPROT: F9D530. "RecName: Full=Xylose isomerase; EC=5.3.1.5" Oct. 19, 2011.

(Continued)

*Primary Examiner* — Christian Fronda
(74) *Attorney, Agent, or Firm* — DLA Piper LLP (US)

(57) ABSTRACT

This disclosure relates to novel xylose isomerases and their uses, particularly in fermentation processes that employ xylose-containing media.

20 Claims, 14 Drawing Sheets

(56) References Cited

OTHER PUBLICATIONS

Ethanol production related xylose isomerase (XI), Seq ID 2, XP002714606, retrieved from EBI accession No. GSP:AZM80432. Database accession No. AZM80432 sequence.
Harhangi, H. R. et al: "Xylose metabolism in the anaerobic fungus *Piromyces* sp. Strain E2 follows the bacterial pathway," Archives of Microbiology, Springer, DE, vol. 180, No. 2, Jun. 13, 2003.
Hector, Ronald E. et al: "Growth and fermentation of D-xylose by *Saccharomyces cerevisiae* expressing a novel D-xylose isomerase originating from the bacterium *Prevotella ruminicola* TC2-24," Biotechnology for Biofuels, Biomed Central Ltd., GB, vol. 6, No. 1, May 30, 2013.
Kuyper, M. et al: "High-level functional expression of a fungal xylose isomerase: The key to efficient ethanolic fermentation of xylose by *Saccharomyces cerevisiae*?" Fems Yeast Research, Wiley-Blackwell Publishing Ltd. GB, NL, vol. 4, No. 1, Oct. 1, 2003.
Accession AEL74969, Mar. 3, 2011.
Chica et al.: "Semi-rational approaches to engineering enzyme activity: combining the benefits of directed evolution and rational design"; Current Opinion in Biotechnology 2005, 16:378-384.
Sen et al.: "Developments in Directed Evolution for. Improving Enzyme Functions"; Appl Biochem Biotechnol (2007) 143:212-223.
Brat, Dawid et al.: "Functional Expression of a Bacterial Xylose Isomerase in *Saccharomyces cerevisiae*"; Applied and Environmental Microbiology, American Society for Microbiology, US, vol. 75, No. 8, Apr. 1, 2009, pp. 2304-2311.
European Search Report dated Aug. 24, 2016 regarding EP 13744924.
Jeffries et al.: "Engineering yeasts for xylose metabolism"; Current Opinion in Iotechnology, vol. 17, No. 3, Jun. 1, 2006, pp. 320-326.
Madhavan, Anjali et al: "Xylose isomerase from polycentric fungus *Orpinomyces*: gene sequencing, cloning, and expression in *Saccharomyces cerevisiae* for bioconversion of xylose to ethanol"; Applied Microbiology and Biotechnology, vol. 82, No. 6, Dec. 3, 2008, pp. 1067-1078.
Van Maris, A. J. A. et al: "Development of Efficient Xylose Fermentation in *Saccharomyces cerevisiae*: Xylose Isomerase as a Key Component"; Advances in Biochemical Engineering, Biotechnology, vol. 108, Jan. 1, 2007, pp. 179-204.
XP002714606: "Ethanol production related xylose isomerase (XI), SEQ ID 2."; Jan. 19, 2012, Database accession No. AZM80432; retrieved from EBI accession No. GSP:AZM80432.

* cited by examiner

SEQUENCE LISTING

```
<160> NUMBER OF SEQ ID NOS: 249

<210> SEQ ID NO 1
<211> LENGTH: 1314
<212> TYPE: DNA
<213> ORGANISM: Unknown
<220> FEATURE:
<223> OTHER INFORMATION: Obtained from environmental sample

<400> SEQUENCE: 1

atggcagtta aagaatattt cccggagata ggcaagatcg cctttgaagg aaaggagtcc      60

aagaacccta tggcattcca ctactacaat ccagagcagg tagtagccgg aaagaaaatg     120

aaagattggt tcaagttcgc tatggcatgg tggcacaccc tctgcgctga aggtggcgac     180

cagttcggtc ctggtaccaa gaaattccct tggaacacag gtgcaactgc actcgaaaga     240

gcaaagaaca aaatggacgc aggtttcgag atcatgagca agctcggtat cgagtatttc     300

tgcttccacg atgttgacct tatcgacgag gctgacactg ttgaagagta cgaggctaac     360

atgaaggcta tcacagctta cgcaaaggag aaaatggccg ctactggcat caaactcctc     420

tggggaacag ccaatgtatt cggcaacaag agatatatga acggcgcttc taccaaccct     480

gacttcaacg tggctgcacg cgctatgctc cagatcaaga acgctatcga cgcaactatc     540

gctctcggtg gtgactgcta tgtattctgg ggcggccgtg agggttacat gagccttctc     600

aacaccgata tgaagagaga gaaagagcac atggctacca tgcttaccat ggcacgcgac     660

tatgctcgtt ctaagggctt caagggtacc ttccttatcg agcctaagcc aatggagccg     720

atgaagcacc agtacgatgt cgatactgag actgtcgtag gtttcctccg cgcccatggt     780

cttgacaagg acttcaaggt aaacatcgag gttaaccacg ctactctcgc aggccacacc     840

ttcgagcacg agctccagtg cgccgttgac gcaggcatgc tcggaagcat cgacgccaac     900

cgtggtgact accagaacgg ctgggatacc gaccagttcc ctatcgacct ctatgagctc     960

gtacaggcta tgatggttat catcaagggc ggcggtctcg tcggcggtac caacttcgac    1020

gccaagaccc gtcgtaactc aacagacctc gaggatatct tcatcgctca tgtatccggc    1080

atggatgtca tggcacgcgc tctcctcatc gctgctgacc ttctcgagaa atctcctatt    1140

cctgcaatgg tcaaggagcg ttacgcttcc tacgactcag gcatgggcaa ggacttcgag    1200

aacggcaagc ttactctcga gcaggttgtc gatttcgcaa gaaagaacgg cgagcctaag    1260

agcaccagcg gaaagcagga gctctacgag tctatcgtca atctctacat ctaa          1314

<210> SEQ ID NO 2
<211> LENGTH: 437
```

```
<212> TYPE: PRT
<213> ORGANISM: Unknown
<220> FEATURE:
<223> OTHER INFORMATION: Obtained from environmental sample

<400> SEQUENCE: 2

Met Ala Val Lys Glu Tyr Phe Pro Glu Ile Gly Lys Ile Ala Phe Glu
1               5                   10                  15

Gly Lys Glu Ser Lys Asn Pro Met Ala Phe His Tyr Tyr Asn Pro Glu
            20                  25                  30

Gln Val Val Ala Gly Lys Lys Met Lys Asp Trp Phe Lys Phe Ala Met
        35                  40                  45

Ala Trp Trp His Thr Leu Cys Ala Glu Gly Gly Asp Gln Phe Gly Pro
    50                  55                  60

Gly Thr Lys Lys Phe Pro Trp Asn Thr Gly Ala Thr Ala Leu Glu Arg
65                  70                  75                  80

Ala Lys Asn Lys Met Asp Ala Gly Phe Glu Ile Met Ser Lys Leu Gly
                85                  90                  95

Ile Glu Tyr Phe Cys Phe His Asp Val Asp Leu Ile Asp Glu Ala Asp
            100                 105                 110

Thr Val Glu Glu Tyr Glu Ala Asn Met Lys Ala Ile Thr Ala Tyr Ala
        115                 120                 125

Lys Glu Lys Met Ala Ala Thr Gly Ile Lys Leu Leu Trp Gly Thr Ala
    130                 135                 140

Asn Val Phe Gly Asn Lys Arg Tyr Met Asn Gly Ala Ser Thr Asn Pro
145                 150                 155                 160

Asp Phe Asn Val Ala Ala Arg Ala Met Leu Gln Ile Lys Asn Ala Ile
                165                 170                 175

Asp Ala Thr Ile Ala Leu Gly Gly Asp Cys Tyr Val Phe Trp Gly Gly
            180                 185                 190

Arg Glu Gly Tyr Met Ser Leu Leu Asn Thr Asp Met Lys Arg Glu Lys
        195                 200                 205

Glu His Met Ala Thr Met Leu Thr Met Ala Arg Asp Tyr Ala Arg Ser
    210                 215                 220

Lys Gly Phe Lys Gly Thr Phe Leu Ile Glu Pro Lys Pro Met Glu Pro
225                 230                 235                 240

Met Lys His Gln Tyr Asp Val Asp Thr Glu Thr Val Val Gly Phe Leu
                245                 250                 255

Arg Ala His Gly Leu Asp Lys Asp Phe Lys Val Asn Ile Glu Val Asn
            260                 265                 270

His Ala Thr Leu Ala Gly His Thr Phe Glu His Glu Leu Gln Cys Ala
        275                 280                 285

Val Asp Ala Gly Met Leu Gly Ser Ile Asp Ala Asn Arg Gly Asp Tyr
    290                 295                 300

Gln Asn Gly Trp Asp Thr Asp Gln Phe Pro Ile Asp Leu Tyr Glu Leu
305                 310                 315                 320

Val Gln Ala Met Met Val Ile Ile Lys Gly Gly Gly Leu Val Gly Gly
                325                 330                 335

Thr Asn Phe Asp Ala Lys Thr Arg Arg Asn Ser Thr Asp Leu Glu Asp
            340                 345                 350

Ile Phe Ile Ala His Val Ser Gly Met Asp Val Met Ala Arg Ala Leu
        355                 360                 365

Leu Ile Ala Ala Asp Leu Leu Glu Lys Ser Pro Ile Pro Ala Met Val
    370                 375                 380
```

Lys Glu Arg Tyr Ala Ser Tyr Asp Ser Gly Met Gly Lys Asp Phe Glu
385 390 395 400

Asn Gly Lys Leu Thr Leu Glu Gln Val Val Asp Phe Ala Arg Lys Asn
405 410 415

Gly Glu Pro Lys Ser Thr Ser Gly Lys Gln Glu Leu Tyr Glu Ser Ile
420 425 430

Val Asn Leu Tyr Ile
435

<210> SEQ ID NO 3
<211> LENGTH: 1314
<212> TYPE: DNA
<213> ORGANISM: Unknown
<220> FEATURE:
<223> OTHER INFORMATION: Obtained from environmental sample

<400> SEQUENCE: 3
atggcaaaca aagagtactt cccggagatc gggaaaatca aattcgaagg caaggattcc 60
aagaacccgc ttgcattcca ttattacaat cctgagcagg tcgtctgcgg caagccgatg 120
aaggactggc tcaagttcgc tatggcatgg tggcacaccc tctgcgcaga gggtagcgac 180
cagttcggcg gacccaccaa gtcattccct tggaacaaag cttcggatcc catcgcaaag 240
gccaagcaga aagtcgacgc cggtttcgag atcatgcaga agctcggtat cggatactat 300
tgcttccacg atgtagacct catcgacgag cccgccacca tcgaggagta tgaggccgat 360
ctcaaggaga tcgtcgctta cctcaaggag aagcaggccc agaccggcat caagctcctt 420
tggggcaccg ccaacgtctt cggtcacaag cggtacatga acggcgcctc caccaaccct 480
gatttcgacg tcgcagcccg cgccatggtc cagatcaaga acgccatgga cgccaccatc 540
gagctcggcg gcgagtgcta tgtcttctgg ggcggccgcg agggctacat gagcctcctc 600
aacaccgaca tgaagcgtga gaagcagcat atggccacca tgctcggcat ggcccgcgac 660
tatgcacgcg gcaagggctt caagggcacc ttcctcatcg agcccaagcc catggagccg 720
accaagcacc agtatgacgt cgacaccgag accgtcatcg gtttcctccg tgccaacggt 780
cttgacaagg acttcaaggt caacatcgag gtcaatcacg ccaccctcgc cggccacacc 840
ttcgagcatg agctccagtg cgccgccgat gccggtctcc tcggatccat cgacgccaac 900
cgcggcgact atcagaacgg ctgggatacc gaccagttcc cgatcgacct ctatgagctc 960
acccaggcca tgatggtcat cctcaagaat ggcggcctcg tcggcggtac caacttcgac 1020
gccaagaccc gtcgcaactc caccgacctg gacgacatca tcatcgccca cgtcagcggt 1080
atggacatca tggcacgcgc actcctcgtc gctgccgacg tcctcaccaa gtccgagctt 1140
cccaagatgc tcaaggagcg ttacgcttcc ttcgactccg gcaagggcaa ggagttcgaa 1200
gagggcaagc tcactctcga gcaggtcgta gagtacgcca agaccaaggg cgagcccaag 1260
gccaccagcg gcaagcagga gctctacgag accatcgtca acatgtacat ctaa 1314

<210> SEQ ID NO 4
<211> LENGTH: 437
<212> TYPE: PRT
<213> ORGANISM: Unknown
<220> FEATURE:
<223> OTHER INFORMATION: Obtained from environmental sample

<400> SEQUENCE: 4

Met Ala Asn Lys Glu Tyr Phe Pro Glu Ile Gly Lys Ile Lys Phe Glu
1 5 10 15

-continued

```
Gly Lys Asp Ser Lys Asn Pro Leu Ala Phe His Tyr Tyr Asn Pro Glu
            20                  25                  30

Gln Val Val Cys Gly Lys Pro Met Lys Asp Trp Leu Lys Phe Ala Met
        35                  40                  45

Ala Trp Trp His Thr Leu Cys Ala Glu Gly Ser Asp Gln Phe Gly Gly
    50                  55                  60

Pro Thr Lys Ser Phe Pro Trp Asn Lys Ala Ser Asp Pro Ile Ala Lys
65                  70                  75                  80

Ala Lys Gln Lys Val Asp Ala Gly Phe Glu Ile Met Gln Lys Leu Gly
                85                  90                  95

Ile Gly Tyr Tyr Cys Phe His Asp Val Asp Leu Ile Asp Glu Pro Ala
            100                 105                 110

Thr Ile Glu Glu Tyr Glu Ala Asp Leu Lys Glu Ile Val Ala Tyr Leu
        115                 120                 125

Lys Glu Lys Gln Ala Gln Thr Gly Ile Lys Leu Leu Trp Gly Thr Ala
    130                 135                 140

Asn Val Phe Gly His Lys Arg Tyr Met Asn Gly Ala Ser Thr Asn Pro
145                 150                 155                 160

Asp Phe Asp Val Ala Ala Arg Ala Met Val Gln Ile Lys Asn Ala Met
                165                 170                 175

Asp Ala Thr Ile Glu Leu Gly Gly Glu Cys Tyr Val Phe Trp Gly Gly
            180                 185                 190

Arg Glu Gly Tyr Met Ser Leu Leu Asn Thr Asp Met Lys Arg Glu Lys
        195                 200                 205

Gln His Met Ala Thr Met Leu Gly Met Ala Arg Asp Tyr Ala Arg Gly
    210                 215                 220

Lys Gly Phe Lys Gly Thr Phe Leu Ile Glu Pro Lys Pro Met Glu Pro
225                 230                 235                 240

Thr Lys His Gln Tyr Asp Val Asp Thr Glu Thr Val Ile Gly Phe Leu
                245                 250                 255

Arg Ala Asn Gly Leu Asp Lys Asp Phe Lys Val Asn Ile Glu Val Asn
            260                 265                 270

His Ala Thr Leu Ala Gly His Thr Phe Glu His Glu Leu Gln Cys Ala
        275                 280                 285

Ala Asp Ala Gly Leu Leu Gly Ser Ile Asp Ala Asn Arg Gly Asp Tyr
    290                 295                 300

Gln Asn Gly Trp Asp Thr Asp Gln Phe Pro Ile Asp Leu Tyr Glu Leu
305                 310                 315                 320

Thr Gln Ala Met Met Val Ile Leu Lys Asn Gly Gly Leu Val Gly Gly
                325                 330                 335

Thr Asn Phe Asp Ala Lys Thr Arg Arg Asn Ser Thr Asp Leu Asp Asp
            340                 345                 350

Ile Ile Ile Ala His Val Ser Gly Met Asp Ile Met Ala Arg Ala Leu
        355                 360                 365

Leu Val Ala Ala Asp Val Leu Thr Lys Ser Glu Leu Pro Lys Met Leu
    370                 375                 380

Lys Glu Arg Tyr Ala Ser Phe Asp Ser Gly Lys Gly Lys Glu Phe Glu
385                 390                 395                 400

Glu Gly Lys Leu Thr Leu Glu Gln Val Val Glu Tyr Ala Lys Thr Lys
                405                 410                 415

Gly Glu Pro Lys Ala Thr Ser Gly Lys Gln Glu Leu Tyr Glu Thr Ile
            420                 425                 430

Val Asn Met Tyr Ile
```

435

<210> SEQ ID NO 5
<211> LENGTH: 1329
<212> TYPE: DNA
<213> ORGANISM: Unknown
<220> FEATURE:
<223> OTHER INFORMATION: Obtained from environmental sample

<400> SEQUENCE: 5
atgaattttt ataaaggcga aaaagaattc ttccccggaa taggaaagat tcagtttgaa 60
ggacgcgagt caaagaaccc gatggcgttt cattattatg acgaaaacaa ggtggtgatg 120
ggtaaaacac tgaaggatca tcttcgtttt gcaatggctt actggcatac gctttgtgcc 180
gaagggggcg accagtttgg cggtggtacg aaaacattcc cctggaatgc tgctgccgac 240
ccgatcagcc gtgccaaata taagatggat gcagcgttcg agtttatgac aaaatgcagc 300
atcccttatt actgtttcca tgatgtggac gtggtggacg aagctcccac gctggctcag 360
tttgaaaaag accttcatac gatggtaggc catgccaaag ggcttcagca ggcaaccgga 420
aaaaaactgt tatggtctac tgccaacgtg ttcagcaaca aacgctatat gaacggggct 480
gccactaatc ctgacttctc ggccgtggct tgtgccggta cgcagatcaa gaatgcgatc 540
gatgcctgta tcgcgctgga cggtgaaaac tatgtgttct ggggcggacg tgaaggatat 600
atgggcttgc tcaataccga tatgaaacgc gaaaaagacc atctggccat gatgctgacg 660
atggcacgcg actatggccg caagaacggt ttcaaaggta ctttcctgat cgagccgaaa 720
ccgatggaac cgaccaagca tcaatatgat gtcgactcgg aaactgtaat cggcttccta 780
cgtcattatg gcctggataa agacttcgcc ctgaatatcg aagtaaatca tgcaaccctg 840
gccggacata cgttcgagca cgaattgcag gctgctgtcg atgccggtat gctgtgcagt 900
atcgatgcca accgtggtga ctaccagaat ggctgggata ccgaccaatt cccgatggac 960
atctacgaac tgactcaggc ttggctggtc attctgcaag gtggtggtct gacaaccggc 1020
ggaacgaact tcgatgccaa gacccgccgc aactcgaccg acctggacga tatcttcctg 1080
gctcatatag gtggtatgga tgcgtttgcc cgtgccctga tcacggctgc tgccatcctt 1140
gaaaactccg attacacgaa gatgcgtgcc gaacgttaca ccagcttcga tggtggcgaa 1200
ggcaaagcgt ttgaagacgg taaactttct ctggaagacc tgcgtacgat cgctctccgc 1260
gacggagaac cgaagatggt cagcggcaaa caggaattat atgagatgat tctcaattta 1320
tacatataa 1329

<210> SEQ ID NO 6
<211> LENGTH: 442
<212> TYPE: PRT
<213> ORGANISM: Unknown
<220> FEATURE:
<223> OTHER INFORMATION: Obtained from environmental sample

<400> SEQUENCE: 6

Met Asn Phe Tyr Lys Gly Glu Lys Glu Phe Phe Pro Gly Ile Gly Lys
1 5 10 15

Ile Gln Phe Glu Gly Arg Glu Ser Lys Asn Pro Met Ala Phe His Tyr
20 25 30

Tyr Asp Glu Asn Lys Val Val Met Gly Lys Thr Leu Lys Asp His Leu
35 40 45

Arg Phe Ala Met Ala Tyr Trp His Thr Leu Cys Ala Glu Gly Gly Asp
50 55 60

```
Gln Phe Gly Gly Gly Thr Lys Thr Phe Pro Trp Asn Ala Ala Ala Asp
65                  70                  75                  80

Pro Ile Ser Arg Ala Lys Tyr Lys Met Asp Ala Ala Phe Glu Phe Met
                85                  90                  95

Thr Lys Cys Ser Ile Pro Tyr Tyr Cys Phe His Asp Val Asp Val Val
            100                 105                 110

Asp Glu Ala Pro Thr Leu Ala Gln Phe Glu Lys Asp Leu His Thr Met
        115                 120                 125

Val Gly His Ala Lys Gly Leu Gln Gln Ala Thr Gly Lys Lys Leu Leu
    130                 135                 140

Trp Ser Thr Ala Asn Val Phe Ser Asn Lys Arg Tyr Met Asn Gly Ala
145                 150                 155                 160

Ala Thr Asn Pro Asp Phe Ser Ala Val Ala Cys Ala Gly Thr Gln Ile
                165                 170                 175

Lys Asn Ala Ile Asp Ala Cys Ile Ala Leu Asp Gly Glu Asn Tyr Val
            180                 185                 190

Phe Trp Gly Gly Arg Glu Gly Tyr Met Gly Leu Leu Asn Thr Asp Met
        195                 200                 205

Lys Arg Glu Lys Asp His Leu Ala Met Met Leu Thr Met Ala Arg Asp
    210                 215                 220

Tyr Gly Arg Lys Asn Gly Phe Lys Gly Thr Phe Leu Ile Glu Pro Lys
225                 230                 235                 240

Pro Met Glu Pro Thr Lys His Gln Tyr Asp Val Asp Ser Glu Thr Val
                245                 250                 255

Ile Gly Phe Leu Arg His Tyr Gly Leu Asp Lys Asp Phe Ala Leu Asn
            260                 265                 270

Ile Glu Val Asn His Ala Thr Leu Ala Gly His Thr Phe Glu His Glu
        275                 280                 285

Leu Gln Ala Ala Val Asp Ala Gly Met Leu Cys Ser Ile Asp Ala Asn
    290                 295                 300

Arg Gly Asp Tyr Gln Asn Gly Trp Asp Thr Asp Gln Phe Pro Met Asp
305                 310                 315                 320

Ile Tyr Glu Leu Thr Gln Ala Trp Leu Val Ile Leu Gln Gly Gly Gly
                325                 330                 335

Leu Thr Thr Gly Gly Thr Asn Phe Asp Ala Lys Thr Arg Arg Asn Ser
            340                 345                 350

Thr Asp Leu Asp Asp Ile Phe Leu Ala His Ile Gly Gly Met Asp Ala
        355                 360                 365

Phe Ala Arg Ala Leu Ile Thr Ala Ala Ala Ile Leu Glu Asn Ser Asp
    370                 375                 380

Tyr Thr Lys Met Arg Ala Glu Arg Tyr Thr Ser Phe Asp Gly Gly Glu
385                 390                 395                 400

Gly Lys Ala Phe Glu Asp Gly Lys Leu Ser Leu Glu Asp Leu Arg Thr
                405                 410                 415

Ile Ala Leu Arg Asp Gly Glu Pro Lys Met Val Ser Gly Lys Gln Glu
            420                 425                 430

Leu Tyr Glu Met Ile Leu Asn Leu Tyr Ile
        435                 440
```

<210> SEQ ID NO 7
<211> LENGTH: 1329
<212> TYPE: DNA
<213> ORGANISM: Unknown
<220> FEATURE:

<223> OTHER INFORMATION: Obtained from environmental sample

<400> SEQUENCE: 7
atgaattact ttaaaggtga gaaagagttc ttcccgggaa tcgggaaaat agagtttgaa 60
ggacgtgaat cgaagaatcc gatggctttt cattactatg acgagaacaa ggttgtcatg 120
gggaagacct tgaaggacca tctgcgtttt gcgatggctt attggcatac gctgtgtgcg 180
gaaggcgccg accagttcgg cggcgggacg aaggcatttc cctggaatac cggggcggat 240
cgtatttccc gtgccaagta taagatggat gctgcttttg agtttatgac gaaatgtaac 300
atcccgtact attgtttcca tgatgtggat gtggtggatg aagctccgac actggccgaa 360
tttgaaaaag acttgcatac gatggtcgaa tatgccaagc agcatcagga ggcaaccggg 420
aaaaaactgt tgtggtctac cgccaatgtg ttcagcaata aacgttatat gaacggggct 480
gccacaaatc cgtatttccc tgctgtcgct tgtgcgggta cgcagatcaa gaatgctatc 540
gacgcttgta ttgccctggg cggcgaaaac tatgtgttct ggggcggtcg tgaagggtat 600
atgagcttgt tgaacaccaa tatgaaacgc gaaaaggaac atctcgccat gatgttgacg 660
atggctcgcg attatgcgcg taagaacggc ttcaaaggta ctttcctggt agagcctaaa 720
ccgatggaac cgaccaaaca tcagtatgat gtggacacag aaactgttat cggcttcctg 780
cgtcattacg gccttgacaa ggactttgcc atcaacatcg aagtgaatca tgctacattg 840
gctggacata cattcgaaca tgagcttcag gcggctgccg atgccggtat gctgtgcagc 900
atcgacgcca accgcggcga ttaccagaat ggttgggaca cggatcagtt cccggtcgac 960
atctacgaac tgacacaggc gtggctggtt atcctcgaag cgggtggcct gactaccggt 1020
ggtacgaact tcgacgccaa gacgcgccgc aactcgactg acctggacga tatcttcctg 1080
gcacacatcg gtggtatgga ttcgtttgcc cgtgctttga tggcggctgc cgatatattg 1140
gaacactccg attacaaaaa gatgcgtgcc gaacgttatg ccagcttcga tcaaggcgac 1200
ggcaagaagt tcgaagatgg taaactcctt ctcgaggacc tccgcaccat cgctcttgcc 1260
tccggcgaac cgaagcaaat cagcgggaaa caggaattgt atgaaatgat tatcaaccag 1320
tacatttaa 1329

<210> SEQ ID NO 8
<211> LENGTH: 442
<212> TYPE: PRT
<213> ORGANISM: Unknown
<220> FEATURE:
<223> OTHER INFORMATION: Obtained from environmental sample

<400> SEQUENCE: 8

Met Asn Tyr Phe Lys Gly Glu Lys Glu Phe Phe Pro Gly Ile Gly Lys
1 5 10 15

Ile Glu Phe Glu Gly Arg Glu Ser Lys Asn Pro Met Ala Phe His Tyr
20 25 30

Tyr Asp Glu Asn Lys Val Val Met Gly Lys Thr Leu Lys Asp His Leu
35 40 45

Arg Phe Ala Met Ala Tyr Trp His Thr Leu Cys Ala Glu Gly Ala Asp
50 55 60

Gln Phe Gly Gly Gly Thr Lys Ala Phe Pro Trp Asn Thr Gly Ala Asp
65 70 75 80

Arg Ile Ser Arg Ala Lys Tyr Lys Met Asp Ala Ala Phe Glu Phe Met
85 90 95

Thr Lys Cys Asn Ile Pro Tyr Tyr Cys Phe His Asp Val Asp Val Val

```
            100                 105                 110

Asp Glu Ala Pro Thr Leu Ala Glu Phe Glu Lys Asp Leu His Thr Met
        115                 120                 125

Val Glu Tyr Ala Lys Gln His Gln Glu Ala Thr Gly Lys Lys Leu Leu
    130                 135                 140

Trp Ser Thr Ala Asn Val Phe Ser Asn Lys Arg Tyr Met Asn Gly Ala
145                 150                 155                 160

Ala Thr Asn Pro Tyr Phe Pro Ala Val Ala Cys Ala Gly Thr Gln Ile
                165                 170                 175

Lys Asn Ala Ile Asp Ala Cys Ile Ala Leu Gly Gly Glu Asn Tyr Val
            180                 185                 190

Phe Trp Gly Gly Arg Glu Gly Tyr Met Ser Leu Leu Asn Thr Asn Met
        195                 200                 205

Lys Arg Glu Lys Glu His Leu Ala Met Met Leu Thr Met Ala Arg Asp
    210                 215                 220

Tyr Ala Arg Lys Asn Gly Phe Lys Gly Thr Phe Leu Val Glu Pro Lys
225                 230                 235                 240

Pro Met Glu Pro Thr Lys His Gln Tyr Asp Val Asp Thr Glu Thr Val
                245                 250                 255

Ile Gly Phe Leu Arg His Tyr Gly Leu Asp Lys Asp Phe Ala Ile Asn
            260                 265                 270

Ile Glu Val Asn His Ala Thr Leu Ala Gly His Thr Phe Glu His Glu
        275                 280                 285

Leu Gln Ala Ala Ala Asp Ala Gly Met Leu Cys Ser Ile Asp Ala Asn
    290                 295                 300

Arg Gly Asp Tyr Gln Asn Gly Trp Asp Thr Asp Gln Phe Pro Val Asp
305                 310                 315                 320

Ile Tyr Glu Leu Thr Gln Ala Trp Leu Val Ile Leu Glu Ala Gly Gly
                325                 330                 335

Leu Thr Thr Gly Gly Thr Asn Phe Asp Ala Lys Thr Arg Arg Asn Ser
            340                 345                 350

Thr Asp Leu Asp Asp Ile Phe Leu Ala His Ile Gly Gly Met Asp Ser
        355                 360                 365

Phe Ala Arg Ala Leu Met Ala Ala Ala Asp Ile Leu Glu His Ser Asp
    370                 375                 380

Tyr Lys Lys Met Arg Ala Glu Arg Tyr Ala Ser Phe Asp Gln Gly Asp
385                 390                 395                 400

Gly Lys Lys Phe Glu Asp Gly Lys Leu Leu Leu Glu Asp Leu Arg Thr
                405                 410                 415

Ile Ala Leu Ala Ser Gly Glu Pro Lys Gln Ile Ser Gly Lys Gln Glu
            420                 425                 430

Leu Tyr Glu Met Ile Ile Asn Gln Tyr Ile
        435                 440
```

<210> SEQ ID NO 9
<211> LENGTH: 1329
<212> TYPE: DNA
<213> ORGANISM: Unknown
<220> FEATURE:
<223> OTHER INFORMATION: Obtained from environmental sample

<400> SEQUENCE: 9

```
atgaattatt ttaaaggtga aaaagagttt ttccctggaa tcgggaaaat agagtttgaa      60

ggacgtgagt cgaagaatcc gatggctttt cattattatg atgaaaacaa ggtcgtaatg     120
```

```
ggcaagacct tgaaagatca cctccgcttt gcaatggctt actggcatac gttgtgcgcg    180

gaaggcgcag accagtttgg cggtggcaca aaatcattcc cctggaatac cgcagcggat    240

cgtatttccc gcgctaaata taaaatggat gctgctttcg agtttatgac caagtgcagt    300

atcccgtact attgtttcca tgatgtggac gtggtggacg aagctccggc actggccgaa    360

tttgaaaagg acctgcatac gatggtggga ttcgccaaac aacaccagga agcaaccgga    420

aagaaactgt tgtggtctac agccaatgta ttcgggcata aacgttatat gaacggagcg    480

gctaccaatc cttatttccc ggctgtcgct tgtgccggta cgcagatcaa gaatgcaatc    540

gacgcctgta tcgagctggg tggagagaac tatgtattct ggggcggacg cgaaggctac    600

atgagcctgc tgaacaccaa tatgaaacgt gaaaaggatc atttggccat gatgctgaca    660

atggcacgcg attatgcccg caagaatggt ttcaagggta ctttcctggt ggaatctaag    720

ccgatggaac cgaccaaaca tcagtatgac gcagatacgg aaaccgtgat cggcttcctg    780

cgccactatg gcctcgacaa ggatttcgct atcaacattg aagtgaacca tgctacattg    840

gccggccata cattcgaaca tgaacttcag gctgctgccg atgccggtat gctgtgcagc    900

atcgatgcaa atagaggcga ctatcagaat ggttgggata cggatcagtt ccccgtagac    960

atttacgaac tgacacaggc ctggctggtt atcctggaag cgggcggact gacaaccgga   1020

ggtacgaact tcgatgcgaa gacccgtcgt aactcgactg acctcgacga tatcttcctg   1080

gcccatatcg gcggtatgga ttcgtttgca cgtgccttga tggcagctgc cgatatcctg   1140

gaacattctg attacaagaa gatgcgtgcc gaacgttacg ccagcttcga ccagggcgac   1200

ggcaagaagt tcgaagacgg caaactcctt ctcgaagacc tgcgcacaat tgcccttgcc   1260

ggcgacgaac cgaagcagat cagcggcaag caggagttgt atgagatgat tatcaatcag   1320

tatatttaa                                                           1329
```

<210> SEQ ID NO 10
<211> LENGTH: 442
<212> TYPE: PRT
<213> ORGANISM: Unknown
<220> FEATURE:
<223> OTHER INFORMATION: Obtained from environmental sample

<400> SEQUENCE: 10

```
Met Asn Tyr Phe Lys Gly Glu Lys Glu Phe Phe Pro Gly Ile Gly Lys
1               5                   10                  15

Ile Glu Phe Glu Gly Arg Glu Ser Lys Asn Pro Met Ala Phe His Tyr
            20                  25                  30

Tyr Asp Glu Asn Lys Val Val Met Gly Lys Thr Leu Lys Asp His Leu
        35                  40                  45

Arg Phe Ala Met Ala Tyr Trp His Thr Leu Cys Ala Glu Gly Ala Asp
    50                  55                  60

Gln Phe Gly Gly Gly Thr Lys Ser Phe Pro Trp Asn Thr Ala Ala Asp
65                  70                  75                  80

Arg Ile Ser Arg Ala Lys Tyr Lys Met Asp Ala Ala Phe Glu Phe Met
                85                  90                  95

Thr Lys Cys Ser Ile Pro Tyr Tyr Cys Phe His Asp Val Asp Val Val
            100                 105                 110

Asp Glu Ala Pro Ala Leu Ala Glu Phe Glu Lys Asp Leu His Thr Met
        115                 120                 125

Val Gly Phe Ala Lys Gln His Gln Glu Ala Thr Gly Lys Lys Leu Leu
    130                 135                 140
```

-continued

```
Trp Ser Thr Ala Asn Val Phe Gly His Lys Arg Tyr Met Asn Gly Ala
145                 150                 155                 160

Ala Thr Asn Pro Tyr Phe Pro Ala Val Ala Cys Ala Gly Thr Gln Ile
                165                 170                 175

Lys Asn Ala Ile Asp Ala Cys Ile Glu Leu Gly Gly Glu Asn Tyr Val
            180                 185                 190

Phe Trp Gly Gly Arg Glu Gly Tyr Met Ser Leu Leu Asn Thr Asn Met
        195                 200                 205

Lys Arg Glu Lys Asp His Leu Ala Met Met Leu Thr Met Ala Arg Asp
    210                 215                 220

Tyr Ala Arg Lys Asn Gly Phe Lys Gly Thr Phe Leu Val Glu Ser Lys
225                 230                 235                 240

Pro Met Glu Pro Thr Lys His Gln Tyr Asp Ala Asp Thr Glu Thr Val
                245                 250                 255

Ile Gly Phe Leu Arg His Tyr Gly Leu Asp Lys Asp Phe Ala Ile Asn
            260                 265                 270

Ile Glu Val Asn His Ala Thr Leu Ala Gly His Thr Phe Glu His Glu
        275                 280                 285

Leu Gln Ala Ala Ala Asp Ala Gly Met Leu Cys Ser Ile Asp Ala Asn
    290                 295                 300

Arg Gly Asp Tyr Gln Asn Gly Trp Asp Thr Asp Gln Phe Pro Val Asp
305                 310                 315                 320

Ile Tyr Glu Leu Thr Gln Ala Trp Leu Val Ile Leu Glu Ala Gly Gly
                325                 330                 335

Leu Thr Thr Gly Gly Thr Asn Phe Asp Ala Lys Thr Arg Arg Asn Ser
            340                 345                 350

Thr Asp Leu Asp Asp Ile Phe Leu Ala His Ile Gly Gly Met Asp Ser
        355                 360                 365

Phe Ala Arg Ala Leu Met Ala Ala Ala Asp Ile Leu Glu His Ser Asp
    370                 375                 380

Tyr Lys Lys Met Arg Ala Glu Arg Tyr Ala Ser Phe Asp Gln Gly Asp
385                 390                 395                 400

Gly Lys Lys Phe Glu Asp Gly Lys Leu Leu Leu Glu Asp Leu Arg Thr
                405                 410                 415

Ile Ala Leu Ala Gly Asp Glu Pro Lys Gln Ile Ser Gly Lys Gln Glu
            420                 425                 430

Leu Tyr Glu Met Ile Ile Asn Gln Tyr Ile
        435                 440
```

<210> SEQ ID NO 11
<211> LENGTH: 1308
<212> TYPE: DNA
<213> ORGANISM: Unknown
<220> FEATURE:
<223> OTHER INFORMATION: Obtained from environmental sample

<400> SEQUENCE: 11

```
atgaaacagt atttcccgaa catctccgcc atcaagtttg agggcgtcga gagcaagaat      60

cccctggctt accgctacta cgaccgcgac cgcgtcgtca tgggtaagaa gatgagcgaa     120

tggtttaagt tcgctatgtg ctggtggcac accctctgcg ccgagggctc cgatcagttc     180

ggtcccggca caaagacctt cccctggaac gccgccgccg accccgtgca ggctgccaag     240

gacaaggccg acgctggctt cgagatcatg cagaaactcg gcatcgagta ctactgcttc     300

cacgacgttg acctcgtggc cgaggctccc gacgtggaga cctacgagaa gaacctcaag     360
```

-continued

```
gagatcgtgg cttatctcaa gcagaaacag gctgagacgg gcatcaagct gctctggggc    420

actgccaacg tcttcggaca caagcgctac atgaacggag cctccacgaa ccccgacttc    480

gatgtcgtgg cacgcgctat cgtgcagatc aagaacgcca tcgatgctac catcgagctg    540

ggcggcacca actacgtctt ctggggcggt cgcgaaggct acatgagcct gctcaacacc    600

gatatgaagc gcgagaagga gcacatggct acgatgttga cgatggcacg cgactatgcc    660

cgttctaagg gattcaaggg cacgttcctc atcgaaccca aacccatgga acccacgaag    720

catcagtacg atgcggacac cgagacggtc atcggattcc tccgtgctca tggtctcgac    780

aaggatttca aggtcaacat cgaggtcaac cacgccacgc tggccggaca cacgttcgag    840

catgagctgg cctgcgccgt agacgccgat atgctcggca gcatcgatgc caatcgcggc    900

gactatcaga acggatggga caccgaccag ttccccatcg accactacga actcacgcag    960

gctatgctgc agatcatccg caacggaggt ttcaaggacg gtggcaccaa ttttgacgct   1020

aagacgcgcc gcaacagcac cgacctcgag gatatcttca tcgctcacgt agcagccatg   1080

gacgccatgg cccacgccct gttgtcggct gccgatatca tcgagaagtc gcccatctgc   1140

acgatggtca aggagcgtta cgccagcttc gatgccggcg aaggcaagcg cttcgaagaa   1200

ggcaagatga ccctcgagga agcctacgag tatggcaaga aggtcgggga gcccaagcag   1260

accagcggaa agcaggagct ctacgaagcc attgtcaata tgtattga                 1308
```

<210> SEQ ID NO 12
<211> LENGTH: 435
<212> TYPE: PRT
<213> ORGANISM: Unknown
<220> FEATURE:
<223> OTHER INFORMATION: Obtained from environmental sample

<400> SEQUENCE: 12

```
Met Lys Gln Tyr Phe Pro Asn Ile Ser Ala Ile Lys Phe Glu Gly Val
1               5                   10                  15

Glu Ser Lys Asn Pro Leu Ala Tyr Arg Tyr Tyr Asp Arg Asp Arg Val
            20                  25                  30

Val Met Gly Lys Lys Met Ser Glu Trp Phe Lys Phe Ala Met Cys Trp
        35                  40                  45

Trp His Thr Leu Cys Ala Glu Gly Ser Asp Gln Phe Gly Pro Gly Thr
    50                  55                  60

Lys Thr Phe Pro Trp Asn Ala Ala Ala Asp Pro Val Gln Ala Ala Lys
65                  70                  75                  80

Asp Lys Ala Asp Ala Gly Phe Glu Ile Met Gln Lys Leu Gly Ile Glu
                85                  90                  95

Tyr Tyr Cys Phe His Asp Val Asp Leu Val Ala Glu Ala Pro Asp Val
            100                 105                 110

Glu Thr Tyr Glu Lys Asn Leu Lys Glu Ile Val Ala Tyr Leu Lys Gln
        115                 120                 125

Lys Gln Ala Glu Thr Gly Ile Lys Leu Leu Trp Gly Thr Ala Asn Val
    130                 135                 140

Phe Gly His Lys Arg Tyr Met Asn Gly Ala Ser Thr Asn Pro Asp Phe
145                 150                 155                 160

Asp Val Val Ala Arg Ala Ile Val Gln Ile Lys Asn Ala Ile Asp Ala
                165                 170                 175

Thr Ile Glu Leu Gly Gly Thr Asn Tyr Val Phe Trp Gly Gly Arg Glu
            180                 185                 190

Gly Tyr Met Ser Leu Leu Asn Thr Asp Met Lys Arg Glu Lys Glu His
```

```
        195                 200                 205

Met Ala Thr Met Leu Thr Met Ala Arg Asp Tyr Ala Arg Ser Lys Gly
    210                 215                 220

Phe Lys Gly Thr Phe Leu Ile Glu Pro Lys Pro Met Glu Pro Thr Lys
225                 230                 235                 240

His Gln Tyr Asp Ala Asp Thr Glu Thr Val Ile Gly Phe Leu Arg Ala
                245                 250                 255

His Gly Leu Asp Lys Asp Phe Lys Val Asn Ile Glu Val Asn His Ala
            260                 265                 270

Thr Leu Ala Gly His Thr Phe Glu His Glu Leu Ala Cys Ala Val Asp
        275                 280                 285

Ala Asp Met Leu Gly Ser Ile Asp Ala Asn Arg Gly Asp Tyr Gln Asn
    290                 295                 300

Gly Trp Asp Thr Asp Gln Phe Pro Ile Asp His Tyr Glu Leu Thr Gln
305                 310                 315                 320

Ala Met Leu Gln Ile Ile Arg Asn Gly Gly Phe Lys Asp Gly Gly Thr
                325                 330                 335

Asn Phe Asp Ala Lys Thr Arg Arg Asn Ser Thr Asp Leu Glu Asp Ile
            340                 345                 350

Phe Ile Ala His Val Ala Ala Met Asp Ala Met Ala His Ala Leu Leu
        355                 360                 365

Ser Ala Ala Asp Ile Ile Glu Lys Ser Pro Ile Cys Thr Met Val Lys
    370                 375                 380

Glu Arg Tyr Ala Ser Phe Asp Ala Gly Glu Gly Lys Arg Phe Glu Glu
385                 390                 395                 400

Gly Lys Met Thr Leu Glu Glu Ala Tyr Glu Tyr Gly Lys Lys Val Gly
                405                 410                 415

Glu Pro Lys Gln Thr Ser Gly Lys Gln Glu Leu Tyr Glu Ala Ile Val
            420                 425                 430

Asn Met Tyr
        435


<210> SEQ ID NO 13
<211> LENGTH: 1317
<212> TYPE: DNA
<213> ORGANISM: Unknown
<220> FEATURE:
<223> OTHER INFORMATION: Obtained from environmental sample

<400> SEQUENCE: 13

atggcaacaa aagagtattt tcccggaata ggaaagatta aattcgaagg taaagagagt      60

atgaacccga tggcatatcg ttactacgat gctgagaagg taatcatggg taagaagatg     120

aaagattggt tgaagtttgc tatggcttgg tggcacactc tctgcgcaga aggtggtgac     180

caattcggtg gcggaacgaa acaattccct tggaatggtg actctgacgc tttgcaagca     240

gctaaaaata aattggatgc aggtttcgaa ttcatgcaga agatgggtat cgaatactat     300

tgcttccacg atgtagacct gatttctgaa ggtgcaagca tcgaagaata cgaagctaac     360

ttgaaagcta tcgtagctta tgcaaaagaa aaacaggctg aaactggtat caagctgttg     420

tggggtactg ctaacgtatt cggtcatgca cgttatatga acggtgctgc taccaatcct     480

gatttcgacg ttgtagcacg cgctgctgtt cagatcaaga acgctattga cgctactatc     540

gaactgggtg gttcaaacta tgtattctgg ggcggtcgcg aaggttacat gtctttgctg     600

aacactgacc agaaacgtga aaaagaacac cttgcaaaga tgttgactat cgctcgtgac     660
```

-continued

```
tatgcacgtg ctcgtggctt caaaggtact ttcctgattg agccgaaacc gatggaaccg    720

acaaaacatc agtatgatgt agatactgaa acagttatcg gcttcctgaa agctcacggt    780

ttggataagg atttcaaagt aaacatcgag gttaatcacg caactttggc tggccatact    840

ttcgaacacg aactggctgt agctgttgac aacggcatgt taggttctat cgacgctaac    900

cgtggtgact accagaacgg ttgggatact gaccaattcc ctatcgataa ctacgaactg    960

actcaagcta tgatgcagat catccgcaac ggtggtttgg gtaatggcgg tactaacttc   1020

gacgctaaga cccgtcgtaa ctctaccgac ctggaagata tcttcatcgc tcacattgca   1080

ggtatggatg ctatggcacg tgctctggaa agtgcagcta aattactgga agaatctcct   1140

tataagaaaa tgttggctga tcgttacgca tcattcgacg gtggcaaggg taaggaattc   1200

gaagaaggca aattgtcttt ggaagatgtt gtagcttatg cgaaagctaa cggcgaaccg   1260

aagcaaacca gcggcaagca agaattgtat gaagcaatcg tgaatatgta ttgctaa      1317
```

```
<210> SEQ ID NO 14
<211> LENGTH: 438
<212> TYPE: PRT
<213> ORGANISM: Unknown
<220> FEATURE:
<223> OTHER INFORMATION: Obtained from environmental sample

<400> SEQUENCE: 14

Met Ala Thr Lys Glu Tyr Phe Pro Gly Ile Gly Lys Ile Lys Phe Glu
1               5                   10                  15

Gly Lys Glu Ser Met Asn Pro Met Ala Tyr Arg Tyr Tyr Asp Ala Glu
            20                  25                  30

Lys Val Ile Met Gly Lys Lys Met Lys Asp Trp Leu Lys Phe Ala Met
        35                  40                  45

Ala Trp Trp His Thr Leu Cys Ala Glu Gly Gly Asp Gln Phe Gly Gly
    50                  55                  60

Gly Thr Lys Gln Phe Pro Trp Asn Gly Asp Ser Asp Ala Leu Gln Ala
65                  70                  75                  80

Ala Lys Asn Lys Leu Asp Ala Gly Phe Glu Phe Met Gln Lys Met Gly
                85                  90                  95

Ile Glu Tyr Tyr Cys Phe His Asp Val Asp Leu Ile Ser Glu Gly Ala
            100                 105                 110

Ser Ile Glu Glu Tyr Glu Ala Asn Leu Lys Ala Ile Val Ala Tyr Ala
        115                 120                 125

Lys Glu Lys Gln Ala Glu Thr Gly Ile Lys Leu Leu Trp Gly Thr Ala
    130                 135                 140

Asn Val Phe Gly His Ala Arg Tyr Met Asn Gly Ala Ala Thr Asn Pro
145                 150                 155                 160

Asp Phe Asp Val Val Ala Arg Ala Ala Val Gln Ile Lys Asn Ala Ile
                165                 170                 175

Asp Ala Thr Ile Glu Leu Gly Gly Ser Asn Tyr Val Phe Trp Gly Gly
            180                 185                 190

Arg Glu Gly Tyr Met Ser Leu Leu Asn Thr Asp Gln Lys Arg Glu Lys
        195                 200                 205

Glu His Leu Ala Lys Met Leu Thr Ile Ala Arg Asp Tyr Ala Arg Ala
    210                 215                 220

Arg Gly Phe Lys Gly Thr Phe Leu Ile Glu Pro Lys Pro Met Glu Pro
225                 230                 235                 240

Thr Lys His Gln Tyr Asp Val Asp Thr Glu Thr Val Ile Gly Phe Leu
                245                 250                 255
```

```
Lys Ala His Gly Leu Asp Lys Asp Phe Lys Val Asn Ile Glu Val Asn
            260                 265                 270

His Ala Thr Leu Ala Gly His Thr Phe Glu His Glu Leu Ala Val Ala
        275                 280                 285

Val Asp Asn Gly Met Leu Gly Ser Ile Asp Ala Asn Arg Gly Asp Tyr
    290                 295                 300

Gln Asn Gly Trp Asp Thr Asp Gln Phe Pro Ile Asp Asn Tyr Glu Leu
305                 310                 315                 320

Thr Gln Ala Met Met Gln Ile Ile Arg Asn Gly Gly Leu Gly Asn Gly
                325                 330                 335

Gly Thr Asn Phe Asp Ala Lys Thr Arg Arg Asn Ser Thr Asp Leu Glu
            340                 345                 350

Asp Ile Phe Ile Ala His Ile Ala Gly Met Asp Ala Met Ala Arg Ala
        355                 360                 365

Leu Glu Ser Ala Ala Lys Leu Leu Glu Glu Ser Pro Tyr Lys Lys Met
    370                 375                 380

Leu Ala Asp Arg Tyr Ala Ser Phe Asp Gly Gly Lys Gly Lys Glu Phe
385                 390                 395                 400

Glu Glu Gly Lys Leu Ser Leu Glu Asp Val Val Ala Tyr Ala Lys Ala
                405                 410                 415

Asn Gly Glu Pro Lys Gln Thr Ser Gly Lys Gln Glu Leu Tyr Glu Ala
            420                 425                 430

Ile Val Asn Met Tyr Cys
        435
```

<210> SEQ ID NO 15
<211> LENGTH: 1314
<212> TYPE: DNA
<213> ORGANISM: Unknown
<220> FEATURE:
<223> OTHER INFORMATION: Obtained from environmental sample

<400> SEQUENCE: 15

```
atggcaaaag agtattttcc tggcgtgaaa aaaatccagt tcgagggtaa ggacagtaag     60

aatccaatgg cttaccgtta ttatgatgca gagaaggtca tcatgggtaa gaagatgaag    120

gattggttga agttcgctat ggcttggtgg cacactttgt gcgctgaggg cgcagaccag    180

ttcggtggcg gtactaagac tttcccttgg aacgaaggtg caaacgcttt ggaagttgct    240

aagaataagg ctgatgctgg tttcgagatt atggagaagc ttggcatcga gtactactgt    300

ttccacgatg tagacctcgt tgaggaggct gcaactatcg aggagtatga ggctaacatg    360

aaggctatcg ttgcttatct taaggagaag caggctgcta ctggcaagaa gcttctttgg    420

ggtactgcta acgtattcgg caacaagcgc tatatgaacg gtgcttctac aaaccctgac    480

ttcgacgttg ttgctcgcgc ttgtgttcag attaagaacg ctatcgacgc tactatcgaa    540

cttggtggta caaactacgt attctggggt ggccgcgagg gttatatgag ccttcttaac    600

acagatatga agcgtgagaa ggagcacatg gcaactatgc ttactaaggc tcgcgactac    660

gctcgttcaa agggctttac tggtacattc cttatcgagc caaagccaat ggaaccatca    720

aagcatcagt atgatgttga tactgagact gtttgtggtt tcttgagggc tcacggtctt    780

gacaaggact tcaaggtaaa catcgaggtt aaccacgcta ctttggctgg tcacacattc    840

gagcacgagt tggctgctgc tgttgataac ggtatgcttg gctctatcga cgctaaccgc    900

ggtgactacc agaacggttg ggatactgac cagttcccta tcgacaactt cgagcttatt    960
```

-continued

```
caggctatga tgcagattat ccgcaacggt ggtcttggca acggtggtac aaacttcgac   1020

gctaagactc gtcgtaactc aactgacctt gaggatatct tcatcgcaca catcgctggt   1080

atggatgcaa tggctcgcgc tcttgagaac gcagcagacc ttttggagaa ctctccaatc   1140

aagaagatgg ttgctgagcg ttacgcttca ttcgacagcg gcaagggtaa ggagttcgag   1200

gaaggcaagt tgagccttgg ggacatcgtt gcttatgcta agcagaacgg tgagcctaag   1260

cagacaagcg gtaagcagga gctttacgag gctatcgtaa acatgtactg ctaa         1314


<210> SEQ ID NO 16
<211> LENGTH: 437
<212> TYPE: PRT
<213> ORGANISM: Unknown
<220> FEATURE:
<223> OTHER INFORMATION: Obtained from environmental sample

<400> SEQUENCE: 16

Met Ala Lys Glu Tyr Phe Pro Gly Val Lys Lys Ile Gln Phe Glu Gly
1               5                   10                  15

Lys Asp Ser Lys Asn Pro Met Ala Tyr Arg Tyr Tyr Asp Ala Glu Lys
            20                  25                  30

Val Ile Met Gly Lys Lys Met Lys Asp Trp Leu Lys Phe Ala Met Ala
        35                  40                  45

Trp Trp His Thr Leu Cys Ala Glu Gly Ala Asp Gln Phe Gly Gly Gly
    50                  55                  60

Thr Lys Thr Phe Pro Trp Asn Glu Gly Ala Asn Ala Leu Glu Val Ala
65                  70                  75                  80

Lys Asn Lys Ala Asp Ala Gly Phe Glu Ile Met Glu Lys Leu Gly Ile
                85                  90                  95

Glu Tyr Tyr Cys Phe His Asp Val Asp Leu Val Glu Glu Ala Ala Thr
            100                 105                 110

Ile Glu Glu Tyr Glu Ala Asn Met Lys Ala Ile Val Ala Tyr Leu Lys
        115                 120                 125

Glu Lys Gln Ala Ala Thr Gly Lys Lys Leu Leu Trp Gly Thr Ala Asn
    130                 135                 140

Val Phe Gly Asn Lys Arg Tyr Met Asn Gly Ala Ser Thr Asn Pro Asp
145                 150                 155                 160

Phe Asp Val Val Ala Arg Ala Cys Val Gln Ile Lys Asn Ala Ile Asp
                165                 170                 175

Ala Thr Ile Glu Leu Gly Gly Thr Asn Tyr Val Phe Trp Gly Gly Arg
            180                 185                 190

Glu Gly Tyr Met Ser Leu Leu Asn Thr Asp Met Lys Arg Glu Lys Glu
        195                 200                 205

His Met Ala Thr Met Leu Thr Lys Ala Arg Asp Tyr Ala Arg Ser Lys
    210                 215                 220

Gly Phe Thr Gly Thr Phe Leu Ile Glu Pro Lys Pro Met Glu Pro Ser
225                 230                 235                 240

Lys His Gln Tyr Asp Val Asp Thr Glu Thr Val Cys Gly Phe Leu Arg
                245                 250                 255

Ala His Gly Leu Asp Lys Asp Phe Lys Val Asn Ile Glu Val Asn His
            260                 265                 270

Ala Thr Leu Ala Gly His Thr Phe Glu His Glu Leu Ala Ala Ala Val
        275                 280                 285

Asp Asn Gly Met Leu Gly Ser Ile Asp Ala Asn Arg Gly Asp Tyr Gln
    290                 295                 300
```

```
Asn Gly Trp Asp Thr Asp Gln Phe Pro Ile Asp Asn Phe Glu Leu Ile
305                 310                 315                 320

Gln Ala Met Met Gln Ile Ile Arg Asn Gly Gly Leu Gly Asn Gly Gly
                325                 330                 335

Thr Asn Phe Asp Ala Lys Thr Arg Arg Asn Ser Thr Asp Leu Glu Asp
            340                 345                 350

Ile Phe Ile Ala His Ile Ala Gly Met Asp Ala Met Ala Arg Ala Leu
        355                 360                 365

Glu Asn Ala Ala Asp Leu Leu Glu Asn Ser Pro Ile Lys Lys Met Val
    370                 375                 380

Ala Glu Arg Tyr Ala Ser Phe Asp Ser Gly Lys Gly Lys Glu Phe Glu
385                 390                 395                 400

Glu Gly Lys Leu Ser Leu Gly Asp Ile Val Ala Tyr Ala Lys Gln Asn
                405                 410                 415

Gly Glu Pro Lys Gln Thr Ser Gly Lys Gln Glu Leu Tyr Glu Ala Ile
            420                 425                 430

Val Asn Met Tyr Cys
        435
```

<210> SEQ ID NO 17
<211> LENGTH: 1317
<212> TYPE: DNA
<213> ORGANISM: Unknown
<220> FEATURE:
<223> OTHER INFORMATION: Obtained from environmental sample

<400> SEQUENCE: 17

```
atggcgacaa aagaatactt tcccggaata gggaaaatca agtttgaggg tgtgaatagc      60

tataatccgc tggcatacag atattacgat gccgagcgca tagtccttgg caagccgatg     120

aaggagtggc tcaagtttgc catggcatgg tggcacacac tctgcgcaga gggtggcgac     180

cagtttggcg gcggtacgaa gaattttccc tggaatggag atcccgatcc ggtacaggcc     240

gcaaaaaaca aagtagacgc cggcttcgaa ttcatgacca agatgggaat agagtatttc     300

tgtttccacg acgtggatct cgtcagcgag gcagcaacca tcgaggagta tgaggccaac     360

ctgaaggaag tggtgggcta catcaaggaa aagcaggccg agacggggat caaaaacctc     420

tggggcactg ccaacgtgtt cagccacgcg cgctacatga acggagccgc caccaacccc     480

gacttcgatg tagtggcccg cgcagccgtg cagatcaaga atgctatcga cgccacgata     540

gccttaggtg gcaccaacta cgtgttctgg ggtggccgtg aaggttacat gagcctgctc     600

aacaccgacc agaagcgcga gaaggagcat ctggcaatga tgctccgcat ggcccgcgac     660

tatgcgcgtg caaaaggctt caccggcacc ttccttatcg agcccaagcc gatggagccc     720

accaagcacc agtatgatgt agacaccgag actgtgatag gcttcctccg tgcccacggc     780

ctcgacaagg acttcaaggt caacatagag gtgaaccacg ccaccctggc cggccatacc     840

ttcgagcatg agctggcagt ggccgtggac aacggtatgc tcggcagcat cgacgccaac     900

cgcggtgact accagaacgg ctgggatacc gaccagttcc ccatcgacaa ctacgagctg     960

acccaggcca tgatgcagat aatacgcaac ggcggcttcg gcaacggcgg atgcaacttc    1020

gacgccaaga cacgccgcaa ctccaccgac ctggaggata tcttcatagc ccacatagca    1080

ggcatggacg ccatggcccg cgccctgctc agcgcagcag aagtgctgga gaaatcgccc    1140

tacaggaaga tgctcgccga gcgctacgca ccgtttgatg ccggccaggg aaaggcattt    1200

gaagagggcg caatgtcgct caccgacctt gtggagtatg ccaaggagca tggcgagccc    1260
```

acacagactt ccggcaagca ggaactctat gaggcaatcg tcaatatgta ttgctaa 1317

<210> SEQ ID NO 18
<211> LENGTH: 438
<212> TYPE: PRT
<213> ORGANISM: Unknown
<220> FEATURE:
<223> OTHER INFORMATION: Obtained from environmental sample

<400> SEQUENCE: 18

```
Met Ala Thr Lys Glu Tyr Phe Pro Gly Ile Gly Lys Ile Lys Phe Glu
1               5                   10                  15

Gly Val Asn Ser Tyr Asn Pro Leu Ala Tyr Arg Tyr Tyr Asp Ala Glu
            20                  25                  30

Arg Ile Val Leu Gly Lys Pro Met Lys Glu Trp Leu Lys Phe Ala Met
        35                  40                  45

Ala Trp Trp His Thr Leu Cys Ala Glu Gly Gly Asp Gln Phe Gly Gly
    50                  55                  60

Gly Thr Lys Asn Phe Pro Trp Asn Gly Asp Pro Asp Pro Val Gln Ala
65                  70                  75                  80

Ala Lys Asn Lys Val Asp Ala Gly Phe Glu Phe Met Thr Lys Met Gly
                85                  90                  95

Ile Glu Tyr Phe Cys Phe His Asp Val Asp Leu Val Ser Glu Ala Ala
            100                 105                 110

Thr Ile Glu Glu Tyr Glu Ala Asn Leu Lys Glu Val Val Gly Tyr Ile
        115                 120                 125

Lys Glu Lys Gln Ala Glu Thr Gly Ile Lys Asn Leu Trp Gly Thr Ala
    130                 135                 140

Asn Val Phe Ser His Ala Arg Tyr Met Asn Gly Ala Ala Thr Asn Pro
145                 150                 155                 160

Asp Phe Asp Val Val Ala Arg Ala Ala Val Gln Ile Lys Asn Ala Ile
                165                 170                 175

Asp Ala Thr Ile Ala Leu Gly Gly Thr Asn Tyr Val Phe Trp Gly Gly
            180                 185                 190

Arg Glu Gly Tyr Met Ser Leu Leu Asn Thr Asp Gln Lys Arg Glu Lys
        195                 200                 205

Glu His Leu Ala Met Met Leu Arg Met Ala Arg Asp Tyr Ala Arg Ala
    210                 215                 220

Lys Gly Phe Thr Gly Thr Phe Leu Ile Glu Pro Lys Pro Met Glu Pro
225                 230                 235                 240

Thr Lys His Gln Tyr Asp Val Asp Thr Glu Thr Val Ile Gly Phe Leu
                245                 250                 255

Arg Ala His Gly Leu Asp Lys Asp Phe Lys Val Asn Ile Glu Val Asn
            260                 265                 270

His Ala Thr Leu Ala Gly His Thr Phe Glu His Glu Leu Ala Val Ala
        275                 280                 285

Val Asp Asn Gly Met Leu Gly Ser Ile Asp Ala Asn Arg Gly Asp Tyr
    290                 295                 300

Gln Asn Gly Trp Asp Thr Asp Gln Phe Pro Ile Asp Asn Tyr Glu Leu
305                 310                 315                 320

Thr Gln Ala Met Met Gln Ile Ile Arg Asn Gly Gly Phe Gly Asn Gly
                325                 330                 335

Gly Cys Asn Phe Asp Ala Lys Thr Arg Arg Asn Ser Thr Asp Leu Glu
            340                 345                 350

Asp Ile Phe Ile Ala His Ile Ala Gly Met Asp Ala Met Ala Arg Ala
```

-continued

```
        355                 360                 365

Leu Leu Ser Ala Ala Glu Val Leu Glu Lys Ser Pro Tyr Arg Lys Met
    370                 375                 380

Leu Ala Glu Arg Tyr Ala Pro Phe Asp Ala Gly Gln Gly Lys Ala Phe
385                 390                 395                 400

Glu Glu Gly Ala Met Ser Leu Thr Asp Leu Val Glu Tyr Ala Lys Glu
                405                 410                 415

His Gly Glu Pro Thr Gln Thr Ser Gly Lys Gln Glu Leu Tyr Glu Ala
            420                 425                 430

Ile Val Asn Met Tyr Cys
        435
```

<210> SEQ ID NO 19
<211> LENGTH: 1320
<212> TYPE: DNA
<213> ORGANISM: Unknown
<220> FEATURE:
<223> OTHER INFORMATION: Obtained from environmental sample

<400> SEQUENCE: 19

```
atggcaacaa aggaatattt tccccatata gggaagatcc agttcaaagg cacggaatcg      60

tacgatccga tgtcgtatcg ttactatgac gccgagcgcg tagttctggg caagcccatg     120

aaggaatggc tgaaattcgc catggcatgg tggcacacat tgtgcgccga gggcggcgac     180

cagttcggcg gcggaacgaa gaagttcccc tggaacgagg gcgaggacgc catgaccatc     240

gccaagcaga aggctgacgc cggcttcgag atcatgcaga agctcggcat cgagtatttc     300

tgcttccacg acatcgacct gatcggcgac ctgggcgacg acatcgagga ctatgagaac     360

cgtatgcacg aaatcaccgc acacctgaag gagaagatgg ccgccacggg catcaagaac     420

ctgtggggca ctgccaacgt gttcggccac gcacgctata tgaacggcgc cgccaccaac     480

cccgacttcg acgttgtggc acgcgcatgt gtgcagatca agaacgccat cgacgccacc     540

atcgctctag gcggtacaaa ctatgtattc tggggcggcc gcgagggcta catgagcctg     600

ctgaacaccg accagaagcg cgagaaagag cacttggcta ccatgctgac catggcacgc     660

gactatgccc gcgccaatgg cttcaccgga acgttcctga tcgagcccaa acccatggag     720

cccagcaagc atcagtatga tgtggatacc gagaccgtaa tcggcttcct gaaggcccac     780

aacctggaca aggacttcaa ggtgaacatc gaggtgaacc atgccactct ggccggccac     840

acattcgagc atgagctggc agtagccgtg gacaacggca tgctgggcag catcgacgcc     900

aaccgcggcg actatcagaa cggctgggac accgaccagt tccccatcga caactatgag     960

ctgacccagg ccatgatgca gataatccgc aacggtggcc tcggcaacgg cggtaccaac    1020

ttcgacgcca agacacgtcg caactccacc gacctggacg acatcttcat cgctcacatc    1080

gccggtatgg acgctatggc ccgcgctccg ctcagcgcag ccgacgtgct tgagaagtcg    1140

ccttacaaga agatgctggc cgaccgctac gcttcattcg acagcggcga gggcaagaag    1200

ttcgaggaag gcaagatgac tctggaggat gtcgtggcct acgccaagaa gaatcccgaa    1260

cccgctcaga ccagcggcaa gcaggaactc tacgaggcca tcatcaacat gtacgcctga    1320
```

<210> SEQ ID NO 20
<211> LENGTH: 439
<212> TYPE: PRT
<213> ORGANISM: Unknown
<220> FEATURE:
<223> OTHER INFORMATION: Obtained from environmental sample

<400> SEQUENCE: 20

Met Ala Thr Lys Glu Tyr Phe Pro His Ile Gly Lys Ile Gln Phe Lys
1 5 10 15

Gly Thr Glu Ser Tyr Asp Pro Met Ser Tyr Arg Tyr Tyr Asp Ala Glu
20 25 30

Arg Val Val Leu Gly Lys Pro Met Lys Glu Trp Leu Lys Phe Ala Met
35 40 45

Ala Trp Trp His Thr Leu Cys Ala Glu Gly Gly Asp Gln Phe Gly Gly
50 55 60

Gly Thr Lys Lys Phe Pro Trp Asn Glu Gly Glu Asp Ala Met Thr Ile
65 70 75 80

Ala Lys Gln Lys Ala Asp Ala Gly Phe Glu Ile Met Gln Lys Leu Gly
85 90 95

Ile Glu Tyr Phe Cys Phe His Asp Ile Asp Leu Ile Gly Asp Leu Gly
100 105 110

Asp Asp Ile Glu Asp Tyr Glu Asn Arg Met His Glu Ile Thr Ala His
115 120 125

Leu Lys Glu Lys Met Ala Ala Thr Gly Ile Lys Asn Leu Trp Gly Thr
130 135 140

Ala Asn Val Phe Gly His Ala Arg Tyr Met Asn Gly Ala Ala Thr Asn
145 150 155 160

Pro Asp Phe Asp Val Val Ala Arg Ala Cys Val Gln Ile Lys Asn Ala
165 170 175

Ile Asp Ala Thr Ile Ala Leu Gly Gly Thr Asn Tyr Val Phe Trp Gly
180 185 190

Gly Arg Glu Gly Tyr Met Ser Leu Leu Asn Thr Asp Gln Lys Arg Glu
195 200 205

Lys Glu His Leu Ala Thr Met Leu Thr Met Ala Arg Asp Tyr Ala Arg
210 215 220

Ala Asn Gly Phe Thr Gly Thr Phe Leu Ile Glu Pro Lys Pro Met Glu
225 230 235 240

Pro Ser Lys His Gln Tyr Asp Val Asp Thr Glu Thr Val Ile Gly Phe
245 250 255

Leu Lys Ala His Asn Leu Asp Lys Asp Phe Lys Val Asn Ile Glu Val
260 265 270

Asn His Ala Thr Leu Ala Gly His Thr Phe Glu His Glu Leu Ala Val
275 280 285

Ala Val Asp Asn Gly Met Leu Gly Ser Ile Asp Ala Asn Arg Gly Asp
290 295 300

Tyr Gln Asn Gly Trp Asp Thr Asp Gln Phe Pro Ile Asp Asn Tyr Glu
305 310 315 320

Leu Thr Gln Ala Met Met Gln Ile Ile Arg Asn Gly Gly Leu Gly Asn
325 330 335

Gly Gly Thr Asn Phe Asp Ala Lys Thr Arg Arg Asn Ser Thr Asp Leu
340 345 350

Asp Asp Ile Phe Ile Ala His Ile Ala Gly Met Asp Ala Met Ala Arg
355 360 365

Ala Pro Leu Ser Ala Ala Asp Val Leu Glu Lys Ser Pro Tyr Lys Lys
370 375 380

Met Leu Ala Asp Arg Tyr Ala Ser Phe Asp Ser Gly Glu Gly Lys Lys
385 390 395 400

Phe Glu Glu Gly Lys Met Thr Leu Glu Asp Val Val Ala Tyr Ala Lys
405 410 415

Lys Asn Pro Glu Pro Ala Gln Thr Ser Gly Lys Gln Glu Leu Tyr Glu
420 425 430

Ala Ile Ile Asn Met Tyr Ala
435

<210> SEQ ID NO 21
<211> LENGTH: 1320
<212> TYPE: DNA
<213> ORGANISM: Unknown
<220> FEATURE:
<223> OTHER INFORMATION: Obtained from environmental sample

<400> SEQUENCE: 21
atggcaacaa aagaattttt tcccgagatt ggtaaaatca agtttgaggg ccgcgaaagc 60
cgcaatcccc tcgcattccg ctactacggc cccgagaaag tcgttcttgg caagaagatg 120
aaagactggt tcaagtttgc gatggcttgg tggcacacac tgtgcgccca gggcaccgac 180
cagtttggtg gcgacaccaa gcagtttccg tggaacactg ccagtgaccc catgcaggcc 240
gccaaggata aggtggatgc cggatttgaa ttcatgacca agatgggcat tgagtacttc 300
tgcttccacg atgtggatct cgtcgccgag gccgccactg tcgaggagta tgaggctaac 360
ctcaagacca tcgtcgccta catcaaagag aaacaagccg agaccggcat caagaacctg 420
tggggcacag ccaacgtatt cggacacaaa cgctacatga acggtgccgc caccaacccc 480
gactttgatg tcgtggcacg cgccatcgtg caaatcaaga acgccatcga cgccaccatc 540
gagttgggcg gcacgagtta cgtcttttgg ggcggccgcg agggccacat gagcctgctc 600
aacaccgacc agaagcgcga gaaggagcac cttgcacgca tgctgaccat ggcacgcgac 660
tatgcccgcg cacgtggttt caacggcacc ttcctcatcg agcccaagcc catggagccg 720
accaagcacc aatatgatgt ggacaccgag accgtcatcg gtttcctgcg tgcccatggt 780
ctggacaagg acttcaaggt caacatcgag gtgaaccacg ctacactggc cggacacacc 840
ttcgagcgcg aactggcagt ggccgtcgac aacggtctac tcggctcaat cgacgccaac 900
cgtggtgact atcagaatgg ttgggacacc gatcagttcc ccatcgacca ctatgagttg 960
gttcagggca tgttgcagat tatccgcaat ggtggtttca ccgacggtgg caccaacttc 1020
gatgccaaga cccgccgcaa ctcgaccgac ctcgaggaca tcttcatcgc ccacatcgcc 1080
gcgatggatg ccatggctca tgcgctggag agtgctgcct ccatcatcga ggagtcgccc 1140
tactgccaga tggtcaagga tcgctatgcc tcatttgact ccggcatcgg caaggacttt 1200
gaggacggca agttgacact ggaacaagcc tacgagtacg gtaagcaagt gggcgaaccc 1260
aagcagacca gtggcaagca agaactgtac gagtcaatca tcaatatgta ttccatttaa 1320

<210> SEQ ID NO 22
<211> LENGTH: 439
<212> TYPE: PRT
<213> ORGANISM: Unknown
<220> FEATURE:
<223> OTHER INFORMATION: Obtained from environmental sample

<400> SEQUENCE: 22

Met Ala Thr Lys Glu Phe Phe Pro Glu Ile Gly Lys Ile Lys Phe Glu
1 5 10 15

Gly Arg Glu Ser Arg Asn Pro Leu Ala Phe Arg Tyr Tyr Gly Pro Glu
20 25 30

Lys Val Val Leu Gly Lys Lys Met Lys Asp Trp Phe Lys Phe Ala Met
35 40 45

```
Ala Trp Trp His Thr Leu Cys Ala Gln Gly Thr Asp Gln Phe Gly Gly
    50                  55                  60

Asp Thr Lys Gln Phe Pro Trp Asn Thr Ala Ser Asp Pro Met Gln Ala
65                  70                  75                  80

Ala Lys Asp Lys Val Asp Ala Gly Phe Glu Phe Met Thr Lys Met Gly
                85                  90                  95

Ile Glu Tyr Phe Cys Phe His Asp Val Asp Leu Val Ala Glu Ala Ala
            100                 105                 110

Thr Val Glu Glu Tyr Glu Ala Asn Leu Lys Thr Ile Val Ala Tyr Ile
        115                 120                 125

Lys Glu Lys Gln Ala Glu Thr Gly Ile Lys Asn Leu Trp Gly Thr Ala
    130                 135                 140

Asn Val Phe Gly His Lys Arg Tyr Met Asn Gly Ala Ala Thr Asn Pro
145                 150                 155                 160

Asp Phe Asp Val Val Ala Arg Ala Ile Val Gln Ile Lys Asn Ala Ile
                165                 170                 175

Asp Ala Thr Ile Glu Leu Gly Gly Thr Ser Tyr Val Phe Trp Gly Gly
            180                 185                 190

Arg Glu Gly His Met Ser Leu Leu Asn Thr Asp Gln Lys Arg Glu Lys
        195                 200                 205

Glu His Leu Ala Arg Met Leu Thr Met Ala Arg Asp Tyr Ala Arg Ala
    210                 215                 220

Arg Gly Phe Asn Gly Thr Phe Leu Ile Glu Pro Lys Pro Met Glu Pro
225                 230                 235                 240

Thr Lys His Gln Tyr Asp Val Asp Thr Glu Thr Val Ile Gly Phe Leu
                245                 250                 255

Arg Ala His Gly Leu Asp Lys Asp Phe Lys Val Asn Ile Glu Val Asn
            260                 265                 270

His Ala Thr Leu Ala Gly His Thr Phe Glu Arg Glu Leu Ala Val Ala
        275                 280                 285

Val Asp Asn Gly Leu Leu Gly Ser Ile Asp Ala Asn Arg Gly Asp Tyr
    290                 295                 300

Gln Asn Gly Trp Asp Thr Asp Gln Phe Pro Ile Asp His Tyr Glu Leu
305                 310                 315                 320

Val Gln Gly Met Leu Gln Ile Ile Arg Asn Gly Gly Phe Thr Asp Gly
                325                 330                 335

Gly Thr Asn Phe Asp Ala Lys Thr Arg Arg Asn Ser Thr Asp Leu Glu
            340                 345                 350

Asp Ile Phe Ile Ala His Ile Ala Ala Met Asp Ala Met Ala His Ala
        355                 360                 365

Leu Glu Ser Ala Ala Ser Ile Ile Glu Glu Ser Pro Tyr Cys Gln Met
    370                 375                 380

Val Lys Asp Arg Tyr Ala Ser Phe Asp Ser Gly Ile Gly Lys Asp Phe
385                 390                 395                 400

Glu Asp Gly Lys Leu Thr Leu Glu Gln Ala Tyr Glu Tyr Gly Lys Gln
                405                 410                 415

Val Gly Glu Pro Lys Gln Thr Ser Gly Lys Gln Glu Leu Tyr Glu Ser
            420                 425                 430

Ile Ile Asn Met Tyr Ser Ile
        435
```

<210> SEQ ID NO 23
<211> LENGTH: 1317

-continued

<212> TYPE: DNA
<213> ORGANISM: Unknown
<220> FEATURE:
<223> OTHER INFORMATION: Obtained from environmental sample

<400> SEQUENCE: 23

```
atggcaacaa aagagtattt tcctggtata ggaaagatta aatttgaagg taaagagagt     60

aagaatccga tggcattccg ctattatgat gccaataaag taatcatggg caagaagatg    120

agcgagtggc tgaagtttgc catggcttgg tggcacacat tgtgcgccga aggtggtgac    180

cagtttggtg gtggaacaaa gactttcccg tggaacgatt cggacaacgc cgtagaagca    240

gccaaccata aagtagatgc cggttttgaa tttatgcaga aaatgggcat cgaatactat    300

tgcttccatg atgtagacct ctgcactgaa gctgctacca ttgaagaata tgaagccaat    360

ctgaaggaaa tagtagccta tccgaaacag aaacaggctg aaacaggtat caaacttctg    420

tggggtacgg caaatgtatt tggtcacaaa cgctatatga atggtgctgc taccaatccg    480

gattttgatg tagtggctcg tgctgctgta cagattaaga atgcgataga cgctacaatt    540

gaactcggtg gtagcaacta cgtgttctgg ggcggccgtg aaggttatat gagcttgctc    600

aatacagacc agaaacgtga gaaagagcat ttggcacaaa tgttgaccat ggctcgtgac    660

tatgctcgtg ccaaaggatt caagggtacc ttcctggttg aacccaaacc gatggaacca    720

actaaacacc agtatgatgt agatacggaa actgtaatcg gcttcctcaa ggctcataat    780

ttggataagg atttcaaggt aaatattgaa gtaaaccatg ctacattggc cggtcatact    840

tttgaacacg aattggctgt tgccgtagac aacgatatgc ttggctctat cgatgccaac    900

cgcggtgact atcagaacgg ttgggatact gaccagttcc ccattgacaa cttcgagctt    960

atccaagcca tgatgcagat tattcgcggt ggtggcttca aagatggtgg tacaaacttc   1020

gacgctaaga ctcgtcgtaa ctctaccgac ctggaagata ttttcattgc acacatcgct   1080

ggtatggatg ctatggcacg tgctttggaa agtgcagcca agttgcttga ggaatctcct   1140

tataagaaaa tgttggctga ccgctatgca tcgttcgata gtggcaaagg taaggagttt   1200

gaagaaggca agctgacatt ggaagacgtt gtagtttatg ccaagcagaa tggcgagcct   1260

aaacagacca gcggtaagca ggaattgtat gaggcaattg taaatatgta tgcctga      1317
```

<210> SEQ ID NO 24
<211> LENGTH: 438
<212> TYPE: PRT
<213> ORGANISM: Unknown
<220> FEATURE:
<223> OTHER INFORMATION: Obtained from environmental sample

<400> SEQUENCE: 24

```
Met Ala Thr Lys Glu Tyr Phe Pro Gly Ile Gly Lys Ile Lys Phe Glu
1               5                   10                  15

Gly Lys Glu Ser Lys Asn Pro Met Ala Phe Arg Tyr Tyr Asp Ala Asn
            20                  25                  30

Lys Val Ile Met Gly Lys Lys Met Ser Glu Trp Leu Lys Phe Ala Met
        35                  40                  45

Ala Trp Trp His Thr Leu Cys Ala Glu Gly Gly Asp Gln Phe Gly Gly
    50                  55                  60

Gly Thr Lys Thr Phe Pro Trp Asn Asp Ser Asp Asn Ala Val Glu Ala
65                  70                  75                  80

Ala Asn His Lys Val Asp Ala Gly Phe Glu Phe Met Gln Lys Met Gly
                85                  90                  95
```

```
Ile Glu Tyr Tyr Cys Phe His Asp Val Asp Leu Cys Thr Glu Ala Ala
            100                 105                 110

Thr Ile Glu Glu Tyr Glu Ala Asn Leu Lys Glu Ile Val Ala Tyr Pro
        115                 120                 125

Lys Gln Lys Gln Ala Glu Thr Gly Ile Lys Leu Leu Trp Gly Thr Ala
    130                 135                 140

Asn Val Phe Gly His Lys Arg Tyr Met Asn Gly Ala Ala Thr Asn Pro
145                 150                 155                 160

Asp Phe Asp Val Val Ala Arg Ala Ala Val Gln Ile Lys Asn Ala Ile
                165                 170                 175

Asp Ala Thr Ile Glu Leu Gly Gly Ser Asn Tyr Val Phe Trp Gly Gly
            180                 185                 190

Arg Glu Gly Tyr Met Ser Leu Leu Asn Thr Asp Gln Lys Arg Glu Lys
        195                 200                 205

Glu His Leu Ala Gln Met Leu Thr Met Ala Arg Asp Tyr Ala Arg Ala
    210                 215                 220

Lys Gly Phe Lys Gly Thr Phe Leu Val Glu Pro Lys Pro Met Glu Pro
225                 230                 235                 240

Thr Lys His Gln Tyr Asp Val Asp Thr Glu Thr Val Ile Gly Phe Leu
                245                 250                 255

Lys Ala His Asn Leu Asp Lys Asp Phe Lys Val Asn Ile Glu Val Asn
            260                 265                 270

His Ala Thr Leu Ala Gly His Thr Phe Glu His Glu Leu Ala Val Ala
        275                 280                 285

Val Asp Asn Asp Met Leu Gly Ser Ile Asp Ala Asn Arg Gly Asp Tyr
    290                 295                 300

Gln Asn Gly Trp Asp Thr Asp Gln Phe Pro Ile Asp Asn Phe Glu Leu
305                 310                 315                 320

Ile Gln Ala Met Met Gln Ile Ile Arg Gly Gly Gly Phe Lys Asp Gly
                325                 330                 335

Gly Thr Asn Phe Asp Ala Lys Thr Arg Arg Asn Ser Thr Asp Leu Glu
            340                 345                 350

Asp Ile Phe Ile Ala His Ile Ala Gly Met Asp Ala Met Ala Arg Ala
        355                 360                 365

Leu Glu Ser Ala Ala Lys Leu Leu Glu Glu Ser Pro Tyr Lys Lys Met
    370                 375                 380

Leu Ala Asp Arg Tyr Ala Ser Phe Asp Ser Gly Lys Gly Lys Glu Phe
385                 390                 395                 400

Glu Glu Gly Lys Leu Thr Leu Glu Asp Val Val Val Tyr Ala Lys Gln
                405                 410                 415

Asn Gly Glu Pro Lys Gln Thr Ser Gly Lys Gln Glu Leu Tyr Glu Ala
            420                 425                 430

Ile Val Asn Met Tyr Ala
        435
```

<210> SEQ ID NO 25
<211> LENGTH: 1317
<212> TYPE: DNA
<213> ORGANISM: Unknown
<220> FEATURE:
<223> OTHER INFORMATION: Obtained from environmental sample

<400> SEQUENCE: 25

```
atggcaacaa aagagtattt tcctggaata ggaaagatta aatttgaagg aaaagagagt      60

aagaacccga tggcattccg ttgctacgat gcagaaaaag ttatcatggg taagagaatg     120
```

```
aaagattggt tgaagtttgc aatggcgtgg tggcatacac tttgtgcaga aggcggtgac    180

caattcggtg gcggtacaaa gagtttcccc cggaacgact atactgataa aattcaggct    240

gctaaaaaca agatggatgc cggttttgag tttatgcaga agatggggat cgaatactat    300

tgttttcacg atgtagacct ctgcacggaa gctgatacca ttgaagaata cgaagctaat    360

ttgaaagaaa tcgtagttta cgcaaagcaa aagcaggtag aaacaggtat caaattattg    420

tggggtactg ccaatgtatt cggtcatgaa cgctatatga atggtgcggc taccaaccca    480

gattttgatg ttgtagcccg tgctgctgtt cagattaaga atgcaattga tgctaccatt    540

gaactaggtg gcttaaacta tgtgttctgg ggtggacgcg aaggttatat gtctttgctg    600

aacactgatc agaaacgtga gaaagaacat cttgcacaaa tgctgaccat tgcccgtgac    660

tatgcccgtg cccgtggctt caaaggtaca ttcttggttg aaccgaaacc gatggaacca    720

accaaacatc aatatgacgt agatacagaa acagttatcg gtttttgaa agctcatgct    780

ttggataaag actttaaagt aaatattgaa gtaaatcatg caacattagc cggtcataca    840

tttgaacacg aactggcagt ggctgtcgac aacggtatgc tgggttctat tgacgctaat    900

cgtggtgatt gtcaaaacgg ttgggataca gaccaatttc ccattgataa ctatgaactg    960

actcaagcca tgatgcagat tattcgtaac ggtggtttgg gcaatggtgg tacgaatttt   1020

gacgctaaaa ctcgccgtaa ttctactgat cttggagata tcttcattgc tcacatcgca   1080

ggtatggatg ctatggcacg tgcattggaa agtgcggcca agttgttgga agaatctccc   1140

tataagaaga tgctggcaga acgttatgca tcctttgaca gcggtaaggg taaagagttt   1200

gaagagggta agttgacctt ggaggatctt gttgcttatg caaaagtcaa tggcgaaccg   1260

aaacaaatca gtggtaaaca agaattgtat gaggcaattg tgaatatgta ttgctaa      1317
```

<210> SEQ ID NO 26
<211> LENGTH: 438
<212> TYPE: PRT
<213> ORGANISM: Unknown
<220> FEATURE:
<223> OTHER INFORMATION: Obtained from environmental sample

<400> SEQUENCE: 26

```
Met Ala Thr Lys Glu Tyr Phe Pro Gly Ile Gly Lys Ile Lys Phe Glu
1               5                   10                  15

Gly Lys Glu Ser Lys Asn Pro Met Ala Phe Arg Cys Tyr Asp Ala Glu
            20                  25                  30

Lys Val Ile Met Gly Lys Arg Met Lys Asp Trp Leu Lys Phe Ala Met
        35                  40                  45

Ala Trp Trp His Thr Leu Cys Ala Glu Gly Gly Asp Gln Phe Gly Gly
    50                  55                  60

Gly Thr Lys Ser Phe Pro Arg Asn Asp Tyr Thr Asp Lys Ile Gln Ala
65                  70                  75                  80

Ala Lys Asn Lys Met Asp Ala Gly Phe Glu Phe Met Gln Lys Met Gly
                85                  90                  95

Ile Glu Tyr Tyr Cys Phe His Asp Val Asp Leu Cys Thr Glu Ala Asp
            100                 105                 110

Thr Ile Glu Glu Tyr Glu Ala Asn Leu Lys Glu Ile Val Val Tyr Ala
        115                 120                 125

Lys Gln Lys Gln Val Glu Thr Gly Ile Lys Leu Leu Trp Gly Thr Ala
    130                 135                 140

Asn Val Phe Gly His Glu Arg Tyr Met Asn Gly Ala Ala Thr Asn Pro
```

-continued

```
145                 150                 155                 160

Asp Phe Asp Val Val Ala Arg Ala Ala Val Gln Ile Lys Asn Ala Ile
                165                 170                 175

Asp Ala Thr Ile Glu Leu Gly Gly Leu Asn Tyr Val Phe Trp Gly Gly
            180                 185                 190

Arg Glu Gly Tyr Met Ser Leu Leu Asn Thr Asp Gln Lys Arg Glu Lys
        195                 200                 205

Glu His Leu Ala Gln Met Leu Thr Ile Ala Arg Asp Tyr Ala Arg Ala
    210                 215                 220

Arg Gly Phe Lys Gly Thr Phe Leu Val Glu Pro Lys Pro Met Glu Pro
225                 230                 235                 240

Thr Lys His Gln Tyr Asp Val Asp Thr Glu Thr Val Ile Gly Phe Leu
                245                 250                 255

Lys Ala His Ala Leu Asp Lys Asp Phe Lys Val Asn Ile Glu Val Asn
            260                 265                 270

His Ala Thr Leu Ala Gly His Thr Phe Glu His Glu Leu Ala Val Ala
        275                 280                 285

Val Asp Asn Gly Met Leu Gly Ser Ile Asp Ala Asn Arg Gly Asp Cys
    290                 295                 300

Gln Asn Gly Trp Asp Thr Asp Gln Phe Pro Ile Asp Asn Tyr Glu Leu
305                 310                 315                 320

Thr Gln Ala Met Met Gln Ile Ile Arg Asn Gly Gly Leu Gly Asn Gly
                325                 330                 335

Gly Thr Asn Phe Asp Ala Lys Thr Arg Arg Asn Ser Thr Asp Leu Gly
            340                 345                 350

Asp Ile Phe Ile Ala His Ile Ala Gly Met Asp Ala Met Ala Arg Ala
        355                 360                 365

Leu Glu Ser Ala Ala Lys Leu Leu Glu Glu Ser Pro Tyr Lys Lys Met
    370                 375                 380

Leu Ala Glu Arg Tyr Ala Ser Phe Asp Ser Gly Lys Gly Lys Glu Phe
385                 390                 395                 400

Glu Glu Gly Lys Leu Thr Leu Glu Asp Leu Val Ala Tyr Ala Lys Val
                405                 410                 415

Asn Gly Glu Pro Lys Gln Ile Ser Gly Lys Gln Glu Leu Tyr Glu Ala
            420                 425                 430

Ile Val Asn Met Tyr Cys
        435


<210> SEQ ID NO 27
<211> LENGTH: 1317
<212> TYPE: DNA
<213> ORGANISM: Unknown
<220> FEATURE:
<223> OTHER INFORMATION: Obtained from environmental sample

<400> SEQUENCE: 27

atggcaacaa aagagtattt tcccggaata ggaaagatta aattcgaagg taaagagagc      60

aagaacccga tggcattccg ttattacgat gccgataaag taatcatggg taagaaaatg     120

agcgaatggc tgaagttcgc catggcatgg tggcacactc tttgcgcaga aggtggtgac     180

cagttcggtg gcggaacaaa gaaattcccc tggaacggtg aggctgacaa ggttcaggct     240

gccaagaaca aaatggacgc cggctttgaa ttcatgcaga aaatgggtat cgaatactac     300

tgcttccacg atgtagacct ctgcgaagaa gccgagacca ttgaagaata cgaagccaac     360

ttgaaggaaa tcgtagcgta tgccaagcag aaacaagcag aaaccggcat caagctgttg     420
```

-continued

```
tggggtactg ccaacgtatt cggccatgcc cgctacatga atggtgcagc caccaacccc    480

gatttcgatg ttgtggcacg tgcagccgtc caaatcaaaa gcgccatcga cgctactatc    540

gagctgggag gttcgaacta tgtgttctgg ggcggtcgcg aaggctacat gtcattgctg    600

aatacagacc agaagcgtga gaaagagcac ctcgcacaga tgttgaccat cgcccgcgac    660

tatgcccgtg cccgtggctt caaaggtacc ttcctgattg aaccgaaacc gatggaacct    720

acaaaacacc agtatgatgt agacaccgaa accgttatcg gcttcttgaa ggcccacaat    780

ctggacaaag atttcaaggt aaacatcgaa gtgaaccacg ctactttggc gggccacacc    840

ttcgagcacg aactcgcagt agccgtagac aacggtatgc tcggctccat cgatgccaac    900

cgtggtgact accagaacgg ctgggataca gaccagttcc ccattgacaa cttcgaactg    960

acccaggcaa tgatgcaaat catccgtaac ggcggctttg gcaatggcgg tacaaacttc   1020

gatgccaaga cccgtcgtaa ctccaccgac ctggaagaca tcttcattgc ccacatcgcc   1080

ggtatggacg tgatggcacg tgcactggaa agtgcagcca aattgcttga agagtctcct   1140

tacaagaaga tgcttgccga ccgctatgct tccttcgaca gtggtaaagg caaggaattc   1200

gaagacggca agctgacact ggaggatttg gcagcttacg caaaagccaa cggtgagccg   1260

aaacagacca gcggcaagca gggattgtat gaggcaatcg taaatatgta ctgctga      1317
```

<210> SEQ ID NO 28
<211> LENGTH: 438
<212> TYPE: PRT
<213> ORGANISM: Unknown
<220> FEATURE:
<223> OTHER INFORMATION: Obtained from environmental sample

<400> SEQUENCE: 28

```
Met Ala Thr Lys Glu Tyr Phe Pro Gly Ile Gly Lys Ile Lys Phe Glu
1               5                   10                  15

Gly Lys Glu Ser Lys Asn Pro Met Ala Phe Arg Tyr Tyr Asp Ala Asp
            20                  25                  30

Lys Val Ile Met Gly Lys Lys Met Ser Glu Trp Leu Lys Phe Ala Met
        35                  40                  45

Ala Trp Trp His Thr Leu Cys Ala Glu Gly Gly Asp Gln Phe Gly Gly
    50                  55                  60

Gly Thr Lys Lys Phe Pro Trp Asn Gly Glu Ala Asp Lys Val Gln Ala
65                  70                  75                  80

Ala Lys Asn Lys Met Asp Ala Gly Phe Glu Phe Met Gln Lys Met Gly
                85                  90                  95

Ile Glu Tyr Tyr Cys Phe His Asp Val Asp Leu Cys Glu Glu Ala Glu
            100                 105                 110

Thr Ile Glu Glu Tyr Glu Ala Asn Leu Lys Glu Ile Val Ala Tyr Ala
        115                 120                 125

Lys Gln Lys Gln Ala Glu Thr Gly Ile Lys Leu Leu Trp Gly Thr Ala
    130                 135                 140

Asn Val Phe Gly His Ala Arg Tyr Met Asn Gly Ala Ala Thr Asn Pro
145                 150                 155                 160

Asp Phe Asp Val Val Ala Arg Ala Ala Val Gln Ile Lys Ser Ala Ile
                165                 170                 175

Asp Ala Thr Ile Glu Leu Gly Gly Ser Asn Tyr Val Phe Trp Gly Gly
            180                 185                 190

Arg Glu Gly Tyr Met Ser Leu Leu Asn Thr Asp Gln Lys Arg Glu Lys
        195                 200                 205
```

Glu His Leu Ala Gln Met Leu Thr Ile Ala Arg Asp Tyr Ala Arg Ala
    210                 215                 220

Arg Gly Phe Lys Gly Thr Phe Leu Ile Glu Pro Lys Pro Met Glu Pro
225                 230                 235                 240

Thr Lys His Gln Tyr Asp Val Asp Thr Glu Thr Val Ile Gly Phe Leu
                245                 250                 255

Lys Ala His Asn Leu Asp Lys Asp Phe Lys Val Asn Ile Glu Val Asn
            260                 265                 270

His Ala Thr Leu Ala Gly His Thr Phe Glu His Glu Leu Ala Val Ala
        275                 280                 285

Val Asp Asn Gly Met Leu Gly Ser Ile Asp Ala Asn Arg Gly Asp Tyr
    290                 295                 300

Gln Asn Gly Trp Asp Thr Asp Gln Phe Pro Ile Asp Asn Phe Glu Leu
305                 310                 315                 320

Thr Gln Ala Met Met Gln Ile Ile Arg Asn Gly Gly Phe Gly Asn Gly
                325                 330                 335

Gly Thr Asn Phe Asp Ala Lys Thr Arg Arg Asn Ser Thr Asp Leu Glu
            340                 345                 350

Asp Ile Phe Ile Ala His Ile Ala Gly Met Asp Val Met Ala Arg Ala
        355                 360                 365

Leu Glu Ser Ala Ala Lys Leu Leu Glu Glu Ser Pro Tyr Lys Lys Met
    370                 375                 380

Leu Ala Asp Arg Tyr Ala Ser Phe Asp Ser Gly Lys Gly Lys Glu Phe
385                 390                 395                 400

Glu Asp Gly Lys Leu Thr Leu Glu Asp Leu Ala Ala Tyr Ala Lys Ala
                405                 410                 415

Asn Gly Glu Pro Lys Gln Thr Ser Gly Lys Gln Gly Leu Tyr Glu Ala
            420                 425                 430

Ile Val Asn Met Tyr Cys
        435

<210> SEQ ID NO 29
<211> LENGTH: 1314
<212> TYPE: DNA
<213> ORGANISM: Unknown
<220> FEATURE:
<223> OTHER INFORMATION: Obtained from environmental sample

<400> SEQUENCE: 29
atgacaaaag agtattttcc aaccattggt aaaattcagt ttgaaggtaa agagagtaag 60
aatccattag catatcgtta ttacgatgct aacaaagtaa taatgggtaa aaagatgagc 120
gaatggctca agtttgcaat ggcatggtgg cacactttgt gtgctgaggg tagcgaccag 180
tttggtcctg gcaccaagtc attcccatgg aacgcatcaa ccgaccgtat gcaggctgca 240
aaagataagg ctgacgcagg cttcgaaatc atgcaaaaac tgggcatcga atactactgt 300
ttccatgatg ttgacctcat cgacccagca gacgatattc caacatacga aaagaatctc 360
aaggaaatcg ttgcatacct caagcaaaaa caggccgaga caggtatcaa attgctatgg 420
ggtacagcta acgtatttgg ccacaagcgt tatatgaacg gtgcatctac caatcctgac 480
tttgacgttg ttgcacgagc tatcgtgcaa atcaagaatg ctatcgatgc aacaatcgaa 540
ctgggcggca cgaactacgt attctggggt ggtcgcgaag gttacatgtc actgctcaac 600
accgaccaaa agcgcgagaa agagcacatg gctaccatgt taggaatggc acgtgactat 660
gcacgttcta aaggctttac tggtactctc cttatcgagc caaagcctat ggaaccaact 720

-continued

```
aagcatcaat acgacgtcga tacagaaact gttattggtt tcctcaaagc tcacggatta    780

gacaaggact tcaaggtaaa tatcgaagtg aaccacgcta cattggctgg ccataccttc    840

gaacatgaat tagcatgtgc tgttgatgca ggtatgcttg gttccatcga tgctaaccgt    900

ggtgatatgc agaatggctg ggatacagat cagttcccta tcaacaatta cgagctcgtt    960

caggccatga tgcagattat ccgcaatggt ggtttcggta acggtggtac aaacttcgac   1020

gctaagacac gtcgtaattc aaccgatttg gaagacatca tcattgctca cgtttcagct   1080

atggatgcta tggcacgtgc tcttgaatgt gctgcagaca ttcttcaaaa ctcacctatt   1140

ccacagatgg tggccaaccg ttatgcaagt tttgacaagg gtataggtaa agatttcgaa   1200

gacggcaagc tcaccctcga gcaagtatac gaatatggta agaccgtcgg cgaaccagct   1260

attacaagcg gcaaacagga gctctacgaa gctatcgtta atatgtattg ctga         1314
```

```
<210> SEQ ID NO 30
<211> LENGTH: 437
<212> TYPE: PRT
<213> ORGANISM: Unknown
<220> FEATURE:
<223> OTHER INFORMATION: Obtained from environmental sample

<400> SEQUENCE: 30

Met Thr Lys Glu Tyr Phe Pro Thr Ile Gly Lys Ile Gln Phe Glu Gly
1               5                   10                  15

Lys Glu Ser Lys Asn Pro Leu Ala Tyr Arg Tyr Tyr Asp Ala Asn Lys
            20                  25                  30

Val Ile Met Gly Lys Lys Met Ser Glu Trp Leu Lys Phe Ala Met Ala
        35                  40                  45

Trp Trp His Thr Leu Cys Ala Glu Gly Ser Asp Gln Phe Gly Pro Gly
    50                  55                  60

Thr Lys Ser Phe Pro Trp Asn Ala Ser Thr Asp Arg Met Gln Ala Ala
65                  70                  75                  80

Lys Asp Lys Ala Asp Ala Gly Phe Glu Ile Met Gln Lys Leu Gly Ile
                85                  90                  95

Glu Tyr Tyr Cys Phe His Asp Val Asp Leu Ile Asp Pro Ala Asp Asp
            100                 105                 110

Ile Pro Thr Tyr Glu Lys Asn Leu Lys Glu Ile Val Ala Tyr Leu Lys
        115                 120                 125

Gln Lys Gln Ala Glu Thr Gly Ile Lys Leu Leu Trp Gly Thr Ala Asn
    130                 135                 140

Val Phe Gly His Lys Arg Tyr Met Asn Gly Ala Ser Thr Asn Pro Asp
145                 150                 155                 160

Phe Asp Val Val Ala Arg Ala Ile Val Gln Ile Lys Asn Ala Ile Asp
                165                 170                 175

Ala Thr Ile Glu Leu Gly Gly Thr Asn Tyr Val Phe Trp Gly Gly Arg
            180                 185                 190

Glu Gly Tyr Met Ser Leu Leu Asn Thr Asp Gln Lys Arg Glu Lys Glu
        195                 200                 205

His Met Ala Thr Met Leu Gly Met Ala Arg Asp Tyr Ala Arg Ser Lys
    210                 215                 220

Gly Phe Thr Gly Thr Leu Leu Ile Glu Pro Lys Pro Met Glu Pro Thr
225                 230                 235                 240

Lys His Gln Tyr Asp Val Asp Thr Glu Thr Val Ile Gly Phe Leu Lys
                245                 250                 255
```

```
Ala His Gly Leu Asp Lys Asp Phe Lys Val Asn Ile Glu Val Asn His
            260                 265                 270

Ala Thr Leu Ala Gly His Thr Phe Glu His Glu Leu Ala Cys Ala Val
        275                 280                 285

Asp Ala Gly Met Leu Gly Ser Ile Asp Ala Asn Arg Gly Asp Met Gln
    290                 295                 300

Asn Gly Trp Asp Thr Asp Gln Phe Pro Ile Asn Asn Tyr Glu Leu Val
305                 310                 315                 320

Gln Ala Met Met Gln Ile Ile Arg Asn Gly Gly Phe Gly Asn Gly Gly
                325                 330                 335

Thr Asn Phe Asp Ala Lys Thr Arg Arg Asn Ser Thr Asp Leu Glu Asp
            340                 345                 350

Ile Ile Ile Ala His Val Ser Ala Met Asp Ala Met Ala Arg Ala Leu
        355                 360                 365

Glu Cys Ala Ala Asp Ile Leu Gln Asn Ser Pro Ile Pro Gln Met Val
    370                 375                 380

Ala Asn Arg Tyr Ala Ser Phe Asp Lys Gly Ile Gly Lys Asp Phe Glu
385                 390                 395                 400

Asp Gly Lys Leu Thr Leu Glu Gln Val Tyr Glu Tyr Gly Lys Thr Val
                405                 410                 415

Gly Glu Pro Ala Ile Thr Ser Gly Lys Gln Glu Leu Tyr Glu Ala Ile
            420                 425                 430

Val Asn Met Tyr Cys
        435
```

<210> SEQ ID NO 31
<211> LENGTH: 1317
<212> TYPE: DNA
<213> ORGANISM: Unknown
<220> FEATURE:
<223> OTHER INFORMATION: Obtained from environmental sample

<400> SEQUENCE: 31

```
atggctaaca aagaattttt ccccggtatt ggtaaaatca aattcgaagg taaagagagc     60

aagaacccca tggcatatcg ttactacgat gctgagaagg tagtccttgg caagaatatg    120

aaagactggt tcaagtttgc gatggcttgg tggcacacat tgtgcgccga gggtagcgac    180

cagtttggtc ccggcactaa gtctttcccc tggaacaccg cagagtgccc catgcaggca    240

gctaaggaca aggttgacgc tggcttcgag ttcatgacca agatgggtat tgaatacttc    300

tgcttccacg atgtagacct cgttgccgag gccgacactg ttgaggagta cgaggctcgc    360

atgaaggaaa tcgttgctta catcaaggag aaggtggccg agactggcat caagaacctg    420

tggggtacag ctaacgtatt tggcaacaag cgctacatga acggtgctgc tactaacccc    480

gactttgacg ttgtggctcg cgctatcgtt caaatcaaga acgctatcga cgctactatc    540

gagctcggtg gtacgtcata cgtattctgg ggcggccgcg agggttacat gagcctcttg    600

aacaccgacc agaagcgtga gaaagagcac ctggctacta tgctcactat ggcacgcgac    660

tacgctcgcg ctaagggttt caagggtaca ttcctcatcg agcccaagcc catggagccc    720

acaaagcacc agtacgatgt tgacactgag actgtaatcg gcttccttaa ggcacacaac    780

cttgacaagg acttcaaggt taacattgag gttaaccacg caactctcgc tggtcacaca    840

tttgagcacg agctcgcttg tgctgttgac gctggcatgc ttggcagcat cgacgctaac    900

cgcggtgact accagaacgg ctgggatact gaccaattcc ccatcgacaa cttcgacctc    960

actcaagcta tgctcgagat catccgcaac gatggtttca aggatggtgg tacaaacttc   1020
```

```
gacgctaaga ctcgccgcaa cagcaccgac ctcgaggata tcttcatcgc acacatcgct   1080

gctatggacg ctatggcacg tgctctcgag agcgctgctg cagtactcga ggagtcagct   1140

ctgccccaaa tgaagaagga ccgctatgca tcgttcgacg ctggcatggg taaggacttc   1200

gaggacggca agctcaccct ggagcaagtt tacgagtatg gtaagaaggt gggcgagccc   1260

aagcagacta gcggcaagca agagctgtat gaggctatcc tcaacatgta cgtataa      1317


<210> SEQ ID NO 32
<211> LENGTH: 438
<212> TYPE: PRT
<213> ORGANISM: Unknown
<220> FEATURE:
<223> OTHER INFORMATION: Obtained from environmental sample

<400> SEQUENCE: 32

Met Ala Asn Lys Glu Phe Phe Pro Gly Ile Gly Lys Ile Lys Phe Glu
1               5                   10                  15

Gly Lys Glu Ser Lys Asn Pro Met Ala Tyr Arg Tyr Tyr Asp Ala Glu
            20                  25                  30

Lys Val Val Leu Gly Lys Asn Met Lys Asp Trp Phe Lys Phe Ala Met
        35                  40                  45

Ala Trp Trp His Thr Leu Cys Ala Glu Gly Ser Asp Gln Phe Gly Pro
    50                  55                  60

Gly Thr Lys Ser Phe Pro Trp Asn Thr Ala Glu Cys Pro Met Gln Ala
65                  70                  75                  80

Ala Lys Asp Lys Val Asp Ala Gly Phe Glu Phe Met Thr Lys Met Gly
                85                  90                  95

Ile Glu Tyr Phe Cys Phe His Asp Val Asp Leu Val Ala Glu Ala Asp
            100                 105                 110

Thr Val Glu Glu Tyr Glu Ala Arg Met Lys Glu Ile Val Ala Tyr Ile
        115                 120                 125

Lys Glu Lys Val Ala Glu Thr Gly Ile Lys Asn Leu Trp Gly Thr Ala
    130                 135                 140

Asn Val Phe Gly Asn Lys Arg Tyr Met Asn Gly Ala Ala Thr Asn Pro
145                 150                 155                 160

Asp Phe Asp Val Val Ala Arg Ala Ile Val Gln Ile Lys Asn Ala Ile
                165                 170                 175

Asp Ala Thr Ile Glu Leu Gly Gly Thr Ser Tyr Val Phe Trp Gly Gly
            180                 185                 190

Arg Glu Gly Tyr Met Ser Leu Leu Asn Thr Asp Gln Lys Arg Glu Lys
        195                 200                 205

Glu His Leu Ala Thr Met Leu Thr Met Ala Arg Asp Tyr Ala Arg Ala
    210                 215                 220

Lys Gly Phe Lys Gly Thr Phe Leu Ile Glu Pro Lys Pro Met Glu Pro
225                 230                 235                 240

Thr Lys His Gln Tyr Asp Val Asp Thr Glu Thr Val Ile Gly Phe Leu
                245                 250                 255

Lys Ala His Asn Leu Asp Lys Asp Phe Lys Val Asn Ile Glu Val Asn
            260                 265                 270

His Ala Thr Leu Ala Gly His Thr Phe Glu His Glu Leu Ala Cys Ala
        275                 280                 285

Val Asp Ala Gly Met Leu Gly Ser Ile Asp Ala Asn Arg Gly Asp Tyr
    290                 295                 300

Gln Asn Gly Trp Asp Thr Asp Gln Phe Pro Ile Asp Asn Phe Asp Leu
```

-continued

```
305                 310                 315                 320

Thr Gln Ala Met Leu Glu Ile Ile Arg Asn Asp Gly Phe Lys Asp Gly
                325                 330                 335

Gly Thr Asn Phe Asp Ala Lys Thr Arg Arg Asn Ser Thr Asp Leu Glu
            340                 345                 350

Asp Ile Phe Ile Ala His Ile Ala Ala Met Asp Ala Met Ala Arg Ala
        355                 360                 365

Leu Glu Ser Ala Ala Ala Val Leu Glu Glu Ser Ala Leu Pro Gln Met
    370                 375                 380

Lys Lys Asp Arg Tyr Ala Ser Phe Asp Ala Gly Met Gly Lys Asp Phe
385                 390                 395                 400

Glu Asp Gly Lys Leu Thr Leu Glu Gln Val Tyr Glu Tyr Gly Lys Lys
                405                 410                 415

Val Gly Glu Pro Lys Gln Thr Ser Gly Lys Gln Glu Leu Tyr Glu Ala
            420                 425                 430

Ile Leu Asn Met Tyr Val
        435
```

<210> SEQ ID NO 33
<211> LENGTH: 1317
<212> TYPE: DNA
<213> ORGANISM: Unknown
<220> FEATURE:
<223> OTHER INFORMATION: Obtained from environmental sample

<400> SEQUENCE: 33

```
atggctaaca aagaattttt cccaggtatt ggtaaaatca aattcgaagg caaagaaagc     60

aagaacccca tggcatatcg tcactacgat gccgagaagg tagtccttgg taagaagatg    120

aaggactggt tcaagtttgc gatggcttgg tggcacactc tgtgcgccga gggtagcgac    180

cagttcggcc ccgtgaccaa gtctttcccc tggaaccagg ccgagtgccc catgcaggct    240

gctaaggaca aggttgacgc cggcttcgag ttcatgacca agatgggtat cgaatacttc    300

tgtttccacg atgtagacct cgttgccgag gccgacaccg ttgaggagta cgaagctcgc    360

atgaaggaaa tcgtggctta catcaaggag aagatggccg agaccggcat caagaacctg    420

tggggtacag ccaacgtatt cggcaacaag cgctacatga acggtgctgc caccaacccc    480

gactttgacg ttgtggctcg cgcaatcgtt cagatcaaga acgccatcga cgctactatc    540

gagctcggcg gtacctctta cgtgttctgg ggcggccgcg agggttacat gactctcttg    600

aacaccgacc agaagcgcga gaaggagcac ctggctacca tgctcaccat ggctcgcgac    660

tatgctcgcg ctaagggctt caagggtaca ttccttatcg agcccaagcc catggagccc    720

accaagcacc agtatgacgt ggataccgag accgttatcg gcttcctcaa ggctcacggc    780

ctggacaagg acttcaaggt gaacatcgag gttaaccatg caactctcgc cggccacaca    840

ttcgagcacg aactcgcttg cgctgttgac gctggcatgc tgggcagcat cgacgctaac    900

cgcggcgact accagaacgg ctgggatacc gaccagttcc ccatcgacaa cttcgacctc    960

actcaggcta tgctcgagat catccgcaac ggtggtttca aggacggtgg tacaaacttc   1020

gacgctaaga cccgtcgcaa cagcaccgat cttgaggaca tcttcatcgc tcacatcgct   1080

gctatggacg caatggcacg cgcgctcgag agcgctgccg ctgtgctcga gcagagcccc   1140

cttccccaga tgaagaaaga ccgctacgca tcgttcgatg ccggcatggg caaggacttc   1200

gaggacggca agctcactct ggagcaggtt tacgagtatg gtaagaaggt aggcgagccc   1260

aagcagacca gcggcaagca ggaactgtac gaggctatcc tcaacatgta tgtataa      1317
```

<210> SEQ ID NO 34
<211> LENGTH: 438
<212> TYPE: PRT
<213> ORGANISM: Unknown
<220> FEATURE:
<223> OTHER INFORMATION: Obtained from environmental sample

<400> SEQUENCE: 34

```
Met Ala Asn Lys Glu Phe Phe Pro Gly Ile Gly Lys Ile Lys Phe Glu
1               5                   10                  15

Gly Lys Glu Ser Lys Asn Pro Met Ala Tyr Arg His Tyr Asp Ala Glu
            20                  25                  30

Lys Val Val Leu Gly Lys Lys Met Lys Asp Trp Phe Lys Phe Ala Met
        35                  40                  45

Ala Trp Trp His Thr Leu Cys Ala Glu Gly Ser Asp Gln Phe Gly Pro
    50                  55                  60

Val Thr Lys Ser Phe Pro Trp Asn Gln Ala Glu Cys Pro Met Gln Ala
65                  70                  75                  80

Ala Lys Asp Lys Val Asp Ala Gly Phe Glu Phe Met Thr Lys Met Gly
                85                  90                  95

Ile Glu Tyr Phe Cys Phe His Asp Val Asp Leu Val Ala Glu Ala Asp
            100                 105                 110

Thr Val Glu Glu Tyr Glu Ala Arg Met Lys Glu Ile Val Ala Tyr Ile
        115                 120                 125

Lys Glu Lys Met Ala Glu Thr Gly Ile Lys Asn Leu Trp Gly Thr Ala
    130                 135                 140

Asn Val Phe Gly Asn Lys Arg Tyr Met Asn Gly Ala Ala Thr Asn Pro
145                 150                 155                 160

Asp Phe Asp Val Val Ala Arg Ala Ile Val Gln Ile Lys Asn Ala Ile
                165                 170                 175

Asp Ala Thr Ile Glu Leu Gly Gly Thr Ser Tyr Val Phe Trp Gly Gly
            180                 185                 190

Arg Glu Gly Tyr Met Thr Leu Leu Asn Thr Asp Gln Lys Arg Glu Lys
        195                 200                 205

Glu His Leu Ala Thr Met Leu Thr Met Ala Arg Asp Tyr Ala Arg Ala
    210                 215                 220

Lys Gly Phe Lys Gly Thr Phe Leu Ile Glu Pro Lys Pro Met Glu Pro
225                 230                 235                 240

Thr Lys His Gln Tyr Asp Val Asp Thr Glu Thr Val Ile Gly Phe Leu
                245                 250                 255

Lys Ala His Gly Leu Asp Lys Asp Phe Lys Val Asn Ile Glu Val Asn
            260                 265                 270

His Ala Thr Leu Ala Gly His Thr Phe Glu His Glu Leu Ala Cys Ala
        275                 280                 285

Val Asp Ala Gly Met Leu Gly Ser Ile Asp Ala Asn Arg Gly Asp Tyr
    290                 295                 300

Gln Asn Gly Trp Asp Thr Asp Gln Phe Pro Ile Asp Asn Phe Asp Leu
305                 310                 315                 320

Thr Gln Ala Met Leu Glu Ile Ile Arg Asn Gly Gly Phe Lys Asp Gly
                325                 330                 335

Gly Thr Asn Phe Asp Ala Lys Thr Arg Arg Asn Ser Thr Asp Leu Glu
            340                 345                 350

Asp Ile Phe Ile Ala His Ile Ala Ala Met Asp Ala Met Ala Arg Ala
        355                 360                 365
```

```
Leu Glu Ser Ala Ala Ala Val Leu Glu Gln Ser Pro Leu Pro Gln Met
    370                 375                 380

Lys Lys Asp Arg Tyr Ala Ser Phe Asp Ala Gly Met Gly Lys Asp Phe
385                 390                 395                 400

Glu Asp Gly Lys Leu Thr Leu Glu Gln Val Tyr Glu Tyr Gly Lys Lys
                405                 410                 415

Val Gly Glu Pro Lys Gln Thr Ser Gly Lys Gln Glu Leu Tyr Glu Ala
            420                 425                 430

Ile Leu Asn Met Tyr Val
        435
```

<210> SEQ ID NO 35
<211> LENGTH: 1320
<212> TYPE: DNA
<213> ORGANISM: Unknown
<220> FEATURE:
<223> OTHER INFORMATION: Obtained from environmental sample

<400> SEQUENCE: 35

```
atgaaagaat attttcctat gacaaaaaaa gttgaatatg agggcgcagc atctaaaaat     60

ccatttgcgt ttaaatacta tgatgccgaa agaattatag caggcaagcc tatgaaagaa    120

catcttaaat ttgctatgag ttggtggcat acactttgtg cgggcggtgc agacccattt    180

ggcacaacaa ctatggacag aacatacggc ggacttaccg acccaatgga aattgcaaag    240

gcaaaagtag atgcaggctt tgagtttatg caaaaactcg gtatagagta tttttgtttt    300

cacgatgcgg atattgcacc ggaaggaagc agttttgttg aaacaaagaa aaacttttgg    360

gaaatagtag attatataca gcaaaagatg aatgaaacag gcataaagtt gctttggggt    420

actgcaaact gctttaatgc tccacgttat atgcacggtg caggaacatc atgcaatgcg    480

cacagttttg catatgcagc cgcacagata aaaaatgcaa ttgaagctac cgttaaactg    540

ggtggaaaag gctatgtttt ctggggcgga agagagggtt atgaaacact tctcaatacg    600

gatatggcac ttgaacttga caatatggca agacttatgc atatggcagt tgattatggc    660

agaagcattg gttttgacgg tgatttttat atcgaaccaa agccaaagga accaacaaaa    720

catcaatatg actttgactc ggcaactgtt ttgggatttt tgagaaagta cggtttagat    780

aaggatttta aacttaatat agaggcaaat catgcgacac ttgcaggtca tacatttgaa    840

catgaattga ctgtagcgcg tataaacggt gcatttggca gcatagatgc aaatagcggc    900

gatcccaatc ttggctggga taccgaccaa ttcccaacag atgtttattc ggcaaccctt    960

tgtatgcttg aagtgataag agcaggcggc tttacaaacg gaggtcttaa ttttgatgca   1020

aaggtcagaa gaggctcatt tacgtttgat gacattgttt atgcatatat cagcggtatg   1080

gacacttttg cgctgggttt tataaaggca tatgaaataa ttgaggacgg cagaatagat   1140

gaatttgtaa aagaaagata cgcaagctat aatacaggca taggcaaaga tattatagat   1200

ggaaaggcaa gccttgaaag tttggaagaa tatattcttt caaatgataa tgttgtaatg   1260

caaagcggca gacaggaata tcttgaaaca gttttgaata atattttgtt taaagcataa   1320
```

<210> SEQ ID NO 36
<211> LENGTH: 439
<212> TYPE: PRT
<213> ORGANISM: Unknown
<220> FEATURE:
<223> OTHER INFORMATION: Obtained from environmental sample

<400> SEQUENCE: 36

```
Met Lys Glu Tyr Phe Pro Met Thr Lys Lys Val Glu Tyr Glu Gly Ala
1               5                   10                  15

Ala Ser Lys Asn Pro Phe Ala Phe Lys Tyr Tyr Asp Ala Glu Arg Ile
            20                  25                  30

Ile Ala Gly Lys Pro Met Lys Glu His Leu Lys Phe Ala Met Ser Trp
        35                  40                  45

Trp His Thr Leu Cys Ala Gly Gly Ala Asp Pro Phe Gly Thr Thr Thr
    50                  55                  60

Met Asp Arg Thr Tyr Gly Gly Leu Thr Asp Pro Met Glu Ile Ala Lys
65                  70                  75                  80

Ala Lys Val Asp Ala Gly Phe Glu Phe Met Gln Lys Leu Gly Ile Glu
                85                  90                  95

Tyr Phe Cys Phe His Asp Ala Asp Ile Ala Pro Glu Gly Ser Ser Phe
            100                 105                 110

Val Glu Thr Lys Lys Asn Phe Trp Glu Ile Val Asp Tyr Ile Gln Gln
        115                 120                 125

Lys Met Asn Glu Thr Gly Ile Lys Leu Leu Trp Gly Thr Ala Asn Cys
    130                 135                 140

Phe Asn Ala Pro Arg Tyr Met His Gly Ala Gly Thr Ser Cys Asn Ala
145                 150                 155                 160

His Ser Phe Ala Tyr Ala Ala Ala Gln Ile Lys Asn Ala Ile Glu Ala
                165                 170                 175

Thr Val Lys Leu Gly Gly Lys Gly Tyr Val Phe Trp Gly Gly Arg Glu
            180                 185                 190

Gly Tyr Glu Thr Leu Leu Asn Thr Asp Met Ala Leu Glu Leu Asp Asn
        195                 200                 205

Met Ala Arg Leu Met His Met Ala Val Asp Tyr Gly Arg Ser Ile Gly
    210                 215                 220

Phe Asp Gly Asp Phe Tyr Ile Glu Pro Lys Pro Lys Glu Pro Thr Lys
225                 230                 235                 240

His Gln Tyr Asp Phe Asp Ser Ala Thr Val Leu Gly Phe Leu Arg Lys
                245                 250                 255

Tyr Gly Leu Asp Lys Asp Phe Lys Leu Asn Ile Glu Ala Asn His Ala
            260                 265                 270

Thr Leu Ala Gly His Thr Phe Glu His Glu Leu Thr Val Ala Arg Ile
        275                 280                 285

Asn Gly Ala Phe Gly Ser Ile Asp Ala Asn Ser Gly Asp Pro Asn Leu
    290                 295                 300

Gly Trp Asp Thr Asp Gln Phe Pro Thr Asp Val Tyr Ser Ala Thr Leu
305                 310                 315                 320

Cys Met Leu Glu Val Ile Arg Ala Gly Gly Phe Thr Asn Gly Gly Leu
                325                 330                 335

Asn Phe Asp Ala Lys Val Arg Arg Gly Ser Phe Thr Phe Asp Asp Ile
            340                 345                 350

Val Tyr Ala Tyr Ile Ser Gly Met Asp Thr Phe Ala Leu Gly Phe Ile
        355                 360                 365

Lys Ala Tyr Glu Ile Ile Glu Asp Gly Arg Ile Asp Glu Phe Val Lys
    370                 375                 380

Glu Arg Tyr Ala Ser Tyr Asn Thr Gly Ile Gly Lys Asp Ile Ile Asp
385                 390                 395                 400

Gly Lys Ala Ser Leu Glu Ser Leu Glu Glu Tyr Ile Leu Ser Asn Asp
                405                 410                 415
```

```
Asn Val Val Met Gln Ser Gly Arg Gln Glu Tyr Leu Glu Thr Val Leu
            420                 425                 430

Asn Asn Ile Leu Phe Lys Ala
        435
```

<210> SEQ ID NO 37
<211> LENGTH: 1323
<212> TYPE: DNA
<213> ORGANISM: Unknown
<220> FEATURE:
<223> OTHER INFORMATION: Obtained from environmental sample

<400> SEQUENCE: 37

```
atgaaagaaa ttttcccaaa tattcctgag attaaattcg aaggaaaaga cagcaaaaat      60

ccttttgctt tccattacta caacccagac caaatcatct taggcaaacc aatgaaagaa     120

cacctcccat tcgctatggc ttggtggcac aatcttggtg caacaggtgt tgatatgttt     180

ggcgctggcc cagctgataa gagtttcggt gctaaagttg gcacaatgga acacgctaag     240

gccaaagtcg atgccggttt cgaattcatg aagaaactcg gtatcagata tttctgcttc     300

catgatgttg acttagttcc agaatgtgca gatatcaaag atacaaacaa agaattagat     360

gaaatcagtg actacatctt agaaaagatg aaaggcacag atattaagtg tttatggggc     420

accgccaata tgttctctaa cccacgcttc tgcaatggtg cgggttccac aaacagtgcg     480

gatgtcttcg ctttcgccgc tgctcaagtt aagaaagcct tagatatcac cgttaaatta     540

ggtggtaggg gttacgtctt ctggggtggt cgtgaaggtt acgaaacatt actcaataca     600

gacgttaaat tcgaacaaga aaacattgct cgtttaatga agatggctgt tgaatatggc     660

cgttccatcg gtttcaaagg cgatttctat atcgaaccaa aaccaaaaga accaatgaaa     720

caccaatatg acttcgacgc cgctacagct attggcttct taagagccca cggcttagac     780

aaagacttca agttgaacat cgaagctaac cacgctacat tagcgggtca tacattccaa     840

cacgatttaa gaatctccgc cattaatggt atgttaggtt ctatcgatgc taaccaaggc     900

gatatgctct taggttggga tacagacgaa ttcccatttg atgtctacag tgcgacacaa     960

tgtatgtacg aagtcttaaa gaatggtggt cttacaggtg gtttcaactt tgactccaaa    1020

acacgtcgtc catcctacac aatggaagat atgttcttag cctatatctt aggtatggat    1080

acattcgctt taggtttaat caaagctgct caaatcatcg aagatggccg tattgatcaa    1140

ttcatcgaaa agaaatattc ttccttccgt gaaacagaaa tcggtcaaaa gatcttaaac    1200

aacaagacaa gcttaaaaga attatccgat tacgcttgca agatgggtgc tccagaactt    1260

ccaggtagtg gtcgtcaaga aatgctcgaa gccatcgtta acgatgtctt attcggcaag    1320

taa                                                                  1323
```

<210> SEQ ID NO 38
<211> LENGTH: 440
<212> TYPE: PRT
<213> ORGANISM: Unknown
<220> FEATURE:
<223> OTHER INFORMATION: Obtained from environmental sample

<400> SEQUENCE: 38

```
Met Lys Glu Ile Phe Pro Asn Ile Pro Glu Ile Lys Phe Glu Gly Lys
1               5                   10                  15

Asp Ser Lys Asn Pro Phe Ala Phe His Tyr Tyr Asn Pro Asp Gln Ile
            20                  25                  30

Ile Leu Gly Lys Pro Met Lys Glu His Leu Pro Phe Ala Met Ala Trp
```

```
        35                  40                  45

Trp His Asn Leu Gly Ala Thr Gly Val Asp Met Phe Gly Ala Gly Pro
    50                  55                  60

Ala Asp Lys Ser Phe Gly Ala Lys Val Gly Thr Met Glu His Ala Lys
65                  70                  75                  80

Ala Lys Val Asp Ala Gly Phe Glu Phe Met Lys Lys Leu Gly Ile Arg
                85                  90                  95

Tyr Phe Cys Phe His Asp Val Asp Leu Val Pro Glu Cys Ala Asp Ile
            100                 105                 110

Lys Asp Thr Asn Lys Glu Leu Asp Glu Ile Ser Asp Tyr Ile Leu Glu
        115                 120                 125

Lys Met Lys Gly Thr Asp Ile Lys Cys Leu Trp Gly Thr Ala Asn Met
    130                 135                 140

Phe Ser Asn Pro Arg Phe Cys Asn Gly Ala Gly Ser Thr Asn Ser Ala
145                 150                 155                 160

Asp Val Phe Ala Phe Ala Ala Ala Gln Val Lys Lys Ala Leu Asp Ile
                165                 170                 175

Thr Val Lys Leu Gly Gly Arg Gly Tyr Val Phe Trp Gly Gly Arg Glu
            180                 185                 190

Gly Tyr Glu Thr Leu Leu Asn Thr Asp Val Lys Phe Glu Gln Glu Asn
        195                 200                 205

Ile Ala Arg Leu Met Lys Met Ala Val Glu Tyr Gly Arg Ser Ile Gly
    210                 215                 220

Phe Lys Gly Asp Phe Tyr Ile Glu Pro Lys Pro Lys Glu Pro Met Lys
225                 230                 235                 240

His Gln Tyr Asp Phe Asp Ala Ala Thr Ala Ile Gly Phe Leu Arg Ala
                245                 250                 255

His Gly Leu Asp Lys Asp Phe Lys Leu Asn Ile Glu Ala Asn His Ala
            260                 265                 270

Thr Leu Ala Gly His Thr Phe Gln His Asp Leu Arg Ile Ser Ala Ile
        275                 280                 285

Asn Gly Met Leu Gly Ser Ile Asp Ala Asn Gln Gly Asp Met Leu Leu
    290                 295                 300

Gly Trp Asp Thr Asp Glu Phe Pro Phe Asp Val Tyr Ser Ala Thr Gln
305                 310                 315                 320

Cys Met Tyr Glu Val Leu Lys Asn Gly Gly Leu Thr Gly Gly Phe Asn
                325                 330                 335

Phe Asp Ser Lys Thr Arg Arg Pro Ser Tyr Thr Met Glu Asp Met Phe
            340                 345                 350

Leu Ala Tyr Ile Leu Gly Met Asp Thr Phe Ala Leu Gly Leu Ile Lys
        355                 360                 365

Ala Ala Gln Ile Ile Glu Asp Gly Arg Ile Asp Gln Phe Ile Glu Lys
    370                 375                 380

Lys Tyr Ser Ser Phe Arg Glu Thr Glu Ile Gly Gln Lys Ile Leu Asn
385                 390                 395                 400

Asn Lys Thr Ser Leu Lys Glu Leu Ser Asp Tyr Ala Cys Lys Met Gly
                405                 410                 415

Ala Pro Glu Leu Pro Gly Ser Gly Arg Gln Glu Met Leu Glu Ala Ile
            420                 425                 430

Val Asn Asp Val Leu Phe Gly Lys
        435                 440
```

<210> SEQ ID NO 39

<211> LENGTH: 1323
<212> TYPE: DNA
<213> ORGANISM: Unknown
<220> FEATURE:
<223> OTHER INFORMATION: Obtained from environmental sample

<400> SEQUENCE: 39

```
atgaaagaaa ttttcccaaa tattcctgag attaaattcg aaggaaaaga cagcaaaaat     60

ccttttgctt tccattacta caacccagac caaatcatct taggtaaacc aatgaaagaa    120

cacctcccat tcgctatggc ttggtggcac aatcttggtg caacaggtgt tgatatgttt    180

ggcgctggcc cagctgataa gagtttcggt gctaaagttg gcacaatgga acacgctaag    240

gccaaagtcg atgccggttt cgaattcatg aagaaacttg gtatcagata tttctgcttc    300

catgatgttg acttagttcc agaatgtgca gatatcaaag atacaaacaa agaattagat    360

gaaatcagtg actacatctt agaaaagatg aaaggcacag atatcaagtg tttatggggc    420

accgccaata tgttctctaa cccacgtttc tgcaatggtg cgggttccac aaacagtgcg    480

gatgtcttcg ctttcgccgc tgctcaagtt aagaaagcct tagatatcac cgttaaatta    540

ggtggtaggg gttacgtctt ctggggtggt cgtgaaggtt acgaaacatt actcaataca    600

gacgttaaat tcgaacaaga aaacattgct cgtttaatga agatggctgt tgaatatggc    660

cgttccatcg gtttcaaagg cgatttctat atcgaaccaa aaccaaaaga accaatgaaa    720

caccaatatg acttcgacgc cgctacagct attggcttct taagagccca cggcttagac    780

aaagacttca agttgaacat cgaagctaac cacgctacat tagcgggtca tacattccaa    840

cacgatttaa gaatctccgc cattaatggt atgttaggtt ctatcgatgc taaccaaggc    900

gatatgctct taggttggga tacagacgaa ttcccatttg atgtctacag tgcgacacaa    960

tgtatgtacg aagtcttaaa gaatggtggt cttacaggtg gtttcaactt tgactccaaa   1020

acacgtcgtc catcctacac aatggaagat atgttcttag cctatatctt aggtatggat   1080

acattcgctt taggtttaat caaagctgct caaatcatcg aagatggccg tattgatcaa   1140

ttcatcgaaa agaaatattc ttccttccgt gaaacagaaa tcggtcaaaa gatcttaaac   1200

aacaagacaa gcttaaaaga attatccgat tacgcttgca agatgggtgc tccagaactt   1260

ccaggtagtg gtcgtcaaga aatgctcgaa gccatcgtta acgatgtctt attcggcaag   1320

taa                                                                  1323
```

<210> SEQ ID NO 40
<211> LENGTH: 440
<212> TYPE: PRT
<213> ORGANISM: Unknown
<220> FEATURE:
<223> OTHER INFORMATION: Obtained from environmental sample

<400> SEQUENCE: 40

```
Met Lys Glu Ile Phe Pro Asn Ile Pro Glu Ile Lys Phe Glu Gly Lys
1               5                   10                  15

Asp Ser Lys Asn Pro Phe Ala Phe His Tyr Tyr Asn Pro Asp Gln Ile
            20                  25                  30

Ile Leu Gly Lys Pro Met Lys Glu His Leu Pro Phe Ala Met Ala Trp
        35                  40                  45

Trp His Asn Leu Gly Ala Thr Gly Val Asp Met Phe Gly Ala Gly Pro
    50                  55                  60

Ala Asp Lys Ser Phe Gly Ala Lys Val Gly Thr Met Glu His Ala Lys
65                  70                  75                  80
```

```
Ala Lys Val Asp Ala Gly Phe Glu Phe Met Lys Lys Leu Gly Ile Arg
                85                  90                  95

Tyr Phe Cys Phe His Asp Val Asp Leu Val Pro Glu Cys Ala Asp Ile
            100                 105                 110

Lys Asp Thr Asn Lys Glu Leu Asp Glu Ile Ser Asp Tyr Ile Leu Glu
        115                 120                 125

Lys Met Lys Gly Thr Asp Ile Lys Cys Leu Trp Gly Thr Ala Asn Met
    130                 135                 140

Phe Ser Asn Pro Arg Phe Cys Asn Gly Ala Gly Ser Thr Asn Ser Ala
145                 150                 155                 160

Asp Val Phe Ala Phe Ala Ala Ala Gln Val Lys Lys Ala Leu Asp Ile
                165                 170                 175

Thr Val Lys Leu Gly Gly Arg Gly Tyr Val Phe Trp Gly Gly Arg Glu
            180                 185                 190

Gly Tyr Glu Thr Leu Leu Asn Thr Asp Val Lys Phe Glu Gln Glu Asn
        195                 200                 205

Ile Ala Arg Leu Met Lys Met Ala Val Glu Tyr Gly Arg Ser Ile Gly
    210                 215                 220

Phe Lys Gly Asp Phe Tyr Ile Glu Pro Lys Pro Lys Glu Pro Met Lys
225                 230                 235                 240

His Gln Tyr Asp Phe Asp Ala Ala Thr Ala Ile Gly Phe Leu Arg Ala
                245                 250                 255

His Gly Leu Asp Lys Asp Phe Lys Leu Asn Ile Glu Ala Asn His Ala
            260                 265                 270

Thr Leu Ala Gly His Thr Phe Gln His Asp Leu Arg Ile Ser Ala Ile
        275                 280                 285

Asn Gly Met Leu Gly Ser Ile Asp Ala Asn Gln Gly Asp Met Leu Leu
    290                 295                 300

Gly Trp Asp Thr Asp Glu Phe Pro Phe Asp Val Tyr Ser Ala Thr Gln
305                 310                 315                 320

Cys Met Tyr Glu Val Leu Lys Asn Gly Gly Leu Thr Gly Gly Phe Asn
                325                 330                 335

Phe Asp Ser Lys Thr Arg Arg Pro Ser Tyr Thr Met Glu Asp Met Phe
            340                 345                 350

Leu Ala Tyr Ile Leu Gly Met Asp Thr Phe Ala Leu Gly Leu Ile Lys
        355                 360                 365

Ala Ala Gln Ile Ile Glu Asp Gly Arg Ile Asp Gln Phe Ile Glu Lys
    370                 375                 380

Lys Tyr Ser Ser Phe Arg Glu Thr Glu Ile Gly Gln Lys Ile Leu Asn
385                 390                 395                 400

Asn Lys Thr Ser Leu Lys Glu Leu Ser Asp Tyr Ala Cys Lys Met Gly
                405                 410                 415

Ala Pro Glu Leu Pro Gly Ser Gly Arg Gln Glu Met Leu Glu Ala Ile
            420                 425                 430

Val Asn Asp Val Leu Phe Gly Lys
        435                 440
```

<210> SEQ ID NO 41
<211> LENGTH: 1326
<212> TYPE: DNA
<213> ORGANISM: Unknown
<220> FEATURE:
<223> OTHER INFORMATION: Obtained from environmental sample

<400> SEQUENCE: 41

-continued

```
atggaatatt tccctttcgt caaatcggtc caatacaagg gaccaacctc aactgaacca     60
ttcgctttca agtactacga tgccaaccgt gtcgttcttg gaaaaccaat gaaagaatgg    120
atgccattcg ctatggcttg gtggcacaac ctcggcgctg ccggtaccga catgttcggc    180
ggcaacacca tggacaagtc ctggggagtc gataaagaaa aagacccaat gggctatgcc    240
aaagccaaag ttgatgccgg cttcgaattc atgcagaaga tgggcatcga atactactgc    300
ttccacgatg tcgacctcgt cccagagtgc gacgacatca ccgttatgta ccagagactc    360
gatgagatcg gtgattacct tctcaagaaa cagaaggaaa ccggtatcaa gcttctttgg    420
tcaaccgcca atgccttcgg acaccgccgt ttcatgaacg gtgctggttc cagcaactcc    480
gccgaagtct attgcttcgc cgccgcccag atcaagaaag ctcttgagct ctgcgtcaaa    540
ctcggtggca aaggctatgt cttctggggt ggacgtgaag gctacgaaac ccttctcaac    600
accgacatga agttcgaaca agagaacatc gccaacctta tgagatgcgc ccgtgactac    660
ggccgcaaga tcggtttcaa aggcgacttc tacatcgaac caaaaccaaa agagccaaca    720
aagcatcagt atgacttcga cgccgctacc gccatcggat tcctccgtca gtacggtctc    780
gacaaagact tcaagatgaa catcgaagcc aaccacgcta ccttagctgg ccacaccttc    840
gaacacgaac tccgcgtctc cgccatgaac ggcatgctcg gttccatcga cgccaacgaa    900
ggcgatatgc tcctcggatg ggatgtcgac cgtttcccag ccaacgtcta tagcgccacc    960
ttcgccatgc tcgaagtcat caaagccggt ggacttaccg gtggcttcaa cttcgacgcc   1020
aagacccgcc gcgcttccaa cacctatgaa gatatgttca aggctttcgt ccttggtatg   1080
gataccttcg ctttaggtct tctcaatgcc gaagccatca tcaaagacgg ccgcatcgac   1140
aagttcgtcg aggatagata tgccagcttc aagaccggca tcggtgctaa ggtccgcgat   1200
cactccgcta cccttgagga tttagctgcc cacgcccttg agaccaaggt ttgcccagat   1260
ccaggcagcg gcgacgagga agaactccag gaaatcctca accagttaat gttcggtaag   1320
aaataa                                                              1326
```

<210> SEQ ID NO 42
<211> LENGTH: 441
<212> TYPE: PRT
<213> ORGANISM: Unknown
<220> FEATURE:
<223> OTHER INFORMATION: Obtained from environmental sample

<400> SEQUENCE: 42

```
Met Glu Tyr Phe Pro Phe Val Lys Ser Val Gln Tyr Lys Gly Pro Thr
1               5                   10                  15

Ser Thr Glu Pro Phe Ala Phe Lys Tyr Tyr Asp Ala Asn Arg Val Val
            20                  25                  30

Leu Gly Lys Pro Met Lys Glu Trp Met Pro Phe Ala Met Ala Trp Trp
        35                  40                  45

His Asn Leu Gly Ala Ala Gly Thr Asp Met Phe Gly Gly Asn Thr Met
    50                  55                  60

Asp Lys Ser Trp Gly Val Asp Lys Glu Lys Asp Pro Met Gly Tyr Ala
65                  70                  75                  80

Lys Ala Lys Val Asp Ala Gly Phe Glu Phe Met Gln Lys Met Gly Ile
                85                  90                  95

Glu Tyr Tyr Cys Phe His Asp Val Asp Leu Val Pro Glu Cys Asp Asp
            100                 105                 110

Ile Thr Val Met Tyr Gln Arg Leu Asp Glu Ile Gly Asp Tyr Leu Leu
        115                 120                 125
```

```
Lys Lys Gln Lys Glu Thr Gly Ile Lys Leu Leu Trp Ser Thr Ala Asn
    130                 135                 140

Ala Phe Gly His Arg Arg Phe Met Asn Gly Ala Gly Ser Ser Asn Ser
145                 150                 155                 160

Ala Glu Val Tyr Cys Phe Ala Ala Ala Gln Ile Lys Lys Ala Leu Glu
                165                 170                 175

Leu Cys Val Lys Leu Gly Gly Lys Gly Tyr Val Phe Trp Gly Gly Arg
            180                 185                 190

Glu Gly Tyr Glu Thr Leu Leu Asn Thr Asp Met Lys Phe Glu Gln Glu
        195                 200                 205

Asn Ile Ala Asn Leu Met Arg Cys Ala Arg Asp Tyr Gly Arg Lys Ile
    210                 215                 220

Gly Phe Lys Gly Asp Phe Tyr Ile Glu Pro Lys Pro Lys Glu Pro Thr
225                 230                 235                 240

Lys His Gln Tyr Asp Phe Asp Ala Ala Thr Ala Ile Gly Phe Leu Arg
                245                 250                 255

Gln Tyr Gly Leu Asp Lys Asp Phe Lys Met Asn Ile Glu Ala Asn His
            260                 265                 270

Ala Thr Leu Ala Gly His Thr Phe Glu His Glu Leu Arg Val Ser Ala
        275                 280                 285

Met Asn Gly Met Leu Gly Ser Ile Asp Ala Asn Glu Gly Asp Met Leu
    290                 295                 300

Leu Gly Trp Asp Val Asp Arg Phe Pro Ala Asn Val Tyr Ser Ala Thr
305                 310                 315                 320

Phe Ala Met Leu Glu Val Ile Lys Ala Gly Gly Leu Thr Gly Gly Phe
                325                 330                 335

Asn Phe Asp Ala Lys Thr Arg Arg Ala Ser Asn Thr Tyr Glu Asp Met
            340                 345                 350

Phe Lys Ala Phe Val Leu Gly Met Asp Thr Phe Ala Leu Gly Leu Leu
        355                 360                 365

Asn Ala Glu Ala Ile Ile Lys Asp Gly Arg Ile Asp Lys Phe Val Glu
    370                 375                 380

Asp Arg Tyr Ala Ser Phe Lys Thr Gly Ile Gly Ala Lys Val Arg Asp
385                 390                 395                 400

His Ser Ala Thr Leu Glu Asp Leu Ala Ala His Ala Leu Glu Thr Lys
                405                 410                 415

Val Cys Pro Asp Pro Gly Ser Gly Asp Glu Glu Glu Leu Gln Glu Ile
            420                 425                 430

Leu Asn Gln Leu Met Phe Gly Lys Lys
        435                 440
```

```
<210> SEQ ID NO 43
<211> LENGTH: 1323
<212> TYPE: DNA
<213> ORGANISM: Unknown
<220> FEATURE:
<223> OTHER INFORMATION: Obtained from environmental sample

<400> SEQUENCE: 43

atgagcgaat tttttaagaa tattccagag attaaattcg aaggaaaaga tagtaaaaat      60

ccatgggcat tcaagtatta caatcctgaa ttgaccatta tgggtaaaaa aatgtctgaa     120

catcttcctt ttgcaatggc ctggtggcat aaccttggcg caaatggagt tgatatgttc     180

ggttcgggaa ccgccgataa atctttcggt caggctccgg gaactatgga gcacgcaaag     240
```

```
gctaaggtag atgcaggtat cgagtttatg aagaaactcg gaatcaagta ctactgctgg    300

catgatgtag accttgttcc tgaagatcca aacgatatca acgtaacaaa caagcgcctt    360

gatgagattt cagattatat ccttgaaaaa acaaagggaa ctgacatcaa gtgtctctgg    420

ggaactgcta acatgttcag taatccccgc tttatgaacg gggcaggctc aacaaactct    480

gctgacgttt actgctttgc agctgcccag gttaaaaagg ctcttgagat taccgtaaag    540

cttggtggcc gcggttatgt attctggggt ggacgcgaag gttatgaaac tcttcttaat    600

acagatgtaa agcttgaaca ggaaaatatt gcaaacctta tgcacatggc agttgattat    660

ggccgttcaa tcggtttcaa gggagacttc tacatcgagc ctaagccaaa ggagccgatg    720

agtcatcagt atgattttga tgccgcaact gcaatcggct tcctccgcca gtatggcctc    780

gacaaagact ttaagatgaa cattgaggct aaccacgctt ctcttgcaaa tcataccttc    840

cagcatgagc tttatatcag ccgcattaac ggaatgcttg gttctgtaga tgctaaccag    900

ggaaatccaa ttctcggctg ggatacagat aacttccctt ggaatgtcta cgacgcaact    960

cttgcaatgt acgaagtact caaggctggt ggacttacag gtggcttcaa ctttgactca   1020

aagaaccgcc gcccatcaaa tacatttgaa gatatgttcc acgcttacat catgggaatg   1080

gacacttttg ctcttggtct tattaaggct gcagaaatta ttgaagacgg aagaatcgat   1140

ggcttcatta aagaaaagta ttcaagctac gaaagtggaa ttggtaagaa gatccgcgac   1200

aagcagacaa ctttggaaga gcttgctgcc cgtgccgcag aaatgaaaaa gccatctgat   1260

ccaggttcag gccgcgagga atatctggaa ggagttgtta acaatatcct ctttcgcgga   1320

taa                                                                 1323
```

```
<210> SEQ ID NO 44
<211> LENGTH: 440
<212> TYPE: PRT
<213> ORGANISM: Unknown
<220> FEATURE:
<223> OTHER INFORMATION: Obtained from environmental sample

<400> SEQUENCE: 44

Met Ser Glu Phe Phe Lys Asn Ile Pro Glu Ile Lys Phe Glu Gly Lys
1               5                   10                  15

Asp Ser Lys Asn Pro Trp Ala Phe Lys Tyr Tyr Asn Pro Glu Leu Thr
            20                  25                  30

Ile Met Gly Lys Lys Met Ser Glu His Leu Pro Phe Ala Met Ala Trp
        35                  40                  45

Trp His Asn Leu Gly Ala Asn Gly Val Asp Met Phe Gly Ser Gly Thr
    50                  55                  60

Ala Asp Lys Ser Phe Gly Gln Ala Pro Gly Thr Met Glu His Ala Lys
65                  70                  75                  80

Ala Lys Val Asp Ala Gly Ile Glu Phe Met Lys Lys Leu Gly Ile Lys
                85                  90                  95

Tyr Tyr Cys Trp His Asp Val Asp Leu Val Pro Glu Asp Pro Asn Asp
            100                 105                 110

Ile Asn Val Thr Asn Lys Arg Leu Asp Glu Ile Ser Asp Tyr Ile Leu
        115                 120                 125

Glu Lys Thr Lys Gly Thr Asp Ile Lys Cys Leu Trp Gly Thr Ala Asn
    130                 135                 140

Met Phe Ser Asn Pro Arg Phe Met Asn Gly Ala Gly Ser Thr Asn Ser
145                 150                 155                 160

Ala Asp Val Tyr Cys Phe Ala Ala Ala Gln Val Lys Lys Ala Leu Glu
```

```
                165                 170                 175

Ile Thr Val Lys Leu Gly Gly Arg Gly Tyr Val Phe Trp Gly Gly Arg
            180                 185                 190

Glu Gly Tyr Glu Thr Leu Leu Asn Thr Asp Val Lys Leu Glu Gln Glu
        195                 200                 205

Asn Ile Ala Asn Leu Met His Met Ala Val Asp Tyr Gly Arg Ser Ile
    210                 215                 220

Gly Phe Lys Gly Asp Phe Tyr Ile Glu Pro Lys Pro Lys Glu Pro Met
225                 230                 235                 240

Ser His Gln Tyr Asp Phe Asp Ala Ala Thr Ala Ile Gly Phe Leu Arg
                245                 250                 255

Gln Tyr Gly Leu Asp Lys Asp Phe Lys Met Asn Ile Glu Ala Asn His
            260                 265                 270

Ala Ser Leu Ala Asn His Thr Phe Gln His Glu Leu Tyr Ile Ser Arg
        275                 280                 285

Ile Asn Gly Met Leu Gly Ser Val Asp Ala Asn Gln Gly Asn Pro Ile
    290                 295                 300

Leu Gly Trp Asp Thr Asp Asn Phe Pro Trp Asn Val Tyr Asp Ala Thr
305                 310                 315                 320

Leu Ala Met Tyr Glu Val Leu Lys Ala Gly Gly Leu Thr Gly Gly Phe
                325                 330                 335

Asn Phe Asp Ser Lys Asn Arg Arg Pro Ser Asn Thr Phe Glu Asp Met
            340                 345                 350

Phe His Ala Tyr Ile Met Gly Met Asp Thr Phe Ala Leu Gly Leu Ile
        355                 360                 365

Lys Ala Ala Glu Ile Ile Glu Asp Gly Arg Ile Asp Gly Phe Ile Lys
    370                 375                 380

Glu Lys Tyr Ser Ser Tyr Glu Ser Gly Ile Gly Lys Lys Ile Arg Asp
385                 390                 395                 400

Lys Gln Thr Thr Leu Glu Glu Leu Ala Ala Arg Ala Ala Glu Met Lys
                405                 410                 415

Lys Pro Ser Asp Pro Gly Ser Gly Arg Glu Glu Tyr Leu Glu Gly Val
            420                 425                 430

Val Asn Asn Ile Leu Phe Arg Gly
        435                 440
```

<210> SEQ ID NO 45
<211> LENGTH: 1323
<212> TYPE: DNA
<213> ORGANISM: Unknown
<220> FEATURE:
<223> OTHER INFORMATION: Obtained from environmental sample

<400> SEQUENCE: 45

```
atgagcgagt tttttaagaa tattcctcaa ataaaatacg aaggaaaaga tagcaaaaat      60

ccctgggcat tcaagtatta caatcctgaa ttgacaatca tgggtaaaaa gatgagcgaa     120

catcttccat tcgcaatggc atggtggcat aaccttggcg caaacggcgt tgatatgttt     180

ggtcagggaa cagcagacaa gtctttcgga cagattcctg gaactatgga gcatgcaaag     240

gctaaggttg atgctggtat agagtttatg aagaagctcg gaatcaaata ttactgctgg     300

cacgatgttg accttgttcc tgaggatcca aacgatatca acgtaactaa caaacgtctg     360

gacgaaattt cagattacat ccttgaaaag acaaaaggaa cagacattaa gtgtctctgg     420

ggaactgcaa acatgttcgg taaccctcgc tttatgaacg gtgcaggctc tacaaactct     480
```

```
gctgacgttt actgttttgc tgccgctcag gtaaaaaagg ctcttgagat tactgtaaag    540

cttggtggcc gaggttatgt tttctggggt ggccgcgaag gttacgaaac tcttctcaat    600

acagacgtaa aacttgaaca ggaaaatatc gcaaacctca tgcatatggc tgttgattat    660

ggccgctcaa tcggtttcaa gggagacttc tacatcgagc ctaagccaaa ggagccaatg    720

agccatcagt atgattttga tgctgcaaca gcaatcggct tcctccgcca gtatggcctc    780

gacaaagatt ttaagatgaa catcgaagct aaccatgcct cacttgcaaa tcacaccttc    840

cagcacgagc tttgtatcag ccgcataaac ggaatgcttg gttctgtaga tgcaaatcag    900

ggaaatccaa ttcttggctg ggatacagat aacttcccat ggaatgttta cgatgcaact    960

ctggcaatgt acgaagttct caaggctggc ggtctaacag gtggcttcaa ctttgactca   1020

aagaaccgtc gcccatcaaa tacttttgaa gatatgttcc acgcttatat catgggtatg   1080

gatacttttg cccttggcct tattaaggct gcagaaatta ttgaagacgg cagaattgac   1140

ggcttcatca aagaaaagta ttcaagcttt gaaagtggaa ttggtaagaa gattcgtgac   1200

aagcagacaa gtttggaaga gcttgcagct cgtgccgctg aaatgaaaaa gccatctgat   1260

ccaggttcag gccgcgagga atacctcgaa ggagttgtta acaacatcct ctttcgcgga   1320

taa                                                                 1323
```

<210> SEQ ID NO 46
<211> LENGTH: 440
<212> TYPE: PRT
<213> ORGANISM: Unknown
<220> FEATURE:
<223> OTHER INFORMATION: Obtained from environmental sample

<400> SEQUENCE: 46

```
Met Ser Glu Phe Phe Lys Asn Ile Pro Gln Ile Lys Tyr Glu Gly Lys
1               5                   10                  15

Asp Ser Lys Asn Pro Trp Ala Phe Lys Tyr Tyr Asn Pro Glu Leu Thr
            20                  25                  30

Ile Met Gly Lys Lys Met Ser Glu His Leu Pro Phe Ala Met Ala Trp
        35                  40                  45

Trp His Asn Leu Gly Ala Asn Gly Val Asp Met Phe Gly Gln Gly Thr
    50                  55                  60

Ala Asp Lys Ser Phe Gly Gln Ile Pro Gly Thr Met Glu His Ala Lys
65                  70                  75                  80

Ala Lys Val Asp Ala Gly Ile Glu Phe Met Lys Lys Leu Gly Ile Lys
                85                  90                  95

Tyr Tyr Cys Trp His Asp Val Asp Leu Val Pro Glu Asp Pro Asn Asp
            100                 105                 110

Ile Asn Val Thr Asn Lys Arg Leu Asp Glu Ile Ser Asp Tyr Ile Leu
        115                 120                 125

Glu Lys Thr Lys Gly Thr Asp Ile Lys Cys Leu Trp Gly Thr Ala Asn
    130                 135                 140

Met Phe Gly Asn Pro Arg Phe Met Asn Gly Ala Gly Ser Thr Asn Ser
145                 150                 155                 160

Ala Asp Val Tyr Cys Phe Ala Ala Ala Gln Val Lys Lys Ala Leu Glu
                165                 170                 175

Ile Thr Val Lys Leu Gly Gly Arg Gly Tyr Val Phe Trp Gly Gly Arg
            180                 185                 190

Glu Gly Tyr Glu Thr Leu Leu Asn Thr Asp Val Lys Leu Glu Gln Glu
        195                 200                 205
```

```
Asn Ile Ala Asn Leu Met His Met Ala Val Asp Tyr Gly Arg Ser Ile
    210                 215                 220

Gly Phe Lys Gly Asp Phe Tyr Ile Glu Pro Lys Pro Lys Glu Pro Met
225                 230                 235                 240

Ser His Gln Tyr Asp Phe Asp Ala Ala Thr Ala Ile Gly Phe Leu Arg
                245                 250                 255

Gln Tyr Gly Leu Asp Lys Asp Phe Lys Met Asn Ile Glu Ala Asn His
            260                 265                 270

Ala Ser Leu Ala Asn His Thr Phe Gln His Glu Leu Cys Ile Ser Arg
        275                 280                 285

Ile Asn Gly Met Leu Gly Ser Val Asp Ala Asn Gln Gly Asn Pro Ile
    290                 295                 300

Leu Gly Trp Asp Thr Asp Asn Phe Pro Trp Asn Val Tyr Asp Ala Thr
305                 310                 315                 320

Leu Ala Met Tyr Glu Val Leu Lys Ala Gly Gly Leu Thr Gly Gly Phe
                325                 330                 335

Asn Phe Asp Ser Lys Asn Arg Arg Pro Ser Asn Thr Phe Glu Asp Met
            340                 345                 350

Phe His Ala Tyr Ile Met Gly Met Asp Thr Phe Ala Leu Gly Leu Ile
        355                 360                 365

Lys Ala Ala Glu Ile Ile Glu Asp Gly Arg Ile Asp Gly Phe Ile Lys
    370                 375                 380

Glu Lys Tyr Ser Ser Phe Glu Ser Gly Ile Gly Lys Lys Ile Arg Asp
385                 390                 395                 400

Lys Gln Thr Ser Leu Glu Glu Leu Ala Ala Arg Ala Ala Glu Met Lys
                405                 410                 415

Lys Pro Ser Asp Pro Gly Ser Gly Arg Glu Glu Tyr Leu Glu Gly Val
            420                 425                 430

Val Asn Asn Ile Leu Phe Arg Gly
        435                 440
```

<210> SEQ ID NO 47
<211> LENGTH: 1311
<212> TYPE: DNA
<213> ORGANISM: Unknown
<220> FEATURE:
<223> OTHER INFORMATION: Obtained from environmental sample

<400> SEQUENCE: 47

```
atgatatttg aaaatattcc cgcaattcct tatgagggtc cgaagagcac aaatccgctg      60

gcgtttaaat tctatgatcc ggacaagatc gttatgggaa agcccatgaa ggagcatctg     120

ccctttgcaa tggcctggtg gcacaacctt ggcgcggccg gaaccgatat gttcgggcgc     180

gataccgccg acaaatcctt cggtgcggta aaaggcacaa tggagcatgc caaagcgaaa     240

gtcgatgccg gctttgagtt catgcagaag ctggggatcc gctatttctg cttccatgat     300

gtggatcttg ttccggaggc ggatgatata aaggagacca accgccgtct ggacgagatc     360

agcgattaca tccttgaaaa gatgaagggc accgatatca agtgcctttg gggcacggcc     420

aatatgttct caaatccgcg ctttatgaac ggcgcaggct cctccaattc tgccgatgta     480

ttcgcttttg cggcagcaca ggccaagaag gccttggatc tgaccgtcaa actcggcggg     540

cgcggctatg tcttctgggg cggacgtgag ggctatgaga cacttctcaa taccgacatg     600

aagttcgagc aggagaatat cgcgaagctc atgcatatgg ctgtcgatta cggccgcagc     660

ataggcttta ccggtgattt ctatatcgag cccaaaccga aagagccgat gaaacaccag     720
```

```
tatgatttcg atgcagccac tgcgataggc ttcctccgcc agtacggact cgataaggac    780

ttcaagctca acatcgaggc aaaccacgcc acactggcag gtcacacttt ccagcacgat    840

ctgcgtgttt ccgcaataaa cggaatgctg ggcagcattg acgccaacca gggcgatatg    900

ctcctcggct gggataccga cgagttcccg ttcaatgtat atgatgcgac catgtgcatg    960

tatgaggtgc tcaagtcaga cgggctcacc ggcggcttta acttcgactc caaatcacgc   1020

cgcccgagct atacggtcga ggatatgttt acaagctata tcctcggcat ggacactttt   1080

gccctcggcc ttctgaaagc ggccgagctt atcgaagacg gaaggcttga cgccttcgtc   1140

aaagaacgct attcaagcta tgagagcggc atcggcgcaa agatccgcag cggagaaacc   1200

gatttgaagg aattggcgga atatgcggac tccctcggag cccccgaact tccgggcagc   1260

ggaaaacagg aacagctcga gagcatagta aatcagatac ttttcggata a            1311
```

<210> SEQ ID NO 48
<211> LENGTH: 436
<212> TYPE: PRT
<213> ORGANISM: Unknown
<220> FEATURE:
<223> OTHER INFORMATION: Obtained from environmental sample

<400> SEQUENCE: 48

```
Met Ile Phe Glu Asn Ile Pro Ala Ile Pro Tyr Glu Gly Pro Lys Ser
1               5                   10                  15

Thr Asn Pro Leu Ala Phe Lys Phe Tyr Asp Pro Asp Lys Ile Val Met
            20                  25                  30

Gly Lys Pro Met Lys Glu His Leu Pro Phe Ala Met Ala Trp Trp His
        35                  40                  45

Asn Leu Gly Ala Ala Gly Thr Asp Met Phe Gly Arg Asp Thr Ala Asp
    50                  55                  60

Lys Ser Phe Gly Ala Val Lys Gly Thr Met Glu His Ala Lys Ala Lys
65                  70                  75                  80

Val Asp Ala Gly Phe Glu Phe Met Gln Lys Leu Gly Ile Arg Tyr Phe
                85                  90                  95

Cys Phe His Asp Val Asp Leu Val Pro Glu Ala Asp Asp Ile Lys Glu
            100                 105                 110

Thr Asn Arg Arg Leu Asp Glu Ile Ser Asp Tyr Ile Leu Glu Lys Met
        115                 120                 125

Lys Gly Thr Asp Ile Lys Cys Leu Trp Gly Thr Ala Asn Met Phe Ser
    130                 135                 140

Asn Pro Arg Phe Met Asn Gly Ala Gly Ser Ser Asn Ser Ala Asp Val
145                 150                 155                 160

Phe Ala Phe Ala Ala Ala Gln Ala Lys Lys Ala Leu Asp Leu Thr Val
                165                 170                 175

Lys Leu Gly Gly Arg Gly Tyr Val Phe Trp Gly Gly Arg Glu Gly Tyr
            180                 185                 190

Glu Thr Leu Leu Asn Thr Asp Met Lys Phe Glu Gln Glu Asn Ile Ala
        195                 200                 205

Lys Leu Met His Met Ala Val Asp Tyr Gly Arg Ser Ile Gly Phe Thr
    210                 215                 220

Gly Asp Phe Tyr Ile Glu Pro Lys Pro Lys Glu Pro Met Lys His Gln
225                 230                 235                 240

Tyr Asp Phe Asp Ala Ala Thr Ala Ile Gly Phe Leu Arg Gln Tyr Gly
                245                 250                 255

Leu Asp Lys Asp Phe Lys Leu Asn Ile Glu Ala Asn His Ala Thr Leu
```

```
            260                 265                 270

Ala Gly His Thr Phe Gln His Asp Leu Arg Val Ser Ala Ile Asn Gly
        275                 280                 285

Met Leu Gly Ser Ile Asp Ala Asn Gln Gly Asp Met Leu Leu Gly Trp
    290                 295                 300

Asp Thr Asp Glu Phe Pro Phe Asn Val Tyr Asp Ala Thr Met Cys Met
305                 310                 315                 320

Tyr Glu Val Leu Lys Ser Asp Gly Leu Thr Gly Gly Phe Asn Phe Asp
                325                 330                 335

Ser Lys Ser Arg Arg Pro Ser Tyr Thr Val Glu Asp Met Phe Thr Ser
            340                 345                 350

Tyr Ile Leu Gly Met Asp Thr Phe Ala Leu Gly Leu Leu Lys Ala Ala
        355                 360                 365

Glu Leu Ile Glu Asp Gly Arg Leu Asp Ala Phe Val Lys Glu Arg Tyr
    370                 375                 380

Ser Ser Tyr Glu Ser Gly Ile Gly Ala Lys Ile Arg Ser Gly Glu Thr
385                 390                 395                 400

Asp Leu Lys Glu Leu Ala Glu Tyr Ala Asp Ser Leu Gly Ala Pro Glu
                405                 410                 415

Leu Pro Gly Ser Gly Lys Gln Glu Gln Leu Glu Ser Ile Val Asn Gln
            420                 425                 430

Ile Leu Phe Gly
        435


<210> SEQ ID NO 49
<211> LENGTH: 1317
<212> TYPE: DNA
<213> ORGANISM: Unknown
<220> FEATURE:
<223> OTHER INFORMATION: Obtained from environmental sample

<400> SEQUENCE: 49

atgagcgagt tttttgccag cattcccaaa attccctttg aaggcaagga cagcgccaat      60

cccctggcgt tcaaatacta cgacgccgac aggatgatac tgggcaagcc catgaaggag     120

caccttccct tcgccatggc ctggtggcac aacctgtgcg ccgcgggcac cgatatgttt     180

ggccgggaca ccgccgacaa gtccttcggc caggtcaagg gcaccatgga acacgccaag     240

gccaaggtgg acgcgggctt tgagttcatg aagaagctgg gcatccgcta cttctgcttc     300

cacgacgtgg acatcgtgcc cgaagccgac gacatcaagg aaaccaaccg ccgtctggac     360

gagatctccg actatatcct ggagaaaatg aaaggcaccg acatccagtg cctgtggggc     420

accgccaaca tgttcggcaa cccccgctat atgaacggcg cgggcagctc caactccgcc     480

gacgtatact gcttcgccgc ggcccagatc aaaaaggccc tggacatcac cgtgaagctg     540

ggcggcaagg gctacgtgtt ctggggcggc cgcgagggct acgagaccct gctgaacacc     600

gatatgaagt tcgagcagga gaacatcgcc cgcctgatgc acatggccgt ggactacggc     660

cgcagcatcg gcttcaccgg cgatttctac atcgagccca agcccaagga gcccatgaag     720

caccagtacg acttcgacgc cgccaccgcc ataggctttt tgcgccagta cggcctggac     780

aaggatttca agctgaacat cgagtccaac cacgccaccc tggcgggcca taccttccag     840

cacgacctgc gcgtttccgc catcaacggc atgctgggct ccatcgacgc caaccagggc     900

gactacctgc tgggctggga taccgacgag ttcccctaca gcgtatacga gaccaccatg     960

tgcatgtacg aggtgctcaa ggccggaggt ctcaccggcg gcttcaattt cgacgccaag    1020
```

```
aaccgccgtc ccagctacac ccccgaggat atgttccacg cctacatcct tgggatggac   1080

agcttcgccc tgggcctgat caaggccgcc gagctcatcg aggacggtcg cctggacgcc   1140

ttcgtccggg accgctacca gagctgggag accggcatcg gcgataagat ccgcaagggc   1200

gagaccacac tggccgagct ggccgagtac gccgcccgga tgggcgcgcc cgcgctgccc   1260

ggcagcggcc gccaggaata cctggagggc gtggtcaaca atatcctgtt caaataa      1317


<210> SEQ ID NO 50
<211> LENGTH: 438
<212> TYPE: PRT
<213> ORGANISM: Unknown
<220> FEATURE:
<223> OTHER INFORMATION: Obtained from environmental sample

<400> SEQUENCE: 50

Met Ser Glu Phe Phe Ala Ser Ile Pro Lys Ile Pro Phe Glu Gly Lys
1               5                   10                  15

Asp Ser Ala Asn Pro Leu Ala Phe Lys Tyr Tyr Asp Ala Asp Arg Met
            20                  25                  30

Ile Leu Gly Lys Pro Met Lys Glu His Leu Pro Phe Ala Met Ala Trp
        35                  40                  45

Trp His Asn Leu Cys Ala Ala Gly Thr Asp Met Phe Gly Arg Asp Thr
    50                  55                  60

Ala Asp Lys Ser Phe Gly Gln Val Lys Gly Thr Met Glu His Ala Lys
65                  70                  75                  80

Ala Lys Val Asp Ala Gly Phe Glu Phe Met Lys Lys Leu Gly Ile Arg
                85                  90                  95

Tyr Phe Cys Phe His Asp Val Asp Ile Val Pro Glu Ala Asp Asp Ile
            100                 105                 110

Lys Glu Thr Asn Arg Arg Leu Asp Glu Ile Ser Asp Tyr Ile Leu Glu
        115                 120                 125

Lys Met Lys Gly Thr Asp Ile Gln Cys Leu Trp Gly Thr Ala Asn Met
    130                 135                 140

Phe Gly Asn Pro Arg Tyr Met Asn Gly Ala Gly Ser Ser Asn Ser Ala
145                 150                 155                 160

Asp Val Tyr Cys Phe Ala Ala Ala Gln Ile Lys Lys Ala Leu Asp Ile
                165                 170                 175

Thr Val Lys Leu Gly Gly Lys Gly Tyr Val Phe Trp Gly Gly Arg Glu
            180                 185                 190

Gly Tyr Glu Thr Leu Leu Asn Thr Asp Met Lys Phe Glu Gln Glu Asn
        195                 200                 205

Ile Ala Arg Leu Met His Met Ala Val Asp Tyr Gly Arg Ser Ile Gly
    210                 215                 220

Phe Thr Gly Asp Phe Tyr Ile Glu Pro Lys Pro Lys Glu Pro Met Lys
225                 230                 235                 240

His Gln Tyr Asp Phe Asp Ala Ala Thr Ala Ile Gly Phe Leu Arg Gln
                245                 250                 255

Tyr Gly Leu Asp Lys Asp Phe Lys Leu Asn Ile Glu Ser Asn His Ala
            260                 265                 270

Thr Leu Ala Gly His Thr Phe Gln His Asp Leu Arg Val Ser Ala Ile
        275                 280                 285

Asn Gly Met Leu Gly Ser Ile Asp Ala Asn Gln Gly Asp Tyr Leu Leu
    290                 295                 300

Gly Trp Asp Thr Asp Glu Phe Pro Tyr Ser Val Tyr Glu Thr Thr Met
305                 310                 315                 320
```

```
Cys Met Tyr Glu Val Leu Lys Ala Gly Gly Leu Thr Gly Gly Phe Asn
                325                 330                 335

Phe Asp Ala Lys Asn Arg Arg Pro Ser Tyr Thr Pro Glu Asp Met Phe
            340                 345                 350

His Ala Tyr Ile Leu Gly Met Asp Ser Phe Ala Leu Gly Leu Ile Lys
        355                 360                 365

Ala Ala Glu Leu Ile Glu Asp Gly Arg Leu Asp Ala Phe Val Arg Asp
    370                 375                 380

Arg Tyr Gln Ser Trp Glu Thr Gly Ile Gly Asp Lys Ile Arg Lys Gly
385                 390                 395                 400

Glu Thr Thr Leu Ala Glu Leu Ala Glu Tyr Ala Ala Arg Met Gly Ala
                405                 410                 415

Pro Ala Leu Pro Gly Ser Gly Arg Gln Glu Tyr Leu Glu Gly Val Val
            420                 425                 430

Asn Asn Ile Leu Phe Lys
        435
```

<210> SEQ ID NO 51
<211> LENGTH: 1320
<212> TYPE: DNA
<213> ORGANISM: Unknown
<220> FEATURE:
<223> OTHER INFORMATION: Obtained from environmental sample

<400> SEQUENCE: 51

```
atgaagacct atttcaaaaa aatccccgtg atcccctacg agggaccgaa gtcccagaat     60

ccgctgtcgt tcaaattcta tgacgcggac cgcatcgttc tcggcaagcc catgaaggag    120

catctgccct tcgccatggc ctggtggcac aatctgggtg ctgccggaac ggacatgttc    180

ggccgcgata ccgccgacaa gtccttcgga gcggagaagg gcaccatgga gcatgccaag    240

gccaaggtgg acgctggctt cgagtttatg aagaaggtgg gcatccggta tttctgcttc    300

catgacgtgg atctggtccc ggaagcggac gacatcaagg agaccaaccg ccgtctcgat    360

gagatcagcg actacatcct caagaagatg aagggcacgg atatcaagtg cctctggggc    420

accgccaaca tgttcggcaa tccccggttc atgaacggcg cgggcagctc caacagcgcg    480

gacgtgttct gctttgccgc ggcccaggtg aagaaggcct tggacatcac cgtcaagctg    540

ggcggccggg gctatgtgtt ctggggcggc cgtgaggggt atgagtccct gctgaacacg    600

gacgtgaagt ttgagcagga gaacatcgcc aagctcatgc accttgccgt ggactacggc    660

cgcagcatcg gcttcaccgg cgatttctac atcgagccca agcccaagga gcccatgaag    720

caccagtacg acttcgatgc cgccaccgcc atcggcttcc tcaggcagta cggcctcgat    780

aaggacttca agatgaacat tgaagccaac cacgcgaccc tggccggcca caccttccag    840

cacgacctca ggatcagcgc catcaacggg atgctgggct ccatcgacgc caaccagggc    900

gacctcctgc tgggatggga caccgacgaa ttccccttca acgtctatga ggccaccatg    960

tgcatgtacg aggtcctcaa ggccggcggc ctcaccggcg gcttcaactt cgactcaaag   1020

aaccgccgtc cctcctacac catggaggat atgttccacg cctacatcct gggcatggac   1080

accttcgccc tgggtcttct caaggccgcg gagctcatcg aggacggtcg gatcgacaaa   1140

ttcgtggagg agcgctacgc cagctacaag accggcatcg gcgccaagat ccgttccggc   1200

gagaccacgc ttcaggagct ggccgcctat gccgacaagt tgggcgcgcc tgcccttccc   1260

ggcagcggcc gtcaggagta cctggagagc atcgtcaacc aggtgctctt cgggatgtga   1320
```

<210> SEQ ID NO 52
<211> LENGTH: 439
<212> TYPE: PRT
<213> ORGANISM: Unknown
<220> FEATURE:
<223> OTHER INFORMATION: Obtained from environmental sample

<400> SEQUENCE: 52

Met Lys Thr Tyr Phe Lys Lys Ile Pro Val Ile Pro Tyr Glu Gly Pro
1               5                   10                  15

Lys Ser Gln Asn Pro Leu Ser Phe Lys Phe Tyr Asp Ala Asp Arg Ile
            20                  25                  30

Val Leu Gly Lys Pro Met Lys Glu His Leu Pro Phe Ala Met Ala Trp
        35                  40                  45

Trp His Asn Leu Gly Ala Ala Gly Thr Asp Met Phe Gly Arg Asp Thr
    50                  55                  60

Ala Asp Lys Ser Phe Gly Ala Glu Lys Gly Thr Met Glu His Ala Lys
65                  70                  75                  80

Ala Lys Val Asp Ala Gly Phe Glu Phe Met Lys Lys Val Gly Ile Arg
                85                  90                  95

Tyr Phe Cys Phe His Asp Val Asp Leu Val Pro Glu Ala Asp Asp Ile
            100                 105                 110

Lys Glu Thr Asn Arg Arg Leu Asp Glu Ile Ser Asp Tyr Ile Leu Lys
        115                 120                 125

Lys Met Lys Gly Thr Asp Ile Lys Cys Leu Trp Gly Thr Ala Asn Met
    130                 135                 140

Phe Gly Asn Pro Arg Phe Met Asn Gly Ala Gly Ser Ser Asn Ser Ala
145                 150                 155                 160

Asp Val Phe Cys Phe Ala Ala Ala Gln Val Lys Lys Ala Leu Asp Ile
                165                 170                 175

Thr Val Lys Leu Gly Gly Arg Gly Tyr Val Phe Trp Gly Gly Arg Glu
            180                 185                 190

Gly Tyr Glu Ser Leu Leu Asn Thr Asp Val Lys Phe Glu Gln Glu Asn
        195                 200                 205

Ile Ala Lys Leu Met His Leu Ala Val Asp Tyr Gly Arg Ser Ile Gly
    210                 215                 220

Phe Thr Gly Asp Phe Tyr Ile Glu Pro Lys Pro Lys Glu Pro Met Lys
225                 230                 235                 240

His Gln Tyr Asp Phe Asp Ala Ala Thr Ala Ile Gly Phe Leu Arg Gln
                245                 250                 255

Tyr Gly Leu Asp Lys Asp Phe Lys Met Asn Ile Glu Ala Asn His Ala
            260                 265                 270

Thr Leu Ala Gly His Thr Phe Gln His Asp Leu Arg Ile Ser Ala Ile
        275                 280                 285

Asn Gly Met Leu Gly Ser Ile Asp Ala Asn Gln Gly Asp Leu Leu Leu
    290                 295                 300

Gly Trp Asp Thr Asp Glu Phe Pro Phe Asn Val Tyr Glu Ala Thr Met
305                 310                 315                 320

Cys Met Tyr Glu Val Leu Lys Ala Gly Gly Leu Thr Gly Gly Phe Asn
                325                 330                 335

Phe Asp Ser Lys Asn Arg Arg Pro Ser Tyr Thr Met Glu Asp Met Phe
            340                 345                 350

His Ala Tyr Ile Leu Gly Met Asp Thr Phe Ala Leu Gly Leu Leu Lys
        355                 360                 365

```
Ala Ala Glu Leu Ile Glu Asp Gly Arg Ile Asp Lys Phe Val Glu Glu
    370                 375                 380

Arg Tyr Ala Ser Tyr Lys Thr Gly Ile Gly Ala Lys Ile Arg Ser Gly
385                 390                 395                 400

Glu Thr Thr Leu Gln Glu Leu Ala Ala Tyr Ala Asp Lys Leu Gly Ala
                405                 410                 415

Pro Ala Leu Pro Gly Ser Gly Arg Gln Glu Tyr Leu Glu Ser Ile Val
            420                 425                 430

Asn Gln Val Leu Phe Gly Met
        435
```

<210> SEQ ID NO 53
<211> LENGTH: 1314
<212> TYPE: DNA
<213> ORGANISM: Unknown
<220> FEATURE:
<223> OTHER INFORMATION: Obtained from environmental sample

<400> SEQUENCE: 53

```
atggctaaag agtattttcc agagattggc aaaatcaagt ttgaaggcaa ggacagcaaa     60

aacccaatgg ctttccacta ctatgacccc gagaaggtga tcatgggcaa gcctatgaaa    120

gactggctcc gcttcgctat ggcatggtgg cacaccctct gcgcagaagg tggcgaccag    180

ttcggtggcg gcactaagaa gttcccttgg aacaacggcg ctgacgctgt agaaatcgca    240

aaacagaagg ctgacgcagg tttcgaaatc atgcagaagc tcggcatccc atatttctgc    300

ttccacgacg tggacctcgt gtctgagggc gcatctgtag aagagtatga ggctaacctc    360

aaggctatca cagactacct cgctgtgaag atgaaggaaa caggcatcaa gctcctgtgg    420

tctactgcca acgtattcgg caacggccgc tacatgaacg gtgcttctac caaccctgac    480

ttcgacgtcg ttgctcgcgc tatcgtgcag attaagaacg ctatcgacgc tggtatcaag    540

ctcggcgctg agaactacgt gttctggggc ggacgcgaag gctacatgag cctcctcaac    600

accgaccaga agcgtgagaa ggagcacatg gccactatgc tcactatggc tcgcgactac    660

gctcgcgcta agggcttcaa gggcacattc ctcatcgagc ctaagccaat ggagccttct    720

aagcaccagt atgacgttga cactgagact gtcatcggct tcctcaaggc acacaacctc    780

gacaaggact tcaaggtgaa catcgaggtg aaccacgcaa ctctcgctgg ccacaccttc    840

gagcacgagc tcgcagtggc agtggacaac aacatgctcg gctctatcga cgctaaccgt    900

ggtgactacc agaatggctg ggatactgac cagttcccaa tcgaccagta cgaactcgtt    960

caggcttgga tggaaatcat ccgtggcggc ggtctcggca ctggcggcac gaacttcgac   1020

gctaagactc gtcgtaactc taccgacctc gaagacatct tcatcgcaca catcgcaggc   1080

atggacgcta tggcacgcgc actcgaatca gctgctaagc tcctcgaaga gtctccatac   1140

aaggcaatga aggcagctcg ctacgcttca ttcgacaacg gtatcggtaa ggacttcgaa   1200

gatggcaagc tcactctcga gcaggcttac gaatacggta agaaggttgg tgagcctaag   1260

cagacttctg gcaagcagga gctctacgaa gccatcgttg caatgtacgc ttaa          1314
```

<210> SEQ ID NO 54
<211> LENGTH: 437
<212> TYPE: PRT
<213> ORGANISM: Unknown
<220> FEATURE:
<223> OTHER INFORMATION: Obtained from environmental sample

<400> SEQUENCE: 54

-continued

```
Met Ala Lys Glu Tyr Phe Pro Glu Ile Gly Lys Ile Lys Phe Glu Gly
1               5                   10                  15

Lys Asp Ser Lys Asn Pro Met Ala Phe His Tyr Tyr Asp Pro Glu Lys
            20                  25                  30

Val Ile Met Gly Lys Pro Met Lys Asp Trp Leu Arg Phe Ala Met Ala
        35                  40                  45

Trp Trp His Thr Leu Cys Ala Glu Gly Gly Asp Gln Phe Gly Gly Gly
    50                  55                  60

Thr Lys Lys Phe Pro Trp Asn Asn Gly Ala Asp Ala Val Glu Ile Ala
65                  70                  75                  80

Lys Gln Lys Ala Asp Ala Gly Phe Glu Ile Met Gln Lys Leu Gly Ile
                85                  90                  95

Pro Tyr Phe Cys Phe His Asp Val Asp Leu Val Ser Glu Gly Ala Ser
            100                 105                 110

Val Glu Glu Tyr Glu Ala Asn Leu Lys Ala Ile Thr Asp Tyr Leu Ala
        115                 120                 125

Val Lys Met Lys Glu Thr Gly Ile Lys Leu Leu Trp Ser Thr Ala Asn
    130                 135                 140

Val Phe Gly Asn Gly Arg Tyr Met Asn Gly Ala Ser Thr Asn Pro Asp
145                 150                 155                 160

Phe Asp Val Val Ala Arg Ala Ile Val Gln Ile Lys Asn Ala Ile Asp
                165                 170                 175

Ala Gly Ile Lys Leu Gly Ala Glu Asn Tyr Val Phe Trp Gly Gly Arg
            180                 185                 190

Glu Gly Tyr Met Ser Leu Leu Asn Thr Asp Gln Lys Arg Glu Lys Glu
        195                 200                 205

His Met Ala Thr Met Leu Thr Met Ala Arg Asp Tyr Ala Arg Ala Lys
    210                 215                 220

Gly Phe Lys Gly Thr Phe Leu Ile Glu Pro Lys Pro Met Glu Pro Ser
225                 230                 235                 240

Lys His Gln Tyr Asp Val Asp Thr Glu Thr Val Ile Gly Phe Leu Lys
                245                 250                 255

Ala His Asn Leu Asp Lys Asp Phe Lys Val Asn Ile Glu Val Asn His
            260                 265                 270

Ala Thr Leu Ala Gly His Thr Phe Glu His Glu Leu Ala Val Ala Val
        275                 280                 285

Asp Asn Asn Met Leu Gly Ser Ile Asp Ala Asn Arg Gly Asp Tyr Gln
    290                 295                 300

Asn Gly Trp Asp Thr Asp Gln Phe Pro Ile Asp Gln Tyr Glu Leu Val
305                 310                 315                 320

Gln Ala Trp Met Glu Ile Ile Arg Gly Gly Gly Leu Gly Thr Gly Gly
                325                 330                 335

Thr Asn Phe Asp Ala Lys Thr Arg Arg Asn Ser Thr Asp Leu Glu Asp
            340                 345                 350

Ile Phe Ile Ala His Ile Ala Gly Met Asp Ala Met Ala Arg Ala Leu
        355                 360                 365

Glu Ser Ala Ala Lys Leu Leu Glu Glu Ser Pro Tyr Lys Ala Met Lys
    370                 375                 380

Ala Ala Arg Tyr Ala Ser Phe Asp Asn Gly Ile Gly Lys Asp Phe Glu
385                 390                 395                 400

Asp Gly Lys Leu Thr Leu Glu Gln Ala Tyr Glu Tyr Gly Lys Lys Val
                405                 410                 415

Gly Glu Pro Lys Gln Thr Ser Gly Lys Gln Glu Leu Tyr Glu Ala Ile
```

-continued 420 425 430

Val Ala Met Tyr Ala
435

<210> SEQ ID NO 55
<211> LENGTH: 1314
<212> TYPE: DNA
<213> ORGANISM: Unknown
<220> FEATURE:
<223> OTHER INFORMATION: Obtained from environmental sample

<400> SEQUENCE: 55
atggctaaag aatttttccc agagattggt aaaatcaagt tcgaaggcaa ggattcaaag 60
aatccaatgg ctttccatta ctatgatgca gagaaggtaa tcatgggcaa acccatgaag 120
gactggctcc gtttcgctat ggcatggtgg cacacactct gtgcagaggg cggcgaccag 180
ttcggtggcg gtacgaagaa gttcccttgg aacgagggtg ctaatgctgt cgagattgct 240
aagcagaagg ctgacgctgg tttcgaaatc atgcagaagc ttggcattcc ttacttctgc 300
ttccacgatg ttgacctcgt ttctgaaggc gcatctgttg aggagtatga ggccaacctc 360
aaggctatca ctgactatct cgcggtgaag atgaaggaga ctggcattaa gctcctgtgg 420
tctactgcca acgtgttcgg caatggccgt tacatgaatg gtgcttccac caaccctgac 480
ttcgacgttg ttgctcgcgc catcgttcag attaagaacg ctatcgatgc aggtatcaag 540
ctcggtgctg agaactatgt gttctggggc ggtcgtgaag gttacatgag cctcctgaac 600
acagaccaga agcgtgagaa ggagcacatg gctactatgc tcactatggc tcgcgactac 660
gctcgcagca agggcttcaa gggtactttc ctcatcgagc ctaagccaat ggagccatct 720
aagcaccagt acgacgttga cacagagact gttatcggct tcctgaaggc acacaacctt 780
gacaaggact tcaaggtgaa catcgaggtg aaccacgcaa cactcgctgg tcacaccttc 840
gagcacgagc tcgctgtggc tgtcgacaac aatatgcttg gttctatcga tgctaaccgc 900
ggtgactacc agaatggttg ggatacggac cagttcccaa ttgaccagta cgagctcgtt 960
caggcttgga tggagatcat ccgtggtggc ggtctcggca caggtggtac aaacttcgac 1020
gctaagactc gtcgtaactc taccgacctc gaggacattt tcattgctca catcgctggt 1080
atggacgcta tggctcgcgc tcttgagtca gcagctaagc tccttgagga gtctccatac 1140
aagaagatga aggctgcccg ttatgcttct ttcgacagcg gcatgggtaa ggactttgag 1200
aacggcaagc tcacactcga acaggtttat gagtatggta agaaggtagg tgagcccaag 1260
cagacttctg gcaagcagga gctcttcgag gcaatcgtgg ccatgtacgc ataa 1314

<210> SEQ ID NO 56
<211> LENGTH: 437
<212> TYPE: PRT
<213> ORGANISM: Unknown
<220> FEATURE:
<223> OTHER INFORMATION: Obtained from environmental sample

<400> SEQUENCE: 56

Met Ala Lys Glu Phe Phe Pro Glu Ile Gly Lys Ile Lys Phe Glu Gly
1 5 10 15

Lys Asp Ser Lys Asn Pro Met Ala Phe His Tyr Tyr Asp Ala Glu Lys
20 25 30

Val Ile Met Gly Lys Pro Met Lys Asp Trp Leu Arg Phe Ala Met Ala
35 40 45

Trp Trp His Thr Leu Cys Ala Glu Gly Gly Asp Gln Phe Gly Gly Gly

```
    50                  55                  60

Thr Lys Lys Phe Pro Trp Asn Glu Gly Ala Asn Ala Val Glu Ile Ala
65                  70                  75                  80

Lys Gln Lys Ala Asp Ala Gly Phe Glu Ile Met Gln Lys Leu Gly Ile
                85                  90                  95

Pro Tyr Phe Cys Phe His Asp Val Asp Leu Val Ser Glu Gly Ala Ser
            100                 105                 110

Val Glu Glu Tyr Glu Ala Asn Leu Lys Ala Ile Thr Asp Tyr Leu Ala
        115                 120                 125

Val Lys Met Lys Glu Thr Gly Ile Lys Leu Leu Trp Ser Thr Ala Asn
    130                 135                 140

Val Phe Gly Asn Gly Arg Tyr Met Asn Gly Ala Ser Thr Asn Pro Asp
145                 150                 155                 160

Phe Asp Val Val Ala Arg Ala Ile Val Gln Ile Lys Asn Ala Ile Asp
                165                 170                 175

Ala Gly Ile Lys Leu Gly Ala Glu Asn Tyr Val Phe Trp Gly Gly Arg
            180                 185                 190

Glu Gly Tyr Met Ser Leu Leu Asn Thr Asp Gln Lys Arg Glu Lys Glu
        195                 200                 205

His Met Ala Thr Met Leu Thr Met Ala Arg Asp Tyr Ala Arg Ser Lys
    210                 215                 220

Gly Phe Lys Gly Thr Phe Leu Ile Glu Pro Lys Pro Met Glu Pro Ser
225                 230                 235                 240

Lys His Gln Tyr Asp Val Asp Thr Glu Thr Val Ile Gly Phe Leu Lys
                245                 250                 255

Ala His Asn Leu Asp Lys Asp Phe Lys Val Asn Ile Glu Val Asn His
            260                 265                 270

Ala Thr Leu Ala Gly His Thr Phe Glu His Glu Leu Ala Val Ala Val
        275                 280                 285

Asp Asn Asn Met Leu Gly Ser Ile Asp Ala Asn Arg Gly Asp Tyr Gln
    290                 295                 300

Asn Gly Trp Asp Thr Asp Gln Phe Pro Ile Asp Gln Tyr Glu Leu Val
305                 310                 315                 320

Gln Ala Trp Met Glu Ile Ile Arg Gly Gly Gly Leu Gly Thr Gly Gly
                325                 330                 335

Thr Asn Phe Asp Ala Lys Thr Arg Arg Asn Ser Thr Asp Leu Glu Asp
            340                 345                 350

Ile Phe Ile Ala His Ile Ala Gly Met Asp Ala Met Ala Arg Ala Leu
        355                 360                 365

Glu Ser Ala Ala Lys Leu Leu Glu Glu Ser Pro Tyr Lys Lys Met Lys
    370                 375                 380

Ala Ala Arg Tyr Ala Ser Phe Asp Ser Gly Met Gly Lys Asp Phe Glu
385                 390                 395                 400

Asn Gly Lys Leu Thr Leu Glu Gln Val Tyr Glu Tyr Gly Lys Lys Val
                405                 410                 415

Gly Glu Pro Lys Gln Thr Ser Gly Lys Gln Glu Leu Phe Glu Ala Ile
            420                 425                 430

Val Ala Met Tyr Ala
        435
```

<210> SEQ ID NO 57
<211> LENGTH: 1314
<212> TYPE: DNA
<213> ORGANISM: Unknown

<220> FEATURE:
<223> OTHER INFORMATION: Obtained from environmental sample

<400> SEQUENCE: 57
atggctaaag agtattttcc agagattggt aaaatcaagt ttgaaggcaa ggattccaag 60
aatccaatgg cattccacta ttatgatgca gagaaagtga ttatgggtaa gcctatgaag 120
gagtggctcc gctttgcaat ggcatggtgg cacacactct gtgcagaggg tggcgaccag 180
tttggtggtg gcactaagaa attcccatgg aacgagggca ctgacgctgt gacgattgct 240
aagcagaagg ctgatgcagg tttcgaaatc atgcagaaac tcggtttccc atatttttgc 300
ttccacgaca ttgacctcgt ttccgaaggc aacagcattg aagagtatga ggctaacctc 360
caggcaatca ctgattatct gaaagtgaag atggaagaga caggcatcaa actcttgtgg 420
tcaactgcca acgtattcgg caatggtcgc tacatgaatg gtgcttccac aaacccagac 480
tttgacgtgg tggctcgtgc catcgttcag attaagaacg caattgacgc tggtatcaaa 540
ctcggtgctg agaactatgt attctggggc ggtcgcgaag gctacatgag ccttctgaac 600
actgaccaga agcgtgagaa ggagcacatg gcaaccatgc tcactatggc tcgcgactac 660
gctcgcagca agggtttcaa gggcactttc ctcattgagc caaagccaat ggagccatct 720
aagcaccagt atgacgttga cacggagact gtcatcggct tcctcaaggc acacaacctc 780
gacaaggatt tcaaggtgaa catcgaagtg aaccacgcta cacttgcagg tcatactttc 840
gagcacgaac ttgctgtggc tgttgacaat ggcatgctcg gttctatcga cgctaaccgt 900
ggtgactatc agaacggttg ggacactgac cagttcccaa tcgaccagta cgaactcgtt 960
caggcttgga tggaaatcat ccgtggtggt ggtctcggca caggtggtac taacttcgat 1020
gctaagactc gtcgtaactc aactgacctc gaggacatct tcatcgcaca catctctggt 1080
atggatgcaa tggcacgtgc tctcgaatcg gcggctaaac ttcttgagga gtctccatac 1140
tgcgctatga agaaggctcg ttacgcttcc ttcgacagcg gcatcggtaa ggacttcgag 1200
gacggcaaac tcacgctcga gcaggcttac gagtacggca agaaagtcgg cgaacccaag 1260
cagacttctg gcaagcagga actctacgag gcaatcgttg ccatgtacgc ataa 1314

<210> SEQ ID NO 58
<211> LENGTH: 437
<212> TYPE: PRT
<213> ORGANISM: Unknown
<220> FEATURE:
<223> OTHER INFORMATION: Obtained from environmental sample

<400> SEQUENCE: 58

Met Ala Lys Glu Tyr Phe Pro Glu Ile Gly Lys Ile Lys Phe Glu Gly
1 5 10 15

Lys Asp Ser Lys Asn Pro Met Ala Phe His Tyr Tyr Asp Ala Glu Lys
20 25 30

Val Ile Met Gly Lys Pro Met Lys Glu Trp Leu Arg Phe Ala Met Ala
35 40 45

Trp Trp His Thr Leu Cys Ala Glu Gly Gly Asp Gln Phe Gly Gly Gly
50 55 60

Thr Lys Lys Phe Pro Trp Asn Glu Gly Thr Asp Ala Val Thr Ile Ala
65 70 75 80

Lys Gln Lys Ala Asp Ala Gly Phe Glu Ile Met Gln Lys Leu Gly Phe
85 90 95

Pro Tyr Phe Cys Phe His Asp Ile Asp Leu Val Ser Glu Gly Asn Ser
100 105 110

```
Ile Glu Glu Tyr Glu Ala Asn Leu Gln Ala Ile Thr Asp Tyr Leu Lys
        115                 120                 125

Val Lys Met Glu Glu Thr Gly Ile Lys Leu Leu Trp Ser Thr Ala Asn
    130                 135                 140

Val Phe Gly Asn Gly Arg Tyr Met Asn Gly Ala Ser Thr Asn Pro Asp
145                 150                 155                 160

Phe Asp Val Val Ala Arg Ala Ile Val Gln Ile Lys Asn Ala Ile Asp
                165                 170                 175

Ala Gly Ile Lys Leu Gly Ala Glu Asn Tyr Val Phe Trp Gly Gly Arg
            180                 185                 190

Glu Gly Tyr Met Ser Leu Leu Asn Thr Asp Gln Lys Arg Glu Lys Glu
        195                 200                 205

His Met Ala Thr Met Leu Thr Met Ala Arg Asp Tyr Ala Arg Ser Lys
    210                 215                 220

Gly Phe Lys Gly Thr Phe Leu Ile Glu Pro Lys Pro Met Glu Pro Ser
225                 230                 235                 240

Lys His Gln Tyr Asp Val Asp Thr Glu Thr Val Ile Gly Phe Leu Lys
                245                 250                 255

Ala His Asn Leu Asp Lys Asp Phe Lys Val Asn Ile Glu Val Asn His
            260                 265                 270

Ala Thr Leu Ala Gly His Thr Phe Glu His Glu Leu Ala Val Ala Val
        275                 280                 285

Asp Asn Gly Met Leu Gly Ser Ile Asp Ala Asn Arg Gly Asp Tyr Gln
    290                 295                 300

Asn Gly Trp Asp Thr Asp Gln Phe Pro Ile Asp Gln Tyr Glu Leu Val
305                 310                 315                 320

Gln Ala Trp Met Glu Ile Ile Arg Gly Gly Gly Leu Gly Thr Gly Gly
                325                 330                 335

Thr Asn Phe Asp Ala Lys Thr Arg Arg Asn Ser Thr Asp Leu Glu Asp
            340                 345                 350

Ile Phe Ile Ala His Ile Ser Gly Met Asp Ala Met Ala Arg Ala Leu
        355                 360                 365

Glu Ser Ala Ala Lys Leu Leu Glu Glu Ser Pro Tyr Cys Ala Met Lys
    370                 375                 380

Lys Ala Arg Tyr Ala Ser Phe Asp Ser Gly Ile Gly Lys Asp Phe Glu
385                 390                 395                 400

Asp Gly Lys Leu Thr Leu Glu Gln Ala Tyr Glu Tyr Gly Lys Lys Val
                405                 410                 415

Gly Glu Pro Lys Gln Thr Ser Gly Lys Gln Glu Leu Tyr Glu Ala Ile
            420                 425                 430

Val Ala Met Tyr Ala
        435
```

<210> SEQ ID NO 59
<211> LENGTH: 1317
<212> TYPE: DNA
<213> ORGANISM: Unknown
<220> FEATURE:
<223> OTHER INFORMATION: Obtained from environmental sample

<400> SEQUENCE: 59

```
atggcaaaag agtatttccc tacgatcggt aagatcgttt atgaaggacc ggagtccaag     60

aaccctatgg catttcatta ctatgacgca gagcgcgtag tagctggtaa aaaaatgaaa    120

gattggatgc gtttcgctat ggcatggtgg cacaccctct gtgcagaagg tgcagaccag    180
```

```
ttcggtggag gcaccaaaca cttcccgtgg agtgaaggtc ccgatgccgt aaccatcgcc    240

aagcagaaag cagacgcagg ttttgagatc atgcagaaac tcggcttccc gtatttctgt    300

ttccatgacg tggatctggt cagcgaaggc agcagcgtag aagagtacga ggcgaacctc    360

gcagccatca ccgattatct caagcagaaa atggacgagt cgggtatcaa actcctttgg    420

tccactgcta acgtattcgg tcacgcccgt tacatgaacg gtgccagcac caatcctgac    480

tttgatgtcg ttgcccgtgc gattgtgcag atcaagaatg ctatcgacgc aggtatcaaa    540

ctcggcgcag agaactacgt cttctggggc ggtcgtgaag gttatatgag cctgctcaat    600

accgaccaga aacgcgagaa agagcatacg gcaatgatgc tgcgtatggc gcgtgactat    660

gcccgcagca aaggtttcaa aggtaccttc ctcatcgaac ccaaacccat ggagccgtcc    720

aagcaccagt atgacgtaga taccgagacg gtgataggtt tcctcaaagc acacggtttg    780

gagaaagact ttaaggtaaa catcgaagtg aaccacgcta ccctcgccgg tcacactttc    840

gagcacgaac tggcagtagc cgtagataac ggcatgctcg gttcgatcga tgccaaccgc    900

ggtgactatc agaacggatg ggataccgac cagttcccca tcgataactt cgaactgacc    960

caagcatgga tgcagatcgt acgtaacggt ggtctcggca caggcggaac gaacttcgac   1020

tccaagaccc gtcgtaactc caccgatctc gaggatatct tcatcgctca catcagtggt   1080

atggacgctt gtgcccgtgc cctattgaat gccgtagaga tcatggagaa atcaccgatc   1140

cctgctatgc tcaaagagcg ttacgcttcc ttcgatagcg gtctgggtaa agatttcgag   1200

gacggcaaac tgacccttga gcaagtctat gagtacggta agaaagtagg cgaacccaaa   1260

caaaccagcg gcaaacaaga actctatgag gctatcgttg ccctctacgc taaataa      1317
```

```
<210> SEQ ID NO 60
<211> LENGTH: 438
<212> TYPE: PRT
<213> ORGANISM: Unknown
<220> FEATURE:
<223> OTHER INFORMATION: Obtained from environmental sample

<400> SEQUENCE: 60

Met Ala Lys Glu Tyr Phe Pro Thr Ile Gly Lys Ile Val Tyr Glu Gly
1               5                   10                  15

Pro Glu Ser Lys Asn Pro Met Ala Phe His Tyr Tyr Asp Ala Glu Arg
            20                  25                  30

Val Val Ala Gly Lys Lys Met Lys Asp Trp Met Arg Phe Ala Met Ala
        35                  40                  45

Trp Trp His Thr Leu Cys Ala Glu Gly Ala Asp Gln Phe Gly Gly Gly
    50                  55                  60

Thr Lys His Phe Pro Trp Ser Glu Gly Pro Asp Ala Val Thr Ile Ala
65                  70                  75                  80

Lys Gln Lys Ala Asp Ala Gly Phe Glu Ile Met Gln Lys Leu Gly Phe
                85                  90                  95

Pro Tyr Phe Cys Phe His Asp Val Asp Leu Val Ser Glu Gly Ser Ser
            100                 105                 110

Val Glu Glu Tyr Glu Ala Asn Leu Ala Ala Ile Thr Asp Tyr Leu Lys
        115                 120                 125

Gln Lys Met Asp Glu Ser Gly Ile Lys Leu Leu Trp Ser Thr Ala Asn
    130                 135                 140

Val Phe Gly His Ala Arg Tyr Met Asn Gly Ala Ser Thr Asn Pro Asp
145                 150                 155                 160
```

-continued

```
Phe Asp Val Val Ala Arg Ala Ile Val Gln Ile Lys Asn Ala Ile Asp
                165                 170                 175

Ala Gly Ile Lys Leu Gly Ala Glu Asn Tyr Val Phe Trp Gly Gly Arg
            180                 185                 190

Glu Gly Tyr Met Ser Leu Leu Asn Thr Asp Gln Lys Arg Glu Lys Glu
        195                 200                 205

His Thr Ala Met Met Leu Arg Met Ala Arg Asp Tyr Ala Arg Ser Lys
    210                 215                 220

Gly Phe Lys Gly Thr Phe Leu Ile Glu Pro Lys Pro Met Glu Pro Ser
225                 230                 235                 240

Lys His Gln Tyr Asp Val Asp Thr Glu Thr Val Ile Gly Phe Leu Lys
                245                 250                 255

Ala His Gly Leu Glu Lys Asp Phe Lys Val Asn Ile Glu Val Asn His
            260                 265                 270

Ala Thr Leu Ala Gly His Thr Phe Glu His Glu Leu Ala Val Ala Val
        275                 280                 285

Asp Asn Gly Met Leu Gly Ser Ile Asp Ala Asn Arg Gly Asp Tyr Gln
    290                 295                 300

Asn Gly Trp Asp Thr Asp Gln Phe Pro Ile Asp Asn Phe Glu Leu Thr
305                 310                 315                 320

Gln Ala Trp Met Gln Ile Val Arg Asn Gly Gly Leu Gly Thr Gly Gly
                325                 330                 335

Thr Asn Phe Asp Ser Lys Thr Arg Arg Asn Ser Thr Asp Leu Glu Asp
            340                 345                 350

Ile Phe Ile Ala His Ile Ser Gly Met Asp Ala Cys Ala Arg Ala Leu
        355                 360                 365

Leu Asn Ala Val Glu Ile Met Glu Lys Ser Pro Ile Pro Ala Met Leu
    370                 375                 380

Lys Glu Arg Tyr Ala Ser Phe Asp Ser Gly Leu Gly Lys Asp Phe Glu
385                 390                 395                 400

Asp Gly Lys Leu Thr Leu Glu Gln Val Tyr Glu Tyr Gly Lys Lys Val
                405                 410                 415

Gly Glu Pro Lys Gln Thr Ser Gly Lys Gln Glu Leu Tyr Glu Ala Ile
            420                 425                 430

Val Ala Leu Tyr Ala Lys
        435


<210> SEQ ID NO 61
<211> LENGTH: 1314
<212> TYPE: DNA
<213> ORGANISM: Unknown
<220> FEATURE:
<223> OTHER INFORMATION: Obtained from environmental sample

<400> SEQUENCE: 61

atgaaagagt atttccctga gatcggtaag atccaatttg aaggcccgga gtccaagaac      60

ccgatggcat ttcactacta tgacgcagag cgcgtcgtag ccggtaaaac aatgaaagag     120

tggatgcgtt tcgctatggc ttggtggcac accctctgtg cggaaggcgg cgaccagttc     180

ggaggcggaa cgaagaagtt cccctggaac gaaggcgcta acgctttgga gatcgccaag     240

cacaaagccg atgcgggatt tgagatcatg cagaaactcg gcatccctta tttctgtttc     300

catgacgtgg atctcatcgc cgagggcggt tcggtagaag agtacgaagc caacctcgct     360

gccatcaccg attacctcaa acagaaaatg gacgagactg gcatcaaact gctgtggtcc     420

acggcgaacg tcttcagcaa cccccgttat atgaacggcg ccagcacgaa ccccgatttc     480
```

```
gatgtagtag cgcgtgccat cgtccagatc aagaacgcta tcgacgccgg tatcaaactc    540
ggagcagaga actatgtctt ctggggtggt cgcgagggct atatgagcct cctcaacact    600
gaccagcgcc gagagaaaga gcatatggct accatgctcc gtatggcgcg tgactacgcg    660
cgtgccaaag gattcaaggg caccttcctc atcgaaccca aaccatgtga gccgtccaaa    720
catcagtatg atgtcgatac cgagaccgtc atcggtttcc tcaaagcgca tggactcgac    780
aaggatttca aagtcaatat cgaggtcaac cacgccaccc tcgcaggcca cacgttcgaa    840
cacgaactgg cttgcgctgt agatgccggc atgctcggtt cgattgacgc caaccgcggt    900
gacgcccaga acggatggga caccgaccag ttccctattg ataacttcga actcacacag    960
gctttcatgc agatcgtccg caacggcggt ttcggaacag gcggtacgaa cttcgacgcc   1020
aagacacgcc gtaactccac cgacttggag gacatcttca tcgcccatat cagcggcatg   1080
gacgcttgcg cacgtgcgtt actcaatgct gtcgaaatcc tcgagaagag cccgattccg   1140
gcgatgctca aagagcgtta tgcttccttt gacggcggca tcggaaagga cttcgaggag   1200
ggaaaactga ctttcgagca ggtctatgag tacggcaaga aagtcggcga acccaaacag   1260
accagcggca aacaggagct ctacgaaacc atcgtcgccc tctatgccaa atag         1314
```

```
<210> SEQ ID NO 62
<211> LENGTH: 437
<212> TYPE: PRT
<213> ORGANISM: Unknown
<220> FEATURE:
<223> OTHER INFORMATION: Obtained from environmental sample

<400> SEQUENCE: 62

Met Lys Glu Tyr Phe Pro Glu Ile Gly Lys Ile Gln Phe Glu Gly Pro
1               5                   10                  15

Glu Ser Lys Asn Pro Met Ala Phe His Tyr Tyr Asp Ala Glu Arg Val
            20                  25                  30

Val Ala Gly Lys Thr Met Lys Glu Trp Met Arg Phe Ala Met Ala Trp
        35                  40                  45

Trp His Thr Leu Cys Ala Glu Gly Gly Asp Gln Phe Gly Gly Gly Thr
    50                  55                  60

Lys Lys Phe Pro Trp Asn Glu Gly Ala Asn Ala Leu Glu Ile Ala Lys
65                  70                  75                  80

His Lys Ala Asp Ala Gly Phe Glu Ile Met Gln Lys Leu Gly Ile Pro
                85                  90                  95

Tyr Phe Cys Phe His Asp Val Asp Leu Ile Ala Glu Gly Gly Ser Val
            100                 105                 110

Glu Glu Tyr Glu Ala Asn Leu Ala Ala Ile Thr Asp Tyr Leu Lys Gln
        115                 120                 125

Lys Met Asp Glu Thr Gly Ile Lys Leu Leu Trp Ser Thr Ala Asn Val
    130                 135                 140

Phe Ser Asn Pro Arg Tyr Met Asn Gly Ala Ser Thr Asn Pro Asp Phe
145                 150                 155                 160

Asp Val Val Ala Arg Ala Ile Val Gln Ile Lys Asn Ala Ile Asp Ala
                165                 170                 175

Gly Ile Lys Leu Gly Ala Glu Asn Tyr Val Phe Trp Gly Gly Arg Glu
            180                 185                 190

Gly Tyr Met Ser Leu Leu Asn Thr Asp Gln Arg Arg Glu Lys Glu His
        195                 200                 205

Met Ala Thr Met Leu Arg Met Ala Arg Asp Tyr Ala Arg Ala Lys Gly
```

```
    210                 215                 220

Phe Lys Gly Thr Phe Leu Ile Glu Pro Lys Pro Cys Glu Pro Ser Lys
225                 230                 235                 240

His Gln Tyr Asp Val Asp Thr Glu Thr Val Ile Gly Phe Leu Lys Ala
                245                 250                 255

His Gly Leu Asp Lys Asp Phe Lys Val Asn Ile Glu Val Asn His Ala
            260                 265                 270

Thr Leu Ala Gly His Thr Phe Glu His Glu Leu Ala Cys Ala Val Asp
        275                 280                 285

Ala Gly Met Leu Gly Ser Ile Asp Ala Asn Arg Gly Asp Ala Gln Asn
    290                 295                 300

Gly Trp Asp Thr Asp Gln Phe Pro Ile Asp Asn Phe Glu Leu Thr Gln
305                 310                 315                 320

Ala Phe Met Gln Ile Val Arg Asn Gly Gly Phe Gly Thr Gly Gly Thr
                325                 330                 335

Asn Phe Asp Ala Lys Thr Arg Arg Asn Ser Thr Asp Leu Glu Asp Ile
            340                 345                 350

Phe Ile Ala His Ile Ser Gly Met Asp Ala Cys Ala Arg Ala Leu Leu
        355                 360                 365

Asn Ala Val Glu Ile Leu Glu Lys Ser Pro Ile Pro Ala Met Leu Lys
    370                 375                 380

Glu Arg Tyr Ala Ser Phe Asp Gly Gly Ile Gly Lys Asp Phe Glu Glu
385                 390                 395                 400

Gly Lys Leu Thr Phe Glu Gln Val Tyr Glu Tyr Gly Lys Lys Val Gly
                405                 410                 415

Glu Pro Lys Gln Thr Ser Gly Lys Gln Glu Leu Tyr Glu Thr Ile Val
            420                 425                 430

Ala Leu Tyr Ala Lys
        435
```

<210> SEQ ID NO 63
<211> LENGTH: 1317
<212> TYPE: DNA
<213> ORGANISM: Unknown
<220> FEATURE:
<223> OTHER INFORMATION: Obtained from environmental sample

<400> SEQUENCE: 63

```
atggcaaaag agtatttccc tacgatcggt aagatcgttt atgaaggacc ggaatccaag      60

aaccctatgg catttcatta ctatgacgca gagcgcgtag tagctggtaa aaaaatgaaa     120

gattggatgc gtttcgctat ggcatggtgg cacaccctct gtgcagaagg tgcagaccag     180

ttcggtggag gcaccaaaca cttcccgtgg aatgaaggtc ccgatgccgt aaccatcgcc     240

aagcagaaag cagacgcagg ttttgagatc atgcagaaac tcggcttccc gtatttctgt     300

ttccatgacg tggatctggt cggcgaaggc agcagcgtag aagagtacga ggcgaacctc     360

gcagccatca ccgattatct caagcagaaa atggacgagt cgggtatcaa actcctttgg     420

tccactgcta acgtattcgg tcacgcccgt tacatgaacg gtgccagcac caatcctgac     480

tttgatgtcg ttgcccgtgc gattgtgcag atcaagaatg ctatcgacgc aggtatcaaa     540

ctcggcgcag agaactacgt cttctggggc ggtcgtgaag gttatatgag cctgctcaac     600

accgaccaga aacgcgagaa agagcatacg gcaatgatgc tgcgtatggc gcgtgactat     660

gcccgcagca aaggtttcaa aggtaccttc ctcatcgaac ccaaacccat ggagccgtcc     720

aagcaccagt atgacgtaga taccgagacg gtgataggtt tcctcaaagc acacggtttg     780
```

```
gagaaagact ttaaggtaaa catcgaagtg aaccacgcta ccctcgccgg tcacactttc    840

gagcacgaac tggcagtagc cgtagataac ggcatgctcg gttcgatcga tgccaaccgc    900

ggtgactatc agaacggatg ggataccgac cagttcccca tcgataactt cgaactgacc    960

caagcatgga tgcagatcgt acgtaacggt ggtctcggca caggcggaac gaacttcgac   1020

tccaagaccc gtcgtaactc caccgatctc gaggatatct tcatcgctca catcagtggt   1080

atggacgctt gtgcccgtgc cctattgaat gccgtagaga tcatggagaa atcaccgatc   1140

cctgctatgc tcaaagagcg ttacgcttcc ttcgatagcg gtctgggtaa agatttcgag   1200

gacggcaaac tgacccttga gcaagtctat gagtacggta agaaagtagg cgaacccaaa   1260

caaaccagcg gcaaacaaga actctatgag gctatcgttg ccctctacgc taaataa      1317
```

<210> SEQ ID NO 64
<211> LENGTH: 438
<212> TYPE: PRT
<213> ORGANISM: Unknown
<220> FEATURE:
<223> OTHER INFORMATION: Obtained from environmental sample

<400> SEQUENCE: 64

```
Met Ala Lys Glu Tyr Phe Pro Thr Ile Gly Lys Ile Val Tyr Glu Gly
1               5                   10                  15

Pro Glu Ser Lys Asn Pro Met Ala Phe His Tyr Tyr Asp Ala Glu Arg
            20                  25                  30

Val Val Ala Gly Lys Lys Met Lys Asp Trp Met Arg Phe Ala Met Ala
        35                  40                  45

Trp Trp His Thr Leu Cys Ala Glu Gly Ala Asp Gln Phe Gly Gly Gly
    50                  55                  60

Thr Lys His Phe Pro Trp Asn Glu Gly Pro Asp Ala Val Thr Ile Ala
65                  70                  75                  80

Lys Gln Lys Ala Asp Ala Gly Phe Glu Ile Met Gln Lys Leu Gly Phe
                85                  90                  95

Pro Tyr Phe Cys Phe His Asp Val Asp Leu Val Gly Glu Gly Ser Ser
            100                 105                 110

Val Glu Glu Tyr Glu Ala Asn Leu Ala Ala Ile Thr Asp Tyr Leu Lys
        115                 120                 125

Gln Lys Met Asp Glu Ser Gly Ile Lys Leu Leu Trp Ser Thr Ala Asn
    130                 135                 140

Val Phe Gly His Ala Arg Tyr Met Asn Gly Ala Ser Thr Asn Pro Asp
145                 150                 155                 160

Phe Asp Val Val Ala Arg Ala Ile Val Gln Ile Lys Asn Ala Ile Asp
                165                 170                 175

Ala Gly Ile Lys Leu Gly Ala Glu Asn Tyr Val Phe Trp Gly Gly Arg
            180                 185                 190

Glu Gly Tyr Met Ser Leu Leu Asn Thr Asp Gln Lys Arg Glu Lys Glu
        195                 200                 205

His Thr Ala Met Met Leu Arg Met Ala Arg Asp Tyr Ala Arg Ser Lys
    210                 215                 220

Gly Phe Lys Gly Thr Phe Leu Ile Glu Pro Lys Pro Met Glu Pro Ser
225                 230                 235                 240

Lys His Gln Tyr Asp Val Asp Thr Glu Thr Val Ile Gly Phe Leu Lys
                245                 250                 255

Ala His Gly Leu Glu Lys Asp Phe Lys Val Asn Ile Glu Val Asn His
            260                 265                 270
```

```
Ala Thr Leu Ala Gly His Thr Phe Glu His Glu Leu Ala Val Ala Val
        275                 280                 285

Asp Asn Gly Met Leu Gly Ser Ile Asp Ala Asn Arg Gly Asp Tyr Gln
    290                 295                 300

Asn Gly Trp Asp Thr Asp Gln Phe Pro Ile Asp Asn Phe Glu Leu Thr
305                 310                 315                 320

Gln Ala Trp Met Gln Ile Val Arg Asn Gly Gly Leu Gly Thr Gly Gly
                325                 330                 335

Thr Asn Phe Asp Ser Lys Thr Arg Arg Asn Ser Thr Asp Leu Glu Asp
            340                 345                 350

Ile Phe Ile Ala His Ile Ser Gly Met Asp Ala Cys Ala Arg Ala Leu
        355                 360                 365

Leu Asn Ala Val Glu Ile Met Glu Lys Ser Pro Ile Pro Ala Met Leu
    370                 375                 380

Lys Glu Arg Tyr Ala Ser Phe Asp Ser Gly Leu Gly Lys Asp Phe Glu
385                 390                 395                 400

Asp Gly Lys Leu Thr Leu Glu Gln Val Tyr Glu Tyr Gly Lys Lys Val
                405                 410                 415

Gly Glu Pro Lys Gln Thr Ser Gly Lys Gln Glu Leu Tyr Glu Ala Ile
            420                 425                 430

Val Ala Leu Tyr Ala Lys
        435


<210> SEQ ID NO 65
<211> LENGTH: 1314
<212> TYPE: DNA
<213> ORGANISM: Unknown
<220> FEATURE:
<223> OTHER INFORMATION: Obtained from environmental sample

<400> SEQUENCE: 65

atgaaagagt atttccctga ggtcggtaag atccaatttg aaggcccgga gtctaagaac     60

ccgatggcat ttcactacta tgacgcagag cgcgtcgtag ccggtaaaac aatgaaagag    120

tggatgcgtt tcgctatggc ttggtggcac accctctgtg cagaaggcgg cgaccagttc    180

ggaggcggaa cgaagcattt cccgtggaat gaaggcgcta acgctttgga gatcgccaaa    240

cacaaagccg atgcgggatt cgagatcatg cagaaactcg gcatccccta tttctgtttc    300

catgacgtgg atctcatcgc cgagggcggt tcggtagaag agtacgaaac caacctcgct    360

gctatcaccg actacctcaa gcagaaaatg gacgagaccg gcatcaaact gctgtggtcc    420

acggcgaacg tgttcagcaa cccccgttat atgaacggcg cgagcacgaa ccccgatttc    480

gatgtagtag cgcgtgccat cgtgcagatc aagaatgcca tcgacgccgg catcaaactg    540

ggcgcagaga actatgtctt ctggggcggt cgcgagggct acatgagcct gctcaacacc    600

gaccagcgcc gcgagaaaga gcatatggct actatgctcc gtatggcgcg tgactacgcg    660

cgtgccaaag gattcaaggg caccttttctc atcgaaccca aaccgtgtga gccgtccaaa    720

catcagtatg atgtcgatac cgagaccgtc atcggtttcc tcaaagcgca tggactcgac    780

aaggatttca aggttaatat cgaggtcaac cacgccaccc tcgcaggcca cacgttcgaa    840

cacgaactgg cttgcgctgt agatgccggc atgctcggtt cgattgacgc caaccgcggt    900

gacgcccaga acggatggga caccgaccag ttccctattg ataacttcga actcacacag    960

gctttcatgc agatcgtccg caacggcggt ttcggaacag gcggtacgaa cttcgacgcc   1020

aagacacgcc gtaactccac cgacttggag gacatcttca tcgcccatat cagcggcatg   1080
```

```
gacgcttgcg cacgtgcgtt gctcaacgcc atcgaaatcc tcgagaagag cccgatcccg   1140

gctatgctca aagaccgtta tgcctccttt gatggcggca tcggaaagga ctttgaggag   1200

ggcaaactga ctttcgagca ggtctatgag tacggcaaga aggtcggaga acccaaacag   1260

accagcggca aacaggagct ctacgaaacc atcgtcgccc tctatgccaa atag         1314


<210> SEQ ID NO 66
<211> LENGTH: 437
<212> TYPE: PRT
<213> ORGANISM: Unknown
<220> FEATURE:
<223> OTHER INFORMATION: Obtained from environmental sample

<400> SEQUENCE: 66

Met Lys Glu Tyr Phe Pro Glu Val Gly Lys Ile Gln Phe Glu Gly Pro
1               5                   10                  15

Glu Ser Lys Asn Pro Met Ala Phe His Tyr Tyr Asp Ala Glu Arg Val
            20                  25                  30

Val Ala Gly Lys Thr Met Lys Glu Trp Met Arg Phe Ala Met Ala Trp
        35                  40                  45

Trp His Thr Leu Cys Ala Glu Gly Gly Asp Gln Phe Gly Gly Gly Thr
    50                  55                  60

Lys His Phe Pro Trp Asn Glu Gly Ala Asn Ala Leu Glu Ile Ala Lys
65                  70                  75                  80

His Lys Ala Asp Ala Gly Phe Glu Ile Met Gln Lys Leu Gly Ile Pro
                85                  90                  95

Tyr Phe Cys Phe His Asp Val Asp Leu Ile Ala Glu Gly Gly Ser Val
            100                 105                 110

Glu Glu Tyr Glu Thr Asn Leu Ala Ala Ile Thr Asp Tyr Leu Lys Gln
        115                 120                 125

Lys Met Asp Glu Thr Gly Ile Lys Leu Leu Trp Ser Thr Ala Asn Val
    130                 135                 140

Phe Ser Asn Pro Arg Tyr Met Asn Gly Ala Ser Thr Asn Pro Asp Phe
145                 150                 155                 160

Asp Val Val Ala Arg Ala Ile Val Gln Ile Lys Asn Ala Ile Asp Ala
                165                 170                 175

Gly Ile Lys Leu Gly Ala Glu Asn Tyr Val Phe Trp Gly Gly Arg Glu
            180                 185                 190

Gly Tyr Met Ser Leu Leu Asn Thr Asp Gln Arg Arg Glu Lys Glu His
        195                 200                 205

Met Ala Thr Met Leu Arg Met Ala Arg Asp Tyr Ala Arg Ala Lys Gly
    210                 215                 220

Phe Lys Gly Thr Phe Leu Ile Glu Pro Lys Pro Cys Glu Pro Ser Lys
225                 230                 235                 240

His Gln Tyr Asp Val Asp Thr Glu Thr Val Ile Gly Phe Leu Lys Ala
                245                 250                 255

His Gly Leu Asp Lys Asp Phe Lys Val Asn Ile Glu Val Asn His Ala
            260                 265                 270

Thr Leu Ala Gly His Thr Phe Glu His Glu Leu Ala Cys Ala Val Asp
        275                 280                 285

Ala Gly Met Leu Gly Ser Ile Asp Ala Asn Arg Gly Asp Ala Gln Asn
    290                 295                 300

Gly Trp Asp Thr Asp Gln Phe Pro Ile Asp Asn Phe Glu Leu Thr Gln
305                 310                 315                 320
```

```
Ala Phe Met Gln Ile Val Arg Asn Gly Gly Phe Gly Thr Gly Gly Thr
                325                 330                 335

Asn Phe Asp Ala Lys Thr Arg Arg Asn Ser Thr Asp Leu Glu Asp Ile
            340                 345                 350

Phe Ile Ala His Ile Ser Gly Met Asp Ala Cys Ala Arg Ala Leu Leu
        355                 360                 365

Asn Ala Ile Glu Ile Leu Glu Lys Ser Pro Ile Pro Ala Met Leu Lys
    370                 375                 380

Asp Arg Tyr Ala Ser Phe Asp Gly Gly Ile Gly Lys Asp Phe Glu Glu
385                 390                 395                 400

Gly Lys Leu Thr Phe Glu Gln Val Tyr Glu Tyr Gly Lys Lys Val Gly
                405                 410                 415

Glu Pro Lys Gln Thr Ser Gly Lys Gln Glu Leu Tyr Glu Thr Ile Val
            420                 425                 430

Ala Leu Tyr Ala Lys
        435


<210> SEQ ID NO 67
<211> LENGTH: 1314
<212> TYPE: DNA
<213> ORGANISM: Unknown
<220> FEATURE:
<223> OTHER INFORMATION: Obtained from environmental sample

<400> SEQUENCE: 67

atgaaagagt atttccctga gatcggtaag atccaatttg aaggcccgga gtccaagaac      60

ccgatggcgt ttcactacta tgacgctgag cgcgtcgtag ccggtaaaac aatgaaagag     120

tggatgcgtt tcgctatggc ttggtggcac accctctgtg cggaaggcgg cgaccagttc     180

ggaggaggaa cgaagaaatt cccctggaac gaaggggcaa acgctttgga gatcgccaag     240

cacaaagccg atgcgggatt cgagatcatg cagaaactcg gcatccctta tttctgtttc     300

catgacgtgg atctcatcgc cgagggcgaa tcggtagaag agtacgaagc caacctcgct     360

gccatcaccg attacctcaa acagaaaatg gacgagaccg gcatcaaact gctgtggtcc     420

acggcgaacg tgttcagcaa cccccgttat atgaacggcg ccagcacgaa ccccgatttc     480

gatgtagtgg cacgcgctat cgtacaaatc aagaacgcta tcgacgccgg tatcaaactc     540

ggagcagaga actatgtctt ctggggcggt cgcgagggct atatgtcgct cctcaacacc     600

gaccagcgcc gagagaaaga gcatatggct actatgctcc gtatggcgcg tgactacgcg     660

cgttccaaag gattcaaggg caccttcctc atcgaaccca aaccgtgtga gccgtccaaa     720

catcagtacg atgtggacac agagaccgtc atcggtttcc ttaaagcgca tggactcgac     780

aaggatttca aagtcaatat cgaggtcaac cacgccaccc tcgcaggcca cacgttcgaa     840

cacgaactgg cttgcgctgt agatgccggc atgctcggtt cgattgacgc caaccgcggt     900

gacgcccaga acggatggga caccgaccaa ttccctattg ataacttcga actcactcag     960

gctttcatgc agatcgtccg caacggcggt ttcggaacag gcggtacgaa cttcgacgcc    1020

aagacacgcc gtaactccac cgacttggag gacatcttca tcgcccatat cagcggcatg    1080

gacgcttgcg ctcgtgcgtt gctcaatgct gtcgaaatcc tcgagaagag cccgatcccg    1140

gctatgctca aagagcgtta tgcttccttt gacggcggca tcggaaagga ctttgaggag    1200

ggcaaactga ctttcgagca ggtctatgag tacggcaaga aggtcggaga acccaaacag    1260

accagcggca aacaggagct ctacgaaacc atcgtcgccc tctatgccaa atga          1314
```

<210> SEQ ID NO 68
<211> LENGTH: 437
<212> TYPE: PRT
<213> ORGANISM: Unknown
<220> FEATURE:
<223> OTHER INFORMATION: Obtained from environmental sample

<400> SEQUENCE: 68

```
Met Lys Glu Tyr Phe Pro Glu Ile Gly Lys Ile Gln Phe Glu Gly Pro
1               5                   10                  15

Glu Ser Lys Asn Pro Met Ala Phe His Tyr Tyr Asp Ala Glu Arg Val
            20                  25                  30

Val Ala Gly Lys Thr Met Lys Glu Trp Met Arg Phe Ala Met Ala Trp
        35                  40                  45

Trp His Thr Leu Cys Ala Glu Gly Gly Asp Gln Phe Gly Gly Gly Thr
    50                  55                  60

Lys Lys Phe Pro Trp Asn Glu Gly Ala Asn Ala Leu Glu Ile Ala Lys
65                  70                  75                  80

His Lys Ala Asp Ala Gly Phe Glu Ile Met Gln Lys Leu Gly Ile Pro
                85                  90                  95

Tyr Phe Cys Phe His Asp Val Asp Leu Ile Ala Glu Gly Glu Ser Val
            100                 105                 110

Glu Glu Tyr Glu Ala Asn Leu Ala Ala Ile Thr Asp Tyr Leu Lys Gln
        115                 120                 125

Lys Met Asp Glu Thr Gly Ile Lys Leu Leu Trp Ser Thr Ala Asn Val
    130                 135                 140

Phe Ser Asn Pro Arg Tyr Met Asn Gly Ala Ser Thr Asn Pro Asp Phe
145                 150                 155                 160

Asp Val Val Ala Arg Ala Ile Val Gln Ile Lys Asn Ala Ile Asp Ala
                165                 170                 175

Gly Ile Lys Leu Gly Ala Glu Asn Tyr Val Phe Trp Gly Gly Arg Glu
            180                 185                 190

Gly Tyr Met Ser Leu Leu Asn Thr Asp Gln Arg Arg Glu Lys Glu His
        195                 200                 205

Met Ala Thr Met Leu Arg Met Ala Arg Asp Tyr Ala Arg Ser Lys Gly
    210                 215                 220

Phe Lys Gly Thr Phe Leu Ile Glu Pro Lys Pro Cys Glu Pro Ser Lys
225                 230                 235                 240

His Gln Tyr Asp Val Asp Thr Glu Thr Val Ile Gly Phe Leu Lys Ala
                245                 250                 255

His Gly Leu Asp Lys Asp Phe Lys Val Asn Ile Glu Val Asn His Ala
            260                 265                 270

Thr Leu Ala Gly His Thr Phe Glu His Glu Leu Ala Cys Ala Val Asp
        275                 280                 285

Ala Gly Met Leu Gly Ser Ile Asp Ala Asn Arg Gly Asp Ala Gln Asn
    290                 295                 300

Gly Trp Asp Thr Asp Gln Phe Pro Ile Asp Asn Phe Glu Leu Thr Gln
305                 310                 315                 320

Ala Phe Met Gln Ile Val Arg Asn Gly Gly Phe Gly Thr Gly Gly Thr
                325                 330                 335

Asn Phe Asp Ala Lys Thr Arg Arg Asn Ser Thr Asp Leu Glu Asp Ile
            340                 345                 350

Phe Ile Ala His Ile Ser Gly Met Asp Ala Cys Ala Arg Ala Leu Leu
        355                 360                 365

Asn Ala Val Glu Ile Leu Glu Lys Ser Pro Ile Pro Ala Met Leu Lys
```

-continued

```
    370                 375                 380

Glu Arg Tyr Ala Ser Phe Asp Gly Gly Ile Gly Lys Asp Phe Glu Glu
385                 390                 395                 400

Gly Lys Leu Thr Phe Glu Gln Val Tyr Glu Tyr Gly Lys Lys Val Gly
                405                 410                 415

Glu Pro Lys Gln Thr Ser Gly Lys Gln Glu Leu Tyr Glu Thr Ile Val
            420                 425                 430

Ala Leu Tyr Ala Lys
        435


<210> SEQ ID NO 69
<211> LENGTH: 1314
<212> TYPE: DNA
<213> ORGANISM: Unknown
<220> FEATURE:
<223> OTHER INFORMATION: Obtained from environmental sample

<400> SEQUENCE: 69

atgaaagagt atttccctga gatcggtaag atccaatttg aaggcccgga gtccaagaac     60

ccgatggcgt ttcactacta tgacgcagag cgcgtagtag ccggtaaaac aatgaaagaa    120

tggatgcgtt tcgccatggc atggtggcac accctctgtg cagaaggcgg cgaccagttc    180

ggaggaggaa cgaagcattt cccgtggaat gaaggcgcta acgctttgga gatcgccaaa    240

cacaaagccg atgcgggatt cgagatcatg cagaaactcg gcatccccta tttctgtttc    300

catgacgtgg atctcatcgc cgagggcgat tcggtggagg agtacgaagc taaccccgct    360

gccatcaccg attacctcaa acagaaaatg gacgagaccg gcatcaaact gctgtggtcc    420

acggcgaacg tcttcagcaa cccccgttac atgaacggtg cgagcacgaa cccggatttc    480

gatgtagtgg cacgcgctat cgtacaaatc aagaacgcta tcgacgccgg tatcaaactc    540

ggagcagaga actatgtctt ctggggcggt cgcgagggct atatgtcgct cctcaacacc    600

gaccagcgtc gcgagaaaga gcatatggct actatgctcc gtatggcgcg tgactacgcg    660

cgtgccaaag gattcaaggg caccttcctc atcgaaccca aaccatgtga gccgtccaaa    720

catcagtacg atgtggacac agagactgtc atcggtttcc tcaaagcgca tggactcgac    780

aaggatttca aagtcaacat cgaggtcaac cacgccaccc tcgcaggtca cacgttcgaa    840

cacgaactgg cttgcgctgt agatgccggc atgctcggtt cgattgacgc caaccgcggt    900

gacgcccaga acggatggga cactgaccag ttccctattg ataacttcga actcacacag    960

gctttcatgc agatcgtccg caacggcggt ttcggaacag gcggtacgaa cttcgacgcc   1020

aagacacgcc gtaactccac cgacttggag gacatcttca tcgcccatat cagcggcatg   1080

gacgcttgtg tccgtgcgtt gctcaacgcc atcgaaatcc tcgagaagag cccgatcccg   1140

gctatgctca aagagcgtta cgcttccttt gacggcggca tcggaaagga ctttgaggat   1200

ggtaaactga ctttcgagca ggtctatgag tacggcaaga aggtcggaga acccaaacag   1260

accagcggca aacaggagct ctacgaaacc atcgtcgccc tctatgccaa gtaa         1314


<210> SEQ ID NO 70
<211> LENGTH: 437
<212> TYPE: PRT
<213> ORGANISM: Unknown
<220> FEATURE:
<223> OTHER INFORMATION: Obtained from environmental sample

<400> SEQUENCE: 70

Met Lys Glu Tyr Phe Pro Glu Ile Gly Lys Ile Gln Phe Glu Gly Pro
```

-continued

```
1               5                   10                  15

Glu Ser Lys Asn Pro Met Ala Phe His Tyr Tyr Asp Ala Glu Arg Val
            20                  25                  30

Val Ala Gly Lys Thr Met Lys Glu Trp Met Arg Phe Ala Met Ala Trp
        35                  40                  45

Trp His Thr Leu Cys Ala Glu Gly Gly Asp Gln Phe Gly Gly Gly Thr
    50                  55                  60

Lys His Phe Pro Trp Asn Glu Gly Ala Asn Ala Leu Glu Ile Ala Lys
65                  70                  75                  80

His Lys Ala Asp Ala Gly Phe Glu Ile Met Gln Lys Leu Gly Ile Pro
                85                  90                  95

Tyr Phe Cys Phe His Asp Val Asp Leu Ile Ala Glu Gly Asp Ser Val
            100                 105                 110

Glu Glu Tyr Glu Ala Asn Pro Ala Ala Ile Thr Asp Tyr Leu Lys Gln
        115                 120                 125

Lys Met Asp Glu Thr Gly Ile Lys Leu Leu Trp Ser Thr Ala Asn Val
    130                 135                 140

Phe Ser Asn Pro Arg Tyr Met Asn Gly Ala Ser Thr Asn Pro Asp Phe
145                 150                 155                 160

Asp Val Val Ala Arg Ala Ile Val Gln Ile Lys Asn Ala Ile Asp Ala
                165                 170                 175

Gly Ile Lys Leu Gly Ala Glu Asn Tyr Val Phe Trp Gly Gly Arg Glu
            180                 185                 190

Gly Tyr Met Ser Leu Leu Asn Thr Asp Gln Arg Arg Glu Lys Glu His
        195                 200                 205

Met Ala Thr Met Leu Arg Met Ala Arg Asp Tyr Ala Arg Ala Lys Gly
    210                 215                 220

Phe Lys Gly Thr Phe Leu Ile Glu Pro Lys Pro Cys Glu Pro Ser Lys
225                 230                 235                 240

His Gln Tyr Asp Val Asp Thr Glu Thr Val Ile Gly Phe Leu Lys Ala
                245                 250                 255

His Gly Leu Asp Lys Asp Phe Lys Val Asn Ile Glu Val Asn His Ala
            260                 265                 270

Thr Leu Ala Gly His Thr Phe Glu His Glu Leu Ala Cys Ala Val Asp
        275                 280                 285

Ala Gly Met Leu Gly Ser Ile Asp Ala Asn Arg Gly Asp Ala Gln Asn
    290                 295                 300

Gly Trp Asp Thr Asp Gln Phe Pro Ile Asp Asn Phe Glu Leu Thr Gln
305                 310                 315                 320

Ala Phe Met Gln Ile Val Arg Asn Gly Gly Phe Gly Thr Gly Gly Thr
                325                 330                 335

Asn Phe Asp Ala Lys Thr Arg Arg Asn Ser Thr Asp Leu Glu Asp Ile
            340                 345                 350

Phe Ile Ala His Ile Ser Gly Met Asp Ala Cys Val Arg Ala Leu Leu
        355                 360                 365

Asn Ala Ile Glu Ile Leu Glu Lys Ser Pro Ile Pro Ala Met Leu Lys
    370                 375                 380

Glu Arg Tyr Ala Ser Phe Asp Gly Gly Ile Gly Lys Asp Phe Glu Asp
385                 390                 395                 400

Gly Lys Leu Thr Phe Glu Gln Val Tyr Glu Tyr Gly Lys Lys Val Gly
                405                 410                 415

Glu Pro Lys Gln Thr Ser Gly Lys Gln Glu Leu Tyr Glu Thr Ile Val
            420                 425                 430
```

Ala Leu Tyr Ala Lys
435

<210> SEQ ID NO 71
<211> LENGTH: 1314
<212> TYPE: DNA
<213> ORGANISM: Unknown
<220> FEATURE:
<223> OTHER INFORMATION: Obtained from environmental sample

<400> SEQUENCE: 71
atgaaagagt atttccctga gatcggaaag atccaattcg aaggcccgga gtccaagaat 60
cctatggcat ttcactacta tgacgcagag cgtgtagtag ccggtaaaac aatgaaagag 120
tggatgcgtt tcgctttggc atggtggcac acgctctgcg cagaaggcgg cgaccagttc 180
ggaggcggca cgaagcattt cccttggaat gaaggtgcaa acgctttgga gatcgccaag 240
cacaaagccg atgcaggctt cgagatcatg cagaaactcg gcatccccta tttctgtttc 300
catgacgtgg atctgatcgc cgagggcggt tcggtagaag agtatgaagc taatttaacg 360
gctatcaccg attacctcaa acagaaaatg gacgagaccg gcatcaaact gctgtggtcc 420
actgcgaacg tgttcggtaa cgcacgttat atgaacggcg cgagcacgaa ccccgatttc 480
gatgtagtgg cacgcgctat cgtgcagatc aagaacgcta tcgacgccgg catcaaactg 540
ggcgcagaga actacgtctt ctggggcggt cgcgagggat atatgtcgct cctgaacacc 600
gaccagaagc gtgagaaaga gcatatggct accatgctcc gtatggcgcg tgactacgcg 660
cgttccaaag gattcaaagg tacgttcctc atcgagccca aaccgtgtga gccgtccaaa 720
catcagtacg acgtggacac tgagaccgtc atcggtttcc tcaaagccca tggtctcggc 780
aaggatttca aagtgaacat cgaggtgaat cacgccaccc tcgcagggca cacgttcgaa 840
cacgaactgg cttgcgccgt agatgccggc atgctcggtt cgatcgacgc caaccgcggt 900
gacgcacaaa acggatggga caccgaccag ttccctattg ataatttcga actcacccag 960
gcattcatgc agatcgtccg caacggcggt ttcggaacag gcggtacgaa cttcgacgcc 1020
aagacacgcc gtaattccac cgacttggag gacatcttca tcgcccatat cagcggcatg 1080
gacgcttgtg cccgtgcgtt gctcaatgct gtcgaaatcc ttgaaaagag cccgatcccg 1140
gcgatgctca aagagcgtta cgcctccttt gacagcggta tgggtaagga ctttgaggag 1200
ggcaagctga ccttcgagca ggtctatgag tacggcaaac aggtcggcga acccaaacag 1260
accagcggca agcaggagct ctacgaaacc atcgtcgccc tctatgccaa atag 1314

<210> SEQ ID NO 72
<211> LENGTH: 437
<212> TYPE: PRT
<213> ORGANISM: Unknown
<220> FEATURE:
<223> OTHER INFORMATION: Obtained from environmental sample

<400> SEQUENCE: 72

Met Lys Glu Tyr Phe Pro Glu Ile Gly Lys Ile Gln Phe Glu Gly Pro
1 5 10 15

Glu Ser Lys Asn Pro Met Ala Phe His Tyr Tyr Asp Ala Glu Arg Val
20 25 30

Val Ala Gly Lys Thr Met Lys Glu Trp Met Arg Phe Ala Leu Ala Trp
35 40 45

Trp His Thr Leu Cys Ala Glu Gly Gly Asp Gln Phe Gly Gly Gly Thr
50 55 60

```
Lys His Phe Pro Trp Asn Glu Gly Ala Asn Ala Leu Glu Ile Ala Lys
65                  70                  75                  80

His Lys Ala Asp Ala Gly Phe Glu Ile Met Gln Lys Leu Gly Ile Pro
                85                  90                  95

Tyr Phe Cys Phe His Asp Val Asp Leu Ile Ala Glu Gly Gly Ser Val
            100                 105                 110

Glu Glu Tyr Glu Ala Asn Leu Thr Ala Ile Thr Asp Tyr Leu Lys Gln
        115                 120                 125

Lys Met Asp Glu Thr Gly Ile Lys Leu Leu Trp Ser Thr Ala Asn Val
    130                 135                 140

Phe Gly Asn Ala Arg Tyr Met Asn Gly Ala Ser Thr Asn Pro Asp Phe
145                 150                 155                 160

Asp Val Val Ala Arg Ala Ile Val Gln Ile Lys Asn Ala Ile Asp Ala
                165                 170                 175

Gly Ile Lys Leu Gly Ala Glu Asn Tyr Val Phe Trp Gly Gly Arg Glu
            180                 185                 190

Gly Tyr Met Ser Leu Leu Asn Thr Asp Gln Lys Arg Glu Lys Glu His
        195                 200                 205

Met Ala Thr Met Leu Arg Met Ala Arg Asp Tyr Ala Arg Ser Lys Gly
    210                 215                 220

Phe Lys Gly Thr Phe Leu Ile Glu Pro Lys Pro Cys Glu Pro Ser Lys
225                 230                 235                 240

His Gln Tyr Asp Val Asp Thr Glu Thr Val Ile Gly Phe Leu Lys Ala
                245                 250                 255

His Gly Leu Gly Lys Asp Phe Lys Val Asn Ile Glu Val Asn His Ala
            260                 265                 270

Thr Leu Ala Gly His Thr Phe Glu His Glu Leu Ala Cys Ala Val Asp
        275                 280                 285

Ala Gly Met Leu Gly Ser Ile Asp Ala Asn Arg Gly Asp Ala Gln Asn
    290                 295                 300

Gly Trp Asp Thr Asp Gln Phe Pro Ile Asp Asn Phe Glu Leu Thr Gln
305                 310                 315                 320

Ala Phe Met Gln Ile Val Arg Asn Gly Gly Phe Gly Thr Gly Gly Thr
                325                 330                 335

Asn Phe Asp Ala Lys Thr Arg Arg Asn Ser Thr Asp Leu Glu Asp Ile
            340                 345                 350

Phe Ile Ala His Ile Ser Gly Met Asp Ala Cys Ala Arg Ala Leu Leu
        355                 360                 365

Asn Ala Val Glu Ile Leu Glu Lys Ser Pro Ile Pro Ala Met Leu Lys
    370                 375                 380

Glu Arg Tyr Ala Ser Phe Asp Ser Gly Met Gly Lys Asp Phe Glu Glu
385                 390                 395                 400

Gly Lys Leu Thr Phe Glu Gln Val Tyr Glu Tyr Gly Lys Gln Val Gly
                405                 410                 415

Glu Pro Lys Gln Thr Ser Gly Lys Gln Glu Leu Tyr Glu Thr Ile Val
            420                 425                 430

Ala Leu Tyr Ala Lys
        435
```

<210> SEQ ID NO 73
<211> LENGTH: 1314
<212> TYPE: DNA
<213> ORGANISM: Unknown
<220> FEATURE:

<223> OTHER INFORMATION: Obtained from environmental sample

<400> SEQUENCE: 73

```
atgaaagagt attttccaca aatcggcaag atcccatttg agggaccaga gtcaaagaac     60
ccaatggcat tccactacta tgacgcagag cgcgtagttg ccggtaagac aatgaaggaa    120
tggatgcgtt tcgctatggc ctggtggcac actctctgtg ctgagggtag cgatcagttc    180
ggccctggta caaagaagtt cccttggaac gagggcgaga cagcccttga gcgcgctaag    240
cacaaggcag atgctggctt cgaggttatg cagaagctcg gcatcccata tttctgcttc    300
cacgatgtag accttatcga cgagggtgct aacgtggctg agtatgaggc aaacctcgct    360
gctatcactg actacctgaa ggagaagatg gaggagactg gcgtaaagct cctctggtct    420
acagccaacg tgttcggtaa cgctcgctat atgaacggtg cttctacaaa tcctgacttc    480
gacgttgtgg ctcgtgccat cgtacagatt aagaacgcta tcgacgctgg tatcaagctt    540
ggtgctgaga actacgtgtt ctggggcggc cgcgagggct acatgagcct tctgaacact    600
gaccagaagc gcgagaagga gcacatggca actatgctcg gcatggctcg cgactatgcc    660
cgcgctaagg gattcaccgg taccttcctc attgagccaa agccaatgga gccaacaaag    720
catcagtatg atgttgacac agagaccgtt atcggtttcc tcaaggctca cggtctggac    780
aaggacttca aggtgaacat cgaggtgaac cacgctactc tcgccggtca caccttcgag    840
cacgagctcg cttgcgctgt tgacgctggt atgctcggtt ctatcgacgc taaccgcggt    900
gacgctcaga acggatggga taccgaccag ttcccaatcg acaacttcga gctgacacag    960
gcttggatgc agattgttcg caatggcggt cttggcacag gtggtaccaa cttcgacgca   1020
aagacccgtc gtaactctac cgacctcgag gacatcttca tcgctcacat ctccggtatg   1080
gacgcttgtg cacgcgctct cctcaacgca gtagagatac tcgagaactc tccaatccca   1140
acaatgctga aggaccgcta tgcaagcttc gactcaggta tgggtaagga cttcgaggac   1200
ggcaagctca cacttgagca ggtttatgag tatggtaaga aggtcgacga gccaaagcag   1260
acctctggta agcaggaact ctatgagacc atcgttgctc tctatgcaaa ataa         1314
```

<210> SEQ ID NO 74
<211> LENGTH: 437
<212> TYPE: PRT
<213> ORGANISM: Unknown
<220> FEATURE:
<223> OTHER INFORMATION: Obtained from environmental sample

<400> SEQUENCE: 74

```
Met Lys Glu Tyr Phe Pro Gln Ile Gly Lys Ile Pro Phe Glu Gly Pro
1               5                   10                  15

Glu Ser Lys Asn Pro Met Ala Phe His Tyr Tyr Asp Ala Glu Arg Val
            20                  25                  30

Val Ala Gly Lys Thr Met Lys Glu Trp Met Arg Phe Ala Met Ala Trp
        35                  40                  45

Trp His Thr Leu Cys Ala Glu Gly Ser Asp Gln Phe Gly Pro Gly Thr
    50                  55                  60

Lys Lys Phe Pro Trp Asn Glu Gly Glu Thr Ala Leu Glu Arg Ala Lys
65                  70                  75                  80

His Lys Ala Asp Ala Gly Phe Glu Val Met Gln Lys Leu Gly Ile Pro
                85                  90                  95

Tyr Phe Cys Phe His Asp Val Asp Leu Ile Asp Glu Gly Ala Asn Val
            100                 105                 110
```

-continued

```
Ala Glu Tyr Glu Ala Asn Leu Ala Ala Ile Thr Asp Tyr Leu Lys Glu
        115                 120                 125

Lys Met Glu Glu Thr Gly Val Lys Leu Leu Trp Ser Thr Ala Asn Val
    130                 135                 140

Phe Gly Asn Ala Arg Tyr Met Asn Gly Ala Ser Thr Asn Pro Asp Phe
145                 150                 155                 160

Asp Val Val Ala Arg Ala Ile Val Gln Ile Lys Asn Ala Ile Asp Ala
                165                 170                 175

Gly Ile Lys Leu Gly Ala Glu Asn Tyr Val Phe Trp Gly Gly Arg Glu
            180                 185                 190

Gly Tyr Met Ser Leu Leu Asn Thr Asp Gln Lys Arg Glu Lys Glu His
        195                 200                 205

Met Ala Thr Met Leu Gly Met Ala Arg Asp Tyr Ala Arg Ala Lys Gly
    210                 215                 220

Phe Thr Gly Thr Phe Leu Ile Glu Pro Lys Pro Met Glu Pro Thr Lys
225                 230                 235                 240

His Gln Tyr Asp Val Asp Thr Glu Thr Val Ile Gly Phe Leu Lys Ala
                245                 250                 255

His Gly Leu Asp Lys Asp Phe Lys Val Asn Ile Glu Val Asn His Ala
            260                 265                 270

Thr Leu Ala Gly His Thr Phe Glu His Glu Leu Ala Cys Ala Val Asp
        275                 280                 285

Ala Gly Met Leu Gly Ser Ile Asp Ala Asn Arg Gly Asp Ala Gln Asn
    290                 295                 300

Gly Trp Asp Thr Asp Gln Phe Pro Ile Asp Asn Phe Glu Leu Thr Gln
305                 310                 315                 320

Ala Trp Met Gln Ile Val Arg Asn Gly Gly Leu Gly Thr Gly Gly Thr
                325                 330                 335

Asn Phe Asp Ala Lys Thr Arg Arg Asn Ser Thr Asp Leu Glu Asp Ile
            340                 345                 350

Phe Ile Ala His Ile Ser Gly Met Asp Ala Cys Ala Arg Ala Leu Leu
        355                 360                 365

Asn Ala Val Glu Ile Leu Glu Asn Ser Pro Ile Pro Thr Met Leu Lys
    370                 375                 380

Asp Arg Tyr Ala Ser Phe Asp Ser Gly Met Gly Lys Asp Phe Glu Asp
385                 390                 395                 400

Gly Lys Leu Thr Leu Glu Gln Val Tyr Glu Tyr Gly Lys Lys Val Asp
                405                 410                 415

Glu Pro Lys Gln Thr Ser Gly Lys Gln Glu Leu Tyr Glu Thr Ile Val
            420                 425                 430

Ala Leu Tyr Ala Lys
        435
```

<210> SEQ ID NO 75
<211> LENGTH: 1320
<212> TYPE: DNA
<213> ORGANISM: Unknown
<220> FEATURE:
<223> OTHER INFORMATION: Obtained from environmental sample

<400> SEQUENCE: 75

```
atggctaaag aatacttccc ctccatcggc aaaatccctt ttgaaggagg cgacagcaaa      60

aatcccctcg ctttccatta ttatgacgcc ggacgcgtgg ttatgggcaa gcccatgaag     120

gaatggctta aattcgccat ggcctggtgg cacacgctgg gccaggcctc cggagacccc     180
```

```
ttcggcggcc agacccgcag ctacgaatgg gacaagggcg aatgccccta ctgccgcgcc    240

aaagccaagg ccgacgccgg ttttgaaatc atgcaaaagc tgggtatcga atacttctgc    300

ttccacgatg tggaccttat cgaggattgc gatgacattg ccgaatacga agcccgcatg    360

aaggacatca cggactacct gctggaaaag atgaaggaga ccggcatcaa gaacctctgg    420

ggcaccgcca atgtcttcgg ccacaagcgc tacatgaacg gcgccggcac caatccgcag    480

ttcgatgtgg tggcccgtgc cgccgtccag atcaagaacg ccctggacgc caccatcaag    540

ctgggcggct ccaactatgt gttctggggc ggccgcgaag gctattacac cctcctcaac    600

acccagatgc agcgggaaaa agaccacctg gccaagttgc tgacggccgc ccgcgactat    660

gcccgcgcca agggcttcaa gggcaccttc ctcattgagc ccaaacccat ggaacccacc    720

aagcaccagt acgacgtgga tacggagacg gtcatcggct tcctccgtgc caacggcctg    780

gacaaggact tcaaggtgaa catcgaggtg aaccacgcca ccctggccgg ccacaccttc    840

gagcatgagc tcaccgtggc ccgcgagaac ggtttcctgg gctccatcgg tgccaaccgc    900

ggcgacgccc agaacggctg ggacacggac cagttccctg tggacccgta cgatcttacc    960

caggccatga tgcaggtgct gctgaacggc ggcttcggca acggcggcac caacttcgac   1020

gccaaactcc gccgctcctc caccgaccct gaggacatct tcatcgccca tatttccgcc   1080

atggatgcca tggcccacgc tttgcttaac gcagctgccg tgctggaaga gagccccctg   1140

tgccagatgg tcaaggagcg ttatgccagc ttcgacggcg gcctcggcaa acagttcgag   1200

gaaggcaagg ctaccctgga agacctgtac gaatacgcca aggtccaggg tgaacccgtt   1260

gtcgcctccg gcaagcagga gctttacgag actctcctga acctgtatgc cgtcaagtaa   1320
```

<210> SEQ ID NO 76
<211> LENGTH: 439
<212> TYPE: PRT
<213> ORGANISM: Unknown
<220> FEATURE:
<223> OTHER INFORMATION: Obtained from environmental sample

<400> SEQUENCE: 76

```
Met Ala Lys Glu Tyr Phe Pro Ser Ile Gly Lys Ile Pro Phe Glu Gly
1               5                   10                  15

Gly Asp Ser Lys Asn Pro Leu Ala Phe His Tyr Tyr Asp Ala Gly Arg
            20                  25                  30

Val Val Met Gly Lys Pro Met Lys Glu Trp Leu Lys Phe Ala Met Ala
        35                  40                  45

Trp Trp His Thr Leu Gly Gln Ala Ser Gly Asp Pro Phe Gly Gly Gln
    50                  55                  60

Thr Arg Ser Tyr Glu Trp Asp Lys Gly Glu Cys Pro Tyr Cys Arg Ala
65                  70                  75                  80

Lys Ala Lys Ala Asp Ala Gly Phe Glu Ile Met Gln Lys Leu Gly Ile
                85                  90                  95

Glu Tyr Phe Cys Phe His Asp Val Asp Leu Ile Glu Asp Cys Asp Asp
            100                 105                 110

Ile Ala Glu Tyr Glu Ala Arg Met Lys Asp Ile Thr Asp Tyr Leu Leu
        115                 120                 125

Glu Lys Met Lys Glu Thr Gly Ile Lys Asn Leu Trp Gly Thr Ala Asn
    130                 135                 140

Val Phe Gly His Lys Arg Tyr Met Asn Gly Ala Gly Thr Asn Pro Gln
145                 150                 155                 160

Phe Asp Val Val Ala Arg Ala Ala Val Gln Ile Lys Asn Ala Leu Asp
```

```
                165                 170                 175

Ala Thr Ile Lys Leu Gly Gly Ser Asn Tyr Val Phe Trp Gly Gly Arg
            180                 185                 190

Glu Gly Tyr Tyr Thr Leu Leu Asn Thr Gln Met Gln Arg Glu Lys Asp
        195                 200                 205

His Leu Ala Lys Leu Leu Thr Ala Ala Arg Asp Tyr Ala Arg Ala Lys
    210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Val Ile Gly Phe Leu Arg
                245                 250                 255

Ala Asn Gly Leu Asp Lys Asp Phe Lys Val Asn Ile Glu Val Asn His
            260                 265                 270

Ala Thr Leu Ala Gly His Thr Phe Glu His Glu Leu Thr Val Ala Arg
        275                 280                 285

Glu Asn Gly Phe Leu Gly Ser Ile Gly Ala Asn Arg Gly Asp Ala Gln
    290                 295                 300

Asn Gly Trp Asp Thr Asp Gln Phe Pro Val Asp Pro Tyr Asp Leu Thr
305                 310                 315                 320

Gln Ala Met Met Gln Val Leu Leu Asn Gly Gly Phe Gly Asn Gly Gly
                325                 330                 335

Thr Asn Phe Asp Ala Lys Leu Arg Arg Ser Ser Thr Asp Pro Glu Asp
            340                 345                 350

Ile Phe Ile Ala His Ile Ser Ala Met Asp Ala Met Ala His Ala Leu
        355                 360                 365

Leu Asn Ala Ala Ala Val Leu Glu Glu Ser Pro Leu Cys Gln Met Val
    370                 375                 380

Lys Glu Arg Tyr Ala Ser Phe Asp Gly Gly Leu Gly Lys Gln Phe Glu
385                 390                 395                 400

Glu Gly Lys Ala Thr Leu Glu Asp Leu Tyr Glu Tyr Ala Lys Val Gln
                405                 410                 415

Gly Glu Pro Val Val Ala Ser Gly Lys Gln Glu Leu Tyr Glu Thr Leu
            420                 425                 430

Leu Asn Leu Tyr Ala Val Lys
        435
```

<210> SEQ ID NO 77
<211> LENGTH: 1320
<212> TYPE: DNA
<213> ORGANISM: Unknown
<220> FEATURE:
<223> OTHER INFORMATION: Obtained from environmental sample

<400> SEQUENCE: 77

```
atggcaaaag agtattttcc gtttaccggt aagattcctt tcgaaggaaa ggacagtaag      60

aatgtaatgg ctttccacta ctacgagcct gagaaggtcg tgatgggaaa gaagatgaag     120

gactggctga agttcgctat ggcttggtgg catacactgg gtggcgcttc tgctgaccag     180

tttggtggtc agactcgttc atacgagtgg gacaaggctg gtgacgctgt tcagcgcgct     240

aaggataaga tggacgctgg cttcgagatc atggacaagc tgggcatcga gtacttctgc     300

ttccacgatg ttgacctcgt tgaagagggt gacaccatcg aggagtatga ggctcgcatg     360

aaggccatca ccgactacgc tcaggagaag atgaagcagt tccccaacat caagctgctc     420

tggggtaccg caaacgtatt cggtaacaag cgctatgcta acggtgcttc taccaacccc     480
```

-continued

```
gacttcgacg tagtggctcg cgccatcgtt cagatcaaga acgctattga tgctaccatc    540

aagctgggtg gtaccaacta tgtgttctgg ggtggtcgtg agggctatat gagtctgctg    600

aacaccgacc agaagcgtga gaaggagcac atggctacta tgctgaccat ggctcgcgac    660

tatgctcgcg ccaagggatt caagggtaca ttcctcattg agccgaagcc catggagccc    720

agcaagcacc agtatgatgt ggatacagag accgttatcg gcttcctgaa ggcacacaac    780

ctggacaagg acttcaaggt gaacatcgag gtgaaccacg ctacactcgc tggtcatacc    840

ttcgagcacg agctggcttg cgctgttgac gctggtatgc ttggttctat cgacgctaac    900

cgtggtgatg ctcagaacgg ttgggatacc gaccagttcc ccatcgacaa ctacgagctg    960

acacaggcta tgctcgagat catccgcaat ggtggtctgg gcaatggtgg taccaacttc   1020

gatgctaaga tccgtcgtaa cagcaccgac ctcgaggatc tcttcatcgc tcacatcagt   1080

ggtatggatg ctatggcacg cgctctgatg aacgctgctg acatccttga gaactctgag   1140

ctgcccgcaa tgaagaaggc tcgctacgca agcttcgacc agggtgttgg taaggacttc   1200

gaagatggca agctgaccct tgagcaggtt tacgagtatg gtaagaaggt gggtgagccc   1260

aagcagactt ctggtaagca ggagaagtac gagaccatcg ttgctctcta tgcaaaataa   1320
```

<210> SEQ ID NO 78
<211> LENGTH: 439
<212> TYPE: PRT
<213> ORGANISM: Unknown
<220> FEATURE:
<223> OTHER INFORMATION: Obtained from environmental sample

<400> SEQUENCE: 78

```
Met Ala Lys Glu Tyr Phe Pro Phe Thr Gly Lys Ile Pro Phe Glu Gly
1               5                   10                  15

Lys Asp Ser Lys Asn Val Met Ala Phe His Tyr Tyr Glu Pro Glu Lys
            20                  25                  30

Val Val Met Gly Lys Lys Met Lys Asp Trp Leu Lys Phe Ala Met Ala
        35                  40                  45

Trp Trp His Thr Leu Gly Gly Ala Ser Ala Asp Gln Phe Gly Gly Gln
    50                  55                  60

Thr Arg Ser Tyr Glu Trp Asp Lys Ala Gly Asp Ala Val Gln Arg Ala
65                  70                  75                  80

Lys Asp Lys Met Asp Ala Gly Phe Glu Ile Met Asp Lys Leu Gly Ile
                85                  90                  95

Glu Tyr Phe Cys Phe His Asp Val Asp Leu Val Glu Glu Gly Asp Thr
            100                 105                 110

Ile Glu Glu Tyr Glu Ala Arg Met Lys Ala Ile Thr Asp Tyr Ala Gln
        115                 120                 125

Glu Lys Met Lys Gln Phe Pro Asn Ile Lys Leu Leu Trp Gly Thr Ala
    130                 135                 140

Asn Val Phe Gly Asn Lys Arg Tyr Ala Asn Gly Ala Ser Thr Asn Pro
145                 150                 155                 160

Asp Phe Asp Val Val Ala Arg Ala Ile Val Gln Ile Lys Asn Ala Ile
                165                 170                 175

Asp Ala Thr Ile Lys Leu Gly Gly Thr Asn Tyr Val Phe Trp Gly Gly
            180                 185                 190

Arg Glu Gly Tyr Met Ser Leu Leu Asn Thr Asp Gln Lys Arg Glu Lys
        195                 200                 205

Glu His Met Ala Thr Met Leu Thr Met Ala Arg Asp Tyr Ala Arg Ala
    210                 215                 220
```

Lys Gly Phe Lys Gly Thr Phe Leu Ile Glu Pro Lys Pro Met Glu Pro
225 230 235 240

Ser Lys His Gln Tyr Asp Val Asp Thr Glu Thr Val Ile Gly Phe Leu
245 250 255

Lys Ala His Asn Leu Asp Lys Asp Phe Lys Val Asn Ile Glu Val Asn
260 265 270

His Ala Thr Leu Ala Gly His Thr Phe Glu His Glu Leu Ala Cys Ala
275 280 285

Val Asp Ala Gly Met Leu Gly Ser Ile Asp Ala Asn Arg Gly Asp Ala
290 295 300

Gln Asn Gly Trp Asp Thr Asp Gln Phe Pro Ile Asp Asn Tyr Glu Leu
305 310 315 320

Thr Gln Ala Met Leu Glu Ile Ile Arg Asn Gly Gly Leu Gly Asn Gly
325 330 335

Gly Thr Asn Phe Asp Ala Lys Ile Arg Arg Asn Ser Thr Asp Leu Glu
340 345 350

Asp Leu Phe Ile Ala His Ile Ser Gly Met Asp Ala Met Ala Arg Ala
355 360 365

Leu Met Asn Ala Ala Asp Ile Leu Glu Asn Ser Glu Leu Pro Ala Met
370 375 380

Lys Lys Ala Arg Tyr Ala Ser Phe Asp Gln Gly Val Gly Lys Asp Phe
385 390 395 400

Glu Asp Gly Lys Leu Thr Leu Glu Gln Val Tyr Glu Tyr Gly Lys Lys
405 410 415

Val Gly Glu Pro Lys Gln Thr Ser Gly Lys Gln Glu Lys Tyr Glu Thr
420 425 430

Ile Val Ala Leu Tyr Ala Lys
435

<210> SEQ ID NO 79
<211> LENGTH: 1320
<212> TYPE: DNA
<213> ORGANISM: Unknown
<220> FEATURE:
<223> OTHER INFORMATION: Obtained from environmental sample

<400> SEQUENCE: 79
atggcaaaag agtattttcc gtttaccggt aagattcctt tcgaaggaaa agagagcaag 60
aacgtaatgg ctttccatta ctatgagcct gaaaaggtgg tcatgggcaa gaaaatgaag 120
gattggctga aattcgccat ggcttggtgg cacaccctcg gtggagccag cgccgaccag 180
ttcggtggac agacccgcag ctatgagtgg gacaaggccg aggatgccgt acagcgtgct 240
aaggacaaga tggacgccgg cttcgagatc atggacaaac tgggcatcga gtatttctgc 300
ttccacgatg tcgacctcgt cgacgagggt gctaccgttg aggagtatga ggctcgcatg 360
aaagccatca ccgactatgc ccaggtcaag atgaaggaat atcccaacat caaactgctc 420
tggggcaccg ccaacgtgtt cggcaacaag cgttatgcca acggcgcttc caccaacccc 480
gacttcgacg tggtggcacg cgctatcgtt cagatcaaga atgccatcga cgctaccatc 540
aagctcggcg gtcagaacta cgtgttctgg ggcggacgcg agggctacat gagcctgctc 600
aataccgatc agaaacgtga gaaggaacac atggccacca tgctcaccat ggcgcgcgac 660
tatgctcgca gcaagggatt caagggcacc ttcctcatcg aacccaaacc catggagcct 720
tccaagcacc agtatgatgt cgacaccgag acggtcatcg gcttcctccg cgcccacaac 780

```
ctcgacaagg acttcaaggt gaacatcgag gtcaaccacg ccacgctcgc cggccacacc    840

ttcgagcacg aactggcttg cgccgtcgac gccggcatgc tcggcagcat cgacgccaac    900

cgcggcgacg cacagaacgg ctgggatacc gaccagttcc ccatcgacaa ctacgaactg    960

acacaggcca tgctggagat catccgcaat ggcggcctcg gcaatggtgg taccaacttc   1020

gacgccaaga tccgtcgtaa cagcaccgac ctcgaagatc tcttcatcgc tcacatcagc   1080

ggtatggatg ccatggctcg cgcgctgctc aacgccgccg ccatcctcga ggagagcgaa   1140

ctgcccgcca tgaagaaggc ccgctacgct tccttcgacg aaggtatcgg caaggacttc   1200

gaagacggca aactcaccct cgagcaggtt tacgagtacg gcaagaaggt aggcgagccc   1260

aagcagacct ccggcaagca agagaagtac gagaccatcg tggctctcta cagcaaataa   1320
```

<210> SEQ ID NO 80
<211> LENGTH: 439
<212> TYPE: PRT
<213> ORGANISM: Unknown
<220> FEATURE:
<223> OTHER INFORMATION: Obtained from environmental sample

<400> SEQUENCE: 80

```
Met Ala Lys Glu Tyr Phe Pro Phe Thr Gly Lys Ile Pro Phe Glu Gly
1               5                   10                  15

Lys Glu Ser Lys Asn Val Met Ala Phe His Tyr Tyr Glu Pro Glu Lys
            20                  25                  30

Val Val Met Gly Lys Lys Met Lys Asp Trp Leu Lys Phe Ala Met Ala
        35                  40                  45

Trp Trp His Thr Leu Gly Gly Ala Ser Ala Asp Gln Phe Gly Gly Gln
    50                  55                  60

Thr Arg Ser Tyr Glu Trp Asp Lys Ala Glu Asp Ala Val Gln Arg Ala
65                  70                  75                  80

Lys Asp Lys Met Asp Ala Gly Phe Glu Ile Met Asp Lys Leu Gly Ile
                85                  90                  95

Glu Tyr Phe Cys Phe His Asp Val Asp Leu Val Asp Glu Gly Ala Thr
            100                 105                 110

Val Glu Glu Tyr Glu Ala Arg Met Lys Ala Ile Thr Asp Tyr Ala Gln
        115                 120                 125

Val Lys Met Lys Glu Tyr Pro Asn Ile Lys Leu Leu Trp Gly Thr Ala
    130                 135                 140

Asn Val Phe Gly Asn Lys Arg Tyr Ala Asn Gly Ala Ser Thr Asn Pro
145                 150                 155                 160

Asp Phe Asp Val Val Ala Arg Ala Ile Val Gln Ile Lys Asn Ala Ile
                165                 170                 175

Asp Ala Thr Ile Lys Leu Gly Gly Gln Asn Tyr Val Phe Trp Gly Gly
            180                 185                 190

Arg Glu Gly Tyr Met Ser Leu Leu Asn Thr Asp Gln Lys Arg Glu Lys
        195                 200                 205

Glu His Met Ala Thr Met Leu Thr Met Ala Arg Asp Tyr Ala Arg Ser
    210                 215                 220

Lys Gly Phe Lys Gly Thr Phe Leu Ile Glu Pro Lys Pro Met Glu Pro
225                 230                 235                 240

Ser Lys His Gln Tyr Asp Val Asp Thr Glu Thr Val Ile Gly Phe Leu
                245                 250                 255

Arg Ala His Asn Leu Asp Lys Asp Phe Lys Val Asn Ile Glu Val Asn
            260                 265                 270
```

-continued

```
His Ala Thr Leu Ala Gly His Thr Phe Glu His Glu Leu Ala Cys Ala
        275                 280                 285

Val Asp Ala Gly Met Leu Gly Ser Ile Asp Ala Asn Arg Gly Asp Ala
    290                 295                 300

Gln Asn Gly Trp Asp Thr Asp Gln Phe Pro Ile Asp Asn Tyr Glu Leu
305                 310                 315                 320

Thr Gln Ala Met Leu Glu Ile Ile Arg Asn Gly Gly Leu Gly Asn Gly
                325                 330                 335

Gly Thr Asn Phe Asp Ala Lys Ile Arg Arg Asn Ser Thr Asp Leu Glu
            340                 345                 350

Asp Leu Phe Ile Ala His Ile Ser Gly Met Asp Ala Met Ala Arg Ala
        355                 360                 365

Leu Leu Asn Ala Ala Ala Ile Leu Glu Glu Ser Glu Leu Pro Ala Met
    370                 375                 380

Lys Lys Ala Arg Tyr Ala Ser Phe Asp Glu Gly Ile Gly Lys Asp Phe
385                 390                 395                 400

Glu Asp Gly Lys Leu Thr Leu Glu Gln Val Tyr Glu Tyr Gly Lys Lys
                405                 410                 415

Val Gly Glu Pro Lys Gln Thr Ser Gly Lys Gln Glu Lys Tyr Glu Thr
            420                 425                 430

Ile Val Ala Leu Tyr Ser Lys
        435
```

<210> SEQ ID NO 81
<211> LENGTH: 1314
<212> TYPE: DNA
<213> ORGANISM: Unknown
<220> FEATURE:
<223> OTHER INFORMATION: Obtained from environmental sample

<400> SEQUENCE: 81

```
atgaaagagt atttcccgca aattggaaag attcccttcg agggaccaga gagcaagagt      60

ccattggcgt tccattatta tgagccggat cgcatggtgc tcggaaagag gatggaggat     120

tggctgaaat tcgccatggc atggtggcac acccttggcc aggccagcgg cgaccagttc     180

ggcggacaga cacgtgagta cgagtgggat aaggctggag atccgataca aagggcaaag     240

gataagatgg acgccggatt cgagatcatg gagaaattgg gtatcaagta cttctgcttc     300

catgatgtgg atctcgtcga ggaagctccc accatcgccg aatatgagga gcgtatgagg     360

atcatcaccg actatgcgct cgagaagatg aaagccactg gcatcaaact cctttggggt     420

acagccaatg ttttcggaca taagagatat atgaatgggg ccgccaccaa cccggagttc     480

ggtgttgtcg ccagggctgc tgtccagatc aagaacgcga tcgacgccac catcaagctg     540

ggaggaacaa actatgtgtt ctggggtggc cgcgagggct acatgagcct gctcaacacc     600

cagatgcaga gggagaagga ccatctcgcc aatatgctca aggctgctcg tgactatgct     660

cgcgccaagg gattcaaggg cacattcctc atcgagccga agccgatgga acctactaag     720

catcagtacg atgtcgacac tgagaccgtg atcggcttcc tccgcgcaaa cggtcttgac     780

aaggatttca aggtcaacat cgaggtcaat cacgccactc ttgcgggtca cactttcgag     840

catgagctcg ccgtggctgt cgacaatggt ctccttggct caatcgatgc gaacagggga     900

gattatcaga acggttggga caccgaccag ttccctgttg atctctttga tttgacccag     960

gccatgctcc agatcatccg taacggaggc ctcggtaatg gtggatccaa cttcgacgcc    1020

aagcttcgcc gtaactccac tgatcctgag gatatattca ttgcccatat ttgcggtatg    1080
```

-continued

```
gacgctatgg ccagggctct ccttgccgcc gccgcgatcg tggaggagtc tcctatcccg   1140

gctatggtca aagagcgtta cgcatccttc gacgaaggtg agggcaagag attcgaggat   1200

ggtaagatga gtctggagga acttgttgat tacgcgaaga ctcacggaga gcccgcccag   1260

aagagtggca aacaggagct ctacgaaacc cttgtcaaca tgtacatcaa ataa         1314
```

<210> SEQ ID NO 82
<211> LENGTH: 437
<212> TYPE: PRT
<213> ORGANISM: Unknown
<220> FEATURE:
<223> OTHER INFORMATION: Obtained from environmental sample

<400> SEQUENCE: 82

```
Met Lys Glu Tyr Phe Pro Gln Ile Gly Lys Ile Pro Phe Glu Gly Pro
1               5                   10                  15

Glu Ser Lys Ser Pro Leu Ala Phe His Tyr Tyr Glu Pro Asp Arg Met
            20                  25                  30

Val Leu Gly Lys Arg Met Glu Asp Trp Leu Lys Phe Ala Met Ala Trp
        35                  40                  45

Trp His Thr Leu Gly Gln Ala Ser Gly Asp Gln Phe Gly Gly Gln Thr
    50                  55                  60

Arg Glu Tyr Glu Trp Asp Lys Ala Gly Asp Pro Ile Gln Arg Ala Lys
65                  70                  75                  80

Asp Lys Met Asp Ala Gly Phe Glu Ile Met Glu Lys Leu Gly Ile Lys
                85                  90                  95

Tyr Phe Cys Phe His Asp Val Asp Leu Val Glu Glu Ala Pro Thr Ile
            100                 105                 110

Ala Glu Tyr Glu Glu Arg Met Arg Ile Ile Thr Asp Tyr Ala Leu Glu
        115                 120                 125

Lys Met Lys Ala Thr Gly Ile Lys Leu Leu Trp Gly Thr Ala Asn Val
    130                 135                 140

Phe Gly His Lys Arg Tyr Met Asn Gly Ala Ala Thr Asn Pro Glu Phe
145                 150                 155                 160

Gly Val Val Ala Arg Ala Ala Val Gln Ile Lys Asn Ala Ile Asp Ala
                165                 170                 175

Thr Ile Lys Leu Gly Gly Thr Asn Tyr Val Phe Trp Gly Gly Arg Glu
            180                 185                 190

Gly Tyr Met Ser Leu Leu Asn Thr Gln Met Gln Arg Glu Lys Asp His
        195                 200                 205

Leu Ala Asn Met Leu Lys Ala Ala Arg Asp Tyr Ala Arg Ala Lys Gly
    210                 215                 220

Phe Lys Gly Thr Phe Leu Ile Glu Pro Lys Pro Met Glu Pro Thr Lys
225                 230                 235                 240

His Gln Tyr Asp Val Asp Thr Glu Thr Val Ile Gly Phe Leu Arg Ala
                245                 250                 255

Asn Gly Leu Asp Lys Asp Phe Lys Val Asn Ile Glu Val Asn His Ala
            260                 265                 270

Thr Leu Ala Gly His Thr Phe Glu His Glu Leu Ala Val Ala Val Asp
        275                 280                 285

Asn Gly Leu Leu Gly Ser Ile Asp Ala Asn Arg Gly Asp Tyr Gln Asn
    290                 295                 300

Gly Trp Asp Thr Asp Gln Phe Pro Val Asp Leu Phe Asp Leu Thr Gln
305                 310                 315                 320

Ala Met Leu Gln Ile Ile Arg Asn Gly Gly Leu Gly Asn Gly Gly Ser
```

```
                325                 330                 335

Asn Phe Asp Ala Lys Leu Arg Arg Asn Ser Thr Asp Pro Glu Asp Ile
            340                 345                 350

Phe Ile Ala His Ile Cys Gly Met Asp Ala Met Ala Arg Ala Leu Leu
        355                 360                 365

Ala Ala Ala Ala Ile Val Glu Glu Ser Pro Ile Pro Ala Met Val Lys
    370                 375                 380

Glu Arg Tyr Ala Ser Phe Asp Glu Gly Glu Gly Lys Arg Phe Glu Asp
385                 390                 395                 400

Gly Lys Met Ser Leu Glu Glu Leu Val Asp Tyr Ala Lys Thr His Gly
                405                 410                 415

Glu Pro Ala Gln Lys Ser Gly Lys Gln Glu Leu Tyr Glu Thr Leu Val
            420                 425                 430

Asn Met Tyr Ile Lys
        435


<210> SEQ ID NO 83
<211> LENGTH: 1320
<212> TYPE: DNA
<213> ORGANISM: Unknown
<220> FEATURE:
<223> OTHER INFORMATION: Obtained from environmental sample

<400> SEQUENCE: 83

atggcaaaag agtattttcc gtttaccggt aagattcctt tcgagggaaa ggacagtaag      60

aatgtaatgg cgttccacta ctacgagccc gagcgcgtgg taatgggcaa gaagatgaag     120

gagtggctga agtttgccat ggcctggtgg cacacgctgg gtggagccag tgccgaccag     180

tttggcggac agacccgcag ctacgagtgg gacaaggctg aagacgccgt gcagcgtgcc     240

aaggacaaga tggatgccgg cttcgagatc atggacaagc tgggcatcga gtatttctgc     300

ttccatgatg tcgatctcgt tgacgagggt gccactgtcg aggagtatga ggctcgcatg     360

caggccatca ccgactatgc gcaggagaag atgaagcagt atcctgccat caagctgctg     420

tggggtacgg ccaatgtctt tggcaacaag cgttatgcca acggtgcctc taccaatccc     480

gacttcgatg tggtggcccg cgccatcgtg cagattaaga atgccattga tgccaccatc     540

aagctgggcg gcagcaacta tgtgttctgg ggcggtcgcg agggctacat gtcgctgctc     600

aacaccgacc agaagcgtga gaaggaacac atggcccgga tgctgaccat ggcccgcgac     660

tatgcccgct cgaagggctt caagggcaac ttcctgattg agcccaagcc catggagccg     720

tcgaagcatc agtacgacgt ggacaccgag acggttatcg gattcctccg cgcacatggc     780

cttgacaagg acttcaaggt gaacatcgag gtgaaccatg ccacgctggc cggtcatacc     840

ttcgagcacg aactggcttg cgccgtagat gccggcatgc tgggcagcat tgatgccaac     900

cgcggcgacg cacagaacgg atgggacacc gaccagttcc ccatcgacaa ctatgagttg     960

acacaggcca tgatggagat tatccgcaat ggcggtctgg gtcttggcgg taccaatttc    1020

gatgccaaga ttcgccgtaa ctccaccgac ctggaagacc tcttcatcgc ccacatcagt    1080

ggcatggacg ccatggctcg tgcgctcctt aatgctgccg acattctgga gaacagcgaa    1140

ctgcccgcca tgaagaaagc gcgctacgcc tcgttcgaca gtggcatggg caaggacttc    1200

gaggacggca aactgaccct tgagcaggtt tacgaatacg gcaaaaaagt cggcgaacct    1260

aagcagacct ccggcaagca ggagaagtac gagaccatcg tggctctcta tgccaagtaa    1320


<210> SEQ ID NO 84
```

<211> LENGTH: 439
<212> TYPE: PRT
<213> ORGANISM: Unknown
<220> FEATURE:
<223> OTHER INFORMATION: Obtained from environmental sample

<400> SEQUENCE: 84

```
Met Ala Lys Glu Tyr Phe Pro Phe Thr Gly Lys Ile Pro Phe Glu Gly
1               5                   10                  15

Lys Asp Ser Lys Asn Val Met Ala Phe His Tyr Tyr Glu Pro Glu Arg
            20                  25                  30

Val Val Met Gly Lys Lys Met Lys Glu Trp Leu Lys Phe Ala Met Ala
        35                  40                  45

Trp Trp His Thr Leu Gly Gly Ala Ser Ala Asp Gln Phe Gly Gly Gln
    50                  55                  60

Thr Arg Ser Tyr Glu Trp Asp Lys Ala Glu Asp Ala Val Gln Arg Ala
65                  70                  75                  80

Lys Asp Lys Met Asp Ala Gly Phe Glu Ile Met Asp Lys Leu Gly Ile
                85                  90                  95

Glu Tyr Phe Cys Phe His Asp Val Asp Leu Val Asp Glu Gly Ala Thr
            100                 105                 110

Val Glu Glu Tyr Glu Ala Arg Met Gln Ala Ile Thr Asp Tyr Ala Gln
        115                 120                 125

Glu Lys Met Lys Gln Tyr Pro Ala Ile Lys Leu Leu Trp Gly Thr Ala
    130                 135                 140

Asn Val Phe Gly Asn Lys Arg Tyr Ala Asn Gly Ala Ser Thr Asn Pro
145                 150                 155                 160

Asp Phe Asp Val Val Ala Arg Ala Ile Val Gln Ile Lys Asn Ala Ile
                165                 170                 175

Asp Ala Thr Ile Lys Leu Gly Gly Ser Asn Tyr Val Phe Trp Gly Gly
            180                 185                 190

Arg Glu Gly Tyr Met Ser Leu Leu Asn Thr Asp Gln Lys Arg Glu Lys
        195                 200                 205

Glu His Met Ala Arg Met Leu Thr Met Ala Arg Asp Tyr Ala Arg Ser
    210                 215                 220

Lys Gly Phe Lys Gly Asn Phe Leu Ile Glu Pro Lys Pro Met Glu Pro
225                 230                 235                 240

Ser Lys His Gln Tyr Asp Val Asp Thr Glu Thr Val Ile Gly Phe Leu
                245                 250                 255

Arg Ala His Gly Leu Asp Lys Asp Phe Lys Val Asn Ile Glu Val Asn
            260                 265                 270

His Ala Thr Leu Ala Gly His Thr Phe Glu His Glu Leu Ala Cys Ala
        275                 280                 285

Val Asp Ala Gly Met Leu Gly Ser Ile Asp Ala Asn Arg Gly Asp Ala
    290                 295                 300

Gln Asn Gly Trp Asp Thr Asp Gln Phe Pro Ile Asp Asn Tyr Glu Leu
305                 310                 315                 320

Thr Gln Ala Met Met Glu Ile Ile Arg Asn Gly Gly Leu Gly Leu Gly
                325                 330                 335

Gly Thr Asn Phe Asp Ala Lys Ile Arg Arg Asn Ser Thr Asp Leu Glu
            340                 345                 350

Asp Leu Phe Ile Ala His Ile Ser Gly Met Asp Ala Met Ala Arg Ala
        355                 360                 365

Leu Leu Asn Ala Ala Asp Ile Leu Glu Asn Ser Glu Leu Pro Ala Met
    370                 375                 380
```

Lys Lys Ala Arg Tyr Ala Ser Phe Asp Ser Gly Met Gly Lys Asp Phe
385 390 395 400

Glu Asp Gly Lys Leu Thr Leu Glu Gln Val Tyr Glu Tyr Gly Lys Lys
405 410 415

Val Gly Glu Pro Lys Gln Thr Ser Gly Lys Gln Glu Lys Tyr Glu Thr
420 425 430

Ile Val Ala Leu Tyr Ala Lys
435

<210> SEQ ID NO 85
<211> LENGTH: 1320
<212> TYPE: DNA
<213> ORGANISM: Unknown
<220> FEATURE:
<223> OTHER INFORMATION: Obtained from environmental sample

<400> SEQUENCE: 85
atggcaaaag agtattttcc gtttacaggt aaaattcctt tcgaaggaaa ggacagtaag 60
aacgtaatgg ctttccacta ctacgagccc gaaaaggtcg tgatgggaaa gaaaatgaaa 120
gactggctga agttcgccat ggcctggtgg cacacactgg gtggcgccag cgccgaccag 180
tttggcggcc agacacgcag ctatgagtgg gacaaggctg ccgatgccgt gcagcgcgca 240
aaggacaaga tggacgccgg cttcgaaatc atggacaagc tgggcatcga gtatttctgc 300
ttccacgacg tggacctcgt tgaggaggga gccaccatcg aggagtatga ggcccgcatg 360
aaggctatca ccgactatgc ccaggagaag atgaaacagt atcccagcat caagctgctc 420
tggggcaccg ccaatgtgtt tggcaacaag cgctacgcca acggcgccag caccaacccc 480
gacttcgacg tcgtggcccg tgccatcgtg cagatcaaga acgccatcga tgccaccatc 540
aagctgggcg gcaccaacta cgtgttctgg ggcggacgcg agggctacat gagcctgctc 600
aacaccgacc agaagcgcga gaaggagcac atggccacca tgctcaccat ggcccgcgac 660
tacgcccgcg caaagggatt caagggcacc ttcctcatcg agcccaagcc catggagccg 720
tcgaagcacc agtacgacgt ggacaccgag accgtcatcg gtttcctgaa ggcccacggt 780
ctggacaagg acttcaaggt gaacatcgag gtgaaccacg ccacgctggc cggccacacc 840
ttcgagcatg agctggcctg cgccgtcgac gccggtatgc tgggcagcat cgatgccaac 900
cgcggcgacg cccagaacgg ctgggacacc gaccagttcc ccatcgacaa cttcgagctc 960
acccaggcca tgatggaaat tatccgcaac ggcggcctcg gcaacggcgg caccaacttc 1020
gacgctaaga tccgccgcaa ctccaccgac ctcgaggacc tcttcatcgc ccacatcagc 1080
ggcatggacg ccatggcccg cgcactgatg aacgctgccg acattatgga gaacagcgag 1140
ctgcccgcca tgaagaaggc acgctacgcc agcttcgacg ccggcatcgg caaggacttt 1200
gaggatggca agctctcgct ggagcaggtc tacgagtatg gcaagaaggt ggaagagccc 1260
aagcagacca gcggcaagca ggagaagtac gagaccatcg tcgccctcta tgccaagtaa 1320

<210> SEQ ID NO 86
<211> LENGTH: 439
<212> TYPE: PRT
<213> ORGANISM: Unknown
<220> FEATURE:
<223> OTHER INFORMATION: Obtained from environmental sample

<400> SEQUENCE: 86

Met Ala Lys Glu Tyr Phe Pro Phe Thr Gly Lys Ile Pro Phe Glu Gly
1 5 10 15

```
Lys Asp Ser Lys Asn Val Met Ala Phe His Tyr Tyr Glu Pro Glu Lys
            20                  25                  30

Val Val Met Gly Lys Lys Met Lys Asp Trp Leu Lys Phe Ala Met Ala
        35                  40                  45

Trp Trp His Thr Leu Gly Gly Ala Ser Ala Asp Gln Phe Gly Gly Gln
    50                  55                  60

Thr Arg Ser Tyr Glu Trp Asp Lys Ala Ala Asp Ala Val Gln Arg Ala
65                  70                  75                  80

Lys Asp Lys Met Asp Ala Gly Phe Glu Ile Met Asp Lys Leu Gly Ile
                85                  90                  95

Glu Tyr Phe Cys Phe His Asp Val Asp Leu Val Glu Glu Gly Ala Thr
            100                 105                 110

Ile Glu Glu Tyr Glu Ala Arg Met Lys Ala Ile Thr Asp Tyr Ala Gln
        115                 120                 125

Glu Lys Met Lys Gln Tyr Pro Ser Ile Lys Leu Leu Trp Gly Thr Ala
    130                 135                 140

Asn Val Phe Gly Asn Lys Arg Tyr Ala Asn Gly Ala Ser Thr Asn Pro
145                 150                 155                 160

Asp Phe Asp Val Val Ala Arg Ala Ile Val Gln Ile Lys Asn Ala Ile
                165                 170                 175

Asp Ala Thr Ile Lys Leu Gly Gly Thr Asn Tyr Val Phe Trp Gly Gly
            180                 185                 190

Arg Glu Gly Tyr Met Ser Leu Leu Asn Thr Asp Gln Lys Arg Glu Lys
        195                 200                 205

Glu His Met Ala Thr Met Leu Thr Met Ala Arg Asp Tyr Ala Arg Ala
    210                 215                 220

Lys Gly Phe Lys Gly Thr Phe Leu Ile Glu Pro Lys Pro Met Glu Pro
225                 230                 235                 240

Ser Lys His Gln Tyr Asp Val Asp Thr Glu Thr Val Ile Gly Phe Leu
                245                 250                 255

Lys Ala His Gly Leu Asp Lys Asp Phe Lys Val Asn Ile Glu Val Asn
            260                 265                 270

His Ala Thr Leu Ala Gly His Thr Phe Glu His Glu Leu Ala Cys Ala
        275                 280                 285

Val Asp Ala Gly Met Leu Gly Ser Ile Asp Ala Asn Arg Gly Asp Ala
    290                 295                 300

Gln Asn Gly Trp Asp Thr Asp Gln Phe Pro Ile Asp Asn Phe Glu Leu
305                 310                 315                 320

Thr Gln Ala Met Met Glu Ile Ile Arg Asn Gly Gly Leu Gly Asn Gly
                325                 330                 335

Gly Thr Asn Phe Asp Ala Lys Ile Arg Arg Asn Ser Thr Asp Leu Glu
            340                 345                 350

Asp Leu Phe Ile Ala His Ile Ser Gly Met Asp Ala Met Ala Arg Ala
        355                 360                 365

Leu Met Asn Ala Ala Asp Ile Met Glu Asn Ser Glu Leu Pro Ala Met
    370                 375                 380

Lys Lys Ala Arg Tyr Ala Ser Phe Asp Ala Gly Ile Gly Lys Asp Phe
385                 390                 395                 400

Glu Asp Gly Lys Leu Ser Leu Glu Gln Val Tyr Glu Tyr Gly Lys Lys
                405                 410                 415

Val Glu Glu Pro Lys Gln Thr Ser Gly Lys Gln Glu Lys Tyr Glu Thr
            420                 425                 430
```

Ile Val Ala Leu Tyr Ala Lys
435

<210> SEQ ID NO 87
<211> LENGTH: 1320
<212> TYPE: DNA
<213> ORGANISM: Unknown
<220> FEATURE:
<223> OTHER INFORMATION: Obtained from environmental sample

<400> SEQUENCE: 87
atggcaaaag agtatttcgc ctttacaggc aagattcctt tcgagggaaa agacagtaag 60
aacgtgatgg ctttccacta ctacgagccg gagcgtgtgg tgatgggcaa gaagatgaag 120
gagtggctga agttcgccat ggcctggtgg cacacactgg gtggcgcatc ggccgaccag 180
ttcggaggcc agacacgcag ctacgagtgg gacaaggccg ccgacgccgt gcagcgcgcc 240
aaggacaaga tggacgccgg cttcgagatt atggacaagc tgggcatcga gtacttctgc 300
ttccacgatg tagacctcgt tgaggagggt gagaccatag ccgagtacga gcgccgcatg 360
aaggaaatca ccgactacgc acaggagaag atgaagcagt tccccaacat caagctgctc 420
tggggcacag ccaacgtgtt cggcaacaag cgctacgcca acggcgcatc gaccaacccc 480
gacttcgacg ttgtggcacg cgccatcgtg cagatcaaga acgccatcga cgccaccatc 540
aagctcggcg gctccaacta tgtgttctgg ggcggacgcg agggctatat gagcctgctc 600
aacaccgacc agaagcgcga gaaggagcac atggccacca tgctcaccat ggcccgcgac 660
tatgcacgcg ccaagggatt caagggcaca ttcctcatcg agccgaagcc catggagccc 720
tcgaagcacc agtacgacgt agacacagag accgtcatcg gcttcctccg tgcacacggg 780
ctggacaagg acttcaaggt gaacatcgag gtaaaccacg ccacactggc cggccacacc 840
ttcgagcacg agctggcttg cgccgtcgac gctggcatgc tgggcagcat cgacgccaac 900
cgtggcgacg cacagaacgg atgggacacc gaccagttcc ccatcgacaa cttcgagctc 960
acacaggcca tgatggaaat catccgcaat ggcggactgg gcaatggcgg caccaacttc 1020
gacgccaaga tccgtcgtaa cagcaccgac ctcgaagacc tcttcatcgc ccacatcagc 1080
ggcatggacg ccatggcacg cgcactgctc aacgctgccg acatcctgga gcacagcgag 1140
ctgcccaaga tgaagaagga gcgctacgcc agcttcgacg caggcatcgg caaggacttc 1200
gaagacggca agctcacact cgagcaggtc tacgagtacg gcaagaaggt cgaagagccc 1260
cgtcagacca gcggcaagca ggagaagtac gagaccatcg tcgccctcta tgccaagtaa 1320

<210> SEQ ID NO 88
<211> LENGTH: 439
<212> TYPE: PRT
<213> ORGANISM: Unknown
<220> FEATURE:
<223> OTHER INFORMATION: Obtained from environmental sample

<400> SEQUENCE: 88

Met Ala Lys Glu Tyr Phe Ala Phe Thr Gly Lys Ile Pro Phe Glu Gly
1 5 10 15

Lys Asp Ser Lys Asn Val Met Ala Phe His Tyr Tyr Glu Pro Glu Arg
20 25 30

Val Val Met Gly Lys Lys Met Lys Glu Trp Leu Lys Phe Ala Met Ala
35 40 45

Trp Trp His Thr Leu Gly Gly Ala Ser Ala Asp Gln Phe Gly Gly Gln
50 55 60

```
Thr Arg Ser Tyr Glu Trp Asp Lys Ala Ala Asp Ala Val Gln Arg Ala
65                  70                  75                  80

Lys Asp Lys Met Asp Ala Gly Phe Glu Ile Met Asp Lys Leu Gly Ile
                85                  90                  95

Glu Tyr Phe Cys Phe His Asp Val Asp Leu Val Glu Glu Gly Glu Thr
            100                 105                 110

Ile Ala Glu Tyr Glu Arg Arg Met Lys Glu Ile Thr Asp Tyr Ala Gln
        115                 120                 125

Glu Lys Met Lys Gln Phe Pro Asn Ile Lys Leu Leu Trp Gly Thr Ala
    130                 135                 140

Asn Val Phe Gly Asn Lys Arg Tyr Ala Asn Gly Ala Ser Thr Asn Pro
145                 150                 155                 160

Asp Phe Asp Val Val Ala Arg Ala Ile Val Gln Ile Lys Asn Ala Ile
                165                 170                 175

Asp Ala Thr Ile Lys Leu Gly Gly Ser Asn Tyr Val Phe Trp Gly Gly
            180                 185                 190

Arg Glu Gly Tyr Met Ser Leu Leu Asn Thr Asp Gln Lys Arg Glu Lys
        195                 200                 205

Glu His Met Ala Thr Met Leu Thr Met Ala Arg Asp Tyr Ala Arg Ala
    210                 215                 220

Lys Gly Phe Lys Gly Thr Phe Leu Ile Glu Pro Lys Pro Met Glu Pro
225                 230                 235                 240

Ser Lys His Gln Tyr Asp Val Asp Thr Glu Thr Val Ile Gly Phe Leu
                245                 250                 255

Arg Ala His Gly Leu Asp Lys Asp Phe Lys Val Asn Ile Glu Val Asn
            260                 265                 270

His Ala Thr Leu Ala Gly His Thr Phe Glu His Glu Leu Ala Cys Ala
        275                 280                 285

Val Asp Ala Gly Met Leu Gly Ser Ile Asp Ala Asn Arg Gly Asp Ala
    290                 295                 300

Gln Asn Gly Trp Asp Thr Asp Gln Phe Pro Ile Asp Asn Phe Glu Leu
305                 310                 315                 320

Thr Gln Ala Met Met Glu Ile Ile Arg Asn Gly Gly Leu Gly Asn Gly
                325                 330                 335

Gly Thr Asn Phe Asp Ala Lys Ile Arg Arg Asn Ser Thr Asp Leu Glu
            340                 345                 350

Asp Leu Phe Ile Ala His Ile Ser Gly Met Asp Ala Met Ala Arg Ala
        355                 360                 365

Leu Leu Asn Ala Ala Asp Ile Leu Glu His Ser Glu Leu Pro Lys Met
    370                 375                 380

Lys Lys Glu Arg Tyr Ala Ser Phe Asp Ala Gly Ile Gly Lys Asp Phe
385                 390                 395                 400

Glu Asp Gly Lys Leu Thr Leu Glu Gln Val Tyr Glu Tyr Gly Lys Lys
                405                 410                 415

Val Glu Glu Pro Arg Gln Thr Ser Gly Lys Gln Glu Lys Tyr Glu Thr
            420                 425                 430

Ile Val Ala Leu Tyr Ala Lys
        435
```

<210> SEQ ID NO 89
<211> LENGTH: 1320
<212> TYPE: DNA
<213> ORGANISM: Unknown
<220> FEATURE:
<223> OTHER INFORMATION: Obtained from environmental sample

<400> SEQUENCE: 89
atggcaaaag agtattttcc gtttactggt aagattcctt tcgagggaaa ggatagtaag 60
aatgtaatgg ctttccacta ttacgagccc gagaaagtcg tgatgggaaa gaagatgaag 120
gactggctga agttcgcaat ggcttggtgg catacactgg gtggtgcatc tgcagaccag 180
ttcggtggag agacccgcag ctacgagtgg agcaaggctg ctgatcccgt tcagcgcgcc 240
aaggacaaga tggacgccgg ctttgagatt atggataagc tgggcatcga gtacttctgt 300
ttccacgata tagacctcgt tcaggaggca gataccattg cagaatatga ggagcgcatg 360
aaggcaatta ccgactatgc tctggagaag atgaagcagt tccccaacat caagttgctc 420
tggggtaccg ctaacgtatt tagcaacaag cgctatatga acggtgcttc taccaatccc 480
gacttcgacg tggtggcccg tgccatcgtt cagatcaaga acgctattga tgcaaccatc 540
aaactcggtg gtaccaacta tgtattctgg ggtggtcgtg agggttacat gagcctattg 600
aataccgacc agaagcgtga aaaggagcac atggcaatga tgctcggtat ggctcgcgac 660
tatgcccgca gcaagggatt caagggtacg ttcctcatcg agccgaagcc gatggagccc 720
tctaagcatc agtatgatgt cgatacggag actgtgattg gtttcctgaa ggcacacggt 780
ctggacaagg acttcaaggt gaacatcgag gtgaaccacg ctacactggc tggtcatacc 840
ttcgagcatg agctggcttg cgctgttgac gcaggtatgc tgggctctat cgacgctaac 900
cgcggtgatg cccagaacgg ctgggatacc gaccagttcc ccatcgacaa ctacgagctg 960
acacaggcta tgatggaaat catccgcaac ggtggtctgg gcaatggtgg taccaacttc 1020
gacgctaaga tccgccgtaa ctctaccgac ctcgaggatc tgttcatcgc tcatatcagt 1080
ggtatggatg ctatggcccg tgctttgttg aatgctgccg acattctgga gaactctgaa 1140
ctgcccgcta tgaagaaggc ccgctacgcc agcttcgaca acggtatcgg taaggacttc 1200
gaggatggca agctgacctt cgagcaggtt tacgaatatg gtaagaaagt tgaagagccg 1260
aagcagacct ctggcaagca ggagaaatac gagaccatcg ttgctctgta tgctaaataa 1320

<210> SEQ ID NO 90
<211> LENGTH: 439
<212> TYPE: PRT
<213> ORGANISM: Unknown
<220> FEATURE:
<223> OTHER INFORMATION: Obtained from environmental sample

<400> SEQUENCE: 90

Met Ala Lys Glu Tyr Phe Pro Phe Thr Gly Lys Ile Pro Phe Glu Gly
1 5 10 15

Lys Asp Ser Lys Asn Val Met Ala Phe His Tyr Tyr Glu Pro Glu Lys
20 25 30

Val Val Met Gly Lys Lys Met Lys Asp Trp Leu Lys Phe Ala Met Ala
35 40 45

Trp Trp His Thr Leu Gly Gly Ala Ser Ala Asp Gln Phe Gly Gly Glu
50 55 60

Thr Arg Ser Tyr Glu Trp Ser Lys Ala Ala Asp Pro Val Gln Arg Ala
65 70 75 80

Lys Asp Lys Met Asp Ala Gly Phe Glu Ile Met Asp Lys Leu Gly Ile
85 90 95

Glu Tyr Phe Cys Phe His Asp Ile Asp Leu Val Gln Glu Ala Asp Thr
100 105 110

Ile Ala Glu Tyr Glu Glu Arg Met Lys Ala Ile Thr Asp Tyr Ala Leu

-continued

```
        115                 120                 125

Glu Lys Met Lys Gln Phe Pro Asn Ile Lys Leu Leu Trp Gly Thr Ala
    130                 135                 140

Asn Val Phe Ser Asn Lys Arg Tyr Met Asn Gly Ala Ser Thr Asn Pro
145                 150                 155                 160

Asp Phe Asp Val Val Ala Arg Ala Ile Val Gln Ile Lys Asn Ala Ile
                165                 170                 175

Asp Ala Thr Ile Lys Leu Gly Gly Thr Asn Tyr Val Phe Trp Gly Gly
            180                 185                 190

Arg Glu Gly Tyr Met Ser Leu Leu Asn Thr Asp Gln Lys Arg Glu Lys
        195                 200                 205

Glu His Met Ala Met Met Leu Gly Met Ala Arg Asp Tyr Ala Arg Ser
    210                 215                 220

Lys Gly Phe Lys Gly Thr Phe Leu Ile Glu Pro Lys Pro Met Glu Pro
225                 230                 235                 240

Ser Lys His Gln Tyr Asp Val Asp Thr Glu Thr Val Ile Gly Phe Leu
                245                 250                 255

Lys Ala His Gly Leu Asp Lys Asp Phe Lys Val Asn Ile Glu Val Asn
            260                 265                 270

His Ala Thr Leu Ala Gly His Thr Phe Glu His Glu Leu Ala Cys Ala
        275                 280                 285

Val Asp Ala Gly Met Leu Gly Ser Ile Asp Ala Asn Arg Gly Asp Ala
    290                 295                 300

Gln Asn Gly Trp Asp Thr Asp Gln Phe Pro Ile Asp Asn Tyr Glu Leu
305                 310                 315                 320

Thr Gln Ala Met Met Glu Ile Ile Arg Asn Gly Gly Leu Gly Asn Gly
                325                 330                 335

Gly Thr Asn Phe Asp Ala Lys Ile Arg Arg Asn Ser Thr Asp Leu Glu
            340                 345                 350

Asp Leu Phe Ile Ala His Ile Ser Gly Met Asp Ala Met Ala Arg Ala
        355                 360                 365

Leu Leu Asn Ala Ala Asp Ile Leu Glu Asn Ser Glu Leu Pro Ala Met
    370                 375                 380

Lys Lys Ala Arg Tyr Ala Ser Phe Asp Asn Gly Ile Gly Lys Asp Phe
385                 390                 395                 400

Glu Asp Gly Lys Leu Thr Phe Glu Gln Val Tyr Glu Tyr Gly Lys Lys
                405                 410                 415

Val Glu Glu Pro Lys Gln Thr Ser Gly Lys Gln Glu Lys Tyr Glu Thr
            420                 425                 430

Ile Val Ala Leu Tyr Ala Lys
        435


<210> SEQ ID NO 91
<211> LENGTH: 1320
<212> TYPE: DNA
<213> ORGANISM: Unknown
<220> FEATURE:
<223> OTHER INFORMATION: Obtained from environmental sample

<400> SEQUENCE: 91

atggcaaaag agtattttcc gtttaccggt aaaattcctt tcgagggaaa ggacagtaag      60

aatgtaatgg ctttccacta ctacgagcct gagcgcgtag tgatgggaaa gaagatgaag     120

gattggttgc gatttgcaat ggcttggtgg cacacactgg gtggcgcttc tgccgaccag     180

tttggtggtc agacccgcag ttacgaatgg gacaaggctg ctgatgctgt tcagcgtgct     240
```

```
aaggacaaga tggatgccgg cttcgagatt atggataagc tgggaatcga gttcttctgc    300

tggcacgata tcgacctcgt tgaagagggt gagaccattg aagagtatga gcgccgcatg    360

aaggctatca ccgactatgc tcttgagaag atgcagcagt atcccaacat caagaacctc    420

tggggaacag ccaatgtgtt tggcaacaag cgttatgcca acggtgccag cacaaaccca    480

gactttgacg tcgttgctcg tgctatcgta cagattaaga atgctatcga cgctactatc    540

aagttgggtg gtcagaatta tgtgttctgg ggtggccgtg agggctacat gagcctgctc    600

aatactgacc agaagcgtga gaaggagcac atggctacaa tgctgaccat ggcacgcgac    660

tatgcccgca gcaagggatt caagggtaac ttcctcattg agcccaagcc catggagccg    720

tcaaagcacc agtatgatgt tgacaccgag accgtatgcg gtttcctgcg tgcccacaac    780

cttgacaagg atttcaaggt aaatatcgag gttaaccatg ctactctggc tggtcatact    840

ttcgagcacg aactggcatg cgctgttgac gctggtatgc ttggttctat cgatgctaac    900

cgtggtgatg cccagaatgg ctgggatacc gaccagttcc ccatcaacaa ctatgaactc    960

actcaggcta tgcttgagat catccgtaat ggtggtctgg gtcttggcgg cacaaacttc   1020

gatgccaaga ttcgtcgtaa ctcaacagat cttgaggatc tcttcatcgc tcacatcagt   1080

ggtatggatg ccatggcccg tgctctgctg aatgctgctg ctattctgga ggagagcgag   1140

ctgcctaaga tgaagaagga gcgttatgct tctttcgatg ccggtatcgg taaggacttc   1200

gaggatggca agcttaccct tgagcaggct tacgagtatg gtaagaaggt tgaggagccc   1260

aagcagactt caggcaagca ggagaagtac gagaccatcg ttgctctgta tgcaaaataa   1320
```

```
<210> SEQ ID NO 92
<211> LENGTH: 439
<212> TYPE: PRT
<213> ORGANISM: Unknown
<220> FEATURE:
<223> OTHER INFORMATION: Obtained from environmental sample

<400> SEQUENCE: 92

Met Ala Lys Glu Tyr Phe Pro Phe Thr Gly Lys Ile Pro Phe Glu Gly
1               5                   10                  15

Lys Asp Ser Lys Asn Val Met Ala Phe His Tyr Tyr Glu Pro Glu Arg
            20                  25                  30

Val Val Met Gly Lys Lys Met Lys Asp Trp Leu Arg Phe Ala Met Ala
        35                  40                  45

Trp Trp His Thr Leu Gly Gly Ala Ser Ala Asp Gln Phe Gly Gly Gln
    50                  55                  60

Thr Arg Ser Tyr Glu Trp Asp Lys Ala Ala Asp Ala Val Gln Arg Ala
65                  70                  75                  80

Lys Asp Lys Met Asp Ala Gly Phe Glu Ile Met Asp Lys Leu Gly Ile
                85                  90                  95

Glu Phe Phe Cys Trp His Asp Ile Asp Leu Val Glu Glu Gly Glu Thr
            100                 105                 110

Ile Glu Glu Tyr Glu Arg Arg Met Lys Ala Ile Thr Asp Tyr Ala Leu
        115                 120                 125

Glu Lys Met Gln Gln Tyr Pro Asn Ile Lys Asn Leu Trp Gly Thr Ala
    130                 135                 140

Asn Val Phe Gly Asn Lys Arg Tyr Ala Asn Gly Ala Ser Thr Asn Pro
145                 150                 155                 160

Asp Phe Asp Val Val Ala Arg Ala Ile Val Gln Ile Lys Asn Ala Ile
                165                 170                 175
```

```
Asp Ala Thr Ile Lys Leu Gly Gly Gln Asn Tyr Val Phe Trp Gly Gly
            180                 185                 190

Arg Glu Gly Tyr Met Ser Leu Leu Asn Thr Asp Gln Lys Arg Glu Lys
        195                 200                 205

Glu His Met Ala Thr Met Leu Thr Met Ala Arg Asp Tyr Ala Arg Ser
    210                 215                 220

Lys Gly Phe Lys Gly Asn Phe Leu Ile Glu Pro Lys Pro Met Glu Pro
225                 230                 235                 240

Ser Lys His Gln Tyr Asp Val Asp Thr Glu Thr Val Cys Gly Phe Leu
                245                 250                 255

Arg Ala His Asn Leu Asp Lys Asp Phe Lys Val Asn Ile Glu Val Asn
            260                 265                 270

His Ala Thr Leu Ala Gly His Thr Phe Glu His Glu Leu Ala Cys Ala
        275                 280                 285

Val Asp Ala Gly Met Leu Gly Ser Ile Asp Ala Asn Arg Gly Asp Ala
    290                 295                 300

Gln Asn Gly Trp Asp Thr Asp Gln Phe Pro Ile Asn Asn Tyr Glu Leu
305                 310                 315                 320

Thr Gln Ala Met Leu Glu Ile Ile Arg Asn Gly Gly Leu Gly Leu Gly
                325                 330                 335

Gly Thr Asn Phe Asp Ala Lys Ile Arg Arg Asn Ser Thr Asp Leu Glu
            340                 345                 350

Asp Leu Phe Ile Ala His Ile Ser Gly Met Asp Ala Met Ala Arg Ala
        355                 360                 365

Leu Leu Asn Ala Ala Ala Ile Leu Glu Glu Ser Glu Leu Pro Lys Met
    370                 375                 380

Lys Lys Glu Arg Tyr Ala Ser Phe Asp Ala Gly Ile Gly Lys Asp Phe
385                 390                 395                 400

Glu Asp Gly Lys Leu Thr Leu Glu Gln Ala Tyr Glu Tyr Gly Lys Lys
                405                 410                 415

Val Glu Glu Pro Lys Gln Thr Ser Gly Lys Gln Glu Lys Tyr Glu Thr
            420                 425                 430

Ile Val Ala Leu Tyr Ala Lys
        435
```

<210> SEQ ID NO 93
<211> LENGTH: 1317
<212> TYPE: DNA
<213> ORGANISM: Unknown
<220> FEATURE:
<223> OTHER INFORMATION: Obtained from environmental sample

<400> SEQUENCE: 93

```
atgaaacagt attttcccca gattggaaag ataccccttcg agggtgtaga gagcaagaat      60

gtgatggctt tccactatta tgagccagaa agagtagtca tgggcaagcc tatgaaagaa     120

tggctgcgct tcgctatggc gtggtggcac acgctggggc aggcgagcgg cgaccccttc     180

ggcggacaga cccgcagcta cgagtgggac cgtgcggccg acgcgctaca gcgcgccaag     240

gacaagatgg atgcgggctt cgagctgatg gagaagcttg gcattgagta cttctgcttc     300

cacgacgtgg acctcgtaga agagggcgcc acggtggagg aatacgagcg gcggatggct     360

gccatcaccg actacgcggt agagaagatg cgcgagcatc ccgagataca ctgcctgtgg     420

ggcacggcca atgtcttcgg ccacaagcgc tacatgaacg gagccgccac caaccccgac     480

ttcgacgtgg tggcgcgtgc ggtggtgcag ataaagaaca gcatcgacgc cacgatcaag     540
```

```
ctgggcggcg agaactatgt gttctggggc ggacgcgagg gatatatgag cctgctcaac    600

accgaccagc gccgcgagaa ggagcacctg gccatgatgc ttgcgaaggc ccgcgactat    660

ggccgcgccc acggcttcaa gggcaccttc ctgatagagc ccaagccgat ggagcccatg    720

aagcaccagt acgacgtgga caccgagacg gtgataggtt tcctgcgtgc ccacggactg    780

gacaaggact tcaaggtgaa catcgaggtg aaccacgcca cgttggcggg ccacacgttc    840

gagcacgagc tggcctgtgc cgtcgatgcc ggcatgctgg gcagcatcga cgccaaccgt    900

ggcgacgcgc agaacggatg ggatacggac cagttcccca tagactgcta cgagctcacg    960

caggcgtgga tggagatcat tcgtggcggc ggcttcacca ccggcggcac caacttcgac   1020

gctaagctgc gccgcaactc gaccgacccc gaggatatct tcatagctca catcagcggc   1080

atggatgcta tggcccgcgc cctgctctgc gccgccgaca tcttggagca cagcgagctg   1140

ccggagatga agcggaagcg ctatgcctcg ttcgacagcg gcatgggcaa ggagttcgaa   1200

gagggcaatc tcagcttcga gcaaatctat gcctacggca agcaggcggg cgaaccggcc   1260

acgaccagcg gcaagcagga gaaatacgaa gccattgttt cactttatac ccgatga      1317


<210> SEQ ID NO 94
<211> LENGTH: 438
<212> TYPE: PRT
<213> ORGANISM: Unknown
<220> FEATURE:
<223> OTHER INFORMATION: Obtained from environmental sample

<400> SEQUENCE: 94

Met Lys Gln Tyr Phe Pro Gln Ile Gly Lys Ile Pro Phe Glu Gly Val
1               5                   10                  15

Glu Ser Lys Asn Val Met Ala Phe His Tyr Tyr Glu Pro Glu Arg Val
            20                  25                  30

Val Met Gly Lys Pro Met Lys Glu Trp Leu Arg Phe Ala Met Ala Trp
        35                  40                  45

Trp His Thr Leu Gly Gln Ala Ser Gly Asp Pro Phe Gly Gly Gln Thr
    50                  55                  60

Arg Ser Tyr Glu Trp Asp Arg Ala Ala Asp Ala Leu Gln Arg Ala Lys
65                  70                  75                  80

Asp Lys Met Asp Ala Gly Phe Glu Leu Met Glu Lys Leu Gly Ile Glu
                85                  90                  95

Tyr Phe Cys Phe His Asp Val Asp Leu Val Glu Glu Gly Ala Thr Val
            100                 105                 110

Glu Glu Tyr Glu Arg Arg Met Ala Ala Ile Thr Asp Tyr Ala Val Glu
        115                 120                 125

Lys Met Arg Glu His Pro Glu Ile His Cys Leu Trp Gly Thr Ala Asn
    130                 135                 140

Val Phe Gly His Lys Arg Tyr Met Asn Gly Ala Ala Thr Asn Pro Asp
145                 150                 155                 160

Phe Asp Val Val Ala Arg Ala Val Val Gln Ile Lys Asn Ser Ile Asp
                165                 170                 175

Ala Thr Ile Lys Leu Gly Gly Glu Asn Tyr Val Phe Trp Gly Gly Arg
            180                 185                 190

Glu Gly Tyr Met Ser Leu Leu Asn Thr Asp Gln Arg Arg Glu Lys Glu
        195                 200                 205

His Leu Ala Met Met Leu Ala Lys Ala Arg Asp Tyr Gly Arg Ala His
    210                 215                 220
```

-continued

```
Gly Phe Lys Gly Thr Phe Leu Ile Glu Pro Lys Pro Met Glu Pro Met
225                 230                 235                 240

Lys His Gln Tyr Asp Val Asp Thr Glu Thr Val Ile Gly Phe Leu Arg
                245                 250                 255

Ala His Gly Leu Asp Lys Asp Phe Lys Val Asn Ile Glu Val Asn His
            260                 265                 270

Ala Thr Leu Ala Gly His Thr Phe Glu His Glu Leu Ala Cys Ala Val
        275                 280                 285

Asp Ala Gly Met Leu Gly Ser Ile Asp Ala Asn Arg Gly Asp Ala Gln
    290                 295                 300

Asn Gly Trp Asp Thr Asp Gln Phe Pro Ile Asp Cys Tyr Glu Leu Thr
305                 310                 315                 320

Gln Ala Trp Met Glu Ile Ile Arg Gly Gly Gly Phe Thr Thr Gly Gly
                325                 330                 335

Thr Asn Phe Asp Ala Lys Leu Arg Arg Asn Ser Thr Asp Pro Glu Asp
            340                 345                 350

Ile Phe Ile Ala His Ile Ser Gly Met Asp Ala Met Ala Arg Ala Leu
        355                 360                 365

Leu Cys Ala Ala Asp Ile Leu Glu His Ser Glu Leu Pro Glu Met Lys
    370                 375                 380

Arg Lys Arg Tyr Ala Ser Phe Asp Ser Gly Met Gly Lys Glu Phe Glu
385                 390                 395                 400

Glu Gly Asn Leu Ser Phe Glu Gln Ile Tyr Ala Tyr Gly Lys Gln Ala
                405                 410                 415

Gly Glu Pro Ala Thr Thr Ser Gly Lys Gln Glu Lys Tyr Glu Ala Ile
            420                 425                 430

Val Ser Leu Tyr Thr Arg
        435
```

<210> SEQ ID NO 95
<211> LENGTH: 1320
<212> TYPE: DNA
<213> ORGANISM: Unknown
<220> FEATURE:
<223> OTHER INFORMATION: Obtained from environmental sample

<400> SEQUENCE: 95

```
atggcaaaag agtattttcc gtttatcggt aaggttcctt tcgaaggaac agagagcaag      60

aacgtgatgg cattccacta ctatgagccc gaaaaggtgg tcatgggtaa gaaaatgaag     120

gactggctga agttcgctat ggcttggtgg cacacactgg gtggtgccag cgccgaccag     180

tttggtggtc agactcgcag ctacgagtgg gacaaggctg ctgatgccgt tcagcgcgcc     240

aaggacaaga tggatgctgg cttcgagatc atggataagc tcggcattga gtacttctgc     300

ttccatgacg tagacctcgt tgaggagggt gaaaccgtcg ctgagtatga ggctcgcatg     360

aaggtcatca ccgactatgc cctggagaag atgcagcagt tccccaacat caaactgctc     420

tggggtactg ctaacgtgtt cggccacaag cgctatgcca acggtgccag caccaatccc     480

gacttcgacg tcgtggcccg tgctatcgtt cagatcaaga atgccatcga tgctaccatt     540

aagctcggcg gtacgaacta tgtgttctgg ggtggtcgtg agggctacat gagccttctc     600

aacaccgacc agaagcgcga gaaggagcac atggcaacga tgctgaccat ggctcgcgac     660

tatgcccgcg ccaagggatt caagggcacg ttcctcatcg agccgaagcc catggagccc     720

tcgaagcatc agtacgacgt cgacaccgag accgtcatcg gcttcctccg tgcccacggt     780

ctggataagg acttcaaggt gaacatcgag gtgaaccacg ccacgctggc cggtcatacc     840
```

```
ttcgagcacg aactggcttg cgccgttgat gccggcatgc tcggctctat cgatgccaac    900

cgcggcgacg ctcagaacgg ctgggacacc gaccagttcc ccatcgacaa ctacgagctc    960

actcaggcca tgatggaaat catccgtaat ggcggtctgg gcaacggcgg cacgaacttc   1020

gatgccaaga tccgtcgtaa cagcaccgac ctcgaggacc tcttcatcgc tcacatcagc   1080

ggcatggatg ccatggcacg cgctctgatg aacgctgctg ccatcctcga agagagcgag   1140

ctgcccgcca tgaagaaggc ccgctatgct tcgttcgacg agggtatcgg caaggacttc   1200

gaggacggca agttgtcact tgagcaggtc tacgaatatg gtaagaaggt tgaggagccc   1260

aagcagacct cgggcaagca ggagaagtac gagaccatcg tggccctcta tgccaagtaa   1320
```

<210> SEQ ID NO 96
<211> LENGTH: 439
<212> TYPE: PRT
<213> ORGANISM: Unknown
<220> FEATURE:
<223> OTHER INFORMATION: Obtained from environmental sample

<400> SEQUENCE: 96

```
Met Ala Lys Glu Tyr Phe Pro Phe Ile Gly Lys Val Pro Phe Glu Gly
1               5                   10                  15

Thr Glu Ser Lys Asn Val Met Ala Phe His Tyr Tyr Glu Pro Glu Lys
            20                  25                  30

Val Val Met Gly Lys Lys Met Lys Asp Trp Leu Lys Phe Ala Met Ala
        35                  40                  45

Trp Trp His Thr Leu Gly Gly Ala Ser Ala Asp Gln Phe Gly Gly Gln
    50                  55                  60

Thr Arg Ser Tyr Glu Trp Asp Lys Ala Ala Asp Ala Val Gln Arg Ala
65                  70                  75                  80

Lys Asp Lys Met Asp Ala Gly Phe Glu Ile Met Asp Lys Leu Gly Ile
                85                  90                  95

Glu Tyr Phe Cys Phe His Asp Val Asp Leu Val Glu Glu Gly Glu Thr
            100                 105                 110

Val Ala Glu Tyr Glu Ala Arg Met Lys Val Ile Thr Asp Tyr Ala Leu
        115                 120                 125

Glu Lys Met Gln Gln Phe Pro Asn Ile Lys Leu Leu Trp Gly Thr Ala
    130                 135                 140

Asn Val Phe Gly His Lys Arg Tyr Ala Asn Gly Ala Ser Thr Asn Pro
145                 150                 155                 160

Asp Phe Asp Val Val Ala Arg Ala Ile Val Gln Ile Lys Asn Ala Ile
                165                 170                 175

Asp Ala Thr Ile Lys Leu Gly Gly Thr Asn Tyr Val Phe Trp Gly Gly
            180                 185                 190

Arg Glu Gly Tyr Met Ser Leu Leu Asn Thr Asp Gln Lys Arg Glu Lys
        195                 200                 205

Glu His Met Ala Thr Met Leu Thr Met Ala Arg Asp Tyr Ala Arg Ala
    210                 215                 220

Lys Gly Phe Lys Gly Thr Phe Leu Ile Glu Pro Lys Pro Met Glu Pro
225                 230                 235                 240

Ser Lys His Gln Tyr Asp Val Asp Thr Glu Thr Val Ile Gly Phe Leu
                245                 250                 255

Arg Ala His Gly Leu Asp Lys Asp Phe Lys Val Asn Ile Glu Val Asn
            260                 265                 270

His Ala Thr Leu Ala Gly His Thr Phe Glu His Glu Leu Ala Cys Ala
```

```
        275                 280                 285

Val Asp Ala Gly Met Leu Gly Ser Ile Asp Ala Asn Arg Gly Asp Ala
    290                 295                 300

Gln Asn Gly Trp Asp Thr Asp Gln Phe Pro Ile Asp Asn Tyr Glu Leu
305                 310                 315                 320

Thr Gln Ala Met Met Glu Ile Ile Arg Asn Gly Gly Leu Gly Asn Gly
                325                 330                 335

Gly Thr Asn Phe Asp Ala Lys Ile Arg Arg Asn Ser Thr Asp Leu Glu
            340                 345                 350

Asp Leu Phe Ile Ala His Ile Ser Gly Met Asp Ala Met Ala Arg Ala
        355                 360                 365

Leu Met Asn Ala Ala Ala Ile Leu Glu Glu Ser Glu Leu Pro Ala Met
    370                 375                 380

Lys Lys Ala Arg Tyr Ala Ser Phe Asp Glu Gly Ile Gly Lys Asp Phe
385                 390                 395                 400

Glu Asp Gly Lys Leu Ser Leu Glu Gln Val Tyr Glu Tyr Gly Lys Lys
                405                 410                 415

Val Glu Glu Pro Lys Gln Thr Ser Gly Lys Gln Glu Lys Tyr Glu Thr
            420                 425                 430

Ile Val Ala Leu Tyr Ala Lys
        435


<210> SEQ ID NO 97
<211> LENGTH: 1320
<212> TYPE: DNA
<213> ORGANISM: Unknown
<220> FEATURE:
<223> OTHER INFORMATION: Obtained from environmental sample

<400> SEQUENCE: 97

atggcaaaag agtattttcc gtttgttggt aagattcctt tcgagggaaa ggatagtaag      60

aatgtaatgg ctttccacta ttacgaacca gagaaggtcg tgatgggaaa gaagatgaag     120

gactggctga agttcgccat ggcatggtgg cacacactgg gacaggccag tgccgacccg     180

tttggaggtc agacccgcag ctacgagtgg gacaaggctg acgatgctgt gcagcgcgca     240

aaggacaaga tggatgccgg atttgagatc atggacaagc tgggcatcga gtacttctgc     300

ttccacgatg tagacctcgt tgaggaggga gcaactgttg aggagtacga ggctcgcatg     360

aaggccatca ccgactatgc attggagaag atgaaagagt atcccaacat caagaacctc     420

tggggtacag ccaatgtatt cagcaacaag cgctatatga acggtgccag caccaacccc     480

gacttcgacg ttgttgcacg tgccatcgta cagataaaga acgccattga cgctaccatc     540

aagctcggcg gtcagaacta cgtgttctgg ggcggacgtg agggatacat gagcctgctc     600

aacaccgacc agaagcgcga gaaggagcac atggcaacca tgctgaccat ggctcgcgac     660

tacgctcgca agaacggttt caagggcaca ttcctcatcg agcctaagcc catggaaccc     720

tcaaagcacc agtacgacgt agacacagag accgtatgcg gtttcctccg cgcccatggt     780

cttgacaagg atttcaaggt gaacattgag gtgaaccacg ctaccctcgc cggccacacc     840

tttgagcatg aactggcttg cgccgtcgac aacggcatgc tcggcagcat cgatgccaac     900

cgcggcgacg ttcagaacgg ctgggacacc gaccagttcc ccatcgacaa ctacgagctg     960

actcaggcca tgctcgaaat catccgcaac ggtggtctgg gcaacggcgg taccaacttc    1020

gacgccaaga tccgtcgtaa ctctaccgac ctcgaggatc tgttcatcgc ccacatcagc    1080

ggtatggacg ccatggcacg tgcactgctc aatgcagcag ccatactgga ggagagcgag    1140
```

ctgcctgcca tgaagaagga gcgttacgcc agcttcgaca gcggcatcgg caaggacttc 1200
gaggacggca agctcacact tgagcaggcc tatgagtatg gtaagaaggt tgaggagcca 1260
aagcagacct ctggcaagca ggagaagtat gagactatag tagccctcta cgctaagtag 1320

<210> SEQ ID NO 98
<211> LENGTH: 439
<212> TYPE: PRT
<213> ORGANISM: Unknown
<220> FEATURE:
<223> OTHER INFORMATION: Obtained from environmental sample

<400> SEQUENCE: 98

Met Ala Lys Glu Tyr Phe Pro Phe Val Gly Lys Ile Pro Phe Glu Gly
1 5 10 15

Lys Asp Ser Lys Asn Val Met Ala Phe His Tyr Tyr Glu Pro Glu Lys
20 25 30

Val Val Met Gly Lys Lys Met Lys Asp Trp Leu Lys Phe Ala Met Ala
35 40 45

Trp Trp His Thr Leu Gly Gln Ala Ser Ala Asp Pro Phe Gly Gly Gln
50 55 60

Thr Arg Ser Tyr Glu Trp Asp Lys Ala Asp Asp Ala Val Gln Arg Ala
65 70 75 80

Lys Asp Lys Met Asp Ala Gly Phe Glu Ile Met Asp Lys Leu Gly Ile
85 90 95

Glu Tyr Phe Cys Phe His Asp Val Asp Leu Val Glu Glu Gly Ala Thr
100 105 110

Val Glu Glu Tyr Glu Ala Arg Met Lys Ala Ile Thr Asp Tyr Ala Leu
115 120 125

Glu Lys Met Lys Glu Tyr Pro Asn Ile Lys Asn Leu Trp Gly Thr Ala
130 135 140

Asn Val Phe Ser Asn Lys Arg Tyr Met Asn Gly Ala Ser Thr Asn Pro
145 150 155 160

Asp Phe Asp Val Val Ala Arg Ala Ile Val Gln Ile Lys Asn Ala Ile
165 170 175

Asp Ala Thr Ile Lys Leu Gly Gly Gln Asn Tyr Val Phe Trp Gly Gly
180 185 190

Arg Glu Gly Tyr Met Ser Leu Leu Asn Thr Asp Gln Lys Arg Glu Lys
195 200 205

Glu His Met Ala Thr Met Leu Thr Met Ala Arg Asp Tyr Ala Arg Lys
210 215 220

Asn Gly Phe Lys Gly Thr Phe Leu Ile Glu Pro Lys Pro Met Glu Pro
225 230 235 240

Ser Lys His Gln Tyr Asp Val Asp Thr Glu Thr Val Cys Gly Phe Leu
245 250 255

Arg Ala His Gly Leu Asp Lys Asp Phe Lys Val Asn Ile Glu Val Asn
260 265 270

His Ala Thr Leu Ala Gly His Thr Phe Glu His Glu Leu Ala Cys Ala
275 280 285

Val Asp Asn Gly Met Leu Gly Ser Ile Asp Ala Asn Arg Gly Asp Val
290 295 300

Gln Asn Gly Trp Asp Thr Asp Gln Phe Pro Ile Asp Asn Tyr Glu Leu
305 310 315 320

Thr Gln Ala Met Leu Glu Ile Ile Arg Asn Gly Gly Leu Gly Asn Gly
325 330 335

```
Gly Thr Asn Phe Asp Ala Lys Ile Arg Arg Asn Ser Thr Asp Leu Glu
            340                 345                 350

Asp Leu Phe Ile Ala His Ile Ser Gly Met Asp Ala Met Ala Arg Ala
        355                 360                 365

Leu Leu Asn Ala Ala Ala Ile Leu Glu Glu Ser Glu Leu Pro Ala Met
    370                 375                 380

Lys Lys Glu Arg Tyr Ala Ser Phe Asp Ser Gly Ile Gly Lys Asp Phe
385                 390                 395                 400

Glu Asp Gly Lys Leu Thr Leu Glu Gln Ala Tyr Glu Tyr Gly Lys Lys
                405                 410                 415

Val Glu Glu Pro Lys Gln Thr Ser Gly Lys Gln Glu Lys Tyr Glu Thr
            420                 425                 430

Ile Val Ala Leu Tyr Ala Lys
        435
```

<210> SEQ ID NO 99
<211> LENGTH: 1317
<212> TYPE: DNA
<213> ORGANISM: Unknown
<220> FEATURE:
<223> OTHER INFORMATION: Obtained from environmental sample

<400> SEQUENCE: 99

```
atgactaaag agtatttccc taccattggc aagattccct ttgagggacc tgaaagcaag      60

aacccgcttg cattccatta ctatgagccc gaccgcctgg tcatgggcaa gaagatgaaa     120

gactggctgc gtttcgccat ggcctggtgg cacaccctgg gccaggcctc cggcgaccag     180

ttcggcggcc agacccgcca ctatgcctgg gatgatccgg attgcccgta tgcacgtgcc     240

aaagccaagg ccgacgccgg tttcgaaatc atgcagaaac tgggcattga attcttctgc     300

ttccacgaca tcgacctggt cgaggatgcc gatgaaatcg ccgagtacga ggcccggatg     360

aaggacatca ccgactatct gctcgtcaag atgaaagaga ccggcatcaa gaacctttgg     420

ggaacggcca acgtatttgg ccacaagcgc tacatgaacg gcgccgccac caaccccgat     480

ttcgacgtgc tggcccgtgc cgccgtccag atcaagaacg ccatcgacgc caccatcaag     540

ttgggcggtc agaactatgt gttctggggc ggccgtgaag gctaccagac cctgctcaat     600

acccagatgc agcgcgagaa ggaacacatg ggccgtatgt tggcactggc ccgcgactat     660

ggccgtgcac acggtttcaa gggcacgttc ctcatcgagc ccaaaccgat ggagccgacc     720

aagcaccagt acgatcagga tacggaaacc gtcatcggct tcctgcgccg ccatggcctc     780

gacaaggact tcaaggtcaa catcgaggtg aaccatgcta ccctggcggg ccacaccttc     840

gagcacgagc tggcttgcgc cgtcgaccac ggcatgctgg gcagcatcga cgccaaccgg     900

ggtgatgccc agaacggctg ggacaccgac cagttcccga tcgataacta tgagctgacg     960

ctggccatgc tccagatcat ccgcaacggc ggcctggcac ccggcggctc gaacttcgat    1020

gcgaagctgc gtcgcaactc caccgatccg gaagatatct tcatcgcgca catcagcgcc    1080

atggatgcca tggcccgcgc cctggtcaat gctgtcgcca ttctcgagga atcgcccatc    1140

ccggccatgg tcagggaacg ttacgcctcg ttcgacagcg gaaagggcag ggaatatgag    1200

gaaggcaggc tgtctctcga agacatcgtg gcctatgcca aagcccacgg cgaaccgaaa    1260

cagatttccg gcaagcagga actctacgaa accatcgtgg ctctctattg caagtag       1317
```

<210> SEQ ID NO 100
<211> LENGTH: 438

<212> TYPE: PRT
<213> ORGANISM: Unknown
<220> FEATURE:
<223> OTHER INFORMATION: Obtained from environmental sample

<400> SEQUENCE: 100

```
Met Thr Lys Glu Tyr Phe Pro Thr Ile Gly Lys Ile Pro Phe Glu Gly
1               5                   10                  15

Pro Glu Ser Lys Asn Pro Leu Ala Phe His Tyr Tyr Glu Pro Asp Arg
            20                  25                  30

Leu Val Met Gly Lys Lys Met Lys Asp Trp Leu Arg Phe Ala Met Ala
        35                  40                  45

Trp Trp His Thr Leu Gly Gln Ala Ser Gly Asp Gln Phe Gly Gly Gln
    50                  55                  60

Thr Arg His Tyr Ala Trp Asp Asp Pro Asp Cys Pro Tyr Ala Arg Ala
65                  70                  75                  80

Lys Ala Lys Ala Asp Ala Gly Phe Glu Ile Met Gln Lys Leu Gly Ile
                85                  90                  95

Glu Phe Phe Cys Phe His Asp Ile Asp Leu Val Glu Asp Ala Asp Glu
            100                 105                 110

Ile Ala Glu Tyr Glu Ala Arg Met Lys Asp Ile Thr Asp Tyr Leu Leu
        115                 120                 125

Val Lys Met Lys Glu Thr Gly Ile Lys Asn Leu Trp Gly Thr Ala Asn
    130                 135                 140

Val Phe Gly His Lys Arg Tyr Met Asn Gly Ala Ala Thr Asn Pro Asp
145                 150                 155                 160

Phe Asp Val Leu Ala Arg Ala Ala Val Gln Ile Lys Asn Ala Ile Asp
                165                 170                 175

Ala Thr Ile Lys Leu Gly Gly Gln Asn Tyr Val Phe Trp Gly Gly Arg
            180                 185                 190

Glu Gly Tyr Gln Thr Leu Leu Asn Thr Gln Met Gln Arg Glu Lys Glu
        195                 200                 205

His Met Gly Arg Met Leu Ala Leu Ala Arg Asp Tyr Gly Arg Ala His
    210                 215                 220

Gly Phe Lys Gly Thr Phe Leu Ile Glu Pro Lys Pro Met Glu Pro Thr
225                 230                 235                 240

Lys His Gln Tyr Asp Gln Asp Thr Glu Thr Val Ile Gly Phe Leu Arg
                245                 250                 255

Arg His Gly Leu Asp Lys Asp Phe Lys Val Asn Ile Glu Val Asn His
            260                 265                 270

Ala Thr Leu Ala Gly His Thr Phe Glu His Glu Leu Ala Cys Ala Val
        275                 280                 285

Asp His Gly Met Leu Gly Ser Ile Asp Ala Asn Arg Gly Asp Ala Gln
    290                 295                 300

Asn Gly Trp Asp Thr Asp Gln Phe Pro Ile Asp Asn Tyr Glu Leu Thr
305                 310                 315                 320

Leu Ala Met Leu Gln Ile Ile Arg Asn Gly Gly Leu Ala Pro Gly Gly
                325                 330                 335

Ser Asn Phe Asp Ala Lys Leu Arg Arg Asn Ser Thr Asp Pro Glu Asp
            340                 345                 350

Ile Phe Ile Ala His Ile Ser Ala Met Asp Ala Met Ala Arg Ala Leu
        355                 360                 365

Val Asn Ala Val Ala Ile Leu Glu Glu Ser Pro Ile Pro Ala Met Val
    370                 375                 380
```

```
Arg Glu Arg Tyr Ala Ser Phe Asp Ser Gly Lys Gly Arg Glu Tyr Glu
385                 390                 395                 400

Glu Gly Arg Leu Ser Leu Glu Asp Ile Val Ala Tyr Ala Lys Ala His
                405                 410                 415

Gly Glu Pro Lys Gln Ile Ser Gly Lys Gln Glu Leu Tyr Glu Thr Ile
            420                 425                 430

Val Ala Leu Tyr Cys Lys
        435


<210> SEQ ID NO 101
<211> LENGTH: 1317
<212> TYPE: DNA
<213> ORGANISM: Unknown
<220> FEATURE:
<223> OTHER INFORMATION: Obtained from environmental sample

<400> SEQUENCE: 101

atggcaaaag agtatttccc gcagatcgga aagatcggct ttgagggtcc tgcaagcaag      60

aacccgctgg cattccatta ttatgacgcc gagcgcgtgg tgatgggtaa acccatgaaa     120

gactggttta aattcgccct cgcgtggtgg cacagcctcg gccaggcctc cggcgacccg     180

ttcggcggcc agacccgctc ctacgagtgg gacaagggcg aatgccccta ctgccgcgcc     240

cgcgccaagg cggacgccgg cttcgagatc atgcaaaagc tcggcatcgg ctatttctgc     300

ttccacgacg tcgacctcat cgaagacacg gacgacatcg ccgaatatga ggcccgcctc     360

aaggacatca cggactacct gctcgaaagg atgcaggaaa ccggcatcaa gaacctctgg     420

ggcacggcca atgtcttcgg tcacaagcgc tacatgaacg gcgccggcac caatccgcag     480

ttcgacatcg tcgcccgcgc tgccgtccag atcaagaacg ccctcgacgc caccatcaag     540

ctcggtggct cgaactacgt cttctggggc ggccgcgaag gttattacac gctgctcaac     600

acccagatgc agcgcgagaa agaccacctc gccaagctcc tcaccgccgc ccgcgactat     660

gcccgcgcca agggcttcca gggcaccttc ctgatcgagc ccaagccgat ggagccgacc     720

aagcaccagt acgatgtcga cacggagact gtaatcggat tcctccgcgc caacggactg     780

gacaaggact tcaaggtcaa catcgaggtc aaccacgcca ccctcgccgg ccataccttc     840

gagcatgagc tgaccgtcgc ccgcgagaac ggattcctcg gcagcatcga cgccaaccgc     900

ggtgacgccc agaacggctg ggacaccgac cagttccccg tggacgccta cgacctcacc     960

caggccatga tgcaggtgct cctgaacggc ggtttcggca acggcggcac caatttcgac    1020

gccaagctcc gtcgcagctc caccgatccc gaggacatct tcatcgccca catcagcgcg    1080

atggacgcca tggcccacgc cctgctgaac gccgcggcca ttctcgagga gagcccgctg    1140

cccgcgatgg tcaaggagcg ttacgcctcc ttcgacagcg gtctcggcaa gcagttcgag    1200

gagggaaagg ccacgctgga ggacctctac gactacgcca aggcccatgg cgagcccgtc    1260

gccgcctccg gcaagcagga actgtgtgaa acttacctga atctgtatgc aaagtaa       1317


<210> SEQ ID NO 102
<211> LENGTH: 438
<212> TYPE: PRT
<213> ORGANISM: Unknown
<220> FEATURE:
<223> OTHER INFORMATION: Obtained from environmental sample

<400> SEQUENCE: 102

Met Ala Lys Glu Tyr Phe Pro Gln Ile Gly Lys Ile Gly Phe Glu Gly
1               5                   10                  15
```

```
Pro Ala Ser Lys Asn Pro Leu Ala Phe His Tyr Tyr Asp Ala Glu Arg
            20                  25                  30

Val Val Met Gly Lys Pro Met Lys Asp Trp Phe Lys Phe Ala Leu Ala
        35                  40                  45

Trp Trp His Ser Leu Gly Gln Ala Ser Gly Asp Pro Phe Gly Gly Gln
    50                  55                  60

Thr Arg Ser Tyr Glu Trp Asp Lys Gly Glu Cys Pro Tyr Cys Arg Ala
65                  70                  75                  80

Arg Ala Lys Ala Asp Ala Gly Phe Glu Ile Met Gln Lys Leu Gly Ile
                85                  90                  95

Gly Tyr Phe Cys Phe His Asp Val Asp Leu Ile Glu Asp Thr Asp Asp
            100                 105                 110

Ile Ala Glu Tyr Glu Ala Arg Leu Lys Asp Ile Thr Asp Tyr Leu Leu
        115                 120                 125

Glu Arg Met Gln Glu Thr Gly Ile Lys Asn Leu Trp Gly Thr Ala Asn
    130                 135                 140

Val Phe Gly His Lys Arg Tyr Met Asn Gly Ala Gly Thr Asn Pro Gln
145                 150                 155                 160

Phe Asp Ile Val Ala Arg Ala Ala Val Gln Ile Lys Asn Ala Leu Asp
                165                 170                 175

Ala Thr Ile Lys Leu Gly Gly Ser Asn Tyr Val Phe Trp Gly Gly Arg
            180                 185                 190

Glu Gly Tyr Tyr Thr Leu Leu Asn Thr Gln Met Gln Arg Glu Lys Asp
        195                 200                 205

His Leu Ala Lys Leu Leu Thr Ala Ala Arg Asp Tyr Ala Arg Ala Lys
    210                 215                 220

Gly Phe Gln Gly Thr Phe Leu Ile Glu Pro Lys Pro Met Glu Pro Thr
225                 230                 235                 240

Lys His Gln Tyr Asp Val Asp Thr Glu Thr Val Ile Gly Phe Leu Arg
                245                 250                 255

Ala Asn Gly Leu Asp Lys Asp Phe Lys Val Asn Ile Glu Val Asn His
            260                 265                 270

Ala Thr Leu Ala Gly His Thr Phe Glu His Glu Leu Thr Val Ala Arg
        275                 280                 285

Glu Asn Gly Phe Leu Gly Ser Ile Asp Ala Asn Arg Gly Asp Ala Gln
    290                 295                 300

Asn Gly Trp Asp Thr Asp Gln Phe Pro Val Asp Ala Tyr Asp Leu Thr
305                 310                 315                 320

Gln Ala Met Met Gln Val Leu Leu Asn Gly Gly Phe Gly Asn Gly Gly
                325                 330                 335

Thr Asn Phe Asp Ala Lys Leu Arg Arg Ser Ser Thr Asp Pro Glu Asp
            340                 345                 350

Ile Phe Ile Ala His Ile Ser Ala Met Asp Ala Met Ala His Ala Leu
        355                 360                 365

Leu Asn Ala Ala Ala Ile Leu Glu Glu Ser Pro Leu Pro Ala Met Val
    370                 375                 380

Lys Glu Arg Tyr Ala Ser Phe Asp Ser Gly Leu Gly Lys Gln Phe Glu
385                 390                 395                 400

Glu Gly Lys Ala Thr Leu Glu Asp Leu Tyr Asp Tyr Ala Lys Ala His
                405                 410                 415

Gly Glu Pro Val Ala Ala Ser Gly Lys Gln Glu Leu Cys Glu Thr Tyr
            420                 425                 430

Leu Asn Leu Tyr Ala Lys
```

435

<210> SEQ ID NO 103
<211> LENGTH: 1317
<212> TYPE: DNA
<213> ORGANISM: Unknown
<220> FEATURE:
<223> OTHER INFORMATION: Obtained from environmental sample

<400> SEQUENCE: 103
atgacaaaag agtatttccc taccatcggc aagatcccct ttgagggacc cgagagcaaa 60 aacccctcg cttttcatta ctatgagccc gaccgcctgg tcatgggcaa gaagatgaaa 120
gactggctgc gtttcgccat ggcctggtgg cacaccctgg gccaggcctc cggcgaccag 180
tttggcggcc agacccgcca ctatgcctgg gatgatccgg attgcccgta tgcacgtgcc 240
aaagccaagg ccgacgccgg tttcgaaatc atgcagaaac tgggcattga attcttctgc 300
ttccacgaca tcgacctgat cgaggatacc gatgacatcg tcgagtatga ggcccggatg 360
aaggacatca ccgactatct gctggtcaag atgaaagaga ccggcatcaa gaatctctgg 420
ggaacggcca acgtattcgg gcacaagcgc tatatgaacg gcgctgccac caaccccgat 480
ttcgacgtgc tggcccgtgc cgccgtccag atcaagaacg ccatcgacgc caccatcaag 540
ctgggcggcc agaattatgt gttctggggc gggcgtgaag gctaccagag cctgctcaat 600
acccagatgc agcgcgaaaa ggaacacatg ggccgtatgt tggcactagc ccgcgactat 660
ggccgtgcac acggtttcaa gggcacgttc ctcatcgagc ccaaaccgat ggagccgacc 720
aagcaccagt acgatcagga tacggagacc gtcatcggtt ttctgcgccg ccatggcctc 780
gacaaggact tcaaggtcaa catcgaggtg aaccatgcta ccctggcggg ccacaccttc 840
gagcacgagc tggcctgcgc cgtcgaccac ggcatgctgg gcagtattga cgccaaccgc 900
ggtgacgccc agaacggctg ggacaccgac cagttcccga tcgataacta tgagctgacg 960
ctggccatgc tccagatcat ccgcaacggc ggcctggcac ccggcggctc gaacttcgat 1020
gcgaagctgc gtcgcaactc caccgatccg gaagatatct tcatcgcgca catcagcgcc 1080
atggatgcca tggcccgcgc cctggtcaac gctgtcgcca ttcttgagga atcgcccatt 1140
ccggacatgg tcaaggagcg ctacgcttcg ttcgacagcg gaaaaggcag ggagtacgaa 1200
gaggggaaac tttccttcga ggacctcgtg gcctatgcca aagcccacgg cgaaccgaaa 1260
cagatttccg gcaagcagga actctacgaa accatcgtgg ctctctattg caagtag 1317

<210> SEQ ID NO 104
<211> LENGTH: 438
<212> TYPE: PRT
<213> ORGANISM: Unknown
<220> FEATURE:
<223> OTHER INFORMATION: Obtained from environmental sample

<400> SEQUENCE: 104

Met Thr Lys Glu Tyr Phe Pro Thr Ile Gly Lys Ile Pro Phe Glu Gly
1 5 10 15

Pro Glu Ser Lys Asn Pro Leu Ala Phe His Tyr Tyr Glu Pro Asp Arg
20 25 30

Leu Val Met Gly Lys Lys Met Lys Asp Trp Leu Arg Phe Ala Met Ala
35 40 45

Trp Trp His Thr Leu Gly Gln Ala Ser Gly Asp Gln Phe Gly Gly Gln
50 55 60

Thr Arg His Tyr Ala Trp Asp Asp Pro Asp Cys Pro Tyr Ala Arg Ala

```
65                  70                  75                  80

Lys Ala Lys Ala Asp Ala Gly Phe Glu Ile Met Gln Lys Leu Gly Ile
                85                  90                  95

Glu Phe Phe Cys Phe His Asp Ile Asp Leu Ile Glu Asp Thr Asp Asp
            100                 105                 110

Ile Val Glu Tyr Glu Ala Arg Met Lys Asp Ile Thr Asp Tyr Leu Leu
        115                 120                 125

Val Lys Met Lys Glu Thr Gly Ile Lys Asn Leu Trp Gly Thr Ala Asn
    130                 135                 140

Val Phe Gly His Lys Arg Tyr Met Asn Gly Ala Ala Thr Asn Pro Asp
145                 150                 155                 160

Phe Asp Val Leu Ala Arg Ala Ala Val Gln Ile Lys Asn Ala Ile Asp
                165                 170                 175

Ala Thr Ile Lys Leu Gly Gly Gln Asn Tyr Val Phe Trp Gly Gly Arg
            180                 185                 190

Glu Gly Tyr Gln Ser Leu Leu Asn Thr Gln Met Gln Arg Glu Lys Glu
        195                 200                 205

His Met Gly Arg Met Leu Ala Leu Ala Arg Asp Tyr Gly Arg Ala His
    210                 215                 220

Gly Phe Lys Gly Thr Phe Leu Ile Glu Pro Lys Pro Met Glu Pro Thr
225                 230                 235                 240

Lys His Gln Tyr Asp Gln Asp Thr Glu Thr Val Ile Gly Phe Leu Arg
                245                 250                 255

Arg His Gly Leu Asp Lys Asp Phe Lys Val Asn Ile Glu Val Asn His
            260                 265                 270

Ala Thr Leu Ala Gly His Thr Phe Glu His Glu Leu Ala Cys Ala Val
        275                 280                 285

Asp His Gly Met Leu Gly Ser Ile Asp Ala Asn Arg Gly Asp Ala Gln
    290                 295                 300

Asn Gly Trp Asp Thr Asp Gln Phe Pro Ile Asp Asn Tyr Glu Leu Thr
305                 310                 315                 320

Leu Ala Met Leu Gln Ile Ile Arg Asn Gly Gly Leu Ala Pro Gly Gly
                325                 330                 335

Ser Asn Phe Asp Ala Lys Leu Arg Arg Asn Ser Thr Asp Pro Glu Asp
            340                 345                 350

Ile Phe Ile Ala His Ile Ser Ala Met Asp Ala Met Ala Arg Ala Leu
        355                 360                 365

Val Asn Ala Val Ala Ile Leu Glu Glu Ser Pro Ile Pro Asp Met Val
    370                 375                 380

Lys Glu Arg Tyr Ala Ser Phe Asp Ser Gly Lys Gly Arg Glu Tyr Glu
385                 390                 395                 400

Glu Gly Lys Leu Ser Phe Glu Asp Leu Val Ala Tyr Ala Lys Ala His
                405                 410                 415

Gly Glu Pro Lys Gln Ile Ser Gly Lys Gln Glu Leu Tyr Glu Thr Ile
            420                 425                 430

Val Ala Leu Tyr Cys Lys
        435
```

<210> SEQ ID NO 105
<211> LENGTH: 1317
<212> TYPE: DNA
<213> ORGANISM: Unknown
<220> FEATURE:
<223> OTHER INFORMATION: Obtained from environmental sample

<400> SEQUENCE: 105

```
atgacaaaag agtatttccc taccatcggc aagatcccct ttgagggacc cgagagcaaa      60

aaccccctcg cttttcatta ctatgagccc gaccgcctgg tcatgggcaa gaagatgaaa     120

gactggctgc gtttcgccat ggcctggtgg cacaccctgg gccaggcctc cggcgaccag     180

tttggcggcc agacccgcca ctatgcctgg gatgatccgg attgcccgta tgcacgtgcc     240

aaagccaagg ccgacgccgg tttcgaaatc atgcagaaac tgggcattga attcttctgc     300

ttccacgaca tcgacctgat cgaggatacc gatgacatcg tcgagtatga ggcccggatg     360

aaggacatca ccgactatct gctggtcaag atgaaagaga ccggcatcaa gaatctctgg     420

ggaacggcca acgtattcgg gcacaagcgc tatatgaacg gcgctgccac caaccccgat     480

ttcgacgtgc tggcccgtgc cgccgcccag atcaagaacg ccatcgacgc caccatcaag     540

ctgggcggcc agaattatgt gttctggggc gggcgtgaag gctaccagag cctgctcaat     600

acccagatgc agcgcgaaaa ggaacacatg ggccgtatgt tggcactagc ccgcgactat     660

ggccgtgcac acggtttcaa gggcacgctc ctcatcgagc ccaaaccgat ggagccgacc     720

aagcaccagt acgatcagga tacggagacc gtcatcggtt ttctgcgccg ccatggcctc     780

gacaaggact tcaaggtcaa catcgaggtg aaccatgcta ccctggcggg ccacaccttc     840

gagcacgagc tggcctgcgc cgtcgaccac ggcatgctgg gcagtattga cgccaaccgc     900

ggtgacgccc aggacggctg ggacaccgac cagttcccga tcgataacta tgagctgacg     960

ctggccatgc tccagatcat ccgcaacggc ggcctggcac ccggcggctc gaacttcgat    1020

gcgaagctgc gtcgcaactc caccgatccg gaagatatct tcatcgcgca catcagcgcc    1080

atggatgcca tggcccgcgc cctggtcaac gctgtcgcca ttcttgagga atcgcccatt    1140

ccggacatgg tcaaggagcg ctacgcttcg ttcgacagcg gaaaaggcag ggagtacgaa    1200

gaggggaaac tttccttcga ggacctcgtg gcctatgcca aagcccacgg cgaaccgaaa    1260

cagatttccg gcaagcagga actctacgaa accatcgtgg ctctctattg caagtag       1317
```

<210> SEQ ID NO 106
<211> LENGTH: 438
<212> TYPE: PRT
<213> ORGANISM: Unknown
<220> FEATURE:
<223> OTHER INFORMATION: Obtained from environmental sample

<400> SEQUENCE: 106

```
Met Thr Lys Glu Tyr Phe Pro Thr Ile Gly Lys Ile Pro Phe Glu Gly
1               5                   10                  15

Pro Glu Ser Lys Asn Pro Leu Ala Phe His Tyr Tyr Glu Pro Asp Arg
            20                  25                  30

Leu Val Met Gly Lys Lys Met Lys Asp Trp Leu Arg Phe Ala Met Ala
        35                  40                  45

Trp Trp His Thr Leu Gly Gln Ala Ser Gly Asp Gln Phe Gly Gly Gln
    50                  55                  60

Thr Arg His Tyr Ala Trp Asp Asp Pro Asp Cys Pro Tyr Ala Arg Ala
65                  70                  75                  80

Lys Ala Lys Ala Asp Ala Gly Phe Glu Ile Met Gln Lys Leu Gly Ile
                85                  90                  95

Glu Phe Phe Cys Phe His Asp Ile Asp Leu Ile Glu Asp Thr Asp Asp
            100                 105                 110

Ile Val Glu Tyr Glu Ala Arg Met Lys Asp Ile Thr Asp Tyr Leu Leu
        115                 120                 125
```

```
Val Lys Met Lys Glu Thr Gly Ile Lys Asn Leu Trp Gly Thr Ala Asn
    130                 135                 140

Val Phe Gly His Lys Arg Tyr Met Asn Gly Ala Ala Thr Asn Pro Asp
145                 150                 155                 160

Phe Asp Val Leu Ala Arg Ala Ala Ala Gln Ile Lys Asn Ala Ile Asp
                165                 170                 175

Ala Thr Ile Lys Leu Gly Gly Gln Asn Tyr Val Phe Trp Gly Gly Arg
            180                 185                 190

Glu Gly Tyr Gln Ser Leu Leu Asn Thr Gln Met Gln Arg Glu Lys Glu
        195                 200                 205

His Met Gly Arg Met Leu Ala Leu Ala Arg Asp Tyr Gly Arg Ala His
    210                 215                 220

Gly Phe Lys Gly Thr Leu Leu Ile Glu Pro Lys Pro Met Glu Pro Thr
225                 230                 235                 240

Lys His Gln Tyr Asp Gln Asp Thr Glu Thr Val Ile Gly Phe Leu Arg
                245                 250                 255

Arg His Gly Leu Asp Lys Asp Phe Lys Val Asn Ile Glu Val Asn His
            260                 265                 270

Ala Thr Leu Ala Gly His Thr Phe Glu His Glu Leu Ala Cys Ala Val
        275                 280                 285

Asp His Gly Met Leu Gly Ser Ile Asp Ala Asn Arg Gly Asp Ala Gln
    290                 295                 300

Asp Gly Trp Asp Thr Asp Gln Phe Pro Ile Asp Asn Tyr Glu Leu Thr
305                 310                 315                 320

Leu Ala Met Leu Gln Ile Ile Arg Asn Gly Gly Leu Ala Pro Gly Gly
                325                 330                 335

Ser Asn Phe Asp Ala Lys Leu Arg Arg Asn Ser Thr Asp Pro Glu Asp
            340                 345                 350

Ile Phe Ile Ala His Ile Ser Ala Met Asp Ala Met Ala Arg Ala Leu
        355                 360                 365

Val Asn Ala Val Ala Ile Leu Glu Glu Ser Pro Ile Pro Asp Met Val
    370                 375                 380

Lys Glu Arg Tyr Ala Ser Phe Asp Ser Gly Lys Gly Arg Glu Tyr Glu
385                 390                 395                 400

Glu Gly Lys Leu Ser Phe Glu Asp Leu Val Ala Tyr Ala Lys Ala His
                405                 410                 415

Gly Glu Pro Lys Gln Ile Ser Gly Lys Gln Glu Leu Tyr Glu Thr Ile
            420                 425                 430

Val Ala Leu Tyr Cys Lys
        435
```

<210> SEQ ID NO 107
<211> LENGTH: 1317
<212> TYPE: DNA
<213> ORGANISM: Unknown
<220> FEATURE:
<223> OTHER INFORMATION: Obtained from environmental sample

<400> SEQUENCE: 107

```
atgacaaaag agtatttccc taccatcggc aagatcccct ttgagggacc cgagagcaaa      60

aaccccctcg cttttcatta ctatgagccc gaccgcctgg tcatgggcaa gaagatgaaa     120

gactggctgc gtttcgccat ggcctggtgg cacaccctgg gccaggcctc cggcgaccag     180

tttggcggcc agacccgcca ctatgcctgg gatgatccgg attgcccgta tgcacgtgcc     240
```

aaagccaagg ccgacgccgg tttcgaaatc atgcagaaac tgggcattga attcttctgc 300
ttccacgaca tcgacctgat cgaggatacc gatgacatcg tcgagtatga ggcccggatg 360
aaggacatca ccgactatct gctggtcaag atgaaagaga ccggcatcaa gaatctctgg 420
ggaacggcca acgtattcgg gcacaagcgc tatatgaacg gcgctgccac caaccccgat 480
ttcgacgtgc tggcccgtgc cgccgtccag atcaagaacg ccatcgacgc caccatcaag 540
ctgggcggcc agaattatgt gttctggggc gggcgtgaag gctaccagag cctgctcaat 600
acccagatgc agcgcgaaaa ggaacacatg ggccgtatgt tggcactagc ccgcgactat 660
ggccgtgcac acggtttcaa gggcacgttc ctcatcgagc ccaaaccgat ggagccgacc 720
aagcaccagt acgatcagga tacggagacc gtcatcggtt ttctgcgccg ccatggcctc 780
gacaaggact tcaaggtcaa catcgaggtg aaccatgcta ccctggcggg ccacaccttc 840
gagcacgagc tggcctgcgc cgtcgaccac ggcatgctgg gcagtattga cgccaaccgc 900
ggtgacgccc agaacggctg ggacaccgac cagttcccga tcgataacta tgagctgacg 960
ctggccatgc tccagatcat ccgcaacggc ggcctggcac ccggcggctc gaacttcgat 1020
gcgaagctgc gtcgcaactc caccgatccg gaagatgtct tcatcgcgca catcagcgcc 1080
atggatgcca tggcccgcgc cctggtcaac gctgtcgcca ttcttgagga atcgcccatt 1140
ccggacatgg tcaaggagcg ctacgcttcg ttcgacagcg gaaaaggcag ggagtacgaa 1200
gaggggaaac tttccttcga ggacctcgtg gcctatgcca aagcccacgg cgaaccgaaa 1260
cagatttccg gcaagcagga actctacgaa accatcgtgg ctctctattg caagtag 1317

<210> SEQ ID NO 108
<211> LENGTH: 438
<212> TYPE: PRT
<213> ORGANISM: Unknown
<220> FEATURE:
<223> OTHER INFORMATION: Obtained from environmental sample

<400> SEQUENCE: 108

Met Thr Lys Glu Tyr Phe Pro Thr Ile Gly Lys Ile Pro Phe Glu Gly
1               5                   10                  15

Pro Glu Ser Lys Asn Pro Leu Ala Phe His Tyr Tyr Glu Pro Asp Arg
            20                  25                  30

Leu Val Met Gly Lys Lys Met Lys Asp Trp Leu Arg Phe Ala Met Ala
        35                  40                  45

Trp Trp His Thr Leu Gly Gln Ala Ser Gly Asp Gln Phe Gly Gly Gln
    50                  55                  60

Thr Arg His Tyr Ala Trp Asp Asp Pro Asp Cys Pro Tyr Ala Arg Ala
65                  70                  75                  80

Lys Ala Lys Ala Asp Ala Gly Phe Glu Ile Met Gln Lys Leu Gly Ile
                85                  90                  95

Glu Phe Phe Cys Phe His Asp Ile Asp Leu Ile Glu Asp Thr Asp Asp
            100                 105                 110

Ile Val Glu Tyr Glu Ala Arg Met Lys Asp Ile Thr Asp Tyr Leu Leu
        115                 120                 125

Val Lys Met Lys Glu Thr Gly Ile Lys Asn Leu Trp Gly Thr Ala Asn
    130                 135                 140

Val Phe Gly His Lys Arg Tyr Met Asn Gly Ala Ala Thr Asn Pro Asp
145                 150                 155                 160

Phe Asp Val Leu Ala Arg Ala Ala Val Gln Ile Lys Asn Ala Ile Asp
                165                 170                 175

```
Ala Thr Ile Lys Leu Gly Gly Gln Asn Tyr Val Phe Trp Gly Gly Arg
            180                 185                 190

Glu Gly Tyr Gln Ser Leu Leu Asn Thr Gln Met Gln Arg Glu Lys Glu
        195                 200                 205

His Met Gly Arg Met Leu Ala Leu Ala Arg Asp Tyr Gly Arg Ala His
    210                 215                 220

Gly Phe Lys Gly Thr Phe Leu Ile Glu Pro Lys Pro Met Glu Pro Thr
225                 230                 235                 240

Lys His Gln Tyr Asp Gln Asp Thr Glu Thr Val Ile Gly Phe Leu Arg
                245                 250                 255

Arg His Gly Leu Asp Lys Asp Phe Lys Val Asn Ile Glu Val Asn His
            260                 265                 270

Ala Thr Leu Ala Gly His Thr Phe Glu His Glu Leu Ala Cys Ala Val
        275                 280                 285

Asp His Gly Met Leu Gly Ser Ile Asp Ala Asn Arg Gly Asp Ala Gln
    290                 295                 300

Asn Gly Trp Asp Thr Asp Gln Phe Pro Ile Asp Asn Tyr Glu Leu Thr
305                 310                 315                 320

Leu Ala Met Leu Gln Ile Ile Arg Asn Gly Gly Leu Ala Pro Gly Gly
                325                 330                 335

Ser Asn Phe Asp Ala Lys Leu Arg Arg Asn Ser Thr Asp Pro Glu Asp
            340                 345                 350

Val Phe Ile Ala His Ile Ser Ala Met Asp Ala Met Ala Arg Ala Leu
        355                 360                 365

Val Asn Ala Val Ala Ile Leu Glu Glu Ser Pro Ile Pro Asp Met Val
    370                 375                 380

Lys Glu Arg Tyr Ala Ser Phe Asp Ser Gly Lys Gly Arg Glu Tyr Glu
385                 390                 395                 400

Glu Gly Lys Leu Ser Phe Glu Asp Leu Val Ala Tyr Ala Lys Ala His
                405                 410                 415

Gly Glu Pro Lys Gln Ile Ser Gly Lys Gln Glu Leu Tyr Glu Thr Ile
            420                 425                 430

Val Ala Leu Tyr Cys Lys
        435
```

<210> SEQ ID NO 109
<211> LENGTH: 1317
<212> TYPE: DNA
<213> ORGANISM: Unknown
<220> FEATURE:
<223> OTHER INFORMATION: Obtained from environmental sample

<400> SEQUENCE: 109

```
atggcaaaag agtatttccc gacaatcgga aagatcccct tcgagggcgt tgagagcaag      60

aatccccttg ctttccatta ttatgacgcc gagcgcgtgg tcatgggcaa gcccatgaag     120

gactggttca agttcgcgat ggcctggtgg cacaccctgg gccaggcttc cgcggacccg     180

ttcggcggcc agacccgctc ctacgagtgg gacaagggcg agtgccccta ctgccgcgcc     240

cgcgccaagg ctgacgccgg cttcgagatc atgcagaagc tcggaatcgg ctactattgc     300

ttccacgaca tcgacctggt ggaggacacc gaggacatcg ccgaatacga ggcccgcatg     360

aaggacatca ccgactacct cgtcgagaag cagaaggaga ccggcatcaa gaacctctgg     420

ggcaccgcga acgtgttcgg caacaagcgc tacatgaacg gcgccgccac gaacccgcag     480

ttcgacatcg tcgcccgcgc ggccctgcag atcaagaacg cgatcgatgc caccatcaag     540
```

-continued

```
ctcggcggca ccggctacgt gttctggggc ggccgggaag gctactacac cctgctgaac    600

acccagatgc agcgcgagaa ggaccacctc gccaagatgc tcaccgccgc ccgcgactac    660

gcccgcgcca acggcttcaa gggcaccttc ctcatcgagc ccaagccgat ggagcccacc    720

aagcaccaat acgacgtgga cacggagacc gtgatcggct tcctccgcgc caatggcctg    780

gacaaggact tcaaggtgaa catcgaggtg aaccacgcca ccctcgccgg ccacaccttc    840

gagcacgagc tcaccgtggc cgttgacaac ggcttcctcg gcagcatcga cgccaaccgc    900

ggcgacgccc agaacggctg ggataccgac cagttcccgg tggatccgta cgatctcacc    960

caggcgatga tccagatcat ccgcaacggc ggcttcaagg acggcggcac caacttcgac   1020

gccaggctcc gccgctcttc caccgacccg gaggacatct tcatcgccca catcagcgcg   1080

atggacgcca tggcccacgc cctgctgaac gccgccgccg tcatcgagga gagcccgctc   1140

tgcgagatgg tcgccaagcg ttacgcttcc ttcgacagcg gcctcggcaa aaagttcgag   1200

gaaggcaagg ccaccctcga ggaactctac gagtatgcca aggcgaacgg tgaggtcaag   1260

gccgaatccg gcaagcagga gctctacgag acccttctga acctctacgc gaaatag      1317


<210> SEQ ID NO 110
<211> LENGTH: 438
<212> TYPE: PRT
<213> ORGANISM: Unknown
<220> FEATURE:
<223> OTHER INFORMATION: Obtained from environmental sample

<400> SEQUENCE: 110

Met Ala Lys Glu Tyr Phe Pro Thr Ile Gly Lys Ile Pro Phe Glu Gly
1               5                   10                  15

Val Glu Ser Lys Asn Pro Leu Ala Phe His Tyr Tyr Asp Ala Glu Arg
            20                  25                  30

Val Val Met Gly Lys Pro Met Lys Asp Trp Phe Lys Phe Ala Met Ala
        35                  40                  45

Trp Trp His Thr Leu Gly Gln Ala Ser Ala Asp Pro Phe Gly Gly Gln
    50                  55                  60

Thr Arg Ser Tyr Glu Trp Asp Lys Gly Glu Cys Pro Tyr Cys Arg Ala
65                  70                  75                  80

Arg Ala Lys Ala Asp Ala Gly Phe Glu Ile Met Gln Lys Leu Gly Ile
                85                  90                  95

Gly Tyr Tyr Cys Phe His Asp Ile Asp Leu Val Glu Asp Thr Glu Asp
            100                 105                 110

Ile Ala Glu Tyr Glu Ala Arg Met Lys Asp Ile Thr Asp Tyr Leu Val
        115                 120                 125

Glu Lys Gln Lys Glu Thr Gly Ile Lys Asn Leu Trp Gly Thr Ala Asn
    130                 135                 140

Val Phe Gly Asn Lys Arg Tyr Met Asn Gly Ala Ala Thr Asn Pro Gln
145                 150                 155                 160

Phe Asp Ile Val Ala Arg Ala Ala Leu Gln Ile Lys Asn Ala Ile Asp
                165                 170                 175

Ala Thr Ile Lys Leu Gly Gly Thr Gly Tyr Val Phe Trp Gly Gly Arg
            180                 185                 190

Glu Gly Tyr Tyr Thr Leu Leu Asn Thr Gln Met Gln Arg Glu Lys Asp
        195                 200                 205

His Leu Ala Lys Met Leu Thr Ala Ala Arg Asp Tyr Ala Arg Ala Asn
    210                 215                 220

Gly Phe Lys Gly Thr Phe Leu Ile Glu Pro Lys Pro Met Glu Pro Thr
```

```
225                 230                 235                 240

Lys His Gln Tyr Asp Val Asp Thr Glu Thr Val Ile Gly Phe Leu Arg
                245                 250                 255

Ala Asn Gly Leu Asp Lys Asp Phe Lys Val Asn Ile Glu Val Asn His
            260                 265                 270

Ala Thr Leu Ala Gly His Thr Phe Glu His Glu Leu Thr Val Ala Val
        275                 280                 285

Asp Asn Gly Phe Leu Gly Ser Ile Asp Ala Asn Arg Gly Asp Ala Gln
    290                 295                 300

Asn Gly Trp Asp Thr Asp Gln Phe Pro Val Asp Pro Tyr Asp Leu Thr
305                 310                 315                 320

Gln Ala Met Ile Gln Ile Ile Arg Asn Gly Gly Phe Lys Asp Gly Gly
                325                 330                 335

Thr Asn Phe Asp Ala Arg Leu Arg Arg Ser Ser Thr Asp Pro Glu Asp
            340                 345                 350

Ile Phe Ile Ala His Ile Ser Ala Met Asp Ala Met Ala His Ala Leu
        355                 360                 365

Leu Asn Ala Ala Ala Val Ile Glu Glu Ser Pro Leu Cys Glu Met Val
    370                 375                 380

Ala Lys Arg Tyr Ala Ser Phe Asp Ser Gly Leu Gly Lys Lys Phe Glu
385                 390                 395                 400

Glu Gly Lys Ala Thr Leu Glu Glu Leu Tyr Glu Tyr Ala Lys Ala Asn
                405                 410                 415

Gly Glu Val Lys Ala Glu Ser Gly Lys Gln Glu Leu Tyr Glu Thr Leu
            420                 425                 430

Leu Asn Leu Tyr Ala Lys
        435


<210> SEQ ID NO 111
<211> LENGTH: 1317
<212> TYPE: DNA
<213> ORGANISM: Unknown
<220> FEATURE:
<223> OTHER INFORMATION: Obtained from environmental sample

<400> SEQUENCE: 111

atggcacaag cgtattttcc taccatcggg aaaatcccct tcgagggacc cgaaagcaag      60

aatcccctgg cattccatta ttatgagccc gaccgcctgg tcctgggcaa gaagatgaag     120

gactggctgc gtttcgccat ggcctggtgg cacacgctgg gccaggcttc cggcgaccag     180

ttcggcggcc agacccgcca ctacgcctgg gacgagcccg ccacgcccct ggaacgggcc     240

aaggccaagg cggatgccgg tttcgagatc atgcagaaac tgggcatcga attcttctgc     300

ttccacgatg tggacctcat cgaagagggc gccacgatcg aggaatacga gcagcggatg     360

cagcagatca cggattatct gctggtcaag atgaaagaga ccggcatccg caacctctgg     420

ggtacggcca acgtgttcgg acacgagcgc tacatgaacg gcgcggccac gaaccccgat     480

ttcgatgtcg tggcccgcgc ggccgtgcag atcaagacgg ccatcgacgc caccatcaag     540

ttgggcggcg agaactatgt gttctggggc ggccgggaag gctatatgag cctgctcaat     600

acgcagatgc accgcgagaa gctgcatctg ggcaagatgc tcgccgcggc ccgcgactac     660

ggacgcgccc acggcttcaa ggggaccttc ctcatcgaac ccaagccgat ggaacccacc     720

aagcatcagt atgaccagga tacggagacg gtcatcggtt tcctgcgccg ctacggcctg     780

gacgaagact tcaaggtgaa catcgaggtc aaccacgcta cgctggccgg ccataccttc     840
```

-continued gaacacgaac tggccacggc ggtcgatgcc ggcctgctgg gcagcatcga cgccaaccgc 900
ggcgacgccc agaacggctg ggataccgac cagttcccga tcgacaacta cgaactgacc 960
ctggcgatgc tgcaggtcat ccgcaacggc ggtctggccc cgggcggctc gaatttcgat 1020
gccaagctcc gccggaactc caccgatccg gaagacatct tcattgccca catcagcgcg 1080
atggatgcga tggcgcgggc cctgctcaat gcggccgccc tctgcgagac gtccccgatt 1140
ccggcgatgg tcaaggcgcg ttacgcttcg ttcgacagcg gcgccggcaa ggatttcgaa 1200
gagggaagga tgacgctgga agacctcgtg gcctatgcca ggacccacgg cgagccgaag 1260
cggacctcgg gcaagcagga actctatgag accctcgtgg cgctttattg caaatag 1317

<210> SEQ ID NO 112
<211> LENGTH: 438
<212> TYPE: PRT
<213> ORGANISM: Unknown
<220> FEATURE:
<223> OTHER INFORMATION: Obtained from environmental sample

<400> SEQUENCE: 112

Met Ala Gln Ala Tyr Phe Pro Thr Ile Gly Lys Ile Pro Phe Glu Gly
1 5 10 15

Pro Glu Ser Lys Asn Pro Leu Ala Phe His Tyr Tyr Glu Pro Asp Arg
20 25 30

Leu Val Leu Gly Lys Lys Met Lys Asp Trp Leu Arg Phe Ala Met Ala
35 40 45

Trp Trp His Thr Leu Gly Gln Ala Ser Gly Asp Gln Phe Gly Gly Gln
50 55 60

Thr Arg His Tyr Ala Trp Asp Glu Pro Ala Thr Pro Leu Glu Arg Ala
65 70 75 80

Lys Ala Lys Ala Asp Ala Gly Phe Glu Ile Met Gln Lys Leu Gly Ile
85 90 95

Glu Phe Phe Cys Phe His Asp Val Asp Leu Ile Glu Glu Gly Ala Thr
100 105 110

Ile Glu Glu Tyr Glu Gln Arg Met Gln Gln Ile Thr Asp Tyr Leu Leu
115 120 125

Val Lys Met Lys Glu Thr Gly Ile Arg Asn Leu Trp Gly Thr Ala Asn
130 135 140

Val Phe Gly His Glu Arg Tyr Met Asn Gly Ala Ala Thr Asn Pro Asp
145 150 155 160

Phe Asp Val Val Ala Arg Ala Ala Val Gln Ile Lys Thr Ala Ile Asp
165 170 175

Ala Thr Ile Lys Leu Gly Gly Glu Asn Tyr Val Phe Trp Gly Gly Arg
180 185 190

Glu Gly Tyr Met Ser Leu Leu Asn Thr Gln Met His Arg Glu Lys Leu
195 200 205

His Leu Gly Lys Met Leu Ala Ala Ala Arg Asp Tyr Gly Arg Ala His
210 215 220

Gly Phe Lys Gly Thr Phe Leu Ile Glu Pro Lys Pro Met Glu Pro Thr
225 230 235 240

Lys His Gln Tyr Asp Gln Asp Thr Glu Thr Val Ile Gly Phe Leu Arg
245 250 255

Arg Tyr Gly Leu Asp Glu Asp Phe Lys Val Asn Ile Glu Val Asn His
260 265 270

Ala Thr Leu Ala Gly His Thr Phe Glu His Glu Leu Ala Thr Ala Val
275 280 285

Asp Ala Gly Leu Leu Gly Ser Ile Asp Ala Asn Arg Gly Asp Ala Gln
    290                 295                 300

Asn Gly Trp Asp Thr Asp Gln Phe Pro Ile Asp Asn Tyr Glu Leu Thr
305                 310                 315                 320

Leu Ala Met Leu Gln Val Ile Arg Asn Gly Gly Leu Ala Pro Gly Gly
                325                 330                 335

Ser Asn Phe Asp Ala Lys Leu Arg Arg Asn Ser Thr Asp Pro Glu Asp
            340                 345                 350

Ile Phe Ile Ala His Ile Ser Ala Met Asp Ala Met Ala Arg Ala Leu
        355                 360                 365

Leu Asn Ala Ala Ala Leu Cys Glu Thr Ser Pro Ile Pro Ala Met Val
    370                 375                 380

Lys Ala Arg Tyr Ala Ser Phe Asp Ser Gly Ala Gly Lys Asp Phe Glu
385                 390                 395                 400

Glu Gly Arg Met Thr Leu Glu Asp Leu Val Ala Tyr Ala Arg Thr His
                405                 410                 415

Gly Glu Pro Lys Arg Thr Ser Gly Lys Gln Glu Leu Tyr Glu Thr Leu
            420                 425                 430

Val Ala Leu Tyr Cys Lys
        435

<210> SEQ ID NO 113
<211> LENGTH: 1317
<212> TYPE: DNA
<213> ORGANISM: Unknown
<220> FEATURE:
<223> OTHER INFORMATION: Obtained from environmental sample

<400> SEQUENCE: 113
atgaccaacg agtattttcc cggaatcggt gtgattccgt ttgaaggaca ggaaagcaag 60
aatcccctgg ctttccatta ttatgacgcc aaccgcgtag tgatgggcaa acccatgaag 120
gaatggttca aatttgccat ggcctggtgg catacgctgg ggcaggcatc ggccgatccc 180
ttcggcggac agacccgctc ctacgcatgg gacaagggcg agtgccctta ctgccgtgcc 240
cgccagaagg ccgacgccgg ctttgaactg atgcagaagc tgggaatcgg ctatttctgc 300
ttccacgatg tgaatatcat cgaggactgc gaggacattg ccgagtatga ggcccgtatg 360
aaggacatca cggactatct gctggtgaag atgaaggaaa cgggcatcaa gaatctgtgg 420
ggcacggcca acgtcttcgg ccacaagcgc tatatgaacg gcgccgccac caacccgcaa 480
ttcgacgtgg tagcccgcgc tgcggtccag atcaagaacg ccctggacgc caccatcaag 540
ctgggcggca gcaattatgt gttctggggc ggccgggaag gctactacac ccttttgaac 600
acgcagatgc agcgggagaa ggaccacctg gcccagatgc tcaaggcggc ccgcgactat 660
gcccgcggca agggattcaa gggcacgttc ctcattgagc ccaagcccat ggagcccacc 720
aagcaccagt acgacgtaga tacggagacc gtgattggtt tcctgcgcgc caacgggctg 780
gacaaggact tcaaggtgaa tatcgaagtg aaccacgcca ccctggccgg ccataccttc 840
gagcacgagc tcaccgtggc ccgcgaaaac ggcttcctgg gcagcatcga cgccaaccgc 900
ggagacgccc agaacggctg ggatacagac cagttccccg tggacgcctt tgacctcacc 960
caggccatga tgcaggtcct gctcaacggc ggattcggca acggcggcac caacttcgac 1020
gccaaactgc gccgttcctc cacggatccc gaggacatct tcatcgccca catcagcgcc 1080
atggacgcca tggcccacgc cctcctgaac gccgccgcca tcctggaaga gagccccatg 1140

```
ccgggcatgg tgaaggagcg ctacgcttcc ttcgacaatg gccttggcaa gaagttcgag   1200

gaaggaaagg ccacgctgga agagctgtac gactatgcca agaagaacgg cgagcctgtg   1260

gccgcttccg gaaagcagga actgtacgaa acgctgctga acctgtacgc caagtaa      1317


<210> SEQ ID NO 114
<211> LENGTH: 438
<212> TYPE: PRT
<213> ORGANISM: Unknown
<220> FEATURE:
<223> OTHER INFORMATION: Obtained from environmental sample

<400> SEQUENCE: 114

Met Thr Asn Glu Tyr Phe Pro Gly Ile Gly Val Ile Pro Phe Glu Gly
1               5                   10                  15

Gln Glu Ser Lys Asn Pro Leu Ala Phe His Tyr Tyr Asp Ala Asn Arg
            20                  25                  30

Val Val Met Gly Lys Pro Met Lys Glu Trp Phe Lys Phe Ala Met Ala
        35                  40                  45

Trp Trp His Thr Leu Gly Gln Ala Ser Ala Asp Pro Phe Gly Gly Gln
    50                  55                  60

Thr Arg Ser Tyr Ala Trp Asp Lys Gly Glu Cys Pro Tyr Cys Arg Ala
65                  70                  75                  80

Arg Gln Lys Ala Asp Ala Gly Phe Glu Leu Met Gln Lys Leu Gly Ile
                85                  90                  95

Gly Tyr Phe Cys Phe His Asp Val Asn Ile Ile Glu Asp Cys Glu Asp
            100                 105                 110

Ile Ala Glu Tyr Glu Ala Arg Met Lys Asp Ile Thr Asp Tyr Leu Leu
        115                 120                 125

Val Lys Met Lys Glu Thr Gly Ile Lys Asn Leu Trp Gly Thr Ala Asn
    130                 135                 140

Val Phe Gly His Lys Arg Tyr Met Asn Gly Ala Ala Thr Asn Pro Gln
145                 150                 155                 160

Phe Asp Val Val Ala Arg Ala Ala Val Gln Ile Lys Asn Ala Leu Asp
                165                 170                 175

Ala Thr Ile Lys Leu Gly Gly Ser Asn Tyr Val Phe Trp Gly Gly Arg
            180                 185                 190

Glu Gly Tyr Tyr Thr Leu Leu Asn Thr Gln Met Gln Arg Glu Lys Asp
        195                 200                 205

His Leu Ala Gln Met Leu Lys Ala Ala Arg Asp Tyr Ala Arg Gly Lys
    210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Val Ile Gly Phe Leu Arg
                245                 250                 255

Ala Asn Gly Leu Asp Lys Asp Phe Lys Val Asn Ile Glu Val Asn His
            260                 265                 270

Ala Thr Leu Ala Gly His Thr Phe Glu His Glu Leu Thr Val Ala Arg
        275                 280                 285

Glu Asn Gly Phe Leu Gly Ser Ile Asp Ala Asn Arg Gly Asp Ala Gln
    290                 295                 300

Asn Gly Trp Asp Thr Asp Gln Phe Pro Val Asp Ala Phe Asp Leu Thr
305                 310                 315                 320

Gln Ala Met Met Gln Val Leu Leu Asn Gly Gly Phe Gly Asn Gly Gly
                325                 330                 335
```

```
Thr Asn Phe Asp Ala Lys Leu Arg Arg Ser Ser Thr Asp Pro Glu Asp
            340                 345                 350

Ile Phe Ile Ala His Ile Ser Ala Met Asp Ala Met Ala His Ala Leu
        355                 360                 365

Leu Asn Ala Ala Ala Ile Leu Glu Glu Ser Pro Met Pro Gly Met Val
    370                 375                 380

Lys Glu Arg Tyr Ala Ser Phe Asp Asn Gly Leu Gly Lys Lys Phe Glu
385                 390                 395                 400

Glu Gly Lys Ala Thr Leu Glu Glu Leu Tyr Asp Tyr Ala Lys Lys Asn
                405                 410                 415

Gly Glu Pro Val Ala Ala Ser Gly Lys Gln Glu Leu Tyr Glu Thr Leu
            420                 425                 430

Leu Asn Leu Tyr Ala Lys
        435
```

<210> SEQ ID NO 115
<211> LENGTH: 1317
<212> TYPE: DNA
<213> ORGANISM: Unknown
<220> FEATURE:
<223> OTHER INFORMATION: Obtained from environmental sample

<400> SEQUENCE: 115

```
atggcaaaag agtatttccc gactatcggc aagattccct tcgagggcgt cgaatccaag     60

aacccgatgg cattccacta ttatgacgcg aaacgcgtcg tgatgggcaa gcccatgaag    120

gactggctca agttcgcgat ggcctggtgg cacaccctgg gacaggcttc cggcgacccg    180

ttcggcggcc agacccgttc ctacgagtgg gacaagggcg agtgccccta ctgccgcgcc    240

aaggccaagg ccgacgccgg tttcgagatc atgcagaaac tgggcatcga gtactactgc    300

ttccatgaca tcgacctggt ggaggacacc gaggacatcg ccgagtacga ggcccgcatg    360

aaggacatca ccgactacct cgtcgagaag cagaaggaga ccggtatcaa gaacctctgg    420

ggcacggcca acgtgttcgg caacaagcgc tacatgaacg gcgccgccac gaacccgcag    480

ttcgacgtcg tcgcccgcgc cgccgtccag atcaagaacg ccatcgacgc caccatcaaa    540

ctcggcggca cctcttacgt gttctggggc ggccgtgaag gctactacac cctcctgaac    600

acccagatgc agcgcgagaa ggaccacctc gccaagatgc tcaccgccgc ccgcgactac    660

gcccgcgccc acggcttcaa gggcaccttc ctcatcgagc ccaagcccat ggagcccacc    720

aagcaccagt acgacgtgga cacggagacc gtgatcggct tcctccgcgc caacggcctg    780

gacaaggact tcaaggtcaa tatcgaagtg aaccacgcca ccctcgccgg ccacaccttc    840

gagcatgagc tcaccgtggc ggtcgataac ggcttcctcg gctccatcga cgccaaccgt    900

ggcgacgccc agaacggctg ggataccgac cagttccccg tggatccgta cgacctcacc    960

caggccatga tgcagatcat ccgcaacggc ggcttcaagg acggcggcac caacttcgac   1020

gccaaactcc gccgctcctc caccgacccg gaggacatct tcatcgccca catcagcgcg   1080

atggacgcca tggcccacgc gctcctgaac gccgccgccg tcatcgagga gagcccgctc   1140

tgcaagatgg tcgaggagcg ctacgcttcc ttcgacagcg gtctcggcaa gcagttcgag   1200

gaaggcaagg ccacccttga ggacctctac gagtatgcca agaagaacgg cgagcccgtc   1260

gtcgcttccg gcaagcagga gctctacgag acccttctga acctctacgc gaagtag      1317
```

<210> SEQ ID NO 116
<211> LENGTH: 438
<212> TYPE: PRT

```
<213> ORGANISM: Unknown
<220> FEATURE:
<223> OTHER INFORMATION: Obtained from environmental sample

<400> SEQUENCE: 116

Met Ala Lys Glu Tyr Phe Pro Thr Ile Gly Lys Ile Pro Phe Glu Gly
1               5                   10                  15

Val Glu Ser Lys Asn Pro Met Ala Phe His Tyr Tyr Asp Ala Lys Arg
            20                  25                  30

Val Val Met Gly Lys Pro Met Lys Asp Trp Leu Lys Phe Ala Met Ala
        35                  40                  45

Trp Trp His Thr Leu Gly Gln Ala Ser Gly Asp Pro Phe Gly Gly Gln
    50                  55                  60

Thr Arg Ser Tyr Glu Trp Asp Lys Gly Glu Cys Pro Tyr Cys Arg Ala
65                  70                  75                  80

Lys Ala Lys Ala Asp Ala Gly Phe Glu Ile Met Gln Lys Leu Gly Ile
                85                  90                  95

Glu Tyr Tyr Cys Phe His Asp Ile Asp Leu Val Glu Asp Thr Glu Asp
            100                 105                 110

Ile Ala Glu Tyr Glu Ala Arg Met Lys Asp Ile Thr Asp Tyr Leu Val
        115                 120                 125

Glu Lys Gln Lys Glu Thr Gly Ile Lys Asn Leu Trp Gly Thr Ala Asn
    130                 135                 140

Val Phe Gly Asn Lys Arg Tyr Met Asn Gly Ala Ala Thr Asn Pro Gln
145                 150                 155                 160

Phe Asp Val Val Ala Arg Ala Ala Val Gln Ile Lys Asn Ala Ile Asp
                165                 170                 175

Ala Thr Ile Lys Leu Gly Gly Thr Ser Tyr Val Phe Trp Gly Gly Arg
            180                 185                 190

Glu Gly Tyr Tyr Thr Leu Leu Asn Thr Gln Met Gln Arg Glu Lys Asp
        195                 200                 205

His Leu Ala Lys Met Leu Thr Ala Ala Arg Asp Tyr Ala Arg Ala His
    210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Val Ile Gly Phe Leu Arg
                245                 250                 255

Ala Asn Gly Leu Asp Lys Asp Phe Lys Val Asn Ile Glu Val Asn His
            260                 265                 270

Ala Thr Leu Ala Gly His Thr Phe Glu His Glu Leu Thr Val Ala Val
        275                 280                 285

Asp Asn Gly Phe Leu Gly Ser Ile Asp Ala Asn Arg Gly Asp Ala Gln
    290                 295                 300

Asn Gly Trp Asp Thr Asp Gln Phe Pro Val Asp Pro Tyr Asp Leu Thr
305                 310                 315                 320

Gln Ala Met Met Gln Ile Ile Arg Asn Gly Gly Phe Lys Asp Gly Gly
                325                 330                 335

Thr Asn Phe Asp Ala Lys Leu Arg Arg Ser Ser Thr Asp Pro Glu Asp
            340                 345                 350

Ile Phe Ile Ala His Ile Ser Ala Met Asp Ala Met Ala His Ala Leu
        355                 360                 365

Leu Asn Ala Ala Ala Val Ile Glu Glu Ser Pro Leu Cys Lys Met Val
    370                 375                 380

Glu Glu Arg Tyr Ala Ser Phe Asp Ser Gly Leu Gly Lys Gln Phe Glu
```

-continued 385 390 395 400

Glu Gly Lys Ala Thr Leu Glu Asp Leu Tyr Glu Tyr Ala Lys Lys Asn
405 410 415

Gly Glu Pro Val Val Ala Ser Gly Lys Gln Glu Leu Tyr Glu Thr Leu
420 425 430

Leu Asn Leu Tyr Ala Lys
435

<210> SEQ ID NO 117
<211> LENGTH: 1317
<212> TYPE: DNA
<213> ORGANISM: Unknown
<220> FEATURE:
<223> OTHER INFORMATION: Obtained from environmental sample

<400> SEQUENCE: 117
atgtcaactg agtatttccc tacaatcggc aagattccct tcgagggacc cgagagcaag 60
aaccccatgg ccttccacta ctatgaaccc gaaaagttgg tgatgggcaa gaagatgaag 120
gactggctgc gtttcgcaat ggcctggtgg cacacccttg gagccgcatc cggcgaccag 180
ttcggcggac agacccgcag ttacgcctgg gacaagggcg actgccctta cagccgcgcc 240
cgcgccaagg tcgacgccgg cttcgagatc atgcagaagc tcggcataga gttcttctgc 300
ttccatgaca tcgacctggt cgaggatacc gacgacatcg ccgagtatga agcccggatg 360
aaagacatca cggactatct gctggaaaag atggaggcta ccggcatcaa gaacctctgg 420
ggcacggcca atgtcttcgg tcacaagcgt tatatgaacg gtgcagccac aaaccccgat 480
ttcgcagtgg tcgcaagggc ggccgtgcag atcaagaacg ccatcgacgc caccatcaag 540
ctgggtggtg agaactatgt gttctggggt ggacgcgagg gttatatgag cctgctcaac 600
acccagatgc agagggagaa ggaacacctt gccaagatgc tcaccgccgc acgtgactat 660
gcacgcgcca aaggtttcaa gggcacgttc ctcatcgaac ccaagccgat ggaacccacc 720
aagcaccagt atgaccagga taccgagacc gttatcggat tcctccgcag ccacggcctg 780
gacaaggact tcaaggtcaa catcgaggtg aaccacgcca ccctggcggg ccataccttc 840
gagcacgaac tggccaccgc cgtcgacaac ggcatgctcg gcagcatcga cgccaaccgc 900
ggagacgccc agaacggctg ggacaccgac cagttcccga tcgacaactt cgagctcacg 960
cttgccatga tgcagataat ccgcaacggc ggcctggcac cgggcggttc gaacttcgac 1020
gcaaagctgc gccgcaattc caccgatccc gaggacatct tcatcgccca catcagcgcg 1080
atggacgcca tggcccgcgc cctcgtcaac gccgccgcca tcctcggcga gtcgcccgtt 1140
ccggctatgg tcaaggaccg ctatgcttcg ttcgactgcg gcaagggcaa ggacttcgaa 1200
gacggcaaac tgactctcga agacatcgtc gcctacgcca gggagaatgg cgagccgaaa 1260
cagatttccg gcaagcagga actctacgaa actatcgtcg ctctttactg caagtaa 1317

<210> SEQ ID NO 118
<211> LENGTH: 438
<212> TYPE: PRT
<213> ORGANISM: Unknown
<220> FEATURE:
<223> OTHER INFORMATION: Obtained from environmental sample

<400> SEQUENCE: 118

Met Ser Thr Glu Tyr Phe Pro Thr Ile Gly Lys Ile Pro Phe Glu Gly
1 5 10 15

Pro Glu Ser Lys Asn Pro Met Ala Phe His Tyr Tyr Glu Pro Glu Lys

-continued

```
            20                  25                  30

Leu Val Met Gly Lys Lys Met Lys Asp Trp Leu Arg Phe Ala Met Ala
        35                  40                  45

Trp Trp His Thr Leu Gly Ala Ala Ser Gly Asp Gln Phe Gly Gly Gln
    50                  55                  60

Thr Arg Ser Tyr Ala Trp Asp Lys Gly Asp Cys Pro Tyr Ser Arg Ala
65                  70                  75                  80

Arg Ala Lys Val Asp Ala Gly Phe Glu Ile Met Gln Lys Leu Gly Ile
                85                  90                  95

Glu Phe Phe Cys Phe His Asp Ile Asp Leu Val Glu Asp Thr Asp Asp
            100                 105                 110

Ile Ala Glu Tyr Glu Ala Arg Met Lys Asp Ile Thr Asp Tyr Leu Leu
        115                 120                 125

Glu Lys Met Glu Ala Thr Gly Ile Lys Asn Leu Trp Gly Thr Ala Asn
    130                 135                 140

Val Phe Gly His Lys Arg Tyr Met Asn Gly Ala Ala Thr Asn Pro Asp
145                 150                 155                 160

Phe Ala Val Val Ala Arg Ala Ala Val Gln Ile Lys Asn Ala Ile Asp
                165                 170                 175

Ala Thr Ile Lys Leu Gly Gly Glu Asn Tyr Val Phe Trp Gly Gly Arg
            180                 185                 190

Glu Gly Tyr Met Ser Leu Leu Asn Thr Gln Met Gln Arg Glu Lys Glu
        195                 200                 205

His Leu Ala Lys Met Leu Thr Ala Ala Arg Asp Tyr Ala Arg Ala Lys
    210                 215                 220

Gly Phe Lys Gly Thr Phe Leu Ile Glu Pro Lys Pro Met Glu Pro Thr
225                 230                 235                 240

Lys His Gln Tyr Asp Gln Asp Thr Glu Thr Val Ile Gly Phe Leu Arg
                245                 250                 255

Ser His Gly Leu Asp Lys Asp Phe Lys Val Asn Ile Glu Val Asn His
            260                 265                 270

Ala Thr Leu Ala Gly His Thr Phe Glu His Glu Leu Ala Thr Ala Val
        275                 280                 285

Asp Asn Gly Met Leu Gly Ser Ile Asp Ala Asn Arg Gly Asp Ala Gln
    290                 295                 300

Asn Gly Trp Asp Thr Asp Gln Phe Pro Ile Asp Asn Phe Glu Leu Thr
305                 310                 315                 320

Leu Ala Met Met Gln Ile Ile Arg Asn Gly Gly Leu Ala Pro Gly Gly
                325                 330                 335

Ser Asn Phe Asp Ala Lys Leu Arg Arg Asn Ser Thr Asp Pro Glu Asp
            340                 345                 350

Ile Phe Ile Ala His Ile Ser Ala Met Asp Ala Met Ala Arg Ala Leu
        355                 360                 365

Val Asn Ala Ala Ala Ile Leu Gly Glu Ser Pro Val Pro Ala Met Val
    370                 375                 380

Lys Asp Arg Tyr Ala Ser Phe Asp Cys Gly Lys Gly Lys Asp Phe Glu
385                 390                 395                 400

Asp Gly Lys Leu Thr Leu Glu Asp Ile Val Ala Tyr Ala Arg Glu Asn
                405                 410                 415

Gly Glu Pro Lys Gln Ile Ser Gly Lys Gln Glu Leu Tyr Glu Thr Ile
            420                 425                 430

Val Ala Leu Tyr Cys Lys
        435
```

<210> SEQ ID NO 119
<211> LENGTH: 1314
<212> TYPE: DNA
<213> ORGANISM: Unknown
<220> FEATURE:
<223> OTHER INFORMATION: Obtained from environmental sample

<400> SEQUENCE: 119
atgtcatatt ttcctactat cggtaacatc ccctttgagg gtgtagagag caagaatccc 60
cttgccttcc attattatga cgcttcccgc gtagttatgg gcaagcccat gaaggagtgg 120
ctcaagtttg ccatggcctg gtggcacacg ctgggtcagg catcggccga ccctttcggc 180
ggacaaaccc gcagctatgc ctgggacaaa ggcgagtgcc cctactgccg tgcccgtgcc 240
aaggccgacg ccggcttcga gctcatgcag aaactgggca tcgagtattt ctgctcccac 300
gacattgacc tcatcgagga ctgcgacgac attgcagagt acgaggcccg tctgaaggac 360
attacggact acctcctgga gaagatgaag aagaccggta tcaagaacct gtggggtacg 420
gccaatgtgt tcggtaacaa gcgttacatg aacggtgctg ctaccaaccc tcagtttgac 480
gttgtggccc gcgctgccgt ccagatcaag aacgccattg acgctaccat caagctgggc 540
ggttccaact atgtgttctg ggtggccgt gagggttact acacgcttct gaacacccag 600
atgcagcgtg agaagaatca cctggctgcc atgctcaagg ctgcccgcga ctatgcccgc 660
gccaacggtt tcaagggcac cttcctcatt gagcccaagc ccatggagcc caccaagcac 720
cagtacgacg tagacacgga gaccgtgatt ggattcctcc gcgccaacgg tctggagaag 780
gacttcaagg tgaacattga ggtgaaccac gctactcttg ccggtcacac cttcgagcac 840
gagctcaccg tggcccgtga gaacggcttc ctgggttcca ttgacgccaa ccgcggagat 900
gcccagaacg gctgggacac cgaccagttc ccggtagatg cctttgacct cacccaggcc 960
atgatgcaga ttctcctcaa cggaggctcc ggcaatggcg gtaccaactt tgacgccaag 1020
ctgcgccgtt cctccaccga ccccgaggac atcttcatcg cgcacatcag cgccatggat 1080
gccatggctc acgccctgct caatgcagct gccgtgctgg aggagagccc gctttgcaag 1140
atggtcaagg agcgttacgc ttccttcgac agcggtcttg gcaagcagtt cgaggaagga 1200
aaggctacgc tggaagatct gtatgcctat gccgtcaaga acggtgagcc cgtggtggct 1260
tccggcaagc aggaactgta cgaaaccttc ctgaacctct atgcaaaatg gtaa 1314

<210> SEQ ID NO 120
<211> LENGTH: 437
<212> TYPE: PRT
<213> ORGANISM: Unknown
<220> FEATURE:
<223> OTHER INFORMATION: Obtained from environmental sample

<400> SEQUENCE: 120

Met Ser Tyr Phe Pro Thr Ile Gly Asn Ile Pro Phe Glu Gly Val Glu
1               5                   10                  15

Ser Lys Asn Pro Leu Ala Phe His Tyr Tyr Asp Ala Ser Arg Val Val
            20                  25                  30

Met Gly Lys Pro Met Lys Glu Trp Leu Lys Phe Ala Met Ala Trp Trp
        35                  40                  45

His Thr Leu Gly Gln Ala Ser Ala Asp Pro Phe Gly Gly Gln Thr Arg
    50                  55                  60

Ser Tyr Ala Trp Asp Lys Gly Glu Cys Pro Tyr Cys Arg Ala Arg Ala
65                  70                  75                  80

Lys Ala Asp Ala Gly Phe Glu Leu Met Gln Lys Leu Gly Ile Glu Tyr
85 90 95

Phe Cys Ser His Asp Ile Asp Leu Ile Glu Asp Cys Asp Asp Ile Ala
100 105 110

Glu Tyr Glu Ala Arg Leu Lys Asp Ile Thr Asp Tyr Leu Leu Glu Lys
115 120 125

Met Lys Lys Thr Gly Ile Lys Asn Leu Trp Gly Thr Ala Asn Val Phe
130 135 140

Gly Asn Lys Arg Tyr Met Asn Gly Ala Ala Thr Asn Pro Gln Phe Asp
145 150 155 160

Val Val Ala Arg Ala Ala Val Gln Ile Lys Asn Ala Ile Asp Ala Thr
165 170 175

Ile Lys Leu Gly Gly Ser Asn Tyr Val Phe Trp Gly Gly Arg Glu Gly
180 185 190

Tyr Tyr Thr Leu Leu Asn Thr Gln Met Gln Arg Glu Lys Asn His Leu
195 200 205

Ala Ala Met Leu Lys Ala Ala Arg Asp Tyr Ala Arg Ala Asn Gly Phe
210 215 220

Lys Gly Thr Phe Leu Ile Glu Pro Lys Pro Met Glu Pro Thr Lys His
225 230 235 240

Gln Tyr Asp Val Asp Thr Glu Thr Val Ile Gly Phe Leu Arg Ala Asn
245 250 255

Gly Leu Glu Lys Asp Phe Lys Val Asn Ile Glu Val Asn His Ala Thr
260 265 270

Leu Ala Gly His Thr Phe Glu His Glu Leu Thr Val Ala Arg Glu Asn
275 280 285

Gly Phe Leu Gly Ser Ile Asp Ala Asn Arg Gly Asp Ala Gln Asn Gly
290 295 300

Trp Asp Thr Asp Gln Phe Pro Val Asp Ala Phe Asp Leu Thr Gln Ala
305 310 315 320

Met Met Gln Ile Leu Leu Asn Gly Gly Ser Gly Asn Gly Gly Thr Asn
325 330 335

Phe Asp Ala Lys Leu Arg Arg Ser Ser Thr Asp Pro Glu Asp Ile Phe
340 345 350

Ile Ala His Ile Ser Ala Met Asp Ala Met Ala His Ala Leu Leu Asn
355 360 365

Ala Ala Ala Val Leu Glu Glu Ser Pro Leu Cys Lys Met Val Lys Glu
370 375 380

Arg Tyr Ala Ser Phe Asp Ser Gly Leu Gly Lys Gln Phe Glu Glu Gly
385 390 395 400

Lys Ala Thr Leu Glu Asp Leu Tyr Ala Tyr Ala Val Lys Asn Gly Glu
405 410 415

Pro Val Val Ala Ser Gly Lys Gln Glu Leu Tyr Glu Thr Phe Leu Asn
420 425 430

Leu Tyr Ala Lys Trp
435

<210> SEQ ID NO 121
<211> LENGTH: 1317
<212> TYPE: DNA
<213> ORGANISM: Unknown
<220> FEATURE:
<223> OTHER INFORMATION: Obtained from environmental sample

<400> SEQUENCE: 121

```
atgtcaactg agtatttccc tacaatcggc aagattccct tcgagggacc cgagagcaag     60

aaccccatgg ccttccacta ctatgaaccc gaaaagttgg tgatgggcaa gaagatgaag    120

gactggctgc gtttcgcaat ggcctggtgg cacacccttg gagccgcatc cggcgaccag    180

ttcggcggac agacccgcag ttacgcctgg gacaagggcg actgccctta cagccgcgcc    240

cgcgccaagg tcgacgccgg cttcgagatc atgcagaagc tcggcataga gttcttctgc    300

ttccatgaca tcgacctggt cgaggatacc gacgacatcg ccgagtatga agcccggatg    360

aaagacatca cggactatct gctggaaaag atggaggtta ccggcatcaa gaacctctgg    420

ggcacggcca atgtcttcgg tcacaagcgt tatatgaacg atgcagccac aaaccccgat    480

ttcgcagtgg tcgcaagggc ggccgtgcag atcaagaacg ccatcgacgc caccatcaag    540

ctgggtggtg agaactatgt gttctggggt ggacgcgagg gttatatgag cctgctcaac    600

acccagatgc agagggagaa ggaacacctt gccaagatgc tcaccgccgc acgtgactat    660

gcacgcgcca aaggtttcaa gggcacgttc ctcatcgaac ccgagccgat ggaacccacc    720

aagcaccagt atgaccagga taccgagacc gttatcggat tcctccgcag ccacggcctg    780

gacaaggact tcaaggtcaa catcgaggtg aaccacgcca ccctggcggg ccataccttc    840

gagcacgaac tggccaccgc cgtcgacaac ggcatgctcg gcagcatcga cgccaaccgc    900

ggagacgccc agaacggctg ggacaccgac cagttcccga tcgacaactt cgagctcacg    960

cttgccatga tgcagataat ccgcaacggc ggcctggcac cgggcggttc gaacttcgac   1020

gcaaagctgc gccgcaattc caccgatccc gaggacatca tcatcgccca catcagcgcg   1080

atggacgcca tggcccgcgc cctcgtcaac gccgccgcca tcctcggcga gtcgcccgtt   1140

ccggctatgg tcaaggaccg ctatgcttcg ttcgactgcg gcaagggcaa ggacttcgaa   1200

gacggcaaac tgactctcga agacatcgtc gcctacgcca gggagaatgg cgagccgaaa   1260

cagatttccg gcaagcagga actctacgaa actatcgtcg ctctttactg caagtaa      1317
```

```
<210> SEQ ID NO 122
<211> LENGTH: 438
<212> TYPE: PRT
<213> ORGANISM: Unknown
<220> FEATURE:
<223> OTHER INFORMATION: Obtained from environmental sample

<400> SEQUENCE: 122

Met Ser Thr Glu Tyr Phe Pro Thr Ile Gly Lys Ile Pro Phe Glu Gly
1               5                   10                  15

Pro Glu Ser Lys Asn Pro Met Ala Phe His Tyr Tyr Glu Pro Glu Lys
            20                  25                  30

Leu Val Met Gly Lys Lys Met Lys Asp Trp Leu Arg Phe Ala Met Ala
        35                  40                  45

Trp Trp His Thr Leu Gly Ala Ala Ser Gly Asp Gln Phe Gly Gly Gln
    50                  55                  60

Thr Arg Ser Tyr Ala Trp Asp Lys Gly Asp Cys Pro Tyr Ser Arg Ala
65                  70                  75                  80

Arg Ala Lys Val Asp Ala Gly Phe Glu Ile Met Gln Lys Leu Gly Ile
                85                  90                  95

Glu Phe Phe Cys Phe His Asp Ile Asp Leu Val Glu Asp Thr Asp Asp
            100                 105                 110

Ile Ala Glu Tyr Glu Ala Arg Met Lys Asp Ile Thr Asp Tyr Leu Leu
        115                 120                 125
```

-continued

```
Glu Lys Met Glu Val Thr Gly Ile Lys Asn Leu Trp Gly Thr Ala Asn
    130                 135                 140

Val Phe Gly His Lys Arg Tyr Met Asn Asp Ala Ala Thr Asn Pro Asp
145                 150                 155                 160

Phe Ala Val Val Ala Arg Ala Ala Val Gln Ile Lys Asn Ala Ile Asp
                165                 170                 175

Ala Thr Ile Lys Leu Gly Gly Glu Asn Tyr Val Phe Trp Gly Gly Arg
            180                 185                 190

Glu Gly Tyr Met Ser Leu Leu Asn Thr Gln Met Gln Arg Glu Lys Glu
        195                 200                 205

His Leu Ala Lys Met Leu Thr Ala Ala Arg Asp Tyr Ala Arg Ala Lys
    210                 215                 220

Gly Phe Lys Gly Thr Phe Leu Ile Glu Pro Glu Pro Met Glu Pro Thr
225                 230                 235                 240

Lys His Gln Tyr Asp Gln Asp Thr Glu Thr Val Ile Gly Phe Leu Arg
                245                 250                 255

Ser His Gly Leu Asp Lys Asp Phe Lys Val Asn Ile Glu Val Asn His
            260                 265                 270

Ala Thr Leu Ala Gly His Thr Phe Glu His Glu Leu Ala Thr Ala Val
        275                 280                 285

Asp Asn Gly Met Leu Gly Ser Ile Asp Ala Asn Arg Gly Asp Ala Gln
    290                 295                 300

Asn Gly Trp Asp Thr Asp Gln Phe Pro Ile Asp Asn Phe Glu Leu Thr
305                 310                 315                 320

Leu Ala Met Met Gln Ile Ile Arg Asn Gly Gly Leu Ala Pro Gly Gly
                325                 330                 335

Ser Asn Phe Asp Ala Lys Leu Arg Arg Asn Ser Thr Asp Pro Glu Asp
            340                 345                 350

Ile Ile Ile Ala His Ile Ser Ala Met Asp Ala Met Ala Arg Ala Leu
        355                 360                 365

Val Asn Ala Ala Ala Ile Leu Gly Glu Ser Pro Val Pro Ala Met Val
    370                 375                 380

Lys Asp Arg Tyr Ala Ser Phe Asp Cys Gly Lys Gly Lys Asp Phe Glu
385                 390                 395                 400

Asp Gly Lys Leu Thr Leu Glu Asp Ile Val Ala Tyr Ala Arg Glu Asn
                405                 410                 415

Gly Glu Pro Lys Gln Ile Ser Gly Lys Gln Glu Leu Tyr Glu Thr Ile
            420                 425                 430

Val Ala Leu Tyr Cys Lys
        435
```

<210> SEQ ID NO 123
<211> LENGTH: 1317
<212> TYPE: DNA
<213> ORGANISM: Unknown
<220> FEATURE:
<223> OTHER INFORMATION: Obtained from environmental sample

<400> SEQUENCE: 123

```
atgaccaacg agtattttcc cggaatcggt gtgattccgt ttgaaggaca ggaaagcaag      60

aatcccctgg ctttccatta ttatgacgcc aaccgcgtag tgatgggcaa acccatgaag     120

gaatggttca aatttgccat ggcctggtgg catacgctgg ggcaggcatc ggccgatccc     180

ttcggcggac agacccgctc ctacgcatgg gacaagggcg agtgccctta ctgccgtgcc     240

cgccagaagg ccgacgccgg ctttgaactg atgcagaagc tgggaatcgg ctatttctgc     300
```

```
ttccacgatg tggatatcat cgaggactgc gaggacattg ccgagtatga ggcccgtatg    360
aaggacatca cggactatct gctggtgaag atgaaggaaa cgggcatcaa gaatctgtgg    420
ggcacggcca acgtcttcgg ccacaagcgc tatatgaacg gcgccgccac caacccgcaa    480
ttcgacgtgg tagcccgcgc tgcggtccag atcaagaacg ccctggacgc caccatcaag    540
ctgggcggca gcaattatgt gttctggggc ggccgggaag gctactacac ccttttgaac    600
acgcagatgc agcgggagaa ggaccacctg gcccagatgc tcaaggcggc ccgcgactat    660
gcccgcggca agggattcaa gggcacgttc ctcattgagc ccaagcccat ggagcccacc    720
aagcaccagt acgacgtaga tacggagacc gtgattggtt tcctgcgcgc caacgggctg    780
gacaaggact tcaaggtgaa tatcgaagtg aaccacgcca ccctggccgg ccataccttc    840
gagcacgagc tcaccgtggc ccgcgaaaac ggcttcctgg gcagcatcga cgccaaccgc    900
ggagacgccc agaacggctg ggatacagac cagttccccg tggacgcctt tgacctcacc    960
caggccatga tgcaggtcct gctcaacggc ggattcggca acggcggcac caacttcgac   1020
gccaaactgc gccgttcctc cacggatccc gaggacatct tcatcgccca catcagcgcc   1080
atggacgcca tggcccacgc cctcctgaac gccgccgcca tcctggaaga gagccccatg   1140
ccgggcatgg tgaaggagcg ctacgcttcc ttcgacaatg gccttggcaa gaagttcgag   1200
gaaggaaagg ccacgctgga agagctgtac gactatgcca agaagaacgg cgagcctgtg   1260
gccgcttccg gaaagcagga actgtacgaa acgctgctga acctgtacgc caagtaa      1317
```

<210> SEQ ID NO 124
<211> LENGTH: 438
<212> TYPE: PRT
<213> ORGANISM: Unknown
<220> FEATURE:
<223> OTHER INFORMATION: Obtained from environmental sample

<400> SEQUENCE: 124

```
Met Thr Asn Glu Tyr Phe Pro Gly Ile Gly Val Ile Pro Phe Glu Gly
1               5                   10                  15

Gln Glu Ser Lys Asn Pro Leu Ala Phe His Tyr Tyr Asp Ala Asn Arg
            20                  25                  30

Val Val Met Gly Lys Pro Met Lys Glu Trp Phe Lys Phe Ala Met Ala
        35                  40                  45

Trp Trp His Thr Leu Gly Gln Ala Ser Ala Asp Pro Phe Gly Gly Gln
    50                  55                  60

Thr Arg Ser Tyr Ala Trp Asp Lys Gly Glu Cys Pro Tyr Cys Arg Ala
65                  70                  75                  80

Arg Gln Lys Ala Asp Ala Gly Phe Glu Leu Met Gln Lys Leu Gly Ile
                85                  90                  95

Gly Tyr Phe Cys Phe His Asp Val Asp Ile Ile Glu Asp Cys Glu Asp
            100                 105                 110

Ile Ala Glu Tyr Glu Ala Arg Met Lys Asp Ile Thr Asp Tyr Leu Leu
        115                 120                 125

Val Lys Met Lys Glu Thr Gly Ile Lys Asn Leu Trp Gly Thr Ala Asn
    130                 135                 140

Val Phe Gly His Lys Arg Tyr Met Asn Gly Ala Ala Thr Asn Pro Gln
145                 150                 155                 160

Phe Asp Val Val Ala Arg Ala Ala Val Gln Ile Lys Asn Ala Leu Asp
                165                 170                 175

Ala Thr Ile Lys Leu Gly Gly Ser Asn Tyr Val Phe Trp Gly Gly Arg
```

-continued

```
            180                 185                 190

Glu Gly Tyr Tyr Thr Leu Leu Asn Thr Gln Met Gln Arg Glu Lys Asp
        195                 200                 205

His Leu Ala Gln Met Leu Lys Ala Ala Arg Asp Tyr Ala Arg Gly Lys
    210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Val Ile Gly Phe Leu Arg
                245                 250                 255

Ala Asn Gly Leu Asp Lys Asp Phe Lys Val Asn Ile Glu Val Asn His
            260                 265                 270

Ala Thr Leu Ala Gly His Thr Phe Glu His Glu Leu Thr Val Ala Arg
        275                 280                 285

Glu Asn Gly Phe Leu Gly Ser Ile Asp Ala Asn Arg Gly Asp Ala Gln
    290                 295                 300

Asn Gly Trp Asp Thr Asp Gln Phe Pro Val Asp Ala Phe Asp Leu Thr
305                 310                 315                 320

Gln Ala Met Met Gln Val Leu Leu Asn Gly Gly Phe Gly Asn Gly Gly
                325                 330                 335

Thr Asn Phe Asp Ala Lys Leu Arg Arg Ser Ser Thr Asp Pro Glu Asp
            340                 345                 350

Ile Phe Ile Ala His Ile Ser Ala Met Asp Ala Met Ala His Ala Leu
        355                 360                 365

Leu Asn Ala Ala Ala Ile Leu Glu Glu Ser Pro Met Pro Gly Met Val
    370                 375                 380

Lys Glu Arg Tyr Ala Ser Phe Asp Asn Gly Leu Gly Lys Lys Phe Glu
385                 390                 395                 400

Glu Gly Lys Ala Thr Leu Glu Glu Leu Tyr Asp Tyr Ala Lys Lys Asn
                405                 410                 415

Gly Glu Pro Val Ala Ala Ser Gly Lys Gln Glu Leu Tyr Glu Thr Leu
            420                 425                 430

Leu Asn Leu Tyr Ala Lys
        435


<210> SEQ ID NO 125
<211> LENGTH: 1317
<212> TYPE: DNA
<213> ORGANISM: Unknown
<220> FEATURE:
<223> OTHER INFORMATION: Obtained from environmental sample

<400> SEQUENCE: 125

atggcaaaag agtatttccc gcagatcgga aagatcggct ttgagggtct tgagagcaag      60

aacccgatgg cattccatta ttatgacgcc gagcgtgtcg tgctcggaaa gaagatgaag     120

gactggctga agttcgcgat ggcctggtgg catacgctcg gacaggcttc cggcgaccca     180

ttcggcggcc agactcgcag ctatgagtgg gacaagggcg agtgccccta ctgccgtgcc     240

cgcgccaagg ccgacgccgg cttcgagctc atgcagaagc tcggcatcga gtacttctgc     300

ttccacgaca tcgacctcat cgaggactgc gacgacatcg acgagtacga ggcccggatg     360

aaggacatca ccgactacct gctggagaag atgaaggaga ccggaatcaa gaatctctgg     420

ggaacggcca acgtcttcgg tcacaagcgc tacatgaacg gcgccgctac caatccgcag     480

tttgaaatcg tcgcccgcgc tgccgtccag atcaagaacg cgctcgacgc caccatcaag     540

ctcggcggct ccaactacgt cttctggggc ggccgcgagg gctattacac gctgctgaat     600
```

```
acccagatgc agcgcgagaa ggaccatctc gccaggctcc ttaccgccgc ccgcgactat    660

gcgcgcgcca aggggttcaa ggggaccttc cccatcgagc cgaagccgat ggagccgacc    720

aagcaccagt atgacgtcga cacggagacc gtcatcggtt tcctccgcca gaatggcctc    780

gacaaggact tcaaggtcaa tatcgaggtg aaccacgcca ccctcgccgg ccataccttc    840

gagcacgagc tgaccgcggc ccgggagaac ggcttcctcg gcagcatcga cgccaaccgc    900

ggcgacgccc agaacggctg ggacaccgac cagttcccgg tggacgcctt cgatctcacg    960

cgggccatga tgcagatcct gctcaatggc ggtttcggca acggcggcac caacttcgac   1020

gccaagctgc gccgcagctc caccgatccc gaggacatct tcatcgccca catcagcgcg   1080

atggacgcca tggcccacgc cctgctgaat gcggccgcca tcctcgagga aagcccgctg   1140

ccggccctgg tcaagcagcg ctatgcgtcc ttcgacagcg gtctcggcaa gcagttcgag   1200

gagggtaagg ccacgctcga ggacctgtac gcatacgcga aggagcacgg cgagcccgtc   1260

gcggcctccg gcaagcagga gctctgcgag acctatctca acctctacgc gaaataa      1317
```

<210> SEQ ID NO 126
<211> LENGTH: 438
<212> TYPE: PRT
<213> ORGANISM: Unknown
<220> FEATURE:
<223> OTHER INFORMATION: Obtained from environmental sample

<400> SEQUENCE: 126

```
Met Ala Lys Glu Tyr Phe Pro Gln Ile Gly Lys Ile Gly Phe Glu Gly
1               5                   10                  15

Leu Glu Ser Lys Asn Pro Met Ala Phe His Tyr Tyr Asp Ala Glu Arg
            20                  25                  30

Val Val Leu Gly Lys Lys Met Lys Asp Trp Leu Lys Phe Ala Met Ala
        35                  40                  45

Trp Trp His Thr Leu Gly Gln Ala Ser Gly Asp Pro Phe Gly Gly Gln
    50                  55                  60

Thr Arg Ser Tyr Glu Trp Asp Lys Gly Glu Cys Pro Tyr Cys Arg Ala
65                  70                  75                  80

Arg Ala Lys Ala Asp Ala Gly Phe Glu Leu Met Gln Lys Leu Gly Ile
                85                  90                  95

Glu Tyr Phe Cys Phe His Asp Ile Asp Leu Ile Glu Asp Cys Asp Asp
            100                 105                 110

Ile Asp Glu Tyr Glu Ala Arg Met Lys Asp Ile Thr Asp Tyr Leu Leu
        115                 120                 125

Glu Lys Met Lys Glu Thr Gly Ile Lys Asn Leu Trp Gly Thr Ala Asn
    130                 135                 140

Val Phe Gly His Lys Arg Tyr Met Asn Gly Ala Ala Thr Asn Pro Gln
145                 150                 155                 160

Phe Glu Ile Val Ala Arg Ala Ala Val Gln Ile Lys Asn Ala Leu Asp
                165                 170                 175

Ala Thr Ile Lys Leu Gly Gly Ser Asn Tyr Val Phe Trp Gly Gly Arg
            180                 185                 190

Glu Gly Tyr Tyr Thr Leu Leu Asn Thr Gln Met Gln Arg Glu Lys Asp
        195                 200                 205

His Leu Ala Arg Leu Leu Thr Ala Ala Arg Asp Tyr Ala Arg Ala Lys
    210                 215                 220

Gly Phe Lys Gly Thr Phe Pro Ile Glu Pro Lys Pro Met Glu Pro Thr
225                 230                 235                 240
```

Lys His Gln Tyr Asp Val Asp Thr Glu Thr Val Ile Gly Phe Leu Arg
245 250 255

Gln Asn Gly Leu Asp Lys Asp Phe Lys Val Asn Ile Glu Val Asn His
260 265 270

Ala Thr Leu Ala Gly His Thr Phe Glu His Glu Leu Thr Ala Ala Arg
275 280 285

Glu Asn Gly Phe Leu Gly Ser Ile Asp Ala Asn Arg Gly Asp Ala Gln
290 295 300

Asn Gly Trp Asp Thr Asp Gln Phe Pro Val Asp Ala Phe Asp Leu Thr
305 310 315 320

Arg Ala Met Met Gln Ile Leu Leu Asn Gly Gly Phe Gly Asn Gly Gly
325 330 335

Thr Asn Phe Asp Ala Lys Leu Arg Arg Ser Ser Thr Asp Pro Glu Asp
340 345 350

Ile Phe Ile Ala His Ile Ser Ala Met Asp Ala Met Ala His Ala Leu
355 360 365

Leu Asn Ala Ala Ala Ile Leu Glu Glu Ser Pro Leu Pro Ala Leu Val
370 375 380

Lys Gln Arg Tyr Ala Ser Phe Asp Ser Gly Leu Gly Lys Gln Phe Glu
385 390 395 400

Glu Gly Lys Ala Thr Leu Glu Asp Leu Tyr Ala Tyr Ala Lys Glu His
405 410 415

Gly Glu Pro Val Ala Ala Ser Gly Lys Gln Glu Leu Cys Glu Thr Tyr
420 425 430

Leu Asn Leu Tyr Ala Lys
435

<210> SEQ ID NO 127
<211> LENGTH: 1317
<212> TYPE: DNA
<213> ORGANISM: Unknown
<220> FEATURE:
<223> OTHER INFORMATION: Obtained from environmental sample

<400> SEQUENCE: 127
atgagtaaag agtattttcc tgggattggc aaaatcccgt atgagggagc cgagagcaag 60
aatgtgatgg cattccacta ttatgatccc gaacgcgtgg tcatgggcaa gaaaatgaaa 120
gactggttca agttcgctat tgcctggtgg catacccctgg ggcaggccag tgctgaccag 180
tttggcggac agacccgttt ctatgaatgg gacaaagccg aggacccctt gcagcgtgcc 240
aaggacaaga tggatgccgg ttttgaaatc atgcagaagc tgggcatcga gtatttctgt 300
ttccatgatg tggacctcat cgaggaggcc gataccatcg aggaatatga agcccgcatg 360
caggcgatta ccgactacgc gctggagaag atgaaggcaa cgggtatcaa gttgctgtgg 420
ggcactgcca acgtgttcgg ccacaagcgt tacatgaacg gcgccgccac caatcccgac 480
ttcaatgtcg tggcacgtgc agccgtgcag atcaagaacg ccctcgatgc taccatcaag 540
ttgggcggaa cgagctacgt cttctggggc ggtcgtgaag gctatcagag cctgctcaac 600
acccagatgc agcgcgagaa gaaccacctg gccaagatgc tcacggcagc ccgtgactat 660
gcccgtgcta agggcttcaa gggcaccttc ctgattgagc ccaagccgat ggaacccacc 720
aagcaccagt atgaccagga caccgagacc gttatcggct tcttgcgtgc caatggcctt 780
gacaaggact ttaaggtcaa cattgaggtc aaccatgcca cgctggctgg ccacaccttt 840
gcacatgagt tggcagtggc tgtggataac ggtatgctgg gcagcatcga tgctaaccgt 900

```
ggtgaccacc agaacggctg ggatacagac cagttcccca tcaacagtta tgaactcacc    960

aatgctatgc tgcagatcat gcacggcggc ggtttcaagg acggcggtac caactttgac   1020

gccaagctgc gccgcaacag taccgacccc gaggacatct ttaccgctca catcagtggt   1080

atggacgctc tggcccgtgc cctgttgagt gctgccgata tccttgagaa gagcgagttg   1140

cctgaaatgc tcaaggaacg ctatgccagc tttgacgcgg gtgaaggcaa gcgctttgag   1200

gatggccaga tgactcttga ggaactggtt gcctatgcca agtcccatgg cgagcctgct   1260

accatcagtg gcaagcagga aaaatatgaa gccatcgtgg ctttgcacgt caagtaa      1317
```

```
<210> SEQ ID NO 128
<211> LENGTH: 438
<212> TYPE: PRT
<213> ORGANISM: Unknown
<220> FEATURE:
<223> OTHER INFORMATION: Obtained from environmental sample

<400> SEQUENCE: 128

Met Ser Lys Glu Tyr Phe Pro Gly Ile Gly Lys Ile Pro Tyr Glu Gly
1               5                   10                  15

Ala Glu Ser Lys Asn Val Met Ala Phe His Tyr Tyr Asp Pro Glu Arg
            20                  25                  30

Val Val Met Gly Lys Lys Met Lys Asp Trp Phe Lys Phe Ala Ile Ala
        35                  40                  45

Trp Trp His Thr Leu Gly Gln Ala Ser Ala Asp Gln Phe Gly Gly Gln
    50                  55                  60

Thr Arg Phe Tyr Glu Trp Asp Lys Ala Glu Asp Pro Leu Gln Arg Ala
65                  70                  75                  80

Lys Asp Lys Met Asp Ala Gly Phe Glu Ile Met Gln Lys Leu Gly Ile
                85                  90                  95

Glu Tyr Phe Cys Phe His Asp Val Asp Leu Ile Glu Glu Ala Asp Thr
            100                 105                 110

Ile Glu Glu Tyr Glu Ala Arg Met Gln Ala Ile Thr Asp Tyr Ala Leu
        115                 120                 125

Glu Lys Met Lys Ala Thr Gly Ile Lys Leu Leu Trp Gly Thr Ala Asn
    130                 135                 140

Val Phe Gly His Lys Arg Tyr Met Asn Gly Ala Ala Thr Asn Pro Asp
145                 150                 155                 160

Phe Asn Val Val Ala Arg Ala Ala Val Gln Ile Lys Asn Ala Leu Asp
                165                 170                 175

Ala Thr Ile Lys Leu Gly Gly Thr Ser Tyr Val Phe Trp Gly Gly Arg
            180                 185                 190

Glu Gly Tyr Gln Ser Leu Leu Asn Thr Gln Met Gln Arg Glu Lys Asn
        195                 200                 205

His Leu Ala Lys Met Leu Thr Ala Ala Arg Asp Tyr Ala Arg Ala Lys
    210                 215                 220

Gly Phe Lys Gly Thr Phe Leu Ile Glu Pro Lys Pro Met Glu Pro Thr
225                 230                 235                 240

Lys His Gln Tyr Asp Gln Asp Thr Glu Thr Val Ile Gly Phe Leu Arg
                245                 250                 255

Ala Asn Gly Leu Asp Lys Asp Phe Lys Val Asn Ile Glu Val Asn His
            260                 265                 270

Ala Thr Leu Ala Gly His Thr Phe Ala His Glu Leu Ala Val Ala Val
        275                 280                 285
```

```
Asp Asn Gly Met Leu Gly Ser Ile Asp Ala Asn Arg Gly Asp His Gln
    290                 295                 300

Asn Gly Trp Asp Thr Asp Gln Phe Pro Ile Asn Ser Tyr Glu Leu Thr
305                 310                 315                 320

Asn Ala Met Leu Gln Ile Met His Gly Gly Gly Phe Lys Asp Gly Gly
                325                 330                 335

Thr Asn Phe Asp Ala Lys Leu Arg Arg Asn Ser Thr Asp Pro Glu Asp
            340                 345                 350

Ile Phe Thr Ala His Ile Ser Gly Met Asp Ala Leu Ala Arg Ala Leu
        355                 360                 365

Leu Ser Ala Ala Asp Ile Leu Glu Lys Ser Glu Leu Pro Glu Met Leu
    370                 375                 380

Lys Glu Arg Tyr Ala Ser Phe Asp Ala Gly Glu Gly Lys Arg Phe Glu
385                 390                 395                 400

Asp Gly Gln Met Thr Leu Glu Glu Leu Val Ala Tyr Ala Lys Ser His
                405                 410                 415

Gly Glu Pro Ala Thr Ile Ser Gly Lys Gln Glu Lys Tyr Glu Ala Ile
            420                 425                 430

Val Ala Leu His Val Lys
        435
```

<210> SEQ ID NO 129
<211> LENGTH: 1329
<212> TYPE: DNA
<213> ORGANISM: Unknown
<220> FEATURE:
<223> OTHER INFORMATION: Obtained from environmental sample

<400> SEQUENCE: 129

```
atgagtaaag agtattatcc tgagattggc aaaatcccgt ttgagggtcc cgagagcaag     60

aatgtgatgg cgttccatta ctatgaaccc gaacgcgtcg tcatgggtaa gaagatgaaa    120

gactggctca agtttgccat gtgctggtgg cacagcctgg gtcaggccag tgccgaccag    180

ttcggcggac agacacgttt ctacgagtgg gacaaggccg atacccccct gcagcgtgcc    240

aaggacaaaa tggatgccgg atttgaaatc atgcagaagt tgggcatcga gtacttctgc    300

ttccacgatg tggacctcat cgaggaggcc gataccatcg aggaatacga ggcccgcatg    360

aaggccatta ccgactatgc gctggagaag atgcaggcca ccggcatcaa gttgctgtgg    420

ggcactgcca atgtgttcgg ccacaagcgc tacatgaacg gcgccgccac caatcccgat    480

ttcaatgtcg tggcacgtgc cgccgtccaa atcaagaatg ccatcgatgc caccatcaag    540

ctgggcggca cgagttacgt cttctggggt ggtcgtgagg gctatcagag tctgctcaac    600

acgcagatgc agcgcgagaa ggaccatctg gcccgcatgc tggcggcagc ccgcgactat    660

ggccgtgccc atggcttcaa gggcactttc ctgatcgagc ccaaacccat ggagcccacc    720

aagcaccagt atgatgtgga caccgagacc gtgctcggct tcctgcgtgc ccacggcctg    780

gacaaggact tcaaggttaa catcgaggtc aatcatgcta cgctggcggg acacactttc    840

agccacgaac tggctgtggc cgtggacaac ggtatgctgg gcagcatcga cgccaaccgc    900

ggcgattatc agaatggctg ggacaccgac cagttcccca tcgacagctt cgagctcacc    960

caggccatgc tgcagatcat gcgcggcggc ggcttcaagg acggaggtac caacttcgat   1020

gccaagctgc gtcgcaacag taccgaccct gaggacatct tcatcgccca catcagcggt   1080

atggatgcca tggcacgcgg cctgttgagc gctgccgcta tcctcgagga tggcgagttg   1140

cccgcgatgc tcaaggcacg ttatgccagc tttgaccagg gcgagggtaa gcgctttgag   1200
```

gacggcgaga tgacgctcga gcagctggtg gattatgcaa aggattatgc caaatcgcac 1260
ggcgagcctg atgtcatcag cggcaagcag gagaagtttg aaaccatcgt ggccctttac 1320
gccaagtaa 1329

<210> SEQ ID NO 130
<211> LENGTH: 442
<212> TYPE: PRT
<213> ORGANISM: Unknown
<220> FEATURE:
<223> OTHER INFORMATION: Obtained from environmental sample

<400> SEQUENCE: 130

Met Ser Lys Glu Tyr Tyr Pro Glu Ile Gly Lys Ile Pro Phe Glu Gly
1 5 10 15

Pro Glu Ser Lys Asn Val Met Ala Phe His Tyr Tyr Glu Pro Glu Arg
20 25 30

Val Val Met Gly Lys Lys Met Lys Asp Trp Leu Lys Phe Ala Met Cys
35 40 45

Trp Trp His Ser Leu Gly Gln Ala Ser Ala Asp Gln Phe Gly Gly Gln
50 55 60

Thr Arg Phe Tyr Glu Trp Asp Lys Ala Asp Thr Pro Leu Gln Arg Ala
65 70 75 80

Lys Asp Lys Met Asp Ala Gly Phe Glu Ile Met Gln Lys Leu Gly Ile
85 90 95

Glu Tyr Phe Cys Phe His Asp Val Asp Leu Ile Glu Glu Ala Asp Thr
100 105 110

Ile Glu Glu Tyr Glu Ala Arg Met Lys Ala Ile Thr Asp Tyr Ala Leu
115 120 125

Glu Lys Met Gln Ala Thr Gly Ile Lys Leu Leu Trp Gly Thr Ala Asn
130 135 140

Val Phe Gly His Lys Arg Tyr Met Asn Gly Ala Ala Thr Asn Pro Asp
145 150 155 160

Phe Asn Val Val Ala Arg Ala Ala Val Gln Ile Lys Asn Ala Ile Asp
165 170 175

Ala Thr Ile Lys Leu Gly Gly Thr Ser Tyr Val Phe Trp Gly Gly Arg
180 185 190

Glu Gly Tyr Gln Ser Leu Leu Asn Thr Gln Met Gln Arg Glu Lys Asp
195 200 205

His Leu Ala Arg Met Leu Ala Ala Ala Arg Asp Tyr Gly Arg Ala His
210 215 220

Gly Phe Lys Gly Thr Phe Leu Ile Glu Pro Lys Pro Met Glu Pro Thr
225 230 235 240

Lys His Gln Tyr Asp Val Asp Thr Glu Thr Val Leu Gly Phe Leu Arg
245 250 255

Ala His Gly Leu Asp Lys Asp Phe Lys Val Asn Ile Glu Val Asn His
260 265 270

Ala Thr Leu Ala Gly His Thr Phe Ser His Glu Leu Ala Val Ala Val
275 280 285

Asp Asn Gly Met Leu Gly Ser Ile Asp Ala Asn Arg Gly Asp Tyr Gln
290 295 300

Asn Gly Trp Asp Thr Asp Gln Phe Pro Ile Asp Ser Phe Glu Leu Thr
305 310 315 320

Gln Ala Met Leu Gln Ile Met Arg Gly Gly Gly Phe Lys Asp Gly Gly
325 330 335

```
Thr Asn Phe Asp Ala Lys Leu Arg Arg Asn Ser Thr Asp Pro Glu Asp
            340                 345                 350

Ile Phe Ile Ala His Ile Ser Gly Met Asp Ala Met Ala Arg Gly Leu
        355                 360                 365

Leu Ser Ala Ala Ala Ile Leu Glu Asp Gly Glu Leu Pro Ala Met Leu
    370                 375                 380

Lys Ala Arg Tyr Ala Ser Phe Asp Gln Gly Glu Gly Lys Arg Phe Glu
385                 390                 395                 400

Asp Gly Glu Met Thr Leu Glu Gln Leu Val Asp Tyr Ala Lys Asp Tyr
                405                 410                 415

Ala Lys Ser His Gly Glu Pro Asp Val Ile Ser Gly Lys Gln Glu Lys
            420                 425                 430

Phe Glu Thr Ile Val Ala Leu Tyr Ala Lys
        435                 440


<210> SEQ ID NO 131
<211> LENGTH: 1317
<212> TYPE: DNA
<213> ORGANISM: Unknown
<220> FEATURE:
<223> OTHER INFORMATION: Obtained from environmental sample

<400> SEQUENCE: 131

atgaccaacg agtattttcc cggaatcggt gtgattccgt ttgaaggaca ggaaagcaag     60

aatcccctgg ctttccatta ttatgacgcc aaccgcgtag tgatgggcaa acccatgaag    120

gaatggttca aatttgccat ggcctggtgg catacgctgg ggcaggcatc ggccgatccc    180

ttcggcggac agacccgctc ctacgcatgg gacaagggcg agtgccctta ctgccgtgcc    240

cgccagaagg ccgacgccgg ctttgaactg atgcagaagc tgggaatcgg ctatttctgc    300

ttccacgatg tggatatcat cgaggactgc gaggacattg ccgagtatga ggcccgtatg    360

aaggacatca cggactatct gctggtgaag atgaaggaaa cgggcatcaa gaatctgtgg    420

ggcacggcca acgtcttcgg ccacaagcgc tatatgaacg gcgccgccac caacccgcaa    480

ttcgacgtgg tagcccgcgc tgcggtccag atcaagaacg ccctggacgc caccatcaag    540

ctgggcggca gcaattatgt gttctggggc ggccgggaag gctactacac ccttttgaac    600

acgcagatgc agcgggagaa ggaccacctg gcccagatgc tcaaggcggc ccgcgactat    660

gcccgcggca agggattcaa gggcacgttc ctcattgagc ccaagcccat ggagcccacc    720

aagcaccagt acgacgtaga tacggagacc gtgattggtt tcctgcgcgc caacgggccg    780

gacaaggact tcaaggtgaa tatcgaagtg aaccacgcca ccctggccgg ccataccttc    840

gagcacgagc tcaccgtggc ccgcgaaaac ggcttcctgg gcagcatcga cgccaaccgc    900

ggagacgccc agaacggctg ggatacagac cagttccccg tggacgcctt tgacctcacc    960

caggccatga tgcaggtcct gctcaacggc ggattcggca acggcggcac caacttcgac   1020

gccaaactgc gccgttcctc cacggatccc gaggacatct tcatcgccca catcagcgcc   1080

atggacgcca tggcccacgc cctcctgaac gccgccgcca tcctggaaga gagccccatg   1140

ccgggcatgg tgaaggagcg ctacgcttcc ttcgacaatg gccttggcaa gaagttcgag   1200

gaaggaaagg ccacgctgga agagctgtac gactatgcca agaagaacgg cgagcctgtg   1260

gccgcttccg gaaagcagga actgtacgaa acgctgctga acctgtacgc caagtaa      1317


<210> SEQ ID NO 132
<211> LENGTH: 438
```

<212> TYPE: PRT
<213> ORGANISM: Unknown
<220> FEATURE:
<223> OTHER INFORMATION: Obtained from environmental sample

<400> SEQUENCE: 132

Met Thr Asn Glu Tyr Phe Pro Gly Ile Gly Val Ile Pro Phe Glu Gly
1               5                   10                  15

Gln Glu Ser Lys Asn Pro Leu Ala Phe His Tyr Tyr Asp Ala Asn Arg
            20                  25                  30

Val Val Met Gly Lys Pro Met Lys Glu Trp Phe Lys Phe Ala Met Ala
        35                  40                  45

Trp Trp His Thr Leu Gly Gln Ala Ser Ala Asp Pro Phe Gly Gly Gln
    50                  55                  60

Thr Arg Ser Tyr Ala Trp Asp Lys Gly Glu Cys Pro Tyr Cys Arg Ala
65                  70                  75                  80

Arg Gln Lys Ala Asp Ala Gly Phe Glu Leu Met Gln Lys Leu Gly Ile
                85                  90                  95

Gly Tyr Phe Cys Phe His Asp Val Asp Ile Ile Glu Asp Cys Glu Asp
            100                 105                 110

Ile Ala Glu Tyr Glu Ala Arg Met Lys Asp Ile Thr Asp Tyr Leu Leu
        115                 120                 125

Val Lys Met Lys Glu Thr Gly Ile Lys Asn Leu Trp Gly Thr Ala Asn
    130                 135                 140

Val Phe Gly His Lys Arg Tyr Met Asn Gly Ala Ala Thr Asn Pro Gln
145                 150                 155                 160

Phe Asp Val Val Ala Arg Ala Ala Val Gln Ile Lys Asn Ala Leu Asp
                165                 170                 175

Ala Thr Ile Lys Leu Gly Gly Ser Asn Tyr Val Phe Trp Gly Gly Arg
            180                 185                 190

Glu Gly Tyr Tyr Thr Leu Leu Asn Thr Gln Met Gln Arg Glu Lys Asp
        195                 200                 205

His Leu Ala Gln Met Leu Lys Ala Ala Arg Asp Tyr Ala Arg Gly Lys
    210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Val Ile Gly Phe Leu Arg
                245                 250                 255

Ala Asn Gly Pro Asp Lys Asp Phe Lys Val Asn Ile Glu Val Asn His
            260                 265                 270

Ala Thr Leu Ala Gly His Thr Phe Glu His Glu Leu Thr Val Ala Arg
        275                 280                 285

Glu Asn Gly Phe Leu Gly Ser Ile Asp Ala Asn Arg Gly Asp Ala Gln
    290                 295                 300

Asn Gly Trp Asp Thr Asp Gln Phe Pro Val Asp Ala Phe Asp Leu Thr
305                 310                 315                 320

Gln Ala Met Met Gln Val Leu Leu Asn Gly Gly Phe Gly Asn Gly Gly
                325                 330                 335

Thr Asn Phe Asp Ala Lys Leu Arg Arg Ser Ser Thr Asp Pro Glu Asp
            340                 345                 350

Ile Phe Ile Ala His Ile Ser Ala Met Asp Ala Met Ala His Ala Leu
        355                 360                 365

Leu Asn Ala Ala Ala Ile Leu Glu Glu Ser Pro Met Pro Gly Met Val
    370                 375                 380

```
Lys Glu Arg Tyr Ala Ser Phe Asp Asn Gly Leu Gly Lys Lys Phe Glu
385                 390                 395                 400

Glu Gly Lys Ala Thr Leu Glu Glu Leu Tyr Asp Tyr Ala Lys Lys Asn
                405                 410                 415

Gly Glu Pro Val Ala Ala Ser Gly Lys Gln Glu Leu Tyr Glu Thr Leu
            420                 425                 430

Leu Asn Leu Tyr Ala Lys
        435
```

<210> SEQ ID NO 133
<211> LENGTH: 1317
<212> TYPE: DNA
<213> ORGANISM: Unknown
<220> FEATURE:
<223> OTHER INFORMATION: Obtained from environmental sample

<400> SEQUENCE: 133

```
atgactaaag agtatttccc ttccgtcggc aagattgcct ttgaaggacc cgaaagcaag     60

aaccctatgg ccttccatta ttatgacgcc aatcgcgtgg taatgggaaa gccgatgaaa    120

gaatggctta aatttgccat ggcctggtgg cacaccctgg gccaggcctc tgcagacccc    180

ttcggcggtc agacccgctc ctacgagtgg gacaagggcg agtgccccta ctgccgcgcc    240

aaggccaagg ccgatgccgg ctttgaactg atgcagaaac tgggcatcga gtatttctgc    300

ttccacgata tagacctggt ggaagactgc gatgatatcg ccgaatacga ggcccgcatg    360

aaggacatca cggactatct cctggagaag atgaaggaaa ccggcatcaa gaacctctgg    420

ggaaccgcca acgtgttcgg ccacaagcgc tatatgaacg gcgccgccac caaccctcag    480

ttcgacatcg tggcccgtgc cgctgtccag atcaagaacg ccctggatgc caccatcaag    540

ctgggcggct ccaactatgt gttctggggc ggccgtgagg gctactatac cctcctgaac    600

acccagatgc agagagagaa ggaccacctg gccaagatgc tcaccgccgc ccgcgactat    660

gcccgtgcca agggcttcaa gggcaccttc ctcatcgaac ccaagccgat ggagcccacc    720

aagcaccagt acgacgtaga tacggagacc gtgatcggct tcctccgcgc caacggcctg    780

gacaaggact tcaaggtgaa tattgaggtg aaccacgcca ccctggccgg ccacaccttc    840

gagcacgagc tcaccgtggc ccgcgagaac ggcttcctgg gcagcatcga cgccaaccgc    900

ggagacgccc agaacggctg ggatacggac cagttccccgg tggatgcctt cgacctcacc    960

caggctatga tgcagatcct tctgaacgga ggcttcggca acggcggtac caacttcgac   1020

gccaaactgc gccgctcctc cacggacccc gaggacatct tcatcgccca catcagcgct   1080

atggatgcca tggcccacgc cctgctgaat gcagccgcca tcctggagga aagcccgctt   1140

ccgaagatgc tgaaagagcg ttatgccagc tttgacggcg gtctgggcaa gaagttcgaa   1200

gaaggcaagg cctctctgga agaactctac gagtatgcca agagcaacgg agagcccgtg   1260

gccgcttccg gcaagcagga gctctgcgaa acgtacctga acctctacgc taagtaa      1317
```

<210> SEQ ID NO 134
<211> LENGTH: 438
<212> TYPE: PRT
<213> ORGANISM: Unknown
<220> FEATURE:
<223> OTHER INFORMATION: Obtained from environmental sample

<400> SEQUENCE: 134

```
Met Thr Lys Glu Tyr Phe Pro Ser Val Gly Lys Ile Ala Phe Glu Gly
1               5                   10                  15
```

```
Pro Glu Ser Lys Asn Pro Met Ala Phe His Tyr Tyr Asp Ala Asn Arg
            20                  25                  30

Val Val Met Gly Lys Pro Met Lys Glu Trp Leu Lys Phe Ala Met Ala
        35                  40                  45

Trp Trp His Thr Leu Gly Gln Ala Ser Ala Asp Pro Phe Gly Gly Gln
    50                  55                  60

Thr Arg Ser Tyr Glu Trp Asp Lys Gly Glu Cys Pro Tyr Cys Arg Ala
65                  70                  75                  80

Lys Ala Lys Ala Asp Ala Gly Phe Glu Leu Met Gln Lys Leu Gly Ile
                85                  90                  95

Glu Tyr Phe Cys Phe His Asp Ile Asp Leu Val Glu Asp Cys Asp Asp
            100                 105                 110

Ile Ala Glu Tyr Glu Ala Arg Met Lys Asp Ile Thr Asp Tyr Leu Leu
        115                 120                 125

Glu Lys Met Lys Glu Thr Gly Ile Lys Asn Leu Trp Gly Thr Ala Asn
    130                 135                 140

Val Phe Gly His Lys Arg Tyr Met Asn Gly Ala Ala Thr Asn Pro Gln
145                 150                 155                 160

Phe Asp Ile Val Ala Arg Ala Ala Val Gln Ile Lys Asn Ala Leu Asp
                165                 170                 175

Ala Thr Ile Lys Leu Gly Gly Ser Asn Tyr Val Phe Trp Gly Gly Arg
            180                 185                 190

Glu Gly Tyr Tyr Thr Leu Leu Asn Thr Gln Met Gln Arg Glu Lys Asp
        195                 200                 205

His Leu Ala Lys Met Leu Thr Ala Ala Arg Asp Tyr Ala Arg Ala Lys
    210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Val Ile Gly Phe Leu Arg
                245                 250                 255

Ala Asn Gly Leu Asp Lys Asp Phe Lys Val Asn Ile Glu Val Asn His
            260                 265                 270

Ala Thr Leu Ala Gly His Thr Phe Glu His Glu Leu Thr Val Ala Arg
        275                 280                 285

Glu Asn Gly Phe Leu Gly Ser Ile Asp Ala Asn Arg Gly Asp Ala Gln
    290                 295                 300

Asn Gly Trp Asp Thr Asp Gln Phe Pro Val Asp Ala Phe Asp Leu Thr
305                 310                 315                 320

Gln Ala Met Met Gln Ile Leu Leu Asn Gly Gly Phe Gly Asn Gly Gly
                325                 330                 335

Thr Asn Phe Asp Ala Lys Leu Arg Arg Ser Ser Thr Asp Pro Glu Asp
            340                 345                 350

Ile Phe Ile Ala His Ile Ser Ala Met Asp Ala Met Ala His Ala Leu
        355                 360                 365

Leu Asn Ala Ala Ala Ile Leu Glu Glu Ser Pro Leu Pro Lys Met Leu
    370                 375                 380

Lys Glu Arg Tyr Ala Ser Phe Asp Gly Gly Leu Gly Lys Lys Phe Glu
385                 390                 395                 400

Glu Gly Lys Ala Ser Leu Glu Glu Leu Tyr Glu Tyr Ala Lys Ser Asn
                405                 410                 415

Gly Glu Pro Val Ala Ala Ser Gly Lys Gln Glu Leu Cys Glu Thr Tyr
            420                 425                 430

Leu Asn Leu Tyr Ala Lys
```

435

<210> SEQ ID NO 135
<211> LENGTH: 1320
<212> TYPE: DNA
<213> ORGANISM: Unknown
<220> FEATURE:
<223> OTHER INFORMATION: Obtained from environmental sample

<400> SEQUENCE: 135
atggctaaag aatacttccc ctccatcggc aaaatccctt ttgaaggagc cgacagcaaa 60
aatcccctcg ctttccatta ttatgacgcc ggacgcgtgg ttatgggcaa gcccatgaag 120
gaatggctta aattcgccat ggcctggtgg cacacgctgg gccaggcctc cggagacccc 180
ttcggcggcc agacccgcag ctacgaatgg gacaagggcg aatgccccta ctgccgcgcc 240
aaggccaagg ccgacgccgg ttttgaaatc atgcaaaagc tgggcatcga atacttctgc 300
ttccacgatg tggaccttat cgaggattgc gatgacattg ccgaatacga agcccgcatg 360
aaggacatca cggactacct gctggaaaag atgaaggaga ccggcatcaa gaacctctgg 420
ggcaccgcca atgtcttcgg ccacaagcgc tacatgaacg gcgccggcac caatccgcag 480
ttcgatgtgg tggcccgtgc cgccgtccag atcaagaacg ccctggacgc caccatcaag 540
ctgggcggct ccaactatgt gttctggggc ggccgcgaag gctattacac cctcctcaac 600
acacagatgc agcgggaaaa agaccacctg gccaagttgc tgacggccgc ccgcgactat 660
gcccgcgcca agggcttcaa gggcaccttc ctcattgagc ccaaacccat ggaacccacc 720
aagcaccagt acgacgtgga tacggagacg gtcatcggct tcctccgtgc caacggcctg 780
gacaaggact tcaaggtgaa catcgaggtg aaccacgcca ccctggccgg ccacaccttc 840
gagcatgagc tcaccgtggc ccgcgagaac ggtttcctgg gctccatcga tgccaaccgc 900
ggcgacgccc agaacggctg ggacacggac cagttccctg tggacccgta cgatcttacc 960
caggccatga tgcaggtgct gctgaacggc ggcttcggca acggcggcac caacttcgac 1020
gccaaactcc gccgctcctc caccgaccct gaggacatct tcatcgccca tatttccgcc 1080
atggatgcca tggcccacgc tttgcttaac gcagctgccg tgctggaaga gagccccctg 1140
tgccagatgg tcaaggagcg ttatgccagc ttcgacgatg gcctcggcaa acagttcgag 1200
gaaggcaagg ctaccctgga agacctgtac gaatacgcca aggcccaggg tgaacccgtt 1260
gtcgcctccg gcaagcagga gctttacgag actctcctga acctgtatgc cgtcaagtaa 1320

<210> SEQ ID NO 136
<211> LENGTH: 439
<212> TYPE: PRT
<213> ORGANISM: Unknown
<220> FEATURE:
<223> OTHER INFORMATION: Obtained from environmental sample

<400> SEQUENCE: 136

Met Ala Lys Glu Tyr Phe Pro Ser Ile Gly Lys Ile Pro Phe Glu Gly
1 5 10 15

Ala Asp Ser Lys Asn Pro Leu Ala Phe His Tyr Tyr Asp Ala Gly Arg
20 25 30

Val Val Met Gly Lys Pro Met Lys Glu Trp Leu Lys Phe Ala Met Ala
35 40 45

Trp Trp His Thr Leu Gly Gln Ala Ser Gly Asp Pro Phe Gly Gly Gln
50 55 60

Thr Arg Ser Tyr Glu Trp Asp Lys Gly Glu Cys Pro Tyr Cys Arg Ala

-continued

```
65                  70                  75                  80

Lys Ala Lys Ala Asp Ala Gly Phe Glu Ile Met Gln Lys Leu Gly Ile
                85                  90                  95

Glu Tyr Phe Cys Phe His Asp Val Asp Leu Ile Glu Asp Cys Asp Asp
            100                 105                 110

Ile Ala Glu Tyr Glu Ala Arg Met Lys Asp Ile Thr Asp Tyr Leu Leu
        115                 120                 125

Glu Lys Met Lys Glu Thr Gly Ile Lys Asn Leu Trp Gly Thr Ala Asn
    130                 135                 140

Val Phe Gly His Lys Arg Tyr Met Asn Gly Ala Gly Thr Asn Pro Gln
145                 150                 155                 160

Phe Asp Val Val Ala Arg Ala Ala Val Gln Ile Lys Asn Ala Leu Asp
                165                 170                 175

Ala Thr Ile Lys Leu Gly Gly Ser Asn Tyr Val Phe Trp Gly Gly Arg
            180                 185                 190

Glu Gly Tyr Tyr Thr Leu Leu Asn Thr Gln Met Gln Arg Glu Lys Asp
        195                 200                 205

His Leu Ala Lys Leu Leu Thr Ala Ala Arg Asp Tyr Ala Arg Ala Lys
    210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Val Ile Gly Phe Leu Arg
                245                 250                 255

Ala Asn Gly Leu Asp Lys Asp Phe Lys Val Asn Ile Glu Val Asn His
            260                 265                 270

Ala Thr Leu Ala Gly His Thr Phe Glu His Glu Leu Thr Val Ala Arg
        275                 280                 285

Glu Asn Gly Phe Leu Gly Ser Ile Asp Ala Asn Arg Gly Asp Ala Gln
    290                 295                 300

Asn Gly Trp Asp Thr Asp Gln Phe Pro Val Asp Pro Tyr Asp Leu Thr
305                 310                 315                 320

Gln Ala Met Met Gln Val Leu Leu Asn Gly Gly Phe Gly Asn Gly Gly
                325                 330                 335

Thr Asn Phe Asp Ala Lys Leu Arg Arg Ser Ser Thr Asp Pro Glu Asp
            340                 345                 350

Ile Phe Ile Ala His Ile Ser Ala Met Asp Ala Met Ala His Ala Leu
        355                 360                 365

Leu Asn Ala Ala Ala Val Leu Glu Glu Ser Pro Leu Cys Gln Met Val
    370                 375                 380

Lys Glu Arg Tyr Ala Ser Phe Asp Asp Gly Leu Gly Lys Gln Phe Glu
385                 390                 395                 400

Glu Gly Lys Ala Thr Leu Glu Asp Leu Tyr Glu Tyr Ala Lys Ala Gln
                405                 410                 415

Gly Glu Pro Val Val Ala Ser Gly Lys Gln Glu Leu Tyr Glu Thr Leu
            420                 425                 430

Leu Asn Leu Tyr Ala Val Lys
        435
```

<210> SEQ ID NO 137
<211> LENGTH: 1317
<212> TYPE: DNA
<213> ORGANISM: Unknown
<220> FEATURE:
<223> OTHER INFORMATION: Obtained from environmental sample

<400> SEQUENCE: 137
atgaccaaag aatatttccc taccgtcggg aagatcccct tcgagggccc cgaaagcaag 60
aaccctatgg cgttccatta ctatgacccc aaccgtctgg tgatgggcaa gaagatgaaa 120
gactggctgc gtttcgccat ggcctggtgg cacaccctcg gccaggcgtc gggcgaccag 180
ttcggcggcc agacccgcag ttatgcgtgg gacgagggag aatgcccgta cgagcgcgcc 240
cgtgccaagg ctgacgccgg cttcgagatc atgcagaaac tcggtatcga gttcttctgc 300
ttccacgaca tcgacctgat cgaggatacc gacgacatcg ccgagtatga ggcccgcctg 360
aaagacatca cggactatct gctcgagaag atgaaagcca ctggcatcaa aaatctctgg 420
ggaacggcca acgtgttcgg ccacaagcgt tgcatgaacg gcgccgccac caacccggac 480
ttcgccgtgc tggcccgcgc tgccgtccag atcaagaacg ccatcgacgc caccatcaag 540
ctgggcggcg agaactatgt gttctggggt ggccgcgaag gctacacgag cctgctcaac 600
acccagatgc agcgtgagaa agagcacctg ggccgcctgc tgtccctggc ccgcgactat 660
ggccgcgccc acggcttcaa gggtaccttc ctgatcgagc ccaagccgat gggaccgacg 720
aaacaccagt acgaccagga tacggaaact gtcatcggtt tcctgcgccg ccacggtcta 780
gacaaggact tcaaggtcaa tatcgaggtg aaccatgcca cgctggcggg ccacaccttc 840
gaacacgaac tggcctgcgc cgtggatcac ggtatgctgg gcagcatcga cgccaaccgc 900
ggtgacgcac agaacggctg ggataccgac cagttcccga tcgacaactt cgagctgacc 960
ctttccatgc tccagatcat ccgcaacggt ggcctggcac ccggcggctc gaatttcgat 1020
gccaagctgc gccgcaactc caccgatccc gaagacattt tcatcgcgca catcagcgcc 1080
atggacgcca tggcccgcgc attggtcaat gcggccgcca tcctggagga gagcgctatt 1140
ccgaagatgg tcaaggagcg ttacgcttcg ttcgacagcg gcaaaggcaa ggaatacgag 1200
gaaggcaagc tgacgctcga agacatcgtg gcctatgcca aggcgaacgg agaaccgaag 1260
cagatttccg gcaaacagga actctacgag acgcttgtcg cactctatag caaataa 1317

<210> SEQ ID NO 138
<211> LENGTH: 438
<212> TYPE: PRT
<213> ORGANISM: Unknown
<220> FEATURE:
<223> OTHER INFORMATION: Obtained from environmental sample

<400> SEQUENCE: 138

Met Thr Lys Glu Tyr Phe Pro Thr Val Gly Lys Ile Pro Phe Glu Gly
1 5 10 15

Pro Glu Ser Lys Asn Pro Met Ala Phe His Tyr Tyr Asp Pro Asn Arg
20 25 30

Leu Val Met Gly Lys Lys Met Lys Asp Trp Leu Arg Phe Ala Met Ala
35 40 45

Trp Trp His Thr Leu Gly Gln Ala Ser Gly Asp Gln Phe Gly Gly Gln
50 55 60

Thr Arg Ser Tyr Ala Trp Asp Glu Gly Glu Cys Pro Tyr Glu Arg Ala
65 70 75 80

Arg Ala Lys Ala Asp Ala Gly Phe Glu Ile Met Gln Lys Leu Gly Ile
85 90 95

Glu Phe Phe Cys Phe His Asp Ile Asp Leu Ile Glu Asp Thr Asp Asp
100 105 110

Ile Ala Glu Tyr Glu Ala Arg Leu Lys Asp Ile Thr Asp Tyr Leu Leu
115 120 125

Glu Lys Met Lys Ala Thr Gly Ile Lys Asn Leu Trp Gly Thr Ala Asn
    130                 135                 140

Val Phe Gly His Lys Arg Cys Met Asn Gly Ala Ala Thr Asn Pro Asp
145                 150                 155                 160

Phe Ala Val Leu Ala Arg Ala Ala Val Gln Ile Lys Asn Ala Ile Asp
                165                 170                 175

Ala Thr Ile Lys Leu Gly Gly Glu Asn Tyr Val Phe Trp Gly Gly Arg
            180                 185                 190

Glu Gly Tyr Thr Ser Leu Leu Asn Thr Gln Met Gln Arg Glu Lys Glu
        195                 200                 205

His Leu Gly Arg Leu Leu Ser Leu Ala Arg Asp Tyr Gly Arg Ala His
    210                 215                 220

Gly Phe Lys Gly Thr Phe Leu Ile Glu Pro Lys Pro Met Gly Pro Thr
225                 230                 235                 240

Lys His Gln Tyr Asp Gln Asp Thr Glu Thr Val Ile Gly Phe Leu Arg
                245                 250                 255

Arg His Gly Leu Asp Lys Asp Phe Lys Val Asn Ile Glu Val Asn His
            260                 265                 270

Ala Thr Leu Ala Gly His Thr Phe Glu His Glu Leu Ala Cys Ala Val
        275                 280                 285

Asp His Gly Met Leu Gly Ser Ile Asp Ala Asn Arg Gly Asp Ala Gln
    290                 295                 300

Asn Gly Trp Asp Thr Asp Gln Phe Pro Ile Asp Asn Phe Glu Leu Thr
305                 310                 315                 320

Leu Ser Met Leu Gln Ile Ile Arg Asn Gly Gly Leu Ala Pro Gly Gly
                325                 330                 335

Ser Asn Phe Asp Ala Lys Leu Arg Arg Asn Ser Thr Asp Pro Glu Asp
            340                 345                 350

Ile Phe Ile Ala His Ile Ser Ala Met Asp Ala Met Ala Arg Ala Leu
        355                 360                 365

Val Asn Ala Ala Ala Ile Leu Glu Glu Ser Ala Ile Pro Lys Met Val
    370                 375                 380

Lys Glu Arg Tyr Ala Ser Phe Asp Ser Gly Lys Gly Lys Glu Tyr Glu
385                 390                 395                 400

Glu Gly Lys Leu Thr Leu Glu Asp Ile Val Ala Tyr Ala Lys Ala Asn
                405                 410                 415

Gly Glu Pro Lys Gln Ile Ser Gly Lys Gln Glu Leu Tyr Glu Thr Leu
            420                 425                 430

Val Ala Leu Tyr Ser Lys
        435

<210> SEQ ID NO 139
<211> LENGTH: 1317
<212> TYPE: DNA
<213> ORGANISM: Unknown
<220> FEATURE:
<223> OTHER INFORMATION: Obtained from environmental sample

<400> SEQUENCE: 139
atgaccaaag ggtatttccc taccatcggc aggattccct tcgagggaac tgaaagcaag 60
aatcccctcg cattccatta ctatgagccc gaccggctcg tactgggcaa gaaaatgaaa 120
gactggctgc gtttcgcgat ggcctggtgg cacaccctgg gccaggcgtc cggcgaccag 180
ttcggcggcc agacccgcag ctatgcctgg gacaaggccg agtgccccta tgagcgcgcc 240

```
aaggccaaag ccgacgccgg cttcgagatc atgcagaaac tcggcatcga gttcttctgt    300

ttccacgaca ttgacctcgt tgaggatacc gacgacatcg ccgagtatga ggcccggatg    360

aaggacatta ccgactatct cctggtcaag atgaaggaga ccggaatcaa gaacctctgg    420

ggtacggcca atgtcttcgg ccacaagcgc tatatgaacg gcgccgccac caatcccgac    480

ttcgacgtgg tggcccgcgc cgccgtccag atcaagaacg ccctcgatgc caccatcaag    540

ctgggcggtg aaaactatgt gttctggggc ggccgcgaag gctatatgag cctgctcaac    600

acgcagatgc agcgtgagaa ggagcacctg ggccggatgc tggtcgccgc ccgcgactac    660

gcccgcgccc acggcttcaa gggtaccttc ctcatcgagc ccaaaccgat ggaaccgacc    720

aagcaccagt acgaccagga tacggaaacc gtgatcggct tccttcgccg ccacggcctg    780

gacaaggatt tcaaggtgaa catcgaagtg aaccacgcca cgctggccgg ccacaccttc    840

gagcacgaac tggccaccgc cgtcgactgc ggcctgctgg gcagcatcga cgccaatcgc    900

ggcgacgctc agaacggctg ggataccgac cagttcccga tcgacaactt cgaactcacg    960

ctggccatgc tgcagattat ccgcaacggc ggtctggcac ccggcggctc gaacttcgac   1020

gccaaactgc gccgtaactc caccgatccg gaagatatct tcatcgccca catcagtgcg   1080

atggacgcga tggcccgtgc gctggtcaac gccgccgcaa tctgggaaga gtctcccatc   1140

ccgcagatga agaaagaacg ctacgcgtcg ttcgacagcg gcaagggcaa ggaattcgaa   1200

gagggcaagc tctgcctcga agacctcgtg gcctatgcca aggcgaacgg agaaccgaaa   1260

cagatctccg gcaggcagga actatatgag accatcgtcg ccctttattg caaatag      1317
```

<210> SEQ ID NO 140
<211> LENGTH: 438
<212> TYPE: PRT
<213> ORGANISM: Unknown
<220> FEATURE:
<223> OTHER INFORMATION: Obtained from environmental sample

<400> SEQUENCE: 140

```
Met Thr Lys Gly Tyr Phe Pro Thr Ile Gly Arg Ile Pro Phe Glu Gly
1               5                   10                  15

Thr Glu Ser Lys Asn Pro Leu Ala Phe His Tyr Tyr Glu Pro Asp Arg
            20                  25                  30

Leu Val Leu Gly Lys Lys Met Lys Asp Trp Leu Arg Phe Ala Met Ala
        35                  40                  45

Trp Trp His Thr Leu Gly Gln Ala Ser Gly Asp Gln Phe Gly Gly Gln
    50                  55                  60

Thr Arg Ser Tyr Ala Trp Asp Lys Ala Glu Cys Pro Tyr Glu Arg Ala
65                  70                  75                  80

Lys Ala Lys Ala Asp Ala Gly Phe Glu Ile Met Gln Lys Leu Gly Ile
                85                  90                  95

Glu Phe Phe Cys Phe His Asp Ile Asp Leu Val Glu Asp Thr Asp Asp
            100                 105                 110

Ile Ala Glu Tyr Glu Ala Arg Met Lys Asp Ile Thr Asp Tyr Leu Leu
        115                 120                 125

Val Lys Met Lys Glu Thr Gly Ile Lys Asn Leu Trp Gly Thr Ala Asn
    130                 135                 140

Val Phe Gly His Lys Arg Tyr Met Asn Gly Ala Ala Thr Asn Pro Asp
145                 150                 155                 160

Phe Asp Val Val Ala Arg Ala Ala Val Gln Ile Lys Asn Ala Leu Asp
                165                 170                 175
```

```
Ala Thr Ile Lys Leu Gly Gly Glu Asn Tyr Val Phe Trp Gly Gly Arg
            180                 185                 190

Glu Gly Tyr Met Ser Leu Leu Asn Thr Gln Met Gln Arg Glu Lys Glu
        195                 200                 205

His Leu Gly Arg Met Leu Val Ala Ala Arg Asp Tyr Ala Arg Ala His
    210                 215                 220

Gly Phe Lys Gly Thr Phe Leu Ile Glu Pro Lys Pro Met Glu Pro Thr
225                 230                 235                 240

Lys His Gln Tyr Asp Gln Asp Thr Glu Thr Val Ile Gly Phe Leu Arg
                245                 250                 255

Arg His Gly Leu Asp Lys Asp Phe Lys Val Asn Ile Glu Val Asn His
            260                 265                 270

Ala Thr Leu Ala Gly His Thr Phe Glu His Glu Leu Ala Thr Ala Val
        275                 280                 285

Asp Cys Gly Leu Leu Gly Ser Ile Asp Ala Asn Arg Gly Asp Ala Gln
    290                 295                 300

Asn Gly Trp Asp Thr Asp Gln Phe Pro Ile Asp Asn Phe Glu Leu Thr
305                 310                 315                 320

Leu Ala Met Leu Gln Ile Ile Arg Asn Gly Gly Leu Ala Pro Gly Gly
                325                 330                 335

Ser Asn Phe Asp Ala Lys Leu Arg Arg Asn Ser Thr Asp Pro Glu Asp
            340                 345                 350

Ile Phe Ile Ala His Ile Ser Ala Met Asp Ala Met Ala Arg Ala Leu
        355                 360                 365

Val Asn Ala Ala Ala Ile Trp Glu Glu Ser Pro Ile Pro Gln Met Lys
    370                 375                 380

Lys Glu Arg Tyr Ala Ser Phe Asp Ser Gly Lys Gly Lys Glu Phe Glu
385                 390                 395                 400

Glu Gly Lys Leu Cys Leu Glu Asp Leu Val Ala Tyr Ala Lys Ala Asn
                405                 410                 415

Gly Glu Pro Lys Gln Ile Ser Gly Arg Gln Glu Leu Tyr Glu Thr Ile
            420                 425                 430

Val Ala Leu Tyr Cys Lys
        435
```

<210> SEQ ID NO 141
<211> LENGTH: 1317
<212> TYPE: DNA
<213> ORGANISM: Unknown
<220> FEATURE:
<223> OTHER INFORMATION: Obtained from environmental sample

<400> SEQUENCE: 141

```
atgaccaacg agtattttcc cggaatcggt gtgattccgt ttgaaggaca ggaaagcaag      60

aatcccatgg ctttccatta ttatgacgcc aaccgcgtag tgatgggcaa acccatgaag     120

gaatggttca aatttgccat ggcctggtgg catacgctgg ggcaggcatc ggccgatccc     180

ttcggcggac agacccgctc ctacgcatgg gacaagggcg agtgccctta ctgccgtgcc     240

cgccagaagg ccgacgccgg ctttgaactg atgcagaagc tgggtatcgg ctatttctgc     300

ttccacgatg tggatatcat cgaggactgc gaagacattg ccgagtatga ggcccgtatg     360

aaggacatca cggactatct gctggtgaag atgaaggaaa cgggcatcaa gaacctgtgg     420

ggcacggcca acgtcttcgg ccacaagcgc tatatgaacg gcgctgccac caacccgcag     480

ttcgacgtgg tggcccgcgc tgcggtccag atcaagaacg ccctggacgc caccatcaag     540
```

```
ctgggcggca gcaattacgt gttctggggc ggccgcgaag gctattatac cctttggaac    600

acgcagatgc ggcgggagaa ggaccacctg gcccagatgc tcaaggcagc ccgtgactat    660

gcccgcggca agggattcaa gggcacgttc ctcattgagc ccaagcccat ggagcccacc    720

aagcaccagt acgacgtaga tacggagacc gtgattggct tcctgcgcgc aaacggactg    780

gacaaggact tcaaggtgaa tatcgaagtg aaccacgcca ccctggccgg ccacaccttc    840

gagcacgaac tcaccgtggc ccgcgaaaac ggcttcctgg gcagcatcga cgccaaccgc    900

ggagacgccc agaacggttg ggatacagac cagttcccca tagatgcctt tgacctcacc    960

caggccatga tgcaggtcct gctcaacggc ggattcggca acggcggcac caacttcgac   1020

gccaaactgc gccgttcctc cacggatccc gaggacatct tcatcgccca catcggcgcc   1080

atggacgcca tggcccacgc cctcctgaac gccgccgcca tcctggaaga gagccccatg   1140

ccgggcatgg tgaaggagcg ctacgcttcc ttcgacaatg gccttggcaa gaagttcgag   1200

gaaggaaagg ccacgctgga agagctgtac gactatgcca agaagaacgg cgagcctgtg   1260

gccgcttccg gcaagcagga actgtacgaa acgctgctga acctgtacgc caagtaa      1317
```

<210> SEQ ID NO 142
<211> LENGTH: 438
<212> TYPE: PRT
<213> ORGANISM: Unknown
<220> FEATURE:
<223> OTHER INFORMATION: Obtained from environmental sample

<400> SEQUENCE: 142

```
Met Thr Asn Glu Tyr Phe Pro Gly Ile Gly Val Ile Pro Phe Glu Gly
1               5                   10                  15

Gln Glu Ser Lys Asn Pro Met Ala Phe His Tyr Tyr Asp Ala Asn Arg
            20                  25                  30

Val Val Met Gly Lys Pro Met Lys Glu Trp Phe Lys Phe Ala Met Ala
        35                  40                  45

Trp Trp His Thr Leu Gly Gln Ala Ser Ala Asp Pro Phe Gly Gly Gln
    50                  55                  60

Thr Arg Ser Tyr Ala Trp Asp Lys Gly Glu Cys Pro Tyr Cys Arg Ala
65                  70                  75                  80

Arg Gln Lys Ala Asp Ala Gly Phe Glu Leu Met Gln Lys Leu Gly Ile
                85                  90                  95

Gly Tyr Phe Cys Phe His Asp Val Asp Ile Ile Glu Asp Cys Glu Asp
            100                 105                 110

Ile Ala Glu Tyr Glu Ala Arg Met Lys Asp Ile Thr Asp Tyr Leu Leu
        115                 120                 125

Val Lys Met Lys Glu Thr Gly Ile Lys Asn Leu Trp Gly Thr Ala Asn
    130                 135                 140

Val Phe Gly His Lys Arg Tyr Met Asn Gly Ala Ala Thr Asn Pro Gln
145                 150                 155                 160

Phe Asp Val Val Ala Arg Ala Ala Val Gln Ile Lys Asn Ala Leu Asp
                165                 170                 175

Ala Thr Ile Lys Leu Gly Gly Ser Asn Tyr Val Phe Trp Gly Gly Arg
            180                 185                 190

Glu Gly Tyr Tyr Thr Leu Trp Asn Thr Gln Met Arg Arg Glu Lys Asp
        195                 200                 205

His Leu Ala Gln Met Leu Lys Ala Ala Arg Asp Tyr Ala Arg Gly Lys
    210                 215                 220

Gly Phe Lys Gly Thr Phe Leu Ile Glu Pro Lys Pro Met Glu Pro Thr
```

-continued

```
225                 230                 235                 240

Lys His Gln Tyr Asp Val Asp Thr Glu Thr Val Ile Gly Phe Leu Arg
                245                 250                 255

Ala Asn Gly Leu Asp Lys Asp Phe Lys Val Asn Ile Glu Val Asn His
            260                 265                 270

Ala Thr Leu Ala Gly His Thr Phe Glu His Glu Leu Thr Val Ala Arg
        275                 280                 285

Glu Asn Gly Phe Leu Gly Ser Ile Asp Ala Asn Arg Gly Asp Ala Gln
    290                 295                 300

Asn Gly Trp Asp Thr Asp Gln Phe Pro Ile Asp Ala Phe Asp Leu Thr
305                 310                 315                 320

Gln Ala Met Met Gln Val Leu Leu Asn Gly Gly Phe Gly Asn Gly Gly
                325                 330                 335

Thr Asn Phe Asp Ala Lys Leu Arg Arg Ser Ser Thr Asp Pro Glu Asp
            340                 345                 350

Ile Phe Ile Ala His Ile Gly Ala Met Asp Ala Met Ala His Ala Leu
        355                 360                 365

Leu Asn Ala Ala Ala Ile Leu Glu Glu Ser Pro Met Pro Gly Met Val
    370                 375                 380

Lys Glu Arg Tyr Ala Ser Phe Asp Asn Gly Leu Gly Lys Lys Phe Glu
385                 390                 395                 400

Glu Gly Lys Ala Thr Leu Glu Glu Leu Tyr Asp Tyr Ala Lys Lys Asn
                405                 410                 415

Gly Glu Pro Val Ala Ala Ser Gly Lys Gln Glu Leu Tyr Glu Thr Leu
            420                 425                 430

Leu Asn Leu Tyr Ala Lys
        435
```

<210> SEQ ID NO 143
<211> LENGTH: 1314
<212> TYPE: DNA
<213> ORGANISM: Unknown
<220> FEATURE:
<223> OTHER INFORMATION: Obtained from environmental sample

<400> SEQUENCE: 143

```
atgaaagaat acttccctac catcggaaaa atccctttcg agggccctca gagcaagaat     60

ccgctcgcat tccattacta tgacgccaac cgcgttgtcg ccggcaaacc catgaaggac    120

tggctcaagt tcgccatggc ttggtggcac accctgggcg cagcatcggc agacccctto    180

ggcggccaga cccgcagcta cgagtgggac aaagccgagt gcccttactg ccgtgcccgt    240

gaaaaggccg acgccggctt cgagatcatg cagaaacttg gaatcgagta cttctgcttc    300

catgacatcg accttgtgga agactgcgag gacattgccg agtacgaggc ccgcatgaag    360

gacatcacgg actacctcct ggagaagatg aaggccaccg gcatcaagaa cctgtggggc    420

accgccaacg tctttggcaa caagcgctac atgaacggcg cagccaccaa ccctcagttc    480

gacatcgttg cccgtgcagc tgtccagatc aagaacgcca tcgacgcaac aatcaagctg    540

ggcggtaccg gttacgtatt ctggggcggc cgcgagggct actacaccct cctgaacacc    600

cagatgcagc gcgagaagga ccaccttgcc aagatgctca ccgcagcccg cgactacgcc    660

cgcgccaagg gattcaaggg cacattcctc atcgagccca agcccatgga gcccaccaag    720

caccagtacg atgttgacac ggaaaccgtc atcggcttcc tccgcgccaa cggcctggac    780

aaggacttca aggtgaacat cgaggtgaac cacgccaccc tggccggcca caccttcgag    840
```

```
cacgagctca ccgtggccgt ggacaacggc ttcctgggca gcatcgacgc aaaccgcggc    900

gacgcccaga acggctggga cactgaccag ttccctgtgg atccttacga cctcacccag    960

gcaatgatgc agattatccg caacggcggc ttcaaggacg gcggcaccaa cttcgacgcc   1020

aaactccgcc gcagctccac ggaccccgag gacatcttca tcgcccacat cagcgcaatg   1080

gatgcaatgg cacacgccct catcaacgct gctgcagtgc ttgaggaaag ccctctgtgc   1140

gagatggttg caaagcgcta cgccagcttt gacagcggtc ttggcaagaa gttcgaggaa   1200

ggcaaagcca ctctcgagga gatctacgag tatgccaaga aggccccggc acccgtcgcc   1260

gcctccggca agcaggagct ctacgagaca ctgctcaatc tgtacgctaa ataa          1314


<210> SEQ ID NO 144
<211> LENGTH: 437
<212> TYPE: PRT
<213> ORGANISM: Unknown
<220> FEATURE:
<223> OTHER INFORMATION: Obtained from environmental sample

<400> SEQUENCE: 144

Met Lys Glu Tyr Phe Pro Thr Ile Gly Lys Ile Pro Phe Glu Gly Pro
1               5                   10                  15

Gln Ser Lys Asn Pro Leu Ala Phe His Tyr Tyr Asp Ala Asn Arg Val
            20                  25                  30

Val Ala Gly Lys Pro Met Lys Asp Trp Leu Lys Phe Ala Met Ala Trp
        35                  40                  45

Trp His Thr Leu Gly Ala Ala Ser Ala Asp Pro Phe Gly Gly Gln Thr
    50                  55                  60

Arg Ser Tyr Glu Trp Asp Lys Ala Glu Cys Pro Tyr Cys Arg Ala Arg
65                  70                  75                  80

Glu Lys Ala Asp Ala Gly Phe Glu Ile Met Gln Lys Leu Gly Ile Glu
                85                  90                  95

Tyr Phe Cys Phe His Asp Ile Asp Leu Val Glu Asp Cys Glu Asp Ile
            100                 105                 110

Ala Glu Tyr Glu Ala Arg Met Lys Asp Ile Thr Asp Tyr Leu Leu Glu
        115                 120                 125

Lys Met Lys Ala Thr Gly Ile Lys Asn Leu Trp Gly Thr Ala Asn Val
    130                 135                 140

Phe Gly Asn Lys Arg Tyr Met Asn Gly Ala Ala Thr Asn Pro Gln Phe
145                 150                 155                 160

Asp Ile Val Ala Arg Ala Ala Val Gln Ile Lys Asn Ala Ile Asp Ala
                165                 170                 175

Thr Ile Lys Leu Gly Gly Thr Gly Tyr Val Phe Trp Gly Gly Arg Glu
            180                 185                 190

Gly Tyr Tyr Thr Leu Leu Asn Thr Gln Met Gln Arg Glu Lys Asp His
        195                 200                 205

Leu Ala Lys Met Leu Thr Ala Ala Arg Asp Tyr Ala Arg Ala Lys Gly
    210                 215                 220

Phe Lys Gly Thr Phe Leu Ile Glu Pro Lys Pro Met Glu Pro Thr Lys
225                 230                 235                 240

His Gln Tyr Asp Val Asp Thr Glu Thr Val Ile Gly Phe Leu Arg Ala
                245                 250                 255

Asn Gly Leu Asp Lys Asp Phe Lys Val Asn Ile Glu Val Asn His Ala
            260                 265                 270

Thr Leu Ala Gly His Thr Phe Glu His Glu Leu Thr Val Ala Val Asp
        275                 280                 285
```

```
Asn Gly Phe Leu Gly Ser Ile Asp Ala Asn Arg Gly Asp Ala Gln Asn
    290                 295                 300

Gly Trp Asp Thr Asp Gln Phe Pro Val Asp Pro Tyr Asp Leu Thr Gln
305                 310                 315                 320

Ala Met Met Gln Ile Ile Arg Asn Gly Gly Phe Lys Asp Gly Gly Thr
                325                 330                 335

Asn Phe Asp Ala Lys Leu Arg Arg Ser Ser Thr Asp Pro Glu Asp Ile
            340                 345                 350

Phe Ile Ala His Ile Ser Ala Met Asp Ala Met Ala His Ala Leu Ile
        355                 360                 365

Asn Ala Ala Ala Val Leu Glu Glu Ser Pro Leu Cys Glu Met Val Ala
    370                 375                 380

Lys Arg Tyr Ala Ser Phe Asp Ser Gly Leu Gly Lys Lys Phe Glu Glu
385                 390                 395                 400

Gly Lys Ala Thr Leu Glu Glu Ile Tyr Glu Tyr Ala Lys Lys Ala Pro
                405                 410                 415

Ala Pro Val Ala Ala Ser Gly Lys Gln Glu Leu Tyr Glu Thr Leu Leu
            420                 425                 430

Asn Leu Tyr Ala Lys
        435
```

<210> SEQ ID NO 145
<211> LENGTH: 1317
<212> TYPE: DNA
<213> ORGANISM: Unknown
<220> FEATURE:
<223> OTHER INFORMATION: Obtained from environmental sample

<400> SEQUENCE: 145

```
atgaccaaag agtatttccc tacaatcgga aagattccct tcgaaggccc ggagagcaag     60

aatccgctgg cattccatta ctatgaaccc gacagaatca tcctcggcag gaagatgaag    120

gactggctgc gcttcgccgt ggcctggtgg cacaccctcg gccaggcgtc cggcgaccag    180

ttcggaggcc agacccgcaa ctatgcgtgg gacgagcccg aatgcccggt agagcgcgcg    240

aaagccaagg ccgacgccgg cttcgagctg atgcagaagc tgggcatcga gtatttctgc    300

ttccacgacg tagacctcat agaggaggcc gcaaccatcg aagaatatga ggagcgcatg    360

ggcatcataa ccgactacct gctcgggaag atgaaggaga caggtatcaa gaacctctgg    420

ggcaccgcca acgtgttcgg ccacaagcgt tacatgaacg gagccgccac caaccccgac    480

ttcgacgtgg tggcccgtgc ggccgtgcag atcaagaacg ccatcgacgc caccatcaag    540

ctgggcggcg agaattacgt attctggggc ggacgcgagg gctatgcaag cctgctcaac    600

actcagatgc agcgcgagaa agaccacctg ggacgcatgc tggctgcagc ccgcgactat    660

ggccgcgccc acggattcaa gggcactttc ctcatcgagc ccaaacccat ggagcctacc    720

aagcaccagt acgaccagga taccgagacc gttatcgcct tcctgcgcag gaacggcctc    780

gacaaggatt tcaaggtaaa catcgaggtg aaccacgcca ccctggcggg ccacaccttc    840

gagcacgaac tggcggtggc agtggacaac ggcctgcttg gcagcatcga cgccaaccgc    900

ggcgacgcgc agaacggatg ggacaccgac cagttcccca tcgacaactt cgagctcacc    960

caggccatgc tgcagataat ccgcaacggc ggactgggaa ccggcggatc gaacttcgac   1020

gccaagctgc gccgcaattc caccgaccct gaggatatct tcatcgccca catcagtgcg   1080

atggacgcca tggcacgcgc gctggcaaac gccgccgcaa tcatcgaaga gagccccatc   1140
```

```
cccgcaatgc tgaaggagcg ctacgcatcg ttcgacagcg gcaagggcaa ggagttcgag   1200

gacggcaaac tgagcctcga agaactggta gcctacgcca aggcgaacgg cgagccgaag   1260

cagatttccg gcaagcagga actctacgaa accatagtgg ccctctattg caagtaa      1317


<210> SEQ ID NO 146
<211> LENGTH: 438
<212> TYPE: PRT
<213> ORGANISM: Unknown
<220> FEATURE:
<223> OTHER INFORMATION: Obtained from environmental sample

<400> SEQUENCE: 146

Met Thr Lys Glu Tyr Phe Pro Thr Ile Gly Lys Ile Pro Phe Glu Gly
1               5                   10                  15

Pro Glu Ser Lys Asn Pro Leu Ala Phe His Tyr Tyr Glu Pro Asp Arg
            20                  25                  30

Ile Ile Leu Gly Arg Lys Met Lys Asp Trp Leu Arg Phe Ala Val Ala
        35                  40                  45

Trp Trp His Thr Leu Gly Gln Ala Ser Gly Asp Gln Phe Gly Gly Gln
    50                  55                  60

Thr Arg Asn Tyr Ala Trp Asp Glu Pro Glu Cys Pro Val Glu Arg Ala
65                  70                  75                  80

Lys Ala Lys Ala Asp Ala Gly Phe Glu Leu Met Gln Lys Leu Gly Ile
                85                  90                  95

Glu Tyr Phe Cys Phe His Asp Val Asp Leu Ile Glu Glu Ala Ala Thr
            100                 105                 110

Ile Glu Glu Tyr Glu Glu Arg Met Gly Ile Ile Thr Asp Tyr Leu Leu
        115                 120                 125

Gly Lys Met Lys Glu Thr Gly Ile Lys Asn Leu Trp Gly Thr Ala Asn
    130                 135                 140

Val Phe Gly His Lys Arg Tyr Met Asn Gly Ala Ala Thr Asn Pro Asp
145                 150                 155                 160

Phe Asp Val Val Ala Arg Ala Ala Val Gln Ile Lys Asn Ala Ile Asp
                165                 170                 175

Ala Thr Ile Lys Leu Gly Gly Glu Asn Tyr Val Phe Trp Gly Gly Arg
            180                 185                 190

Glu Gly Tyr Ala Ser Leu Leu Asn Thr Gln Met Gln Arg Glu Lys Asp
        195                 200                 205

His Leu Gly Arg Met Leu Ala Ala Ala Arg Asp Tyr Gly Arg Ala His
    210                 215                 220

Gly Phe Lys Gly Thr Phe Leu Ile Glu Pro Lys Pro Met Glu Pro Thr
225                 230                 235                 240

Lys His Gln Tyr Asp Gln Asp Thr Glu Thr Val Ile Ala Phe Leu Arg
                245                 250                 255

Arg Asn Gly Leu Asp Lys Asp Phe Lys Val Asn Ile Glu Val Asn His
            260                 265                 270

Ala Thr Leu Ala Gly His Thr Phe Glu His Glu Leu Ala Val Ala Val
        275                 280                 285

Asp Asn Gly Leu Leu Gly Ser Ile Asp Ala Asn Arg Gly Asp Ala Gln
    290                 295                 300

Asn Gly Trp Asp Thr Asp Gln Phe Pro Ile Asp Asn Phe Glu Leu Thr
305                 310                 315                 320

Gln Ala Met Leu Gln Ile Ile Arg Asn Gly Gly Leu Gly Thr Gly Gly
                325                 330                 335
```

```
Ser Asn Phe Asp Ala Lys Leu Arg Arg Asn Ser Thr Asp Pro Glu Asp
            340                 345                 350

Ile Phe Ile Ala His Ile Ser Ala Met Asp Ala Met Ala Arg Ala Leu
        355                 360                 365

Ala Asn Ala Ala Ala Ile Ile Glu Glu Ser Pro Ile Pro Ala Met Leu
    370                 375                 380

Lys Glu Arg Tyr Ala Ser Phe Asp Ser Gly Lys Gly Lys Glu Phe Glu
385                 390                 395                 400

Asp Gly Lys Leu Ser Leu Glu Glu Leu Val Ala Tyr Ala Lys Ala Asn
                405                 410                 415

Gly Glu Pro Lys Gln Ile Ser Gly Lys Gln Glu Leu Tyr Glu Thr Ile
            420                 425                 430

Val Ala Leu Tyr Cys Lys
        435
```

<210> SEQ ID NO 147
<211> LENGTH: 1317
<212> TYPE: DNA
<213> ORGANISM: Unknown
<220> FEATURE:
<223> OTHER INFORMATION: Obtained from environmental sample

<400> SEQUENCE: 147

```
atggcacaag aatacttccc taccattggg aaaatcccct tcgagggcac tgagagcaag     60

aatcccccttg ctttccatta ctatgagccg gagcgcattg tctgcggcaa acccatgaaa    120

gaatggctca agtttgccat ggcctggtgg cacacgctgg ggcaggcatc ggccgatccc    180

ttcggcggcc aaacccgcag ctatgcctgg gataagggcg aatgccccta ctgccgtgcc    240

cgcgccaagg cggacgccgg cttcgagatt atgcaaaagc tgggcatcga gtacttctgc    300

ttccacgata tcgacctggt agaagactgt gacgatattg cggaatacga agcccgcatg    360

aaggacatca cggactacct cctggagaag atgaaggaaa ccggtatcaa gaacctctgg    420

ggcaccgcca atgtgtttgg tcacaagcgc tacatgaacg gcgccgccac caacccgcag    480

tttgacgtag tggcccgtgc cgctgttcag attaagaacg ccattgacgc caccatcaag    540

ttgggcggtg ccaattacgt gttctggggc ggccgcgagg gctattacag cctcctgaac    600

acccagatgc agcgggagaa ggaccacctg gccaagctgc tcacggcagc ccgcgactat    660

gcccgcgcca acggcttcaa gggaaccttc ctgattgagc ccaagcccat ggagcccacc    720

aagcaccagt acgacgtgga tacggagacg gtcattggct tcctccgcgc caacggcctg    780

gacaaggact tcaaggtgaa tatcgaggtg aaccacgcca cgttggccgg ccacaccttt    840

gagcacgagc tcaccgtggc ccgcgagaac ggcttcctgg gcagcatcga cgccaaccgc    900

ggcgatgccc agaacggctg ggatacggac cagttcccgg tagacgctta tgagctcacc    960

caggccatga tgcaggtgct cctgaacgga ggcttcggca acggcggcac caacttcgac   1020

gccaagctgc gccgctcctc cacggacccg gaggacatct tcatcgccca tatcagtgcg   1080

atggatgcca tggcccacgc cctgctcaac gccgccgccg tgctggagga aagccccctg   1140

tgccagatgg tgaaggagcg ctacgccagc tttgacagcg gtccgggcaa gcagttcgag   1200

gaaggaaagg ccaccctgga ggacctgtac aactacgcca aagccaccgg tgaacccgtg   1260

gttgcctccg gcaagcagga actttacgag accctcctga acctctatgc aaagtag      1317
```

<210> SEQ ID NO 148
<211> LENGTH: 438
<212> TYPE: PRT

<213> ORGANISM: Unknown
<220> FEATURE:
<223> OTHER INFORMATION: Obtained from environmental sample

<400> SEQUENCE: 148

```
Met Ala Gln Glu Tyr Phe Pro Thr Ile Gly Lys Ile Pro Phe Glu Gly
1               5                   10                  15

Thr Glu Ser Lys Asn Pro Leu Ala Phe His Tyr Tyr Glu Pro Glu Arg
            20                  25                  30

Ile Val Cys Gly Lys Pro Met Lys Glu Trp Leu Lys Phe Ala Met Ala
        35                  40                  45

Trp Trp His Thr Leu Gly Gln Ala Ser Ala Asp Pro Phe Gly Gly Gln
    50                  55                  60

Thr Arg Ser Tyr Ala Trp Asp Lys Gly Glu Cys Pro Tyr Cys Arg Ala
65                  70                  75                  80

Arg Ala Lys Ala Asp Ala Gly Phe Glu Ile Met Gln Lys Leu Gly Ile
                85                  90                  95

Glu Tyr Phe Cys Phe His Asp Ile Asp Leu Val Glu Asp Cys Asp Asp
            100                 105                 110

Ile Ala Glu Tyr Glu Ala Arg Met Lys Asp Ile Thr Asp Tyr Leu Leu
        115                 120                 125

Glu Lys Met Lys Glu Thr Gly Ile Lys Asn Leu Trp Gly Thr Ala Asn
    130                 135                 140

Val Phe Gly His Lys Arg Tyr Met Asn Gly Ala Ala Thr Asn Pro Gln
145                 150                 155                 160

Phe Asp Val Val Ala Arg Ala Ala Val Gln Ile Lys Asn Ala Ile Asp
                165                 170                 175

Ala Thr Ile Lys Leu Gly Gly Ala Asn Tyr Val Phe Trp Gly Gly Arg
            180                 185                 190

Glu Gly Tyr Tyr Ser Leu Leu Asn Thr Gln Met Gln Arg Glu Lys Asp
        195                 200                 205

His Leu Ala Lys Leu Leu Thr Ala Ala Arg Asp Tyr Ala Arg Ala Asn
    210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Val Ile Gly Phe Leu Arg
                245                 250                 255

Ala Asn Gly Leu Asp Lys Asp Phe Lys Val Asn Ile Glu Val Asn His
            260                 265                 270

Ala Thr Leu Ala Gly His Thr Phe Glu His Glu Leu Thr Val Ala Arg
        275                 280                 285

Glu Asn Gly Phe Leu Gly Ser Ile Asp Ala Asn Arg Gly Asp Ala Gln
    290                 295                 300

Asn Gly Trp Asp Thr Asp Gln Phe Pro Val Asp Ala Tyr Glu Leu Thr
305                 310                 315                 320

Gln Ala Met Met Gln Val Leu Leu Asn Gly Gly Phe Gly Asn Gly Gly
                325                 330                 335

Thr Asn Phe Asp Ala Lys Leu Arg Arg Ser Ser Thr Asp Pro Glu Asp
            340                 345                 350

Ile Phe Ile Ala His Ile Ser Ala Met Asp Ala Met Ala His Ala Leu
        355                 360                 365

Leu Asn Ala Ala Ala Val Leu Glu Glu Ser Pro Leu Cys Gln Met Val
    370                 375                 380

Lys Glu Arg Tyr Ala Ser Phe Asp Ser Gly Pro Gly Lys Gln Phe Glu
```

-continued 385 390 395 400

Glu Gly Lys Ala Thr Leu Glu Asp Leu Tyr Asn Tyr Ala Lys Ala Thr
405 410 415

Gly Glu Pro Val Val Ala Ser Gly Lys Gln Glu Leu Tyr Glu Thr Leu
420 425 430

Leu Asn Leu Tyr Ala Lys
435

<210> SEQ ID NO 149
<211> LENGTH: 1317
<212> TYPE: DNA
<213> ORGANISM: Unknown
<220> FEATURE:
<223> OTHER INFORMATION: Obtained from environmental sample

<400> SEQUENCE: 149
atggcacaag aatacttccc taccattggg aaaatcccct tcgagggcac tgagagcaag 60
aatccccttg ctttccatta ctatgagccg gagcgcattg tctgcggcaa acccatgaaa 120
gaatggctca agtttgccat ggcctggtgg cacacgctgg ggcaggcatc ggccgatccc 180
ttcggcggcc aaacccgcag ctatgcctgg gataagggcg aatgccccta ctgccgtgcc 240
cgtgccaagg cggacgccgg ttttgagatt atgcaaaagc tgggcatcga gtacttctgc 300
ttccacgata tcgacctggt agaagactgt gacgatattg cggaatacga agcccgcatg 360
aaggacatca cggactacct cctggagaag atgaaggaaa ccggcatcaa gaacctctgg 420
ggcaccgcca atgtgtttgg tcacaagcgc tacatgaacg gcgccggcac caatccgcag 480
tttgacgtgg tggcccgtgc tgccgtgcaa atcaagaacg ccattgacgc caccatcaag 540
ttgggcggtg ccaattacgt gttctggggc ggccgcgagg gctattacag cctcctgaac 600
acccagatgc agcgggagaa ggaccacctg gccaagctgc tcacggcagc ccgcgactat 660
gcccgcgcca acggcttcaa gggaaccttc ctgattgagc ccaagcccat ggagcccacc 720
aagcaccagt acgacgtgga tacggagacg gtcattggct tcctccgcgc caacggcctg 780
gacaaggact tcaaggtgaa tatcgaggtg aaccacgcca cgctggccgg ccacaccttt 840
gagcacgaac tcaccgtggc ccgcgagaac ggcttcctgg gcagcatcga cgccaaccgc 900
ggcgatgccc agaacggctg ggatacggac cagttcccgg tagacgctta tgagctcacc 960
caggccatga tgcaggtgct cctgaacgga ggcttcggca acggcggcac caacttcgac 1020
gccaagctgc gccgctcctc cacggacctg gaggacatct tcatcgccca tatcagtgcg 1080
atggatgcca tggcccacgc cctgctcaac gccgccgccg tgctggagga aagccccctg 1140
tgccagatgg tgaaggagcg ctacgccagc tttgacagcg gtccgggcaa gcagttcgag 1200
gaaggaaagg ccaccctgga ggacctgtac aactacgcca aagccaacgg tgaacccgtg 1260
gttgcctccg gcaagcagga actttacgag accctcctga acctctatgc aaagtag 1317

<210> SEQ ID NO 150
<211> LENGTH: 438
<212> TYPE: PRT
<213> ORGANISM: Unknown
<220> FEATURE:
<223> OTHER INFORMATION: Obtained from environmental sample

<400> SEQUENCE: 150

Met Ala Gln Glu Tyr Phe Pro Thr Ile Gly Lys Ile Pro Phe Glu Gly
1 5 10 15

Thr Glu Ser Lys Asn Pro Leu Ala Phe His Tyr Tyr Glu Pro Glu Arg

-continued

```
            20                  25                  30

Ile Val Cys Gly Lys Pro Met Lys Glu Trp Leu Lys Phe Ala Met Ala
        35                  40                  45

Trp Trp His Thr Leu Gly Gln Ala Ser Ala Asp Pro Phe Gly Gly Gln
    50                  55                  60

Thr Arg Ser Tyr Ala Trp Asp Lys Gly Glu Cys Pro Tyr Cys Arg Ala
65                  70                  75                  80

Arg Ala Lys Ala Asp Ala Gly Phe Glu Ile Met Gln Lys Leu Gly Ile
                85                  90                  95

Glu Tyr Phe Cys Phe His Asp Ile Asp Leu Val Glu Asp Cys Asp Asp
            100                 105                 110

Ile Ala Glu Tyr Glu Ala Arg Met Lys Asp Ile Thr Asp Tyr Leu Leu
        115                 120                 125

Glu Lys Met Lys Glu Thr Gly Ile Lys Asn Leu Trp Gly Thr Ala Asn
    130                 135                 140

Val Phe Gly His Lys Arg Tyr Met Asn Gly Ala Gly Thr Asn Pro Gln
145                 150                 155                 160

Phe Asp Val Val Ala Arg Ala Ala Val Gln Ile Lys Asn Ala Ile Asp
                165                 170                 175

Ala Thr Ile Lys Leu Gly Gly Ala Asn Tyr Val Phe Trp Gly Gly Arg
            180                 185                 190

Glu Gly Tyr Tyr Ser Leu Leu Asn Thr Gln Met Gln Arg Glu Lys Asp
        195                 200                 205

His Leu Ala Lys Leu Leu Thr Ala Ala Arg Asp Tyr Ala Arg Ala Asn
    210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Val Ile Gly Phe Leu Arg
                245                 250                 255

Ala Asn Gly Leu Asp Lys Asp Phe Lys Val Asn Ile Glu Val Asn His
            260                 265                 270

Ala Thr Leu Ala Gly His Thr Phe Glu His Glu Leu Thr Val Ala Arg
        275                 280                 285

Glu Asn Gly Phe Leu Gly Ser Ile Asp Ala Asn Arg Gly Asp Ala Gln
    290                 295                 300

Asn Gly Trp Asp Thr Asp Gln Phe Pro Val Asp Ala Tyr Glu Leu Thr
305                 310                 315                 320

Gln Ala Met Met Gln Val Leu Leu Asn Gly Gly Phe Gly Asn Gly Gly
                325                 330                 335

Thr Asn Phe Asp Ala Lys Leu Arg Arg Ser Ser Thr Asp Leu Glu Asp
            340                 345                 350

Ile Phe Ile Ala His Ile Ser Ala Met Asp Ala Met Ala His Ala Leu
        355                 360                 365

Leu Asn Ala Ala Ala Val Leu Glu Glu Ser Pro Leu Cys Gln Met Val
    370                 375                 380

Lys Glu Arg Tyr Ala Ser Phe Asp Ser Gly Pro Gly Lys Gln Phe Glu
385                 390                 395                 400

Glu Gly Lys Ala Thr Leu Glu Asp Leu Tyr Asn Tyr Ala Lys Ala Asn
                405                 410                 415

Gly Glu Pro Val Val Ala Ser Gly Lys Gln Glu Leu Tyr Glu Thr Leu
            420                 425                 430

Leu Asn Leu Tyr Ala Lys
        435
```

<210> SEQ ID NO 151
<211> LENGTH: 1317
<212> TYPE: DNA
<213> ORGANISM: Unknown
<220> FEATURE:
<223> OTHER INFORMATION: Obtained from environmental sample

<400> SEQUENCE: 151
atggcaaaag aatatttccc taccatcggc aagattcctt ttgaaggaac cgacagcaag 60
agtcccctcg ccttccatta ctatgacgcc cagcgcgttg tgatgggcaa acccatgaag 120
gaatggctca agttcgccat ggcctggtgg cacaccctgg gccaggcatc ggccgacccc 180
ttcggcggtc agacccgcca ctatgcctgg gatgaaggcg aatgccccta ctgccgcgcc 240
aaagccaagg ccgacgccgg cttcgagatc atgcagaaac tgggcatcga gtacttctgc 300
ttccacgatg tggacctggt ggaagactgc gacgacatcg ccgagtacga agcccgcatg 360
aaggacatca cggactacct gctggagaag atgaaggaaa ccggcatcaa gaacctctgg 420
ggcacggcca atgtgttcgg ccacaagcgt tacatgaacg gcgccgggac caacccgcag 480
tttgacattg tggcccgcgc tgccgtccag atcaaaaacg ccctggacgc caccatcaag 540
ctgggcggtt ccaactacgt gttctggggc agccgcgaag gctactacac cctcctgaac 600
acccagatgc agcgggagaa agaccacctg gccaagctcc tgaccgccgc ccgcgactac 660
gcccgcgcca aaggcttcaa gggaaccttc ctcatcgagc ccaaacccat ggagcccacc 720
aagcaccagt acgacgtgga caccgagacc gtaatcggct tcctgcgtgc caacggcctg 780
gacaaggact tcaaggtgaa catcgaggtg aaccacgcca ccctggctgg ccacaccttc 840
gagcacgaac tcaccgtcgc ccgtgaaaac ggcttcctcg gatcgatcga cgccaaccgc 900
ggcgacgccc agaacggctg ggacaccgac cagttccccg tagacgccta tgacctcacc 960
caggccatga tgcaggtgct gctgaacggc ggtttcggca atggcggtac caacttcgac 1020
gccaagctcc gccgctcctc cacggatccg gaagacatct tcatcgccca catcagcgcc 1080
atggacgcca tggcccacgc cctgctgaac gccgccgccg tgctggaaga aagcccgctt 1140
cccgccatgg cgaaagagcg ctacgcctcc tttgacagcg gacttggcaa gaagttcgaa 1200
gagggaaagg ccaccctcga agagctgtac gactatgcca aggctaacga cgcccctgtc 1260
gccgcctccg gcaagcagga actttacgaa accttcttga acctctatgc aaaatag 1317

<210> SEQ ID NO 152
<211> LENGTH: 438
<212> TYPE: PRT
<213> ORGANISM: Unknown
<220> FEATURE:
<223> OTHER INFORMATION: Obtained from environmental sample

<400> SEQUENCE: 152

Met Ala Lys Glu Tyr Phe Pro Thr Ile Gly Lys Ile Pro Phe Glu Gly
1               5                   10                  15

Thr Asp Ser Lys Ser Pro Leu Ala Phe His Tyr Tyr Asp Ala Gln Arg
            20                  25                  30

Val Val Met Gly Lys Pro Met Lys Glu Trp Leu Lys Phe Ala Met Ala
        35                  40                  45

Trp Trp His Thr Leu Gly Gln Ala Ser Ala Asp Pro Phe Gly Gly Gln
    50                  55                  60

Thr Arg His Tyr Ala Trp Asp Glu Gly Glu Cys Pro Tyr Cys Arg Ala
65                  70                  75                  80

```
Lys Ala Lys Ala Asp Ala Gly Phe Glu Ile Met Gln Lys Leu Gly Ile
                85                  90                  95

Glu Tyr Phe Cys Phe His Asp Val Asp Leu Val Glu Asp Cys Asp Asp
            100                 105                 110

Ile Ala Glu Tyr Glu Ala Arg Met Lys Asp Ile Thr Asp Tyr Leu Leu
        115                 120                 125

Glu Lys Met Lys Glu Thr Gly Ile Lys Asn Leu Trp Gly Thr Ala Asn
    130                 135                 140

Val Phe Gly His Lys Arg Tyr Met Asn Gly Ala Gly Thr Asn Pro Gln
145                 150                 155                 160

Phe Asp Ile Val Ala Arg Ala Ala Val Gln Ile Lys Asn Ala Leu Asp
                165                 170                 175

Ala Thr Ile Lys Leu Gly Gly Ser Asn Tyr Val Phe Trp Gly Ser Arg
            180                 185                 190

Glu Gly Tyr Tyr Thr Leu Leu Asn Thr Gln Met Gln Arg Glu Lys Asp
        195                 200                 205

His Leu Ala Lys Leu Leu Thr Ala Ala Arg Asp Tyr Ala Arg Ala Lys
    210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Val Ile Gly Phe Leu Arg
                245                 250                 255

Ala Asn Gly Leu Asp Lys Asp Phe Lys Val Asn Ile Glu Val Asn His
            260                 265                 270

Ala Thr Leu Ala Gly His Thr Phe Glu His Glu Leu Thr Val Ala Arg
        275                 280                 285

Glu Asn Gly Phe Leu Gly Ser Ile Asp Ala Asn Arg Gly Asp Ala Gln
    290                 295                 300

Asn Gly Trp Asp Thr Asp Gln Phe Pro Val Asp Ala Tyr Asp Leu Thr
305                 310                 315                 320

Gln Ala Met Met Gln Val Leu Leu Asn Gly Gly Phe Gly Asn Gly Gly
                325                 330                 335

Thr Asn Phe Asp Ala Lys Leu Arg Arg Ser Ser Thr Asp Pro Glu Asp
            340                 345                 350

Ile Phe Ile Ala His Ile Ser Ala Met Asp Ala Met Ala His Ala Leu
        355                 360                 365

Leu Asn Ala Ala Ala Val Leu Glu Glu Ser Pro Leu Pro Ala Met Ala
    370                 375                 380

Lys Glu Arg Tyr Ala Ser Phe Asp Ser Gly Leu Gly Lys Lys Phe Glu
385                 390                 395                 400

Glu Gly Lys Ala Thr Leu Glu Glu Leu Tyr Asp Tyr Ala Lys Ala Asn
                405                 410                 415

Asp Ala Pro Val Ala Ala Ser Gly Lys Gln Glu Leu Tyr Glu Thr Phe
            420                 425                 430

Leu Asn Leu Tyr Ala Lys
        435
```

<210> SEQ ID NO 153
<211> LENGTH: 1317
<212> TYPE: DNA
<213> ORGANISM: Unknown
<220> FEATURE:
<223> OTHER INFORMATION: Obtained from environmental sample

<400> SEQUENCE: 153

```
atggcaaaac agtattttcc gcaaatcgga aagattaaat tcgaaggaac agagagcaag     60

aatccgcttg cgttccatta ttatgacgca aacagggtag tcctcggaaa ggcaatggag    120

gagtggctca agttcgcaat ggcttggtgg catactctcg gacaggcttc cggagaccag    180

ttcggcggcc agacccgcag ctacgagtgg gatcttgcag ccacccccga gcagcgcgca    240

aaggacaagc tcgacgccgg cttcgaaata atggagaaac ttggaatcaa gtatttctgt    300

ttccacgatg ttgaccttat cgaagacagc gacgatattg cgacatatga ggctcgtctc    360

aaggacctta cagactacgc tgcagagcag atgaagctcc acgacatcaa gctcctctgg    420

ggtacagcga atgtattcgg caacaagcgc tacatgaacg gtgcggctac aaaccctgat    480

ttcgatgtag ttgcccgcgc agccgttcag attaagaacg ctatcgacgc gaccatcaag    540

ctcggtggta ccagctatgt attctggggc ggtcgtgagg gatatcagag cctgctcaac    600

actcagatgc agcgtgagaa ggaccacctc gcaaccatgc ttacaatcgc tcgcgactat    660

gctcgcagca agggctttac cggaaccttc cttatcgagc ctaagccgat ggagcctaca    720

aaacaccagt acgacgtaga tacagagact gttgtcggct tcctcaaggc acacggcctg    780

gacaaggact tcaaggtaaa tatcgaggtt aaccacgcaa ctctcgcagg ccacaccttc    840

gagcacgaac tcaccgttgc tgtggataac ggaatgctcg gttctatcga cgctaaccgc    900

ggtgatgcac agaacggctg ggatacagac cagttccctg taagcgctga ggagcttacc    960

ctcgctatga tgcagattat ccgtaatggt ggccttggca acggaggatc caacttcgac   1020

gcaaagcttc gccgcaactc taccgatcct gaagacatct tcatcgcaca catctgcggt   1080

atggatgcaa tggcacacgc tctcctcaat gcagctgcaa ttatcgagga gtctcctatc   1140

cctacaatgg ttaaggagcg ttacgcttcc ttcgacagcg gtatgggtaa ggacttcgag   1200

gatggaaagc ttaccctcga ggatctctac agctacggcg tgaagaacgg agagccaaag   1260

cagaccagcg caaagcagga gctctatgag actctcatga atatctattg caagtaa      1317
```

```
<210> SEQ ID NO 154
<211> LENGTH: 438
<212> TYPE: PRT
<213> ORGANISM: Unknown
<220> FEATURE:
<223> OTHER INFORMATION: Obtained from environmental sample

<400> SEQUENCE: 154

Met Ala Lys Gln Tyr Phe Pro Gln Ile Gly Lys Ile Lys Phe Glu Gly
1               5                   10                  15

Thr Glu Ser Lys Asn Pro Leu Ala Phe His Tyr Tyr Asp Ala Asn Arg
            20                  25                  30

Val Val Leu Gly Lys Ala Met Glu Glu Trp Leu Lys Phe Ala Met Ala
        35                  40                  45

Trp Trp His Thr Leu Gly Gln Ala Ser Gly Asp Gln Phe Gly Gly Gln
    50                  55                  60

Thr Arg Ser Tyr Glu Trp Asp Leu Ala Ala Thr Pro Glu Gln Arg Ala
65                  70                  75                  80

Lys Asp Lys Leu Asp Ala Gly Phe Glu Ile Met Glu Lys Leu Gly Ile
                85                  90                  95

Lys Tyr Phe Cys Phe His Asp Val Asp Leu Ile Glu Asp Ser Asp Asp
            100                 105                 110

Ile Ala Thr Tyr Glu Ala Arg Leu Lys Asp Leu Thr Asp Tyr Ala Ala
        115                 120                 125
```

-continued

```
Glu Gln Met Lys Leu His Asp Ile Lys Leu Leu Trp Gly Thr Ala Asn
    130                 135                 140

Val Phe Gly Asn Lys Arg Tyr Met Asn Gly Ala Ala Thr Asn Pro Asp
145                 150                 155                 160

Phe Asp Val Val Ala Arg Ala Ala Val Gln Ile Lys Asn Ala Ile Asp
                165                 170                 175

Ala Thr Ile Lys Leu Gly Gly Thr Ser Tyr Val Phe Trp Gly Gly Arg
            180                 185                 190

Glu Gly Tyr Gln Ser Leu Leu Asn Thr Gln Met Gln Arg Glu Lys Asp
        195                 200                 205

His Leu Ala Thr Met Leu Thr Ile Ala Arg Asp Tyr Ala Arg Ser Lys
    210                 215                 220

Gly Phe Thr Gly Thr Phe Leu Ile Glu Pro Lys Pro Met Glu Pro Thr
225                 230                 235                 240

Lys His Gln Tyr Asp Val Asp Thr Glu Thr Val Val Gly Phe Leu Lys
                245                 250                 255

Ala His Gly Leu Asp Lys Asp Phe Lys Val Asn Ile Glu Val Asn His
            260                 265                 270

Ala Thr Leu Ala Gly His Thr Phe Glu His Glu Leu Thr Val Ala Val
        275                 280                 285

Asp Asn Gly Met Leu Gly Ser Ile Asp Ala Asn Arg Gly Asp Ala Gln
    290                 295                 300

Asn Gly Trp Asp Thr Asp Gln Phe Pro Val Ser Ala Glu Glu Leu Thr
305                 310                 315                 320

Leu Ala Met Met Gln Ile Ile Arg Asn Gly Gly Leu Gly Asn Gly Gly
                325                 330                 335

Ser Asn Phe Asp Ala Lys Leu Arg Arg Asn Ser Thr Asp Pro Glu Asp
            340                 345                 350

Ile Phe Ile Ala His Ile Cys Gly Met Asp Ala Met Ala His Ala Leu
        355                 360                 365

Leu Asn Ala Ala Ala Ile Ile Glu Glu Ser Pro Ile Pro Thr Met Val
    370                 375                 380

Lys Glu Arg Tyr Ala Ser Phe Asp Ser Gly Met Gly Lys Asp Phe Glu
385                 390                 395                 400

Asp Gly Lys Leu Thr Leu Glu Asp Leu Tyr Ser Tyr Gly Val Lys Asn
                405                 410                 415

Gly Glu Pro Lys Gln Thr Ser Ala Lys Gln Glu Leu Tyr Glu Thr Leu
            420                 425                 430

Met Asn Ile Tyr Cys Lys
        435
```

<210> SEQ ID NO 155
<211> LENGTH: 1317
<212> TYPE: DNA
<213> ORGANISM: Unknown
<220> FEATURE:
<223> OTHER INFORMATION: Obtained from environmental sample

<400> SEQUENCE: 155

```
atggcaaaag aatttttttcc acaagtaggc aagattccat ttgagggtcc tgaaagtact      60

aacgtactcg cattccacta ctatgatcca gaacgcgaag ttcttggtaa gaaaatgaaa     120

gattggctga agtatgctat ggcttggtgg cacacactcg gtcaggcaag tggcgaccaa     180

ttcggtggtc aaactcgttc gtatgaatgg gatgaagccg acgatgttct tcaacgcgca     240

aaggataaaa tggatgctgg ttttgaattg atgaccaaac ttggcattga atactactgc     300
```

```
ttccatgatg tcgaccttat tgaagaaggt gcaacaattg aagaatatga agctcgtatg    360

caagctatca ccgactacgc attagaaaaa caaaaagaaa ccggcattaa gctcctttgg    420

ggtactgcta atgtgtttgg tcataagcgt tatatgaatg gtgcggcaac aaaccctgac    480

tttgatgtag tggctcgcgc tgctgtacaa atcaagaacg ctatcgatgc aactatcaag    540

cttggtggtc aaaactatgt attctggggt ggccgcgaag gttatatgag tttgctcaac    600

actcaaatgc aacgcgaaaa agaccacttg gcaaagatgc ttaccgcagc tcgcgactat    660

gctcgtgcta agggcttcaa gggtacattc ctcgttgaac ctaagcctat ggaaccaact    720

aagcatcaat atgataccga tacagaaact gtgattggtt tcctccgtgc aaatggtctt    780

gaaaaagact tcaaggtgaa cattgaagtg aaccatgcta ctctcgctca gcacactttc    840

gaacacgaac tcgctgtggc tgtcgacaat ggcatgctcg gttctatcga cgctaaccgt    900

ggcgatgctc aaaatggctg ggataccgac caattcccaa tcgacaacta cgaactcacc    960

ctcgctatgc tccaaatcat tcgcaatggt ggtcttggca atggcggtag caacctcgac   1020

gctaagattc gtcgtaatag caccgacctt gaagacctct ttatcgctca catcagtggt   1080

atggatgcta tggctcgtgc acttctcaat gctgctgcaa tcgttgaaaa gagcgaaatt   1140

cctgctatgt tgaagcagcg ttatgcaagc tctgatgcag gtatgggtaa ggacttcgaa   1200

gaaggaaaac tcactctcga acaactcgta gactatgcta aggctaacgg cgaacctgct   1260

acagtaagcg gcaagcaaga aaagtatgaa actctcgttg ctctctacgc taagtaa      1317


<210> SEQ ID NO 156
<211> LENGTH: 438
<212> TYPE: PRT
<213> ORGANISM: Unknown
<220> FEATURE:
<223> OTHER INFORMATION: Obtained from environmental sample

<400> SEQUENCE: 156

Met Ala Lys Glu Phe Phe Pro Gln Val Gly Lys Ile Pro Phe Glu Gly
1               5                   10                  15

Pro Glu Ser Thr Asn Val Leu Ala Phe His Tyr Tyr Asp Pro Glu Arg
            20                  25                  30

Glu Val Leu Gly Lys Lys Met Lys Asp Trp Leu Lys Tyr Ala Met Ala
        35                  40                  45

Trp Trp His Thr Leu Gly Gln Ala Ser Gly Asp Gln Phe Gly Gly Gln
    50                  55                  60

Thr Arg Ser Tyr Glu Trp Asp Glu Ala Asp Asp Val Leu Gln Arg Ala
65                  70                  75                  80

Lys Asp Lys Met Asp Ala Gly Phe Glu Leu Met Thr Lys Leu Gly Ile
                85                  90                  95

Glu Tyr Tyr Cys Phe His Asp Val Asp Leu Ile Glu Glu Gly Ala Thr
            100                 105                 110

Ile Glu Glu Tyr Glu Ala Arg Met Gln Ala Ile Thr Asp Tyr Ala Leu
        115                 120                 125

Glu Lys Gln Lys Glu Thr Gly Ile Lys Leu Leu Trp Gly Thr Ala Asn
    130                 135                 140

Val Phe Gly His Lys Arg Tyr Met Asn Gly Ala Ala Thr Asn Pro Asp
145                 150                 155                 160

Phe Asp Val Val Ala Arg Ala Ala Val Gln Ile Lys Asn Ala Ile Asp
                165                 170                 175

Ala Thr Ile Lys Leu Gly Gly Gln Asn Tyr Val Phe Trp Gly Gly Arg
```

-continued

```
            180                 185                 190

Glu Gly Tyr Met Ser Leu Leu Asn Thr Gln Met Gln Arg Glu Lys Asp
        195                 200                 205

His Leu Ala Lys Met Leu Thr Ala Ala Arg Asp Tyr Ala Arg Ala Lys
    210                 215                 220

Gly Phe Lys Gly Thr Phe Leu Val Glu Pro Lys Pro Met Glu Pro Thr
225                 230                 235                 240

Lys His Gln Tyr Asp Thr Asp Thr Glu Thr Val Ile Gly Phe Leu Arg
                245                 250                 255

Ala Asn Gly Leu Glu Lys Asp Phe Lys Val Asn Ile Glu Val Asn His
            260                 265                 270

Ala Thr Leu Ala Gln His Thr Phe Glu His Glu Leu Ala Val Ala Val
        275                 280                 285

Asp Asn Gly Met Leu Gly Ser Ile Asp Ala Asn Arg Gly Asp Ala Gln
    290                 295                 300

Asn Gly Trp Asp Thr Asp Gln Phe Pro Ile Asp Asn Tyr Glu Leu Thr
305                 310                 315                 320

Leu Ala Met Leu Gln Ile Ile Arg Asn Gly Gly Leu Gly Asn Gly Gly
                325                 330                 335

Ser Asn Leu Asp Ala Lys Ile Arg Arg Asn Ser Thr Asp Leu Glu Asp
            340                 345                 350

Leu Phe Ile Ala His Ile Ser Gly Met Asp Ala Met Ala Arg Ala Leu
        355                 360                 365

Leu Asn Ala Ala Ala Ile Val Glu Lys Ser Glu Ile Pro Ala Met Leu
    370                 375                 380

Lys Gln Arg Tyr Ala Ser Ser Asp Ala Gly Met Gly Lys Asp Phe Glu
385                 390                 395                 400

Glu Gly Lys Leu Thr Leu Glu Gln Leu Val Asp Tyr Ala Lys Ala Asn
                405                 410                 415

Gly Glu Pro Ala Thr Val Ser Gly Lys Gln Glu Lys Tyr Glu Thr Leu
            420                 425                 430

Val Ala Leu Tyr Ala Lys
        435
```

<210> SEQ ID NO 157
<211> LENGTH: 1317
<212> TYPE: DNA
<213> ORGANISM: Unknown
<220> FEATURE:
<223> OTHER INFORMATION: Obtained from environmental sample

<400> SEQUENCE: 157

```
atgactaaag agtatttccc gggaatcgga aagattccgt ttgaaggaac caagagcaag      60

aaccccctgg ccttccatta ttataacgcc tcccaggtag cgatgggcaa gcccatgaag     120

gactggctca agtatgccat ggcctggtgg cacaccctgg gccaggcctc tgcagacccc     180

tttggcggcc agacccgctc ctacgaatgg gacaagggcg agtgccctta ttgccgcgcc     240

aagcagaagg ccgatgccgg ctttgagctc atgcagaagc tgggcatcga gtactactgc     300

ttccacgacg tggacatcat cgaggactgc gaggacattg ccgagtacga ggcccgcatg     360

aaggacatca cggactacct gctggagaag cagaaagaga ccggcatcaa gaacctctgg     420

ggcaccgcca acgtgtttgg ccacaagcgc tacatgaacg gcgccgccac caaccctcag     480

tttgacattg tggcccgtgc cgccgtccag atcaagaacg ccctggatgc caccatcaag     540

ctgggtggta ccaactacgt gttctggggt ggccgcgaag gctactacac gctgctcaac     600
```

-continued acccagatgc agcgggagaa gaaccacctg gccaagatgc tcaccgccgc ccgcgactac 660
gcccgcgcca agggcttcaa gggcaccttc ctcattgagc ccaaacccat ggagcccacc 720
aagcaccagt acgacgtgga caccgagacc gtgattggtt tcatccgcgc caacggcctg 780
gacaaggact tcaaggtaaa cattgaggta aaccacgcca ccctggccgg ccacaccttt 840
gagcacgagc tcaccgtggc ccgcgagaac ggcttcctgg gctccatcga cgccaaccgc 900
ggagatgccc agaacggctg ggatacggac cagttcccca tcgacgccct ggatctcacc 960
caggctatga tgcaggtcat cctcaacggt ggcttcggca atggcggcac caactttgac 1020
gccaagctcc gccgctcctc caccgatccc gaggacatct tcatcgccca catcagcgcc 1080
atggatgcca tggcacacgc cctcctgaac gcagccgcca tcctggaaga gagccccctg 1140
cccgccatgg tcaaggagcg ttacgcttcc ttcgacagcg gtctgggcaa gaagttcgaa 1200
gaaggcaagg cctccctgga agaactttac gaatatgcca agaagaatgg agagcccgtg 1260
gccgcttccg gcaaacagga gctctgcgaa acttacttga acctctatgc aaagtag 1317

<210> SEQ ID NO 158
<211> LENGTH: 438
<212> TYPE: PRT
<213> ORGANISM: Unknown
<220> FEATURE:
<223> OTHER INFORMATION: Obtained from environmental sample

<400> SEQUENCE: 158

Met Thr Lys Glu Tyr Phe Pro Gly Ile Gly Lys Ile Pro Phe Glu Gly
1               5                   10                  15

Thr Lys Ser Lys Asn Pro Leu Ala Phe His Tyr Tyr Asn Ala Ser Gln
            20                  25                  30

Val Ala Met Gly Lys Pro Met Lys Asp Trp Leu Lys Tyr Ala Met Ala
        35                  40                  45

Trp Trp His Thr Leu Gly Gln Ala Ser Ala Asp Pro Phe Gly Gly Gln
    50                  55                  60

Thr Arg Ser Tyr Glu Trp Asp Lys Gly Glu Cys Pro Tyr Cys Arg Ala
65                  70                  75                  80

Lys Gln Lys Ala Asp Ala Gly Phe Glu Leu Met Gln Lys Leu Gly Ile
                85                  90                  95

Glu Tyr Tyr Cys Phe His Asp Val Asp Ile Ile Glu Asp Cys Glu Asp
            100                 105                 110

Ile Ala Glu Tyr Glu Ala Arg Met Lys Asp Ile Thr Asp Tyr Leu Leu
        115                 120                 125

Glu Lys Gln Lys Glu Thr Gly Ile Lys Asn Leu Trp Gly Thr Ala Asn
    130                 135                 140

Val Phe Gly His Lys Arg Tyr Met Asn Gly Ala Ala Thr Asn Pro Gln
145                 150                 155                 160

Phe Asp Ile Val Ala Arg Ala Ala Val Gln Ile Lys Asn Ala Leu Asp
                165                 170                 175

Ala Thr Ile Lys Leu Gly Gly Thr Asn Tyr Val Phe Trp Gly Gly Arg
            180                 185                 190

Glu Gly Tyr Tyr Thr Leu Leu Asn Thr Gln Met Gln Arg Glu Lys Asn
        195                 200                 205

His Leu Ala Lys Met Leu Thr Ala Ala Arg Asp Tyr Ala Arg Ala Lys
    210                 215                 220

Gly Phe Lys Gly Thr Phe Leu Ile Glu Pro Lys Pro Met Glu Pro Thr
225                 230                 235                 240

```
Lys His Gln Tyr Asp Val Asp Thr Glu Thr Val Ile Gly Phe Ile Arg
                245                 250                 255

Ala Asn Gly Leu Asp Lys Asp Phe Lys Val Asn Ile Glu Val Asn His
            260                 265                 270

Ala Thr Leu Ala Gly His Thr Phe Glu His Glu Leu Thr Val Ala Arg
        275                 280                 285

Glu Asn Gly Phe Leu Gly Ser Ile Asp Ala Asn Arg Gly Asp Ala Gln
    290                 295                 300

Asn Gly Trp Asp Thr Asp Gln Phe Pro Ile Asp Ala Leu Asp Leu Thr
305                 310                 315                 320

Gln Ala Met Met Gln Val Ile Leu Asn Gly Gly Phe Gly Asn Gly Gly
                325                 330                 335

Thr Asn Phe Asp Ala Lys Leu Arg Arg Ser Ser Thr Asp Pro Glu Asp
            340                 345                 350

Ile Phe Ile Ala His Ile Ser Ala Met Asp Ala Met Ala His Ala Leu
        355                 360                 365

Leu Asn Ala Ala Ala Ile Leu Glu Glu Ser Pro Leu Pro Ala Met Val
    370                 375                 380

Lys Glu Arg Tyr Ala Ser Phe Asp Ser Gly Leu Gly Lys Lys Phe Glu
385                 390                 395                 400

Glu Gly Lys Ala Ser Leu Glu Glu Leu Tyr Glu Tyr Ala Lys Lys Asn
                405                 410                 415

Gly Glu Pro Val Ala Ala Ser Gly Lys Gln Glu Leu Cys Glu Thr Tyr
            420                 425                 430

Leu Asn Leu Tyr Ala Lys
        435
```

<210> SEQ ID NO 159
<211> LENGTH: 1317
<212> TYPE: DNA
<213> ORGANISM: Unknown
<220> FEATURE:
<223> OTHER INFORMATION: Obtained from environmental sample

<400> SEQUENCE: 159

```
atgactaaag agtatttccc gggaatcgga aagattccgt ttgaaggaac caagagcaag     60

aaccccctgg ccttccatta ttataacgcc tcccaggtag tgatgggcaa gcccatgaag    120

gactggctca agtatgccat ggcctggtgg cacaccctgg gccaggcctc tgcagacccc    180

tttggcggcc agacccgctc ctacgaatgg gacaagggcg agtgcccgta ctgccgcgcc    240

aagcagaagg ccgatgccgg ctttgagctc atgcagaagc tgggcatcga gtactactgc    300

ttccacgacg tggacatcat cgaggactgc gaggacattg ccgagtacga ggcccgcatg    360

aaggacatca cggactacct gctggagaag cagaaagaga ccggcatcaa gaacctctgg    420

ggcaccgcca acgtgtttgg ccacaagcgc tacatgaacg gcgccgccac caaccctcag    480

tttgacattg tggcccgtgc cgccgtccag atcaagaacg ccctggatgc caccatcaaa    540

ctgggtggta ccaactacgt gttctggggt ggccgcgaag gctactacac gctgctcaac    600

acccagatgc agcgggagaa gaaccacctg gccaagatgc tcaccgccgc ccgcgactac    660

gcccgcgcca agggcttcaa gggcaccttc ctcattgagc ccaaacccat ggagcccacc    720

aagcaccagt acgacgtgga caccgagacc gtgattggtt tcatccgcgc caacggcctg    780

gacaaggact tcaaggtaaa cattgaggta aaccacgcca ccctggccgg ccacaccttt    840

gagcacgagc tcaccgtggc ccgcgagaac ggcttcctgg gctccatcga cgccaaccgc    900
```

```
ggagatgccc agaacggctg ggatacggac cagttcccca tcgacgccct ggatctcacc    960

caggctatga tgcaggtcat cctcaacggt ggcttcggca atggcggcac caactttgac   1020

gccaagctcc gccgctcctc caccgatccc gaggacatct tcatcgccca catcagcgcc   1080

atggatgcca tggcacacgc cctcctgaac gcagccgcca tcctggaaga gagccccctg   1140

cccgccatgg tcaaggagcg ttacgcttcc ttcgacagcg gtctgggcaa gaagttcgaa   1200

gaaggcaagg cctccctgga agaactttac gaatatgcca agaagaatgg agagcccgtg   1260

gccgcttccg gcaaacagga gctctgcgaa acttacttga acctctatgc aaagtag      1317


<210> SEQ ID NO 160
<211> LENGTH: 438
<212> TYPE: PRT
<213> ORGANISM: Unknown
<220> FEATURE:
<223> OTHER INFORMATION: Obtained from environmental sample

<400> SEQUENCE: 160

Met Thr Lys Glu Tyr Phe Pro Gly Ile Gly Lys Ile Pro Phe Glu Gly
1               5                   10                  15

Thr Lys Ser Lys Asn Pro Leu Ala Phe His Tyr Tyr Asn Ala Ser Gln
            20                  25                  30

Val Val Met Gly Lys Pro Met Lys Asp Trp Leu Lys Tyr Ala Met Ala
        35                  40                  45

Trp Trp His Thr Leu Gly Gln Ala Ser Ala Asp Pro Phe Gly Gly Gln
    50                  55                  60

Thr Arg Ser Tyr Glu Trp Asp Lys Gly Glu Cys Pro Tyr Cys Arg Ala
65                  70                  75                  80

Lys Gln Lys Ala Asp Ala Gly Phe Glu Leu Met Gln Lys Leu Gly Ile
                85                  90                  95

Glu Tyr Tyr Cys Phe His Asp Val Asp Ile Ile Glu Asp Cys Glu Asp
            100                 105                 110

Ile Ala Glu Tyr Glu Ala Arg Met Lys Asp Ile Thr Asp Tyr Leu Leu
        115                 120                 125

Glu Lys Gln Lys Glu Thr Gly Ile Lys Asn Leu Trp Gly Thr Ala Asn
    130                 135                 140

Val Phe Gly His Lys Arg Tyr Met Asn Gly Ala Ala Thr Asn Pro Gln
145                 150                 155                 160

Phe Asp Ile Val Ala Arg Ala Ala Val Gln Ile Lys Asn Ala Leu Asp
                165                 170                 175

Ala Thr Ile Lys Leu Gly Gly Thr Asn Tyr Val Phe Trp Gly Gly Arg
            180                 185                 190

Glu Gly Tyr Tyr Thr Leu Leu Asn Thr Gln Met Gln Arg Glu Lys Asn
        195                 200                 205

His Leu Ala Lys Met Leu Thr Ala Ala Arg Asp Tyr Ala Arg Ala Lys
    210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Val Ile Gly Phe Ile Arg
                245                 250                 255

Ala Asn Gly Leu Asp Lys Asp Phe Lys Val Asn Ile Glu Val Asn His
            260                 265                 270

Ala Thr Leu Ala Gly His Thr Phe Glu His Glu Leu Thr Val Ala Arg
        275                 280                 285
```

```
Glu Asn Gly Phe Leu Gly Ser Ile Asp Ala Asn Arg Gly Asp Ala Gln
    290                 295                 300

Asn Gly Trp Asp Thr Asp Gln Phe Pro Ile Asp Ala Leu Asp Leu Thr
305                 310                 315                 320

Gln Ala Met Met Gln Val Ile Leu Asn Gly Gly Phe Gly Asn Gly Gly
                325                 330                 335

Thr Asn Phe Asp Ala Lys Leu Arg Arg Ser Ser Thr Asp Pro Glu Asp
            340                 345                 350

Ile Phe Ile Ala His Ile Ser Ala Met Asp Ala Met Ala His Ala Leu
        355                 360                 365

Leu Asn Ala Ala Ala Ile Leu Glu Glu Ser Pro Leu Pro Ala Met Val
    370                 375                 380

Lys Glu Arg Tyr Ala Ser Phe Asp Ser Gly Leu Gly Lys Lys Phe Glu
385                 390                 395                 400

Glu Gly Lys Ala Ser Leu Glu Glu Leu Tyr Glu Tyr Ala Lys Lys Asn
                405                 410                 415

Gly Glu Pro Val Ala Ala Ser Gly Lys Gln Glu Leu Cys Glu Thr Tyr
            420                 425                 430

Leu Asn Leu Tyr Ala Lys
        435
```

<210> SEQ ID NO 161
<211> LENGTH: 1317
<212> TYPE: DNA
<213> ORGANISM: Unknown
<220> FEATURE:
<223> OTHER INFORMATION: Obtained from environmental sample

<400> SEQUENCE: 161

```
atggcaaaag agtatttccc gactatcggc aagattccct tcgagggcgt cgaatccaag      60

aacccgatgg cattccacta ctatgacgcg aaccgcgtcg tgatgggcaa gcccatgaag     120

gactggctca agttcgcgat ggcctggtgg cacaccctgg gacaggcttc cggcgacccg     180

ttcggcggcc agacccgttc ctacgagtgg gacaagggcg agtgccccta ctgccgcgcc     240

aaggccaagg ccgacgccgg cttcgagatc atgcagaagc tcggtatcga gtactactgc     300

ttccatgaca tcgacctcgt ggaggacacc gaggacatcg ccgagtacga ggcccgcatg     360

aaggacatca ccgactacct cgtcgagaag cagaaggaaa ccggcatcaa gaacctctgg     420

ggcacggcca acgtgttcgg caacaagcgc tacatgaacg gcgccgccac gaacccgcag     480

ttcgacgtcg tcgcccgcgc cgccgtccag atcaagaacg ccatcgacgc caccatcaag     540

ctcggcggta ccggttacgt gttctggggc ggccgtgaag gctactacac cctcctgaac     600

acccagatgc agcgcgagaa ggaccacctc gccaagatgc tcaccgccgc ccgcgactac     660

gcccgcgccc acggcttcca gggcaccttc ctcatcgagc ccaagcccat ggagcccacc     720

aagcaccagt acgacgtgga cacggagacc gtgatcggct tcctgcgcgc caacggtctg     780

gacaaggact tcaaggtcaa tatcgaggtg aaccacgcca ccctcgccgg ccacaccttc     840

gagcacgagc tcaccgtggc tgtcgataac ggcttcctcg gctccatcga cgccaaccgc     900

ggcgacgccc agaacggctg ggacaccgac cagttccccg tggacccgta cgacctcacc     960

caggccatga tgcagatcat ccgcaacggc ggtttcaagg acggcggcac caacttcgac    1020

gccaagctcc gccgctcttc caccgacccg gaggacatct tcatcgccca catcagcgcg    1080

atggacgcca tggcccacgc cctgctgaac gccgccgccg tcatcgagga gagcccgctc    1140

tgcaagatgg tcgaggagcg ctacgcttcc ttcgacagcg gcctcggcaa gcagttcgag    1200
```

gaaggcaagg ccaccctcga ggacctctac gagtatgcca agaagaatgg cgagcccgtc 1260
gtcgcctccg gcaagcagga gctctacgag acgctgctga acctttacgc gaagtag 1317

<210> SEQ ID NO 162
<211> LENGTH: 438
<212> TYPE: PRT
<213> ORGANISM: Unknown
<220> FEATURE:
<223> OTHER INFORMATION: Obtained from environmental sample

<400> SEQUENCE: 162

Met Ala Lys Glu Tyr Phe Pro Thr Ile Gly Lys Ile Pro Phe Glu Gly
1 5 10 15

Val Glu Ser Lys Asn Pro Met Ala Phe His Tyr Tyr Asp Ala Asn Arg
20 25 30

Val Val Met Gly Lys Pro Met Lys Asp Trp Leu Lys Phe Ala Met Ala
35 40 45

Trp Trp His Thr Leu Gly Gln Ala Ser Gly Asp Pro Phe Gly Gly Gln
50 55 60

Thr Arg Ser Tyr Glu Trp Asp Lys Gly Glu Cys Pro Tyr Cys Arg Ala
65 70 75 80

Lys Ala Lys Ala Asp Ala Gly Phe Glu Ile Met Gln Lys Leu Gly Ile
85 90 95

Glu Tyr Tyr Cys Phe His Asp Ile Asp Leu Val Glu Asp Thr Glu Asp
100 105 110

Ile Ala Glu Tyr Glu Ala Arg Met Lys Asp Ile Thr Asp Tyr Leu Val
115 120 125

Glu Lys Gln Lys Glu Thr Gly Ile Lys Asn Leu Trp Gly Thr Ala Asn
130 135 140

Val Phe Gly Asn Lys Arg Tyr Met Asn Gly Ala Ala Thr Asn Pro Gln
145 150 155 160

Phe Asp Val Val Ala Arg Ala Ala Val Gln Ile Lys Asn Ala Ile Asp
165 170 175

Ala Thr Ile Lys Leu Gly Gly Thr Gly Tyr Val Phe Trp Gly Gly Arg
180 185 190

Glu Gly Tyr Tyr Thr Leu Leu Asn Thr Gln Met Gln Arg Glu Lys Asp
195 200 205

His Leu Ala Lys Met Leu Thr Ala Ala Arg Asp Tyr Ala Arg Ala His
210 215 220

Gly Phe Gln Gly Thr Phe Leu Ile Glu Pro Lys Pro Met Glu Pro Thr
225 230 235 240

Lys His Gln Tyr Asp Val Asp Thr Glu Thr Val Ile Gly Phe Leu Arg
245 250 255

Ala Asn Gly Leu Asp Lys Asp Phe Lys Val Asn Ile Glu Val Asn His
260 265 270

Ala Thr Leu Ala Gly His Thr Phe Glu His Glu Leu Thr Val Ala Val
275 280 285

Asp Asn Gly Phe Leu Gly Ser Ile Asp Ala Asn Arg Gly Asp Ala Gln
290 295 300

Asn Gly Trp Asp Thr Asp Gln Phe Pro Val Asp Pro Tyr Asp Leu Thr
305 310 315 320

Gln Ala Met Met Gln Ile Ile Arg Asn Gly Gly Phe Lys Asp Gly Gly
325 330 335

Thr Asn Phe Asp Ala Lys Leu Arg Arg Ser Ser Thr Asp Pro Glu Asp

```
            340                 345                 350

Ile Phe Ile Ala His Ile Ser Ala Met Asp Ala Met Ala His Ala Leu
        355                 360                 365

Leu Asn Ala Ala Ala Val Ile Glu Glu Ser Pro Leu Cys Lys Met Val
    370                 375                 380

Glu Glu Arg Tyr Ala Ser Phe Asp Ser Gly Leu Gly Lys Gln Phe Glu
385                 390                 395                 400

Glu Gly Lys Ala Thr Leu Glu Asp Leu Tyr Glu Tyr Ala Lys Lys Asn
                405                 410                 415

Gly Glu Pro Val Val Ala Ser Gly Lys Gln Glu Leu Tyr Glu Thr Leu
            420                 425                 430

Leu Asn Leu Tyr Ala Lys
        435


<210> SEQ ID NO 163
<211> LENGTH: 1317
<212> TYPE: DNA
<213> ORGANISM: Unknown
<220> FEATURE:
<223> OTHER INFORMATION: Obtained from environmental sample

<400> SEQUENCE: 163

atggcaaaag agtatttccc gacaatcggt aagatcccct tcgagggacc cgagtccaag      60

aacccgatgg cattccacta ctatgacgcg gagcgcgtgg tgatgggcaa gaagatgaag     120

gactggttca agttcgcgat ggcctggtgg cacaccctgg gccaggcttc cgccgacccg     180

ttcggcggcc agacccgctc ctacgagtgg gacaagggcg aaggcccctg ctcccgcgcc     240

cgcgccaagg ctgacgccgg tttcgagatc atgcagaaac tgggcatcgg ctactactgc     300

ttccacgaca tcgacctggt ggaggacacc gaggacatcg ccgagtatga agcccgcatg     360

aaggacatca ccgactacct cgtggagaag cagaaggaga ccggcatcaa gaacctctgg     420

ggcacggcca acgtattcgg caacaagccc tacatgaacg gcgccgccac gaacccgcag     480

ttcgacatcg ccgcccgcgc ggccctgcag accaagaacg ccatcgatgc caccatcaag     540

ctgggcggca ccggttacgt gttctggggc ggccgtgaag gctactacac cctcctgaac     600

acccagatgc agcgcgagaa ggaccacctt gccaagatgc tcaccgcggc tcgcgactat     660

gcccgcgccc acggcttcaa gggcaccttc ttcatcgagc cgaaaccgat ggagcccacc     720

aagcaccagt acgacgtgga cacggagacc gtgatcggct tcctccgcgc caacggcctg     780

gacaaggact tcaaggtgaa catcgaagtg aaccacgcca ccctcgccgg ccacaccttc     840

gagcacgggc tcaccgtggc cgttgacaac ggcttcctcg gcagcatcga cgccaaccgc     900

ggagacgccc agaacggctg ggataccgac cagttcccgg tggatccgta cgacctcacc     960

caggcgatga tccagatcat ccgcaatggc ggcttcaagg acggcggtac caacttcgac    1020

gccaagctcc gccgctcttc caccgacccg gaggacatct tcatcgccca catcagcgcg    1080

atggacgcca tggcccacgc cctgctgaac gccgccgccg tgctcgagga gagcccgctc    1140

tgcgagatgg ttgcaaagcg ttacgcttcc ttcgacagcg gtctcggcaa gaagttcgag    1200

gaaggcaacg ccaccctcga ggaactctac gagtacgcca aggcgaaggg cgaggtcgtt    1260

gccgaatccg gcaagcagga actctacgag accctgctga acctctacgc gaagtag       1317


<210> SEQ ID NO 164
<211> LENGTH: 438
<212> TYPE: PRT
<213> ORGANISM: Unknown
```

<220> FEATURE:
<223> OTHER INFORMATION: Obtained from environmental sample

<400> SEQUENCE: 164

```
Met Ala Lys Glu Tyr Phe Pro Thr Ile Gly Lys Ile Pro Phe Glu Gly
1               5                   10                  15

Pro Glu Ser Lys Asn Pro Met Ala Phe His Tyr Tyr Asp Ala Glu Arg
            20                  25                  30

Val Val Met Gly Lys Lys Met Lys Asp Trp Phe Lys Phe Ala Met Ala
        35                  40                  45

Trp Trp His Thr Leu Gly Gln Ala Ser Ala Asp Pro Phe Gly Gly Gln
    50                  55                  60

Thr Arg Ser Tyr Glu Trp Asp Lys Gly Glu Gly Pro Cys Ser Arg Ala
65                  70                  75                  80

Arg Ala Lys Ala Asp Ala Gly Phe Glu Ile Met Gln Lys Leu Gly Ile
                85                  90                  95

Gly Tyr Tyr Cys Phe His Asp Ile Asp Leu Val Glu Asp Thr Glu Asp
            100                 105                 110

Ile Ala Glu Tyr Glu Ala Arg Met Lys Asp Ile Thr Asp Tyr Leu Val
        115                 120                 125

Glu Lys Gln Lys Glu Thr Gly Ile Lys Asn Leu Trp Gly Thr Ala Asn
    130                 135                 140

Val Phe Gly Asn Lys Pro Tyr Met Asn Gly Ala Ala Thr Asn Pro Gln
145                 150                 155                 160

Phe Asp Ile Ala Ala Arg Ala Ala Leu Gln Thr Lys Asn Ala Ile Asp
                165                 170                 175

Ala Thr Ile Lys Leu Gly Gly Thr Gly Tyr Val Phe Trp Gly Gly Arg
            180                 185                 190

Glu Gly Tyr Tyr Thr Leu Leu Asn Thr Gln Met Gln Arg Glu Lys Asp
        195                 200                 205

His Leu Ala Lys Met Leu Thr Ala Ala Arg Asp Tyr Ala Arg Ala His
    210                 215                 220

Gly Phe Lys Gly Thr Phe Phe Ile Glu Pro Lys Pro Met Glu Pro Thr
225                 230                 235                 240

Lys His Gln Tyr Asp Val Asp Thr Glu Thr Val Ile Gly Phe Leu Arg
                245                 250                 255

Ala Asn Gly Leu Asp Lys Asp Phe Lys Val Asn Ile Glu Val Asn His
            260                 265                 270

Ala Thr Leu Ala Gly His Thr Phe Glu His Gly Leu Thr Val Ala Val
        275                 280                 285

Asp Asn Gly Phe Leu Gly Ser Ile Asp Ala Asn Arg Gly Asp Ala Gln
    290                 295                 300

Asn Gly Trp Asp Thr Asp Gln Phe Pro Val Asp Pro Tyr Asp Leu Thr
305                 310                 315                 320

Gln Ala Met Ile Gln Ile Ile Arg Asn Gly Gly Phe Lys Asp Gly Gly
                325                 330                 335

Thr Asn Phe Asp Ala Lys Leu Arg Arg Ser Ser Thr Asp Pro Glu Asp
            340                 345                 350

Ile Phe Ile Ala His Ile Ser Ala Met Asp Ala Met Ala His Ala Leu
        355                 360                 365

Leu Asn Ala Ala Ala Val Leu Glu Glu Ser Pro Leu Cys Glu Met Val
    370                 375                 380

Ala Lys Arg Tyr Ala Ser Phe Asp Ser Gly Leu Gly Lys Lys Phe Glu
385                 390                 395                 400
```

```
Glu Gly Asn Ala Thr Leu Glu Glu Leu Tyr Glu Tyr Ala Lys Ala Lys
                405                 410                 415

Gly Glu Val Val Ala Glu Ser Gly Lys Gln Glu Leu Tyr Glu Thr Leu
            420                 425                 430

Leu Asn Leu Tyr Ala Lys
        435


<210> SEQ ID NO 165
<211> LENGTH: 1317
<212> TYPE: DNA
<213> ORGANISM: Unknown
<220> FEATURE:
<223> OTHER INFORMATION: Obtained from environmental sample

<400> SEQUENCE: 165

atggcaaaag agtatttccc gacaatcgga aagatcccct tcgagggcgc tgagagcaag      60

aatccccttg ctttccacta ttatgacgcc gagcgtgtgg tcatgggcaa gcccatgaag     120

gactggttca agttcgcgat ggcctggtgg cacaccctgg gccaggcttc cgccgacccg     180

ttcggcggcc agacccgctc ctacgagtgg gacaagggcg agtgccccta ctgccgcgcc     240

cgccagaagg ctgacgccgg tttcgagatc atgcagaagc tcggcatcgg ctactactgc     300

ttccacgaca tcgacctggt cgaggacacc gaggacatcg ccgagtacga ggcccgcatg     360

aaggacatca ccgactacct cgtcgagaag cagaaggaga ccggcatcaa gaacctctgg     420

ggcacggcca acgtgttcgg caacaagcgc tacatgaacg gcgccgccac gaacccgcag     480

ttcgacatcg tcgcccacgc ggccctgcag atcaagaacg cgatcggcgc caccatcaag     540

ctcggcggca ccggttacgt gttctggggc ggccgtgaag gttactacac cctcctgaac     600

acccagatgc agcgcgagaa ggaccacctc gccaagatgc tcaccgccgc ccgcgactac     660

gcccgcgcca acggcttcaa gggcaccttc ctcatcgagc cgaagccgat ggagcccacc     720

aagcaccagt atgacgtgga cacggagacc gtgatcggct tcctccgcgc caacggcctg     780

gacaaggact tcaaggtgaa catcgaggtg aaccacgcca ccctcgccgg ccacaccttc     840

gagcacgagc tcaccgtggc ggtcgacaac ggcttcctcg gcagcatcga cgccaaccgc     900

ggtgacgccc agaacggctg ggataccgac cagttcccgg tggatccgta cgatctcacc     960

caggcgatga tccagatcat ccgcaacggc ggcttcaagg atggcggcac caacttcgac    1020

gccaagctcc gccgctcttc caccgacccg gaggacatct tcatcgccca catcagcgcg    1080

atggacgcca tggcccacgc cctgctgaac gccgccgccg tcatcgagga gagcccgctc    1140

tgcgagatgg tcgccaagcg ctacgcttcc ttcgacagcg gtctcggcaa gaagttcgag    1200

gaaggcaacg ccaccctcga ggaactctac gagtacgcca aggcgaacgg tgaggtcaag    1260

gccgaatccg gcaagcagga gctctacgag acccttctga acctctacgc gaaatag       1317


<210> SEQ ID NO 166
<211> LENGTH: 438
<212> TYPE: PRT
<213> ORGANISM: Unknown
<220> FEATURE:
<223> OTHER INFORMATION: Obtained from environmental sample

<400> SEQUENCE: 166

Met Ala Lys Glu Tyr Phe Pro Thr Ile Gly Lys Ile Pro Phe Glu Gly
1               5                   10                  15

Ala Glu Ser Lys Asn Pro Leu Ala Phe His Tyr Tyr Asp Ala Glu Arg
            20                  25                  30
```

```
Val Val Met Gly Lys Pro Met Lys Asp Trp Phe Lys Phe Ala Met Ala
        35                  40                  45

Trp Trp His Thr Leu Gly Gln Ala Ser Ala Asp Pro Phe Gly Gly Gln
    50                  55                  60

Thr Arg Ser Tyr Glu Trp Asp Lys Gly Glu Cys Pro Tyr Cys Arg Ala
65                  70                  75                  80

Arg Gln Lys Ala Asp Ala Gly Phe Glu Ile Met Gln Lys Leu Gly Ile
                85                  90                  95

Gly Tyr Tyr Cys Phe His Asp Ile Asp Leu Val Glu Asp Thr Glu Asp
            100                 105                 110

Ile Ala Glu Tyr Glu Ala Arg Met Lys Asp Ile Thr Asp Tyr Leu Val
        115                 120                 125

Glu Lys Gln Lys Glu Thr Gly Ile Lys Asn Leu Trp Gly Thr Ala Asn
    130                 135                 140

Val Phe Gly Asn Lys Arg Tyr Met Asn Gly Ala Ala Thr Asn Pro Gln
145                 150                 155                 160

Phe Asp Ile Val Ala His Ala Ala Leu Gln Ile Lys Asn Ala Ile Gly
                165                 170                 175

Ala Thr Ile Lys Leu Gly Gly Thr Gly Tyr Val Phe Trp Gly Gly Arg
            180                 185                 190

Glu Gly Tyr Tyr Thr Leu Leu Asn Thr Gln Met Gln Arg Glu Lys Asp
        195                 200                 205

His Leu Ala Lys Met Leu Thr Ala Ala Arg Asp Tyr Ala Arg Ala Asn
    210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Val Ile Gly Phe Leu Arg
                245                 250                 255

Ala Asn Gly Leu Asp Lys Asp Phe Lys Val Asn Ile Glu Val Asn His
            260                 265                 270

Ala Thr Leu Ala Gly His Thr Phe Glu His Glu Leu Thr Val Ala Val
        275                 280                 285

Asp Asn Gly Phe Leu Gly Ser Ile Asp Ala Asn Arg Gly Asp Ala Gln
    290                 295                 300

Asn Gly Trp Asp Thr Asp Gln Phe Pro Val Asp Pro Tyr Asp Leu Thr
305                 310                 315                 320

Gln Ala Met Ile Gln Ile Ile Arg Asn Gly Gly Phe Lys Asp Gly Gly
                325                 330                 335

Thr Asn Phe Asp Ala Lys Leu Arg Arg Ser Ser Thr Asp Pro Glu Asp
            340                 345                 350

Ile Phe Ile Ala His Ile Ser Ala Met Asp Ala Met Ala His Ala Leu
        355                 360                 365

Leu Asn Ala Ala Ala Val Ile Glu Glu Ser Pro Leu Cys Glu Met Val
    370                 375                 380

Ala Lys Arg Tyr Ala Ser Phe Asp Ser Gly Leu Gly Lys Lys Phe Glu
385                 390                 395                 400

Glu Gly Asn Ala Thr Leu Glu Glu Leu Tyr Glu Tyr Ala Lys Ala Asn
                405                 410                 415

Gly Glu Val Lys Ala Glu Ser Gly Lys Gln Glu Leu Tyr Glu Thr Leu
            420                 425                 430

Leu Asn Leu Tyr Ala Lys
        435
```

<210> SEQ ID NO 167
<211> LENGTH: 1317
<212> TYPE: DNA
<213> ORGANISM: Unknown
<220> FEATURE:
<223> OTHER INFORMATION: Obtained from environmental sample

<400> SEQUENCE: 167

```
atggcaaaag agtatttccc cactatcggg aagattcctt tcgaaggagt cgagagcaag      60

aacccccttg cattccatta ttatgacgca aaccgcatgg tcatgggcaa gcccatgaag     120

gactggttca agttcgccat ggcatggtgg cacaccctgg gacaggcctc cgcagacccg     180

ttcggcggcc agacccgctc ctacgaatgg gacaagggcg aatgccccta ctgccgcgcc     240

agggcaaagg ccgatgccgg cttcgagatc atgcagaaac tgggtatcga gtatttctgc     300

ttccatgaca tcgacctggt agaggactgc gacgacatcg ccgagtacga ggcccgcatg     360

aaggacatca cggactatct cctggagaag atgaaggaaa ccggcatcaa gaacctctgg     420

ggcaccgcca acgtgttcgg caacaagcgt tacatgaacg gcgccggcac caatccgcag     480

ttcgacgtag tggcccgcgc tgccgtccag atcaagaacg ccatcgacgc caccatcaag     540

ctcggcggtt ccaactatgt gttctggggc ggccgtgaag gatactacac cctgctgaac     600

acccagatgc agcgcgagaa ggaccacctc ggcaaactgc tcaccgccgc ccgcgactat     660

gcccgcaaga acggcttcaa gggcaccttc ctcatcgagc ccaagccgat ggagcccacc     720

aagcaccagt acgacgtaga cacggagacc gtgatcggct tcctccgcgc caacggcctg     780

gagaaagact tcaaggtgaa catcgaggtg aaccacgcca ccctggccgg ccataccttc     840

gagcatgaac tcaccgtggc cgtggacaac ggcttcctgg gatccatcga cgccaaccgc     900

ggcgacgccc agaacggctg ggatacggac cagttcccgg tagacccgta cgacctcacc     960

caggccatga tgcagatcat ccgcaacggc ggcctcggca acggcggtac caacttcgac    1020

gccaaactgc gccgttcctc caccgatcct gaggacatct tcatcgccca catcagcgcc    1080

atggacgcca tggcccacgc cctgctcaac gcagccgccg tgctggaaga aagtccgctc    1140

tgtgagatgg tcaaggagcg ctacgcttcc ttcgacagcg gtctcggcaa gaagttcgaa    1200

gagggcaagg ctaccctgga agaaatctac gagtatgcca agaagagcgg cgaacccgtg    1260

gtcgcttccg gcaagcagga gctctacgaa accctgctga acctctacgc caagtag      1317
```

<210> SEQ ID NO 168
<211> LENGTH: 438
<212> TYPE: PRT
<213> ORGANISM: Unknown
<220> FEATURE:
<223> OTHER INFORMATION: Obtained from environmental sample

<400> SEQUENCE: 168

```
Met Ala Lys Glu Tyr Phe Pro Thr Ile Gly Lys Ile Pro Phe Glu Gly
1               5                   10                  15

Val Glu Ser Lys Asn Pro Leu Ala Phe His Tyr Tyr Asp Ala Asn Arg
            20                  25                  30

Met Val Met Gly Lys Pro Met Lys Asp Trp Phe Lys Phe Ala Met Ala
        35                  40                  45

Trp Trp His Thr Leu Gly Gln Ala Ser Ala Asp Pro Phe Gly Gly Gln
    50                  55                  60

Thr Arg Ser Tyr Glu Trp Asp Lys Gly Glu Cys Pro Tyr Cys Arg Ala
65                  70                  75                  80
```

```
Arg Ala Lys Ala Asp Ala Gly Phe Glu Ile Met Gln Lys Leu Gly Ile
                85                  90                  95

Glu Tyr Phe Cys Phe His Asp Ile Asp Leu Val Glu Asp Cys Asp Asp
            100                 105                 110

Ile Ala Glu Tyr Glu Ala Arg Met Lys Asp Ile Thr Asp Tyr Leu Leu
        115                 120                 125

Glu Lys Met Lys Glu Thr Gly Ile Lys Asn Leu Trp Gly Thr Ala Asn
    130                 135                 140

Val Phe Gly Asn Lys Arg Tyr Met Asn Gly Ala Gly Thr Asn Pro Gln
145                 150                 155                 160

Phe Asp Val Val Ala Arg Ala Ala Val Gln Ile Lys Asn Ala Ile Asp
                165                 170                 175

Ala Thr Ile Lys Leu Gly Gly Ser Asn Tyr Val Phe Trp Gly Gly Arg
            180                 185                 190

Glu Gly Tyr Tyr Thr Leu Leu Asn Thr Gln Met Gln Arg Glu Lys Asp
        195                 200                 205

His Leu Gly Lys Leu Leu Thr Ala Ala Arg Asp Tyr Ala Arg Lys Asn
    210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Val Ile Gly Phe Leu Arg
                245                 250                 255

Ala Asn Gly Leu Glu Lys Asp Phe Lys Val Asn Ile Glu Val Asn His
            260                 265                 270

Ala Thr Leu Ala Gly His Thr Phe Glu His Glu Leu Thr Val Ala Val
        275                 280                 285

Asp Asn Gly Phe Leu Gly Ser Ile Asp Ala Asn Arg Gly Asp Ala Gln
    290                 295                 300

Asn Gly Trp Asp Thr Asp Gln Phe Pro Val Asp Pro Tyr Asp Leu Thr
305                 310                 315                 320

Gln Ala Met Met Gln Ile Ile Arg Asn Gly Gly Leu Gly Asn Gly Gly
                325                 330                 335

Thr Asn Phe Asp Ala Lys Leu Arg Arg Ser Ser Thr Asp Pro Glu Asp
            340                 345                 350

Ile Phe Ile Ala His Ile Ser Ala Met Asp Ala Met Ala His Ala Leu
        355                 360                 365

Leu Asn Ala Ala Ala Val Leu Glu Glu Ser Pro Leu Cys Glu Met Val
    370                 375                 380

Lys Glu Arg Tyr Ala Ser Phe Asp Ser Gly Leu Gly Lys Lys Phe Glu
385                 390                 395                 400

Glu Gly Lys Ala Thr Leu Glu Glu Ile Tyr Glu Tyr Ala Lys Lys Ser
                405                 410                 415

Gly Glu Pro Val Val Ala Ser Gly Lys Gln Glu Leu Tyr Glu Thr Leu
            420                 425                 430

Leu Asn Leu Tyr Ala Lys
        435
```

<210> SEQ ID NO 169
<211> LENGTH: 1317
<212> TYPE: DNA
<213> ORGANISM: Unknown
<220> FEATURE:
<223> OTHER INFORMATION: Obtained from environmental sample

<400> SEQUENCE: 169

```
atggctaaag aatacttccc ctccatcggc aaaatccctt ttgaaggagg cgacagcaaa     60

aatcccctcg ctttccatta ttatgacgcc ggacgcgtgg ttatgggcaa gcccatgaag    120

gaatggctta aattcgccat ggcctggtgg cacacgctgg gccaggcctc cggagacccc    180

ttcggcggcc agacccgcag ctacgaatgg gacaagggcg aatgccccta ctgccgcgcc    240

aaagccaagg ccgacgccgg ttttgaaatc atgcaaaagc tgggtatcga atacttctgc    300

ttccacgatg tggaccttat cgaggattgc gatgacattg ccgaatacga agcccgcatg    360

aaggacatca cggactacct gctggaaaag atgaaggaga ccggcatcaa gaacctctgg    420

ggcaccgcca atgtcttcgg ccacaagcgc tacatgaacg gcgccgccac gaacccgcag    480

ttcgacgtgg tcgcccgcgc cgccgtccag atcaagaacg cgattgacgc caccatcaag    540

ctcggcggta ccagttatgt attctggggc ggccgcgagg gctactacac cctcctgaac    600

acccagatgc agcgtgagaa agaccacctg gccaagatgc tcaccgcagc ccgcgactac    660

gcccgcgcca agggcttcaa gggcaccttc ctcatcgagc ccaagccgat ggagcccacc    720

aagcaccagt acgacgttga cacggagacc gtgatcggct ccctgcgcgc caacggcctg    780

gacaaggact tcaaggtgaa catcgaggtg aaccacgcca ccctggccgg ccacaccttc    840

gagcacgaac tcaccgtggc tgttgacaac ggcttcctgg gctccatcga cgccaaccgc    900

ggcgacgccc agaacggctg ggatacggac cagttcccgg tagacccgta cgacctcacc    960

caggccatga tgcagattat ccgcaacggc ggcttcaagg acggcggcac caacttcgat   1020

gccaaactgc gccgctcttc caccgatccg gaagacatct tcatcgccca catcagcgct   1080

atggatgcca tggcacacgc cctgctcaac gccgccgccg tgctggaaga gagcccgctg   1140

tgcaacatgg tcaaggagcg ttacgccggc ttcgacagcg gccttggcaa gaagttcgag   1200

gaagggaagg caacgctgga ggaaatctat gactatgcca agaagagcgg cgaacccgtc   1260

gtggcttccg gcaagcagga actctacgaa accatcctga acctctatgc caagtag      1317
```

```
<210> SEQ ID NO 170
<211> LENGTH: 438
<212> TYPE: PRT
<213> ORGANISM: Unknown
<220> FEATURE:
<223> OTHER INFORMATION: Obtained from environmental sample

<400> SEQUENCE: 170

Met Ala Lys Glu Tyr Phe Pro Ser Ile Gly Lys Ile Pro Phe Glu Gly
1               5                   10                  15

Gly Asp Ser Lys Asn Pro Leu Ala Phe His Tyr Tyr Asp Ala Gly Arg
            20                  25                  30

Val Val Met Gly Lys Pro Met Lys Glu Trp Leu Lys Phe Ala Met Ala
        35                  40                  45

Trp Trp His Thr Leu Gly Gln Ala Ser Gly Asp Pro Phe Gly Gly Gln
    50                  55                  60

Thr Arg Ser Tyr Glu Trp Asp Lys Gly Glu Cys Pro Tyr Cys Arg Ala
65                  70                  75                  80

Lys Ala Lys Ala Asp Ala Gly Phe Glu Ile Met Gln Lys Leu Gly Ile
                85                  90                  95

Glu Tyr Phe Cys Phe His Asp Val Asp Leu Ile Glu Asp Cys Asp Asp
            100                 105                 110

Ile Ala Glu Tyr Glu Ala Arg Met Lys Asp Ile Thr Asp Tyr Leu Leu
        115                 120                 125

Glu Lys Met Lys Glu Thr Gly Ile Lys Asn Leu Trp Gly Thr Ala Asn
```

```
    130                 135                 140

Val Phe Gly His Lys Arg Tyr Met Asn Gly Ala Ala Thr Asn Pro Gln
145                 150                 155                 160

Phe Asp Val Val Ala Arg Ala Ala Val Gln Ile Lys Asn Ala Ile Asp
                165                 170                 175

Ala Thr Ile Lys Leu Gly Gly Thr Ser Tyr Val Phe Trp Gly Gly Arg
            180                 185                 190

Glu Gly Tyr Tyr Thr Leu Leu Asn Thr Gln Met Gln Arg Glu Lys Asp
        195                 200                 205

His Leu Ala Lys Met Leu Thr Ala Ala Arg Asp Tyr Ala Arg Ala Lys
    210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Val Ile Gly Ser Leu Arg
                245                 250                 255

Ala Asn Gly Leu Asp Lys Asp Phe Lys Val Asn Ile Glu Val Asn His
            260                 265                 270

Ala Thr Leu Ala Gly His Thr Phe Glu His Glu Leu Thr Val Ala Val
        275                 280                 285

Asp Asn Gly Phe Leu Gly Ser Ile Asp Ala Asn Arg Gly Asp Ala Gln
    290                 295                 300

Asn Gly Trp Asp Thr Asp Gln Phe Pro Val Asp Pro Tyr Asp Leu Thr
305                 310                 315                 320

Gln Ala Met Met Gln Ile Ile Arg Asn Gly Gly Phe Lys Asp Gly Gly
                325                 330                 335

Thr Asn Phe Asp Ala Lys Leu Arg Arg Ser Ser Thr Asp Pro Glu Asp
            340                 345                 350

Ile Phe Ile Ala His Ile Ser Ala Met Asp Ala Met Ala His Ala Leu
        355                 360                 365

Leu Asn Ala Ala Ala Val Leu Glu Glu Ser Pro Leu Cys Asn Met Val
    370                 375                 380

Lys Glu Arg Tyr Ala Gly Phe Asp Ser Gly Leu Gly Lys Lys Phe Glu
385                 390                 395                 400

Glu Gly Lys Ala Thr Leu Glu Glu Ile Tyr Asp Tyr Ala Lys Lys Ser
                405                 410                 415

Gly Glu Pro Val Val Ala Ser Gly Lys Gln Glu Leu Tyr Glu Thr Ile
            420                 425                 430

Leu Asn Leu Tyr Ala Lys
        435
```

<210> SEQ ID NO 171
<211> LENGTH: 1317
<212> TYPE: DNA
<213> ORGANISM: Unknown
<220> FEATURE:
<223> OTHER INFORMATION: Obtained from environmental sample

<400> SEQUENCE: 171

```
atgtcaaaag agtatttccc tacaatcggc agggtcccct tcgagggacc tgagagcaag      60

aatccgctgg cgttccacta ttacgagccg gaccggctcg tcctgggcag gaaaatgaag     120

gactggctgc gcttcgcaat ggcctggtgg catacgctcg ggcaggcttc cggcgaccag     180

ttcggcggac agacctgcac atacgcctgg gatgaaggcg agtgtcccgt ctgccgggca     240

aaggccaagg ctgacgccgg ctttgaactg atgcagaaac tgggcatcgg gtatttctgc     300
```

```
ttccacgacg tggacctggt cgaggaggcc gacaccattg aagaatacga ggagcggatg    360

cggatcatca ccgactacct gctcgagaag atggaagaga ccggcatccg caatctctgg    420

ggaaccgcca atgtcttcgg acacaagcgc tatatgaacg gcgccgccac caatcccgac    480

ttcgacgtcg tggcccgtgc cgcggtccag atcaagaatg ccatcgatgc caccatcaaa    540

ctgggtggtg agaactatgt gttctggggt ggccgcgagg gctatacgag cctgctcaac    600

acgcagatgc accgggaaaa acaccacctc ggaaatatgc tcagggcagc ccgcgactat    660

ggccgtgccc acggtttcaa gggaacgttc ctgatcgagc ccaagccgat ggagccgacc    720

aagcatcagt acgaccagga tacggagacg gtcatcggtt tcctgcgctg tcacggcctg    780

gacaaggatt tcaaggtgaa catcgaggtg aaccacgcca cgctcgccgg acacaccttc    840

gagcacgaac tggccactgc ggtcgatgcc ggcctgctgg gcagcatcga tgccaaccgc    900

ggcgacgccc agaacggctg ggataccgac cagttcccga tcgacaacta cgaactcacg    960

ctggcgatgc tgcagatcat ccgcaatggc ggactcgcac ccggcggatc gaacttcgat   1020

gccaagttgc gccgcaattc caccgatccg gaagacatct tcatcgccca catcagcgcg   1080

atggacgcga tggcccgtgc cctgctcaat gcggcggcca tctggaccga atcgccgatt   1140

caggatatgg tcagggaccg ctatgcttcc ttcgacagcg gaaagggcag ggagttcgag   1200

gaaggcagac tcagtctgga agacctcgtg gcctatgcga aggagcacgg tgagccgcgc   1260

cagatctccg gcaggcagga actttatgaa accatcgtag cgctttactg caggtaa      1317
```

<210> SEQ ID NO 172
<211> LENGTH: 438
<212> TYPE: PRT
<213> ORGANISM: Unknown
<220> FEATURE:
<223> OTHER INFORMATION: Obtained from environmental sample

<400> SEQUENCE: 172

```
Met Ser Lys Glu Tyr Phe Pro Thr Ile Gly Arg Val Pro Phe Glu Gly
1               5                   10                  15

Pro Glu Ser Lys Asn Pro Leu Ala Phe His Tyr Tyr Glu Pro Asp Arg
            20                  25                  30

Leu Val Leu Gly Arg Lys Met Lys Asp Trp Leu Arg Phe Ala Met Ala
        35                  40                  45

Trp Trp His Thr Leu Gly Gln Ala Ser Gly Asp Gln Phe Gly Gly Gln
    50                  55                  60

Thr Cys Thr Tyr Ala Trp Asp Glu Gly Glu Cys Pro Val Cys Arg Ala
65                  70                  75                  80

Lys Ala Lys Ala Asp Ala Gly Phe Glu Leu Met Gln Lys Leu Gly Ile
                85                  90                  95

Gly Tyr Phe Cys Phe His Asp Val Asp Leu Val Glu Glu Ala Asp Thr
            100                 105                 110

Ile Glu Glu Tyr Glu Glu Arg Met Arg Ile Ile Thr Asp Tyr Leu Leu
        115                 120                 125

Glu Lys Met Glu Glu Thr Gly Ile Arg Asn Leu Trp Gly Thr Ala Asn
    130                 135                 140

Val Phe Gly His Lys Arg Tyr Met Asn Gly Ala Ala Thr Asn Pro Asp
145                 150                 155                 160

Phe Asp Val Val Ala Arg Ala Ala Val Gln Ile Lys Asn Ala Ile Asp
                165                 170                 175

Ala Thr Ile Lys Leu Gly Gly Glu Asn Tyr Val Phe Trp Gly Gly Arg
            180                 185                 190
```

```
Glu Gly Tyr Thr Ser Leu Leu Asn Thr Gln Met His Arg Glu Lys His
        195                 200                 205

His Leu Gly Asn Met Leu Arg Ala Ala Arg Asp Tyr Gly Arg Ala His
    210                 215                 220

Gly Phe Lys Gly Thr Phe Leu Ile Glu Pro Lys Pro Met Glu Pro Thr
225                 230                 235                 240

Lys His Gln Tyr Asp Gln Asp Thr Glu Thr Val Ile Gly Phe Leu Arg
                245                 250                 255

Cys His Gly Leu Asp Lys Asp Phe Lys Val Asn Ile Glu Val Asn His
            260                 265                 270

Ala Thr Leu Ala Gly His Thr Phe Glu His Glu Leu Ala Thr Ala Val
        275                 280                 285

Asp Ala Gly Leu Leu Gly Ser Ile Asp Ala Asn Arg Gly Asp Ala Gln
    290                 295                 300

Asn Gly Trp Asp Thr Asp Gln Phe Pro Ile Asp Asn Tyr Glu Leu Thr
305                 310                 315                 320

Leu Ala Met Leu Gln Ile Ile Arg Asn Gly Gly Leu Ala Pro Gly Gly
                325                 330                 335

Ser Asn Phe Asp Ala Lys Leu Arg Arg Asn Ser Thr Asp Pro Glu Asp
            340                 345                 350

Ile Phe Ile Ala His Ile Ser Ala Met Asp Ala Met Ala Arg Ala Leu
        355                 360                 365

Leu Asn Ala Ala Ala Ile Trp Thr Glu Ser Pro Ile Gln Asp Met Val
    370                 375                 380

Arg Asp Arg Tyr Ala Ser Phe Asp Ser Gly Lys Gly Arg Glu Phe Glu
385                 390                 395                 400

Glu Gly Arg Leu Ser Leu Glu Asp Leu Val Ala Tyr Ala Lys Glu His
                405                 410                 415

Gly Glu Pro Arg Gln Ile Ser Gly Arg Gln Glu Leu Tyr Glu Thr Ile
            420                 425                 430

Val Ala Leu Tyr Cys Arg
        435
```

<210> SEQ ID NO 173
<211> LENGTH: 1317
<212> TYPE: DNA
<213> ORGANISM: Unknown
<220> FEATURE:
<223> OTHER INFORMATION: Obtained from environmental sample

<400> SEQUENCE: 173

```
atgactaaag agtatttccc gggaatcgga acgattccgt ttgaaggaac caagagcaag     60

aaccccctgg ccttccatta ttataacgcc tcccaggtag tgatgggcaa gcccatgaag    120

gactggctca agtatgccat ggcctggtgg cacaccctgg gccaggcctc tgcagacccc    180

tttggcggcc agacccgctc ctacgaatgg gacaagggcg agtgcccgta ctgccgcgcc    240

aagcagaagg ccgatgccgg ctttgagctc atgcagaagc tgggcatcga gtactactgc    300

ttccacgacg tggacatcat cgaggactgc gaggacattg ccgagtacga ggcccgcatg    360

aaggacatca cggactacct gctggagaag cagaaagaga ccggcatcaa gaacctctgg    420

ggcaccgcca acgtgtttgg ccacaagcgc tacatgaacg gcgccgccac caaccctcag    480

tttgacattg tggcccgtgc cgccgtccag atcaagaacg ccctggatgc cgccatcaaa    540

ctgggtggta ccaactacgt gttctggggt ggccgcgaag gctactacac gctgctcaac    600
```

```
acccagatgc agcgggagaa gaaccacctg gccaagatgc tcaccgccgc ccgcgactac    660

gcccgcgcca agggcttcaa gggcaccttc ctcattgagc ccaaacccat ggagcccacc    720

aagcaccagt acgacgtgga caccgagacc gtgattggtt tcatccgcgc caacggcctg    780

gacaaggact tcaaggtaaa cattgaggta aaccacgcca ccctggccgg ccacaccttt    840

gagcacgagc tcaccgtggc ccgcgagaac ggcttcctgg gctccatcga cgccaaccgc    900

ggagatgccc agaacggctg ggatacggac cagttcccca tcgacgccct ggatctcacc    960

caggctatga tgcaggtcat cctcaacggt ggcttcggca atggcggcac caactttgac   1020

gccaagctcc gccgctcctc caccgatccc gaggacatct tcatcgccca catcagcgcc   1080

atggatgcca tggcacacgc cctcctgaac gcagccgcca tcctggaaga gagccccctg   1140

cccgccatgg tcaaggagcg ttacgcttcc ttcgacagcg gtctgggcaa gaagttcgaa   1200

gaaggcaagg cctccctgga agaactttac gaatatgcca agaagaatgg agagcccgtg   1260

gccgcttccg gcaaacagga gctctgcgaa acttacttga acctctatgc aaagtag      1317
```

```
<210> SEQ ID NO 174
<211> LENGTH: 438
<212> TYPE: PRT
<213> ORGANISM: Unknown
<220> FEATURE:
<223> OTHER INFORMATION: Obtained from environmental sample

<400> SEQUENCE: 174

Met Thr Lys Glu Tyr Phe Pro Gly Ile Gly Thr Ile Pro Phe Glu Gly
1               5                   10                  15

Thr Lys Ser Lys Asn Pro Leu Ala Phe His Tyr Tyr Asn Ala Ser Gln
            20                  25                  30

Val Val Met Gly Lys Pro Met Lys Asp Trp Leu Lys Tyr Ala Met Ala
        35                  40                  45

Trp Trp His Thr Leu Gly Gln Ala Ser Ala Asp Pro Phe Gly Gly Gln
    50                  55                  60

Thr Arg Ser Tyr Glu Trp Asp Lys Gly Glu Cys Pro Tyr Cys Arg Ala
65                  70                  75                  80

Lys Gln Lys Ala Asp Ala Gly Phe Glu Leu Met Gln Lys Leu Gly Ile
                85                  90                  95

Glu Tyr Tyr Cys Phe His Asp Val Asp Ile Ile Glu Asp Cys Glu Asp
            100                 105                 110

Ile Ala Glu Tyr Glu Ala Arg Met Lys Asp Ile Thr Asp Tyr Leu Leu
        115                 120                 125

Glu Lys Gln Lys Glu Thr Gly Ile Lys Asn Leu Trp Gly Thr Ala Asn
    130                 135                 140

Val Phe Gly His Lys Arg Tyr Met Asn Gly Ala Ala Thr Asn Pro Gln
145                 150                 155                 160

Phe Asp Ile Val Ala Arg Ala Ala Val Gln Ile Lys Asn Ala Leu Asp
                165                 170                 175

Ala Ala Ile Lys Leu Gly Gly Thr Asn Tyr Val Phe Trp Gly Gly Arg
            180                 185                 190

Glu Gly Tyr Tyr Thr Leu Leu Asn Thr Gln Met Gln Arg Glu Lys Asn
        195                 200                 205

His Leu Ala Lys Met Leu Thr Ala Ala Arg Asp Tyr Ala Arg Ala Lys
    210                 215                 220

Gly Phe Lys Gly Thr Phe Leu Ile Glu Pro Lys Pro Met Glu Pro Thr
225                 230                 235                 240
```

```
Lys His Gln Tyr Asp Val Asp Thr Glu Thr Val Ile Gly Phe Ile Arg
                245                 250                 255

Ala Asn Gly Leu Asp Lys Asp Phe Lys Val Asn Ile Glu Val Asn His
            260                 265                 270

Ala Thr Leu Ala Gly His Thr Phe Glu His Glu Leu Thr Val Ala Arg
        275                 280                 285

Glu Asn Gly Phe Leu Gly Ser Ile Asp Ala Asn Arg Gly Asp Ala Gln
    290                 295                 300

Asn Gly Trp Asp Thr Asp Gln Phe Pro Ile Asp Ala Leu Asp Leu Thr
305                 310                 315                 320

Gln Ala Met Met Gln Val Ile Leu Asn Gly Gly Phe Gly Asn Gly Gly
                325                 330                 335

Thr Asn Phe Asp Ala Lys Leu Arg Arg Ser Ser Thr Asp Pro Glu Asp
            340                 345                 350

Ile Phe Ile Ala His Ile Ser Ala Met Asp Ala Met Ala His Ala Leu
        355                 360                 365

Leu Asn Ala Ala Ala Ile Leu Glu Glu Ser Pro Leu Pro Ala Met Val
    370                 375                 380

Lys Glu Arg Tyr Ala Ser Phe Asp Ser Gly Leu Gly Lys Lys Phe Glu
385                 390                 395                 400

Glu Gly Lys Ala Ser Leu Glu Glu Leu Tyr Glu Tyr Ala Lys Lys Asn
                405                 410                 415

Gly Glu Pro Val Ala Ala Ser Gly Lys Gln Glu Leu Cys Glu Thr Tyr
            420                 425                 430

Leu Asn Leu Tyr Ala Lys
        435


<210> SEQ ID NO 175
<211> LENGTH: 1308
<212> TYPE: DNA
<213> ORGANISM: Unknown
<220> FEATURE:
<223> OTHER INFORMATION: Obtained from environmental sample

<400> SEQUENCE: 175

gtgactgatt tcttcaaggg catcgcgccc gtcaagtttg aggggccgca gagctccaat     60

ccgctggcct atcgccacta taacaaggac gaaatcgtcc tcggcaagcg gatggaagac    120

catatccgtc ccggcgttgc ctattggcac accttcgcct atgagggcgg cgatccgttt    180

ggcggccgca ccttcgatcg cccctggttc gacaagggta tggacggcgc ccgcctcaag    240

gccgacgtgg ccttcgaact gttcgacctg ctcgacgttc ctttcttctg tttccacgat    300

gctgatatcg ctcccgaagg cgcaacgctg gccgagagca accgcaatgt gcgcgagatt    360

ggcgagatct tcgctcgcaa gatggaaacc agccgcacca agctgctctg ggtacggca     420

aacctgttct ccaatcgccg ctacatggcc ggcgccgcca ccaacccgga cccggaaatc    480

ttcgcctatg ccgctgggca ggtgaagaac gtgctggaac tgacccacga actgggcggc    540

gccaactatg tgctgtgggg cggtcgcgag ggttatgaaa ccctgctcaa caccaagatc    600

ggccaggaaa tggaccagat gggccgtttt ctgtcgatgg tcgtcgagca tgccgaaaag    660

atcggcttca agggccagat cctgatcgag cccaagccgc aggagccgag caagcaccag    720

tatgacttcg acgttgcaac cgtttacggc ttcctcaaga agtatggtct cgaaaccaag    780

gtgaagtgca atatcgaggt cggccatgcc ttcctcgcca atcactcctt cgagcatgaa    840

ctggctttgg ccgcatcgct gggcattctc ggctcggtcg acgccaatcg caacgatcta    900
```

-continued

```
cagtccggct gggataccga ccagttcccc aataatgtcc ccgaaaccgc actcgccttc    960

tatcagattc tcaaggcggg cggactgggc aatggcggct ggaacttcga cgcccgcgtg   1020

cgccgccagt cacttgatcc ggccgacctg ctgcacggcc atatcggcgg cctcgacgtg   1080

ctggcgcgcg gcctcaaggc cgccgcggcg ctgatcgagg acggcaccta tgacaaggtc   1140

gtcgacgccc gctatgccgg ctggaaccag ggcctgggca aggatatcct tggtggcaag   1200

ctgaaccttg ccgacctggc tgccaaggtc gacgccgaaa acctcaaccc gcagcctagg   1260

tccggccagc aggaatatct cgaaaacctg atcaaccggt tcgtttag                1308
```

<210> SEQ ID NO 176
<211> LENGTH: 435
<212> TYPE: PRT
<213> ORGANISM: Unknown
<220> FEATURE:
<223> OTHER INFORMATION: Obtained from environmental sample

<400> SEQUENCE: 176

```
Met Thr Asp Phe Phe Lys Gly Ile Ala Pro Val Lys Phe Glu Gly Pro
1               5                   10                  15

Gln Ser Ser Asn Pro Leu Ala Tyr Arg His Tyr Asn Lys Asp Glu Ile
            20                  25                  30

Val Leu Gly Lys Arg Met Glu Asp His Ile Arg Pro Gly Val Ala Tyr
        35                  40                  45

Trp His Thr Phe Ala Tyr Glu Gly Gly Asp Pro Phe Gly Gly Arg Thr
    50                  55                  60

Phe Asp Arg Pro Trp Phe Asp Lys Gly Met Asp Gly Ala Arg Leu Lys
65                  70                  75                  80

Ala Asp Val Ala Phe Glu Leu Phe Asp Leu Leu Asp Val Pro Phe Phe
                85                  90                  95

Cys Phe His Asp Ala Asp Ile Ala Pro Glu Gly Ala Thr Leu Ala Glu
            100                 105                 110

Ser Asn Arg Asn Val Arg Glu Ile Gly Glu Ile Phe Ala Arg Lys Met
        115                 120                 125

Glu Thr Ser Arg Thr Lys Leu Leu Trp Gly Thr Ala Asn Leu Phe Ser
    130                 135                 140

Asn Arg Arg Tyr Met Ala Gly Ala Ala Thr Asn Pro Asp Pro Glu Ile
145                 150                 155                 160

Phe Ala Tyr Ala Ala Gly Gln Val Lys Asn Val Leu Glu Leu Thr His
                165                 170                 175

Glu Leu Gly Gly Ala Asn Tyr Val Leu Trp Gly Gly Arg Glu Gly Tyr
            180                 185                 190

Glu Thr Leu Leu Asn Thr Lys Ile Gly Gln Glu Met Asp Gln Met Gly
        195                 200                 205

Arg Phe Leu Ser Met Val Val Glu His Ala Glu Lys Ile Gly Phe Lys
    210                 215                 220

Gly Gln Ile Leu Ile Glu Pro Lys Pro Gln Glu Pro Ser Lys His Gln
225                 230                 235                 240

Tyr Asp Phe Asp Val Ala Thr Val Tyr Gly Phe Leu Lys Lys Tyr Gly
                245                 250                 255

Leu Glu Thr Lys Val Lys Cys Asn Ile Glu Val Gly His Ala Phe Leu
            260                 265                 270

Ala Asn His Ser Phe Glu His Glu Leu Ala Leu Ala Ala Ser Leu Gly
        275                 280                 285

Ile Leu Gly Ser Val Asp Ala Asn Arg Asn Asp Leu Gln Ser Gly Trp
```

```
    290                 295                 300

Asp Thr Asp Gln Phe Pro Asn Asn Val Pro Glu Thr Ala Leu Ala Phe
305                 310                 315                 320

Tyr Gln Ile Leu Lys Ala Gly Gly Leu Gly Asn Gly Gly Trp Asn Phe
                325                 330                 335

Asp Ala Arg Val Arg Arg Gln Ser Leu Asp Pro Ala Asp Leu Leu His
            340                 345                 350

Gly His Ile Gly Gly Leu Asp Val Leu Ala Arg Gly Leu Lys Ala Ala
        355                 360                 365

Ala Ala Leu Ile Glu Asp Gly Thr Tyr Asp Lys Val Val Asp Ala Arg
    370                 375                 380

Tyr Ala Gly Trp Asn Gln Gly Leu Gly Lys Asp Ile Leu Gly Gly Lys
385                 390                 395                 400

Leu Asn Leu Ala Asp Leu Ala Ala Lys Val Asp Ala Glu Asn Leu Asn
                405                 410                 415

Pro Gln Pro Arg Ser Gly Gln Gln Glu Tyr Leu Glu Asn Leu Ile Asn
            420                 425                 430

Arg Phe Val
        435


<210> SEQ ID NO 177
<211> LENGTH: 23
<212> TYPE: PRT
<213> ORGANISM: Unknown
<220> FEATURE:
<223> OTHER INFORMATION: Obtained from environmental sample

<400> SEQUENCE: 177

Gly Cys Ile Gly Cys Ile Cys Ala Arg Gly Ala Arg Gly Gly Asn Ala
1               5                   10                  15

Thr Tyr Gly Thr Val Thr Thr
            20


<210> SEQ ID NO 178
<211> LENGTH: 8
<212> TYPE: PRT
<213> ORGANISM: Unknown
<220> FEATURE:
<223> OTHER INFORMATION: Obtained from environmental sample

<400> SEQUENCE: 178

Ala Ala Gln Glu Gly Ile Val Phe
1               5


<210> SEQ ID NO 179
<211> LENGTH: 23
<212> TYPE: PRT
<213> ORGANISM: Unknown
<220> FEATURE:
<223> OTHER INFORMATION: Obtained from environmental sample

<400> SEQUENCE: 179

Gly Cys Asp Ala Thr Tyr Thr Cys Asn Gly Cys Arg Ala Thr Arg Thr
1               5                   10                  15

Ala Cys Ala Thr Ser Gly Gly
            20


<210> SEQ ID NO 180
<211> LENGTH: 8
<212> TYPE: PRT
<213> ORGANISM: Unknown
```

<220> FEATURE:
<223> OTHER INFORMATION: Obtained from environmental sample

<400> SEQUENCE: 180

Pro Met Tyr Ile Ala Glu Ile Ala
1 5

<210> SEQ ID NO 181
<211> LENGTH: 60
<212> TYPE: DNA
<213> ORGANISM: Unknown
<220> FEATURE:
<223> OTHER INFORMATION: Obtained from environmental sample

<400> SEQUENCE: 181
ggcgcgcctc tagaaagctt acgcgtgagc tccctgcagg gatatcggta ccgcggccgc 60

<210> SEQ ID NO 182
<211> LENGTH: 53
<212> TYPE: DNA
<213> ORGANISM: Unknown
<220> FEATURE:
<223> OTHER INFORMATION: Obtained from environmental sample

<400> SEQUENCE: 182
caccattaat taaagctttg taaatatgat gagagaataa tataaatcaa acg 53

<210> SEQ ID NO 183
<211> LENGTH: 57
<212> TYPE: DNA
<213> ORGANISM: Unknown
<220> FEATURE:
<223> OTHER INFORMATION: Obtained from environmental sample

<400> SEQUENCE: 183
ggcgcgcctc tagaaagctt aatcgacaag aacacttcta tttatatagg tatgaaa 57

<210> SEQ ID NO 184
<211> LENGTH: 57
<212> TYPE: DNA
<213> ORGANISM: Unknown
<220> FEATURE:
<223> OTHER INFORMATION: Obtained from environmental sample

<400> SEQUENCE: 184
gcagggatat cggtacccac cagcggccgc tgaagaaggt ttatttcgtt tcgctgt 57

<210> SEQ ID NO 185
<211> LENGTH: 38
<212> TYPE: DNA
<213> ORGANISM: Unknown
<220> FEATURE:
<223> OTHER INFORMATION: Obtained from environmental sample

<400> SEQUENCE: 185
caccattaat taacccaggt gagactggat gctccata 38

<210> SEQ ID NO 186
<211> LENGTH: 60
<212> TYPE: DNA
<213> ORGANISM: Unknown
<220> FEATURE:
<223> OTHER INFORMATION: Obtained from environmental sample

<400> SEQUENCE: 186
gcctctagaa agcttacgcg tgagctccct gcagggatat cggtacccac cagcggccgc 60

<210> SEQ ID NO 187
<211> LENGTH: 60
<212> TYPE: DNA
<213> ORGANISM: Unknown
<220> FEATURE:
<223> OTHER INFORMATION: Obtained from environmental sample

<400> SEQUENCE: 187
cgctggtggg taccgatatc cctgcaggga gctcacgcgt aagctttcta gaggcgcgcc 60

<210> SEQ ID NO 188
<211> LENGTH: 200
<212> TYPE: DNA
<213> ORGANISM: Unknown
<220> FEATURE:
<223> OTHER INFORMATION: Obtained from environmental sample

<400> SEQUENCE: 188
tgcgtgtgcc gcgagtccac gtctactcgc gaaccgagtg caggcgggtc ttcggccagg 60
acggccgtgc gtgaccccgg ccgccagacg aaacggaccg cgctcgccag acgctaccca 120
gcccgttcat gccggccgcg agccgacctg tctcggtcgc ttcgacgcac gcgcggtcct 180
ttcgggtact cgcctaagac 200

<210> SEQ ID NO 189
<211> LENGTH: 39
<212> TYPE: DNA
<213> ORGANISM: Unknown
<220> FEATURE:
<223> OTHER INFORMATION: Obtained from environmental sample

<400> SEQUENCE: 189
caatagcggc cgcggtacct gcgtgtgccg cgagtccac 39

<210> SEQ ID NO 190
<211> LENGTH: 34
<212> TYPE: DNA
<213> ORGANISM: Unknown
<220> FEATURE:
<223> OTHER INFORMATION: Obtained from environmental sample

<400> SEQUENCE: 190
tgttaggatc cgtcttaggc gagtacccga aagg 34

<210> SEQ ID NO 191
<211> LENGTH: 37
<212> TYPE: DNA
<213> ORGANISM: Unknown
<220> FEATURE:
<223> OTHER INFORMATION: Obtained from environmental sample

<400> SEQUENCE: 191
caataggatc caggcatatt tatggtgaag aataagt 37

<210> SEQ ID NO 192
<211> LENGTH: 35
<212> TYPE: DNA
<213> ORGANISM: Unknown
<220> FEATURE:
<223> OTHER INFORMATION: Obtained from environmental sample

<400> SEQUENCE: 192
tgttactcga gaaatcatta cgaccgagat tcccg 35

<210> SEQ ID NO 193
<211> LENGTH: 31
<212> TYPE: DNA
<213> ORGANISM: Unknown
<220> FEATURE:
<223> OTHER INFORMATION: Obtained from environmental sample

<400> SEQUENCE: 193
caatactcga gtgcgtgtgc cgcgagtcca c 31

<210> SEQ ID NO 194
<211> LENGTH: 36
<212> TYPE: DNA
<213> ORGANISM: Unknown
<220> FEATURE:
<223> OTHER INFORMATION: Obtained from environmental sample

<400> SEQUENCE: 194
tgttagcggc cgcgtcttag gcgagtaccc gaaagg 36

<210> SEQ ID NO 195
<211> LENGTH: 32
<212> TYPE: DNA
<213> ORGANISM: Unknown
<220> FEATURE:
<223> OTHER INFORMATION: Obtained from environmental sample

<400> SEQUENCE: 195
actagtggat ccctcgaggt cgacgtttaa ac 32

<210> SEQ ID NO 196
<211> LENGTH: 64
<212> TYPE: DNA
<213> ORGANISM: Unknown
<220> FEATURE:
<223> OTHER INFORMATION: Obtained from environmental sample

<400> SEQUENCE: 196
caccaggcgc gcctctagaa agcttacgcg tagtttatca ttatcaatac tgccatttca 60
aaga 64

<210> SEQ ID NO 197
<211> LENGTH: 57
<212> TYPE: DNA
<213> ORGANISM: Unknown
<220> FEATURE:
<223> OTHER INFORMATION: Obtained from environmental sample

<400> SEQUENCE: 197
aacgtcgacc tcgagggatc cactagttcg aaactaagtt cttggtgttt taaaact 57

<210> SEQ ID NO 198
<211> LENGTH: 58
<212> TYPE: DNA
<213> ORGANISM: Unknown
<220> FEATURE:
<223> OTHER INFORMATION: Obtained from environmental sample

<400> SEQUENCE: 198
gtggatccct cgaggtcgac gtttaaacat tgaattgaat tgaaatcgat agatcaat 58

<210> SEQ ID NO 199
<211> LENGTH: 69
<212> TYPE: DNA
<213> ORGANISM: Unknown

<220> FEATURE:
<223> OTHER INFORMATION: Obtained from environmental sample

<400> SEQUENCE: 199
caccagcggc cgcggtaccg atatccctgc agggagctcg aaatatcgaa tgggaaaaaa 60
aaactggat 69

<210> SEQ ID NO 200
<211> LENGTH: 25
<212> TYPE: DNA
<213> ORGANISM: Unknown
<220> FEATURE:
<223> OTHER INFORMATION: Obtained from environmental sample

<400> SEQUENCE: 200
acagggataa caaagtttct ccagc 25

<210> SEQ ID NO 201
<211> LENGTH: 25
<212> TYPE: DNA
<213> ORGANISM: Unknown
<220> FEATURE:
<223> OTHER INFORMATION: Obtained from environmental sample

<400> SEQUENCE: 201
cataccaagt catgcgttac cagag 25

<210> SEQ ID NO 202
<211> LENGTH: 25
<212> TYPE: DNA
<213> ORGANISM: Unknown
<220> FEATURE:
<223> OTHER INFORMATION: Obtained from environmental sample

<400> SEQUENCE: 202
tttcccattc gatatttcga gctcc 25

<210> SEQ ID NO 203
<211> LENGTH: 25
<212> TYPE: DNA
<213> ORGANISM: Unknown
<220> FEATURE:
<223> OTHER INFORMATION: Obtained from environmental sample

<400> SEQUENCE: 203
cataccaagt catgcgttac cagag 25

<210> SEQ ID NO 204
<211> LENGTH: 7
<212> TYPE: PRT
<213> ORGANISM: Artificial Sequence
<220> FEATURE:
<223> OTHER INFORMATION: Sequence Motif
<220> FEATURE:
<221> NAME/KEY: MISC_FEATURE
<222> LOCATION: (1)..(1)
<223> OTHER INFORMATION: Can be either Leu or Ile
<220> FEATURE:
<221> NAME/KEY: MISC_FEATURE
<222> LOCATION: (6)..(6)
<223> OTHER INFORMATION: Can be any two amino acids

<400> SEQUENCE: 204

Xaa Glu Pro Lys Pro Xaa Pro
1 5

<210> SEQ ID NO 205
<211> LENGTH: 10
<212> TYPE: PRT
<213> ORGANISM: Artificial Sequence
<220> FEATURE:
<223> OTHER INFORMATION: Sequence Motif
<220> FEATURE:
<221> NAME/KEY: MISC_FEATURE
<222> LOCATION: (1)..(1)
<223> OTHER INFORMATION: Can be either Phe or Leu
<220> FEATURE:
<221> NAME/KEY: MISC_FEATURE
<222> LOCATION: (4)..(4)
<223> OTHER INFORMATION: Can be any amino acid but Lys
<220> FEATURE:
<221> NAME/KEY: MISC_FEATURE
<222> LOCATION: (6)..(6)
<223> OTHER INFORMATION: Can be either Leu, Ile, or Val
<220> FEATURE:
<221> NAME/KEY: MISC_FEATURE
<222> LOCATION: (7)..(7)
<223> OTHER INFORMATION: Can be any amino acid
<220> FEATURE:
<221> NAME/KEY: MISC_FEATURE
<222> LOCATION: (8)..(8)
<223> OTHER INFORMATION: Can be either Asp or Pro
<220> FEATURE:
<221> NAME/KEY: MISC_FEATURE
<222> LOCATION: (9)..(9)
<223> OTHER INFORMATION: Can be any amino acid
<220> FEATURE:
<221> NAME/KEY: MISC_FEATURE
<222> LOCATION: (10)..(10)
<223> OTHER INFORMATION: Can be either Asp, Gly, or Glu

<400> SEQUENCE: 205

Xaa His Asp Xaa Asp Xaa Xaa Xaa Xaa Xaa
1               5                   10

<210> SEQ ID NO 206
<211> LENGTH: 12
<212> TYPE: PRT
<213> ORGANISM: Artificial Sequence
<220> FEATURE:
<223> OTHER INFORMATION: Sequence Motif
<220> FEATURE:
<221> NAME/KEY: MISC_FEATURE
<222> LOCATION: (2)..(2)
<223> OTHER INFORMATION: Can be either Phe or Tyr
<220> FEATURE:
<221> NAME/KEY: MISC_FEATURE
<222> LOCATION: (3)..(3)
<223> OTHER INFORMATION: Can be either Ala, Ser, or Thr
<220> FEATURE:
<221> NAME/KEY: MISC_FEATURE
<222> LOCATION: (4)..(4)
<223> OTHER INFORMATION: Can be either Met, Leu, Val, or Ile
<220> FEATURE:
<221> NAME/KEY: MISC_FEATURE
<222> LOCATION: (5)..(5)
<223> OTHER INFORMATION: Can be either Ala or Ser
<220> FEATURE:
<221> NAME/KEY: MISC_FEATURE
<222> LOCATION: (6)..(6)
<223> OTHER INFORMATION: Can be either Trp, Tyr, Phe, or Leu
<220> FEATURE:
<221> NAME/KEY: MISC_FEATURE
<222> LOCATION: (8)..(8)
<223> OTHER INFORMATION: Can be either His or Thr
<220> FEATURE:
<221> NAME/KEY: MISC_FEATURE
<222> LOCATION: (10)..(10)
<223> OTHER INFORMATION: Can be either Leu, Phe, Met, or Gly

<400> SEQUENCE: 206

Pro Xaa Xaa Xaa Xaa Xaa Trp Xaa Asn Xaa Gly Ala 1 5 10

<210> SEQ ID NO 207
<211> LENGTH: 11
<212> TYPE: PRT
<213> ORGANISM: Artificial Sequence
<220> FEATURE:
<223> OTHER INFORMATION: Sequence Motif
<220> FEATURE:
<221> NAME/KEY: MISC_FEATURE
<222> LOCATION: (2)..(2)
<223> OTHER INFORMATION: Can be either Phe or Tyr
<220> FEATURE:
<221> NAME/KEY: MISC_FEATURE
<222> LOCATION: (3)..(3)
<223> OTHER INFORMATION: Can be either Ala or Ser
<220> FEATURE:
<221> NAME/KEY: MISC_FEATURE
<222> LOCATION: (4)..(4)
<223> OTHER INFORMATION: Can be any two amino acids
<220> FEATURE:
<221> NAME/KEY: MISC_FEATURE
<222> LOCATION: (5)..(5)
<223> OTHER INFORMATION: Can be either Trp, Tyr, Phe, or Leu
<220> FEATURE:
<221> NAME/KEY: MISC_FEATURE
<222> LOCATION: (7)..(7)
<223> OTHER INFORMATION: Can be either His or Thr
<220> FEATURE:
<221> NAME/KEY: MISC_FEATURE
<222> LOCATION: (8)..(8)
<223> OTHER INFORMATION: Can be any amino acid but Thr or Val
<220> FEATURE:
<221> NAME/KEY: MISC_FEATURE
<222> LOCATION: (9)..(9)
<223> OTHER INFORMATION: Can be any amino acid

<400> SEQUENCE: 207

Pro Xaa Xaa Xaa Xaa Trp Xaa Xaa Xaa Gly Ala
1 5 10

<210> SEQ ID NO 208
<211> LENGTH: 11
<212> TYPE: PRT
<213> ORGANISM: Artificial Sequence
<220> FEATURE:
<223> OTHER INFORMATION: Sequence Motif
<220> FEATURE:
<221> NAME/KEY: MISC_FEATURE
<222> LOCATION: (1)..(1)
<223> OTHER INFORMATION: Can be either Gly, Ser, or Asn
<220> FEATURE:
<221> NAME/KEY: MISC_FEATURE
<222> LOCATION: (2)..(2)
<223> OTHER INFORMATION: Can be either Ile, Val, or Ala
<220> FEATURE:
<221> NAME/KEY: MISC_FEATURE
<222> LOCATION: (4)..(4)
<223> OTHER INFORMATION: Can be either Tyr, Phe, His, or Gly
<220> FEATURE:
<221> NAME/KEY: MISC_FEATURE
<222> LOCATION: (5)..(5)
<223> OTHER INFORMATION: Can be either Phe, Tyr, Leu, Ile, or Val
<220> FEATURE:
<221> NAME/KEY: MISC_FEATURE
<222> LOCATION: (7)..(7)
<223> OTHER INFORMATION: Can be either Phe or Trp
<220> FEATURE:
<221> NAME/KEY: MISC_FEATURE
<222> LOCATION: (10)..(10)
<223> OTHER INFORMATION: Can be any amino acid

<400> SEQUENCE: 208

Xaa Xaa Arg Xaa Xaa Cys Xaa His Asp Xaa Asp
1 5 10

```
<210> SEQ ID NO 209
<211> LENGTH: 11
<212> TYPE: PRT
<213> ORGANISM: Artificial Sequence
<220> FEATURE:
<223> OTHER INFORMATION: Sequence Motif
<220> FEATURE:
<221> NAME/KEY: MISC_FEATURE
<222> LOCATION: (2)..(2)
<223> OTHER INFORMATION: Can be either Ala, Ser, Thr, or Cys
<220> FEATURE:
<221> NAME/KEY: MISC_FEATURE
<222> LOCATION: (3)..(3)
<223> OTHER INFORMATION: Can be either Asn or Lys
<220> FEATURE:
<221> NAME/KEY: MISC_FEATURE
<222> LOCATION: (4)..(4)
<223> OTHER INFORMATION: Can be any amino acid but Leu
<220> FEATURE:
<221> NAME/KEY: MISC_FEATURE
<222> LOCATION: (6)..(6)
<223> OTHER INFORMATION: Can be any amino acid
<220> FEATURE:
<221> NAME/KEY: MISC_FEATURE
<222> LOCATION: (7)..(7)
<223> OTHER INFORMATION: Can be either Asn, Asp, or His
<220> FEATURE:
<221> NAME/KEY: MISC_FEATURE
<222> LOCATION: (8)..(8)
<223> OTHER INFORMATION: Can be either Pro, Arg, Lys, Ala, or Gly
<220> FEATURE:
<221> NAME/KEY: MISC_FEATURE
<222> LOCATION: (9)..(9)
<223> OTHER INFORMATION: Can be either Arg, Val, or Ala
<220> FEATURE:
<221> NAME/KEY: MISC_FEATURE
<222> LOCATION: (10)..(10)
<223> OTHER INFORMATION: Can be either Phe or Tyr

<400> SEQUENCE: 209

Thr Xaa Xaa Xaa Phe Xaa Xaa Xaa Xaa Xaa Cys
1               5                   10


<210> SEQ ID NO 210
<211> LENGTH: 13
<212> TYPE: PRT
<213> ORGANISM: Artificial Sequence
<220> FEATURE:
<223> OTHER INFORMATION: Sequence Motif
<220> FEATURE:
<221> NAME/KEY: MISC_FEATURE
<222> LOCATION: (1)..(1)
<223> OTHER INFORMATION: Can be either Trp, Phe, or Tyr
<220> FEATURE:
<221> NAME/KEY: MISC_FEATURE
<222> LOCATION: (3)..(3)
<223> OTHER INFORMATION: Can be either Thr, Gln, Val, or Ile
<220> FEATURE:
<221> NAME/KEY: MISC_FEATURE
<222> LOCATION: (5)..(5)
<223> OTHER INFORMATION: Can be any amino acid
<220> FEATURE:
<221> NAME/KEY: MISC_FEATURE
<222> LOCATION: (6)..(6)
<223> OTHER INFORMATION: Can be either Phe or Tyr
<220> FEATURE:
<221> NAME/KEY: MISC_FEATURE
<222> LOCATION: (7)..(7)
<223> OTHER INFORMATION: Can be either Pro or Phe
<220> FEATURE:
<221> NAME/KEY: MISC_FEATURE
<222> LOCATION: (8)..(8)
<223> OTHER INFORMATION: Can be any amino acid but Thr
<220> FEATURE:
<221> NAME/KEY: MISC_FEATURE
```

<222> LOCATION: (9)..(9)
<223> OTHER INFORMATION: Can be any combination of 2, 3 or 4 amino acids
<220> FEATURE:
<221> NAME/KEY: MISC_FEATURE
<222> LOCATION: (10)..(10)
<223> OTHER INFORMATION: Can be either Tyr, Phe, or His
<220> FEATURE:
<221> NAME/KEY: MISC_FEATURE
<222> LOCATION: (12)..(12)
<223> OTHER INFORMATION: Can be either Ala, Thr, or Leu

<400> SEQUENCE: 210

Xaa Asp Xaa Asp Xaa Xaa Xaa Xaa Xaa Xaa Ser Xaa Thr
1 5 10

<210> SEQ ID NO 211
<211> LENGTH: 9
<212> TYPE: PRT
<213> ORGANISM: Artificial Sequence
<220> FEATURE:
<223> OTHER INFORMATION: Sequence Motif
<220> FEATURE:
<221> NAME/KEY: MISC_FEATURE
<222> LOCATION: (3)..(3)
<223> OTHER INFORMATION: Can be either Asn or His
<220> FEATURE:
<221> NAME/KEY: MISC_FEATURE
<222> LOCATION: (6)..(6)
<223> OTHER INFORMATION: Can be either Ser or Ala

<400> SEQUENCE: 211

Gly Phe Xaa Phe Asp Xaa Lys Thr Arg
1 5

<210> SEQ ID NO 212
<211> LENGTH: 13
<212> TYPE: PRT
<213> ORGANISM: Artificial Sequence
<220> FEATURE:
<223> OTHER INFORMATION: Sequence Motif
<220> FEATURE:
<221> NAME/KEY: MISC_FEATURE
<222> LOCATION: (3)..(3)
<223> OTHER INFORMATION: Can be any amino acid
<220> FEATURE:
<221> NAME/KEY: MISC_FEATURE
<222> LOCATION: (6)..(6)
<223> OTHER INFORMATION: Can be either Arg or Lys
<220> FEATURE:
<221> NAME/KEY: MISC_FEATURE
<222> LOCATION: (7)..(7)
<223> OTHER INFORMATION: Can be any 2 amino acids
<220> FEATURE:
<221> NAME/KEY: MISC_FEATURE
<222> LOCATION: (9)..(9)
<223> OTHER INFORMATION: Can be either Trp, Tyr, or Phe
<220> FEATURE:
<221> NAME/KEY: MISC_FEATURE
<222> LOCATION: (10)..(10)
<223> OTHER INFORMATION: Can be either Asp, Asn, or Gly
<220> FEATURE:
<221> NAME/KEY: MISC_FEATURE
<222> LOCATION: (11)..(11)
<223> OTHER INFORMATION: Can be any 2 or 3 amino acids
<220> FEATURE:
<221> NAME/KEY: MISC_FEATURE
<222> LOCATION: (12)..(12)
<223> OTHER INFORMATION: Can be either Asp, Asn, Glu, Gly, or Thr
<220> FEATURE:
<221> NAME/KEY: MISC_FEATURE
<222> LOCATION: (13)..(13)
<223> OTHER INFORMATION: Can be either Ala or Thr

<400> SEQUENCE: 212

```
Phe Gly Xaa Gln Thr Xaa Xaa Glu Xaa Xaa Xaa Xaa Xaa
1               5                   10


<210> SEQ ID NO 213
<211> LENGTH: 13
<212> TYPE: PRT
<213> ORGANISM: Artificial Sequence
<220> FEATURE:
<223> OTHER INFORMATION: Sequence Motif
<220> FEATURE:
<221> NAME/KEY: MISC_FEATURE
<222> LOCATION: (3)..(3)
<223> OTHER INFORMATION: Can be any amino acid
<220> FEATURE:
<221> NAME/KEY: MISC_FEATURE
<222> LOCATION: (6)..(6)
<223> OTHER INFORMATION: Can be either Arg or Lys
<220> FEATURE:
<221> NAME/KEY: MISC_FEATURE
<222> LOCATION: (7)..(7)
<223> OTHER INFORMATION: Can be any 2 amino acids
<220> FEATURE:
<221> NAME/KEY: MISC_FEATURE
<222> LOCATION: (9)..(9)
<223> OTHER INFORMATION: Can be either Trp, Tyr, or Phe
<220> FEATURE:
<221> NAME/KEY: MISC_FEATURE
<222> LOCATION: (10)..(10)
<223> OTHER INFORMATION: Can be either Asp, Asn, or Gly
<220> FEATURE:
<221> NAME/KEY: MISC_FEATURE
<222> LOCATION: (11)..(11)
<223> OTHER INFORMATION: Can be any 3 amino acids
<220> FEATURE:
<221> NAME/KEY: MISC_FEATURE
<222> LOCATION: (12)..(12)
<223> OTHER INFORMATION: Can be any amino acid but Cys
<220> FEATURE:
<221> NAME/KEY: MISC_FEATURE
<222> LOCATION: (13)..(13)
<223> OTHER INFORMATION: Can be any amino acid but Pro

<400> SEQUENCE: 213

Phe Gly Xaa Gln Thr Xaa Xaa Glu Xaa Xaa Xaa Xaa Xaa
1               5                   10


<210> SEQ ID NO 214
<211> LENGTH: 15
<212> TYPE: PRT
<213> ORGANISM: Artificial Sequence
<220> FEATURE:
<223> OTHER INFORMATION: Sequence Motif
<220> FEATURE:
<221> NAME/KEY: MISC_FEATURE
<222> LOCATION: (1)..(1)
<223> OTHER INFORMATION: Can be either Phe or Trp
<220> FEATURE:
<221> NAME/KEY: MISC_FEATURE
<222> LOCATION: (4)..(4)
<223> OTHER INFORMATION: Can be any amino acid
<220> FEATURE:
<221> NAME/KEY: MISC_FEATURE
<222> LOCATION: (6)..(6)
<223> OTHER INFORMATION: Can be either Leu, Val, or Ile
<220> FEATURE:
<221> NAME/KEY: MISC_FEATURE
<222> LOCATION: (7)..(7)
<223> OTHER INFORMATION: Can be any amino acid
<220> FEATURE:
<221> NAME/KEY: MISC_FEATURE
<222> LOCATION: (8)..(8)
<223> OTHER INFORMATION: Can be either Asp or Glu
<220> FEATURE:
<221> NAME/KEY: MISC_FEATURE
<222> LOCATION: (11)..(11)
<223> OTHER INFORMATION: Can be any amino acid but Pro
```

<220> FEATURE:
<221> NAME/KEY: MISC_FEATURE
<222> LOCATION: (12)..(12)
<223> OTHER INFORMATION: Can be either Thr, Ser, or Asp
<220> FEATURE:
<221> NAME/KEY: MISC_FEATURE
<222> LOCATION: (13)..(13)
<223> OTHER INFORMATION: Can be either Ile or Val
<220> FEATURE:
<221> NAME/KEY: MISC_FEATURE
<222> LOCATION: (14)..(14)
<223> OTHER INFORMATION: Can be either Glu or Ala

<400> SEQUENCE: 214

Xaa His Asp Xaa Asp Xaa Xaa Xaa Glu Gly Xaa Xaa Xaa Xaa Glu
1               5                   10                  15

<210> SEQ ID NO 215
<211> LENGTH: 1008
<212> TYPE: DNA
<213> ORGANISM: Saccharomyces cerevisiae

<400> SEQUENCE: 215
atgtctgaac cagctcaaaa gaaacaaaag gttgctaaca actctctaga acaattgaaa 60
gcctccggca ctgtcgttgt tgccgacact ggtgatttcg gctctattgc caagtttcaa 120
cctcaagact ccacaactaa cccatcattg atcttggctg ctgccaagca accaacttac 180
gccaagttga tcgatgttgc cgtggaatac ggtaagaagc atggtaagac caccgaagaa 240
caagtcgaaa atgctgtgga cagattgtta gtcgaattcg gtaaggagat cttaaagatt 300
gttccaggca gagtctccac cgaagttgat gctagattgt cttttgacac tcaagctacc 360
attgaaaagg ctagacatat cattaaattg tttgaacaag aaggtgtctc caaggaaaga 420
gtccttatta aaattgcttc cacttgggaa ggtattcaag ctgccaaaga attggaagaa 480
aaggacggta tccactgtaa tttgactcta ttattctcct tcgttcaagc agttgcctgt 540
gccgaggccc aagttacttt gatttcccca tttgttggta gaattctaga ctggtacaaa 600
tccagcactg gtaaagatta caagggtgaa gccgacccag gtgttatttc cgtcaagaaa 660
atctacaact actacaagaa gtacggttac aagactattg ttatgggtgc ttctttcaga 720
agcactgacg aaatcaaaaa cttggctggt gttgactatc taacaatttc tccagcttta 780
ttggacaagt tgatgaacag tactgaacct ttcccaagag ttttggaccc tgtctccgct 840
aagaaggaag ccggcgacaa gatttcttac atcagcgacg aatctaaatt cagattcgac 900
ttgaatgaag acgctatggc cactgaaaaa ttgtccgaag gtatcagaaa attctctgcc 960
gatattgtta ctctattcga cttgattgaa aagaaagtta ccgcttaa 1008

<210> SEQ ID NO 216
<211> LENGTH: 1803
<212> TYPE: DNA
<213> ORGANISM: Saccharomyces cerevisiae

<400> SEQUENCE: 216
atgttgtgtt cagtaattca gagacagaca agagaggttt ccaacacaat gtctttagac 60
tcatactatc ttgggtttga tctttcgacc caacaactga aatgtctcgc cattaaccag 120
gacctaaaaa ttgtccattc agaaacagtg gaatttgaaa aggatcttcc gcattatcac 180
acaaagaagg gtgtctatat acacggcgac actatcgaat gtcccgtagc catgtggtta 240
gaggctctag atctggttct ctcgaaatat cgcgaggcta aatttccatt gaacaaagtt 300
atggccgtct cagggtcctg ccagcagcac gggtctgtct actggtcctc ccaagccgaa 360

```
tctctgttag agcaattgaa taagaaaccg gaaaaagatt tattgcacta cgtgagctct    420
gtagcatttg caaggcaaac cgccccccaat tggcaagacc acagtactgc aaagcaatgt    480
caagagtttg aagagtgcat aggtgggcct gaaaaaatgg ctcaattaac agggtccaga    540
gcccatttta gatttactgg tcctcaaatt ctgaaaattg cacaattaga accagaagct    600
tacgaaaaaa caaagaccat ttctttagtg tctaattttt tgacttctat cttagtgggc    660
catcttgttg aattagagga ggcagatgcc tgtggtatga acctttatga tatacgtgaa    720
agaaaattca gtgatgagct actacatcta attgatagtt cttctaagga taaaactatc    780
agacaaaaat taatgagagc acccatgaaa aatttgatag cgggtaccat ctgtaaatat    840
tttattgaga agtacggttt caatacaaac tgcaaggtct ctcccatgac tggggataat    900
ttagccacta tatgttcttt acccctgcgg aagaatgacg ttctcgtttc cctaggaaca    960
agtactacag ttcttctggt caccgataag tatcacccct ctccgaacta tcatcttttc   1020
attcatccaa ctctgccaaa ccattatatg ggtatgattt gttattgtaa tggttctttg   1080
gcaagggaga ggataagaga cgagttaaac aaagaacggg aaaataatta tgagaagact   1140
aacgattgga ctctttttaa tcaagctgtg ctagatgact cagaaagtag tgaaaatgaa   1200
ttaggtgtat attttcctct gggggagatc gttcctagcg taaaagccat aaacaaaagg   1260
gttatcttca atccaaaaac gggtatgatt gaaagagagg tggccaagtt caaagacaag   1320
aggcacgatg ccaaaaatat tgtagaatca caggctttaa gttgcagggt aagaatatct   1380
cccctgcttt cggattcaaa cgcaagctca caacagagac tgaacgaaga tacaatcgtg   1440
aagtttgatt acgatgaatc tccgctgcgg gactacctaa ataaaaggcc agaaaggact   1500
ttttttgtag gtggggcttc taaaaacgat gctattgtga agaagtttgc tcaagtcatt   1560
ggtgctacaa agggtaattt taggctagaa acaccaaact catgtgccct tggtggttgt   1620
tataaggcca tgtggtcatt gttatatgac tctaataaaa ttgcagttcc ttttgataaa   1680
tttctgaatg acaattttcc atggcatgta atggaaagca tatccgatgt ggataatgaa   1740
aattgggatc gctataattc caagattgtc cccttaagcg aactggaaaa gactctcatc   1800
taa                                                                 1803
```

<210> SEQ ID NO 217
<211> LENGTH: 2043
<212> TYPE: DNA
<213> ORGANISM: Saccharomyces cerevisiae

<400> SEQUENCE: 217

```
atgactcaat tcactgacat tgataagcta gccgtctcca ccataagaat tttggctgtg     60
gacaccgtat ccaaggccaa ctcaggtcac ccaggtgctc cattgggtat ggcaccagct    120
gcacacgttc tatggagtca aatgcgcatg aacccaacca acccagactg gatcaacaga    180
gatagatttg tcttgtctaa cggtcacgcg gtcgctttgt tgtattctat gctacatttg    240
actggttacg atctgtctat tgaagacttg aaacagttca gacagttggg ttccagaaca    300
ccaggtcatc ctgaatttga gttgccaggt gttgaagtta ctaccggtcc attaggtcaa    360
ggtatctcca acgctgttgg tatggccatg gctcaagcta acctggctgc cacttacaac    420
aagccgggct ttaccttgtc tgacaactac acctatgttt tcttgggtga cggttgtttg    480
caagaaggta tttcttcaga agcttcctcc ttggctggtc atttgaaatt gggtaacttg    540
attgccatct acgatgacaa caagatcact atcgatggtg ctaccagtat ctcattcgat    600
```

-continued gaagatgttg ctaagagata cgaagcctac ggttgggaag ttttgtacgt agaaaatggt 660
aacgaagatc tagccggtat tgccaaggct attgctcaag ctaagttatc caaggacaaa 720
ccaactttga tcaaaatgac cacaaccatt ggttacggtt ccttgcatgc cggctctcac 780
tctgtgcacg gtgccccatt gaaagcagat gatgttaaac aactaaagag caaattcggt 840
ttcaacccag acaagtcctt tgttgttcca caagaagttt acgaccacta ccaaaagaca 900
attttaaagc caggtgtcga agccaacaac aagtggaaca agttgttcag cgaataccaa 960
aagaaattcc cagaattagg tgctgaattg gctagaagat tgagcggcca actacccgca 1020
aattgggaat ctaagttgcc aacttacacc gccaaggact ctgccgtggc cactagaaaa 1080
ttatcagaaa ctgttcttga ggatgtttac aatcaattgc cagagttgat tggtggttct 1140
gccgatttaa caccttctaa cttgaccaga tggaaggaag cccttgactt ccaacctcct 1200
tcttccggtt caggtaacta ctctggtaga tacattaggt acggtattag agaacacgct 1260
atgggtgcca taatgaacgg tatttcagct ttcggtgcca actacaaacc atacggtggt 1320
actttcttga acttcgtttc ttatgctgct ggtgccgtta gattgtccgc tttgtctggc 1380
cacccagtta tttgggttgc tacacatgac tctatcggtg tcggtgaaga tggtccaaca 1440
catcaaccta ttgaaacttt agcacacttc agatccctac caaacattca agtttggaga 1500
ccagctgatg gtaacgaagt ttctgccgcc tacaagaact ctttagaatc caagcatact 1560
ccaagtatca ttgctttgtc cagacaaaac ttgccacaat tggaaggtag ctctattgaa 1620
agcgcttcta agggtggtta cgtactacaa gatgttgcta acccagatat tattttagtg 1680
gctactggtt ccgaagtgtc tttgagtgtt gaagctgcta agactttggc cgcaaagaac 1740
atcaaggctc gtgttgtttc tctaccagat ttcttcactt ttgacaaaca acccctagaa 1800
tacagactat cagtcttacc agacaacgtt ccaatcatgt ctgttgaagt tttggctacc 1860
acatgttggg gcaaatacgc tcatcaatcc ttcggtattg acagatttgg tgcctccggt 1920
aaggcaccag aagtcttcaa gttcttcggt ttcaccccag aaggtgttgc tgaaagagct 1980
caaaagacca ttgcattcta taagggtgac aagctaattt ctcctttgaa aaaagctttc 2040
taa 2043

<210> SEQ ID NO 218
<211> LENGTH: 717
<212> TYPE: DNA
<213> ORGANISM: Saccharomyces cerevisiae

<400> SEQUENCE: 218
atggtcaaac caattatagc tcccagtatc cttgcttctg acttcgccaa cttgggttgc 60
gaatgtcata aggtcatcaa cgccggcgca gattggttac atatcgatgt catggacggc 120
cattttgttc caaacattac tctgggccaa ccaattgtta cctccctacg tcgttctgtg 180
ccacgccctg gcgatgctag caacacagaa aagaagccca ctgcgttctt cgattgtcac 240
atgatggttg aaaatcctga aaaatgggtc gacgattttg ctaaatgtgg tgctgaccaa 300
tttacgttcc actacgaggc cacacaagac cctttgcatt tagttaagtt gattaagtct 360
aagggcatca aagctgcatg cgccatcaaa cctggtactt ctgttgacgt tttatttgaa 420
ctagctcctc atttggatat ggctcttgtt atgactgtgg aacctgggtt tggaggccaa 480
aaattcatgg aagacatgat gccaaaagtg gaaactttga gagccaagtt cccccatttg 540
aatatccaag tcgatggtgg tttgggcaag gagaccatcc cgaaagccgc caaagccggt 600
gccaacgtta ttgtcgctgg taccagtgtt ttcactgcag ctgacccgca cgatgttatc 660
tccttcatga aagaagaagt ctcgaaggaa ttgcgttcta gagatttgct agattag 717

<210> SEQ ID NO 219
<211> LENGTH: 777
<212> TYPE: DNA
<213> ORGANISM: Saccharomyces cerevisiae

<400> SEQUENCE: 219
atggctgccg gtgtcccaaa aattgatgcg ttagaatctt tgggcaatcc tttggaggat 60
gccaagagag ctgcagcata cagagcagtt gatgaaaatt taaaatttga tgatcacaaa 120
attattggaa ttggtagtgg tagcacagtg gtttatgttg ccgaaagaat tggacaatat 180
ttgcatgacc ctaaatttta tgaagtagcg tctaaattca tttgcattcc aacaggattc 240
caatcaagaa acttgatttt ggataacaag ttgcaattag gctccattga acagtatcct 300
cgcattgata tagcgtttga cggtgctgat gaagtggatg agaatttaca attaattaaa 360
ggtggtggtg cttgtctatt tcaagaaaaa ttggttagta ctagtgctaa aaccttcatt 420
gtcgttgctg attcaagaaa aaagtcacca aaacatttag gtaagaactg gaggcaaggt 480
gttcccattg aaattgtacc ttcctcatac gtgagggtca agaatgatct attagaacaa 540
ttgcatgctg aaaaagttga catcagacaa ggaggttctg ctaaagcagg tcctgttgta 600
actgacaata ataacttcat tatcgatgcg gatttcggtg aaatttccga tccaagaaaa 660
ttgcatagag aaatcaaact gttagtgggc gtggtggaaa caggtttatt catcgacaac 720
gcttcaaaag cctacttcgg taattctgac ggtagtgttg aagttaccga aaagtga 777

<210> SEQ ID NO 220
<211> LENGTH: 1725
<212> TYPE: DNA
<213> ORGANISM: Saccharomyces cerevisiae

<400> SEQUENCE: 220
atggcagttg aggagaacaa tatgcctgtt gtttcacagc aaccccaagc tggtgaagac 60
gtgatctctt cactcagtaa agattcccat ttaagcgcac aatctcaaaa gtattctaat 120
gatgaattga aagccggtga gtcagggtct gaaggctccc aaagtgttcc tatagagata 180
cccaagaagc ccatgtctga atatgttacc gtttccttgc tttgtttgtg tgttgccttc 240
ggcggcttca tgtttggctg ggataccggt actatttctg ggtttgttgt ccaaacagac 300
tttttgagaa ggtttggtat gaaacataag gatggtaccc actatttgtc aaacgtcaga 360
acaggtttaa tcgtcgccat tttcaatatt ggctgtgcct ttggtggtat tatactttcc 420
aaaggtggag atatgtatgg ccgtaaaaag ggtctttcga ttgtcgtctc ggtttatata 480
gttggtatta tcattcaaat tgcctctatc aacaagtggt accaatattt cattggtaga 540
atcatatctg gtttgggtgt cggcggcatc gccgtcttat gtcctatgtt gatctctgaa 600
attgctccaa agcacttgag aggcacacta gtttcttgtt atcagctgat gattactgca 660
ggtatctttt tgggctactg tactaattac ggtacaaaga gctattcgaa ctcagttcaa 720
tggagagttc cattagggct atgtttcgct tggtcattat ttatgattgg cgctttgacg 780
ttagttcctg aatccccacg ttatttatgt gaggtgaata aggtagaaga cgccaagcgt 840
tccattgcta agtctaacaa ggtgtcacca gaggatcctg ccgtccaggc agagttagat 900
ctgatcatgg ccggtataga agctgaaaaa ctggctggca atgcgtcctg gggggaatta 960
ttttccacca agaccaaagt atttcaacgt ttgttgatgg gtgtgtttgt tcaaatgttc 1020
caacaattaa ccggtaacaa ttattttttc tactacggta ccgttatttt caagtcagtt 1080
ggcctggatg attcctttga aacatccatt gtcattggtg tagtcaactt tgcctccact 1140
ttctttagtt tgtggactgt cgaaaacttg ggacatcgta aatgtttact tttgggcgct 1200
gccactatga tggcttgtat ggtcatctac gcctctgttg gtgttactag attatatcct 1260
cacggtaaaa gccagccatc ttctaaaggt gccggtaact gtatgattgt ctttacctgt 1320
ttttatattt tctgttatgc cacaacctgg gcgccagttg cctgggtcat cacagcagaa 1380
tcattcccac tgagagtcaa gtcgaaatgt atggcgttgg cctctgcttc caattgggta 1440
tgggggttct tgattgcatt tttcacccca ttcatcacat ctgccattaa cttctactac 1500
ggttatgtct tcatgggctg tttggttgcc atgttttttt atgtcttttt ctttgttcca 1560
gaaactaaag gcctatcgtt agaagaaatt caagaattat gggaagaagg tgttttacct 1620
tggaaatctg aaggctggat tccttcatcc agaagaggta ataattacga tttagaggat 1680
ttacaacatg acgacaaacc gtggtacaag gccatgctag aataa 1725

<210> SEQ ID NO 221
<211> LENGTH: 37
<212> TYPE: DNA
<213> ORGANISM: Unknown
<220> FEATURE:
<223> OTHER INFORMATION: Obtained from environmental sample

<400> SEQUENCE: 221
caccattaat taacccgggg cacctgtcac tttggaa 37

<210> SEQ ID NO 222
<211> LENGTH: 51
<212> TYPE: DNA
<213> ORGANISM: Unknown
<220> FEATURE:
<223> OTHER INFORMATION: Obtained from environmental sample

<400> SEQUENCE: 222
cgcgtaagct ttctagaggc gcgccaagct tttacactct tgaccagcgc a 51

<210> SEQ ID NO 223
<211> LENGTH: 57
<212> TYPE: DNA
<213> ORGANISM: Unknown
<220> FEATURE:
<223> OTHER INFORMATION: Obtained from environmental sample

<400> SEQUENCE: 223
ccgctggtgg gtaccgatat ccctgcaggg agctcacgcg taagctttct agaggcg 57

<210> SEQ ID NO 224
<211> LENGTH: 56
<212> TYPE: DNA
<213> ORGANISM: Unknown
<220> FEATURE:
<223> OTHER INFORMATION: Obtained from environmental sample

<400> SEQUENCE: 224
ctgcagggat atcggtaccc accagcggcc gcaggccttg ggtgcttgct ggcgaa 56

<210> SEQ ID NO 225
<211> LENGTH: 48
<212> TYPE: DNA
<213> ORGANISM: Unknown
<220> FEATURE:
<223> OTHER INFORMATION: Obtained from environmental sample

<400> SEQUENCE: 225
acctctgcat gcgaattctt aagacaaata aaatttatag agacttgt 48

<210> SEQ ID NO 226
<211> LENGTH: 36
<212> TYPE: DNA
<213> ORGANISM: Unknown
<220> FEATURE:
<223> OTHER INFORMATION: Obtained from environmental sample

<400> SEQUENCE: 226
gtcttaagaa ttcgcatgca gaggtagttt caaggt 36

<210> SEQ ID NO 227
<211> LENGTH: 39
<212> TYPE: DNA
<213> ORGANISM: Unknown
<220> FEATURE:
<223> OTHER INFORMATION: Obtained from environmental sample

<400> SEQUENCE: 227
caccattaat taatacgtat ttctcgccga gaaaaactt 39

<210> SEQ ID NO 228
<211> LENGTH: 25
<212> TYPE: DNA
<213> ORGANISM: Unknown
<220> FEATURE:
<223> OTHER INFORMATION: Obtained from environmental sample

<400> SEQUENCE: 228
ccccatcgac aactacgagc tcact 25

<210> SEQ ID NO 229
<211> LENGTH: 25
<212> TYPE: DNA
<213> ORGANISM: Unknown
<220> FEATURE:
<223> OTHER INFORMATION: Obtained from environmental sample

<400> SEQUENCE: 229
caacttgccg tcctcgaagt ccttg 25

<210> SEQ ID NO 230
<211> LENGTH: 25
<212> TYPE: DNA
<213> ORGANISM: Unknown
<220> FEATURE:
<223> OTHER INFORMATION: Obtained from environmental sample

<400> SEQUENCE: 230
cgagcctgag aaggtcgtga tggga 25

<210> SEQ ID NO 231
<211> LENGTH: 25
<212> TYPE: DNA
<213> ORGANISM: Unknown
<220> FEATURE:
<223> OTHER INFORMATION: Obtained from environmental sample

<400> SEQUENCE: 231
tacgtcgaag tcggggttgg tagaa 25

<210> SEQ ID NO 232

<211> LENGTH: 21
<212> TYPE: DNA
<213> ORGANISM: Unknown
<220> FEATURE:
<223> OTHER INFORMATION: Obtained from environmental sample

<400> SEQUENCE: 232
agtcacatca agatcgttta t 21

<210> SEQ ID NO 233
<211> LENGTH: 21
<212> TYPE: DNA
<213> ORGANISM: Unknown
<220> FEATURE:
<223> OTHER INFORMATION: Obtained from environmental sample

<400> SEQUENCE: 233
gcacggaata tgggactact t 21

<210> SEQ ID NO 234
<211> LENGTH: 21
<212> TYPE: DNA
<213> ORGANISM: Unknown
<220> FEATURE:
<223> OTHER INFORMATION: Obtained from environmental sample

<400> SEQUENCE: 234
actccacttc aagtaagagt t 21

<210> SEQ ID NO 235
<211> LENGTH: 27
<212> TYPE: DNA
<213> ORGANISM: Unknown
<220> FEATURE:
<223> OTHER INFORMATION: Obtained from environmental sample

<400> SEQUENCE: 235
gaacaaaaac ctgcaggaaa cgaagat 27

<210> SEQ ID NO 236
<211> LENGTH: 31
<212> TYPE: DNA
<213> ORGANISM: Unknown
<220> FEATURE:
<223> OTHER INFORMATION: Obtained from environmental sample

<400> SEQUENCE: 236
gctctaattt gtgagtttag tatacatgca t 31

<210> SEQ ID NO 237
<211> LENGTH: 1338
<212> TYPE: DNA
<213> ORGANISM: Unknown
<220> FEATURE:
<223> OTHER INFORMATION: Obtained from environmental sample

<400> SEQUENCE: 237
ttaattaagt taattacctt ttttgcgagg catatttatg gtgaagaata agttttgacc 60
atcaaagaag gttaatgtgg ctgtggtttc agggtccata aagcttttca attcatcatt 120
ttttttttat tctttttttt gattccggtt tccttgaaat ttttttgatt cggtaatctc 180
cgaacagaag gaagaacgaa ggaaggagca cagacttaga ttggtatata tacgcatatg 240
tagtgttgaa gaaacatgaa attgcccagt attcttaacc caactgcaca gaacaaaaac 300
ctgcaggaaa cgaagataaa tcatgtcgaa agctacatat aaggaacgtg ctgctactca 360
tcctagtcct gttgctgcca agctatttaa tatcatgcac gaaaagcaaa caaacttgtg 420
tgcttcattg gatgttcgta ccaccaagga attactggag ttagttgaag cattaggtcc 480
caaaatttgt ttactaaaaa cacatgtgga tatcttgact gatttttcca tggagggcac 540
agttaagccg ctaaaggcat tatccgccaa gtacaatttt ttactcttcg aagacagaaa 600
atttgctgac attggtaata cagtcaaatt gcagtactct gcgggtgtat acagaatagc 660
agaatgggca gacattacga atgcacacgg tgtggtgggc ccaggtattg ttagcggttt 720
gaagcaggcg gcagaagaag taacaaagga acctagaggc cttttgatgt tagcagaatt 780
gtcatgcaag ggctccctag ctactggaga atatactaag ggtactgttg acattgcgaa 840
gagcgacaaa gattttgtta tcggctttat tgctcaaaga gacatgggtg gaagagatga 900
aggttacgat tggttgatta tgacacccgg tgtgggttta gatgacaagg gagacgcatt 960
gggtcaacag tatagaaccg tggatgatgt ggtctctaca ggatctgaca ttattattgt 1020
tggaagagga ctatttgcaa agggaaggga tgctaaggta gagggtgaac gttacagaaa 1080
agcaggctgg gaagcatatt tgagaagatg cggccagcaa aactaaaaaa ctgtattata 1140
agtaaatgca tgtatactaa actcacaaat tagagcttca atttaattat atcagttatt 1200
acccgggaat ctcggtcgta atgattttta taatgacgaa aaaaaaaaaa ttggaaagaa 1260
aaagcttcat ggcctttata aaaaggaacc atccaatacc tcgccagaac caagtaacag 1320
tattttacgg ttaattaa 1338

<210> SEQ ID NO 238
<211> LENGTH: 1314
<212> TYPE: DNA
<213> ORGANISM: Unknown
<220> FEATURE:
<223> OTHER INFORMATION: Obtained from environmental sample

<400> SEQUENCE: 238
atggctaagg aatacttccc agaaattggt aagattaagt tcgaaggtaa ggactctaag 60
aacccaatgg ctttccacta ctacgaccca gaaaaggtta ttatgggtaa gccaatgaag 120
gactggttga gattcgctat ggcttggtgg cacaccttgt gtgctgaagg tggtgaccaa 180
ttcggtggtg gtactaagaa gttcccatgg aacaacggtg ctgacgctgt tgaaattgct 240
aagcaaaagg ctgacgctgg tttcgaaatt atgcaaaagt tgggtattcc atacttctgt 300
ttccacgacg ttgacttggt ttctgaaggt gcttctgttg aagaatacga agctaacttg 360
aaggctatta ccgactactt ggctgttaag atgaaggaaa ccggaattaa gttgttgtgg 420
tctaccgcta acgttttcgg taacggtaga tacatgaacg gtgcttctac caacccagac 480
ttcgacgttg ttgctagagc tattgttcaa attaagaacg ctattgacgc tggtattaag 540
ttgggtgctg aaaactacgt tttctggggt ggtagagaag gttacatgtc tttgttgaac 600
accgaccaaa agagagaaaa ggaacacatg gctaccatgt tgaccatggc tagagactac 660
gctagagcta agggtttcaa gggtactttc ttgattgaac caaagccaat ggaaccatct 720
aagcaccaat acgacgttga caccgaaacc gttattggtt tcttgaaggc tcacaacttg 780
gacaaggact tcaaggttaa cattgaagtt aaccacgcta ccttggctgg tcacaccttc 840
gaacacgaat tggctgttgc tgttgacaac aacatgttgg gttctattga cgctaacaga 900
ggtgactacc aaaacggttg ggacaccgac caattcccaa ttgaccaata cgaattggtt 960
caagcttgga tggaaattat tagaggtggt ggtttgggta caggtggtac taacttcgac 1020
gctaagacca gaagaaactc taccgacttg gaagacattt tcattgctca cattgctggt 1080
atggacgcta tggctagagc tttggaatct gctgctaagt tgttggaaga atctccatac 1140
aaggctatga aggctgctag atacgcttct ttcgacaacg gtattggtaa ggacttcgaa 1200
gacggtaagt tgaccttgga acaagcttac gaatacggta agaaggttgg tgaaccaaag 1260
caaacctctg gtaagcaaga attgtacgaa gctattgttg ctatgtacgc ttaa 1314

<210> SEQ ID NO 239
<211> LENGTH: 1314
<212> TYPE: DNA
<213> ORGANISM: Unknown
<220> FEATURE:
<223> OTHER INFORMATION: Obtained from environmental sample

<400> SEQUENCE: 239
atggctaagg aatacttccc agaaattggt aagattaagt tcgaaggtaa ggactctaag 60
aacccaatgg ctttccacta ctacgacgct gaaaaggtta ttatgggtaa gccaatgaag 120
gaatggttga gattcgctat ggcttggtgg cacaccttgt gtgctgaagg tggtgaccaa 180
ttcggtggtg gtactaagaa gttcccatgg aacgaaggta ctgacgctgt taccattgct 240
aagcaaaagg ctgacgctgg tttcgaaatt atgcaaaagt tgggtttccc atacttctgt 300
ttccacgaca ttgacttggt ttctgaaggt aactctattg aagaatacga agctaacttg 360
caagctatta ccgactactt gaaggttaag atggaagaaa ccggaattaa gttgttgtgg 420
tctaccgcta acgttttcgg taacggtaga tacatgaacg gtgcttctac caacccagac 480
ttcgacgttg ttgctagagc tattgttcaa attaagaacg ctattgacgc tggtattaag 540
ttgggtgctg aaaactacgt ttctggggt ggtagagaag gttacatgtc tttgttgaac 600
accgaccaaa agagagaaaa ggaacacatg gctaccatgt tgaccatggc tagagactac 660
gctagatcta agggtttcaa gggtactttc ttgattgaac caaagccaat ggaaccatct 720
aagcaccaat acgacgttga caccgaaacc gttattggtt tcttgaaggc tcacaacttg 780
gacaaggact tcaaggttaa cattgaagtt aaccacgcta ccttggctgg tcacaccttc 840
gaacacgaat tggctgttgc tgttgacaac ggtatgttgg gttctattga cgctaacaga 900
ggtgactacc aaaacggttg ggacaccgac caattcccaa ttgaccaata cgaattggtt 960
caagcttgga tggaaattat tagaggtggt ggtttgggta ctggtggtac aaacttcgac 1020
gctaagacca gaagaaactc taccgacttg gaagacattt tcattgctca catttctggt 1080
atggacgcta tggctagagc tttggaatct gctgctaagt tgttggaaga atctccatac 1140
tgtgctatga agaaggctag atacgcttct ttcgactctg gtattggtaa ggacttcgaa 1200
gacggtaagt tgaccttgga acaagcttac gaatacggta agaaggttgg tgaaccaaag 1260
caaacctctg gtaagcaaga attgtacgaa gctattgttg ctatgtacgc ttaa 1314

<210> SEQ ID NO 240
<211> LENGTH: 21
<212> TYPE: DNA
<213> ORGANISM: Unknown
<220> FEATURE:
<223> OTHER INFORMATION: Obtained from environmental sample

<400> SEQUENCE: 240
tacttggctg ttaagatgaa g 21

<210> SEQ ID NO 241
<211> LENGTH: 22

<212> TYPE: DNA
<213> ORGANISM: Unknown
<220> FEATURE:
<223> OTHER INFORMATION: Obtained from environmental sample

<400> SEQUENCE: 241
atctagcagc cttcatagcc tt 22

<210> SEQ ID NO 242
<211> LENGTH: 22
<212> TYPE: DNA
<213> ORGANISM: Unknown
<220> FEATURE:
<223> OTHER INFORMATION: Obtained from environmental sample

<400> SEQUENCE: 242
cgaaggtact gacgctgtta cc 22

<210> SEQ ID NO 243
<211> LENGTH: 22
<212> TYPE: DNA
<213> ORGANISM: Unknown
<220> FEATURE:
<223> OTHER INFORMATION: Obtained from environmental sample

<400> SEQUENCE: 243
cgaaagaagc gtatctagcc tt 22

<210> SEQ ID NO 244
<211> LENGTH: 1320
<212> TYPE: DNA
<213> ORGANISM: Unknown
<220> FEATURE:
<223> OTHER INFORMATION: Obtained from environmental sample

<400> SEQUENCE: 244
atggctaagg aatatttccc attcaccggt aagattccat tcgaaggtaa ggactctaag 60
aacgttatgg ctttccacta ttatgaacca gaaaaggttg ttatgggtaa gaagatgaag 120
gactggttga agttcgctat ggcttggtgg cacaccttgg gtggtgcttc tgctgaccaa 180
ttcggtggtc aaaccagatc ttatgaatgg gacaaggctg gtgacgctgt tcaaagagct 240
aaggacaaga tggacgctgg tttcgaaatt atggacaagt tgggtattga atatttctgt 300
ttccacgacg ttgacttggt tgaagaaggt gacaccattg aagaatatga agctagaatg 360
aaggctatta ccgactatgc tcaagaaaag atgaagcaat tcccaaacat taagttgttg 420
tggggtactg ctaacgtttt cggtaacaag agatatgcta acggtgcttc taccaaccca 480
gacttcgacg ttgttgctag agctattgtt caaattaaga acgctattga tgctaccatt 540
aagttgggtg gtactaacta tgttttctgg ggtggtagag aaggttatat gtctttgttg 600
aacaccgacc aaaagagaga aaaggaacac atggctacca tgttgaccat ggctagagac 660
tatgctagag ctaagggttt caagggtact ttcttgattg aaccaaagcc aatggaacca 720
tctaagcacc aatatgacgt tgacaccgaa accgttattg gtttcttgaa ggctcacaac 780
ttggacaagg acttcaaggt taacattgaa gttaaccacg ctaccttggc tggtcacacc 840
ttcgaacacg aattggcttg tgctgttgac gctggtatgt tgggttctat tgacgctaac 900
agaggtgacg ctcaaaacgg ttgggacacc gaccaattcc caattgacaa ctatgaattg 960
acccaagcta tgttggaaat tattagaaac ggtggtttgg gtaacggtgg aaccaacttc 1020
gacgctaaga ttagaagaaa ctctaccgac ttggaagact tgttcattgc tcacatttct 1080

-continued ggtatggacg ctatggctag agctttgatg aacgctgctg acattttgga aaactctgaa 1140
ttgccagcta tgaagaaggc tagatatgct tctttcgacc aaggtgttgg taaggacttc 1200
gaagacggta agttgacctt ggaacaagtt tatgaatatg gtaagaaggt tggtgaacca 1260
aagcaaacct ctggtaagca agaaaagtat gaaaccattg ttgctttgta tgctaagtaa 1320

<210> SEQ ID NO 245
<211> LENGTH: 1320
<212> TYPE: DNA
<213> ORGANISM: Unknown
<220> FEATURE:
<223> OTHER INFORMATION: Obtained from environmental sample

<400> SEQUENCE: 245
atggctaagg aatatttccc attcattggt aaggttccat tcgaaggtac tgaatctaag 60
aacgttatgg ctttccacta ttatgaacca gaaaaggttg ttatgggtaa gaagatgaag 120
gactggttga agttcgctat ggcttggtgg cacaccttgg gtggtgcttc tgctgaccaa 180
ttcggtggtc aaaccagatc ttatgaatgg gacaaggctg ctgacgctgt tcaaagagct 240
aaggacaaga tggacgctgg tttcgaaatt atggacaagt tgggtattga atatttctgt 300
ttccacgacg ttgacttggt tgaagaaggt gaaaccgttg ctgaatatga agctagaatg 360
aaggttatta ccgactatgc tttggaaaag atgcaacaat tcccaaacat taagttgttg 420
tggggtactg ctaacgtttt cggtcacaag agatatgcta acggtgcttc taccaaccca 480
gacttcgacg ttgttgctag agctattgtt caaattaaga acgctattga tgctaccatt 540
aagttgggtg gtactaacta tgttttctgg ggtggtagag aaggttatat gtctttgttg 600
aacaccgacc aaaagagaga aaaggaacac atggctacca tgttgaccat ggctagagac 660
tatgctagag ctaagggttt caagggtact ttcttgattg aaccaaagcc aatggaacca 720
tctaagcacc aatatgacgt tgacaccgaa accgttattg gtttcttgag ggctcacggt 780
ttggacaagg acttcaaggt taacattgaa gttaaccacg ctaccttggc tggtcacacc 840
ttcgaacacg aattggcttg tgctgttgac gctggtatgt tgggttctat tgacgctaac 900
agaggtgacg ctcaaaacgg ttgggacacc gaccaattcc caattgacaa ctatgaattg 960
acccaagcta tgatggaaat tattagaaac ggtggtttgg gtaacggtgg aaccaacttc 1020
gacgctaaga ttagaagaaa ctctaccgac ttggaagact tgttcattgc tcacatttct 1080
ggtatggacg ctatggctag agctttgatg aacgctgctg ctattttgga agaatctgaa 1140
ttgccagcta tgaagaaggc tagatatgct tctttcgacg aaggtattgg taaggacttc 1200
gaagacggta agttgtcttt ggaacaagtt tatgaatatg gtaagaaggt tgaagaacca 1260
aagcaaacct ctggtaagca agaaaagtat gaaaccattg ttgctttgta tgctaagtaa 1320

<210> SEQ ID NO 246
<211> LENGTH: 1323
<212> TYPE: DNA
<213> ORGANISM: Unknown
<220> FEATURE:
<223> OTHER INFORMATION: Obtained from environmental sample

<400> SEQUENCE: 246
atgaaggaaa ttttcccaaa cattccagaa attaagttcg aaggtaagga ctctaagaac 60
ccattcgctt tccactatta taacccagac caaattattt tgggtaagcc aatgaaggaa 120
cacttgccat tcgctatggc ttggtggcac aacttgggtg ctaccggtgt tgacatgttc 180
ggtgctggtc cagctgacaa gtctttcggt gctaaggttg gtactatgga acacgctaag 240

```
gctaaggttg acgctggttt cgaattcatg aagaagttgg gtattagata tttctgtttc    300

cacgacgttg acttggttcc agaatgtgct gacattaagg acaccaacaa ggaattggac    360

gaaatttctg actatatttt ggaaaagatg aagggtactg acattaagtg tttgtggggt    420

actgctaaca tgttctctaa cccaagattc tgtaacggtg ctggttctac caactctgct    480

gacgttttcg ctttcgctgc tgctcaagtt aagaaggctt tggacattac cgttaagttg    540

ggtggtagag gttatgtttt ctggggtggt agagaaggtt atgaaacctt gttgaacacc    600

gacgttaagt tcgaacaaga aaacattgct agattgatga agatggctgt tgaatatggt    660

agatctattg gtttcaaggg tgacttctat attgaaccaa agccaaagga accaatgaag    720

caccaatatg acttcgacgc tgctaccgct attggtttct tgagggctca cggtttggac    780

aaggacttca agttgaacat tgaagctaac cacgctacct tggctggtca caccttccaa    840

cacgacttga gaatttctgc tattaacggt atgttgggtt ctattgacgc taaccaaggt    900

gacatgttgt tgggttggga caccgacgaa ttcccattcg acgtttattc tgctacccaa    960

tgtatgtatg aagttttgaa gaacggtggt ttgaccggtg gtttcaactt cgactctaag   1020

accagaagac catcttatac catggaagac atgttcttgg cttatatttt gggtatggac   1080

accttcgctt tgggtttgat taaggctgct caaattattg aagacggtag aattgaccaa   1140

ttcattgaaa agaagtattc ttctttcaga gaaaccgaaa ttggtcaaaa gattttgaac   1200

aacaagacct ctttgaagga attgtctgac tatgcttgta agatgggtgc tccagaattg   1260

ccaggttctg gtagacaaga aatgttggaa gctattgtta acgacgtttt gttcggtaag   1320

taa                                                                 1323
```

<210> SEQ ID NO 247
<211> LENGTH: 1320
<212> TYPE: DNA
<213> ORGANISM: Unknown
<220> FEATURE:
<223> OTHER INFORMATION: Obtained from environmental sample

<400> SEQUENCE: 247

```
atggctaagg aatactttcc attcaccgga aagataccat ttgaaggtaa agattctaaa     60

aacgtaatgg cttttcatta ttacgaacca gaaaaagttg ttatgggcaa aaagatgaaa    120

gattggttga aatttgcgat ggcttggtgg catacactcg gggagcttc cgctgatcaa    180

tttggcggac aaaccagatc atacgaatgg gataaagcag gcgatgccgt gcagagagca    240

aaggataaaa tggatgctgg tttcgaaatt atggataagc taggtatcga atacttctgc    300

ttccatgacg tcgatttggt tgaagagggc gatactatcg aggaatacga ggcgagaatg    360

aaggctataa cagactacgc ccaggagaaa atgaaacaat ttcctaacat caaattactc    420

tggggtactg ccaatgtgtt tggtaacaaa agatacgcaa acggggcttc aactaatcct    480

gacttcgatg ttgttgcaag agccattgtt caaatcaaaa acgcgataga cgctactatt    540

aaactaggtg gcacgaatta cgtcttttgg ggtggaaggg aaggttacat gtctctgctt    600

aatacagatc agaagagaga gaaggaacac atggcaacaa tgctcactat ggcccgtgac    660

tacgcaagag caaaaggttt taagggcact ttccttatcg aaccaaagcc tatggaacca    720

tcaaaacacc aatatgatgt tgacacagaa actgtgatcg gctttttgaa agctcataac    780

ttggacaagg atttcaaagt aaacattgaa gttaatcatg ctacactagc aggacacaca    840

tttgaacacg aactggcctg tgcggtagat gcagggatgc tgggttctat cgacgctaat    900
```

```
agaggggatg ctcaaaatgg ttgggatacc gatcaatttc caatcgacaa ttacgaatta    960

acacaagcta tgttggagat tattagaaat ggaggtttgg gtaatggggg tacaaacttc   1020

gatgctaaga ttcgtcgaaa ttccacagac ttagaagatt tgttcattgc gcatatatct   1080

ggtatggatg ctatggccag agcattaatg aatgccgctg acatcttaga aaacagtgaa   1140

cttccagcaa tgaaaaaggc cagatatgcc tctttcgatc aaggtgtagg aaaagatttt   1200

gaggacggca agttgacttt agaacaagtc tatgaatacg gtaaaaaggt cggcgaacct   1260

aagcaaacca gcggaaagca agagaaatac gagactatcg tggctcttta tgcaaaataa   1320
```

<210> SEQ ID NO 248
<211> LENGTH: 1320
<212> TYPE: DNA
<213> ORGANISM: Unknown
<220> FEATURE:
<223> OTHER INFORMATION: Obtained from environmental sample

<400> SEQUENCE: 248

```
atggccaagg agtacttccc ttttatcggc aaggtcccat ttgaagggac agaatccaaa     60

aacgtcatgg cttttcacta ctatgaacct gagaaggtag ttatgggtaa aaagatgaaa    120

gattggttga agtttgcaat ggcatggtgg catactttgg gtggggcctc tgctgatcaa    180

tttggaggac aaactagatc atacgaatgg gataaagcag ctgatgccgt tcaaagagcc    240

aaagataaaa tggatgccgg gttcgaaatc atggacaaat tgggtatcga atatttctgc    300

ttccatgatg tagaccttgt tgaggagggt gaaaccgtcg ctgaatatga ggcgagaatg    360

aaggttatta cggattacgc actagaaaag atgcagcagt ttccaaacat aaaactattg    420

tggggtactg ctaatgtttt cggacataaa cgttacgcta acggagcttc cactaatcca    480

gactttgatg ttgtcgcgag agctatcgtt caaatcaaaa atgcaatcga tgctacaatt    540

aagttaggag ggacaaatta cgtgttctgg ggtggtagag aaggttacat gagcctgctt    600

aatacagatc aaaagagaga aaaggagcac atggcaacaa tgctaacaat ggctagagat    660

tatgcccgag ctaagggctt caaaggcact tttctgatag aacctaaacc aatggaacca    720

tctaaacacc aatacgatgt agacaccgaa actgtaatag gcttccttcg tgcacatggt    780

ttggataaag attttaaggt gaacattgaa gtgaatcatg ctactttagc cggtcacact    840

tttgaacatg aattagcatg tgctgttgat gcgggaatgt tgggttctat cgatgccaac    900

agaggcgacg cccaaaatgg ttgggacaca gaccagtttc ctattgacaa ttacgaactc    960

acccaagcta tgatggaaat tatcaggaat gggggactgg gaaatggtgg tacgaacttt   1020

gatgcgaaga taaggagaaa ctctactgac ttagaagatt tgtttatagc acatatttca   1080

ggtatggacg ctatggcaag agctttaatg aatgccgcag caatcttgga ggaaagtgaa   1140

ctcccagcta tgaaaaaggc aagatacgca agttttgatg agggtattgg caaagacttc   1200

gaagatggta aactatcttt agaacaagtg tacgagtatg gcaaaaaggt agaggaacca   1260

aaacaaacat caggcaaaca agagaaatat gaaacaattg tcgctcttta cgcgaagtaa   1320
```

<210> SEQ ID NO 249
<211> LENGTH: 1323
<212> TYPE: DNA
<213> ORGANISM: Unknown
<220> FEATURE:
<223> OTHER INFORMATION: Obtained from environmental sample

<400> SEQUENCE: 249

```
atgaaggaaa tcttccctaa catcccagag atcaaattcg aaggcaaaga ctctaaaaat     60
```

-continued

```
ccatttgcct tccactatta caacccagac cagatcattt taggtaaacc aatgaaggag        120

cacttgccat ttgctatggc ttggtggcat aatctaggcg ccactggtgt tgatatgttt        180

ggtgcaggcc ctgcggacaa atctttcgga gctaaagtag gaactatgga acatgcaaaa        240

gcgaaagttg atgctgggtt tgagttcatg aagaaattag gaatcagata tttctgcttt        300

catgatgttg acttggttcc tgagtgtgct gacattaagg atacaaacaa ggaacttgat        360

gaaatctctg actacatttt ggaaaagatg aaaggtactg acataaagtg tttgtggggc        420

acggctaata tgttttccaa tccaagattt tgtaacggcg ctggctcaac taattcagca        480

gatgtctttg cattcgctgc tgcacaagtc aagaaagcac ttgacattac agtcaaactg        540

ggtgggagag gatacgtttt ctggggtggt agagaaggct acgaaacatt gttgaataca        600

gacgttaagt ttgaacaaga gaatattgca aggttaatga aaatggcagt ggaatatggg        660

cgttctatag gttttaaagg tgatttctac attgagccaa aaccaaagga acctatgaaa        720

catcaatacg atttcgatgc cgcaacagca ataggtttcc ttagagccca cgggttggat        780

aaagacttta agctcaatat cgaagccaac cacgcaacac ttgcaggcca tacatttcaa        840

catgatctta gaatatctgc tattaacgga atgctcggct caattgatgc caatcagggt        900

gatatgctac taggttggga tactgatgag tttccatttg atgtatactc cgctacacaa        960

tgcatgtatg aggtgttgaa aaatggtggt ctgaccggtg gcttcaactt cgatagtaag       1020

accagacgtc cttcatacac tatggaagat atgtttctgg cgtatatctt aggtatggac       1080

acatttgctt taggtctaat caaagccgct caaatcattg aagatggcag aattgaccag       1140

tttatagaaa agaaatactc cagttttcga gaaaccgaaa tcggacaaaa gattctcaat       1200

aacaaaactt cattgaagga attatctgat tacgcctgta agatgggtgc gccagaatta       1260

cctggaagcg gtagacaaga gatgcttgaa gctatcgtga atgatgtatt gtttggaaaa       1320

taa                                                                     1323
```

XYLOSE ISOMERASES AND THEIR USES

1. BACKGROUND

The efficient, commercial production of biofuels from plant material, such as sugarcane, requires the fermentation of pentoses, such as xylose. Xylose in plant material typically comes from lignocellulose, which is a matrix composed of cellulose, hemicelluloses, and lignin. Lignocellulose is broken down either by acid hydrolysis or enzymatic reaction, yielding xylose in addition to other monosaccharides, such as glucose (Maki et al., 2009, Int. J. Biol. Sci. 5:500-516).

Fungi, especially *Saccharomyces cerevisiae*, are commercially relevant microorganisms that ferment sugars into biofuels such as ethanol. However, *S. cerevisiae* does not endogenously metabolize xylose, requiring genetic modifications that allow it to convert xylose into xylulose. Other organisms, whose usefulness in ethanol production is limited, are able to metabolize xylose (Nevigot, 2008, Micobiol. Mol. Biol. Rev. 72:379-412).

Two pathways have been identified for the metabolism of xylose to xylulose in microorganisms: the xylose reductase (XR, EC 1.1.1.307)/xylitol dehydrogenase (XDH, EC 1.1.1.9, 1.1.1.10 and 1.1.1.B19) pathway and the xylose isomerase (XI, EC 5.3.1.5) pathway. Use of the XR/XDH pathway for xylose metabolism creates an imbalance of cofactors (excess NADH and NADP+) limiting the potential output of this pathway for the production of ethanol. The XI pathway, on the otherhand, converts xylose to xylulose in a single step and does not create a cofactor imbalance (Young et al., 2010, Biotechnol. Biofuels 3:24-36).

Because *S. cerevisiae* does not possess a native XI, it has been desirable to search for an XI in another organism to insert into *S. cerevisiae* for the purpose of biofuels production. Several XI genes have been discovered, although little or no enzymatic activity upon expression in *S. cerevisiae* has been a common problem. The XI from *Piromyces* sp. E2 was the first heterologously expressed XI in *S. cerevisiae* whose enzymatic activity could be observed (WO 03/062430).

2. SUMMARY

Due to the physiology of *S. cerevisiae* and the process of commercial biofuel production, there are other characteristics besides activity that are valuable in a commercially useful XI. During fermentation, the pH of the yeast cell and its environment can become more acidic (Rosa and Sa-Correia, 1991, Appl. Environ. Microbiol. 57:830-835). The ability of the XI to function in an acidic environment is therefore highly desirable. Therefore, there is a still a need in the art for XI enzymes with enhanced activity to convert xylose to xylulose for biofuels production under a broader range of commercially relevant conditions.

The present disclosure relates to novel xylose isomerases. The xylose isomerases have desirable characteristics for xylose fermentation, such as high activity, tolerance to acidic conditions (i.e., pH levels below 7, e.g., pH 6.5 or pH 6), or both.

The present disclosure has multiple aspects. In one aspect, the disclosure is directed to XI polypeptides. The polypeptides of the disclosure typically comprise amino acid sequences having at least 70%, 75%, 80%, 85%, 90%, 93%, 95%, 96%, 98%, 99% or 100% sequence identity to any of the XI polypeptides of Table 1, or the catalytic domain or dimerization domain thereof, or are encoded by nucleic acid sequences comprising nucleotide sequences having at least 70%, 75%, 80%, 85%, 90%, 93%, 95%, 96%, 98%, 99% or 100% sequence identity to any of the nucleic acids of Table 1:

TABLE 1

| SEQ ID NO: | Clone No. | Organism Classification | Type of Sequence | Catalytic Domain | Dimerization Domain |
|---|---|---|---|---|---|
| 1 | 1754MI2_001 | *Bacteroidales* | DNA | | |
| 2 | 1754MI2_001 | *Bacteroidales* | Amino Acid | 2-376 | 377-437 |
| 3 | 5586MI6_004 | *Bacteroidales* | DNA | | |
| 4 | 5586MI6_004 | *Bacteroidales* | Amino Acid | 2-376 | 377-437 |
| 5 | 5749MI1_003 | *Bacteroidales* | DNA | | |
| 6 | 5749MI1_003 | *Bacteroidales* | Amino Acid | 2-381 | 382-442 |
| 7 | 5750MI1_003 | *Bacteroidales* | DNA | | |
| 8 | 5750MI1_003 | *Bacteroidales* | Amino Acid | 2-381 | 382-442 |
| 9 | 5750MI2_003 | *Bacteroidales* | DNA | | |
| 10 | 5750MI2_003 | *Bacteroidales* | Amino Acid | 2-381 | 382-442 |
| 11 | 5586MI5_004 | *Bacteroides* | DNA | | |
| 12 | 5586MI5_004 | *Bacteroides* | Amino Acid | 2-375 | 376-435 |
| 13 | 5586MI202_004 | *Bacteroides* | DNA | | |
| 14 | 5586MI202_004 | *Bacteroides* | Amino Acid | 2-377 | 378-438 |
| 15 | 5586MI211_003 | *Bacteroides* | DNA | | |
| 16 | 5586MI211_003 | *Bacteroides* | Amino Acid | 2-376 | 377-437 |
| 17 | 5606MI1_005 | *Bacteroides* | DNA | | |
| 18 | 5606MI1_005 | *Bacteroides* | Amino Acid | 2-377 | 378-438 |
| 19 | 5606MI2_003 | *Bacteroides* | DNA | | |
| 20 | 5606MI2_003 | *Bacteroides* | Amino Acid | 2-378 | 379-439 |
| 21 | 5610MI3_003 | *Bacteroides* | DNA | | |
| 22 | 5610MI3_003 | *Bacteroides* | Amino Acid | 2-377 | 378-439 |
| 23 | 5749MI2_004 | *Bacteroides* | DNA | | |
| 24 | 5749MI2_004 | *Bacteroides* | Amino Acid | 2-377 | 378-438 |
| 25 | 5750MI3_003 | *Bacteroides* | DNA | | |
| 26 | 5750MI3_003 | *Bacteroides* | Amino Acid | 2-377 | 378-438 |
| 27 | 5750MI4_003 | *Bacteroides* | DNA | | |
| 28 | 5750MI4_003 | *Bacteroides* | Amino Acid | 2-377 | 378-438 |
| 29 | 5751MI4_002 | *Bacteroides* | DNA | | |
| 30 | 5751MI4_002 | *Bacteroides* | Amino Acid | 2-376 | 377-437 |
| 31 | 5751MI5_003 | *Bacteroides* | DNA | | |
| 32 | 5751MI5_003 | *Bacteroides* | Amino Acid | 2-377 | 378-438 |

TABLE 1-continued

| SEQ ID NO: | Clone No. | Organism Classification | Type of Sequence | Catalytic Domain | Dimerization Domain |
|---|---|---|---|---|---|
| 33 | 5751MI6_004 | *Bacteroides* | DNA | | |
| 34 | 5751MI6_004 | *Bacteroides* | Amino Acid | 2-377 | 378-438 |
| 35 | 5586MI22_003 | *Clostridiales* | DNA | | |
| 36 | 5586MI22_003 | *Clostridiales* | Amino Acid | 2-375 | 376-439 |
| 37 | 1753MI4_001 | *Firmicutes* | DNA | | |
| 38 | 1753MI4_001 | *Firmicutes* | Amino Acid | 2-374 | 375-440 |
| 39 | 1753MI6_001 | *Firmicutes* | DNA | | |
| 40 | 1753MI6_001 | *Firmicutes* | Amino Acid | 2-374 | 375-440 |
| 41 | 1753MI35_004 | *Firmicutes* | DNA | | |
| 42 | 1753MI35_004 | *Firmicutes* | Amino Acid | 2-375 | 376-441 |
| 43 | 1754MI9_004 | *Firmicutes* | DNA | | |
| 44 | 1754MI9_004 | *Firmicutes* | Amino Acid | 2-375 | 376-440 |
| 45 | 1754MI22_004 | *Firmicutes* | DNA | | |
| 46 | 1754MI22_004 | *Firmicutes* | Amino Acid | 2-375 | 376-440 |
| 47 | 727MI1_002 | *Firmicutes* | DNA | | |
| 48 | 727MI1_002 | *Firmicutes* | Amino Acid | 2-372 | 373-436 |
| 49 | 727MI9_005 | *Firmicutes* | DNA | | |
| 50 | 727MI9_005 | *Firmicutes* | Amino Acid | 2-374 | 375-438 |
| 51 | 727MI27_002 | *Firmicutes* | DNA | | |
| 52 | 727MI27_002 | *Firmicutes* | Amino Acid | 2-374 | 375-439 |
| 53 | 1753MI2_006 | *Neocallimastigales* | DNA | | |
| 54 | 1753MI2_006 | *Neocallimastigales* | Amino Acid | 2-376 | 377-437 |
| 55 | 5586MI3_005 | *Neocallimastigales* | DNA | | |
| 56 | 5586MI3_005 | *Neocallimastigales* | Amino Acid | 2-376 | 377-437 |
| 57 | 5586MI91_002 | *Neocallimastigales* | DNA | | |
| 58 | 5586MI91_002 | *Neocallimastigales* | Amino Acid | 2-376 | 377-437 |
| 59 | 5586MI194_003 | *Neocallimastigales* | DNA | | |
| 60 | 5586MI194_003 | *Neocallimastigales* | Amino Acid | 2-376 | 377-438 |
| 61 | 5586MI198_003 | *Neocallimastigales* | DNA | | |
| 62 | 5586MI198_003 | *Neocallimastigales* | Amino Acid | 2-375 | 376-437 |
| 63 | 5586MI201_003 | *Neocallimastigales* | DNA | | |
| 64 | 5586MI201_003 | *Neocallimastigales* | Amino Acid | 2-376 | 377-438 |
| 65 | 5586MI204_002 | *Neocallimastigales* | DNA | | |
| 66 | 5586M1204_002 | *Neocallimastigales* | Amino Acid | 2-375 | 376-437 |
| 67 | 5586MI207_002 | *Neocallimastigales* | DNA | | |
| 68 | 5586MI207_002 | *Neocallimastigales* | Amino Acid | 2-375 | 376-437 |
| 69 | 5586MI209_003 | *Neocallimastigales* | DNA | | |
| 70 | 5586MI209_003 | *Neocallimastigales* | Amino Acid | 2-375 | 376-437 |
| 71 | 5586MI214_002 | *Neocallimastigales* | DNA | | |
| 72 | 5586MI214_002 | *Neocallimastigales* | Amino Acid | 2-375 | 376-437 |
| 73 | 5751MI3_001 | *Neocallimastigales* | DNA | | |
| 74 | 5751MI3_001 | *Neocallimastigales* | Amino Acid | 2-375 | 376-437 |
| 75 | 5753MI3_002 | *Prevotella* | DNA | | |
| 76 | 5753MI3_002 | *Prevotella* | Amino Acid | 2-376 | 377-439 |
| 77 | 1754MI1_001 | *Prevotella* | DNA | | |
| 78 | 1754MI1_001 | *Prevotella* | Amino Acid | 2-377 | 378-439 |
| 79 | 1754MI3_007 | *Prevotella* | DNA | | |
| 80 | 1754MI3_007 | *Prevotella* | Amino Acid | 2-377 | 378-439 |
| 81 | 1754MI5_009 | *Prevotella* | DNA | | |
| 82 | 1754MI5_009 | *Prevotella* | Amino Acid | 2-375 | 376-437 |
| 83 | 5586MI1_003 | *Prevotella* | DNA | | |
| 84 | 5586MI1_003 | *Prevotella* | Amino Acid | 2-377 | 378-439 |
| 85 | 5586MI2_006 | *Prevotella* | DNA | | |
| 86 | 5586MI2_006 | *Prevotella* | Amino Acid | 2-377 | 378-439 |
| 87 | 5586MI8_003 | *Prevotella* | DNA | | |
| 88 | 5586MI8_003 | *Prevotella* | Amino Acid | 2-377 | 378-439 |
| 89 | 5586MI14_003 | *Prevotella* | DNA | | |
| 90 | 5586MI14_003 | *Prevotella* | Amino Acid | 2-377 | 378-439 |
| 91 | 5586MI26_003 | *Prevotella* | DNA | | |
| 92 | 5586MI26_003 | *Prevotella* | Amino Acid | 2-377 | 378-439 |
| 93 | 5586MI86_001 | *Prevotella* | DNA | | |
| 94 | 5586MI86_001 | *Prevotella* | Amino Acid | 2-376 | 377-438 |
| 95 | 5586MI108_002 | *Prevotella* | DNA | | |
| 96 | 5586MI108_002 | *Prevotella* | Amino Acid | 2-377 | 378-439 |
| 97 | 5586MI182_004 | *Prevotella* | DNA | | |
| 98 | 5586MI182_004 | *Prevotella* | Amino Acid | 2-377 | 378-439 |
| 99 | 5586MI193_004 | *Prevotella* | DNA | | |
| 100 | 5586MI193_004 | *Prevotella* | Amino Acid | 2-376 | 377-438 |
| 101 | 5586MI195_003 | *Prevotella* | DNA | | |
| 102 | 5586MI195_003 | *Prevotella* | Amino Acid | 2-376 | 377-438 |
| 103 | 5586MI216_003 | *Prevotella* | DNA | | |
| 104 | 5586MI216_003 | *Prevotella* | Amino Acid | 2-376 | 377-438 |
| 105 | 5586MI197_003 | *Prevotella* | DNA | | |
| 106 | 5586MI197_003 | *Prevotella* | Amino Acid | 2-376 | 377-438 |
| 107 | 5586MI199_003 | *Prevotella* | DNA | | |
| 108 | 5586MI199_003 | *Prevotella* | Amino Acid | 2-376 | 377-438 |
| 109 | 5586MI200_003 | *Prevotella* | DNA | | |

TABLE 1-continued

| SEQ ID NO: | Clone No. | Organism Classification | Type of Sequence | Catalytic Domain | Dimerization Domain |
|---|---|---|---|---|---|
| 110 | 5586MI200_003 | *Prevotella* | Amino Acid | 2-376 | 377-438 |
| 111 | 5586MI203_003 | *Prevotella* | DNA | | |
| 112 | 5586MI203_003 | *Prevotella* | Amino Acid | 2-376 | 377-438 |
| 113 | 5586MI205_004 | *Prevotella* | DNA | | |
| 114 | 5586MI205_004 | *Prevotella* | Amino Acid | 2-376 | 377-438 |
| 115 | 5586MI206_004 | *Prevotella* | DNA | | |
| 116 | 5586MI206_004 | *Prevotella* | Amino Acid | 2-376 | 377-438 |
| 117 | 5586MI208_003 | *Prevotella* | DNA | | |
| 118 | 5586MI208_003 | *Prevotella* | Amino Acid | 2-376 | 377-438 |
| 119 | 5586MI210_002 | *Prevotella* | DNA | | |
| 120 | 5586MI210_002 | *Prevotella* | Amino Acid | 2-374 | 375-437 |
| 121 | 5586MI212_002 | *Prevotella* | DNA | | |
| 122 | 5586MI212_002 | *Prevotella* | Amino Acid | 2-376 | 377-438 |
| 123 | 5586MI213_003 | *Prevotella* | DNA | | |
| 124 | 5586MI213_003 | *Prevotella* | Amino Acid | 2-376 | 377-438 |
| 125 | 5586MI215_003 | *Prevotella* | DNA | | |
| 126 | 5586MI215_003 | *Prevotella* | Amino Acid | 2-376 | 377-438 |
| 127 | 5607MI1_003 | *Prevotella* | DNA | | |
| 128 | 5607MI1_003 | *Prevotella* | Amino Acid | 2-376 | 377-438 |
| 129 | 5607MI2_003 | *Prevotella* | DNA | | |
| 130 | 5607MI2_003 | *Prevotella* | Amino Acid | 2-376 | 377-442 |
| 131 | 5607MI3_003 | *Prevotella* | DNA | | |
| 132 | 5607MI3_003 | *Prevotella* | Amino Acid | 2-376 | 377-438 |
| 133 | 5607MI4_005 | *Prevotella* | DNA | | |
| 134 | 5607MI4_005 | *Prevotella* | Amino Acid | 2-376 | 377-438 |
| 135 | 5607MI5_002 | *Prevotella* | DNA | | |
| 136 | 5607MI5_002 | *Prevotella* | Amino Acid | 2-376 | 377-439 |
| 137 | 5607MI6_002 | *Prevotella* | DNA | | |
| 138 | 5607MI6_002 | *Prevotella* | Amino Acid | 2-376 | 377-438 |
| 139 | 5607MI7_002 | *Prevotella* | DNA | | |
| 140 | 5607MI7_002 | *Prevotella* | Amino Acid | 2-376 | 377-438 |
| 141 | 5608MI1_004 | *Prevotella* | DNA | | |
| 142 | 5608MI1_004 | *Prevotella* | Amino Acid | 2-376 | 377-438 |
| 143 | 5608MI2_002 | *Prevotella* | DNA | | |
| 144 | 5608MI2_002 | *Prevotella* | Amino Acid | 2-375 | 376-437 |
| 145 | 5608MI3_004 | *Prevotella* | DNA | | |
| 146 | 5608MI3_004 | *Prevotella* | Amino Acid | 2-376 | 377-438 |
| 147 | 5609MI1_005 | *Prevotella* | DNA | | |
| 148 | 5609MI1_005 | *Prevotella* | Amino Acid | 2-376 | 377-438 |
| 149 | 5610MI1_003 | *Prevotella* | DNA | | |
| 150 | 5610MI1_003 | *Prevotella* | Amino Acid | 2-376 | 377-438 |
| 151 | 5610MI2_004 | *Prevotella* | DNA | | |
| 152 | 5610MI2_004 | *Prevotella* | Amino Acid | 2-376 | 377-438 |
| 153 | 5751MI1_003 | *Prevotella* | DNA | | |
| 154 | 5751MI1_003 | *Prevotella* | Amino Acid | 2-376 | 377-438 |
| 155 | 5751MI2_003 | *Prevotella* | DNA | | |
| 156 | 5751MI2_003 | *Prevotella* | Amino Acid | 2-376 | 377-438 |
| 157 | 5752MI1_003 | *Prevotella* | DNA | | |
| 158 | 5752MI1_003 | *Prevotella* | Amino Acid | 2-376 | 377-438 |
| 159 | 5752MI2_003 | *Prevotella* | DNA | | |
| 160 | 5752MI2_003 | *Prevotella* | Amino Acid | 2-376 | 377-438 |
| 161 | 5752MI3_002 | *Prevotella* | DNA | | |
| 162 | 5752MI3_002 | *Prevotella* | Amino Acid | 2-376 | 377-438 |
| 163 | 5752MI5_003 | *Prevotella* | DNA | | |
| 164 | 5752MI5_003 | *Prevotella* | Amino Acid | 2-376 | 377-438 |
| 165 | 5752MI6_004 | *Prevotella* | DNA | | |
| 166 | 5752MI6_004 | *Prevotella* | Amino Acid | 2-376 | 377-438 |
| 167 | 5753MI1_002 | *Prevotella* | DNA | | |
| 168 | 5753MI1_002 | *Prevotella* | Amino Acid | 2-376 | 377-438 |
| 169 | 5753MI2_002 | *Prevotella* | DNA | | |
| 170 | 5753MI2_002 | *Prevotella* | Amino Acid | 2-376 | 377-438 |
| 171 | 5753MI4_002 | *Prevotella* | DNA | | |
| 172 | 5753MI4_002 | *Prevotella* | Amino Acid | 2-376 | 377-438 |
| 173 | 5752MI4_004 | *Prevotella* | DNA | | |
| 174 | 5752MI4_004 | *Prevotella* | Amino Acid | 2-376 | 377-438 |
| 175 | 727MI4_006 | *Rhizobiales* | DNA | | |
| 176 | 727MI4_006 | *Rhizobiales* | Amino Acid | 2-373 | 374-435 |

In specific embodiments, a polypeptide of the disclosure comprises an amino acid sequence having:

(1) (a) at least 97% or 98% sequence identity to SEQ ID NO:78 or the catalytic domain thereof (amino acids 2-377 of SEQ ID NO:78) and/or (b) at least 80%, 85%, 90%, 93% or 95% sequence identity to SEQ ID NO:78 or the catalytic domain thereof (amino acids 2-377 of SEQ ID NO:78) and further comprises (i) SEQ ID NO:212 or SEQ ID NO:213 and/or (ii) SEQ ID NO:214;

(2) (a) at least 95%, 97% or 98% sequence identity to SEQ ID NO:96 or the catalytic domain thereof (amino acids 2-377 of SEQ ID NO:96) and/or (b) at least 80%, 85%, 90%, 93% or 95% sequence identity to SEQ ID NO:96 or the catalytic domain thereof (amino acids 2-377 of SEQ ID NO:96) and further comprises (i) SEQ ID NO:212 or SEQ ID NO:213 and/or (ii) SEQ ID NO:214;

(3) at least 80%, 85%, 90%, 93%, 95%, 97% or 98% sequence identity to SEQ ID NO:38 or the catalytic domain thereof (amino acids 2-374 of SEQ ID NO:38), and optionally further comprises one, two, three, four or all five of (i) SEQ ID NO:206 or SEQ ID NO:207; (ii) SEQ ID NO:208; (iii) SEQ ID NO:209; (iv) SEQ ID NO:210; and (iv) SEQ ID NO:211;

(4) at least 80%, 85%, 90%, 93%, 95%, 97% or 98% sequence identity to SEQ ID NO:2 or the catalytic domain thereof (amino acids 2-374 of SEQ ID NO:2);

(5) at least 93%, 95%, 97% or 98% sequence identity to SEQ ID NO:58 or the catalytic domain thereof (amino acids 2-376 of SEQ ID NO:58), (6) at least 80%, 85%, 90%, 93%, 95%, 97% or 98% sequence identity to SEQ ID NO:42 or the catalytic domain thereof (amino acids 2-375 of SEQ ID NO:42), and optionally further comprises one, two or all three of (i) SEQ ID NO:206 or SEQ ID NO:207; (ii) SEQ ID NO:210; and (iii) SEQ ID NO:211;

(7) (a) at least 97% or 98% sequence identity to SEQ ID NO:84 or the catalytic domain thereof (amino acids 2-376 of SEQ ID NO:84), and/or (b) at least 80%, 85%, 90%, 93% or 95% sequence identity to SEQ ID NO:84 or the catalytic domain thereof (amino acids 2-376 of SEQ ID NO:84) and further comprises (i) SEQ ID NO:212 or SEQ ID NO:213 and/or (ii) SEQ ID NO:214;

(8) (a) at least 97% or 98% sequence identity to SEQ ID NO:80 or the catalytic domain thereof (amino acids 2-377 of SEQ ID NO:80) and/or (b) at least 80%, 85%, 90%, 93% or 95% sequence identity to SEQ ID NO:80 or the catalytic domain thereof (amino acids 2-377 of SEQ ID NO:80) and further comprises (i) SEQ ID NO:212 or SEQ ID NO:213 and/or (ii) SEQ ID NO:214;

(9) at least 93%, 95%, 97% or 98% sequence identity to SEQ ID NO:54 or the catalytic domain thereof (amino acids 2-376 of SEQ ID NO:54);

(10) at least 80%, 85%, 90%, 93%, 95%, 97% or 98% sequence identity to SEQ ID NO:46 or the catalytic domain thereof (amino acids 2-376 of SEQ ID NO:46), and optionally further comprises SEQ ID NO:206 or SEQ ID NO:207;

(11) at least 90%, 93%, 95%, 97% or 98% sequence identity to SEQ ID NO:16 or the catalytic domain thereof (amino acids 2-376 of SEQ ID NO:16);

(12) at least 85%, 90%, 93%, 95%, 97% or 98% sequence identity to SEQ ID NO:82 or the catalytic domain thereof (amino acids 2-375 of SEQ ID NO:82); and/or

(13) at least 90%, 93%, 95%, 97% or 98% sequence identity to SEQ ID NO:32 or the catalytic domain thereof (amino acids 2-377 of SEQ ID NO:32).

The XIs of the disclosure can be characterized in terms of their activity. In some embodiments, a XI of the disclosure has at least 1.3 times the activity of the *Orpinomyces* sp. XI assigned Genbank Accession No. 169733248 ("Op-XI") at pH 7.5, for example using the assay described in any of Examples 4, 6 and 7. In certain specific embodiments, a XI of the disclosure has an activity ranging from 1.25 to 3.0 times, from 1.5 to 3 times, from 1.5 to 2.25 times, or from 1.75 to 3 times the activity of Op-XI at pH 7.5.

The XIs of the disclosure can also be characterized in terms of their tolerance to acidic environments (e.g., at a pH of 6.5 or 6). In some embodiments, a XI of the disclosure has at least 1.9 times the activity of the Op-XI at pH 6, for example using the assay described in Example 7. In certain specific embodiments, a XI of the disclosure has an activity ranging from 1.9 to 4.1 times, from 2.4 to 4.1 times, from 2.4 to 3.9 times, or 2.4 to 4.1 times the activity of Op-XI at pH 6.

Tolerance to acidic environments can also be characterized as a ratio of activity at pH 6 to activity at pH 7.5 ("a pH 6 to pH 7.5 activity ratio"), for example as measured using the assay of Example 7. In some embodiments, the pH 6 to pH 7.5 activity ratio is at least 0.5 or at least 0.6. In various embodiments, the pH 6 to pH 7.5 activity ratio is 0.5-0.9 or 0.6-0.9.

In another aspect, the disclosure is directed to a nucleic acid which encodes a XI polypeptide of the disclosure. In various embodiments, the nucleic acid comprises a nucleotide sequence with at least 50%, 60%, 70%, 75%, 80%, 85%, 90%, 93%, 95%, 96%, 98%, 99% or 100% sequence identity to the nucleotide sequence of any one of SEQ ID NOS:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, and 175, or the portion of any of the foregoing sequences encoding a XI catalytic domain or dimerization domain.

The nucleic acids of the disclosure can be codon optimized, e.g., for expression in eukaryotic organisms such as yeast or filamentous fungi. Exemplary codon optimized open reading frames for expression in *S. cerevisiae* are SEQ ID NO:238 (encoding a XI of SEQ ID NO:54), SEQ ID NO:239 (encoding a XI of SEQ ID NO:58), SEQ ID NO:244 (encoding a XI of SEQ ID NO:78), SEQ ID NO:245 (encoding a XI of SEQ ID NO:96), SEQ ID NO:246 (encoding a XI of SEQ ID NO:38), SEQ ID NO:247 (encoding a XI of SEQ ID NO:78), SEQ ID NO:248 (encoding a XI of SEQ ID NO:96), and SEQ ID NO:249 (encoding a XI of SEQ ID NO:38). In various embodiments, the disclosure provides nucleic acids comprising nucleotide sequences having at least 70%, at least 75%, at least 80%, at least 85%, at least 90%, at least 93%, at least 95%, at least 96%, at least 98%, or at least 99% sequence identity, or having 100% sequence identity, to the nucleotide sequence of any one of SEQ ID NOs:238, 239, 244, 245, 246, 247, 248 and 249, or the portion of any of the foregoing sequences encoding a XI catalytic domain or dimerization domain.

In other aspects, the disclosure is directed to a vector comprising a XI-encoding nucleotide sequence, for example a vector having an origin of replication and/or a promoter sequence operably linked to the XI-encoding nucleotide sequence. The promoter sequence can be one that is operable in a eukaryotic cell, for example in a fungal cell. In some embodiments, the promoter is operable in yeast (e.g., *S. cerevisiae*) or filamentous fungi.

In yet another aspect, the disclosure is directed to a recombinant cell comprising a nucleic acid that encodes a XI polypeptide. Particularly, the cell is engineered to express any of the XI polypeptides described herein. The recombinant cell may be of any species, and is preferably a eukaryotic cell, for example a yeast cell. Suitable genera of yeast include *Saccharomyces, Kluyveromyces, Candida, Pichia, Schizosaccharomyces, Hansenula, Klockera, Schwanniomyces, Issatchenkia* and *Yarrowia*. In specific embodiments, the recombinant cell is a *S. cerevisiae, S. bulderi, S. barnetti,*

*S. exiguus, S. uvarum, S. diastaticus, K. lactis, I. orientalis, K. marxianusor K. fragilis*. Suitable genera of filamentous fungi include *Aspergillus, Penicillium, Rhizopus, Chrysosporium, Myceliophthora, Trichoderma, Humicola, Acremonium* and *Fusarium*. In specific embodiments, the recombinant cell is an *Aspergillus niger, Aspergillus oryzae, Trichoderma reesei, Penicillium chrysogenum, Myceliophthora thermophila*, or *Rhizopus oryzae*.

The recombinant cell may also be mutagenized or engineered to include modifications other than the recombinant expression of XI, particularly those that make the cell more suited to utilize xylose in a fermentation pathway. Exemplary additional modifications create one, two, three, four, five or even more of the following phenotypes: (a) increase in xylose transport into the cell; (b) increase in aerobic growth rate on xylose; (c) increase in xylulose kinase activity; (d) increase in flux through the pentose phosphate pathway into glycolysis, (e) decrease in aldose reductase activity, (f) decrease in sensitivity to catabolite repression, (g) increase in tolerance to biofuels, e.g., ethanol, (h) increase tolerance to intermediate production (e.g., xylitol), (i) increase in temperature tolerance, (j) osmolarity of organic acids, and (k) a reduced production of byproducts.

Increases in activity can be achieved by increased expression levels, for example expression of a hexose or pentose (e.g., xylose) transporter, a xylulose kinase, a glycolytic enzyme, or an ethanologenic enzyme is increased. The increased expression levels are achieved by overexpressing an endogenous protein or by expressing a heterologous protein.

Other modifications to the recombinant cell that are part of the disclosure are modifications that decrease the activity of genes or pathways in the recombinant cell. Preferably, the expression levels of one, two, three or more of the genes for hexose kinase, MIG-1, MIG-2, XR, aldose reductase, and XDH are reduced. Reducing gene activity can be achieved by a targeted deletion or disruption of the gene (and optionally reintroducing the gene under the control of a different promoter that drives lower levels of expression or inducible expression).

In yet other aspects, the disclosure is directed to methods of producing fermentation products, for example one or more of ethanol, butanol, diesel, lactic acid, 3-hydroxypropionic acid, acrylic acid, acetic acid, succinic acid, citric acid, malic acid, fumaric acid, itaconic acid, an amino acid, 1,3-propane-diol, ethylene, glycerol, a β-lactam antibiotic and a cephalosporin. Typically, a cell that recombinantly expresses a XI of the disclosure is cultured in a xylose-containing medium, for example a medium supplemented with a lignocellulosic hydrolysate. The media may also contain glucose, arabinose, or other sugars, particularly those derived from lignocellulose. The media may be of any pH, particularly a pH between 3.0 and 9.0, preferably between 4.0 and 8.0, more preferably between 5.0 and 8.0, even more preferably between 6.0 and 7.5. The culture may occur in any media where the culture is under anaerobic or aerobic conditions, preferably under anaerobic conditions for production of compounds mentioned above and aerobically for biomass/cellular production. Optionally, the methods further comprise recovering the fermentation product produced by the recombinant cell.

3. BRIEF DESCRIPTION OF THE FIGURES

Figure 8:
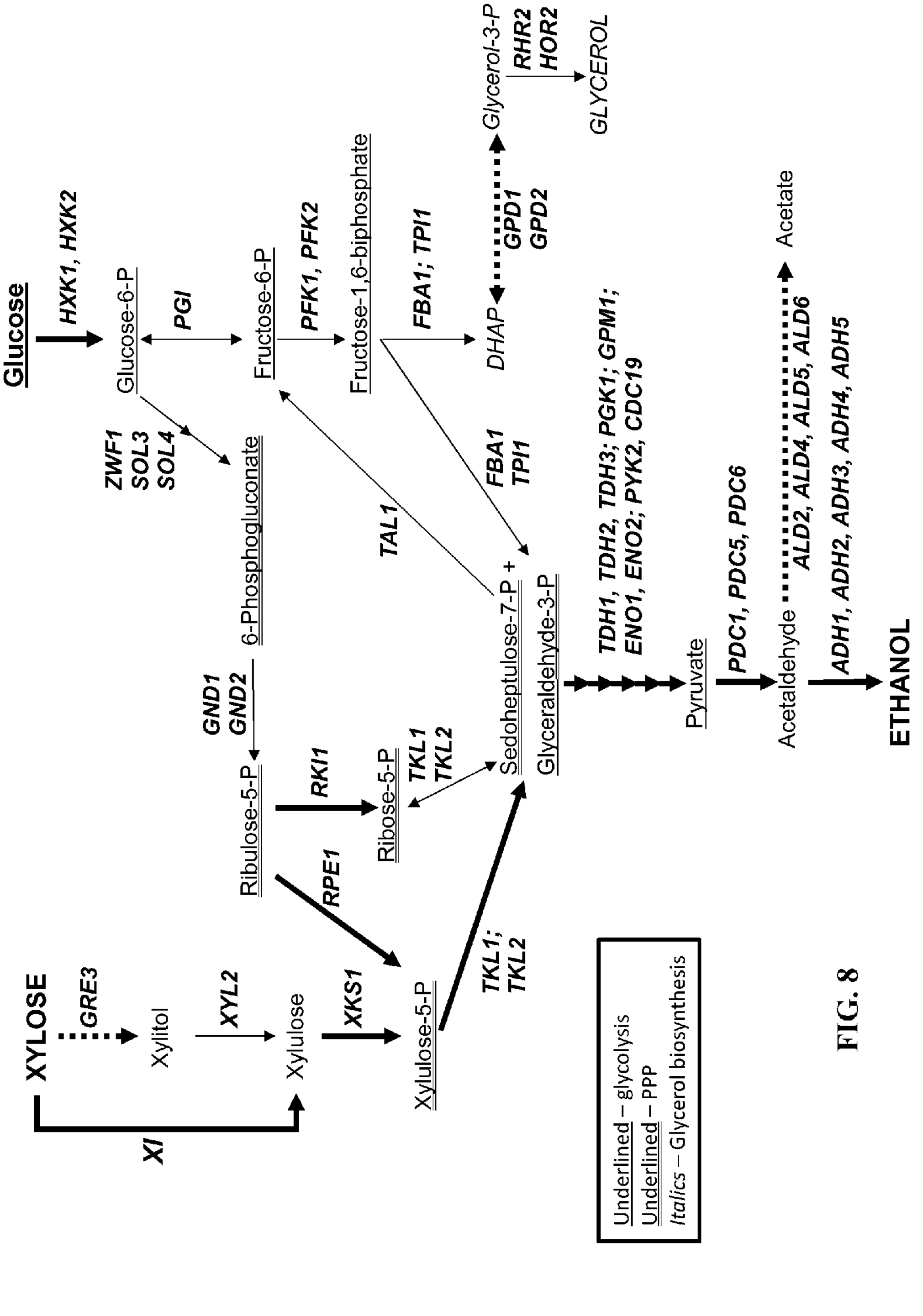

FIG. 8: Production of ethanol from glycolytic and pentose phosphate ("PPP") pathways. Not all steps are shown. For example, glyceraldehyde-3-phosphate is converted to pyruvate via a series of glycolytic steps: (1) glyceraldehyde-3-phosphate to 3-phospho-D-glycerol-phosphate catalyzed by glyceraldehyde-3-phosphate dehydrogenase (TDH1-3); (2) 3-phospho-D-glycerol-phosphate to 3-phosphoglycerate catalyzed by 3-phosphoglycerate kinase (PGK1); (3) 3-phosphoglycerate to 2-phosphoglycerate catalyzed by phosphoglycerate mutase (GPM1); (4) 2-phosphoglycerate to phosphoenolpyruvate catalyzed by *enolase* (ENO1; ENO2); and (5) phosphoenolpyruvate to pyruvate calatyzed by pyruvate kinase (PYK2; CDC19). Other abbreviations: DHAP=dihydroxy-acetone-phosphate; GPD=Glycerol-3-phosphate dehydrogenase; RHR2/HOR2=DL-glycerol-3-phosphatase; XI=xylose isomerase; GRE=xylose reductase/aldose reductase; XYL=xylitol dehydrogenase; XKS=xylulokinase; PDC=pyruvate decarboxylase; ADH=alcohol dehydrogenase; ALD=aldehyde dehydrogenase; HXK=hexokinase; PGI=phosphoglucose isomerase; PFK=phosphofructokinase; FBA=aldolase; TPI=triosephosphate isomerase; ZWF=glucose-6 phosphate dehydrogenase; SOL=6-phosphogluconolactonase; GND=6-phosphogluconate dehydrogenase; RPE=D-ribulose-5-Phosphate 3-epimerase; RKI=ribose-5-phosphate ketol-isomerase; TKL=transketolase; TAL=transaldolase. Heavy dashed arrows indicate reactions and corresponding enzymes that can be reduced or eliminated to increase xylose utilization, particularly in the production of ethanol, and heavy solid arrows indicate reactions and corresponding enzymes that can be increased to increase xylose utilization, particularly in the production of ethanol. The enzymes shown in FIG. 8 are encoded by *S. cerevisiae* genes. The *S. cerevisiae* genes are used for exemplification purposes. Analogous enzymes and modifications in other organisms are within the scope of the present disclosure.

4. DETAILED DESCRIPTION

4.1 Xylose Isomerase Polypeptides

A "xylose isomerase" or "XI" is an enzyme that catalyzes the direct isomerisation of D-xylose into D-xylulose and/or vice versa. This class of enzymes is also known as D-xylose ketoisomerases. A xylose isomerase herein may also be capable of catalyzing the conversion between D-glucose and D-fructose (and accordingly may therefore be referred to as a glucose isomerase).

A "XI polypeptide of the disclosure" or a "XI of the disclosure" is a xylose isomerase having an amino acid sequence that is related to any one of SEQ ID NOs:2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, or 176. In some embodiments, the xylose isomerase of the disclosure has an amino acid sequence that is at least about 70%, at least 80%, at least 90%, at least 95%, at least 96%, at least 98%, or at least 99% sequence identity thereto, or to a catalytic or dimerization domain thereof. The xylose isomerase of the disclosure can also have 100% sequence identity to one of the foregoing sequences.

The disclosure provides isolated, synthetic or recombinant XI polypeptides comprising an amino acid sequence having at least about 80%, e.g., at least about 81%, 82%, 83%, 84%, 85%, 86%, 87%, 88%, 89%, 90%, 91%, 92%, 93%, 94%, 95%, 96%, 97%, 98%, 99%, or complete (100%) sequence identity to a polypeptide of SEQ ID NO:2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, or 176, over a region of at least about 10, e.g., at least about 15, 20, 25, 30, 35, 40, 45, 50, 55, 60, 65, 70, 75, 80, 85, 90, 95, 100, 125, 150, 175, 200, 225, 250, 275, 300, 325, or 350 residues, or over the full length of the polypeptide, over the length of catalytic domain, or over the length of the dimerization domain.

The XI polypeptides of the disclosure can be encoded by a nucleic acid sequence having at least about 80%, about 85%, about 86%, about 87%, about 88%, about 89%, or about 90% sequence identity to 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, or 175, or by a nucleic acid sequence capable of hybridizing under high stringency conditions to a complement of SEQ ID NO:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, or 175, or to a fragment thereof. Exemplary nucleic acids of the disclosure are described in Section 4.2 below.

In specific embodiments, a polypeptide of the disclosure comprises an amino acid sequence having:

(1) (a) at least 97% or 98% sequence identity to SEQ ID NO:78 or the catalytic domain thereof (amino acids 2-377 of SEQ ID NO:78) and/or (b) at least 80%, 85%, 90%, 93% or 95% sequence identity to SEQ ID NO:78 or the catalytic domain thereof (amino acids 2-377 of SEQ ID NO:78) and further comprises (i) SEQ ID NO:212 or SEQ ID NO:213 and/or (ii) SEQ ID NO:214;

(2) (a) at least 95%, 97% or 98% sequence identity to SEQ ID NO:96 or the catalytic domain thereof (amino acids 2-377 of SEQ ID NO:96) and/or (b) at least 80%, 85%, 90%, 93% or 95% sequence identity to SEQ ID NO:96 or the catalytic domain thereof (amino acids 2-377 of SEQ ID NO:96) and further comprises (i) SEQ ID NO:212 or SEQ ID NO:213 and/or (ii) SEQ ID NO:214;

(3) at least 80%, 85%, 90%, 93%, 95%, 97% or 98% sequence identity to SEQ ID NO:38 or the catalytic domain thereof (amino acids 2-374 of SEQ ID NO:38), and optionally further comprises one, two, three, four or all five of (i) SEQ ID NO:206 or SEQ ID NO:207; (ii) SEQ ID NO:208; (iii) SEQ ID NO:209; (iv) SEQ ID NO:210; and (iv) SEQ ID NO:211;

(4) at least 80%, 85%, 90%, 93%, 95%, 97% or 98% sequence identity to SEQ ID NO:2 or the catalytic domain thereof (amino acids 2-374 of SEQ ID NO:2);

(5) at least 93%, 95%, 97% or 98% sequence identity to SEQ ID NO:58 or the catalytic domain thereof (amino acids 2-376 of SEQ ID NO:58), (6) at least 80%, 85%, 90%, 93%, 95%, 97% or 98% sequence identity to SEQ ID NO:42 or the catalytic domain thereof (amino acids 2-375 of SEQ ID NO:42), and optionally further comprises one, two or all three of (i) SEQ ID NO:206 or SEQ ID NO:207; (ii) SEQ ID NO:210; and (iii) SEQ ID NO:211;

(7) (a) at least 97% or 98% sequence identity to SEQ ID NO:84 or the catalytic domain thereof (amino acids 2-376 of SEQ ID NO:84), and/or (b) at least 80%, 85%, 90%, 93% or 95% sequence identity to SEQ ID NO:84 or the catalytic domain thereof (amino acids 2-376 of SEQ ID NO:84) and further comprises (i) SEQ ID NO:212 or SEQ ID NO:213 and/or (ii) SEQ ID NO:214;

(8) (a) at least 97% or 98% sequence identity to SEQ ID NO:80 or the catalytic domain thereof (amino acids 2-377 of SEQ ID NO:80) and/or (b) at least 80%, 85%, 90%, 93% or 95% sequence identity to SEQ ID NO:80 or the catalytic domain thereof (amino acids 2-377 of SEQ ID NO:80) and further comprises (i) SEQ ID NO:212 or SEQ ID NO:213 and/or (ii) SEQ ID NO:214;

(9) at least 93%, 95%, 97% or 98% sequence identity to SEQ ID NO:54 or the catalytic domain thereof (amino acids 2-376 of SEQ ID NO:54);

(10) at least 80%, 85%, 90%, 93%, 95%, 97% or 98% sequence identity to SEQ ID NO:46 or the catalytic domain thereof (amino acids 2-376 of SEQ ID NO:46), and optionally further comprises SEQ ID NO:206 or SEQ ID NO:207;

(11) at least 90%, 93%, 95%, 97% or 98% sequence identity to SEQ ID NO:16 or the catalytic domain thereof (amino acids 2-376 of SEQ ID NO:16);

(12) at least 85%, 90%, 93%, 95%, 97% or 98% sequence identity to SEQ ID NO:82 or the catalytic domain thereof (amino acids 2-375 of SEQ ID NO:82); and/or

(13) at least 90%, 93%, 95%, 97% or 98% sequence identity to SEQ ID NO:32 or the catalytic domain thereof (amino acids 2-377 of SEQ ID NO:32).

An example of an algorithm that is suitable for determining sequence similarity is the BLAST algorithm, which is described in Altschul et al., 1990, J. Mol. Biol. 215:403-410. Software for performing BLAST analyses is publicly available through the National Center for Biotechnology Information. This algorithm involves first identifying high scoring sequence pairs (HSPs) by identifying short words of length W in the query sequence that either match or satisfy some positive-valued threshold score T when aligned with a word of the same length in a database sequence. These initial neighborhood word hits act as starting points to find longer HSPs containing them. The word hits are expanded in both directions along each of the two sequences being compared for as far as the cumulative alignment score can be increased. Extension of the word hits is stopped when: the cumulative alignment score falls off by the quantity X from a maximum achieved value; the cumulative score goes to zero or below; or the end of either sequence is reached. The BLAST algorithm parameters W, T, and X determine the sensitivity and speed of the alignment. The BLAST program uses as defaults a word length (W) of 11, the BLOSUM62 scoring matrix (see Henikoff & Henikoff, 1992, Proc. Nat'l. Acad. Sci. USA 89:10915-10919) alignments (B) of 50, expectation (E) of 10, M'5, N'-4, and a comparison of both strands.

Any of the amino acid sequences described herein can be produced together or in conjunction with at least 1, e.g., at least (or up to) 2, 3, 5, 10, or 20 heterologous amino acids flanking each of the C- and/or N-terminal ends of the specified amino acid sequence, and or deletions of at least 1, e.g., at least (or up to) 2, 3, 5, 10, or 20 amino acids from the C- and/or N-terminal ends of a XI of the disclosure.

The XIs of the disclosure can be characterized in terms of their activity. In some embodiments, a XI of the disclosure has at least 1.3 times the activity of the *Orpinomyces* sp. XI assigned Genbank Accession No. 169733248 ("Op-XI") at pH 7.5, for example using the assay described in any of Examples 4, 6 and 7. In certain specific embodiments, a XI of the disclosure has an activity ranging from 1.25 to 3.0 times, from 1.5 to 3 times, from 1.5 to 2.25 times, or from 1.75 to 3 times the activity of Op-XI at pH 7.5.

The XIs of the disclosure can also be characterized in terms of their tolerance to acidic environments (e.g., at a pH of 6.5 or 6). In some embodiments, a XI of the disclosure has at least 1.9 times the activity of the Op-XI at pH 6, for example using the assay described in Example 7. In certain specific embodiments, a XI of the disclosure has an activity ranging from 1.9 to 4.1 times, from 2.4 to 4.1 times, from 2.4 to 3.9 times, or 2.4 to 4.1 times the activity of Op-XI at pH6.

Tolerance to acidic environments can also be characterized as a ratio of activity at pH 6 to activity at pH 7.5 ("a pH 6 to pH 7.5 activity ratio"), for example as measured using the assay of Example 7. In some embodiments, the pH 6 to pH 7.5 activity ratio is at least 0.5 or at least 0.6. In various embodiments, the pH 6 to pH 7.5 activity ratio is 0.5-0.9 or 0.6-0.9.

The xylose isomerases of the disclosure can have one or more (e.g., up to 2, 3, 5, 10, or 20) conservative amino acid substitutions relative to the polypeptide of SEQ ID NO:2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, or 176 or to the portion thereof of discussed above. The conservative substitutions can be chosen from among a group having a similar side chain to the reference amino acid. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Accordingly, exemplary conservative substitutions for each of the naturally occurring amino acids are as follows: ala to ser; arg to lys; asn to gln or his; asp to glu; cys to ser or ala; gln to asn; glu to asp; gly to pro; his to asn or gin; ile to leu or val; leu to ile or val; lys to arg; gln or glu; met to leu or ile; phe to met, leu or tyr; ser to thr; thr to ser; trp to tyr; tyr to trp or phe; and, val to ile or leu.

The present disclosure also provides a fusion protein that includes at least a portion (e.g., a fragment or domain) of a XI polypeptide of the disclosure attached to one or more fusion segments, which are typically heterologous to the XI polypeptide. Suitable fusion segments include, without limitation, segments that can provide other desirable biological activity or facilitate purification of the XI polypeptide (e.g., by affinity chromatography). Fusion segments can be joined to the amino or carboxy terminus of a XI polypeptide. The fusion segments can be susceptible to cleavage.

4.2 Xylose Isomerase Nucleic Acids

A "XI nucleic acid of the disclosure" is a nucleic acid encoding a xylose isomerase of the disclosure. In certain embodiments, the xylose isomerase nucleic acid of the disclosure is encoded by a nucleotide sequence of any one of SEQ ID NOs:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, or 175, or a sequence having at least about 50%, at least 60%, at least 70%, at least 80%, at least 90%, at least 95%, at least 96%, at least 98%, or at least 99% sequence identity thereto. The xylose isomerase nucleic acid of the disclosure can also have 100% sequence identity to one of the foregoing sequences.

The present disclosure provides nucleic acids encoding a polypeptide of the disclosure, for example one described in Section 4.1 above. The disclosure provides isolated, synthetic or recombinant nucleic acids comprising a nucleic acid sequence having at least about 70%, e.g., at least about 71%, 72%, 73%, 74%, 75%, 76%, 77%, 78%, 79%, 80%, 81%, 82%, 83%, 84%, 85%, 86%, 87%, 88%; 89%, 90%, 91%, 92%, 93%, 94%, 95%, 96%, 97%, 98%, or 99%, or complete (100%) sequence identity to a nucleic acid of SEQ ID NO:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, or 175, over a region of at least about 10, e.g., at least about 15, 20, 25, 30, 35, 40, 45, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, or 2000 nucleotides.

Nucleic acids of the disclosure also include isolated, synthetic or recombinant nucleic acids encoding a XI polypeptide having the sequence of SEQ ID NO:2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, or 176, and subsequences thereof (e.g., a conserved domain or a catalytic domain), and variants thereof.

To increase the likelihood that a XI polypeptide is recombinantly expressed, a XI nucleic acid may be adapted to optimize its codon usage to that of the chosen cell. Several methods for codon optimization are known in the art. For expression in yeast, an exemplary method to optimize codon usage of the nucleotide sequences to that of the yeast is a codon pair optimization technology as disclosed in WO 2006/077258 and/or WO 2008/000632. WO2008/000632 addresses codon-pair optimization. Codon-pair optimization is a method wherein the nucleotide sequences encoding a polypeptide are modified with respect to their codon-usage, in particular the codon-pairs that are used, to obtain improved expression of the nucleotide sequence encoding the polypeptide and/or improved production of the encoded polypeptide. Codon pairs are defined as a set of two subsequent triplets (codons) in a coding sequence. Boles codon optimization (see Table 2 of Wiedemann and Boles, 2008, Appl. Environ. Microbiol. 74:2043-2050) can also be used to optimize expression and activity of XIs in yeast. Alternatively, the XI sequence can be optimized using commercially available software, such as Gene Designer (DNA2.0). Preferably, codon optimized sequences avoid nucleotide repeats and restriction sites that are utilized in cloning the XI nucleic acids, by adjusting the settings in commercial software or by manually altering the sequences to substitute codons that introduce undesired sequences, for example with highly utilized codons in the organism of interest. Exemplary codon optimized open reading frames for expression in *S. cerevisiae* are SEQ ID NO:238 (encoding a XI of SEQ ID NO:54), SEQ ID NO:239 (encoding a XI of SEQ ID NO:58), SEQ ID NO:244 (encoding a XI of SEQ ID NO:78), SEQ ID NO:245 (encoding a XI of SEQ ID NO:96), SEQ ID NO:246 (encoding a XI of SEQ ID NO:38), SEQ ID NO:247 (encoding a XI of SEQ ID NO:78), SEQ ID NO:248 (encoding a XI of SEQ ID NO:96), and SEQ ID NO:249 (encoding a XI of SEQ ID NO:38). In various embodiments, the disclosure provides nucleic acids comprising nucleotide sequences having at least 70%, at least 75%, at least 80%, at least 85%, at least 90%, at least 93%, at least 95%, at least 96%, at least 98%, or at least 99% sequence identity, or having 100% sequence identity, to the nucleotide sequence of any one of SEQ ID NOs:238, 239, 244, 245, 246, 247, 248 and 249, or the portion of any of the foregoing sequences encoding a XI catalytic domain or dimerization domain.

4.3 Host Cells and Recombinant Expression

The disclosure also provides host cells transformed with a XI nucleic acid and recombinant host cells engineered to express XI polypeptides. The XI nucleic acid construct may be extrachromosomal, on a plasmid, which can be a low copy plasmid or a high copy plasmid. The nucleic acid construct may be maintained episomally and thus comprise a sequence for autonomous replication, such as an autosomal replication sequence. Alternatively, a XI nucleic acid may be integrated in one or more copies into the genome of the cell. Integration into the cell's genome may occur at random by non-homologous recombination but preferably, the nucleic acid construct may be integrated into the cell's genome by homologous recombination as is well known in the art. In certain embodiments, the host cell is bacterial or fungal (e.g., a yeast or a filamentous fungus).

Suitable host cells of the bacterial genera include, but are not limited to, cells of *Escherichia, Bacillus, Lactobacillus, Pseudomonas,* and *Streptomyces*. Suitable cells of bacterial species include, but are not limited to, cells of *Escherichia coli, Bacillus subtilis, Bacillus licheniformis, Lactobacillus brevis, Pseudomonas aeruginosa,* and *Streptomyces lividans*.

Suitable host cells of the genera of yeast include, but are not limited to, cells of *Saccharomyces, Kluyveromyces, Candida, Pichia, Schizosaccharomyces, Hansenula, Klockera, Schwanniomyces, Phaffia, Issatchenkia* and *Yarrowia*. In specific embodiments, the recombinant cell is a *S. cerevisiae, C. albicans, S. pombe, S. bulderi, S. barnetti, S. exiguus, S. uvarum, S. diastaticus, H. polymorpha, K. lactis, I. orientalis, K. marxianus, K. fragilis, P. pastoris, P. canadensis, K. marxianus* or *P. rhodozyma*. Exemplary yeast strains that are suitable for recombinant XI expression include, but are not limited to, Lallemand LYCC 6391, Lallemand LYCC 6939, Lallemand LYCC 6469, (all from Lallemand, Inc., Montreal, Canada); NRRL YB-1952 (ARS (NRRL) Collection, U.S. Department of Agriculture); and BY4741.

Suitable host cells of filamentous fungi include all filamentous forms of the subdivision Eumycotina. Suitable cells of filamentous fungal genera include, but are not limited to, cells of *Acremonium, Aspergillus, Aureobasidium, Bjerkandera, Ceriporiopsis, Chrysoporium, Coprinus, Coriolus, Corynascus, Chaetomium, Cryptococcus, Filobasidium, Fusarium, Gibberella, Humicola, Hypocrea, Magnaporthe, Mucor, Myceliophthora, Neocallimastix, Neurospora, Paecilomyces, Penicillium, Phanerochaete, Phlebia, Piromyces, Pleurotus, Scytaldium, Schizophyllum, Sporotrichum, Talaromyces, Thermoascus, Thielavia, Tolypocladium, Trametes,* and *Trichoderma*. In certain aspects, the recombinant cell is a *Trichoderma* sp. (e.g., *Trichoderma reesei*), *Penicillium* sp., *Humicola* sp. (e.g., *Humicola insolens*); *Aspergillus* sp. (e.g., *Aspergillus niger*), *Chrysosporium* sp., *Fusarium* sp., or *Hypocrea* sp. Suitable cells can also include cells of various anamorph and teleomorph forms of these filamentous fungal genera.

Suitable cells of filamentous fungal species include, but are not limited to, cells of *Aspergillus awamori, Aspergillus fumigatus, Aspergillus foetidus, Aspergillus japonicus, Aspergillus nidulans, Aspergillus niger, Aspergillus oryzae, Chrysosporium lucknowense, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Coprinus cinereus, Coriolus hirsutus, Humicola insolens, Humicola lanuginosa, Mucor miehei, Myceliophthora thermophila, Neurospora crassa, Neurospora intermedia, Penicillium purpurogenum, Penicillium canescens, Penicillium solitum, Penicillium funiculosum, Phanerochaete chrysosporium, Phlebia radiate, Pleurotus eryngii, Talaromyces flavus, Thielavia terrestris, Trametes villosa, Trametes versicolor, Trichoderma harzianum, Trichoderma koningii, Trichoderma longibrachiatum, Trichoderma reesei,* and *Trichoderma viride*.

Typically, for recombinant expression, the XI nucleic acid will be operably linked to one or more nucleic acid sequences capable of providing for or aiding the transcription and/or translation of the XI sequence, for example a promoter operable in the organism in which the XI is to be expressed. The promoters can be homologous or heterologous, and constitutive or inducible.

Preferably, the XI polypeptide is expressed in the cytosol and therefore lacks a mitochondrial or peroxisomal targeting signal.

Where recombinant expression in a filamentous fungal host is desired, the promoter can be a fungal promoter (including but not limited to a filamentous fungal promoter), a promoter operable in plant cells, a promoter operable in mammalian cells.

As described in U.S. provisional application No. 61/553,901, filed Oct. 31, 2011, the contents of which are hereby incorporated in their entireties, promoters that are constitutively active in mammalian cells (which can derived from a mammalian genome or the genome of a mammalian virus) are capable of eliciting high expression levels in filamentous fungi such as *Trichoderma reesei*. An exemplary promoter is the cytomegalovirus ("CMV") promoter.

As described in U.S. provisional application No. 61/553,897, filed Oct. 31, 2011, the contents of which are hereby incorporated in their entireties, promoters that are constitutively active in plant cells (which can derived from a plant genome or the genome of a plant virus) are capable of eliciting high expression levels in filamentous fungi such as *Trichoderma reesei*. Exemplary promoters are the cauliflower mosaic virus ("CaMV") 35S promoter or the *Commelina* yellow mottle virus ("CoYMV") promoter.

Mammalian, mammalian viral, plant and plant viral promoters can drive particularly high expression when the associated 5' UTR sequence (i.e., the sequence which begins at the transcription start site and ends one nucleotide (nt) before the start codon), normally associated with the mammalian or mammalian viral promoter is replaced by a fungal 5' UTR sequence.

The source of the 5' UTR can vary provided it is operable in the filamentous fungal cell. In various embodiments, the 5' UTR can be derived from a yeast gene or a filamentous fungal gene. The 5' UTR can be from the same species, one other component in the expression cassette (e.g., the promoter or the XI coding sequence), or from a different species. The 5' UTR can be from the same species as the filamentous fungal cell that the expression construct is intended to operate in. In an exemplary embodiment, the 5' UTR comprises a sequence corresponding to a fragment of a 5' UTR from a *T. reesei* glyceraldehyde-3-phosphate dehydrogenase (gpd). In a specific embodiment, the 5' UTR is not naturally associated with the CMV promoter Examples of other promoters that can be used include, but are not limited to, a cellulase promoter, a xylanase promoter, the 1818 promoter (previously identified as a highly expressed protein by EST mapping *Trichoderma*). For example, the promoter can suitably be a cellobiohydrolase, endoglucanase, or β-glucosidase promoter. A particularly suitable promoter can be, for example, a *T. reesei* cellobiohydrolase, endoglucanase, or β-glucosidase promoter. Non-limiting examples of promoters include a cbh1, cbh2, egl1, egl2, egl3, egl4, egl5, pki1, gpd1, xyn1, or xyn2 promoter.

For recombinant expression in yeast, suitable promoters for *S. cerevisiae* include the MFα1 promoter, galactose inducible promoters such as the GAL1, GAL7 and GAL10 promoters, glycolytic enzyme promoters including the TPI and PGK promoters, the TDH3 promoter, the TEF1 promoter, the TRP1 promoter, the CYCI promoter, the CUP1 promoter, the PHO5 promoter, the ADH1 promoter, and the HSP promoter. Promoters that are active at different stage of growth or production (e.g., idiophase or trophophase) can also be used (see, e.g., Puig et al., 1996, Biotechnology Letters 18(8):887-892; Puig and Pérez-Ortin, 2000, Systematic and Applied Microbiology 23(2): 300-303; Simon et al., 2001, Cell 106:697-708; Wittenberg and Reed, 2005, Oncogene 24:2746-2755). A suitable promoter in the genus *Pichia* sp. is the AOXI (methanol utilization) promoter.

The engineered host cells can be cultured in conventional nutrient media modified as appropriate for activating promoters, selecting transformants, or amplifying the nucleic acid sequence encoding the XI polypeptide. Culture conditions, such as temperature, pH and the like, are those previously used with the host cell selected for expression, and will be apparent to those skilled in the art. As noted, many references are available for the culture and production of many cells, including cells of bacterial and fungal origin. Cell culture media in general are set forth in Atlas and Parks (eds.), 1993, The Handbook of Microbiological Media, CRC Press, Boca Raton, Fla., which is incorporated herein by reference. For recombinant expression in filamentous fungal cells, the cells are cultured in a standard medium containing physiological salts and nutrients, such as described in Pourquie et al., 1988, Biochemistry and Genetics of Cellulose Degradation, eds. Aubert, et al., Academic Press, pp. 71-86; and Ilmen et al., 1997, Appl. Environ. Microbiol. 63:1298-1306. Culture conditions are also standard, e.g., cultures are incubated at 30° C. in shaker cultures or fermenters until desired levels of XI expression are achieved. Preferred culture conditions for a given filamentous fungus may be found in the scientific literature and/or from the source of the fungi such as the American Type Culture Collection (ATCC). After fungal growth has been established, the cells are exposed to conditions effective to cause or permit the expression of a XI.

In cases where a XI coding sequence is under the control of an inducible promoter, the inducing agent, e.g., a sugar, metal salt or antibiotics, is added to the medium at a concentration effective to induce XI expression.

In addition to recombinant expression of a XI polypeptide, a host cell of the disclosure may further include one or more genetic modifications that increase the cell's ability to utilize xylose as a substrate in a fermentation process. Exemplary additional modifications create one, two, three, four, five or even more of the following phenotypes: (a) increase in xylose transport into the cell; (b) increase in aerobic growth rate on xylose; (c) increase in xylulose kinase activity; (d) increase in flux through the pentose phosphate pathway into glycolysis, (e) modulating in aldose reductase activity, (f) decrease in sensitivity to catabolite repression, (g) increase in tolerance to biofuels, e.g., ethanol, (h) increase tolerance to intermediate production (for example xylitol), (i) increase in temperature tolerance, (j) osmolarity of organic acids, and (k) a reduced production of byproducts.

As illustrated below, a modification that results in one or more of the foregoing phenotypes can be a result of increasing or decreasing expression of an endogenous protein (e.g., by at least a factor of about 1.1, about 1.2, about 1.5, about 2, about 5, about 10 or about 20) or a result of introducing expression of a heterologous polypeptide. For avoidance of doubt, "decreasing" or "reducing" gene expression encompasses eliminating expression. Decreasing (or reducing) the expression of an endogenous protein can be accomplished by inactivating one or more (or all) endogenous copies of a gene in a cell. A gene can be inactivated by deletion of at least part of the gene or by disruption of the gene. This can be achieved by deleting the some or all of a gene coding sequence or regulatory sequence whose deletion results in a reduction of gene expression in the cell. Examples of modifications that increase xylose utilization or yield of fermentation product are described below.

Increasing Xylose Transport:

Xylose transport can be increased directly or indirectly. For example, a recombinant cell may include one or more genetic modifications that result in expression of a xylose transporter. Exemplary transporters include, but are not limited to GXF1, SUT1 and At6g59250 from *Candida intermedia, Pichia stipitis* (now renamed *Scheffersomyces stipitis*; the terms are used interchangeably herein) and *Arabidopsis thaliana*, respectively (Runquist et al., 2010, Biotechnol. Biofuels 3:5), as well as HXT4, HXT5, HXT7, GAL2, AGT1, and GXF2 (see, e.g., Matsushika et al., 2009, Appl. Microbiol. Biotechnol. 84:37-53). Other transporters include PsAraT, SUT2-4 and XUT1-5 from *P. stiptis*; GXS1 from *Candida intermedia*; XylHP and DEHAOD02167 from *Debaryomyces hansenii*; and YALI0C06424 from *Yarrowia lipolytica* (see, e.g., Young et al., 2011, Appl. Environ. Microbiol. 77:3311-3319). Xylose transport can also be increased by (over-) expression of low-affinity hexose transporters, which are capable of non-selectively transporting sugars, including xylose, into the cell once glucose levels are low (e.g., 0.2-1.0 g/1); and includes CgHXT1-CgHXT5 from *Colletotrichum graminicola*. The foregoing modifications can be made singly or in combinations of two, three or more modifications.

Increasing Xylulose Kinase Activity:

Xylulose kinase activity can be increased by overexpression of a xylulose kinase, e.g., xylulose kinase (XKS1; *Saccharomyces* genome database ("SGD") accession no. YGR194C) of *S. cerevisiae*, particularly where the recombinant cell is a yeast cell. In one embodiment, a *S. cerevisiae* cell is engineered to include at least 2 additional copies of xylulose kinase under the control of a strong constitutive promoter such as TDH3, TEF1 or PGK1. In another embodiment, overexpression of an endogenous xylulose kinase was engineered. This xylulose kinase having improved kinetic activities through the use of protein engineering techniques known by those skilled in the art.

Increasing Flux Through the Pentose Phosphate Pathway:

This can be achieved by increasing expression of one or more genes in the pentose phosphate pathway, for example *S. cerevisiae* transaldolase TAL1 (SGD accession no. YLR354C), transketolase TKL1 (SGD accession no. YPR074C), ribulose 5-phosphate epimerase RPE1 (SGD accession no. YJL121C) and ribose-5-phosphate ketoisomerase RKI1 (SGD accession no. YOR095C) and/or one or more genes to increase glycolytic flux, for example *S. cerevisiae* pyruvate kinase PYK1/CDC19 (SGD accession no. YAL038W), pyruvate decarboxylase PDC1 (SGD accession no. YLR044C), pyruvate decarboxylase PDC5 (SGD accession no. YLR134W), pyruvate decarboxylase PDC6 (SGD accession no. YGR087C), the alcohol dehydrogenases ADH1-5 (SGD accession nos. YOL086C, YMR303C, YMR083W, YGL256W, and YBR145W, respectively), and hexose kinase HXK1-2 (SGD accession nos. YFR053C and YGL253W, respectively). In one embodiment, the yeast cell has one additional copy each of TAL1, TKL1, RPE1 and RKI1 from *S. cerevisiae* under the control of strong constitutive promoters (e.g., PGK1, TDH3, TEF1); and may also include improvements to glycolytic flux (e.g., increased copies of genes such as PYK1, PDC1, PDC5, PDC6, ADH1-5) and glucose-6-phosphate and hexokinase. The foregoing modifications can be made singly or in combinations of two, three or more modifications.

Modulating Aldose Reductase Activity:

A recombinant cell can include one or more genetic modifications that increase or reduce (unspecific) aldose reductase (sometimes called aldo-keto reductase) activity. Aldose reductase activity can be reduced by one or more genetic modifications that reduce the expression of or inactivate a gene encoding an aldose reductase, for example *S. cerevisiae* GRE3 (SGD accession no. YHR104W).

In certain embodiments, GRE3 expression is reduced. In one aspect, the recombinant cell is a yeast cell in which the GRE3 gene is deleted. Deletion of GRE3 decreased xylitol yield by 49% and biomass production by 31%, but increased ethanol yield by 19% (Traff-Bjerre et al., 2004, Yeast 21:141-150). In another aspect, the recombinant cell is a yeast cell which has a reduction in expression of GRE3. Reducing GRE3 expression has been shown to result in a two-fold decrease in by-product (i.e., xylitol) formation and an associated improvement in ethanol yield (Traff et al., 2001, Appl. Environ. Microbiol. 67:5668-5674).

In another embodiment, the recombinant cell is a cell (optionally but not necessarily a yeast cell) in which GRE3 is overexpressed. In a study analyzing the effect of GRE3 overexpression in *S. cerevisiae* to investigate the effect on xylose utilization, an increase of about 30% in xylose consumption and about 120% in ethanol production was noted (Traff-Bjerre et al., 2004, Yeast 21:141-150).

Decreasing Xylose Reductase Activity:

A recombinant cell may include one or more genetic modifications that reduce xylose reductase activity. Xylose reductase activity can be reduced by one or more genetic modifications that reduce the expression of or inactivate a gene encoding a xylose reductase.

Decreasing Sensitivity to Catabolite Repression:

Glucose and other sugars, such as galactose or maltose, are able to cause carbon catabolite repression in Crabtree-positive yeast, such as *S. cerevisiae*. In one study, xylose was found to decrease the derepression of various enzymes of an engineered *S. cerevisiae* strain capable of xylose utilization by at least 10-fold in the presence of ethanol. Xylose also impaired the derepression of galactokinase and invertase (Belinchon & Gancedo, 2003, Arch. Microbiol. 180:293-297). In certain embodiments, in order to reduce catabolite sensitivity, yeast can include one or more genetic modifications that reduce expression of one or more of GRR1 (SGD accession no. YJR090C), the gene assigned SGD accession no. YLR042C, GAT1 (SGD accession no. YKR067W) and/or one or more genetic modifications that decrease expression of one or more of SNF1 (SGD accession no. YDR477W), SNF4 (SGD accession no. YGL115W), MIG1 (SGD accession no. YGL035C) and CRE1 (SGD accession no. YJL127C). In further embodiments, yeast can include one or more genetic modifications that result in overexpression of the pentose phosphate pathway enzymes. In yet further embodiments, yeast can include one or more genetic modifications that reduce expression of hexo-/glucokinase. In yet a further embodiment, yeast can include one or more genetic modifications that modulate the activity of one or more GATA factors, for example GAT1, DAL80 (SGD accession no. YKR034W), GZF3 (SGD accession no. YJL110C) and GLN3 (SGD accession no. YER040W). The foregoing modifications can be made singly or in combinations of two, three or more modifications.

Increasing Tolerance to Biofuels (e.g., Ethanol), Pathway Intermediates (e.g., Xylitol), Organic Acids and Temperature:

For efficient bioethanol production from lignocellulosic biomass, it is useful to improve cellular tolerance to toxic compounds released during the pretreatment of biomass. In one study, the gene encoding PHO13 (SGD accession no. YDL236W), a protein with alkaline phosphatase activity, was disrupted. This resulted in improved ethanol production from xylose in the presence of three major inhibitors (i.e., acetic acid, formic acid and furfural). Further, the specific ethanol productivity of the mutant in the presence of 90 mM furfural was four fold higher (Fujitomi et al., 2012, Biores. Tech., 111:161-166). Thus, in one embodiment, yeast has one or more genetic modifications that reduce PHO13 expression. In other embodiments, yeast, bacterial and fungal cells are evolved under selective conditions to identify strains that can withstand higher temperatures, higher levels of intermediates, higher levels of organic acids and/or higher levels of biofuels (e.g., ethanol). In yet other embodiments, yeast are engineered to reduce expression of FPS1 (SGD accession no. YLL043W); overexpress unsaturated lipid and ergosterol biosynthetic pathways; reduce expression of PHO13 and/or SSK2 (SGD accession no. YNR031C); modulate global transcription factor cAMP receptor protein, through increasing or decreasing expression; increase expression of MSN2 (SGD accession no. YMR037C), RCN1 (SGD accession no. YKL159C), RSA3 (SGD accession no. YLR221C), CDC19 and/or ADH1; or increase expression of Rice ASR1. The foregoing modifications can be made singly or in combinations of two, three or more modifications.

Reducing Production of Byproducts:

Glycerol is one of the main byproducts in C6 ethanol production. Reducing glycerol is desirable for increasing xylose utilization by yeast. Production of glycerol can be reduced by deleting the gene encoding the FPS1 channel protein, which mediates glycerol export, and GPD2 (SGD accession no. YOL059W), which encodes glycerol-3-phosphate dehydrogenase; optionally along with overexpression of GLT1 (SGD accession no. YDL171C) and GLN1 (SGD accession no. YPR035W). In one study, FPS1 and GPD2 were knocked-out in one *S. cerevisiae* strain, and in another were replaced by overexpression of GLT1 and GLN1, which encode glutamate synthase and glutamine synthetase, respectively. When grown under microaerobic conditions, these strains showed ethanol yield improvements of 13.17% and 6.66%, respectively. Conversely, glycerol, acetic acid and pyruvic acid were found to all decrease, with glycerol down 37.4% and 41.7%, respectively (Zhang and Chen, 2008, Chinese J. Chem. Eng. 16:620-625).

Production of glycerol can also be reduced by deleting the NADH-dependent glycerol-3-phosphate dehydrogenase 1 (GPD1; SGD accession no. YDL022W) and/or the NADPH-dependent glutamate dehydrogenase 1 (GDH1; SGD accession no. YOR375C). Sole deletion of GPD1 or GDH1 reduces glycerol production, and double deletion results in a 46.4% reduction of glycerol production as compared to wild-type *S. cerevisiae* (Kim et al., 2012, Bioproc. Biosys. Eng. 35:49-54). Deleting FPS1 can decrease production of glycerol for osmoregulatory reasons.

Reducing production of acetate can also increase xylose utilization. Deleting ALD6 (SGD accession no. YPL061W) can decrease production of acetate.

ADH2 can also be deleted to reduce or eliminate acetylaldehyde formation from ethanol and thereby increase ethanol yield.

The foregoing modifications to reduce byproduct formation can be made singly or in combinations of two, three or more modifications.

In addition to ethanol production, a recombinant XI-expressing cell of the disclosure can be suitable for the production of non-ethanolic fermentation products. Such non-ethanolic fermentation products include in principle any bulk or fine chemical that is producible by a eukaryotic microorganism such as a yeast or a filamentous fungus. Such fermentation products may be, for example, butanol, lactic acid, 3-hydroxy-propionic acid, acrylic acid, acetic acid, succinic acid, citric acid, malic acid, fumaric acid, itaconic acid, an amino acid, 1,3-propane-diol, ethylene, glycerol, a β-lactam antibiotic or a cephalosporin. A preferred modified host cell of the disclosure for production of non-ethanolic fermentation products is a host cell that contains a genetic modification that results in decreased alcohol dehydrogenase activity.

Cells expressing the XI polypeptides of the disclosure can be grown under batch, fed-batch or continuous fermentations conditions. Classical batch fermentation is a closed system, wherein the compositions of the medium is set at the beginning of the fermentation and is not subject to artificial alternations during the fermentation. A variation of the batch system is a fed-batch fermentation in which the substrate is added in increments as the fermentation progresses. Fed-batch systems are useful when catabolite repression is likely to inhibit the metabolism of the cells and where it is desirable to have limited amounts of substrate in the medium. Batch and fed-batch fermentations are common and well known in the art. Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in log phase growth. Continuous fermentation systems strive to maintain steady state growth conditions. Methods for modulating nutrients and growth factors for continuous fermentation processes as well as techniques for maximizing the rate of product formation are well known in the art of industrial microbiology.

4.4 Fermentation Methods

A further aspect the disclosure relates to fermentation processes in which the recombinant XI-expressing cells are used for the fermentation of carbon source comprising a source of xylose. Thus, in certain embodiments, the disclosure provides a process for producing a fermentation product by (a) fermenting a medium containing a source of xylose with a recombinant XI-expressing cell as defined herein above, under conditions in which the cell ferments xylose to the fermentation product, and optionally, (b) recovery of the fermentation product. In some embodiments, the fermentation product is an alcohol (e.g., ethanol, butanol, etc.), a fatty alcohol (e.g., a C8-C20 fatty alcohol), a fatty acid (e.g., a C8-C20 fatty acid), lactic acid, 3-hydroxypropionic acid, acrylic acid, acetic acid, succinic acid, citric acid, malic acid, fumaric acid, an amino acid, 1,3-propanediol, itaconic acid, ethylene, glycerol, and a β-lactam antibiotic such as Penicillin G or Penicillin V and fermentative derivatives thereof and cephalosporins. The fermentation process may be an aerobic or an anaerobic fermentation process.

In addition to a source of xylose the carbon source in the fermentation medium may also comprise a source of glucose. The source of xylose or glucose may be xylose or glucose as such or may be any carbohydrate oligo- or polymer comprising xylose or glucose units, such as e.g., lignocellulose, xylans, cellulose, starch and the like. Most microorganisms possess carbon catabolite repression that results in sequential consumption of mixed sugars derived from the lignocellulose, reducing the efficacy of the overall process. To increase the efficiency of fermentation, microorganisms that are capable of simultaneous consumption of mixed sugars (e.g., glucose and xylose) have been developed, for example by rendering them less sensitive to glucose repression (see, e.g., Kim et al., 2010, Appl. Microbiol. Biotechnol. 88:1077-85 and Ho et al., 1999, Adv. Biochem. Eng. Biotechnol. 65:163-92). Such cells can be used for recombinant XI expression and in the fermentation methods of the disclosure.

The fermentation process is preferably run at a temperature that is optimal for the recombinant XI-expressing cells. Thus, for most yeasts or fungal host cells, the fermentation process is performed at a temperature which is less than 38° C., unless temperature tolerant mutant strains are used, in which case the temperature may be higher. For most yeast or filamentous fungal host cells, the fermentation process is suitably performed at a temperature which is lower than 35° C., 33° C., 30° C. or 28° C. Optionally, the temperature is higher than 20° C., 22° C., or 25° C.

An exemplary process is a process for the production of ethanol, whereby the process comprises the steps of: (a) fermenting a medium containing a source of xylose with a transformed host cell as defined above, whereby the host cell ferments xylose to ethanol; and optionally, (b) recovery of the ethanol. The fermentation medium can also comprise a source of glucose that is also fermented to ethanol. The source of xylose can be sugars produced from biomass or agricultural wastes. Many processes for the production of monomeric sugars such as glucose generated from lignocellulose are well known, and are suitable for use herein. In brief, the cellulolytic material may be enzymatically, chemically, and/or physically hydrolyzed to a glucose and xylose containing fraction. Alternatively, the recombinant XI-expressing cells of the disclosure can be further transformed with one or more genes encoding for enzymes effective for hydrolysis of complex substrates such as lignocellulose, and include but are not limited to cellulases, hemicellulases, peroxidases, laccases, chitinases, proteases, and pectinases. The recombinant cells of the disclosure can then be fermented under anaerobic in the presence of glucose and xylose. Where the recombinant cell is a yeast cell, the fermentation techniques and conditions described for example, by Wyman (1994, Biores. Technol. 50:3-16) and Olsson and Hahn-Hagerdal (1996, Enzyme Microb. Technol. 18:312-331) can be used. After completion of the fermentation, the ethanol may be recovered and optionally purified or distilled. Solid residue containing lignin may be discarded or burned as a fuel.

The fermentation process may be run under aerobic and anaerobic conditions. In some embodiments, the process is carried out under microaerobic or oxygen limited conditions. Fermentation can be carried out in a batch, fed-batch, or continuous configuration within (bio)reactors.

5. EXAMPLES

5.1 Materials and Methods

5.1.1 Yeast Culture

Unless stated otherwise for a particular example, yeast transformants were grown in SC-ura media with about 2% glucose at 30° C. for about 24 hours. The media contains approx. 20 g agar, approx. 134 g BD Difco™ Yeast Nitrogen Base without amino acids (BD, Franklin Lakes, N.J., and approx. 2 g SC amino-acid mix containing about 85 mg of the following amino acids unless noted (quantity listed in parentheses): L-Adenine (21.0), L-Alanine, L-Arginine, L-Asparagine, L-Aspartic Acid, L-Cysteine, Glutamine, L-Glutamic Acid, Glycine, L-Histidine, Myo-Inositol, L-Isoleucine, L-Leucine (173.4), L-Lysine, L-Methionine, p-Aminobenzoic Acid (8.6), L-Phenylalanine, L-Proline, L-Serine, L-Threonine, L-Tryptophan, L-Tyrosine, L-Valine).

5.1.2 Xylose Isomerase Activity

XI activity in cell lysates was determined using a method based on that of Kersters-Hilderson et al., 1986, Enzyme Microb. Technol. 9:145-148, in which enzymatic conversion of xylose to xylulose by the XI is coupled with the enzymatic conversion of the product (xylulose) to xylitol via the enzyme sorbitol dehydrogenase (SDH). SDH activity requires the oxidation of NADH to $NAD^+$. The rate of oxidation of NADH is directly proportional to the rate of SDH conversion of D-xylulose to D-xylitol and is measured by the decrease in absorbance at 340 nm One unit of enzyme activity as measured by this assay is a decrease of 1 mole of NADH per minute under assay conditions. All reactions, solutions, plates, and spectrophotometer were equilibrated to about 35° C. prior to use. Assays were performed either on fresh lysates immediately after preparation or lysates that had been frozen at −20° C. immediately after preparation. Assays were performed using a BioTek Model: Synergy H1 Hybrid Reader spectrophotometer and 96-well plates (Corning, Model #Costar® #3598). All spectrophotometric readings were performed at 340 nm. A standard curve of NADH was generated with each assay with concentrations ranging from 0 to about 0.6 mM.

The reaction buffer used for experiments at pH 7.5 was about 100 mM Tris-HCl (pH 7.5). The assay mix was prepared as follows: reaction buffer to which was added about 10 mM $MgCl_2$, 0.15 mM NADH and 0.05 mg/ml SDH (Roche, catalog #50-720-3313). For experiments where activity was also measured at pH 6, the buffer was changed to about 100 mM sodium phosphate, pH 6. The assay mix for the entire experiment was then prepared as follows: about 10 mM $MgCl_2$, 1.2 mM NADH and 0.02 mg/ml SDH.

Any sample dilutions were performed using the reaction buffer as diluent. Reactions were set up by aliquotting about 90 μl of assay mix into each well of the plates. About 10 μl of each XI sample was added to the wells. The reactions were started by the addition of about 100 μl substrate solution (about 1 M D-xylose). Reactions were mixed and read immediately using kinetic assay mode for about 10 minutes. Volumetric activity (VA) units are in milli-absorbance (mA) units per minute per ml of lysate added to the reactions (mA/min/ml). Background VA rates of negative control wells (no enzyme added) were subtracted from VA of samples. Determination of fold improvement over positive control (FIOPC) was obtained by dividing the VA of the XI-samples by the VA observed for a control (*Orpinomyces* xylose isomerase, NCBI:169733248 (Op-XI)) expressed using the same host and expression vector. In some characterizations, the slope of an NADH standard curve was used to convert VA (mA/min) to μmole-NADH/min (or Units). If protein quantitation was performed, specific activities (SA) were calculated where the units for SA are (mole $NADH^+$/min/mg, or U/mg lysate protein). All activities listed (VA or SA) account for any dilutions, volumes of lysate added, and protein concentrations for the lysates assayed.

5.2 Example 2: Activity-Based Discovery Screen for Xylose Isomerases

Libraries used for the activity-based discovery ("ABD") screen were in the format of excised phagemids. These libraries were constructed as described in U.S. Pat. No.

6,280,926. Sources for these libraries were environmental rumen samples collected from the foregut of deceased herbivores.

An *Escherichia coli* screening strain was constructed to identify genes from the environmental libraries encoding xylose isomerase activity. Specifically, *E. coli* strain SEL700, a MG1655 derivative that is recA$^-$, phage lambda resistant and contains an F' plasmid, was complemented with plasmid pJC859, a derivative of pBR322 containing the *E. coli* recA gene (Kokjohn et al., 1987, J. Bacteriol. 169:1499-1508) to generate a wild-type recA phenotype.

Figure 1A:
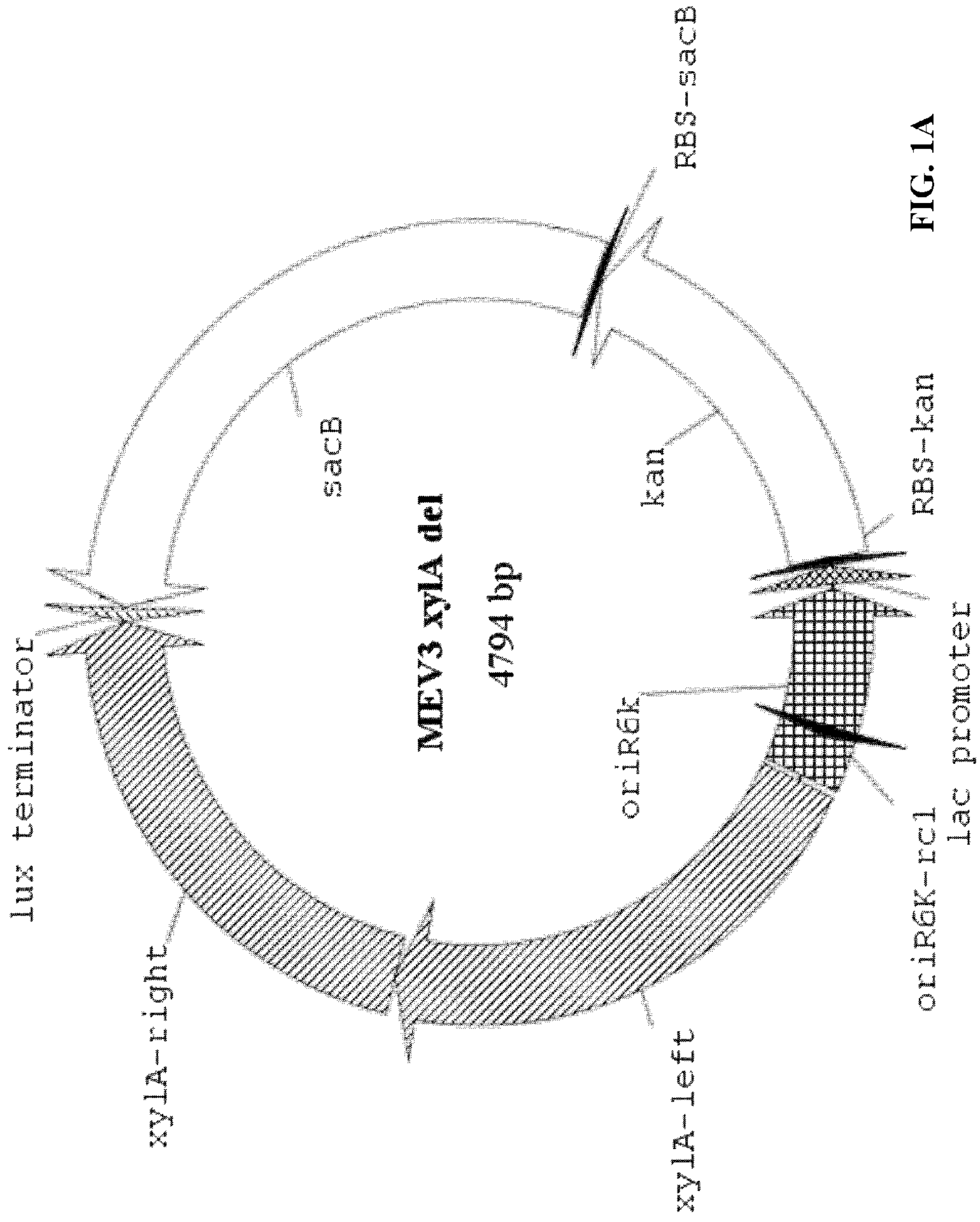
FIGS. 1A-1B are maps for the vector pMEV-ΔxylA (MEV3 xylA del) and PCR-BluntII-TOPO-xylA, respectively, used in the activity-based screen for XIs.

A two-step marker exchange procedure was then used to delete the entire coding sequence of the endogenous *xy/A* xylose isomerase gene. Briefly, pMEV3, a plasmid with a pir-dependent replicon (ori6RK) encoding kanamycin-resistance and the sacB levansucrase, was used as a vector for construction of the xylA deletion plasmid. A fragment of DNA containing the flanking regions of the xylA gene (0.7 kb of sequence 5' and 0.9 kb of sequence 3' of xylA) and containing BsaI restriction sites was generated by overlap extension PCR using primers, ligated to pMEV3 digested with BbsI, and transformed into *E. coli* by electroporation. Clones were confirmed by sequencing, resulting in plasmid pMEV3-ΔxylA (FIG. 1A).

Figure 2:
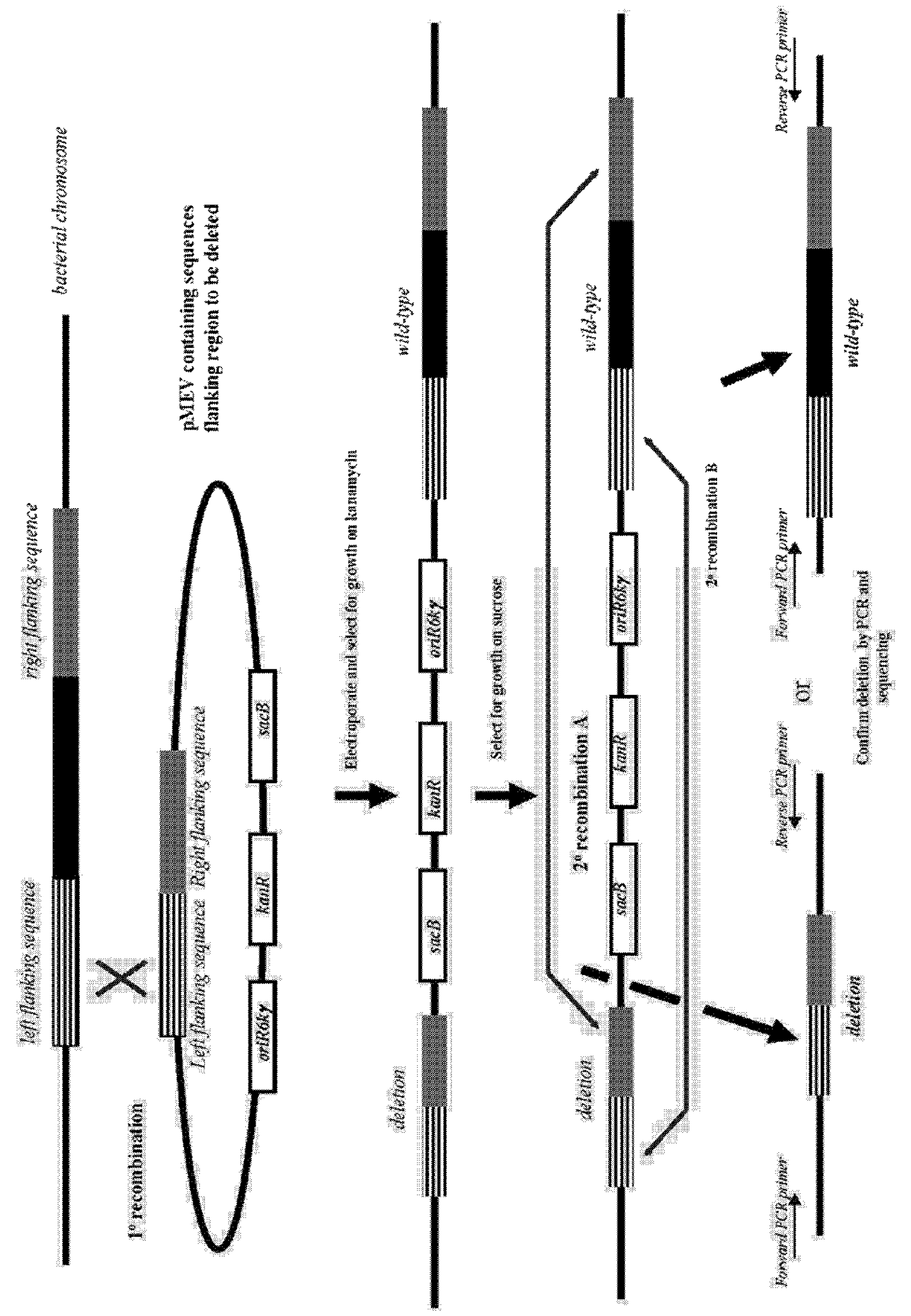
FIG. 2 illustrates the experimental strategy for the two-step marker exchange approach.

The pMEV3-ΔxylA plasmid was then transformed into strain *E. coli* strain SEL700 (MG1655 Δ$^r$, Δ(recA-srl)306, srl-301::Tn10-84(Tets), [F' proAB, lacI$^q$, ZΔM15, Tn10 (Tet$^r$)] pJC859). Single-crossover events were selected for by plating on LB agar plates containing kanamycin (final concentration, about 50 μg/ml). After confirmation of integration of pMEV3-ΔxylA on the chromosome, a second crossover event was selected for by growth on LB agar media containing sucrose (FIG. 2). Colonies displaying resistance to kanamycin and the ability to grow on sucrose were screened both by PCR characterization with primers flanking the *xy/A* gene to confirm gene deletion and by growth on a modified MacConkey media (ABD media), comprised of: MacConkey Agar Base (Difco™ #281810) (approximate formula per liter: Pancreatic Digest of Gelatin (17.0 g) Peptones (meat and casein) (3.0 g), Bile Salts No. 3 (1.5 g), Sodium Chloride (5.0 g), Agar (13.5 g), Neutral Red (0.03 g), Crystal Violet (1.0 g, Xylose (30.0 g) and Kanamycin (50 mg). The ABD media contained neutral red, a pH indicator that turns red at a pH <6.8. Colonies of mutants lacking xylA appeared white on this media while colonies with restored xylose metabolism ability appeared red in color due to the fermentation of xylose to xylulose, which lowered the pH of the media surrounding those colonies.

Following the successful deletion of xylA, the resulting strain was cured of pJC859 by the following method: The xylA deletion strain was grown for about 24 hours in LB media containing tetracycline at a final concentration, about 20 μg/ml, at around 37° C. The next day the cells were subcultured (1:100 dilution) into LB tetracycline (at the same concentration) media and incubated at about three different temperatures (30, 37, and 42° C.). Cells were passaged the same way as above for about two more days. Dilutions of the resulting cultures were plated on LB plates to isolate single colonies. Colonies were replica plated onto LB agar plates with and without Carbenicillin (at about 100 μg/ml, final concentration). Carbenicillin resistant colonies were deemed to still contain vector pJC859 whereas carbenicillin sensitive colonies were cured of pJC859, restoring the recA genotype of strain SEL700. This strain, SEL700 ΔxylA, was used for the ABD screening.

Figure 1B:
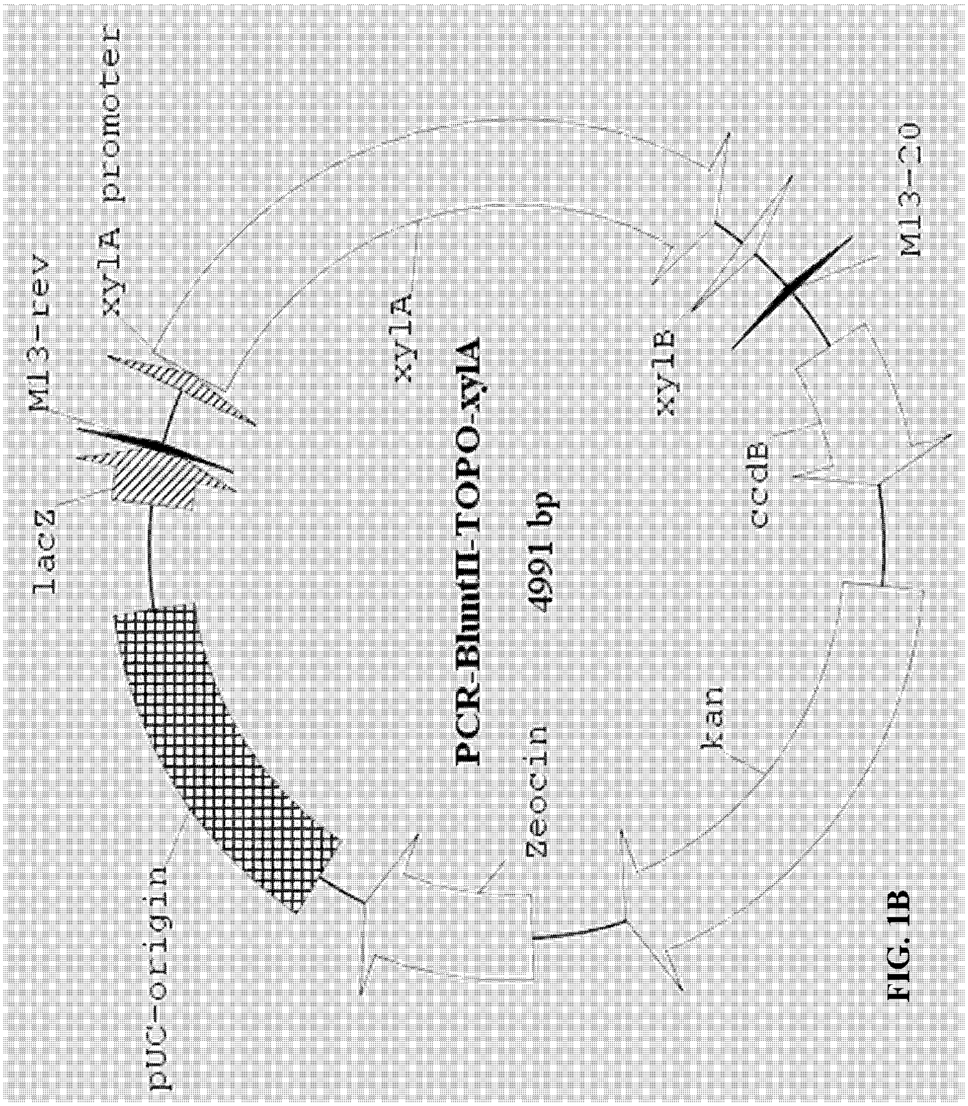

The ABD screening method was verified by creating a positive control strain by PCR amplification of the xylA gene from *E. coli* K12 and cloning into the PCR-BluntII TOPO vector (Invitrogen, Carlsbad, Calif.) using standard procedures. This vector (PCR-BluntII-TOPO-xylA, FIG. 1B) was then transformed into the screening strain (SEL700 ΔxylA). Complementation of the xylose phenotype was verified by growth of transformants on ABD media and appearance of red halos indicating xylose utilization.

The libraries were screened for XI activity by infecting strain SEL700 ΔxylA with the excised phagemid libraries. Infected cells were plated onto ABD media and only colonies with red "halos" (indicating xylose fermentation), were carried forward. Positives were purified to single colonies, and regrown on ABD media to confirm phenotype.

5.3 Example 2:Sequence-Based Discovery for Xylose Isomerases

Libraries used for sequence-based discovery ("SBD") were in the format of genomic DNA (gDNA) extractions. These libraries were constructed as described in U.S. Pat. No. 6,280,926. Sources for these libraries were samples collected from the guts of deceased herbivores.

XI genes often exist in conserved gene clusters (Dodd et al., 2011, Molecular Microbiol. 79:292-304). In order to obtain full length XI gene sequences from metagenomic samples, primers were designed to both upstream and downstream conserved DNA sequences found in several Bacteroides species, typically xylulose kinase and xylose permease, respectively. These flanking DNA sequences were obtained from public databases. Sample genomic DNA was extracted from eleven different animal rumen samples. Left flanking consensus primer has the sequence 5'-GCIGCICARGARGGNATYGTVTT-3' (SEQ ID NO:177) (this primer codes for the amino acid motif AAQEGIV(F) (SEQ ID NO:178)). Right flanking consensus primer has the sequence 5'-GCDATYTCNGCRATRTACATSGG-3' (SEQ ID NO:179) (this primer codes for the amino acid motif PMYIAEIA (SEQ ID NO:180)). PCR reactions were carried out using touchdown cycling conditions, and hot start Platinum® Taq DNA polymerase (Invitrogen, Carlsbad, Calif.). PCR products of expected size were purified and subcloned into pCR4-TOPO vector system (Invitrogen, Carlsbad, Calif.). Positive colonies from the TOPO-based PCR libraries were transformed into TOP10 (Invitrogen, Carlsbad, Calif.) and the transformants grown on LB agar plates with kanamycin (about 25 μg/ml final concentration). Resistant colonies were picked and inoculated into 2 columns each of a 96-deep well plate in about 1.2 ml LB kanamycin (25 μg/ml final concentration) media per well. Cultures were grown overnight at about 30° C. The next day plasmids were purified and inserts sequenced. Sequence analysis revealed multiple full length XI genes. Identification of putative ORFs was done by identifying start and stop codons for the longest protein coding region, and subsequent manual curation based on homology to published xylose isomerase DNA sequences.

5.4 Example 3: XI Sequence Analysis

Plasmids from both ABD and SBD screens were purified and vector inserts were sequenced using an ABI 3730xl DNA Analyzer and ABI BigDye® v3.1 cycle sequencing chemistry. Identification of putative ORFs was done by identifying start and stop codons for the longest protein coding region, and subsequent manual curation based on homology to published xylose isomerase DNA sequences. The XI ORF identified are set forth in Table 2 below, which indicates the sequences and source organism classification for each XI determined from either the ABD or SBD libraries as well as their assigned sequence identifiers. The putative catalytic domains (based on sequence alignments with other XIs) are underlined.

TABLE 2

| Clone No. | Class of organism | Type of Sequence | SEQ ID NO: | Sequence |
|---|---|---|---|---|
| 1754MI2_001 | *Bacteroidales* | DNA | 1 | ATGGCAGTTAAAGAATATTTCCCGGAGATAGGCAAGATCGCCTTTGAAGGAAAGGAGTCC<br>AAGAACCCTATGGCATTCCACTACTACAATCCAGAGCAGGTAGTAGCCGGAAAGAAAATG<br>AAAGATTGGTTCAAGTTCGCTATGGCATGGTGGCACACCCTCTGCGCTGAAGGTGGCGAC<br>CAGTTCGGTCCTGGTACCAAGAAATTCCCTTGGAACACAGGTGCAACTGCACTCGAAAGA<br>GCAAAGAACAAAATGGACGCAGGTTTCGAGATCATGAGCAAGCTCGGTATCGAGTATTTC<br>TGCTTCCACGATGTTGACCTTATCGACGAGGCTGACACTGTTGAAGAGTACGAGGCTAAC<br>ATGAAGGCTATCACAGCTTACGCAAAGGAGAAAATGGCCGCTACTGGCATCAAACTCCTC<br>TGGGGAACAGCCAATGTATTCGGCAACAAGAGATATATGAACGGCGCTTCTACCAACCCT<br>GACTTCAACGTGGCTGCACGCGCTATGCTCCAGATCAAGAACGCTATCGACGCAACTATC<br>GCTCTCGGTGGTGACTGCTATGTATTCTGGGGCGGCCGTGAGGGTTACATGAGCCTTCTC<br>AACACCGATATGAAGAGAGAGAAAGAGCACATGGCTACCATGCTTACCATGGCACGCGAC<br>TATGCTCGTTCTAAGGGCTTCAAGGGTACCTTCCTTATCGAGCCTAAGCCAATGGAGCCG<br>ATGAAGCACCAGTACGATGTCGATACTGAGACTGTCGTAGGTTTCCTCCGCGCCCATGGT<br>CTTGACAAGGACTTCAAGGTAAACATCGAGGTTAACCACGCTACTCTCGCAGGCCACACC<br>TTCGAGCACGAGCTCCAGTGCGCCGTTGACGCAGGCATGCTCGGAAGCATCGACGCCAAC<br>CGTGGTGACTACCAGAACGGCTGGGATACCGACCAGTTCCCTATCGACCTCTATGAGCTC<br>GTACAGGCTATGATGGTTATCATCAAGGGCGGCGGTCTCGTCGGCGGTACCAACTTCGAC<br>GCCAAGACCCGTCGTAACTCAACAGACCTCGAGGATATCTTCATCGCTCATGTATCCGGC<br>ATGGATGTCATGGCACGCGCTCTCCTCATCGCTGCTGACCTTCTCGAGAAATCTCCTATT<br>CCTGCAATGGTCAAGGAGCGTTACGCTTCCTACGACTCAGGCATGGGCAAGGACTTCGAG<br>AACGGCAAGCTTACTCTCGAGCAGGTTGTCGATTTCGCAAGAAAGAACGGCGAGCCTAAG<br>AGCACCAGCGGAAAGCAGGAGCTCTACGAGTCTATCGTCAATCTCTACATCTAA |
| 1754MI2_001 | *Bacteroidales* | Amino Acid | 2 | MAVKEYFPEIGKIAFEGKESKNPMAFHYYNPEQVVAGKKMKDWFKFAMAWWHTLCAEGGD<br>QFGPGTKKFPWNTGATALERAKNKMDAGFEIMSKLGIEYFCFHDVDLIDEADTVEEYEAN<br>MKAITAYAKEKMAATGIKLLWGTANVFGNKRYMNGASTNDDFNVAARAMLQIKNAIDATI<br>ALGGPCYVFWGGREGYMSLLNTDMKREKEHMATMLTMARDYARSKGFKGTFLIEPKPMEP<br>MKHQYDVDTETVVGFLRAHGLDKDFKVNIEVNHATLAGHTFEHELQCAVDAGMLGSIDAN<br>RGDYQNGWDTDQFPIDLYELVQAMMVIIKGGGLVGGTNFDAKTRRNSTDLEDIFIAHVSG<br>MDVMARALLIAADLLEKSPIPAMVKERYASYDSGMGKDFENGKLTLEQVVDFARKNGEPK<br>STSGKQELYESIVNLYI |
| 5586MI6_004 | *Bacteroidales* | DNA | 3 | ATGGCAAACAAAGAGTACTTCCCGGAGATCGGGAAAATCAAATTCGAAGGCAAGGATTCC<br>AAGAACCCGCTTGCATTCCATTATTACAATCCTGAGCAGGTCGTCTGCGGCAAGCCGATG<br>AAGGACTGGCTCAAGTTCGCTATGGCATGGTGGCACACCCTCTGCGCAGAGGGTAGCGAC<br>CAGTTCGGCGGACCCACCAAGTCATTCCCTTGGAACAAAGCTTCGGATCCCATCGCAAAG<br>GCCAAGCAGAAAGTCGACGCCGGTTTCGAGATCATGCAGAAGCTCGGTATCGGATACTAT<br>TGCTTCCACGATGTAGACCTCATCGACGAGCCCGCCACCATCGAGGAGTATGAGGCCGAT<br>CTCAAGGAGATCGTCGCTTACCTCAAGGAGAAGCAGGCCCAGACCGGCATCAAGCTCCTT<br>TGGGGCACCGCCAACGTCTTCGGTCACAAGCGGTACATGAACGGCGCCTCCACCAACCCT<br>GATTTCGACGTCGCAGCCCGCGCCATGGTCCAGATCAAGAACGCCATGGACGCCACCATC<br>GAGCTCGGCGGCGAGTGCTATGTCTTCTGGGGCGGCCGCGAGGGCTACATGAGCCTCCTC<br>AACACCGACATGAAGCGTGAGAAGCAGCATATGGCCACCATGCTCGGCATGGCCCGCGAC<br>TATGCACGCGGCAAGGGCTTCAAGGGCACCTTCCTCATCGAGCCCAAGCCCATGGAGCCG<br>ACCAAGCACCAGTATGACGTCGACACCGAGACCGTCATCGGTTTCCTCCGTGCCAACGGT<br>CTTGACAAGGACTTCAAGGTCAACATCGAGGTCAATCACGCCACCCTCGCCGGCCACACC<br>TTCGAGCATGAGCTCCAGTGCGCCGCCGATGCCGGTCTCCTCGGATCCATCGACGCCAAC<br>CGCGGCGACTATCAGAACGGCTGGGATACCGACCAGTTCCCGATCGACCTCTATGAGCTC<br>ACCCAGGCCATGATGGTCATCCTCAAGAATGGCGGCCTCGTCGGCGGTACCAACTTCGAC<br>GCCAAGACCCGTCGCAACTCCACCGACCTGGACGACATCATCATCGCCCACGTCAGCGGT<br>ATGGACATCATGGCACGCGCACTCCTCGTCGCTGCCGACGTCCTCACCAAGTCCGAGCTT<br>CCCAAGATGCTCAAGGAGCGTTACGCTTCCTTCGACTCCGGCAAGGGCAAGGAGTTCGAA<br>GAGGGCAAGCTCACTCTCGAGCAGGTCGTAGAGTACGCCAAGACCAAGGGCGAGCCCAAG<br>GCCACCAGCGGCAAGCAGGAGCTCTACGAGACCATCGTCAACATGTACATCTAA |
| 5586MI6_004 | *Bacteroidales* | Amino Acid | 4 | MANKEYFPEIGKIKFEGKDSKNPLAFHYYNPEQVVCGKPMKDWLKFAMAWWHTLCAEGSD<br>QFGGPTKSFPWNKASDPIAKAKQKVDAGFEIMQKLGIGYYCFHDVDLIDEPATIEEYEAD<br>LKEIVAYLKEKQAQTGIKLLWGTANVFGHKRYMNGASTNPDFDVAARAMVQIKNAMDATI<br>ELGGECYVFWGGREGYMSLLNTDMKREKQHMATMLGMARDYARGKGFKGTFLIEPKPMEP<br>TKHQYDVDTETVIGFLRANGLDKDFKVNIEVNHATLAGHTFEHELQCAADAGLLGSIDAN<br>RGDYQNGWDTDQFPIDLYELTQAMMVILKNGGLVGGTNFDAKTRRNSTDLDDIIIAHVSG<br>MDIMARALLVAADVLTKSELPKMLKERYASFDSGKGKEFEEGKLTLEQVVEYAKTKGEPK<br>ATSGKQELYETIVNMYI |
| 5749MI1_003 | *Bacteroidales* | DNA | 5 | ATGAATTTTTATAAAGGCGAAAAAGAATTCTTCCCCGGAATAGGAAAGATTCAGTTTGAA<br>GGACGCGAGTCAAAGAACCCGATGGCGTTTCATTATTATGACGAAAACAAGGTGGTGATG<br>GGTAAAACACTGAAGGATCATCTTCGTTTTGCAATGGCTTACTGGCATACGCTTTGTGCC<br>GAAGGGGGCGACCAGTTTGGCGGTGGTACGAAAACATTCCCCTGGAATGCTGCTGCCGAC<br>CCGATCAGCCGTGCCAAATATAAGATGGATGCAGCGTTCGAGTTTATGACAAAATGCAGC<br>ATCCCTTATTACTGTTTCCATGATGTGGACGTGGTGGACGAAGCTCCCACGCTGGCTCAG |

TABLE 2-continued

| Clone No. | Class of organism | Type of Sequence | SEQ ID NO: | Sequence |
|---|---|---|---|---|
| | | | | TTTGAAAAAGACCTTCATACGATGGTAGGCCATGCCAAAGGGCTTCAGCAGGCAACCGGA<br>AAAAAACTGTTATGGTCTACTGCCAACGTGTTCAGCAACAAACGCTATATGAACGGGGCT<br>GCCACTAATCCTGACTTCTCGGCCGTGGCTTGTGCCGGTACGCAGATCAAGAATGCGATC<br>GATGCCTGTATCGCGCTGGACGGTGAAAACTATGTGTTCTGGGGCGGACGTGAAGGATAT<br>ATGGGCTTGCTCAATACCGATATGAAACGCGAAAAAGACCATCTGGCCATGATGCTGACG<br>ATGGCACGCGACTATGGCCGCAAGAACGGTTTCAAAGGTACTTTCCTGATCGAGCCGAAA<br>CCGATGGAACCGACCAAGCATCAATATGATGTCGACTCGGAAACTGTAATCGGCTTCCTA<br>CGTCATTATGGCCTGGATAAAGACTTCGCCCTGAATATCGAAGTAAATCATGCAACCCTG<br>GCCGGACATACGTTCGAGCACGAATTGCAGGCTGCTGTCGATGCCGGTATGCTGTGCAGT<br>ATCGATGCCAACCGTGGTGACTACCAGAATGGCTGGGATACCGACCAATTCCCGATGGAC<br>ATCTACGAACTGACTCAGGCTTGGCTGGTCATTCTGCAAGGTGGTGGTCTGACAACCGGC<br>GGAACGAACTTCGATGCCAAGACCCGCCGCAACTCGACCGACCTGGACGATATCTTCCTG<br>GCTCATATAGGTGGTATGGATGCGTTTGCCCGTGCCCTGATCACGGCTGCTGCCATCCTT<br>GAAAACTCCGATTACACGAAGATGCGTGCCGAACGTTACACCAGCTTCGATGGTGGCGAA<br>GGCAAAGCGTTTGAAGACGGTAAACTTTCTCTGGAAGACCTGCGTACGATCGCTCTCCGC<br>GACGGAGAACCGAAGATGGTCAGCGGCAAACAGGAATTATATGAGATGATTCTCAATTTA<br>TACATATAA |
| 5749MI1_ 003 | *Bacteroidales* | Amino Acid | 6 | MNFYKGEKEFFPGIGKIQFEGRESKNPMAFHYYDENKVVMGKTLKDHLRFAMAYWHTLCA<br>EGGDQFGGGTKTFPWNAAADPISRAKYKMDAAFEFMTKCSIPYYCFHDVDVVDEAPTLAQ<br>FEKDLHTMVGHAKGLQQATGKKLLWSTANVFSNKRYMNGAATNPDFSAVACAGTQIKNAI<br>DACIALDGENYVFWGGREGYMGLLNTDMKREKDHLAMMLTMARDYGRKNGFKGTFLIEPK<br>PMEPTKHQYDVDSETVIGFLRHYGLDKPFALNIEVNHATLAGHTFEHELQAAVDAGMLCS<br>IDANRGDYQNGWDTDQFPMDIYELTQAWLVILQGGGLTTGGTNFDAKTRRNSTDLDDIFL<br>AHIGGMDAFARALITAAILENSDYTKMRAERYTSFDGGEGKAFEDGKLSLEDLRTIALR<br>DGEPKMVSGKQELYEMILNLYI |
| 5750MI1_ 003 | *Bacteroidales* | DNA | 7 | ATGAATTACTTTAAAGGTGAGAAAGAGTTCTTCCCGGGAATCGGGAAAATAGAGTTTGAA<br>GGACGTGAATCGAAGAATCCGATGGCTTTTCATTACTATGACGAGAACAAGGTTGTCATG<br>GGGAAGACCTTGAAGGACCATCTGCGTTTTGCGATGGCTTATTGGCATACGCTGTGTGCG<br>GAAGGCGCCGACCAGTTCGGCGGCGGGACGAAGGCATTTCCCTGGAATACCGGGGCGGAT<br>CGTATTTCCCGTGCCAAGTATAAGATGGATGCTGCTTTTGAGTTTATGACGAAATGTAAC<br>ATCCCGTACTATTGTTTCCATGATGTGGATGTGGTGGATGAAGCTCCGACACTGGCCGAA<br>TTTGAAAAAGACTTGCATACGATGGTCGAATATGCCAAGCAGCATCAGGAGGCAACCGGG<br>AAAAAACTGTTGTGGTCTACCGCCAATGTGTTCAGCAATAAACGTTATATGAACGGGGCT<br>GCCACAAATCCGTATTTCCCTGCTGTCGCTTGTGCGGGTACGCAGATCAAGAATGCTATC<br>GACGCTTGTATTGCCCTGGGCGGCGAAAACTATGTGTTCTGGGGCGGTCGTGAAGGGTAT<br>ATGAGCTTGTTGAACACCAATATGAAACGCGAAAAGGAACATCTCGCCATGATGTTGACG<br>ATGGCTCGCGATTATGCGCGTAAGAACGGCTTCAAAGGTACTTTCCTGGTAGAGCCTAAA<br>CCGATGGAACCGACCAAACATCAGTATGATGTGGACACAGAAACTGTTATCGGCTTCCTG<br>CGTCATTACGGCCTTGACAAGGACTTTGCCATCAACATCGAAGTGAATCATGCTACATTG<br>GCTGGACATACATTCGAACATGAGCTTCAGGCGGCTGCCGATGCCGGTATGCTGTGCAGC<br>ATCGACGCCAACCGCGGCGATTACCAGAATGGTTGGGACACGGATCAGTTCCCGGTCGAC<br>ATCTACGAACTGACACAGGCGTGGCTGGTTATCCTCGAAGCGGGTGGCCTGACTACCGGT<br>GGTACGAACTTCGACGCCAAGACGCGCCGCAACTCGACTGACCTGGACGATATCTTCCTG<br>GCACACATCGGTGGTATGGATTCGTTTGCCCGTGCTTTGATGGCGGCTGCCGATATATTG<br>GAACACTCCGATTACAAAAAGATGCGTGCCGAACGTTATGCCAGCTTCGATCAAGGCGAC<br>GGCAAGAAGTTCGAAGATGGTAAACTCCTTCTCGAGGACCTCCGCACCATCGCTCTTGCC<br>TCCGGCGAACCGAAGCAAATCAGCGGGAAACAGGAATTGTATGAAATGATTATCAACCAG<br>TACATTTAA |
| 5750MI1_ 003 | *Bacteroidales* | Amino Acid | 8 | MNYFKGEKEFFPGIGKIEFEGRESKNPMAFHYYDENKVVMGKTLKDHLRFAMAYWHTLCA<br>EGADQFGGGTKAFPWNTGADRISRAKYKMDAAFEFMTKCNIPYYCFHDVDVVDEAPTLAE<br>FEKDLHTMVEYAKQHQEATGKKLLWSTANVFSNKRYMNGAATNPYFPAVACAGTQIKNAI<br>DACIALGGENYVFWGGREGYMSLLNTNMKREKEHLAMMLTMARDYARKNGFKGTFLVEPK<br>PMEPTKHQYDVDTETVIGFLRHYGLDKPFAINIEVNHATLAGHTFEHELQAAADAGMLCS<br>IDANRGDYQNGWDTDQFPVDIYELTQAWLVILEAGGLTTGGTNFDAKTRRNSTDLDDIFL<br>AHIGGMDSFARALMAAADILEHSDYKKMRAERYASFDQGDGKKFEDGKLLLEDLRTIALA<br>SGEPKQISGKQELYEMIINQYI |
| 5750MI2_ 003 | *Bacteroidales* | DNA | 9 | ATGAATTATTTTAAAGGTGAAAAAGAGTTTTTCCCTGGAATCGGGAAAATAGAGTTTGAA<br>GGACGTGAGTCGAAGAATCCGATGGCTTTTCATTATTATGATGAAAACAAGGTCGTAATG<br>GGCAAGACCTTGAAAGATCACCTCCGCTTTGCAATGGCTTACTGGCATACGTTGTGCGCG<br>GAAGGCGCAGACCAGTTTGGCGGTGGCACAAAATCATTCCCCTGGAATACCGCAGCGGAT<br>CGTATTTCCCGCGCTAAATATAAAATGGATGCTGCTTTCGAGTTTATGACCAAGTGCAGT<br>ATCCCGTACTATTGTTTCCATGATGTGGACGTGGTGGACGAAGCTCCGGCACTGGCCGAA<br>TTTGAAAAGGACCTGCATACGATGGTGGGATTCGCCAAACAACACCAGGAAGCAACCGGA<br>AAGAAACTGTTGTGGTCTACAGCCAATGTATTCGGGCATAAACGTTATATGAACGGAGCG<br>GCTACCAATCarTATTTCCCGGCTGTCGCTTGTGCCGGTACGCAGATCAAGAATGCAATC<br>GACGCCTGTATCGAGCTGGGTGGAGAGAACTATGTATTCTGGGGCGGACGCGAAGGCTAC<br>ATGAGCCTGCTGAACACCAATATGAAACGTGAAAAGGATCATTTGGCCATGATGCTGACA<br>ATGGCACGCGATTATGCCCGCAAGAATGGTTTCAAGGGTACTTTCCTGGTGGAATCTAAG<br>CCGATGGAACCGACCAAACATCAGTATGACGCAGATACGGAAACCGTGATCGGCTTCCTG<br>CGCCACTATGGCCTCGACAAGGATTTCGCTATCAACATTGAAGTGAACCATGCTACATTG<br>GCCGGCCATACATTCGAACATGAACTTCAGGCTGCTGCCGATGCCGGTATGCTGTGCAGC<br>ATCGATGCAAATAGAGGCGACTATCAGAATGGTTGGGATACGGATCAGTTCCCCGTAGAC |

TABLE 2-continued

| Clone No. | Class of organism | Type of Sequence | SEQ ID NO: | Sequence |
|---|---|---|---|---|
| | | | | ATTTACGAACTGACACAGGCCTGGCTGGTTATCCTGGAAGCGGGCGGACTGACAACCGGA<br>GGTACGAACTTCGATGCGAAGACCCGTCGTAACTCGACTGACCTCGACGATATCTTCCTG<br>GCCCATATCGGCGGTATGGATTCGTTTGCACGTGCCTTGATGGCAGCTGCCGATATCCTG<br>GAACATTCTGATTACAAGAAGATGCGTGCCGAACGTTACGCCAGCTTCGACCAGGGCGAC<br>GGCAAGAAGTTCGAAGACGGCAAACTCCTTCTCGAAGACCTGCGCACAATTGCCCTTGCC<br>GGCGACGAACCGAAGCAGATCAGCGGCAAGCAGGAGTTGTATGAGATGATTATCAATCAG<br>TATATTTAA |
| 5750MI2_003 | *Bacteroidales* | Amino Acid | 10 | MNYFKGEKEFFPGIGKIEFEGRESKNPMAFHYYDENKVVMGKTLKDHLRFAMAYWHTLCA<br>EGADQFGGGTKSFPWNTAADRISRAKYKMDAAFEFMTKCSIPYYCFHDVDVVDEAPALAE<br>FEKDLHTMVGFAKQHQEATGKKLLWSTANVFGHKRYMNGAATNPYFPAVACAGTQIKNAI<br>DACIELGGENYVFWGGREGYMSLLNTNMKREKDHLAMMLTMARDYARKNGFKGTFLVESK<br>PMEPTKHQYDADTETVIGFLRHYGLDKDFAINIEVNHATLAGHTFEHELQAAADAGMLCS<br>IDANRGDYQNGWDTDQFPVDIYELTQAWLVILEAGGLTTGGTNFDAKTRRNSTDLDDIFL<br>AHIGGMDSFARALMAAADILEHSDYKKMRAERYASFDQGDGKKFEDGKLLLEDLRTIALA<br>GDEPKQISGKQELYEMIINQYI |
| 5586MI5_004 | *Bacteroides* | DNA | 11 | ATGAAACAGTATTTCCCGAACATCTCCGCCATCAAGTTTGAGGGCGTCGAGAGCAAGAAT<br>CCCCTGGCTTACCGCTACTACGACCGCGACCGCGTCGTCATGGGTAAGAAGATGAGCGAA<br>TGGTTTAAGTTCGCTATGTGCTGGTGGCACACCCTCTGCGCCGAGGGCTCCGATCAGTTC<br>GGTCCCGGCACAAAGACCTTCCCCTGGAACGCCGCCGCCGACCCCGTGCAGGCTGCCAAG<br>GACAAGGCCGACGCTGGCTTCGAGATCATGCAGAAACTCGGCATCGAGTACTACTGCTTC<br>CACGACGTTGACCTCGTGGCCGAGGCTCCCGACGTGGAGACCTACGAGAAGAACCTCAAG<br>GAGATCGTGGCTTATCTCAAGCAGAAACAGGCTGAGACGGGCATCAAGCTGCTCTGGGGC<br>ACTGCCAACGTCTTCGGACACAAGCGCTACATGAACGGAGCCTCCACGAACCCCGACTTC<br>GATGTCGTGGCACGCGCTATCGTGCAGATCAAGAACGCCATCGATGCTACCATCGAGCTG<br>GGCGGCACCAACTACGTCTTCTGGGGCGGTCGCGAAGGCTACATGAGCCTGCTCAACACC<br>GATATGAAGCGCGAGAAGGAGCACATGGCTACGATGTTGACGATGGCACGCGACTATGCC<br>CGTTCTAAGGGATTCAAGGGCACGTTCCTCATCGAACCCAAACCCATGGAACCCACGAAG<br>CATCAGTACGATGCGGACACCGAGACGGTCATCGGATTCCTCCGTGCTCATGGTCTCGAC<br>AAGGATTTCAAGGTCAACATCGAGGTCAACCACGCCACGCTGGCCGGACACACGTTCGAG<br>CATGAGCTGGCCTGCGCCGTAGACGCCGATATGCTCGGCAGCATCGATGCCAATCGCGGC<br>GACTATCAGAACGGATGGGACACCGACCAGTTCCCCATCGACCACTACGAACTCACGCAG<br>GCTATGCTGCAGATCATCCGCAACGGAGGTTTCAAGGACGGTGGCACCAATTTTGACGCT<br>AAGACGCGCCGCAACAGCACCGACCTCGAGGATATCTTCATCGCTCACGTAGCAGCCATG<br>GACGCCATGGCCCACGCCCTGTTGTCGGCTGCCGATATCATCGAGAAGTCGCCCATCTGC<br>ACGATGGTCAAGGAGCGTTACGCCAGCTTCGATGCCGGCGAAGGCAAGCGCTTCGAAGAA<br>GGCAAGATGACCCTCGAGGAAGCCTACGAGTATGGCAAGAAGGTCGGGGAGCCCAAGCAG<br>ACCAGCGGAAAGCAGGAGCTCTACGAAGCCATTGTCAATATGTATTGA |
| 5586MI5_004 | *Bacteroides* | Amino Acid | 12 | MKQYFPNISAIKFEGVESKNPLAYRYYDRDRVVMGKKMSEWFKFAMCWWHTLCAEGSDQF<br>GPGTKTFPWNAAADPVQAAKDKADAGFEIMQKLGIEYYCFHDVDLVAEAPDVETYEKNLK<br>EIVAYLKQKQAETGIKLLWGTANVFGHKRYMNGASTNPDFDVVARAIVQIKNAIDATIEL<br>GGTNYVFWGGREGYMSLLNTDMKREKEHMATMLTMARDYARSKGFKGTFLIEPKPMEPTK<br>HQYDADTETVIGFLRAHGLDKDFKVNIEVNHATLAGHTFEHELACAVDADMLGSIDANRG<br>DYQNGWDTDQFPIDHYELTQAMLQIIRNGGFKDGGTNFDAKTRRNSTDLEDIFIAHVAAM<br>DAMAHALLSAADIIEKSPICTMVKERYASFDAGEGKRFEEGKMTLEEAYEYGKKVGEPKQ<br>TSGKQELYEAIVNMY |
| 5586MI202_004 | *Bacteroides* | DNA | 13 | ATGGCAACAAAAGAGTATTTTCCCGGAATAGGAAAGATTAAATTCGAAGGTAAAGAGAGT<br>ATGAACCCGATGGCATATCGTTACTACGATGCTGAGAAGGTAATCATGGGTAAGAAGATG<br>AAAGATTGGTTGAAGTTTGCTATGGCTTGGTGGCACACTCTCTGCGCAGAAGGTGGTGAC<br>CAATTCGGTGGCGGAACGAAACAATTCCCTTGGAATGGTGACTCTGACGCTTTGCAAGCA<br>GCTAAAAATAAATTGGATGCAGGTTTCGAATTCATGCAGAAGATGGGTATCGAATACTAT<br>TGCTTCCACGATGTAGACCTGATTTCTGAAGGTGCAAGCATCGAAGAATACGAAGCTAAC<br>TTGAAAGCTATCGTAGCTTATGCAAAAGAAAAACAGGCTGAAACTGGTATCAAGCTGTTG<br>TGGGGTACTGCTAACGTATTCGGTCATGCACGTTATATGAACGGTGCTGCTACCAATCCT<br>GATTTCGACGTTGTAGCACGCGCTGCTGTTCAGATCAAGAACGCTATTGACGCTACTATC<br>GAACTGGGTGGTTCAAACTATGTATTCTGGGGCGGTCGCGAAGGTTACATGTCTTTGCTG<br>AACACTGACCAGAAACGTGAAAAAGAACACCTTGCAAAGATGTTGACTATCGCTCGTGAC<br>TATGCACGTGCTCGTGGCTTCAAAGGTACTTTCCTGATTGAGCCGAAACCGATGGAACCG<br>ACAAAACATCAGTATGATGTAGATACTGAAACAGTTATCGGCTTCCTGAAAGCTCACGGT<br>TTGGATAAGGATTTCAAAGTAAACATCGAGGTTAATCACGCAACTTTGGCTGGCCATACT<br>TTCGAACACGAACTGGCTGTAGCTGTTGACAACGGCATGTTAGGTTCTATCGACGCTAAC<br>CGTGGTGACTACCAGAACGGTTGGGATACTGACCAATTCCCTATCGATAACTACGAACTG<br>ACTCAAGCTATGATGCAGATCATCCGCAACGGTGGTTTGGGTAATGGCGGTACTAACTTC<br>GACGCTAAGACCCGTCGTAACTCTACCGACCTGGAAGATATCTTCATCGCTCACATTGCA<br>GGTATGGATGCTATGGCACGTGCTCTGGAAAGTGCAGCTAAATTACTGGAAGAATCTCCT<br>TATAAGAAAATGTTGGCTGATCGTTACGCATCATTCGACGGTGGCAAGGGTAAGGAATTC<br>GAAGAAGGCAAATTGTCTTTGGAAGATGTTGTAGCTTATGCGAAAGCTAACGGCGAACCG<br>AAGCAAACCAGCGGCAAGCAAGAATTGTATGAAGCAATCGTGAATATGTATTGCTAA |
| 5586MI202_004 | *Bacteroides* | Amino Acid | 14 | MATKEYFPGIGKIKFEGKESMNPMAYRYYDAEKVIMGKKMKDWLKFAMAWWHTLCAEGGD<br>QFGGGTKQFPWNGDSDALQAAKNKLDAGFEFMQKMGIETYCFHDVDLISEGASIEEYEAN<br>LKAIVAYAKEKQAETGIKLLWGTANVFGHARYMNGAATNPDFDVVARAAVQIKNAIDATI<br>ELGGSNYVFWGGREGYMSLLNTDQKREKEHLAKMLTIARDYARARGFKGTFLIEPKPMEP |

TABLE 2-continued

| Clone No. | Class of organism | Type of Sequence | SEQ ID NO: | Sequence |
|---|---|---|---|---|
| | | | | TKHQYDVDTETVIGFLKAHGLDKDFKVNIEVNHATLAGHTFEHELAVAVDNGMLGSIDAN<br>RGDYQNGWDTDQFPIDNYELTQAMMQIIRNGGLGNGGTNFDAKTRRNSTDLEDIFIAHIA<br>GMDAMARALESAAKLLEESPYKKMLADRYASFDGGKGKEFEEGKLSLEDVVAYAKANGEP<br>KQTSGKQELYEAIVNMYC |
| 5586MI211_003 | *Bacteroides* | DNA | 15 | ATGGCAAAAGAGTATTTTCCTGGCGTGAAAAAAATCCAGTTCGAGGGTAAGGACAGTAAG<br>AATCCAATGGCTTACCGTTATTATGATGCAGAGAAGGTCATCATGGGTAAGAAGATGAAG<br>GATTGGTTGAAGTTCGCTATGGCTTGGTGGCACACTTTGTGCGCTGAGGGCGCAGACCAG<br>TTCGGTGGCGGTACTAAGACTTTCCCTTGGAACGAAGGTGCAAACGCTTTGGAAGTTGCT<br>AAGAATAAGGCTGATGCTGGTTTCGAGATTATGGAGAAGCTTGGCATCGAGTACTACTGT<br>TTCCACGATGTAGACCTCGTTGAGGAGGCTGCAACTATCGAGGAGTATGAGGCTAACATG<br>AAGGCTATCGTTGCTTATCTTAAGGAGAAGCAGGCTGCTACTGGCAAGAAGCTTCTTTGG<br>GGTACTGCTAACGTATTCGGCAACAAGCGCTATATGAACGGTGCTTCTACAAACCCTGAC<br>TTCGACGTTGTTGCTCGCGCTTGTGTTCAGATTAAGAACGCTATCGACGCTACTATCGAA<br>CTTGGTGGTACAAACTACGTATTCTGGGGTGGCCGCGAGGGTTATATGAGCCTTCTTAAC<br>ACAGATATGAAGCGTGAGAAGGAGCACATGGCAACTATGCTTACTAAGGCTCGCGACTAC<br>GCTCGTTCAAAGGGCTTTACTGGTACATTCCTTATCGAGCCAAAGCCAATGGAACCATCA<br>AAGCATCAGTATGATGTTGATACTGAGACTGTTTGTGGTTTCTTGAGGGCTCACGGTCTT<br>GACAAGGACTTCAAGGTAAACATCGAGGTTAACCACGCTACTTTGGCTGGTCACACATTC<br>GAGCACGAGTTGGCTGCTGCTGTTGATAACGGTATGCTTGGCTCTATCGACGCTAACCGC<br>GGTGACTACCAGAACGGTTGGGATACTGACCAGTTCCCTATCGACAACTTCGAGCTTATT<br>CAGGCTATGATGCAGATTATCCGCAACGGTGGTCTTGGCAACGGTGGTACAAACTTCGAC<br>GCTAAGACTCGTCGTAACTCAACTGACCTTGAGGATATCTTCATCGCACACATCGCTGGT<br>ATGGATGCAATGGCTCGCGCTCTTGAGAACGCAGCAGACCTTTTGGAGAACTCTCCAATC<br>AAGAAGATGGTTGCTGAGCGTTACGCTTCATTCGACAGCGGCAAGGGTAAGGAGTTCGAG<br>GAAGGCAAGTTGAGCCTTGGGGACATCGTTGCTTATGCTAAGCAGAACGGTGAGCCTAAG<br>CAGACAAGCGGTAAGCAGGAGCTTTACGAGGCTATCGTAAACATGTACTGCTAA |
| 5586MI211_003 | *Bacteroides* | Amino Acid | 16 | MAKEYFPGVKKIQFEGKDSKNPMAYRYYDAEKVIMGKKMKDWLKFAMAWWHTLCAEGADQ<br>FGGGTKTFPWNEGANALEVAKNKADAGFEIMEKLGIEYYCFHDVDLVEEAATIEEYEANM<br>KAIVAYLKEKQAATGKKLLWGTANVFGNKRYMNGASTNPDFDVVARACVQIKNAIDATIE<br>LGGTNYVFWGGREGYMSLLNTDMKREKEHMATMLTKARDYARSKGFTGTFLIEPKPMEPS<br>KHQYDVDTETVCGFLRAHGLDKDFKVNIEVNHATLAGHTFEHELAAAVDNGMLGSIDANR<br>GDYQNGWDTDQFPIDNFELIQAMMQIIRNGGLGNGGTNFDAKTRRNSTDLEDIFIAHIAG<br>MDAMARALENAADLLENSPIKKMVAERYASFDSGKGKEFEEGKLSLGDIVAYAKQNGEPK<br>QTSGKQELYEAIVNMYC |
| 5606MI1_005 | *Bacteroides* | DNA | 17 | ATGGCGACAAAAGAATACTTTCCCGGAATAGGGAAAATCAAGTTTGAGGGTGTGAATAGC<br>TATAATCCGCTGGCATACAGATATTACGATGCCGAGCGCATAGTCCTTGGCAAGCCGATG<br>AAGGAGTGGCTCAAGTTTGCCATGGCATGGTGGCACACACTCTGCGCAGAGGGTGGCGAC<br>CAGTTTGGCGGCGGTACGAAGAATTTTCCCTGGAATGGAGATCCCGATCCGGTACAGGCC<br>GCAAAAAACAAAGTAGACGCCGGCTTCGAATTCATGACCAAGATGGGAATAGAGTATTTC<br>TGTTTCCACGACGTGGATCTCGTCAGCGAGGCAGCAACCATCGAGGAGTATGAGGCCAAC<br>CTGAAGGAAGTGGTGGGCTACATCAAGGAAAAGCAGGCCGAGACGGGGATCAAAAACCTC<br>TGGGGCACTGCCAACGTGTTCAGCCACGCGCGCTACATGAACGGAGCCGCCACCAACCCC<br>GACTTCGATGTAGTGGCCCGCGCAGCCGTGCAGATCAAGAATGCTATCGACGCCACGATA<br>GCCTTAGGTGGCACCAACTACGTGTTCTGGGGTGGCCGTGAAGGTTACATGAGCCTGCTC<br>AACACCGACCAGAAGCGCGAGAAGGAGCATCTGGCAATGATGCTCCGCATGGCCCGCGAC<br>TATGCGCGTGCAAAAGGCTTCACCGGCACCTTCCTTATCGAGCCCAAGCCGATGGAGCCC<br>ACCAAGCACCAGTATGATGTAGACACCGAGACTGTGATAGGCTTCCTCCGTGCCCACGGC<br>CTCGACAAGGACTTCAAGGTCAACATAGAGGTGAACCACGCCACCCTGGCCGGCCATACC<br>TTCGAGCATGAGCTGGCAGTGGCCGTGGACAACGGTATGCTCGGCAGCATCGACGCCAAC<br>CGCGGTGACTACCAGAACGGCTGGGATACCGACCAGTTCCCCATCGACAACTACGAGCTG<br>ACCCAGGCCATGATGCAGATAATACGCAACGGCGGCTTCGGCAACGGCGGATGCAACTTC<br>GACGCCAAGACACGCCGCAACTCCACCGACCTGGAGGATATCTTCATAGCCCACATAGCA<br>GGCATGGACGCCATGGCCCGCGCCCTGCTCAGCGCAGCAGAAGTGCTGGAGAAATCGCCC<br>TACAGGAAGATGCTCGCCGAGCGCTACGCACCGTTTGATGCCGGCCAGGGAAAGGCATTT<br>GAAGAGGGCGCAATGTCGCTCACCGACCTTGTGGAGTATGCCAAGGAGCATGGCGAGCCC<br>ACACAGACTTCCGGCAAGCAGGAACTCTATGAGGCAATCGTCAATATGTATTGCTAA |
| 5606MI1_005 | *Bacteroides* | Amino Acid | 18 | MATKEYFPGIGKIKFEGVNSYNPLAYRYYDAERIVLGKPMKEWLKFAMAWWHTLCAEGGD<br>QFGGGTKNFPWNGDPDPVQAAKNKVDAGFEFMTKMGIEYFCFHDVDLVSEAATIEEYEAN<br>LKEVVGYIKEKQAETGIKNLWGTANVFSHARYMNGAATNPDFDVVARAAVQIKNATDATI<br>ALGGTNYVFWGGREGYMSLLNTDQKREKEHLAMMLRMARDYARAKGFTGTFLIEPKPMEP<br>TKHQYDVDTETVIGFLRAHGLDKDFKVNIEVNHATLAGHTFEHELAVAVDNGMLGSIDAN<br>RGDYQNGWDTDQFPIDNYELTQAMMQIIRNGGFGNGGCNFDAKTRRNSTDLEDIFIAHIA<br>GMDAMARALLSAAEVLEKSPYRKMLAERYAPFDAGQGKAFEEGAMSLTDLVEYAKEHGEP<br>TQTSGKQELYEAIVNMYC |
| 5606MI2_003 | *Bacteroides* | DNA | 19 | ATGGCAACAAAGGAATATTTTCCCCATATAGGGAAGATCCAGTTCAAAGGCACGGAATCG<br>TACGATCCGATGTCGTATCGTTACTATGACGCCGAGCGCGTAGTTCTGGGCAAGCCCATG<br>AAGGAATGGCTGAAATTCGCCATGGCATGGTGGCACACATTGTGCGCCGAGGGCGGCGAC<br>CAGTTCGGCGGCGGAACGAAGAAGTTCCCCTGGAACGAGGGCGAGGACGCCATGACCATC<br>GCCAAGCAGAAGGCTGACGCCGGCTTCGAGATCATGCAGAAGCTCGGCATCGAGTATTTC<br>TGCTTCCACGACATCGACCTGATCGGCGACCTGGGCGACGACATCGAGGACTATGAGAAC<br>CGTATGCACGAAATCACCGCACACCTGAAGGAGAAGATGGCCGCCACGGGCATCAAGAAC |

TABLE 2-continued

| Clone No. | Class of organism | Type of Sequence | SEQ ID NO: | Sequence |
|---|---|---|---|---|
| | | | | CTGTGGGGCACTGCCAACGTGTTCGGCCACGCACGCTATATGAACGGCGCCGCCACCAAC<br>CCCGACTTCGACGTTGTGGCACGCGCATGTGTGCAGATCAAGAACGCCATCGACGCCACC<br>ATCGCTCTAGGCGGTACAAACTATGTATTCTGGGGCGGCCGCGAGGGCTACATGAGCCTG<br>CTGAACACCGACCAGAAGCGCGAGAAAGAGCACTTGGCTACCATGCTGACCATGGCACGC<br>GACTATGCCCGCGCCAATGGCTTCACCGGAACGTTCCTGATCGAGCCCAAACCCATGGAG<br>CCCAGCAAGCATCAGTATGATGTGGATACCGAGACCGTAATCGGCTTCCTGAAGGCCCAC<br>AACCTGGACAAGGACTTCAAGGTGAACATCGAGGTGAACCATGCCACTCTGGCCGGCCAC<br>ACATTCGAGCATGAGCTGGCAGTAGCCGTGGACAACGGCATGCTGGGCAGCATCGACGCC<br>AACCGCGGCGACTATCAGAACGGCTGGGACACCGACCAGTTCCCCATCGACAACTATGAG<br>CTGACCCAGGCCATGATGCAGATAATCCGCAACGGTGGCCTCGGCAACGGCGGTACCAAC<br>TTCGACGCCAAGACACGTCGCAACTCCACCGACCTGGACGACATCTTCATCGCTCACATC<br>GCCGGTATGGACGCTATGGCCCGCGCTCCGCTCAGCGCAGCCGACGTGCTTGAGAAGTCG<br>CCTTACAAGAAGATGCTGGCCGACCGCTACGCTTCATTCGACAGCGGCGAGGGCAAGAAG<br>TTCGAGGAAGGCAAGATGACTCTGGAGGATGTCGTGGCCTACGCCAAGAAGAATCCCGAA<br>CCCGCTCAGACCAGCGGCAAGCAGGAACTCTACGAGGCCATCATCAACATGTACGCCTGA |
| 5606MI2_<br>003 | *Bacteroides* | Amino Acid | 20 | MATKEYFPHIGKIQFKGTESTDPMSYRYTDAERVVLGKPMKEWLKFAMAWWHTLCAEGGD<br>QFGGGTKKFPWNEGEDAMTIAKQKADAGFEIMQKLGIEYFCFHDIDLIGDLGDDIEDYEN<br>RMHEITAHLKEKMAATGIKNLWGTANVFGHARTMNGAATNPDFDVVARACVQIKNAIDAT<br>IALGGTNYVFWGGREGYMSLLNTDQKREKEHLATMLTMARDTARANGFTGTFLIEPKPME<br>PSKHQYDVDTETVIGFLKAHNLDKDFKVNIEVNHATLAGHTFEHELAVAVDNGMLGSIDA<br>NRGDYQNGWDTDQFPIDNYELTQAMMQIIRNGGLGNGGTNFDAKTRRNSTDLDDIFIAHI<br>AGMDAMARAPLSAADVLEKSPTKKMLADRTASFDSGEGKKFEEGKMTLEDVVAYAKKNPE<br>PAQTSGKQELYEAIINMYA |
| 5610MI3_<br>003 | *Bacteroides* | DNA | 21 | ATGGCAACAAAAGAATTTTTTCCCGAGATTGGTAAAATCAAGTTTGAGGGCCGCGAAAGC<br>CGCAATCCCCTCGCATTCCGCTACTACGGCCCCGAGAAAGTCGTTCTTGGCAAGAAGATG<br>AAAGACTGGTTCAAGTTTGCGATGGCTTGGTGGCACACACTGTGCGCCCAGGGCACCGAC<br>CAGTTTGGTGGCGACACCAAGCAGTTTCCGTGGAACACTGCCAGTGACCCCATGCAGGCC<br>GCCAAGGATAAGGTGGATGCCGGATTTGAATTCATGACCAAGATGGGCATTGAGTACTTC<br>TGCTTCCACGATGTGGATCTCGTCGCCGAGGCCGCCACTGTCGAGGAGTATGAGGCTAAC<br>CTCAAGACCATCGTCGCCTACATCAAAGAGAAACAAGCCGAGACCGGCATCAAGAACCTG<br>TGGGGCACAGCCAACGTATTCGGACACAAACGCTACATGAACGGTGCCGCCACCAACCCC<br>GACTTTGATGTCGTGGCACGCGCCATCGTGCAAATCAAGAACGCCATCGACGCCACCATC<br>GAGTTGGGCGGCACGAGTTACGTCTTTTGGGGCGGCCGCGAGGGCCACATGAGCCTGCTC<br>AACACCGACCAGAAGCGCGAGAAGGAGCACCTTGCACGCATGCTGACCATGGCACGCGAC<br>TATGCCCGCGCACGTGGTTTCAACGGCACCTTCCTCATCGAGCCCAAGCCCATGGAGCCG<br>ACCAAGCACCAATATGATGTGGACACCGAGACCGTCATCGGTTTCCTGCGTGCCCATGGT<br>CTGGACAAGGACTTCAAGGTCAACATCGAGGTGAACCACGCTACACTGGCCGGACACACC<br>TTCGAGCGCGAACTGGCAGTGGCCGTCGACAACGGTCTACTCGGCTCAATCGACGCCAAC<br>CGTGGTGACTATCAGAATGGTTGGGACACCGATCAGTTCCCCATCGACCACTATGAGTTG<br>GTTCAGGGCATGTTGCAGATTATCCGCAATGGTGGTTTCACCGACGGTGGCACCAACTTC<br>GATGCCAAGACCCGCCGCAACTCGACCGACCTCGAGGACATCTTCATCGCCCACATCGCC<br>GCGATGGATGCCATGGCTCATGCGCTGGAGAGTGCTGCCTCCATCATCGAGGAGTCGCCC<br>TACTGCCAGATGGTCAAGGATCGCTATGCCTCATTTGACTCCGGCATCGGCAAGGACTTT<br>GAGGACGGCAAGTTGACACTGGAACAAGCCTACGAGTACGGTAAGCAAGTGGGCGAACCC<br>AAGCAGACCAGTGGCAAGCAAGAACTGTACGAGTCAATCATCAATATGTATTCCATTTAA |
| 5610MI3_<br>003 | *Bacteroides* | Amino Acid | 22 | MATKEFFPEIGKIKFEGRESRNPLAFRYYGPEKVVLGKKMKDWFKFAMAWWHTLCAQGTD<br>QFGGDTKQFPWNTASDDMQAAKDKVDAGFEFMTKMGIEYFCFHDVDLVAEAATVEEYEAN<br>LKTIVAYIKEKQAETGIKNLWGTANVFGHKRYMNGAATNPDFDVVARAIVQIKNAIDATI<br>ELGGTSYVFWGGREGHMSLLNTDQKREKEHLARMLTMARDYARARGFNGTFLIEPKPMEP<br>TKHQYEVETETVIGFLRAHGLDKEEKVNIEVNHATLAGHTFERELAVAVDNGLLGSIDAN<br>RGDYQNGWDTDQFPIDHYELVQGMLQIIRNGGFTDGGTNFDAKTRRNSTDLEDIFIAHIA<br>AMDAMAHALESAASIIEESPYCQMVKDRYASFDSGIGKDFEDGKLTLEQAYEYGKQVGEP<br>KQTSGKQELYESIINMYSI |
| 5749MI2_<br>004 | *Bacteroides* | DNA | 23 | ATGGCAACAAAAGAGTATTTTCCTGGTATAGGAAAGATTAAATTTGAAGGTAAAGAGAGT<br>AAGAATCCGATGGCATTCCGCTATTATGATGCCAATAAAGTAATCATGGGCAAGAAGATG<br>AGCGAGTGGCTGAAGTTTGCCATGGCTTGGTGGCACACATTGTGCGCCGAAGGTGGTGAC<br>CAGTTTGGTGGTGGAACAAAGACTTTCCCGTGGAACGATTCGGACAACGCCGTAGAAGCA<br>GCCAACCATAAAGTAGATGCCGGTTTTGAATTTATGCAGAAAATGGGCATCGAATACTAT<br>TGCTTCCATGATGTAGACCTCTGCACTGAAGCTGCTACCATTGAAGAATATGAAGCCAAT<br>CTGAAGGAAATAGTAGCCTATCCGAAACAGAAACAGGCTGAAACAGGTATCAAACTTCTG<br>TGGGGTACGGCAAATGTATTTGGTCACAAACGCTATATGAATGGTGCTGCTACCAATCCG<br>GATTTTGATGTAGTGGCTCGTGCTGCTGTACAGATTAAGAATGCGATAGACGCTACAATT<br>GAACTCGGTGGTAGCAACTACGTGTTCTGGGGCGGCCGTGAAGGTTATATGAGCTTGCTC<br>AATACAGACCAGAAACGTGAGAAAGAGCATTTGGCACAAATGTTGACCATGGCTCGTGAC<br>TATGCTCGTGCCAAAGGATTCAAGGGTACCTTCCTGGTTGAACCCAAACCGATGGAACCA<br>ACTAAACACCAGTATGATGTAGATACGGAAACTGTAATCGGCTTCCTCAAGGCTCATAAT<br>TTGGATAAGGATTTCAAGGTAAATATTGAAGTAAACCATGCTACATTGGCCGGTCATACT<br>TTTGAACACGAATTGGCTGTTGCCGTAGACAACGATATGCTTGGCTCTATCGATGCCAAC<br>CGCGGTGACTATCAGAACGGTTGGGATACTGACCAGTTCCCCATTGACAACTTCGAGCTT<br>ATCCAAGCCATGATGCAGATTATTCGCGGTGGTGGCTTCAAAGATGGTGGTACAAACTTC<br>GACGCTAAGACTCGTCGTAACTCTACCGACCTGGAAGATATTTTCATTGCACACATCGCT<br>GGTATGGATGCTATGGCACGTGCTTTGGAAAGTGCAGCCAAGTTGCTTGAGGAATCTCCT |

TABLE 2-continued

| Clone No. | Class of organism | Type of Sequence | SEQ ID NO: | Sequence |
|---|---|---|---|---|
| | | | | TATAAGAAAATGTTGGCTGACCGCTATGCATCGTTCGATAGTGGCAAAGGTAAGGAGTTT<br>GAAGAAGGCAAGCTGACATTGGAAGACGTTGTAGTTTATGCCAAGCAGAATGGCGAGCCT<br>AAACAGACCAGCGGTAAGCAGGAATTGTATGAGGCAATTGTAAAATATGTATGCCTGA |
| 5749MI2_ 004 | *Bacteroides* | Amino Acid | 24 | MATKEYFPGIGKIKFEGKESKNPMAFRYYDANKVIMGKKMSEWLKFAMAWWHTLCAEGGD<br>QFGGGTKTFPWNDSDNAVEAANHKVDAGFEFMQKMGIEYYCFHDVDLCTEAATIEEYEAN<br>LKEIVAYPKQKQAETGIKLLWGTANVFGHKRYMNGAATNPDFDVVARAAVQIKNAIDATI<br>ELGGSNYVFWGGREGYMSLLNTDQKREKEHLAQMLTMARDYARAKGFKGTFLVEPKPMEP<br>TKHQYDVDTETVIGFLKAHNLDKDFKVNIEVNHATLAGHTFEHELAVAVDNDMLGSIDAN<br>RGDYQNGWDTDQFPIDNFELIQAMMQIIRGGGFKDGGTNFDAKTRRNSTDLEDIFIAHIA<br>GMDAMARALESAAKLLEESPYKKMLADRYASFDSGKGKEFEEGKLTLEDVVVYAKQNGEP<br>KQTSGKQELYEAIVNMYA |
| 5750MI3_ 003 | *Bacteroides* | DNA | 25 | ATGGCAACAAAAGAGTATTTTCCTGGAATAGGAAAGATTAAATTTGAAGGAAAAGAGAGT<br>AAGAACCCGATGGCATTCCGTTGCTACGATGCAGAAAAAGTTATCATGGGTAAGAGAATG<br>AAAGATTGGTTGAAGTTTGCAATGGCGTGGTGGCATACACTTTGTGCAGAAGGCGGTGAC<br>CAATTCGGTGGCGGTACAAAGAGTTTCCCCCGGAACGACTATACTGATAAAATTCAGGCT<br>GCTAAAAACAAGATGGATGCCGGTTTTGAGTTTATGCAGAAGATGGGGATCGAATACTAT<br>TGTTTTCACGATGTAGACCTCTGCACGGAAGCTGATACCATTGAAGAATACGAAGCTAAT<br>TTGAAAGAAATCGTAGTTTACGCAAAGCAAAAGCAGGTAGAAACAGGTATCAAATTATTG<br>TGGGGTACTGCCAATGTATTCGGTCATGAACGCTATATGAATGGTGCGGCTACCAACCCA<br>GATTTTGATGTTGTAGCCCGTGCTGCTGTTCAGATTAAGAATGCAATTGATGCTACCATT<br>GAACTAGGTGGCTTAAACTATGTGTTCTGGGGTGGACGCGAAGGTTATATGTCTTTGCTG<br>AACACTGATCAGAAACGTGAGAAAGAACATCTTGCACAAATGCTGACCATTGCCCGTGAC<br>TATGCCCGTGCCCGTGGCTTCAAAGGTACATTCTTGGTTGAACCGAAACCGATGGAACCA<br>ACCAAACATCAATATGACGTAGATACAGAAACAGTTATCGGTTTTTTGAAAGCTCATGCT<br>TTGGATAAAGACTTTAAAGTAAATATTGAAGTAAATCATGCAACATTAGCCGGTCATACA<br>TTTGAACACGAACTGGCAGTGGCTGTCGACAACGGTATGCTGGGTTCTATTGACGCTAAT<br>CGTGGTGATTGTCAAAACGGTTGGGATACAGACCAATTTCCCATTGATAACTATGAACTG<br>ACTCAAGCCATGATGCAGATTATTCGTAACGGTGGTTTGGGCAATGGTGGTACGAATTTT<br>GACGCTAAAACTCGCCGTAATTCTACTGATCTTGGAGATATCTTCATTGCTCACATCGCA<br>GGTATGGATGCTATGGCACGTGCATTGGAAAGTGCGGCCAAGTTGTTGGAAGAATCTCCC<br>TATAAGAAGATGCTGGCAGAACGTTATGCATCCTTTGACAGCGGTAAGGGTAAAGAGTTT<br>GAAGAGGGTAAGTTGACCTTGGAGGATCTTGTTGCTTATGCAAAAGTCAATGGCGAACCG<br>AAACAAATCAGIGGTAAACAAGAATTGTATGAGGCAATTGTGAATATGTATTGCTAA |
| 5750MI3_ 003 | *Bacteroides* | Amino Acid | 26 | MATKEYFPGIGKIKFEGKESKNPMAFRCYDAEKVIMGKRMKDWLKFAMAWWHTLCAEGGD<br>QFGGGTKSFPRNDYTDKIQAAKNKMDAGFEFMQKMGIEYYCFHDVDLCTEADTIEEYEAN<br>LKEIVVYAKQKQVETGIKLLWGTANVFGHERYMNGAATNPDFDVVARAAVQIKNAIDATI<br>ELGGLNYVFWGGREGYMSLLNTDQKREKEHLAQMLTIARDYARARGFKGTFLVEPKPMEP<br>TKHQYDVDTETVIGFLKAHALDKDFKVNIEVNHATLAGHTFEHELAVAVDNGMLGSIDAN<br>RGDCQNGWDTDQFPIDNYELTQAMMQIIRNGGLGNGGTNFDAKTRRNSTDLGDIFIAHIA<br>GMDAMARALESAAKLLEESPYKKMLAERYASFDSGKGKEFEEGKLTLEDLVAYAKVNGEP<br>KQISGKQELYEAIVNMYC |
| 5750MI4_ 003 | *Bacteroides* | DNA | 27 | ATGGCAACAAAAGAGTATTTTCCCGGAATAGGAAAGATTAAATTCGAAGGTAAAGAGAGC<br>AAGAACCCGATGGCATTCCGTTATTACGATGCCGATAAAGTAATCATGGGTAAGAAAATG<br>AGCGAATGGCTGAAGTTCGCCATGGCATGGTGGCACACTCTTTGCGCAGAAGGTGGTGAC<br>CAGTTCGGTGGCGGAACAAAGAAATTCCCCTGGAACGGTGAGGCTGACAAGGTTCAGGCT<br>GCCAAGAACAAAATGGACGCCGGCTTTGAATTCATGCAGAAAATGGGTATCGAATACTAC<br>TGCTTCCACGATGTAGACCTCTGCGAAGAAGCCGAGACCATTGAAGAATACGAAGCCAAC<br>TTGAAGGAAATCGTAGCGTATGCCAAGCAGAAACAAGCAGAAACCGGCATCAAGCTGTTG<br>TGGGGTACTGCCAACGTATTCGGCCATGCCCGCTACATGAATGGTGCAGCCACCAACCCC<br>GATTTCGATGTTGTGGCACGTGCAGCCGTCCAAATCAAAAGCGCCATCGACGCTACTATC<br>GAGCTGGGAGGTTCGAACTATGTGTTCTGGGGCGGTCGCGAAGGCTACATGTCATTGCTG<br>AATACAGACCAGAAGCGTGAGAAAGAGCACCTCGCACAGATGTTGACCATCGCCCGCGAC<br>TATGCCCGTGCCCGTGGCTTCAAAGGTACCTTCCTGATTGAACCGAAACCGATGGAACCT<br>ACAAAACACCAGTATGATGTAGACACCGAAACCGTTATCGGCTTCTTGAAGGCCCACAAT<br>CTGGACAAAGATTTCAAGGTAAACATCGAAGTGAACCACGCTACTTTGGCGGGCCACACC<br>TTCGAGCACGAACTCGCAGTAGCCGTAGACAACGGTATGCTCGGCTCCATCGATGCCAAC<br>CGTGGTGACTACCAGAACGGCTGGGATACAGACCAGTTCCCCATTGACAACTTCGAACTG<br>ACCCAGGCAATGATGCAAATCATCCGTAACGGCGGCTTTGGCAATGGCGGTACAAACTTC<br>GATGCCAAGACCCGTCGTAACICCACCGACCTGGAAGACATCTTCATTGCCCACATCGCC<br>GGTATGGACGTGATGGCACGTGCACTGGAAAGTGCAGCCAAATTGCTTGAAGAGTCTCCT<br>TACAAGAAGATGCTTGCCGACCGCTATGCTTCCTTCGACAGTGGTAAAGGCAAGGAATTC<br>GAAGACGGCAAGCTGACACTGGAGGATTTGGCAGCTTACGCAAAAGCCAACGGTGAGCCG<br>AAACAGACCAGCGGCAAGCAGGGATTGTATGAGGCAATCGTAAATATGTACTGCTGA |
| 5750MI4_ 003 | *Bacteroides* | Amino Acid | 28 | MATKEYFPGIGKIKFEGKESKNPMAFRYYDADKVIMGKKMSEWLKFAMAWWHTLCAEGGD<br>QFGGGTKKFPWNGEADKVQAAKNKMDAGFEFMQKMGIEYYCFHDVDLCEEAETIEEYEAN<br>LKEIVAYAKQKQAETGIKLLWGTANVFGHARYMNGAATNPDFDVVARAAVQIKSAIDATI<br>ELGGSNYVFWGGREGYMSLLNTDQKREKEHLAQMLTIARDYARARGFKGTFLIEPKPMEP<br>TKHQYDVDTETVIGFLKAHNLDKDFKVNIEVNHATLAGHTFEHELAVAVDNGMLGSIDAN<br>RGDYQNGWDTDQFPIDNFELTQAMMQIIRNGGFGNGGTNFDAKTRRNSTDLEDIFIAHIA<br>GMDVMARALESAAKLLEESPYKKMLADRYASFDSGKGKEFEDGKLTLEDLAAYAKANGEP<br>KQTSGKQGLYEAIVNMYC |

TABLE 2-continued

| Clone No. | Class of organism | Type of Sequence | SEQ ID NO: | Sequence |
|---|---|---|---|---|
| 5751MI4_002 | *Bacteroides* | DNA | 29 | ATGACAAAAGAGTATTTTCCAACCATTGGTAAAATTCAGTTTGAAGGTAAAGAGAGTAAG<br>AATCCATTAGCATATCGTTATTACGATGCTAACAAAGTAATAATGGGTAAAAAGATGAGC<br>GAATGGCTCAAGTTTGCAATGGCATGGTGGCACACTTTGTGTGCTGAGGGTAGCGACCAG<br>TTTGGTCCTGGCACCAAGTCATTCCCATGGAACGCATCAACCGACCGTATGCAGGCTGCA<br>AAAGATAAGGCTGACGCAGGCTTCGAAATCATGCAAAAACTGGGCATCGAATACTACTGT<br>TTCCATGATGTTGACCTCATCGACCCAGCAGACGATATTCCAACATACGAAAAGAATCTC<br>AAGGAAATCGTTGCATACCTCAAGCAAAAACAGGCCGAGACAGGTATCAAATTGCTATGG<br>GGTACAGCTAACGTATTTGGCCACAAGCGTTATATGAACGGTGCATCTACCAATCCTGAC<br>TTTGACGTTGTTGCACGAGCTATCGTGCAAATCAAGAATGCTATCGATGCAACAATCGAA<br>CTGGGCGGCACGAACTACGTATTCTGGGGTGGTCGCGAAGGTTACATGTCACTGCTCAAC<br>ACCGACCAAAAGCGCGAGAAAGAGCACATGGCTACCATGTTAGGAATGGCACGTGACTAT<br>GCACGTTCTAAAGGCTTTACTGGTACTCTCCTTATCGAGCCAAAGCCTATGGAACCAACT<br>AAGCATCAATACGACGTCGATACAGAAACTGTTATTGGTTTCCTCAAAGCTCACGGATTA<br>GACAAGGACTTCAAGGTAAATATCGAAGTGAACCACGCTACATTGGCTGGCCATACCTTC<br>GAACATGAATTAGCATGTGCTGTTGATGCAGGTATGCTTGGTTCCATCGATGCTAACCGT<br>GGTGATATGCAGAATGGCTGGGATACAGATCAGTTCCCTATCAACAATTACGAGCTCGTT<br>CAGGCCATGATGCAGATTATCCGCAATGGTGGTTTCGGTAACGGTGGTACAAACTTCGAC<br>GCTAAGACACGTCGTAATTCAACCGATTTGGAAGACATCATCATTGCTCACGTTTCAGCT<br>ATGGATGCTATGGCACGTGCTCTTGAATGTGCTGCAGACATTCTTCAAAACTCACCTATT<br>CCACAGATGGTGGCCAACCGTTATGCAAGTTTTGACAAGGGTATAGGTAAAGATTTCGAA<br>GACGGCAAGCTCACCCTCGAGCAAGTATACGAATATGGTAAGACCGTCGGCGAACCAGCT<br>ATTACAAGCGGCAAACAGGAGCTCTACGAAGCTATCGTTAATATGTATTGCTGA |
| 5751MI4_002 | *Bacteroides* | Amino Acid | 30 | MTKEYFPTIGKIQFEGKESKNPLAYRYYDANKVIMGKKMSEWLKFAMAWWHTLCAEGSDQ<br>FGPGTKSFPWNASTDRMQAAKDKADAGFEIMQKLGIEYYCFHDVDLIDPADDIPTYEKNL<br>KEIVAYLKQKQAETGIKLLWGTANVFGHKRYMNGASTNPDFDVVARAIVQIKNAIDATIE<br>LGGTNYVFWGGREGYMSLLNTDQKREKEHMATMLGMARDYARSKGFTGTLLIEPKPMEPT<br>KHQYDVDTETVIGFLKAHGLDKDFKVNIEVNHATLAGHTFEHELACAVDAGMLGSIDANR<br>GDMQNGWDTDQFPINNYELVQAMMQIIRNGGFGNGGTNFDAKTRRNSTDLEDIIIAHVSA<br>MDAMARALECAADILQNSPIPQMVANRYASFDKGIGKDFEDGKLTLEQVYEYGKTVGEPA<br>ITSGKQELYEAIVNMYC |
| 5751MI5_003 | *Bacteroides* | DNA | 31 | ATGGCTAACAAAGAATTTTTCCCCGGTATTGGTAAAATCAAATTCGAAGGTAAAGAGAGC<br>AAGAACCCCATGGCATATCGTTACTACGATGCTGAGAAGGTAGTCCTTGGCAAGAATATG<br>AAAGACTGGTTCAAGTTTGCGATGGCTTGGTGGCACACATTGTGCGCCGAGGGTAGCGAC<br>CAGTTTGGTCCCGGCACTAAGTCTTTCCCCTGGAACACCGCAGAGTGCCCCATGCAGGCA<br>GCTAAGGACAAGGTTGACGCTGGCTTCGAGTTCATGACCAAGATGGGTATTGAATACTTC<br>TGCTTCCACGATGTAGACCTCGTTGCCGAGGCCGACACTGTTGAGGAGTACGAGGCTCGC<br>ATGAAGGAAATCGTTGCTTACATCAAGGAGAAGGTGGCCGAGACTGGCATCAAGAACCTG<br>TGGGGTACAGCTAACGTATTTGGCAACAAGCGCTACATGAACGGTGCTGCTACTAACCCC<br>GACTTTGACGTTGTGGCTCGCGCTATCGTTCAAATCAAGAACGCTATCGACGCTACTATC<br>GAGCTCGGTGGTACGTCATACGTATTCTGGGGCGGCCGCGAGGGTTACATGAGCCTCTTG<br>AACACCGACCAGAAGCGTGAGAAAGAGCACCTGGCTACTATGCTCACTATGGCACGCGAC<br>TACGCTCGCGCTAAGGGTTTCAAGGGTACATTCCTCATCGAGCCCAAGCCCATGGAGCCC<br>ACAAAGCACCAGTACGATGTTGACACTGAGACTGTAATCGGCTTCCTTAAGGCACACAAC<br>CTTGACAAGGACTTCAAGGTTAACATTGAGGTTAACCACGCAACTCTCGCTGGTCACACA<br>TTTGAGCACGAGCTCGCTTGTGCTGTTGACGCTGGCATGCTTGGCAGCATCGACGCTAAC<br>CGCGGTGACTACCAGAACGGCTGGGATACTGACCAATTCCCCATCGACAACTTCGACCTC<br>ACTCAAGCTATGCTCGAGATCATCCGCAACGATGGTTTCAAGGATGGTGGTACAAACTTC<br>GACGCTAAGACTCGCCGCAACAGCACCGACCTCGAGGATATCTTCATCGCACACATCGCT<br>GCTATGGACGCTATGGCACGTGCTCTCGAGAGCGCTGCTGCAGTACTCGAGGAGTCAGCT<br>CTGCCCCAAATGAAGAAGGACCGCTATGCATCGTTCGACGCTGGCATGGGTAAGGACTTC<br>GAGGACGGCAAGCTCACCCTGGAGCAAGTTTACGAGTATGGTAAGAAGGTGGGCGAGCCC<br>AAGCAGACTAGCGGCAAGCAAGAGCTGTATGAGGCTATCCTCAACATGTACGTATAA |
| 5751MI5_003 | *Bacteroides* | Amino Acid | 32 | MANKEFFPGIGKIKFEGKESKNPMAYRYYDAEKVVLGKNMKDWFKFAMAWWHTLCAEGSD<br>QFGPGTKSFPWNTAECPMQAAKDKVDAGFEFMTKMGIEYFCFHDVDLVAEADTVEEYEAR<br>MKEIVAYIKEKVAETGIKNLWGTANVFGNKRYMNGAATNPDFDVVARAIVQIKNAIDATI<br>ELGGTSYVFWGGREGYMSLLNTDQKREKEHLATMLTMARDYARAKGFKGTFLIEPKPMEP<br>TKHQYDVDTETVIGFLKAHNLDKDFKVNIEVNHATLAGHTFEHELACAVDAGMLGSIDAN<br>RGDYQNGWDTDQFPIDNFDLTQAMLEIIRNDGFKDGGTNFDAKTRRNSTDLEDIFIAHIA<br>AMDAMARALESAAAVLEESALPQMKKDRYASFDAGMGKDFEDGKLTLEQVYEYGKKVGEP<br>KQTSGKQELYEAILNMYV |
| 5751MI6_004 | *Bacteroides* | DNA | 33 | ATGGCTAACAAAGAATTTTTCCCAGGTATTGGTAAAATCAAATTCGAAGGCAAAGAAAGC<br>AAGAACCCCATGGCATATCGTCACTACGATGCCGAGAAGGTAGTCCTTGGTAAGAAGATG<br>AAGGACTGGTTCAAGTTTGCGATGGCTTGGTGGCACACTCTGTGCGCCGAGGGTAGCGAC<br>CAGTTCGGCCCCGTGACCAAGTCTTTCCCCTGGAACCAGGCCGAGTGCCCCATGCAGGCT<br>GCTAAGGACAAGGTTGACGCCGGCTTCGAGTTCATGACCAAGATGGGTATCGAATACTTC<br>TGTTTCCACGATGTAGACCTCGTTGCCGAGGCCGACACCGTTGAGGAGTACGAAGCTCGC<br>ATGAAGGAAATCGTGGCTTACATCAAGGAGAAGATGGCCGAGACCGGCATCAAGAACCTG<br>TGGGGTACAGCCAACGTATTCGGCAACAAGCGCTACATGAACGGTGCTGCCACCAACCCC<br>GACTTTGACGTTGTGGCTCGCGCAATCGTTCAGATCAAGAACGCCATCGACGCTACTATC<br>GAGCTCGGCGGTACCTCTTACGTGTTCTGGGGCGGCCGCGAGGGTTACATGACTCTCTTG<br>AACACCGACCAGAAGCGCGAGAAGGAGCACCTGGCTACCATGCTCACCATGGCTCGCGAC |

TABLE 2-continued

| Clone No. | Class of organism | Type of Sequence | SEQ ID NO: | Sequence |
|---|---|---|---|---|
| | | | | TATGCTCGCGCTAAGGGCTTCAAGGGTACATTCCTTATCGAGCCCAAGCCCATGGAGCCC<br>ACCAAGCACCAGTATGACGTGGATACCGAGACCGTTATCGGCTTCCTCAAGGCTCACGGC<br>CTGGACAAGGACTTCAAGGTGAACATCGAGGTTAACCATGCAACTCTCGCCGGCCACACA<br>TTCGAGCACGAACTCGCTTGCGCTGTTGACGCTGGCATGCTGGGCAGCATCGACGCTAAC<br>CGCGGCGACTACCAGAACGGCTGGGATACCGACCAGTTCCCCATCGACAACTTCGACCTC<br>ACTCAGGCTATGCTCGAGATCATCCGCAACGGTGGTTTCAAGGACGGTGGTACAAACTTC<br>GACGCTAAGACCCGTCGCAACAGCACCGATCTTGAGGACATCTTCATCGCTCACATCGCT<br>GCTATGGACGCAATGGCACGCGCGCTCGAGAGCGCTGCCGCTGTGCTCGAGCAGAGCCCC<br>CTTCCCCAGATGAAGAAAGACCGCTACGCATCGTTCGATGCCGGCATGGGCAAGGACTTC<br>GAGGACGGCAAGCTCACTCTGGAGCAGGTTTACGAGTATGGTAAGAAGGTAGGCGAGCCC<br>AAGCAGACCAGCGGCAAGCAGGAACTGTACGAGGCTATCCTCAACATGTATGTATAA |
| 5751MI6_ 004 | *Bacteroides* | Amino Acid | 34 | MANKEFFPGIGKIKFEGKESKNPMAYRHYDAEKVVLGKKMKDWFKFAMAWWHTLCAEGSD<br>QFGPVTKSFPWNQAECPMQAAKDKVDAGFEFMTKMGIEYFCFHDVDLVAEADTVEEYEAR<br>MKEIVAYIKEKMAETGIKNLWGTANVFGNKRYMNGAATNPDFDVVARAIVQIKNAIDATI<br>ELGGTSYVFWGGREGYMTLLNTDQKREKEHLATMLTMARDYARAKGFKGTFLIEPKPMEP<br>TKHQYDVDTETVIGFLKAHGLDKDFKVNIEVNHATLAGHTFEHELACAVDAGMLGSIDAN<br>RGDYQNGWDTDQFPIDNFDLTQAMLEIIRNGGFKDGGTNFDAKTRRNSTDLEDIFIAHIA<br>AMDAMARALESAAAVLEQSPLPQMKKDRYASFDAGMGKDFEDGKLTLEQVYEYGKKVGEP<br>KQTSGKQELYEAILNMYV |
| 5586MI22_ 003 | *Clostridiales* | DNA | 35 | ATGAAAGAATATTTTCCTATGACAAAAAAAGTTGAATATGAGGGCGCAGCATCTAAAAAT<br>CCATTTGCGTTTAAATACTATGATGCCGAAAGAATTATAGCAGGCAAGCCTATGAAAGAA<br>CATCTTAAATTTGCTATGAGTTGGTGGCATACACTTTGTGCGGGCGGTGCAGACCCATTT<br>GGCACAACAACTATGGACAGAACATACGGCGGACTTACCGACCCAATGGAAATTGCAAAG<br>GCAAAAGTAGATGCAGGCTTTGAGTTTATGCAAAAACTCGGTATAGAGTATTTTTGTTTT<br>CACGATGCGGATATTGCACCGGAAGGAAGCAGTTTTGTTGAAACAAAGAAAAACTTTTGG<br>GAAATAGTAGATTATATACAGCAAAAGATGAATGAAACAGGCATAAAGTTGCTTTGGGGT<br>ACTGCAAACTGCTTTAATGCTCCACGTTATATGCACGGTGCAGGAACATCATGCAATGCG<br>CACAGTTTTGCATATGCAGCCGCACAGATAAAAAATGCAATTGAAGCTACCGTTAAACTG<br>GGTGGAAAAGGCTATGTTTTCTGGGGCGGAAGAGAGGGTTATGAAACACTTCTCAATACG<br>GATATGGCACTTGAACTTGACAATATGGCAAGACTTATGCATATGGCAGTTGATTATGGC<br>AGAAGCATTGGTTTTGACGGTGATTTTTATATCGAACCAAAGCCAAAGGAACCAACAAAA<br>CATCAATATGACTTTGACTCGGCAACTGTTTTGGGATTTTTGAGAAAGTACGGTTTAGAT<br>AAGGATTTTAAACTTAATATAGAGGCAAATCATGCGACACTTGCAGGTCATACATTTGAA<br>CATGAATTGACTGTAGCGCGTATAAACGGTGCATTTGGCAGCATAGATGCAAATAGCGGC<br>GATCCCAATCTTGGCTGGGATACCGACCAATTCCCAACAGATGTTTATTCGGCAACCCTT<br>TGTATGCTTGAAGTGATAAGAGCAGGCGGCTTTACAAACGGAGGTCTTAATTTTGATGCA<br>AAGGTCAGAAGAGGCTCATTTACGTTTGATGACATTGTTTATGCATATATCAGCGGTATG<br>GACACTTTTGCGCTGGGTTTTATAAAGGCATATGAAATAATTGAGGACGGCAGAATAGAT<br>GAATTTGTAAAAGAAAGATACGCAAGCTATAATACAGGCATAGGCAAAGATATTATAGAT<br>GGAAAGGCAAGCCTTGAAAGTTTGGAAGAATATATTCTTTCAAATGATAATGTTGTAATG<br>CAAAGCGGCAGACAGGAATATCTTGAAACAGTTTTGAATAATATTTTGTTTAAAGCATAA |
| 5586MI22_ 003 | *Clostridiales* | Amino Acid | 36 | MKEYFPMTKKVEYEGAASKNDFAFKYYDAERIIAGKPMKEHLKFAMSWWHTLCAGGADPF<br>GTTTMDRTYGGLTDPMEIAKAKVDAGFEFMQKLGIEYFCFHDADIAPEGSSFVETKKNFW<br>EIVDYIQQKMNETGIKLLWGTANCFNAPRYMHGAGTSCNAHSFAYAAAQIKNAIEATVKL<br>GGKGYVFWGGREGYETLLNTDMALELDNMARLMHMAVDYGRSIGFDGDFYIEPKPKEPTK<br>HQYDFDSATVLGFLRKYGLDKDFKLNIEANHATLAGHTFEHELTVARINGAFGSIDANSG<br>DPNLGWDTDQFPTDVYSATLCMLEVIRAGGFTNGGLNFDAKVRRGSFTFDDIVYAYISGM<br>DTFALGFIKAYEIIEDGRIDEFVKERYASYNTGIGKDIIDGKASLESLEEYILSNDNVVM<br>QSGRQEYLETVLNNILFKA |
| 1753MI4_ 001 | *Firmicutes* | DNA | 37 | ATGAAAGAAATTTTCCCAAATATTCCTGAGATTAAATTCGAAGGAAAAGACAGCAAAAAT<br>CCTTTTGCTTTCCATTACTACAACCCAGACCAAATCATCTTAGGCAAACCAATGAAAGAA<br>CACCTCCCATTCGCTATGGCTTGGTGGCACAATCTTGGTGCAACAGGTGTTGATATGTTT<br>GGCGCTGGCCCAGCTGATAAGAGTTTCGGTGCTAAAGTTGGCACAATGGAACACGCTAAG<br>GCCAAAGTCGATGCCGGTTTCGAATTCATGAAGAAACTCGGTATCAGATATTTCTGCTTC<br>CATGATGTTGACTTAGTTCCAGAATGTGCAGATATCAAAGATACAAACAAAGAATTAGAT<br>GAAATCAGTGACTACATCTTAGAAAAGATGAAAGGCACAGATATTAAGTGTTTATGGGGC<br>ACCGCCAATATGTTCTCTAACCCACGCTTCTGCAATGGIGCGGGTTCCACAAACAGTGCG<br>GATGTCTTCGCTTTCGCCGCTGCTCAAGTTAAGAAAGCCTTAGATATCACCGTTAAATTA<br>GGTGGTAGGGGTTACGTCTTCTGGGGTGGTCGTGAAGGTTACGAAACATTACTCAATACA<br>GACGTTAAATTCGAACAAGAAAACATTGCTCGTTTAATGAAGATGGCTGTTGAATATGGC<br>CGTTCCATCGGTTTCAAAGGCGATTTCTATATCGAACCAAAACCAAAAGAACCAATGAAA<br>CACCAATATGACTTCGACGCCGCTACAGCTATTGGCTTCTTAAGAGCCCACGGCTTAGAC<br>AAAGACTTCAAGTTGAACATCGAAGCTAACCACGCTACATTAGCGGGTCATACATTCCAA<br>CACGATTTAAGAATCTCCGCCATTAATGGTATGTTAGGTTCTATCGATGCTAACCAAGGC<br>GATATGCTCTTAGGTTGGGATACAGACGAATTCCCATTTGATGTCTACAGTGCGACACAA<br>TGTATGTACGAAGTCTTAAAGAATGGTGGTCTTACAGGTGGTTTCAACTTTGACTCCAAA<br>ACACGTCGTCCATCCTACACAATGGAAGATATGTTCTTAGCCTATATCTTAGGTATGGAT<br>ACATTCGCTTTAGGTTTAATCAAAGCTGCTCAAATCATCGAAGATGGCCGTATTGATCAA<br>TTCATCGAAAAGAAATATTCTTCCTTCCGTGAAACAGAAATCGGTCAAAAGATCTTAAAC<br>AACAAGACAAGCTTAAAAGAATTATCCGATTACGCTTGCAAGATGGGTGCTCCAGAACTT<br>CCAGGTAGTGGTCGTCAAGAAATGCTCGAAGCCATCGTTAACGATGTCTTATTCGGCAAG<br>TAA |

TABLE 2-continued

| Clone No. | Class of organism | Type of Sequence | SEQ ID NO: | Sequence |
|---|---|---|---|---|
| 1753MI4_ 001 | *Firmicutes* | Amino Acid | 38 | MKEIFPNIPEIKFEGKDSKNPFAFHYYNPDQIILGKPMKEHLPFAMAWWHNLGATGVDMF<br>GAGPADKSFGAKVGTMEHAKAKVDAGFEFMKKLGIRYFCFHDVDLVPECADIKDTNKELD<br>EISDYILEKMKGTDIKCLWGTANMFSNPRFCNGAGSTNSADVFAFAAAQVKKALDITVKL<br>GGRGYVFWGGREGYETLLNTDVKFEQENIARLMKMAVEYGRSIGFKGDFYIEPKPKEPMK<br>HQYDFDAATAIGFLRAHGLDKDFKLNIEANHATLAGHTFQHDLRISAINGMLGSIDANQG<br>DMLLGWDTDEFPFDVYSATQCMYEVLKNGGLTGGFNFDSKTRRPSYTMEDMFLAYILGMD<br>TFALGLIKAAQIIEDGRIDQFIEKKYSSFRETEIGQKILNNKTSLKELSDYACKMGAPEL<br>PGSGRQEMLEAIVNDVLFGK |
| 1753MI6_ 001 | *Firmicutes* | DNA | 39 | ATGAAAGAAATTTTCCCAAATATTCCTGAGATTAAATTCGAAGGAAAAGACAGCAAAAAT<br>CCTTTTGCTTTCCATTACTACAACCCAGACCAAATCATCTTAGGTAAACCAATGAAAGAA<br>CACCTCCCATTCGCTATGGCTTGGTGGCACAATCTTGGTGCAACAGGTGTTGATATGTTT<br>GGCGCTGGCCCAGCTGATAAGAGTTTCGGTGCTAAAGTTGGCACAATGGAACACGCTAAG<br>GCCAAAGTCGATGCCGGTTTCGAATTCATGAAGAAACTTGGTATCAGATATTTCTGCTTC<br>CATGATGTTGACTTAGTTCCAGAATGTGCAGATATCAAAGATACAAACAAAGAATTAGAT<br>GAAATCAGTGACTACATCTTAGAAAAGATGAAAGGCACAGATATCAAGTGTTTATGGGGC<br>ACCGCCAATATGTTCTCTAACCCACGTTTCTGCAATGGTGCGGGTTCCACAAACAGTGCG<br>GATGTCTTCGCTTTCGCCGCTGCTCAAGTTAAGAAAGCCTTAGATATCACCGTTAAATTA<br>GGTGGTAGGGGTTACGTCTTCTGGGGTGGTCGTGAAGGTTACGAAACATTACTCAATACA<br>GACGTTAAATTCGAACAAGAAAACATTGCTCGTTTAATGAAGATGGCTGTTGAATATGGC<br>CGTTCCATCGGTTTCAAAGGCGATTTCTATATCGAACCAAAACCAAAAGAACCAATGAAA<br>CACCAATATGACTTCGACGCCGCTACAGCTATTGGCTTCTTAAGAGCCCACGGCTTAGAC<br>AAAGACTTCAAGTTGAACATCGAAGCTAACCACGCTACATTAGCGGGTCATACATTCCAA<br>CACGATTTAAGAATCTCCGCCATTAATGGTATGTTAGGTTCTATCGATGCTAACCAAGGC<br>GATATGCTCTTAGGTTGGGATACAGACGAATTCCCATTTGATGTCTACAGTGCGACACAA<br>TGTATGTACGAAGTCTTAAAGAATGGTGGTCTTACAGGTGGTTTCAACTTTGACTCCAAA<br>ACACGTCGTCCATCCTACACAATGGAAGATATGTTCTTAGCCTATATCTTAGGTATGGAT<br>ACATTCGCTTTAGGTTTAATCAAAGCTGCTCAAATCATCGAAGATGGCCGTATTGATCAA<br>TTCATCGAAAAGAAATATTCTTCCTTCCGTGAAACAGAAATCGGTCAAAAGATCTTAAAC<br>AACAAGACAAGCTTAAAAGAATTATCCGATTACGCTTGCAAGATGGGTGCTCCAGAACTT<br>CCAGGTAGTGGTCGTCAAGAAATGCTCGAAGCCATCGTTAACGATGTCTTATTCGGCAAG<br>TAA |
| 1753MI6_ 001 | *Firmicutes* | Amino Acid | 40 | MKEIFPNIPEIKFEGKDSKNPFAFHYYNPDQIILGKDMKEHLPFAMAWWHNLGATGVDMF<br>GAGPADKSFGAKVGTMEHAKAKVDAGFEFMKKLGIRYFCFHDVDLVPECADIKDTNKELD<br>EISDYILEKMKGTDIKCLWGTANMFSNPRFCNGAGSTNSADVFAFAAAQVKKALDITVKL<br>GGRGYVFWGGREGYETLLNTDVKFEQENIARLMKMAVEYGRSIGFKGDFYIEPKPKEPMK<br>HQYDFDAATAIGFLRAHGLDKDFKLNIEANHATLAGHTFQHDLRISAINGMLGSIDANQG<br>DMLLGWDTDEFPFDVYSATQCMYEVLKNGGLTGGFNFDSKTRRDSYTMEDMFLAYILGMD<br>TFALGLIKAAQIIEDGRIDQFIEKKYSSFRETEIGQKILNNKTSLKELSDYACKMGAPEL<br>PGSGRQEMLEAIVNDVLFGK |
| 1753MI35_ 004 | *Firmicutes* | DNA | 41 | ATGGAATATTTCCCTTTCGTCAAATCGGTCCAATACAAGGGACCAACCTCAACTGAACCA<br>TTCGCTTTCAAGTACTACGATGCCAACCGTGTCGTTCTTGGAAAACCAATGAAAGAATGG<br>ATGCCATTCGCTATGGCTTGGTGGCACAACCTCGGCGCTGCCGGTACCGACATGTTCGGC<br>GGCAACACCATGGACAAGTCCTGGGGAGTCGATAAAGAAAAAGACCCAATGGGCTATGCC<br>AAAGCCAAAGTTGATGCCGGCTTCGAATTCATGCAGAAGATGGGCATCGAATACTACTGC<br>TTCCACGATGTCGACCTCGTCCCAGAGTGCGACGACATCACCGTTATGTACCAGAGACTC<br>GATGAGATCGGTGATTACCTTCTCAAGAAACAGAAGGAAACCGGTATCAAGCTTCTTTGG<br>TCAACCGCCAATGCCTTCGGACACCGCCGTTTCATGAACGGTGCTGGTTCCAGCAACTCC<br>GCCGAAGTCTATTGCTTCGCCGCCGCCCAGATCAAGAAAGCTCTTGAGCTCTGCGTCAAA<br>CTCGGTGGCAAAGGCTATGTCTTCTGGGGTGGACGTGAAGGCTACGAAACCCTTCTCAAC<br>ACCGACATGAAGTTCGAACAAGAGAACATCGCCAACCTTATGAGATGCGCCCGTGACTAC<br>GGCCGCAAGATCGGTTTCAAAGGCGACTTCTACATCGAACCAAAACCAAAAGAGCCAACA<br>AAGCATCAGTATGACTTCGACGCCGCTACCGCCATCGGATTCCTCCGTCAGTACGGTCTC<br>GACAAAGACTTCAAGATGAACATCGAAGCCAACCACGCTACCTTAGCTGGCCACACCTTC<br>GAACACGAACTCCGCGTCTCCGCCATGAACGGCATGCTCGGTTCCATCGACGCCAACGAA<br>GGCGATATGCTCCTCGGATGGGATGTCGACCGTTTCCCAGCCAACGTCTATAGCGCCACC<br>TTCGCCATGCTCGAAGTCATCAAAGCCGGTGGACTTACCGGTGGCTTCAACTTCGACGCC<br>AAGACCCGCCGCGCTTCCAACACCTATGAAGATATGTTCAAGGCTTTCGTCCTTGGTATG<br>GATACCTTCGCTTTAGGTCTTCTCAATGCCGAAGCCATCATCAAAGACGGCCGCATCGAC<br>AAGTTCGTCGAGGATAGATATGCCAGCTTCAAGACCGGCATCGGTGCTAAGGTCCGCGAT<br>CACTCCGCTACCCTTGAGGATTTAGCTGCCCACGCCCTTGAGACCAAGGTTTGCCCAGAT<br>CCAGGCAGCGGCGACGAGGAAGAACTCCAGGAAATCCTCAACCAGTTAATGTTCGGTAAG<br>AAATAA |
| 1753MI35_ 004 | *Firmicutes* | Amino Acid | 42 | MEYFPFVKSVQYKGPTSTEPFAFKYYDANRVVLGKPMKEWMPFAMAWWHNLGAAGTDMFG<br>GNTMDKSWGVDKEKDPMGYAKAKVDAGFEFMQKMGIEYYCFHDVDLVPECDDITVMYQRL<br>DEIGDYLLKKQKETGIKLLWSTANAFGHRRFMNGAGSSNSAEVYCFAAAQIKKALELCVK<br>LGGKGYVFWGGREGYETLLNTDMKFEQENIANLMRCARDYGRKIGFKGDFYIEPKPKEPT<br>KHQYDFDAATAIGFLRQYGLDKDFKMNIEANHATLAGHTFEHELRVSAMNGMLGSIDANE<br>GDMLLGWDVDRFPANVYSATFAMLEVIKAGGLTGGFNFDAKTRRASNTYEDMFKAFVLGM<br>DTFALGLLNAEAIIKDGRIDKFVEDRYASFKTGIGAKVRDHSATLEDLAAHALETKVCPD<br>PGSGDEEELQEILNQLMFGKK |

TABLE 2-continued

| Clone No. | Class of organism | Type of Sequence | SEQ ID NO: | Sequence |
|---|---|---|---|---|
| 1754MI9_ 004 | *Firmicutes* | DNA | 43 | ATGAGCGAATTTTTTAAGAATATTCCAGAGATTAAATTCGAAGGAAAAGATAGTAAAAAT<br>CCATGGGCATTCAAGTATTACAATCCTGAATTGACCATTATGGGTAAAAAAATGTCTGAA<br>CATCTTCCTTTTGCAATGGCCTGGTGGCATAACCTTGGCGCAAATGGAGTTGATATGTTC<br>GGTTCGGGAACCGCCGATAAATCTTTCGGTCAGGCTCCGGGAACTATGGAGCACGCAAAG<br>GCTAAGGTAGATGCAGGTATCGAGTTTATGAAGAAACTCGGAATCAAGTACTACTGCTGG<br>CATGATGTAGACCTTGTTCCTGAAGATCCAAACGATATCAACGTAACAAACAAGCGCCTT<br>GATGAGATTTCAGATTATATCCTTGAAAAAACAAAGGGAACTGACATCAAGTGTCTCTGG<br>GGAACTGCTAACATGTTCAGTAATCCCCGCTTTATGAACGGGGCAGGCTCAACAAACTCT<br>GCTGACGTTTACTGCTTTGCAGCTGCCCAGGTTAAAAAGGCTCTTGAGATTACCGTAAAG<br>CTTGGTGGCCGCGGTTATGTATTCTGGGGTGGACGCGAAGGTTATGAAACTCTTCTTAAT<br>ACAGATGTAAAGCTTGAACAGGAAAATATTGCAAACCTTATGCACATGGCAGTTGATTAT<br>GGCCGTTCAATCGGTTTCAAGGGAGACTTCTACATCGAGCCTAAGCCAAAGGAGCCGATG<br>AGTCATCAGTATGATTTTGATGCCGCAACTGCAATCGGCTTCCTCCGCCAGTATGGCCTC<br>GACAAAGACTTTAAGATGAACATTGAGGCTAACCACGCTTCTCTTGCAAATCATACCTTC<br>CAGCATGAGCTTTATATCAGCCGCATTAACGGAATGCTTGGTTCTGTAGATGCTAACCAG<br>GGAAATCCAATTCTCGGCTGGGATACAGATAACTTCCCTTGGAATGTCTACGACGCAACT<br>CTTGCAATGTACGAAGTACTCAAGGCTGGTGGACTTACAGGTGGCTTCAACTTTGACTCA<br>AAGAACCGCCGCCCATCAAATACATTTGAAGATATGTTCCACGCTTACATCATGGGAATG<br>GACACTTTTGCTCTTGGTCTTATTAAGGCTGCAGAAATTATTGAAGACGGAAGAATCGAT<br>GGCTTCATTAAAGAAAAGTATTCAAGCTACGAAAGTGGAATTGGTAAGAAGATCCGCGAC<br>AAGCAGACAACTTTGGAAGAGCTTGCTGCCCGTGCCGCAGAAATGAAAAAGCCATCTGAT<br>CCAGGTTCAGGCCGCGAGGAATATCTGGAAGGAGTTGTTAACAATATCCTCTTTCGCGGA<br>TAA |
| 1754MI9_ 004 | *Firmicutes* | Amino Acid | 44 | MSEFFKNIPEIKFEGKDSKNPWAFKYYNPELTIMGKKMSEHLPFAMAWWHNLGANGVDMF<br>GSGTADKSFGQAPGTMEHAKAKVDAGIEFMKKLGIKYYCWHDVDINPEDPNDINVTNKRL<br>DEISDYILEKTKGTDIKCLWGTANMFSNPRFMNGAGSTNSADVYCFAAAQVKKALEITVK<br>LGGRGYVFWGGREGYETLLNTDVKLEQENIANLMHMAVDYGRSIGFKGDFYIEPKPKEPM<br>SHQYDFDAATAIGFLRQYGLDKDFKMNIEANHASLANHTFQHELYISRINGMLGSVDANQ<br>GNPILGWDTDNFPWNVYDATLAMYEVLKAGGLTGGFNFDSKNRRPSNTFEDMFHAYIMGM<br>DTFALGLIKAAEIIEDGRIDGFIKEKYSSYESGIGKKIRDKQTTLEELAARAAEMKKPSD<br>PGSGREEYLEGVVNNILFRG |
| 1754MI22_ 004 | *Firmicutes* | DNA | 45 | ATGAGCGAGTTTTTTAAGAATATTCCTCAAATAAAATACGAAGGAAAAGATAGCAAAAAT<br>CCCTGGGCATTCAAGTATTACAATCCTGAATTGACAATCATGGGTAAAAAGATGAGCGAA<br>CATCTTCCATTCGCAATGGCATGGTGGCATAACCTTGGCGCAAACGGCGTTGATATGTTT<br>GGTCAGGGAACAGCAGACAAGTCTTTCGGACAGATTCCTGGAACTATGGAGCATGCAAAG<br>GCTAAGGTTGATGCTGGTATAGAGTTTATGAAGAAGCTCGGAATCAAATATTACTGCTGG<br>CACGATGTTGACCTTGTTCCTGAGGATCCAAACGATATCAACGTAACTAACAAACGTCTG<br>GACGAAATTTCAGATTACATCCTTGAAAAGACAAAAGGAACAGACATTAAGTGTCTCTGG<br>GGAACTGCAAACATGTTCGGTAACCCTCGCTTTATGAACGGTGCAGGCTCTACAAACTCT<br>GCTGACGTTTACTGTTTTGCTGCCGCTCAGGTAAAAAAGGCTCTTGAGATTACTGTAAAG<br>CTTGGTGGCCGAGGTTATGTTTTCTGGGGTGGCCGCGAAGGTTACGAAACTCTTCTCAAT<br>ACAGACGTAAAACTTGAACAGGAAAATATCGCAAACCTCATGCATATGGCTGTTGATTAT<br>GGCCGCTCAATCGGTTTCAAGGGAGACTTCTACATCGAGCCTAAGCCAAAGGAGCCAATG<br>AGCCATCAGTATGATTTTGATGCTGCAACAGCAATCGGCTTCCTCCGCCAGTATGGCCTC<br>GACAAAGATTTTAAGATGAACATCGAAGCTAACCATGCCTCACTTGCAAATCACACCTTC<br>CAGCACGAGCTTTGTATCAGCCGCATAAACGGAATGCTTGGTTCTGTAGATGCAAATCAG<br>GGAAATCCAATTCTTGGCTGGGATACAGATAACTTCCCATGGAATGTTTACGATGCAACT<br>CTGGCAATGTACGAAGTTCTCAAGGCTGGCGGTCTAACAGGTGGCTTCAACTTTGACTCA<br>AAGAACCGICGCCCATCAAATACTTTTGAAGAIATGTTCCACGCTTATATCATGGGTATG<br>GATACTTTTGCCCTTGGCCTTATTAAGGCTGCAGAAATTATTGAAGACGGCAGAATTGAC<br>GGCTTCATCAAAGAAAAGTATTCAAGCTTTGAAAGTGGAATTGGTAAGAAGATTCGTGAC<br>AAGCAGACAAGTTTGGAAGAGCTTGCAGCTCGTGCCGCTGAAATGAAAAAGCCATCTGAT<br>CCAGGTTCAGGCCGCGAGGAATACCTCGAAGGAGTTGTTAACAACATCCTCTTTCGCGGA<br>TAA |
| 1754MI22_ 004 | *Firmicutes* | Amino Acid | 46 | MSEFFKNIPQIKYEGKDSKNPWAFKYYNPELTIMGKKMSEHLPFAMAWWHNLGANGVDMF<br>GQGTADKSFGQIPGTMEHAKAKVDAGIEFMKKLGIKYYCWHDVDLVPEDPNDINVTNKRL<br>DEISDYILEKTKGTDIKCLWGTANMFGNPRFMNGAGSTNSADVYCFAAAQVKKALEITVK<br>LGGRGYVFWGGREGYETLLNTDVKLEQENIANLMHMAVDYGRSIGFKGDFYIEPKPKEPM<br>SHQYDFDAATAIGFLRQYGLDKDFKMNIEANHASLANHTFQHELCISRINGMLGSVDANQ<br>GNPILGWDTDNFPWNVYDATLAMYEVLKAGGLTGGFNFDSKNRRDSNTFEDMFHAYIMGM<br>DTFALGLIKAAEIIEPGRIDGFIKEKYSSFESGIGKKIRDKQTSLEELAARAAEMKKPSD<br>RGSGREEYLEGVVNNILFRG |
| 727MI1_ 002 | *Firmicutes* | DNA | 47 | ATGATATTTGAAAATATTCCCGCAATTCCTTATGAGGGTCCGAAGAGCACAAATCCGCTG<br>GCGTTTAAATTCTATGATCCGGACAAGATCGTTATGGGAAAGCCCATGAAGGAGCATCTG<br>CCCTTTGCAATGGCCTGGTGGCACAACCTTGGCGCGGCCGGAACCGATATGTTCGGGCGC<br>GATACCGCCGACAAATCCTTCGGTGCGGTAAAAGGCACAATGGAGCATGCCAAAGCGAAA<br>GTCGATGCCGGCTTTGAGTTCATGCAGAAGCTGGGGATCCGCTATTTCTGCTTCCATGAT<br>GTGGATCTTGTTCCGGAGGCGGATGATATAAAGGAGACCAACCGCCGTCTGGACGAGATC<br>AGCGATTACATCCTTGAAAAGATGAAGGGCACCGATATCAAGTGCCTTTGGGGCACGGCC<br>AATATGTTCTCAAATCCGCGCTTTATGAACGGCGCAGGCTCCTCCAATTCTGCCGATGTA<br>TTCGCTTTTGCGGCAGCACAGGCCAAGAAGGCCTTGGATCTGACCGTCAAACTCGGCGGG<br>CGCGGCTATGTCTTCTGGGGCGGACGTGAGGGCTATGAGACACTTCTCAATACCGACATG |

TABLE 2-continued

| Clone No. | Class of organism | Type of Sequence | SEQ ID NO: | Sequence |
|---|---|---|---|---|
| | | | | AAGTTCGAGCAGGAGAATATCGCGAAGCTCATGCATATGGCTGTCGATTACGGCCGCAGC<br>ATAGGCTTTACCGGTGATTTCTATATCGAGCCCAAACCGAAAGAGCCGATGAAACACCAG<br>TATGATTTCGATGCAGCCACTGCGATAGGCTTCCTCCGCCAGTACGGACTCGATAAGGAC<br>TTCAAGCTCAACATCGAGGCAAACCACGCCACACTGGCAGGTCACACTTTCCAGCACGAT<br>CTGCGTGTTTCCGCAATAAACGGAATGCTGGGCAGCATTGACGCCAACCAGGGCGATATG<br>CTCCTCGGCTGGGATACCGACGAGTTCCCGTTCAATGTATATGATGCGACCATGTGCATG<br>TATGAGGTGCTCAAGTCAGACGGGCTCACCGGCGGCTTTAACTTCGACTCCAAATCACGC<br>CGCCCGAGCTATACGGTCGAGGATATGTTTACAAGCTATATCCTCGGCATGGACACTTTT<br>GCCCTCGGCCTTCTGAAAGCGGCCGAGCTTATCGAAGACGGAAGGCTTGACGCCTTCGTC<br>AAAGAACGCTATTCAAGCTATGAGAGCGGCATCGGCGCAAAGATCCGCAGCGGAGAAACC<br>GATTTGAAGGAATTGGCGGAATATGCGGACTCCCTCGGAGCCCCCGAACTTCCGGGCAGC<br>GGAAAACAGGAACAGCTCGAGAGCATAGTAAATCAGATACTTTTCGGATAA |
| 727MI1_ 002 | *Firmicutes* | Amino Acid | 48 | MIFENIPAIPYEGPKSTNPLAFKFTDPDKIVMGKPMKEHLPFAMAWWHNLGAAGTDMFGR<br>DTADKSFGAVKGTMEHAKAKVDAGFEFMQKLGIRYFCFHDVDLVPEADDIKETNRRLDEI<br>SDYILEKMKGTDIKCLWGTANMFSNPRFMNGAGSSNSADVFAFAAAQAKKALDLTVKLGG<br>RGYVFWGGREGYETLLNTDMKFEQENIAKLMHMAVDYGRSIGFTGDFYIEPKPKEPMKHQ<br>YDFDAATAIGFLRQYGLDKDFKLNIEANHATLAGHTFQHDLRVSAINGMLGSIDANQGDM<br>LLGWDTDEFPFNVYDATMCMYEVLKSDGLTGGFNFDSKSRRPSYTVEDMFTSYILGMDTF<br>ALGLLKAAELIEDGRLDAFVKERYSSYESGIGAKIRSGETDLKELAEYADSLGAPELPGS<br>GKQEQLESIVNQILFG |
| 727MI9_ 005 | *Firmicutes* | DNA | 49 | ATGAGCGAGTTTTTGCCAGCATTCCCAAAATTCCCTTTGAAGGCAAGGACAGCGCCAAT<br>CCCCTGGCGTTCAAATACTACGACGCCGACAGGATGATACTGGGCAAGCCCATGAAGGAG<br>CACCTTCCCTTCGCCATGGCCTGGTGGCACAACCTGTGCGCCGCGGGCACCGATATGTTT<br>GGCCGGGACACCGCCGACAAGTCCTTCGGCCAGGTCAAGGGCACCATGGAACACGCCAAG<br>GCCAAGGTGGACGCGGGCTTTGAGTTCATGAAGAAGCTGGGCATCCGCTACTTCTGCTTC<br>CACGACGTGGACATCGTGCCCGAAGCCGACGACATCAAGGAAACCAACCGCCGTCTGGAC<br>GAGATCTCCGACTATATCCTGGAGAAAATGAAAGGCACCGACATCCAGTGCCTGTGGGGC<br>ACCGCCAACATGTTCGGCAACCCCCGCTATATGAACGGCGCGGGCAGCTCCAACTCCGCC<br>GACGTATACTGCTTCGCCGCGGCCCAGATCAAAAAGGCCCTGGACATCACCGTGAAGCTG<br>GGCGGCAAGGGCTACGTGTTCTGGGGCGGCCGCGAGGGCTACGAGACCCTGCTGAACACC<br>GATATGAAGTTCGAGCAGGAGAACATCGCCCGCCTGATGCACATGGCCGTGGACTACGGC<br>CGCAGCATCGGCTTCACCGGCGATTTCTACATCGAGCCCAAGCCCAAGGAGCCCATGAAG<br>CACCAGTACGACTTCGACGCCGCCACCGCCATAGGCTTTTTGCGCCAGTACGGCCTGGAC<br>AAGGATTTCAAGCTGAACATCGAGTCCAACCACGCCACCCTGGCGGGCCATACCTTCCAG<br>CACGACCTGCGCGTTTCCGCCATCAACGGCATGCTGGGCTCCATCGACGCCAACCAGGGC<br>GACTACCTGCTGGGCTGGGATACCGACGAGTTCCCCTACAGCGTATACGAGACCACCATG<br>TGCATGTACGAGGTGCTCAAGGCCGGAGGTCTCACCGGCGGCTTCAATTTCGACGCCAAG<br>AACCGCCGTCCCAGCTACACCCCCGAGGATATGTTCCACGCCTACATCCTTGGGATGGAC<br>AGCTTCGCCCTGGGCCTGATCAAGGCCGCCGAGCTCATCGAGGACGGTCGCCTGGACGCC<br>TTCGTCCGGGACCGCTACCAGAGCTGGGAGACCGGCATCGGCGATAAGATCCGCAAGGGC<br>GAGACCACACTGGCCGAGCTGGCCGAGTACGCCGCCCGGATGGGCGCGCCCGCGCTGCCC<br>GGCAGCGGCCGCCAGGAATACCTGGAGGGCGTGGTCAACAATATCCTGTTCAAATAA |
| 727MI9_ 005 | *Firmicutes* | Amino Acid | 50 | MSEFFASIPKIPFEGKDSANDLAFKYYDADRMILGKPMKEHLDFAMAWWHNLCAAGTDMF<br>GRDTADKSFGQVKGTMEHAKAKVDAGFEFMKKLGIRYFCFHDVDIVPEADDIKETNRRLD<br>EISDYILEKMKGTDIQCLWGTANMFGNPRYMNGAGSSNSADVYCFAAAQIKKALDITVKL<br>GGKGYVFWGGREGYETLLNTDMKFEQENIARLMHMAVDYGRSIGFTGDFYIEPKPKEPMK<br>HQYDFDAATAIGFLRQYGLDKDFKLNIESNHATLAGHTFQHDLRVSAINGMLGSIDANQG<br>DYLLGWDTDEFPYSVYETTMCMYEVLKAGGLTGGFNFDAKNRRPSYTPEDMFHAYILGMD<br>SFALGLIKAAELIEDGRLDAFVRDRYQSWETGIGEKIRKGETTLAELAEYAARMGAPALP<br>GSGRQEYLEGVVNNILFK |
| 727MI27_ 002 | *Firmicutes* | DNA | 51 | ATGAAGACCTATTTCAAAAAAATCCCCGTGATCCCCTACGAGGGACCGAAGTCCCAGAAT<br>CCGCTGTCGTTCAAATTCTATGACGCGGACCGCATCGTTCTCGGCAAGCCCATGAAGGAG<br>CATCTGCCCTTCGCCATGGCCTGGTGGCACAATCTGGGTGCTGCCGGAACGGACATGTTC<br>GGCCGCGATACCGCCGACAAGTCCTTCGGAGCGGAGAAGGGCACCATGGAGCATGCCAAG<br>GCCAAGGTGGACGCTGGCTTCGAGTTTATGAAGAAGGTGGGCATCCGGTATTTCTGCTTC<br>CATGACGTGGATCTGGTCCCGGAAGCGGACGACATCAAGGAGACCAACCGCCGTCTCGAT<br>GAGATCAGCGACTACATCCTCAAGAAGATGAAGGGCACGGATATCAAGTGCCTCTGGGGC<br>ACCGCCAACATGTTCGGCAATCCCCGGTTCATGAACGGCGCGGGCAGCTCCAACAGCGCG<br>GACGTGTTCTGCTTTGCCGCGGCCCAGGTGAAGAAGGCCTTGGACATCACCGTCAAGCTG<br>GGCGGCCGGGGCTATGTGTTCTGGGGCGGCCGTGAGGGGTATGAGTCCCTGCTGAACACG<br>GACGTGAAGTTTGAGCAGGAGAACATCGCCAAGCTCATGCACCTTGCCGTGGACTACGGC<br>CGCAGCATCGGCTTCACCGGCGATTTCTACATCGAGCCCAAGCCCAAGGAGCCCATGAAG<br>CACCAGTACGACTTCGATGCCGCCACCGCCATCGGCTTCCTCAGGCAGTACGGCCTCGAT<br>AAGGACTTCAAGATGAACATTGAAGCCAACCACGCGACCCTGGCCGGCCACACCTTCCAG<br>CACGACCTCAGGATCAGCGCCATCAACGGGATGCTGGGCTCCATCGACGCCAACCAGGGC<br>GACCTCCTGCTGGGATGGGACACCGACGAATTCCCCTTCAACGTCTATGAGGCCACCATG<br>TGCATGTACGAGGTCCTCAAGGCCGGCGGCCTCACCGGCGGCTTCAACTTCGACTCAAAG<br>AACCGCCGTCCCTCCTACACCATGGAGGATATGTTCCACGCCTACATCCTGGGCATGGAC<br>ACCTTCGCCCTGGGTCTTCTCAAGGCCGCGGAGCTCATCGAGGACGGTCGGATCGACAAA<br>TTCGTGGAGGAGCGCTACGCCAGCTACAAGACCGGCATCGGCGCCAAGATCCGTTCCGGC<br>GAGACCACGCTTCAGGAGCTGGCCGCCTATGCCGACAAGTTGGGCGCGCCTGCCCTTCCC<br>GGCAGCGGCCGTCAGGAGTACCTGGAGAGCATCGTCAACCAGGTGCTCTTCGGGATGTGA |

TABLE 2-continued

| Clone No. | Class of organism | Type of Sequence | SEQ ID NO: | Sequence |
|---|---|---|---|---|
| 727MI27_002 | *Firmicutes* | Amino Acid | 52 | MKTYFKKIPVIPYEGPKSQNPLSFKFYDADRIVLGKPMKEHLPFAMAWWHNLGAAGTDMF<br>GRDTADKSFGAEKGTMEHAKAKVDAGFEFMKKVGIRYFCFHDVDLVPEADDIKETNRRLD<br>EISDYILKKMKGTDIKCLWGTANMFGNPRFMNGAGSSNSADVFCFAAAQVKKALDITVKL<br>GGRGYVFWGGREGYESLLNTDVKFEQENIAKLMHLAVDYGRSIGFTGDFYIEPKPKEPMK<br>HQYDFDAATAIGFLRQYGLDKDFKMNIEANHATLAGHTFQHDLRISAINGMLGSIDANQG<br>DLLLGWDTDEFPFNVYEATMCMYEVLKAGGLTGGFNFDSKNRRPSYTMEDMFHAYILGMD<br>TFALGLLKAAELIEDGRIDKFVEERYASYKTGIGAKIRSGETTLQELAAYADKLGAPALP<br>GSGRQEYLESIVNQVLFGM |
| 1753MI2_006 | *Neocalli-mastigales* | DNA | 53 | ATGGCTAAAGAGTATTTTCCAGAGATTGGCAAAATCAAGTTTGAAGGCAAGGACAGCAAA<br>AACCCAATGGCTTTCCACTACTATGACCCCGAGAAGGTGATCATGGGCAAGCCTATGAAA<br>GACTGGCTCCGCTTCGCTATGGCATGGTGGCACACCCTCTGCGCAGAAGGTGGCGACCAG<br>TTCGGTGGCGGCACTAAGAAGTTCCCTTGGAACAACGGCGCTGACGCTGTAGAAATCGCA<br>AAACAGAAGGCTGACGCAGGTTTCGAAATCATGCAGAAGCTCGGCATCCCATATTTCTGC<br>TTCCACGACGTGGACCTCGTGTCTGAGGGCGCATCTGTAGAAGAGTATGAGGCTAACCTC<br>AAGGCTATCACAGACTACCTCGCTGTGAAGATGAAGGAAACAGGCATCAAGCTCCTGTGG<br>TCTACTGCCAACGTATTCGGCAACGGCCGCTACATGAACGGTGCTTCTACCAACCCTGAC<br>TTCGACGTCGTTGCTCGCGCTATCGTGCAGATTAAGAACGCTATCGACGCTGGTATCAAG<br>CTCGGCGCTGAGAACTACGTGTTCTGGGGCGGACGCGAAGGCTACATGAGCCTCCTCAAC<br>ACCGACCAGAAGCGTGAGAAGGAGCACATGGCCACTATGCTCACTATGGCTCGCGACTAC<br>GCTCGCGCTAAGGGCTTCAAGGGCACATTCCTCATCGAGCCTAAGCCAATGGAGCCTTCT<br>AAGCACCAGTATGACGTTGACACTGAGACTGTCATCGGCTTCCTCAAGGCACACAACCTC<br>GACAAGGACTTCAAGGTGAACATCGAGGTGAACCACGCAACTCTCGCTGGCCACACCTTC<br>GAGCACGAGCTCGCAGTGGCAGTGGACAACAACATGCTCGGCTCTATCGACGCTAACCGT<br>GGTGACTACCAGAATGGCTGGGATACTGACCAGTTCCCAATCGACCAGTACGAACTCGTT<br>CAGGCTTGGATGGAAATCATCCGTGGCGGCGGTCTCGGCACTGGCGGCACGAACTTCGAC<br>GCTAAGACTCGTCGTAACTCTACCGACCTCGAAGACATCTTCATCGCACACATCGCAGGC<br>ATGGACGCTATGGCACGCGCACTCGAATCAGCTGCTAAGCTCCTCGAAGAGTCTCCATAC<br>AAGGCAATGAAGGCAGCTCGCTACGCTTCATTCGACAACGGTATCGGTAAGGACTTCGAA<br>GATGGCAAGCTCACTCTCGAGCAGGCTTACGAATACGGTAAGAAGGTTGGTGAGCCTAAG<br>CAGACTTCTGGCAAGCAGGAGCTCTACGAAGCCATCGTTGCAATGTACGCTTAA |
| 1753MI2_006 | *Neocalli-mastigales* | Amino Acid | 54 | MAKEYFPEIGKIKFEGKDSKNPMAFHYYDPEKVIMGKPMKDWLRFAMAWWHTLCAEGGDQ<br>FGGGTKKFPWNNGADAVEIAKQKADAGFEIMQKLGIPYFCFHDVDLVSEGASVEEYEANL<br>KAITDYLAVKMKETGIKLLWSTANVFGNGRYMNGASTNPDFDVVARAIVQIKNAIDAGIK<br>LGAENYVFWGGREGYMSLLNTDQKREKEHMATMLTMARDYARAKGFKGTFLIEPKPMEPS<br>KHQYDVDTETVIGFLKAHNLDKDFKVNIEVNHATLAGHTFEHELAVAVDNNMLGSIDANR<br>GDYQNGWDTDQFPIDQYELVQAWMEIIRGGGLGTGGTNFDAKTRRNSTDLEDIFIAHIAG<br>MDAMARALESAAKLLEESPYKAMKAARYASFDNGIGKDFEDGKLTLEQAYEYGKKVGEPK<br>QTSGKQELYEAIVAMYA |
| 5586MI3_005 | *Neocalli-mastigales* | DNA | 55 | ATGGCTAAAGAATTTTTCCCAGAGATTGGTAAAATCAAGTTCGAAGGCAAGGATTCAAAG<br>AATCCAATGGCTTTCCATTACTATGATGCAGAGAAGGTAATCATGGGCAAACCCATGAAG<br>GACTGGCTCCGTTTCGCTATGGCATGGTGGCACACACTCTGTGCAGAGGGCGGCGACCAG<br>TTCGGTGGCGGTACGAAGAAGTTCCCTTGGAACGAGGGTGCTAATGCTGTCGAGATTGCT<br>AAGCAGAAGGCTGACGCTGGTTTCGAAATCATGCAGAAGCTTGGCATTCCTTACTTCTGC<br>TTCCACGATGTTGACCTCGTTTCTGAAGGCGCATCTGTTGAGGAGTATGAGGCCAACCTC<br>AAGGCTATCACTGACTATCTCGCGGTGAAGATGAAGGAGACTGGCATTAAGCTCCTGTGG<br>TCTACTGCCAACGTGTTCGGCAATGGCCGTTACATGAATGGTGCTTCCACCAACCCTGAC<br>TTCGACGTTGTTGCTCGCGCCATCGTTCAGATTAAGAACGCTATCGATGCAGGTATCAAG<br>CTCGGTGCTGAGAACTATGTGTTCTGGGGCGGTCGTGAAGGTTACATGAGCCTCCTGAAC<br>ACAGACCAGAAGCGTGAGAAGGAGCACATGGCTACTATGCTCACTATGGCTCGCGACTAC<br>GCTCGCAGCAAGGGCTTCAAGGGTACTTTCCTCATCGAGCCTAAGCCAATGGAGCCATCT<br>AAGCACCAGTACGACGTTGACACAGAGACTGTTATCGGCTTCCTGAAGGCACACAACCTT<br>GACAAGGACTTCAAGGTGAACATCGAGGTGAACCACGCAACACTCGCTGGICACACCTTC<br>GAGCACGAGCTCGCTGTGGCTGTCGACAACAATATGCTTGGTTCTATCGATGCTAACCGC<br>GGTGACTACCAGAATGGTTGGGATACGGACCAGTTCCCAATTGACCAGTACGAGCTCGTT<br>CAGGCTTGGATGGAGATCATCCGTGGTGGCGGTCTCGGCACAGGTGGTACAAACTTCGAC<br>GCTAAGACTCGTCGTAACTCTACCGACCTCGAGGACATTTTCATTGCTCACATCGCTGGT<br>ATGGACGCTATGGCTCGCGCTCTTGAGTCAGCAGCTAAGCTCCTTGAGGAGTCTCCATAC<br>AAGAAGATGAAGGCTGCCCGTTATGCTTCTTTCGACAGCGGCATGGGTAAGGACTTTGAG<br>AACGGCAAGCTCACACTCGAACAGGTTTATGAGTATGGTAAGAAGGTAGGTGAGCCCAAG<br>CAGACTTCTGGCAAGCAGGAGCTCTTCGAGGCAATCGTGGCCATGTACGCATAA |
| 5586MI3_005 | *Neocalli-mastigales* | Amino Acid | 56 | MAKEFFPEIGKIKFEGKDSKNPMAFHYYDAEKVIMGKPMKDWLRFAMAWWHTLCAEGGDQ<br>FGGGTKKFPWNEGANAVEIAKQKADAGFEIMQKLGIPYFCFHDVDLVSEGASVEEYEANL<br>KAITDYLAVKMKETGIKLLWSTANVFGNGRYMNGASTNPDFDVVARAIVQIKNAIDAGIK<br>LGAENYVFWGGREGYMSLLNTDQKREKEHMATMLTMARDYARSKGFKGTFLIEPKPMEPS<br>KHQYDVDTETVIGFLKAHNLDKDFKVNIEVNHATLAGHTFEHELAVAVDNNMLGSIDANR<br>GDYQNGWDTDQFPIDQYELVQAWMEIIRGGGLGTGGTNFDAKTRRNSTDLEDIFIAHIAG<br>MDAMARALESAAKLLEESPYKKMKAARYASFDSGMGKDFENGKLTLEQVYEYGKKVGEPK<br>QTSGKQELFEAIVAMYA |
| 5586MI91_002 | *Neocalli-mastigales* | DNA | 57 | ATGGCTAAAGAGTATTTTCCAGAGATTGGTAAAATCAAGTTTGAAGGCAAGGATTCCAAG<br>AATCCAATGGCATTCCACTATTATGATGCAGAGAAAGTGATTATGGGTAAGCCTATGAAG |

TABLE 2-continued

| Clone No. | Class of organism | Type of Sequence | SEQ ID NO: | Sequence |
|---|---|---|---|---|
| | | | | GAGTGGCTCCGCTTTGCAATGGCATGGTGGCACACACTCTGTGCAGAGGGIGGCGACCAG<br>TTTGGTGGTGGCACTAAGAAATTCCCATGGAACGAGGGCACTGACGCTGTGACGATTGCT<br>AAGCAGAAGGCTGATGCAGGTTTCGAAATCATGCAGAAACTCGGTTTCCCATATTTTTGC<br>TTCCACGACATTGACCTCGTTTCCGAAGGCAACAGCATTGAAGAGTATGAGGCTAACCTC<br>CAGGCAATCACTGATTATCTGAAAGTGAAGATGGAAGAGACAGGCATCAAACTCTTGTGG<br>TCAACTGCCAACGTATTCGGCAATGGTCGCTACATGAATGGTGCTTCCACAAACCCAGAC<br>TTTGACGTGGTGGCTCGTGCCATCGTTCAGATTAAGAACGCAATTGACGCTGGTATCAAA<br>CTCGGTGCTGAGAACTATGTATTCTGGGGCGGTCGCGAAGGCTACATGAGCCTTCTGAAC<br>ACTGACCAGAAGCGTGAGAAGGAGCACATGGCAACCATGCTCACTATGGCTCGCGACTAC<br>GCTCGCAGCAAGGGTTTCAAGGGCACTTTCCTCATTGAGCCAAAGCCAATGGAGCCATCT<br>AAGCACCAGTATGACGTTGACACGGAGACTGTCATCGGCTTCCTCAAGGCACACAACCTC<br>GACAAGGATTTCAAGGTGAACATCGAAGTGAACCACGCTACACTTGCAGGTCATACTTTC<br>GAGCACGAACTTGCTGTGGCTGTTGACAATGGCATGCTCGGTTCTATCGACGCTAACCGT<br>GGTGACTATCAGAACGGTTGGGACACTGACCAGTTCCCAATCGACCAGTACGAACTCGTT<br>CAGGCTTGGATGGAAATCATCCGTGGTGGTGGTCTCGGCACAGGTGGTACTAACTTCGAT<br>GCTAAGACTCGTCGTAACTCAACTGACCTCGAGGACATCTTCATCGCACACATCTCTGGT<br>ATGGATGCAATGGCACGTGCTCTCGAATCGGCGGCTAAACTTCTTGAGGAGTCTCCATAC<br>TGCGCTATGAAGAAGGCTCGTTACGCTTCCTTCGACAGCGGCATCGGTAAGGACTTCGAG<br>GACGGCAAACTCACGCTCGAGCAGGCTTACGAGTACGGCAAGAAAGTCGGCGAACCCAAG<br>CAGACTTCTGGCAAGCAGGAACTCTACGAGGCAATCGTTGCCATGTACGCATAA |
| 5586MI91_002 | *Neocallimastigales* | Amino Acid | 58 | MAKEYFPEIGKIKFEGKDSKNPMAFHYYDAEKVIMGKPMKEWLRFAMAWWHTLCAEGGDQ<br>FGGGTKKFPWNEGTDAVTIAKQKADAGFEIMQKLGFPYFCFHDIDLVSEGNSIEEYEANL<br>QAITDYLKVKMEETGIKLLWSTANVFGNGRYMNGASTNPDFDVVARAIVQIKNAIDAGIK<br>LGAENYVFWGGREGYMSLLNTDQKREKEHMATMLTMARDYARSKGFKGTFLIEPKPMEPS<br>KHQYDVDTETVIGFLKAHNLDKDFKVNIEVNHATLAGHTFEHELAVAVDNGMLGSIDANR<br>GDYQNGWDTDQFPIDQYELVQAWMEIIRGGGLGTGGTNFDAKTRRNSTDLEDIFIAHISG<br>MDAMARALESAAKLLEESPYCAMKKARYASFDSGIGKDFEDGKLTLEQATEYGKKVGEPK<br>QTSGKQELYEAIVAMYA |
| 5586MI194_003 | *Neocallimastigales* | DNA | 59 | ATGGCAAAAGAGTATTTCCCTACGATCGGTAAGATCGTTTATGAAGGACCGGAGTCCAAG<br>AACCCTATGGCATTTCATTACTATGACGCAGAGCGCGTAGTAGCTGGTAAAAAAATGAAA<br>GATTGGATGCGTTTCGCTATGGCATGGTGGCACACCCTCTGTGCAGAAGGTGCAGACCAG<br>TTCGGTGGAGGCACCAAACACTTCCCGTGGAGTGAAGGTCCCGATGCCGTAACCATCGCC<br>AAGCAGAAAGCAGACGCAGGTTTTGAGATCATGCAGAAACTCGGCTTCCCGTATTTCTGT<br>TTCCATGACGTGGATCTGGTCAGCGAAGGCAGCAGCGTAGAAGAGTACGAGGCGAACCTC<br>GCAGCCATCACCGATTATCTCAAGCAGAAAATGGACGAGTCGGGTATCAAACTCCTTTGG<br>TCCACTGCTAACGTATTCGGTCACGCCCGTTACATGAACGGTGCCAGCACCAATCCTGAC<br>TTTGATGTCGTTGCCCGTGCGATTGTGCAGATCAAGAATGCTATCGACGCAGGTATCAAA<br>CTCGGCGCAGAGAACTACGTCTTCTGGGGCGGTCGTGAAGGTTATATGAGCCTGCTCAAT<br>ACCGACCAGAAACGCGAGAAAGAGCATACGGCAATGATGCTGCGTATGGCGCGTGACTAT<br>GCCCGCAGCAAAGGTTTCAAAGGTACCTTCCTCATCGAACCCAAACCCATGGAGCCGTCC<br>AAGCACCAGTATGACGTAGATACCGAGACGGTGATAGGTTTCCTCAAAGCACACGGTTTG<br>GAGAAAGACTTTAAGGTAAACATCGAAGTGAACCACGCTACCCTCGCCGGTCACACTTTC<br>GAGCACGAACTGGCAGTAGCCGTAGATAACGGCATGCTCGGTTCGATCGATGCCAACCGC<br>GGTGACTATCAGAACGGATGGGATACCGACCAGTTCCCCATCGATAACTTCGAACTGACC<br>CAAGCATGGATGCAGATCGTACGTAACGGTGGTCTCGGCACAGGCGGAACGAACTTCGAC<br>TCCAAGACCCGTCGTAACTCCACCGATCTCGAGGATATCTTCATCGCTCACATCAGTGGT<br>ATGGACGCTTGTGCCCGTGCCCTATTGAATGCCGTAGAGATCATGGAGAAATCACCGATC<br>CCTGCTATGCTCAAAGAGCGTTACGCTTCCTTCGATAGCGGTCTGGGTAAAGATTTCGAG<br>GACGGCAAACTGACCCTTGAGCAAGTCTATGAGTACGGTAAGAAAGTAGGCGAACCCAAA<br>CAAACCAGCGGCAAACAAGAACTCTATGAGGCTATCGTTGCCCTCTACGCTAAATAA |
| 5586MI194_003 | *Neocallimastigales* | Amino Acid | 60 | MAKEYFPTIGKIVYEGPESKNPMAFHYYDAERVVAGKKMKDWMRFAMAWWHTLCAEGADQ<br>FGGGYKHFPWSEGPDAVYIAKQKADAGFEIMQKLGFPYPCFHDVELVSEGSSVEEYEANL<br>AAITDYLKQKMDESGIKLLWSTANVFGHARYMNGASTNPDFDVVARAIVQIKNAIDAGIK<br>LGAENYVFWGGREGYMSLLNTDQKREKEHTAMMLRMARDTARSKGFKGTFLIEPKPMEPS<br>KHQYDVDTETVIGFLKAHGLEKDFKVNIEVNHATLAGHTFEHELAVAVDNGMLGSIDANR<br>GDYQNGWDTDQFPIDNFELTQAWMQIVRNGGLGTGGTNFDSKTRRNSTDLEDIFIAHISG<br>MDACARALLNAVEIMEKSPIPAMLKERYASFDSGLGKEFEDGKLYLEQVYEYGKKVGEPK<br>QTSGKQELYEAIVALYAK |
| 5586MI198_003 | *Neocallimastigales* | DNA | 61 | ATGAAAGAGTATTTCCCTGAGATCGGTAAGATCCAATTTGAAGGCCCGGAGTCCAAGAAC<br>CCGATGGCATTTCACTACTATGACGCAGAGCGCGTCGTAGCCGGTAAAACAATGAAAGAG<br>TGGATGCGTTTCGCTATGGCTTGGTGGCACACCCTCTGTGCGGAAGGCGGCGACCAGTTC<br>GGAGGCGGAACGAAGAAGTTCCCCTGGAACGAAGGCGCTAACGCTTTGGAGATCGCCAAG<br>CACAAAGCCGATGCGGGATTTGAGATCATGCAGAAACTCGGCATCCCTTATTTCTGTTTC<br>CATGACGTGGATCTCATCGCCGAGGGCGGTTCGGTAGAAGAGTACGAAGCCAACCTCGCT<br>GCCATCACCGATTACCTCAAACAGAAAATGGACGAGACTGGCATCAAACTGCTGTGGTCC<br>ACGGCGAACGTCTTCAGCAACCCCCGTTATATGAACGGCGCCAGCACGAACCCCGATTTC<br>GATGTAGTAGCGCGTGCCATCGTCCAGATCAAGAACGCTATCGACGCCGGTATCAAACTC<br>GGAGCAGAGAACTATGTCTTCTGGGGTGGTCGCGAGGGCTATATGAGCCTCCTCAACACT<br>GACCAGCGCCGAGAGAAAGAGCATATGGCTACCATGCTCCGTATGGCGCGTGACTACGCG<br>CGTGCCAAAGGATTCAAGGGCACCTTCCTCATCGAACCCAAACCATGTGAGCCGTCCAAA<br>CATCAGTATGATGTCGATACCGAGACCGTCATCGGTTTCCTCAAAGCGCATGGACTCGAC<br>AAGGATTTCAAAGTCAATATCGAGGTCAACCACGCCACCCTCGCAGGCCACACGTTCGAA |

TABLE 2-continued

| Clone No. | Class of organism | Type of Sequence | SEQ ID NO: | Sequence |
|---|---|---|---|---|
| | | | | CACGAACTGGCTTGCGCTGTAGATGCCGGCATGCTCGGTTCGATTGACGCCAACCGCGGT<br>GACGCCCAGAACGGATGGGACACCGACCAGTTCCCTATTGATAACTTCGAACTCACACAG<br>GCTTTCATGCAGATCGTCCGCAACGGCGGTTTCGGAACAGGCGGYACGAACTTCGACGCC<br>AAGACACGCCGTAACTCCACCGACTTGGAGGACATCTTCATCGCCCATATCAGCGGCATG<br>GACGCTTGCGCACGTGCGTTACTCAATGCTGTCGAAATCCTCGAGAAGAGCCCGATTCCG<br>GCGATGCTCAAAGAGCGTTATGCTTCCTTTGACGGCGGCATCGGAAAGGACTTCGAGGAG<br>GGAAAACTGACTTTCGAGCAGGTCTATGAGTACGGCAAGAAAGTCGGCGAACCCAAACAG<br>ACCAGCGGCAAACAGGAGCTCTACGAAACCATCGTCGCCCTCTATGCCAAATAG |
| 5586MI198_003 | *Neocallimastigales* | Amino Acid | 62 | MKEYFPEIGKIQFEGPESKNPMAFHYYDAERVVAGKTMKEWMRFAMAWWHTLCAEGGDQF<br>GGGTKKFPWNEGANALETAKHKADAGFEIMQKLGIPYFCFHDVDLIAEGGSVEEYEANLA<br>AITDYLKQKMDETGIKLLWSTANVFSNPRYMNGASTNPDFDVVARAIVQIKNAIDAGIKL<br>GAENYVFWGGREGYMSLLNTDQRREKEHMATMLRMARDYARAKGFKGTFLIEPKPCEPSK<br>HQYDVDTETVIGFLKAHGLDKDPKVNIEVNHATLAGHTFEHELACAVDAGMLGSIDANRG<br>DAQNGWDYDQFPIDNFELTQAFMQIVRNGGFGTGGTNFDAKTRRNSTDLEDIFIAHISGM<br>DACARALLNAVEILEKSPIPAMLKERYASPDGGIGKDFEEGKLTFEQVYEYGKKVGEPKQ<br>TSGKQELYETIVALYAK |
| 5586MI201_003 | *Neocallimastigales* | DNA | 63 | ATGGCAAAAGAGTATTTCCCTACGATCGGTAAGATCGTTTATGAAGGACCGGAATCCAAG<br>AACCCTATGGCATTTCATTACTATGACGCAGAGCGCGTAGTAGCTGGTAAAAAAATGAAA<br>GATTGGATGCGTTTCGCTATGGCATGGTGGCACACCCYCTGTGCAGAAGGTGCAGACCAG<br>TTCGGTGGAGGCACCAAACACTTCCCGTGGAATGAAGGTCCCGATGCCGTAACCATCGCC<br>AAGCAGAAAGCAGACGCAGGTTTTGAGATCATGCAGAAACTCGGCTTCCCGTATTTCTGT<br>TTCCATGACGTGGATCTGGTCGGCGAAGGCAGCAGCGTAGAAGAGTACGAGGCGAACCTC<br>GCAGCCATCACCGATTATCTCAAGCAGAAAATGGACGAGTCGGGTATCAAACTCCTTTGG<br>TCCACTGCTAACGTATTCGGTCACGCCCGTTACATGAACGGTGCCAGCACCAATCCTGAC<br>TTTGATGTCGTTGCCCGTGCGATTGTGCAGATCAAGAATGCTATCGACGCAGGTATCAAA<br>CTCGGCGCAGAGAACTACGTCTTCTGGGGCGGTCGTGAAGGTTATATGAGCCTGCTCAAC<br>ACCGACCAGAAACGCGAGAAAGAGCATACGGCAATGATGCTGCGTATGGCGCGTGACTAT<br>GCCCGCAGCAAAGGTTTCAAAGGTACCTTCCTCATCGAACCCAAACCCATGGAGCCGTCC<br>AAGCACCAGTATGACGTAGATACCGAGACGGTGATAGGTTTCCTCAAAGCACACGGTTTG<br>GAGAAAGACTTTAAGGTAAACATCGAAGTGAACCACGCTACCCTCGCCGGICACACTTTC<br>GAGCACGAACTGGCAGTAGCCGTAGATAACGGCATGCTCGGTTCGATCGATGCCAACCGC<br>GGTGACTATCAGAACGGATGGGATACCGACCAGTTCCCCATCGATAACTTCGAACTGACC<br>CAAGCATGGATGCAGATCGTACGTAACGGTGGTCTCGGCACAGGCGGAACGAACTTCGAC<br>TCCAAGACCCGTCGTAACTCCACCGATCTCGAGGATATCTTCATCGCTCACATCAGTGGT<br>ATGGACGCTTGTGCCCGTGCCCTATTGAATGCCGTAGAGATCATGGAGAAATCACCGATC<br>CCTGCTATGCTCAAAGAGCGTTACGCTTCCTTCGATAGCGGTCTGGGTAAAGATTTCGAG<br>GACGGCAAACTGACCCTTGAGCAAGTCTATGAGTACGGTAAGAAAGTAGGCGAACCCAAA<br>CAAACCAGCGGCAAACAAGAACTCTATGAGGCTATCGTTGCCCTCTACGCTAAATAA |
| 5586MI201_003 | *Neocallimastigales* | Amino Acid | 64 | MAKEYFPTIGKIVYEGPESKNPMAFHYYDAERVVAGKKMKDWMRFAMAWWHTLCAEGADQ<br>FGGGTKHFPWNEGPDAVTIAKQKADAGFEIMQKLGFPYFCFHDVDINGEGSSVEEYEANL<br>AAITDYLKQKMDESGIKLLWSTANVFGHARYMNGASTNPDFDVVARAIVQIKNAIDAGIK<br>LGAENYVFWGGREGYMSLLNTDQKREKEHTAMMLRMARDYARSKGFKGTFLIEPKPMEPS<br>KHQYDVDTETVIGFLKAHGLEKDFKVNIEVNHATLAGHTFEHELAVAVDNGMLGSIDANR<br>GDYQNGWDTDQFPIDNFELTQAWMQIVRNGGLGTGGTNFDSKTRRNSTDLEDIFIAHISG<br>MDACARALLNAVEIMEKSPIPAMLKERYASFDSGLGKDFEDGKLTLEQVYEYGKKVGEPK<br>QTSGKQELYEAIVALYAK |
| 5586MI204_002 | *Neocallimastigales* | DNA | 65 | ATGAAAGAGTATTTCCCTGAGGTCGGTAAGATCCAATTTGAAGGCCCGGAGTCTAAGAAC<br>CCGATGGCATTTCACTACTATGACGCAGAGCGCGTCGTAGCCGGTAAAACAATGAAAGAG<br>TGGATGCGTTTCGCTATGGCTTGGTGGCACACCCTCTGTGCAGAAGGCGGCGACCAGTTC<br>GGAGGCGGAACGAAGCATTTCCCGTGGAATGAAGGCGCTAACGCTTTGGAGATCGCCAAA<br>CACAAAGCCGATGCGGGATTCGAGATCATGCAGAAACTCGGCATCCCCTATTTCTGTTTC<br>CATGACGTGGATCTCATCGCCGAGGGCGGTTCGGTAGAAGAGTACGAAACCAACCTCGCT<br>GCTATCACCGACTACCTCAAGCAGAAAATGGACGAGACCGGCATCAAACTGCTGTGGTCC<br>ACGGCGAACGTGTTCAGCAACCCCCGTTATATGAACGGCGCGAGCACGAACCCCGATTTC<br>GATGTAGTAGCGCGTGCCATCGTGCAGATCAAGAATGCCATCGACGCCGGCATCAAACTG<br>GGCGCAGAGAACTATGTCTTCTGGGGCGGTCGCGAGGGCTACATGAGCCTGCTCAACACC<br>GACCAGCGCCGCGAGAAAGAGCATATGGCTACTATGCTCCGTATGGCGCGTGACTACGCG<br>CGTGCCAAAGGATTCAAGGGCACCTTTCTCATCGAACCCAAACCGTGTGAGCCGTCCAAA<br>CATCAGTATGATGTCGATACCGAGACCGTCATCGGTTTCCTCAAAGCGCATGGACTCGAC<br>AAGGATTTCAAGGTTAATATCGAGGTCAACCACGCCACCCTCGCAGGCCACACGTTCGAA<br>CACGAACTGGCTTGCGCTGTAGATGCCGGCATGCTCGGTTCGATTGACGCCAACCGCGGT<br>GACGCCCAGAACGGATGGGACACCGACCAGTTCCCTATTGATAACTTCGAACTCACACAG<br>GCTTTCATGCAGATCGTCCGCAACGGCGGTTTCGGAACAGGCGGTACGAACTTCGACGCC<br>AAGACACGCCGTAACTCCACCGACTTGGAGGACATCTTCATCGCCCATATCAGCGGCATG<br>GACGCTTGCGCACGTGCGTTGCTCAACGCCATCGAAATCCTCGAGAAGAGCCCGATCCCG<br>GCTATGCTCAAAGACCGTTATGCCTCCTTTGATGGCGGCATCGGAAAGGACTTTGAGGAG<br>GGCAAACTGACTTTCGAGCAGGTCTATGAGTACGGCAAGAAGGTCGGAGAACCCAAACAG<br>ACCAGCGGCAAACAGGAGCTCTACGAAACCATCGTCGCCCTCTATGCCAAATAG |
| 5586MI204_002 | *Neocallimastigales* | Amino Acid | 66 | MKEYFPEVGKIQFEGPESKNPMAFHYYDAERVVAGKTMKEWMRFAMAWWHTLCAEGGDQF<br>GGGTKHFPWNEGANALEIAKHKADAGFEIMQKLGIPYFCFHDVDLIAEGGSVEEYETNLA<br>AITDYLKQKMDETGIKLLWSTANVFSNPRYMNGASTNPDFDVVARAIVQIKNAIDAGIKL |

TABLE 2-continued

| Clone No. | Class of organism | Type of Sequence | SEQ ID NO: | Sequence |
|---|---|---|---|---|
| | | | | GAENYVFWGGREGYMSLLNTDQRREKEHMATMLRMARDYARAKGFKGTFLIEPKPCEPSK<br>HQYDVDTETVIGFLKAHGLDKDFKVNIEVNHATLAGHTFEHELACAVDAGMLGSIDANRG<br>DAQNGWDTDQFPIDNFELTQAFMQIVRNGGFGTGGTNFDAKTRRNSTDLEDIFIAHISGM<br>DACARALLNAIEILEKSPIPAMLKDRYASFDGGIGKPFEEGKLTFEQVYEYGKKVGEPKQ<br>TSGKQELYETIVALYAK |
| 5586MI207_002 | *Neocallimastigales* | DNA | 67 | ATGAAAGAGTATTTCCCTGAGATCGGTAAGATCCAATTTGAAGGCCCGGAGTCCAAGAAC<br>CCGATGGCGTTTCACTACTATGACGCTGAGCGCGTCGTAGCCGGTAAAACAATGAAAGAG<br>TGGATGCGTTTCGCTATGGCTTGGTGGCACACCCTCTGTGCGGAAGGCGGCGACCAGTTC<br>GGAGGAGGAACGAAGAAATTCCCCTGGAACGAAGGGGCAAACGCTTTGGAGATCGCCAAG<br>CACAAAGCCGATGCGGGATTCGAGATCATGCAGAAACTCGGCATCCCTTATTTCTGTTTC<br>CATGACGTGGATCTCATCGCCGAGGGCGAATCGGTAGAAGAGTACGAAGCCAACCTCGCT<br>GCCATCACCGATTACCTCAAACAGAAAATGGACGAGACCGGCATCAAACTGCTGTGGTCC<br>ACGGCGAACGTGTTCAGCAACCCCCGTTATATGAACGGCGCCAGCACGAACCCCGATTTC<br>GATGTAGTGGCACGCGCTATCGTACAAATCAAGAACGCTATCGACGCCGGTATCAAACTC<br>GGAGCAGAGAACTATGTCTTCTGGGGCGGTCGCGAGGGCTATATGTCGCTCCTCAACACC<br>GACCAGCGCCGAGAGAAAGAGCATATGGCTACTATGCTCCGTATGGCGCGTGACTACGCG<br>CGTTCCAAAGGATTCAAGGGCACCTTCCTCATCGAACCCAAACCGTGTGAGCCGTCCAAA<br>CATCAGTACGATGTGGACACAGAGACCGTCATCGGTTTCCTTAAAGCGCATGGACTCGAC<br>AAGGATTTCAAAGTCAATATCGAGGTCAACCACGCCACCCTCGCAGGCCACACGTTCGAA<br>CACGAACTGGCTTGCGCTGTAGATGCCGGCATGCTCGGTTCGATTGACGCCAACCGCGGT<br>GACGCCCAGAACGGATGGGACACCGACCAATTCCCTATTGATAACTTCGAACTCACTCAG<br>GCTTTCATGCAGATCGTCCGCAACGGCGGTTTCGGAACAGGCGGTACGAACTTCGACGCC<br>AAGACACGCCGTAACTCCACCGACTTGGAGGACATCTTCATCGCCCATATCAGCGGCATG<br>GACGCTTGCGCTCGTGCGTTGCTCAATGCTGTCGAAATCCTCGAGAAGAGCCCGATCCCG<br>GCTATGCTCAAAGAGCGTTATGCTTCCTTTGACGGCGGCATCGGAAAGGACTTTGAGGAG<br>GGCAAACTGACTTTCGAGCAGGTCTATGAGTACGGCAAGAAGGTCGGAGAACCCAAACAG<br>ACCAGCGGCAAACAGGAGCTCTACGAAACCATCGTCGCCCTCTATGCCAAATGA |
| 5586MI207_002 | *Neocallimastigales* | Amino Acid | 68 | MKEYFPEIGKIQFEGPESKNPMAFHYYDAERVVAGKTMKEWMRFAMAWWHTLCAEGGDQF<br>GGGTKKFPWNEGANALEIAKHKADAGFEIMQKLGIPYFCFHDVDLIAEGESVEEYEANLA<br>AITDYLKQKMDETGIKLLWSTANVFSNPRYMNGASTNPDFDVVARAIVQIKNAIDAGIKL<br>GAENYVFWGGREGYMSLLNTDQRREKEHMATMLRMARDYARSKGFKGTFLIEPKPCEPSK<br>HQYDVDTETVIGFLKAHGLDKDFKVNIEVNHATLAGHTFEHELACAVDAGMLGSIDANRG<br>DAQNGWDTDQFPIDNFELTQAFMQIVRNGGFGTGGTNFDAKTRRNSTDLEDIFIAHISGM<br>DACARALLNAVEILEKSPIPAMLKERYASFDGGIGKDFEEGKLTFEQVYEYGKKVGEPKQ<br>TSGKQELYETIVALYAK |
| 5586MI209_003 | *Neocallimastigales* | DNA | 69 | ATGAAAGAGTATTTCCCTGAGATCGGTAAGATCCAATTTGAAGGCCCGGAGTCCAAGAAC<br>CCGATGGCGTTTCACTACTATGACGCAGAGCGCGTGTAGTAGCCGGTAAAACAATGAAAGAA<br>TGGATGCGTTTCGCCATGGCATGGTGGCACACCCTCTGTGCAGAAGGCGGCGACCAGTTC<br>GGAGGAGGAACGAAGCATTTCCCGTGGAATGAAGGCGCTAACGCTTTGGAGATCGCCAAA<br>CACAAAGCCGATGCGGGATTCGAGATCATGCAGAAACTCGGCATCCCCTATTTCTGTTTC<br>CATGACGTGGATCTCATCGCCGAGGGCGATTCGGTGGAGGAGTACGAAGCTAACCCCGCT<br>GCCATCACCGATTACCTCAAACAGAAAATGGACGAGACCGGCATCAAACTGCTGTGGTCC<br>ACGGCGAACGTCTTCAGCAACCCCCGTTACATGAACGGTGCGAGCACGAACCCGGATTTC<br>GATGTAGTGGCACGCGCTATCGTACAAATCAAGAACGCTATCGACGCCGGTATCAAACTC<br>GGAGCAGAGAACTATGTCTTCTGGGGCGGTCGCGAGGGCTATATGTCGCTCCTCAACACC<br>GACCAGCGTCGCGAGAAAGAGCATATGGCTACTATGCTCCGTATGGCGCGTGACTACGCG<br>CGTGCCAAAGGATTCAAGGGCACCTTCCTCATCGAACCCAAACCATGTGAGCCGTCCAAA<br>CATCAGTACGATGTGGACACAGAGACTGTCATCGGTTTCCTCAAAGCGCATGGACTCGAC<br>AAGGATTTCAAAGTCAACATCGAGGTCAACCACGCCACCCTCGCAGGTCACACGTTCGAA<br>CACGAACTGGCTTGCGCTGTAGATGCCGGCATGCTCGGTTCGATTGACGCCAACCGCGGT<br>GACGCCCAGAACGGATGGGACACTGACCAGTTCCCTATTGATAACTTCGAACTCACACAG<br>GCTTTCATGCAGATCGTCCGCAACGGCGGTTTCGGAACAGGCGGTACGAACTTCGACGCC<br>AAGACACGCCGTAACTCCACCGACTTGGAGGACATCTTCATCGCCCATATCAGCGGCATG<br>GACGCTTGTGTCCGTGCGTTGCTCAACGCCATCGAAATCCTCGAGAAGAGCCCGATCCCG<br>GCTATGCTCAAAGAGCGTTACGCTTCCTTTGACGGCGGCATCGGAAAGGACTTTGAGGAT<br>GGTAAACTGACTTTCGAGCAGGTCTATGAGTACGGCAAGAAGGTCGGAGAACCCAAACAG<br>ACCAGCGGCAAACAGGAGCTCTACGAAACCATCGTCGCCCTCTATGCCAAGTAA |
| 5586MI209_003 | *Neocallimastigales* | Amino Acid | 70 | MKEYFPEIGKIQFEGPESKNPMAFHYYDAERVVAGKTMKEWMRFAMAWWHTLCAEGGDQF<br>GGGTKHFPWNEGANALEIAKHKADAGFEIMQKLGIPYFCFHDVDLIAEGDSVEEYEANPA<br>AITDYLKQKMDETGIKLLWSTANVFSNPRYMNGASTNPDFDVVARAIVQIKNAIDAGIKL<br>GAENYVFWGGREGYMSLLNTDQRREKEHMATMLRMARDYARAKGFKGTFLIEPKPCEPSK<br>HQYDVDTETVIGFLKAHGLDKDFKVNIEVNHATLAGHTFEHELACAVDAGMLGSIDANRG<br>DAQNGWDTDQFPIDNFELTQAFMQIVRNGGFGTGGTNFDAKTRRNSTDLEDIFIAHISGM<br>DACVRALLNAIEILEKSPIPAMLKERYASFDGGIGKDFEDGKLTFEQVTEYGKKVGEPKQ<br>TSGKQELYETIVALYAK |
| 5586MI214_002 | *Neocallimastigales* | DNA | 71 | ATGAAAGAGTATTTCCCTGAGATCGGAAAGATCCAATTCGAAGGCCCGGAGTCCAAGAAT<br>CCTATGGCATTTCACTACTATGACGCAGAGCGTGTAGTAGCCGGTAAAACAATGAAAGAG<br>TGGATGCGTTTCGCTTTGGCATGGTGGCACACGCTCTGCGCAGAAGGCGGCGACCAGTTC<br>GGAGGCGGCACGAAGCATTTCCCTTGGAATGAAGGTGCAAACGCTTTGGAGATCGCCAAG<br>CACAAAGCCGATGCAGGCTTCGAGATCATGCAGAAACTCGGCATCCCCTATTTCTGTTTC<br>CATGACGTGGATCTGATCGCCGAGGGCGGTTCGGTAGAAGAGTATGAAGCTAATTTAACG |

TABLE 2-continued

| Clone No. | Class of organism | Type of Sequence | SEQ ID NO: | Sequence |
|---|---|---|---|---|
| | | | | GCTATCACCGATTACCTCAAACAGAAAATGGACGAGACCGGCATCAAACTGCTGTGGTCC<br>ACTGCGAACGTGTTCGGTAACGCACGTTATATGAACGGCGCGAGCACGAACCCCGATTTC<br>GATGTAGTGGCACGCGCTATCGTGCAGATCAAGAACGCTATCGACGCCGGCATCAAACTG<br>GGCGCAGAGAACTACGTCTTCTGGGGCGGTCGCGAGGGATATATGTCGCTCCTGAACACC<br>GACCAGAAGCGTGAGAAAGAGCATATGGCTACCATGCTCCGTATGGCGCGTGACTACGCG<br>CGTTCCAAAGGATTCAAAGGTACGTTCCTCATCGAGCCCAAACCGTGTGAGCCGTCCAAA<br>CATCAGTACGACGTGGACACTGAGACCGTCATCGGTTTCCTCAAAGCCCATGGTCTCGGC<br>AAGGATTTCAAAGTGAACATCGAGGTGAATCACGCCACCCTCGCAGGGCACACGTTCGAA<br>CACGAACTGGCTTGCGCCGTAGATGCCGGCATGCTCGGTTCGATCGACGCCAACCGCGGT<br>GACGCACAAAACGGATGGGACACCGACCAGTTCCCTATTGATAATTTCGAACTCACCCAG<br>GCATTCATGCAGATCGTCCGCAACGGCGGTTTCGGAACAGGCGGTACGAACTTCGACGCC<br>AAGACACGCCGTAATTCCACCGACTTGGAGGACATCTTCATCGCCCATATCAGCGGCATG<br>GACGCTTGTGCCCGTGCGTTGCTCAATGCTGTCGAAATCCTTGAAAAGAGCCCGATCCCG<br>GCGATGCTCAAAGAGCGTTACGCCTCCTTTGACAGCGGTATGGGTAAGGACTTTGAGGAG<br>GGCAAGCTGACCTTCGAGCAGGTCTATGAGTACGGCAAACAGGTCGGCGAACCCAAACAG<br>ACCAGCGGCAAGCAGGAGCTCTACGAAACCATCGTCGCCCTCTATGCCAAATAG |
| 5586MI214_002 | *Neocallimastigales* | Amino Acid | 72 | MKEYFPEIGKIQFEGPESKNPMAFHYYDAERVVAGKTMKEWMRFALAWWHTLCAEGGDQF<br>GGGTKHFPWNEGANALEIAKHKADAGFEIMQKLGIPYFCFHDVDLIAEGGSVEEYEANLT<br>AITDYLKQKMDETGIKLLWSTANVFGNARYMNGASTNPDFDVVARAIVQIKNAIDAGIKL<br>GAENYVFWGGREGYMSLLNTDQKREKEHMATMLRMARDYARSKGFKGTFLTEPKPCEPSK<br>HQYDVDTETVIGFLKAHGLGKDPKVNIEVNHATLAGHTFEHELACAVDAGMLGSIDANRG<br>DAQNGWDTDQFPIDNFELTQAFMQIVRNGGFGTGGTNFDAKTRRNSTDLEDIFIAHISGM<br>DACARALLNAVEILEKSPIPAMLKERYASFDSGMGKDFEEGKLTFEQVYEYGKQVGEPKQ<br>TSGKQELYETIVALYAK |
| 5751MI3_001 | *Neocallimastigales* | DNA | 73 | ATGAAAGAGTATTTTCCACAAATCGGCAAGATCCCATTTGAGGGACCAGAGTCAAAGAAC<br>CCAATGGCATTCCACTACTATGACGCAGAGCGCGTAGTTGCCGGTAAGACAATGAAGGAA<br>TGGATGCGTTTCGCTATGGCCTGGTGGCACACTCTCTGTGCTGAGGGTAGCGATCAGTTC<br>GGCCCTGGTACAAAGAAGTTCCCTTGGAACGAGGGCGAGACAGCCCTTGAGCGCGCTAAG<br>CACAAGGCAGATGCTGGCTTCGAGGTTATGCAGAAGCTCGGCATCCCATATTTCTGCTTC<br>CACGATGTAGACCTTATCGACGAGGGTGCTAACGTGGCTGAGTATGAGGCAAACCTCGCT<br>GCTATCACTGACTACCTGAAGGAGAAGATGGAGGAGACTGGCGTAAAGCTCCTCTGGTCT<br>ACAGCCAACGTGTTCGGTAACGCTCGCTATATGAACGGTGCTTCTACAAATCCTGACTTC<br>GACGTTGTGGCTCGTGCCATCGTACAGATTAAGAACGCTATCGACGCTGGTATCAAGCTT<br>GGTGCTGAGAACTACGTGTTCTGGGGCGGCCGCGAGGGCTACATGAGCCTTCTGAACACT<br>GACCAGAAGCGCGAGAAGGAGCACATGGCAACTATGCTCGGCATGGCTCGCGACTATGCC<br>CGCGCTAAGGGATTCACCGGTACCTTCCTCATTGAGCCAAAGCCAATGGAGCCAACAAAG<br>CATCAGTATGATGTTGACACAGAGACCGTTATCGGTTTCCTCAAGGCTCACGGTCTGGAC<br>AAGGACTTCAAGGTGAACATCGAGGTGAACCACGCTACTCTCGCCGGTCACACCTTCGAG<br>CACGAGCTCGCTTGCGCTGTTGACGCTGGTATGCTCGGTTCTATCGACGCTAACCGCGGT<br>GACGCTCAGAACGGATGGGATACCGACCAGTTCCCAATCGACAACTTCGAGCTGACACAG<br>GCTTGGATGCAGATTGTTCGCAATGGCGGTCTTGGCACAGGTGGTACCAACTTCGACGCA<br>AAGACCCGTCGTAACTCTACCGACCTCGAGGACATCTTCATCGCTCACATCTCCGGTATG<br>GACGCTTGTGCACGCGCTCTCCTCAACGCAGTAGAGATACTCGAGAACTCTCCAATCCCA<br>ACAATGCTGAAGGACCGCTATGCAAGCTTCGACTCAGGTATGGGTAAGGACTTCGAGGAC<br>GGCAAGCTCACACTTGAGCAGGTTTATGAGTATGGTAAGAAGGTCGACGAGCCAAAGCAG<br>ACCTCTGGTAAGCAGGAACTCTATGAGACCATCGTTGCTCTCTATGCAAAATAA |
| 5751MI3_001 | *Neocallimastigales* | Amino Acid | 74 | MKEYFPQIGKIPFEGPESKNPMAFHYYDAERVVAGKTMKEWMPFAMAWWHTLCAEGSDQF<br>GPGTKKFPWNEGETALERAKHKADAGFEVMQKLGIPYFCFHDVDLIDEGANVAEYEANLA<br>AITDYLKEKMEETGVKLLWSTANVFGNARYMNGASTNPDFDVVARAIVQIKNAIDAGIKL<br>GAENYVFWGGREGYMSLLNTDQKREKEHMATMLGMARDYARAKGFTGTFLIEPKPMEPTK<br>HQYDVDTETVIGFLKAHGLDKDFKVNIEVNHATLAGHTFEHELACAVDAGMLGSIDANRG<br>DAQNGWDTDQFPIDNFELTQAWMQIVRNGGLGTGGTNFDAKTRRNSTDLEDIFIAHISGM<br>DACARALLNAVEILENSPIPTMLKDRYASFDSGMGKDFEDGKLTLEQVYEYGKKVDEPKQ<br>TSGKQELYETIVALYAK |
| 5753MI3_002 | *Prevotella* | DNA | 75 | ATGGCTAAAGAATACTTCCCCTCCATCGGCAAAATCCCTTTTGAAGGAGGCGACAGCAAA<br>AATCCCCTCGCTTTCCATTATTATGACGCCGGACGCGTGGTTATGGGCAAGCCCATGAAG<br>GAATGGCTTAAATTCGCCATGGCCTGGTGGCACACGCTGGGCCAGGCCTCCGGAGACCCC<br>TTCGGCGGCCAGACCCGCAGCTACGAATGGGACAAGGGCGAATGCCCCTACTGCCGCGCC<br>AAAGCCAAGGCCGACGCCGGTTTTGAAATCATGCAAAAGCTGGGTATCGAATACTTCTGC<br>TTCCACGATGTGGACCTTATCGAGGATTGCGATGACATTGCCGAATACGAAGCCCGCATG<br>AAGGACATCACGGACTACCTGCTGGAAAAGATGAAGGAGACCGGCATCAAGAACCTCTGG<br>GGCACCGCCAATGTCTTCGGCCACAAGCGCTACATGAACGGCGCCGGCACCAATCCGCAG<br>TTCGATGTGGIGGCCCGTGCCGCCGTCCAGATCAAGAACGCCCTGGACGCCACCATCAAG<br>CTGGGCGGCTCCAACTATGTGTTCTGGGGCGGCCGCGAAGGCTATTACACCCTCCTCAAC<br>ACCCAGATGCAGCGGGAAAAAGACCACCTGGCCAAGTTGCTGACGGCCGCCCGCGACTAT<br>GCCCGCGCCAAGGGCTTCAAGGGCACCTTCCTCATTGAGCCCAAACCCATGGAACCCACC<br>AAGCACCAGTACGACGTGGATACGGAGACGGTCATCGGCTTCCTCCGTGCCAACGGCCTG<br>GACAAGGACTTCAAGGTGAACATCGAGGTGAACCACGCCACCCTGGCCGGCCACACCTIC<br>GAGCATGAGCTCACCGTGGCCCGCGAGAACGGTTTCCTGGGCTCCATCGGTGCCAACCGC<br>GGCGACGCCCAGAACGGCTGGGACACGGACCAGTTCCCTGTGGACCCGTACGATCTTACC<br>CAGGCCATGATGCAGGTGCTGCTGAACGGCGGCTTCGGCAACGGCGGCACCAACTTCGAC<br>GCCAAACTCCGCCGCTCCTCCACCGACCCTGAGGACATCTTCATCGCCCATATTTCCGCC |

TABLE 2-continued

| Clone No. | Class of organism | Type of Sequence | SEQ ID NO: | Sequence |
|---|---|---|---|---|
| | | | | ATGGATGCCATGGCCCACGCTTTGCTTAACGCAGCTGCCGTGCTGGAAGAGAGCCCCCTG<br>TGCCAGATGGTCAAGGAGCGTTATGCCAGCTTCGACGGCGGCCTCGGCAAACAGTTCGAG<br>GAAGGCAAGGCTACCCTGGAAGACCTGTACGAATACGCCAAGGTCCAGGGTGAACCCGTT<br>GTCGCCTCCGGCAAGCAGGAGCTTTACGAGACTCTCCTGAACCTGTATGCCGTCAAGTAA |
| 5753MI3_002 | *Prevotella* | Amino Acid | 76 | MAKEYFPSIGKIPFEGGDSKNPLAFHYYDAGRVVMGKPMKEWLKFAMAWWHTLGQASGDP<br>FGGQTRSYEWDKGECPYCRAKAKADAGFEIMQKLGIEYFCFHDVDLIEDCDDIAEYEARM<br>KDITDYLLEKMKETGIKNLWGTANVFGHKRYMNGAGTNPQFDVVARAAVQIKNALDATIK<br>LGGSNYVFWGGREGYYTLLNTQMQREKDHLAKLLTAARDYARAKGFKGTFLIEPKPMEPT<br>KHQYDVDTETVIGFLRANGLDKDFKVNIEVNHATLAGHTFEHELTVARENGFLGSIGANR<br>GDAQNGWDTDQFPVDPYDLTQAMMQVLLNGGFGNGGTNFDAKLRRSSTDPEDIFIAHISA<br>MDAMAHALLNAAAVLEESPLCQMVKERYASFDGGLGKQFEEGKATLEDLYEYAKVQGEPV<br>VASGKQELYETLLNLYAVK |
| 1754MI1_001 | *Prevotella* | DNA | 77 | ATGGCAAAAGAGTATTTTCCGTTTACCGGTAAGATTCCTTTCGAAGGAAAGGACAGTAAG<br>AATGTAATGGCTTTCCACTACTACGAGCCTGAGAAGGTCGTGATGGGAAAGAAGATGAAG<br>GACTGGCTGAAGTTCGCTATGGCTTGGTGGCATACACTGGGTGGCGCTTCTGCTGACCAG<br>TTTGGTGGTCAGACTCGTTCATACGAGTGGGACAAGGCTGGTGACGCTGTTCAGCGCGCT<br>AAGGATAAGATGGACGCTGGCTTCGAGATCATGGACAAGCTGGGCATCGAGTACTTCTGC<br>TTCCACGATGTTGACCTCGTTGAAGAGGGTGACACCATCGAGGAGTATGAGGCTCGCATG<br>AAGGCCATCACCGACTACGCTCAGGAGAAGATGAAGCAGTTCCCCAACATCAAGCTGCTC<br>TGGGGTACCGCAAACGTATTCGGTAACAAGCGCTATGCTAACGGTGCTTCTACCAACCCC<br>GACTTCGACGTAGTGGCTCGCGCCATCGTTCAGATCAAGAACGCTATTGATGCTACCATC<br>AAGCTGGGTGGTACCAACTATGTGTTCTGGGGTGGTCGTGAGGGCTATATGAGTCTGCTG<br>AACACCGACCAGAAGCGTGAGAAGGAGCACATGGCTACTATGCTGACCATGGCTCGCGAC<br>TATGCTCGCGCCAAGGGATTCAAGGGTACATTCCTCATTGAGCCGAAGCCCATGGAGCCC<br>AGCAAGCACCAGTATGATGTGGATACAGAGACCGTTATCGGCTTCCTGAAGGCACACAAC<br>CTGGACAAGGACTTCAAGGTGAACATCGAGGTGAACCACGCTACACTCGCTGGTCATACC<br>TTCGAGCACGAGCTGGCTTGCGCTGTTGACGCTGGTATGCTTGGTTCTATCGACGCTAAC<br>CGTGGTGATGCTCAGAACGGTTGGGATACCGACCAGTTCCCCATCGACAACTACGAGCTG<br>ACACAGGCTATGCTCGAGATCATCCGCAATGGIGGTCTGGGCAATGGTGGTACCAACTTC<br>GATGCTAAGATCCGTCGTAACAGCACCGACCTCGAGGATCTCTTCATCGCTCACATCAGT<br>GGTATGGATGCTATGGCACGCGCTCTGATGAACGCTGCTGACATCCTTGAGAACTCTGAG<br>CTGCCCGCAATGAAGAAGGCTCGCTACGCAAGCTTCGACCAGGGTGTTGGTAAGGACTTC<br>GAAGATGGCAAGCTGACCCIIGAGCAGGTITACGAGTATGGTAAGAAGGTGGGTGAGCCC<br>AAGCAGACTTCTGGTAAGCAGGAGAAGTACGAGACCATCGTTGCTCTCTATGCAAAATAA |
| 1754MI1_001 | *Prevotella* | Amino Acid | 78 | MAKEYFPFTGKIPFEGKDSKNVMAFHYTEPEKVVMGKKMKDWLKFAMAWWHTLGGASADQ<br>FGGQTRSYEWDKAGDAVQRAKDKMDAGFEIMDKLGIEYFCFHDVDLVEEGDTIEEYEARM<br>KAITDYAQEKMKQFPNIKLLWGTANVFGNKRYANGASTNPDFDVVARAIVQIKNAIDATI<br>KLGGTNYVFWGGREGYMSLLNTDQKREKEHMATMLTMARDYARAKGFKGTFLIEPKPMEP<br>SKHQYDVDTETVIGFLKAHNLDKPFKVNIEVNHATLAGHTFEHELACAVDAGMLGSIDAN<br>RGDAQNGWDTDQFPIDNYELTQAMLEIIRNGGLGNGGTNFDAKIRRNSTDLEDLFIAHIS<br>GMDAMARALMNAADILENSELPAMKKARYASFDQGVGKDFEDGKLTLEQVYEYGKKVGEP<br>KQTSGKQEKYETIVALYAK |
| 1754MI3_007 | *Prevotella* | DNA | 79 | ATGGCAAAAGAGTATTTTCCGTTTACCGGTAAGATTCCTTTCGAAGGAAAAGAGAGCAAG<br>AACGTAATGGCTTTCCATTACTATGAGCCTGAAAAGGTGGTCATGGGCAAGAAAATGAAG<br>GATTGGCTGAAATTCGCCATGGCTTGGTGGCACACCCTCGGTGGAGCCAGCGCCGACCAG<br>TTCGGTGGACAGACCCGCAGCTATGAGTGGGACAAGGCCGAGGATGCCGTACAGCGTGCT<br>AAGGACAAGATGGACGCCGGCTTCGAGATCATGGACAAACTGGGCATCGAGTATTTCTGC<br>TTCCACGATGTCGACCTCGTCGACGAGGGTGCTACCGTTGAGGAGTATGAGGCTCGCATG<br>AAAGCCATCACCGACTATGCCCAGGTCAAGATGAAGGAATATCCCAACATCAAACTGCTC<br>TGGGGCACCGCCAACGTGTTCGGCAACAAGCGTTATGCCAACGGCGCTTCCACCAACCCC<br>GACTTCGACGTGGTGGCACGCGCTATCGTTCAGATCAAGAATGCCATCGACGCTACCATC<br>AAGCTCGGCGGTCAGAACTACGTGTTCTGGGGCGGACGCGAGGGCTACATGAGCCTGCTC<br>AATACCGATCAGAAACGTGAGAAGGAACACATGGCCACCATGCTCACCATGGCGCGCGAC<br>TATGCTCGCAGCAAGGGATTCAAGGGCACCTTCCTCATCGAACCCAAACCCATGGAGCCT<br>TCCAAGCACCAGTATGATGTCGACACCGAGACGGTCATCGGCTTCCTCCGCGCCCACAAC<br>CTCGACAAGGACTTCAAGGTGAACATCGAGGTCAACCACGCCACGCTCGCCGGCCACACC<br>TTCGAGCACGAACTGGCTTGCGCCGTCGACGCCGGCATGCTCGGCAGCATCGACGCCAAC<br>CGCGGCGACGCACAGAACGGCTGGGATACCGACCAGTTCCCCATCGACAACTACGAACTG<br>ACACAGGCCATGCTGGAGATCATCCGCAATGGCGGCCTCGGCAATGGTGGTACCAACTTC<br>GACGCCAAGATCCGTCGTAACAGCACCGACCTCGAAGATCTCTTCATCGCTCACATCAGC<br>GGTATGGATGCCATGGCTCGCGCGCTGCTCAACGCCGCCGCCATCCTCGAGGAGAGCGAA<br>CTGCCCGCCATGAAGAAGGCCCGCTACGCTTCCTTCGACGAAGGTATCGGCAAGGACTTC<br>GAAGACGGCAAACTCACCCTCGAGCAGGTTTACGAGTACGGCAAGAAGGTAGGCGAGCCC<br>AAGCAGACCTCCGGCAAGCAAGAGAAGTACGAGACCATCGTGGCTCTCTACAGCAAATAA |
| 1754MI3_007 | *Prevotella* | Amino Acid | 80 | MAKEYFPFTGKIPFEGKESKNVMAFHYYEPEKVVMGKKMKDWLKFAMAWWHTLGGASADQ<br>FGGQTRSYEWDKAEDAVQRAKDKMDAGFEIMDKLGIEYFCFHDVDLVDEGATVEEYEARM<br>KAITDYAQVKMKEYPNIKLLWGTANVFGNKRYANGASTNPDFDVVARAIVQIKNAIDATI<br>KLGGQNYVFWGGREGYMSLLNTDQKREKEHMATMLTMARDYARSKGFKGTFLIEPKPMEP<br>SKHQYDVDTETVIGFLRAHNLDKDFKVNIEVNHATLAGHTFEHELACAVDAGMLGSIDAN |

TABLE 2-continued

| Clone No. | Class of organism | Type of Sequence | SEQ ID NO: | Sequence |
|---|---|---|---|---|
| | | | | RGDAQNGWDTDQFPIDNYELTQAMLEIIRNGGLGNGGTNFDAKIRRNSTDLEDLFIAHIS<br>GMDAMARALLNAAAILEESELPAMKKARYASFDEGIGKDFEDGKLTLEQVYEYGKKVGEP<br>KQTSGKQEKYETIVALYSK |
| 1754MI5_<br>009 | *Prevotella* | DNA | 81 | ATGAAAGAGTATTTCCCGCAAATTGGAAAGATTCCCTTCGAGGGACCAGAGAGCAAGAGT<br>CCATTGGCGTTCCATTATTATGAGCCGGATCGCATGGTGCTCGGAAAGAGGATGGAGGAT<br>TGGCTGAAATTCGCCATGGCATGGTGGCACACCCTTGGCCAGGCCAGCGGCGACCAGTTC<br>GGCGGACAGACACGTGAGTACGAGTGGGATAAGGCTGGAGATCCGATACAAAGGGCAAAG<br>GATAAGATGGACGCCGGATTCGAGATCATGGAGAAATTGGGTATCAAGTACTTCTGCTTC<br>CATGATGTGGATCTCGTCGAGGAAGCTCCCACCATCGCCGAATATGAGGAGCGTATGAGG<br>ATCATCACCGACTATGCGCTCGAGAAGATGAAAGCCACTGGCATCAAACTCCTTTGGGGT<br>ACAGCCAATGTTTTCGGACATAAGAGATATATGAATGGGGCCGCCACCAACCCGGAGTTC<br>GGTGTTGTCGCCAGGGCTGCTGTCCAGATCAAGAACGCGATCGACGCCACCATCAAGCTG<br>GGAGGAACAAACTATGTGTTCTGGGGTGGCCGCGAGGGCTACATGAGCCTGCTCAACACC<br>CAGATGCAGAGGGAGAAGGACCATCTCGCCAATATGCTCAAGGCTGCTCGTGACTATGCT<br>CGCGCCAAGGGATTCAAGGGCACATTCCTCATCGAGCCGAAGCCGATGGAACCTACTAAG<br>CATCAGTACGATGTCGACACTGAGACCGTGATCGGCTTCCTCCGCGCAAACGGTCTTGAC<br>AAGGATTTCAAGGTCAACATCGAGGTCAATCACGCCACTCTTGCGGGTCACACTTTCGAG<br>CATGAGCTCGCCGTGGCTGTCGACAATGGTCTCCTTGGCTCAATCGATGCGAACAGGGGA<br>GATTATCAGAACGGTTGGGACACCGACCAGTTCCCTGTTGATCTCTTTGATTTGACCCAG<br>GCCATGCTCCAGATCATCCGTAACGGAGGCCTCGGTAATGGIGGATCCAACTTCGACGCC<br>AAGCTTCGCCGTAACTCCACTGATCCTGAGGATATATTCATTGCCCATATTTGCGGTATG<br>GACGCTATGGCCAGGGCTCTCCTTGCCGCCGCCGCGATCGTGGAGGAGTCTCCTATCCCG<br>GCTATGGTCAAAGAGCGTTACGCATCCTTCGACGAAGGTGAGGGCAAGAGATTCGAGGAT<br>GGTAAGATGAGTCTGGAGGAACTTGTTGATTACGCGAAGACTCACGGAGAGCCCGCCCAG<br>AAGAGTGGCAAACAGGAGCTCTACGAAACCCTTGTCAACATGTACATCAAATAA |
| 1754MI5_<br>009 | *Prevotella* | Amino Acid | 82 | MKEYFPQIGKIPFEGPESKSPLAFHYYEPDRMVDGKRMEDWLKFAMAWWHTLGQASGDQF<br>GGQTREYEWDKAGDPIQRAKDKMDAGFEIMEKLGIKYFCFHDVDLVEEAPTIAEYEERMR<br>IITDYALEKMKATGIKLLWGTANVFGHKRYMNGAATNPEFGVVARAAVQIKNAIDATIKL<br>GGTNYVFWGGREGYMSLLNTQMQREKDHLANMLKAARDYARAKGFKGTFLIEPKPMEPTK<br>HQYDVDTETVIGFLRANGLDKDFKVNIEVNHATLAGHTFEHELAVAVDNGLLGSIDANRG<br>DYQNGWDTDQFPVDDFDLTQAMLQIIRNGGLGNGGSNFDAKLRRNSTDPEDIFIAHICGM<br>DAMARADDAAAAIVEESPIPAMVKERYASFDEGEGKRFEDGKMSDEELVDTAKTHGEPAQ<br>KSGKQELYETLVNMYIK |
| 5586MI1_<br>003 | *Prevotella* | DNA | 83 | ATGGCAAAAGAGTATTTTCCGTTTACCGGTAAGATTCCTTTCGAGGGAAAGGACAGTAAG<br>AATGTAATGGCGTTCCACTACTACGAGCCCGAGCGCGTGGTAATGGGCAAGAAGATGAAG<br>GAGTGGCTGAAGTTTGCCATGGCCTGGTGGCACACGCTGGGTGGAGCCAGTGCCGACCAG<br>TTTGGCGGACAGACCCGCAGCTACGAGTGGGACAAGGCTGAAGACGCCGTGCAGCGTGCC<br>AAGGACAAGATGGATGCCGGCTTCGAGATCATGGACAAGCTGGGCATCGAGTATTTCTGC<br>TTCCATGATGTCGATCTCGTTGACGAGGGTGCCACTGTCGAGGAGTATGAGGCTCGCATG<br>CAGGCCATCACCGACTATGCGCAGGAGAAGATGAAGCAGTATCCTGCCATCAAGCTGCTG<br>TGGGGTACGGCCAATGTCTTTGGCAACAAGCGTTATGCCAACGGTGCCTCTACCAATCCC<br>GACTTCGATGTGGTGGCCCGCGCCATCGTGCAGATTAAGAATGCCATTGATGCCACCATC<br>AAGCTGGGCGGCAGCAACTATGTGTTCTGGGGCGGTCGCGAGGGCTACATGTCGCTGCTC<br>AACACCGACCAGAAGCGTGAGAAGGAACACATGGCCCGGATGCTGACCATGGCCCGCGAC<br>TATGCCCGCTCGAAGGGCTTCAAGGGCAACTTCCTGATTGAGCCCAAGCCCATGGAGCCG<br>TCGAAGCATCAGTACGACGTGGACACCGAGACGGTTATCGGATTCCTCCGCGCACATGGC<br>CTTGACAAGGACTTCAAGGTGAACATCGAGGTGAACCATGCCACGCTGGCCGGTCATACC<br>TTCGAGCACGAACTGGCTTGCGCCGTAGATGCCGGCATGCTGGGCAGCATTGATGCCAAC<br>CGCGGCGACGCACAGAACGGATGGGACACCGACCAGTTCCCCATCGACAACTATGAGTTG<br>ACACAGGCCATGATGGAGATTATCCGCAATGGCGGTCTGGGTCTTGGCGGTACCAATTTC<br>GATGCCAAGATTCGCCGTAACTCCACCGACCTGGAAGACCTCTTCATCGCCCACATCAGT<br>GGCATGGACGCCATGGCTCGTGCGCTCCTTAATGCTGCCGACATTCTGGAGAACAGCGAA<br>CTGCCCGCCATGAAGAAAGCGCGCTACGCCTCGTTCGACAGTGGCATGGGCAAGGACTTC<br>GAGGACGGCAAACTGACCCTTGAGCAGGTTTACGAATACGGCAAAAAAGTCGGCGAACCT<br>AAGCAGACCTCCGGCAAGCAGGAGAAGTACGAGACCATCGTGGCTCTCTATGCCAAGTAA |
| 5586MI1_<br>003 | *Prevotella* | Amino Acid | 84 | MAKEYFPFTGKIPFEGKDSKNVMAFHYTEPERVVMGKKMKEWLKFAMAWWHTLGGASADQ<br>FGGQTRSYEWDKAEDAVQRAKDKMDAGFEIMDKDGIEYFCFHDVDLVDEGATVEEYEARM<br>QAITDYAQEKMKQYPAIKLLWGTANVFGNKRYANGASTNPDFDVVARAIVQIKNAIDATI<br>KLGGSNYVFWGGREGYMSLLNTDQKREKEHMARMLTMARDYARSKGFKGNFLIEPKPMEP<br>SKHQYDVDTETVIGFDRAHGLDKDEKVNIEVNHATLAGHTFEHELACAVDAGMLGSIDAN<br>RGDAQNGWDTDQFPIDNYELTQAMMEIIRNGGLGLGGTNFDAKIRRNSTDLEDLFIAHIS<br>GMDAMARALLNAADILENSELPAMKKARYASFDSGMGKDFEDGKLTLEQVYEYGKKVGEP<br>KQTSGKQEKTETIVADYAK |
| 5586MI2_<br>006 | *Prevotella* | DNA | 85 | ATGGCAAAAGAGTATTTTCCGTTTACAGGTAAAATTCCTTTCGAAGGAAAGGACAGTAAG<br>AACGTAATGGCTTTCCACTACTACGAGCCCGAAAAGGTCGTGATGGGAAAGAAAATGAAA<br>GACTGGCTGAAGTTCGCCATGGCCTGGTGGCACACACTGGGTGGCGCCAGCGCCGACCAG<br>TTTGGCGGCCAGACACGCAGCTATGAGTGGGACAAGGCTGCCGATGCCGTGCAGCGCGCA<br>AAGGACAAGATGGACGCCGGCTTCGAAATCATGGACAAGCTGGGCATCGAGTATTTCTGC<br>TTCCACGACGTGGACCTCGTTGAGGAGGGAGCCACCATCGAGGAGTATGAGGCCCGCATG<br>AAGGCTATCACCGACTATGCCCAGGAGAAGATGAAACAGTATCCCAGCATCAAGCTGCTC<br>TGGGGCACCGCCAATGTGTTTGGCAACAAGCGCTACGCCAACGGCGCCAGCACCAACCCC |

TABLE 2-continued

| Clone No. | Class of organism | Type of Sequence | SEQ ID NO: | Sequence |
|---|---|---|---|---|
| | | | | GACTTCGACGTCGTGGCCCGTGCCATCGTGCAGATCAAGAACGCCATCGATGCCACCATC<br>AAGCTGGGCGGCACCAACTACGTGTTCTGGGGCGGACGCGAGGGCTACATGAGCCTGCTC<br>AACACCGACCAGAAGCGCGAGAAGGAGCACATGGCCACCATGCTCACCATGGCCCGCGAC<br>TACGCCCGCGCAAAGGGATTCAAGGGCACCTTCCTCATCGAGCCCAAGCCCATGGAGCCG<br>TCGAAGCACCAGTACGACGTGGACACCGAGACCGTCATCGGTTTCCTGAAGGCCCACGGT<br>CTGGACAAGGACTTCAAGGTGAACATCGAGGTGAACCACGCCACGCTGGCCGGCCACACC<br>TTCGAGCATGAGCTGGCCTGCGCCGTCGACGCCGGTATGCTGGGCAGCATCGATGCCAAC<br>CGCGGCGACGCCCAGAACGGCTGGGACACCGACCAGTTCCCCATCGACAACTTCGAGCTC<br>ACCCAGGCCATGATGGAAATTATCCGCAACGGCGGCCTCGGCAACGGCGGCACCAACTTC<br>GACGCTAAGATCCGCCGCAACTCCACCGACCTCGAGGACCTCTTCATCGCCCACATCAGC<br>GGCATGGACGCCATGGCCCGCGCACTGATGAACGCTGCCGACATTATGGAGAACAGCGAG<br>CTGCCCGCCATGAAGAAGGCACGCTACGCCAGCTTCGACGCCGGCATCGGCAAGGACTTT<br>GAGGATGGCAAGCTCTCGCTGGAGCAGGTCTACGAGTATGGCAAGAAGGTGGAAGAGCCC<br>AAGCAGACCAGCGGCAAGCAGGAGAAGTACGAGACCATCGTCGCCCTCTATGCCAAGTAA |
| 5586MI2_ 006 | *Prevotella* | Amino Acid | 86 | MAKEYFPFTGKIPFEGKDSKNVMAFHYYEPEKVVMGKKMKDWLKFAMAWWHTLGGASADQ<br>FGGQTRSYEWDKAADAVQRAKDKMDAGFEIMDKLGIEYFCFHDVDLVEEGATIEEYEARM<br>KAITDYAQEKMKQYPSIKLLWGTANVFGNKRYANGASTNPDFDVVARAIVQIKNAIDATI<br>KLGGTNYVFWGGREGYMSLLNTDQKREKEHMATMLTMARDYARAKGFKGTFLIEPKPMEP<br>SKHQYDVDTETVIGFLKAHGLDKDFKVNIEVNHATLAGHTFEHELACAVDAGMLGSIDAN<br>RGDAQNGWDTDQFPIDNFELTQAMMEIIRNGGLGNGGTNFDAKIRRNSTDLEDLFIAHIS<br>GMDAMARALMNAADIMENSELPAMKKARYASFDAGIGKDFEDGKLSLEQVYEYGKKVEEP<br>KQTSGKQEKYETIVALYAK |
| 5586MI8_ 003 | *Prevotella* | DNA | 87 | ATGGCAAAAGAGTATTTCGCCTTTACAGGCAAGATTCCTTTCGAGGGAAAAGACAGTAAG<br>AACGTGATGGCTTTCCACTACTACGAGCCGGAGCGTGTGGTGATGGGCAAGAAGATGAAG<br>GAGTGGCTGAAGTTCGCCATGGCCTGGTGGCACACACTGGGTGGCGCATCGGCCGACCAG<br>TTCGGAGGCCAGACACGCAGCTACGAGTGGGACAAGGCCGCCGACGCCGTGCAGCGCGCC<br>AAGGACAAGATGGACGCCGGCTTCGAGATTATGGACAAGCTGGGCATCGAGTACTTCTGC<br>TTCCACGATGTAGACCTCGTTGAGGAGGGTGAGACCATAGCCGAGTACGAGCGCCGCATG<br>AAGGAAATCACCGACTACGCACAGGAGAAGATGAAGCAGTTCCCCAACATCAAGCTGCTC<br>TGGGGCACAGCCAACGTGTTCGGCAACAAGCGCTACGCCAACGGCGCATCGACCAACCCC<br>GACTTCGACGTTGTGGCACGCGCCATCGTGCAGATCAAGAACGCCATCGACGCCACCATC<br>AAGCTCGGCGGCTCCAACTATGTGTTCTGGGGCGGACGCGAGGGCTATATGAGCCTGCTC<br>AACACCGACCAGAAGCGCGAGAAGGAGCACATGGCCACCATGCTCACCATGGCCCGCGAC<br>TATGCACGCGCCAAGGGATTCAAGGGCACATTCCTCATCGAGCCGAAGCCCATGGAGCCC<br>TCGAAGCACCAGTACGACGTAGACACAGAGACCGTCATCGGCTTCCTCCGTGCACACGGG<br>CTGGACAAGGACTTCAAGGTGAACATCGAGGTAAACCACGCCACACTGGCCGGCCACACC<br>TTCGAGCACGAGCTGGCTTGCGCCGTCGACGCTGGCATGCTGGGCAGCATCGACGCCAAC<br>CGTGGCGACGCACAGAACGGATGGGACACCGACCAGTTCCCCATCGACAACTTCGAGCTC<br>ACACAGGCCATGATGGAAATCATCCGCAATGGCGGACTGGGCAATGGCGGCACCAACTTC<br>GACGCCAAGATCCGTCGTAACAGCACCGACCTCGAAGACCTCTTCATCGCCCACATCAGC<br>GGCATGGACGCCATGGCACGCGCACTGCTCAACGCTGCCGACATCCTGGAGCACAGCGAG<br>CTGCCCAAGATGAAGAAGGAGCGCTACGCCAGCTTCGACGCAGGCATCGGCAAGGACTTC<br>GAAGACGGCAAGCTCACACTCGAGCAGGTCTACGAGTACGGCAAGAAGGTCGAAGAGCCC<br>CGTCAGACCAGCGGCAAGCAGGAGAAGTACGAGACCATCGTCGCCCTCTATGCCAAGTAA |
| 5586MI8_ 003 | *Prevotella* | Amino Acid | 88 | MAKEYFAFTGKIPFEGKDSKNVMAFHYTEPERVVMGKKMKEWLKFAMAWWHTLGGASADQ<br>FGGQTRSYEWDKAADAVQRAKDKMDAGFEIMDKLGIEYFCFHDVDLVEEGETIAEYERRM<br>KEITDYAQEKMKQFPNIKLLWGTANVFGNKRYANGASTNPDFDVVARAIVQIKNAIDATI<br>KLGGSNYVFWGGREGYMSLLNTDQKREKEHMATMLTMARDYARAKGFKGTFLIEPKPMEP<br>SKHQYDVDTETVIGFLRAHGLDKDFKVNIEVNHATLAGHTFEHELACAVDAGMLGSIDAN<br>RGDAQNGWDTDQFPIDNFELTQAMMEIIRNGGLGNGGTNFDAKIRRNSTDLEDLFIAHIS<br>GMDAMARALLNAADILEHSELPKMKKERYASFDAGIGKDFEDGKLTLEQVYEYGKKVEEP<br>RQTSGKQEKYETIVALYAK |
| 5586MI14_ 003 | *Prevotella* | DNA | 89 | ATGGCAAAAGAGTATTTTCCGTTTACTGGTAAGATTCCTTTCGAGGGAAAGGATAGTAAG<br>AATGTAATGGCTTTCCACTATTACGAGCCCGAGAAAGTCGTGATGGGAAAGAAGATGAAG<br>GACTGGCTGAAGTTCGCAATGGCTTGGTGGCATACACTGGGTGGTGCATCTGCAGACCAG<br>TTCGGTGGAGAGACCCGCAGCTACGAGTGGAGCAAGGCTGCTGATCCCGTTCAGCGCGCC<br>AAGGACAAGATGGACGCCGGCTTTGAGATTATGGATAAGCTGGGCATCGAGTACTTCTGT<br>TTCCACGATATAGACCTCGTTCAGGAGGCAGATACCATTGCAGAATATGAGGAGCGCATG<br>AAGGCAATTACCGACTATGCTCTGGAGAAGATGAAGCAGTTCCCCAACATCAAGTTGCTC<br>TGGGGTACCGCTAACGTATTTAGCAACAAGCGCTATATGAACGGTGCTTCTACCAATCCC<br>GACTTCGACGTGGTGGCCCGTGCCATCGTTCAGATCAAGAACGCTATTGATGCAACCATC<br>AAACTCGGTGGTACCAACTATGTATTCTGGGGTGGTCGTGAGGGTTACATGAGCCTATTG<br>AATACCGACCAGAAGCGTGAAAAGGAGCACATGGCAATGATGCTCGGTATGGCTCGCGAC<br>TATGCCCGCAGCAAGGGATTCAAGGGTACGTTCCTCATCGAGCCGAAGCCGATGGAGCCC<br>TCTAAGCATCAGTATGATGTCGATACGGAGACTGTGATTGGTTTCCTGAAGGCACACGGT<br>CTGGACAAGGACTTCAAGGTGAACATCGAGGTGAACCACGCTACACTGGCTGGTCATACC<br>TTCGAGCATGAGCTGGCTTGCGCTGTTGACGCAGGTATGCTGGGCTCTATCGACGCTAAC<br>CGCGGTGATGCCCAGAACGGCTGGGATACCGACCAGTTCCCCATCGACAACTACGAGCTG<br>ACACAGGCTATGATGGAAATCATCCGCAACGGTGGTCTGGGCAATGGTGGTACCAACTIC<br>GACGCTAAGATCCGCCGTAACTCTACCGACCTCGAGGATCTGTTCATCGCTCATATCAGT<br>GGTATGGATGCTATGGCCCGTGCTTTGTTGAATGCTGCCGACATTCTGGAGAACTCTGAA<br>CTGCCCGCTATGAAGAAGGCCCGCTACGCCAGCTTCGACAACGGTATCGGTAAGGACTTC |

TABLE 2-continued

| Clone No. | Class of organism | Type of Sequence | SEQ ID NO: | Sequence |
|---|---|---|---|---|
| | | | | GAGGATGGCAAGCTGACCTTCGAGCAGGTTTACGAATATGGTAAGAAAGTTGAAGAGCCG<br>AAGCAGACCTCTGGCAAGCAGGAGAAATACGAGACCATCGTTGCTCTGTATGCTAAATAA |
| 5586MI14_ 003 | *Prevotella* | Amino Acid | 90 | MAKEYFPFTGKIPFEGKDSKNVMAFHYYEPEKVVMGKKMKDWLKFAMAWWHTLGGASADQ<br>FGGETRSYEWSKAADPVQRAKDKMDAGFEIMDKLGIEYFCFHDIDLVQEADTIAEYEERM<br>KAITDYALEKMKQFPNIKLLWGTANVFSNKRYMNGASTNPDFDVVARAIVQIKNAIDATI<br>KLGGTNYVFWGGREGYMSLLNTDQKREKEHMAMMLGMARDYARSKGFKGTFLIEPKPMEP<br>SKHQYDVDTETVIGFLKAHGLDKDFKVNIEVNHATLAGHTFEHELACAVDAGMLGSIDAN<br>RGDAQNGWDTDQFPIDNYELTQAMMEIIRNGGLGNGGTNFDAKIRRNSTDLEDLFIAHIS<br>GMDAMARALLNAADILENSELPAMKKARYASFDNGIGKDFEDGKLTFEQVYEYGKKVEEP<br>KQTSGKQEKYETIVALYAK |
| 5586MI26_ 003 | *Prevotella* | DNA | 91 | ATGGCAAAAGAGTATTTTCCGTTTACCGGTAAAATTCCTTTCGAGGGAAAGGACAGTAAG<br>AATGTAATGGCTTTCCACTACTACGAGCCTGAGCGCGTAGTGATGGGAAAGAAGATGAAG<br>GATTGGTTGCGATTTGCAATGGCTTGGTGGCACACACTGGGTGGCGCTTCTGCCGACCAG<br>TTTGGTGGTCAGACCCGCAGTTACGAATGGGACAAGGCTGCTGATGCTGTICAGCGTGCT<br>AAGGACAAGATGGATGCCGGCTTCGAGATTATGGATAAGCTGGGAATCGAGTICTTCTGC<br>TGGCACGATATCGACCTCGTTGAAGAGGGTGAGACCATTGAAGAGTATGAGCGCCGCATG<br>AAGGCTATCACCGACTATGCTCTTGAGAAGATGCAGCAGTATCCCAACATCAAGAACCTC<br>TGGGGAACAGCCAATGTGTTTGGCAACAAGCGTTATGCCAACGGTGCCAGCACAAACCCA<br>GACTTTGACGTCGTTGCTCGTGCTATCGTACAGATTAAGAATGCTATCGACGCTACTATC<br>AAGTTGGGTGGTCAGAATTATGTGTTCTGGGGTGGCCGTGAGGGCTACATGAGCCTGCTC<br>AATACTGACCAGAAGCGTGAGAAGGAGCACATGGCTACAATGCTGACCATGGCACGCGAC<br>TATGCCCGCAGCAAGGGATTCAAGGGTAACTTCCTCATTGAGCCCAAGCCCATGGAGCCG<br>TCAAAGCACCAGTATGATGTTGACACCGAGACCGTATGCGGTTTCCTGCGTGCCCACAAC<br>CTTGACAAGGATTTCAAGGTAAATATCGAGGTTAACCATGCTACTCTGGCTGGTCATACT<br>TTCGAGCACGAACTGGCATGCGCTGTTGACGCTGGTATGCTTGGTTCTATCGATGCTAAC<br>CGTGGTGATGCCCAGAATGGCTGGGATACCGACCAGTTCCCCATCAACAACTATGAACTC<br>ACTCAGGCTATGCTTGAGATCATCCGTAATGGTGGTCTGGGTCTTGGCGGCACAAACTTC<br>GATGCCAAGATTCGTCGTAACTCAACAGATCTTGAGGATCTCTTCATCGCTCACATCAGT<br>GGTATGGATGCCATGGCCCGTGCTCTGCTGAATGCTGCTGCTATTCTGGAGGAGAGCGAG<br>CTGCCTAAGATGAAGAAGGAGCGTTATGCTTCTTTCGATGCCGGTATCGGTAAGGACTTC<br>GAGGATGGCAAGCTTACCCTTGAGCAGGCTTACGAGTATGGTAAGAAGGTTGAGGAGCCC<br>AAGCAGACTTCAGGCAAGCAGGAGAAGTACGAGACCATCGTTGCTCTGTATGCAAAATAA |
| 5586MI26_ 003 | *Prevotella* | Amino Acid | 92 | MAKEYFPFTGKIPFEGKDSKNVMAFHYYEPERVVMGKKMKDWLRFAMAWWHTLGGASADQ<br>FGGQTRSYEWDKAADAVQRAKDKMDAGFEIMDKLGIEFFCWHDIDLVEEGETIEEYERRM<br>KAITDYALEKMQQYPNIKNLWGTANVFGNKRYANGASTNPDFDVVARAIVQIKNAIDATI<br>KLGGQNYVFWGGREGYMSLLNTDQKREKEHMATMLTMARDYARSKGFKGNFLIEPKPMEP<br>SKHQYDVDTETVCGFLRAHNLDKDFKVNIEVNHATLAGHTFEHELACAVDAGMLGSIDAN<br>RGDAQNGWDTDQFPINNYELTQAMLEIIRNGGLGLGGTNFDAKIRRNSTDLEDLFIAHIS<br>GMDAMARALLNAAAILEESELPKMKKERYASFDAGIGKDFEDGKLTLEQAYEYGKKVEEP<br>KQTSGKQEKYETIVALYAK |
| 5586MI86_ 001 | *Prevotella* | DNA | 93 | ATGAAACAGTATTTTCCCCAGATTGGAAAGATACCCTTCGAGGGTGTAGAGAGCAAGAAT<br>GTGATGGCTTTCCACTATTATGAGCCAGAAAGAGTAGTCATGGGCAAGCCTATGAAAGAA<br>TGGCTGCGCTTCGCTATGGCGTGGTGGCACACGCTGGGGCAGGCGAGCGGCGACCCCTTC<br>GGCGGACAGACCCGCAGCTACGAGTGGGACCGTGCGGCCGACGCGCTACAGCGCGCCAAG<br>GACAAGATGGATGCGGGCTTCGAGCTGATGGAGAAGCTTGGCATTGAGTACTTCTGCTTC<br>CACGACGTGGACCTCGTAGAAGAGGGCGCCACGGTGGAGGAATACGAGCGGCGGATGGCT<br>GCCATCACCGACTACGCGGTAGAGAAGATGCGCGAGCATCCCGAGATACACTGCCTGTGG<br>GGCACGGCCAATGTCTTCGGCCACAAGCGCTACATGAACGGAGCCGCCACCAACCCCGAC<br>TTCGACGTGGTGGCGCGTGCGGTGGTGCAGATAAAGAACAGCATCGACGCCACGATCAAG<br>CTGGGCGGCGAGAACTATGTGTTCTGGGGCGGACGCGAGGGATATATGAGCCTGCTCAAC<br>ACCGACCAGCGCCGCGAGAAGGAGCACCTGGCCATGATGCTTGCGAAGGCCCGCGACTAT<br>GGCCGCGCCCACGGCTTCAAGGGCACCTTCCTGATAGAGCCCAAGCCGATGGAGCCCATG<br>AAGCACCAGTACGACGTGGACACCGAGACGGTGATAGGTTTCCTGCGTGCCCACGGACTG<br>GACAAGGACTTCAAGGTGAACATCGAGGTGAACCACGCCACGTTGGCGGGCCACACGTTC<br>GAGCACGAGCTGGCCTGTGCCGTCGATGCCGGCATGCTGGGCAGCATCGACGCCAACCGT<br>GGCGACGCGCAGAACGGATGGGATACGGACCAGTTCCCCATAGACTGCTACGAGCTCACG<br>CAGGCGTGGATGGAGATCATTCGTGGCGGCGGCTTCACCACCGGCGGCACCAACTTCGAC<br>GCTAAGCTGCGCCGCAACTCGACCGACCCCGAGGATATCTTCATAGCTCACATCAGCGGC<br>ATGGATGCTATGGCCCGCGCCCTGCTCTGCGCCGCCGACATCTTGGAGCACAGCGAGCTG<br>CCGGAGATGAAGCGGAAGCGCTATGCCTCGTTCGACAGCGGCATGGGCAAGGAGTTCGAA<br>GAGGGCAATCTCAGCTTCGAGCAAATCTATGCCTACGGCAAGCAGGCGGGCGAACCGGCC<br>ACGACCAGCGGCAAGCAGGAGAAATACGAAGCCATTGTTTCACTTTATACCCGATGA |
| 5586MI86_ 001 | *Prevotella* | Amino Acid | 94 | MKQYFPQIGKIPFEGVESKNVMAFHYYEPERVVMGKPMKEWLRFAMAWWHTLGQASGDPF<br>GGQTRSYEWDRAADALQRAKDKMDAGFELMEKLGIEYFCFHDVDINEEGATVEEYERRMA<br>AITDYAVEKMREHPEIHCLWGTANVFGHKRYMNGAATNPDFDVVARAVVQIKNSIDATIK<br>LGGENYVFWGGREGYMSLLNTDQRREKEHLAMMLAKARDYGRAHGFKGTFLIEPKPMEPM<br>KHQYDVDTETVIGFLRAHGLDKDFKVNIEVNHATLAGHTFEHELACAVDAGMLGSIDANR<br>GDAQNGWDTDQFPIDCYELTQAWMEIIRGGGFTTGGTNFDAKLRRNSTDPEDIFIAHISG<br>MDAMARALLCAADILEESELPEMKRKRYASFDSGMGKEFEEGNLSFEQIYAYGKQAGEPA<br>TTSGKQEKYEAIVSLYTR |

TABLE 2-continued

| Clone No. | Class of organism | Type of Sequence | SEQ ID NO: | Sequence |
|---|---|---|---|---|
| 5586MI108_002 | *Prevotella* | DNA | 95 | ATGGCAAAAGAGTATTTTCCGTTTATCGGTAAGGTTCCTTTCGAAGGAACAGAGAGCAAG<br>AACGTGATGGCATTCCACTACTATGAGCCCGAAAAGGTGGTCATGGGTAAGAAAATGAAG<br>GACTGGCTGAAGTTCGCTATGGCTTGGTGGCACACACTGGGTGGTGCCAGCGCCGACCAG<br>TTTGGTGGTCAGACTCGCAGCTACGAGTGGGACAAGGCTGCTGATGCCGTTCAGCGCGCC<br>AAGGACAAGATGGATGCTGGCTTCGAGATCATGGATAAGCTCGGCATTGAGTACTTCTGC<br>TTCCATGACGTAGACCTCGTTGAGGAGGGTGAAACCGTCGCTGAGTATGAGGCTCGCATG<br>AAGGTCATCACCGACTATGCCCTGGAGAAGATGCAGCAGTTCCCCAACATCAAACTGCTC<br>TGGGGTACTGCTAACGTGTTCGGCCACAAGCGCTATGCCAACGGTGCCAGCACCAATCCC<br>GACTTCGACGTCGTGGCCCGTGCTATCGTTCAGATCAAGAATGCCATCGATGCTACCATT<br>AAGCTCGGCGGTACGAACTATGTGTTCTGGGGTGGTCGTGAGGGCTACATGAGCCTTCTC<br>AACACCGACCAGAAGCGCGAGAAGGAGCACATGGCAACGATGCTGACCATGGCTCGCGAC<br>TATGCCCGCGCCAAGGGATTCAAGGGCACGTTCCTCATCGAGCCGAAGCCCATGGAGCCC<br>TCGAAGCATCAGTACGACGTCGACACCGAGACCGTCATCGGCTTCCTCCGTGCCCACGGT<br>CTGGATAAGGACTTCAAGGTGAACATCGAGGTGAACCACGCCACGCTGGCCGGTCATACC<br>TTCGAGCACGAACTGGCTTGCGCCGTTGATGCCGGCATGCTCGGCTCTATCGATGCCAAC<br>CGCGGCGACGCTCAGAACGGCTGGGACACCGACCAGTTCCCCATCGACAACTACGAGCTC<br>ACTCAGGCCATGATGGAAATCATCCGTAATGGCGGTCTGGGCAACGGCGGCACGAACTTC<br>GATGCCAAGATCCGTCGTAACAGCACCGACCTCGAGGACCTCTTCATCGCTCACATCAGC<br>GGCATGGATGCCATGGCACGCGCTCTGATGAACGCTGCTGCCATCCTCGAAGAGAGCGAG<br>CTGCCCGCCATGAAGAAGGCCCGCTATGCTTCGTTCGACGAGGGTATCGGCAAGGACTTC<br>GAGGACGGCAAGTTGTCACTTGAGCAGGTCTACGAATATGGTAAGAAGGTTGAGGAGCCC<br>AAGCAGACCTCGGGCAAGCAGGAGAAGTACGAGACCATCGTGGCCCTCTATGCCAAGTAA |
| 5586MI108_002 | *Prevotella* | Amino Acid | 96 | MAKEYFPFIGKVPFEGTESKNVMAFHYYEPEKVVMGKKMKDWLKFAMAWWHTLGGASADQ<br>FGGQTRSYEWDKAADAVQRAKDKMDAGFEIMDKLGIEYFCFHDVDLVEEGETVAEYEARM<br>KVITDYALEKMQQFPNIKLLWGTANVFGHKRYANGASTNPDFDVVARAIVQIKNAIDATI<br>KLGGTNYVFWGGREGYMSLLNTDQKREKEHMATMLTMARDYARAKGFKGTFLIEPKPMEP<br>SKHQYDVDTETVIGFLRAHGLDKDFKVNIEVNHATLAGHTFEHELACAVDAGMLGSIDAN<br>RGDAQNGWDTDQFPIDNYELTQAMMEIIRNGGLGNGGTNFDAKIRRNSTDLEDLFIAHIS<br>GMDAMARALMNAAAILEESELPAMKKARYASFDEGIGKDFEDGKLSLEQVYEYGKKVEEP<br>KQTSGKQEKYETIVALYAK |
| 5586MI182_004 | *Prevotella* | DNA | 97 | ATGGCAAAAGAGTATTTTCCGTTTGTTGGTAAGATTCCTTTCGAGGGAAAGGATAGTAAG<br>AATGTAATGGCTTTCCACTATTACGAACCAGAGAAGGTCGTGATGGGAAAGAAGATGAAG<br>GACTGGCTGAAGTTCGCCATGGCATGGTGGCACACACTGGGACAGGCCAGTGCCGACCCG<br>TTTGGAGGTCAGACCCGCAGCTACGAGTGGGACAAGGCTGACGATGCTGTGCAGCGCGCA<br>AAGGACAAGATGGATGCCGGATTTGAGATCATGGACAAGCTGGGCATCGAGTACTTCTGC<br>TTCCACGATGTAGACCTCGTTGAGGAGGGAGCAACTGTTGAGGAGTACGAGGCTCGCATG<br>AAGGCCATCACCGACTATGCATTGGAGAAGATGAAAGAGTATCCCAACATCAAGAACCTC<br>TGGGGTACAGCCAATGTATTCAGCAACAAGCGCTATATGAACGGTGCCAGCACCAACCCC<br>GACTTCGACGTTGTTGCACGTGCCATCGTACAGATAAAGAACGCCATTGACGCTACCATC<br>AAGCTCGGCGGTCAGAACTACGTGTTCTGGGGCGGACGTGAGGGATACATGAGCCTGCTC<br>AACACCGACCAGAAGCGCGAGAAGGAGCACATGGCAACCATGCTGACCATGGCTCGCGAC<br>TACGCTCGCAAGAACGGTTTCAAGGGCACATTCCTCATCGAGCCTAAGCCCATGGAACCC<br>TCAAAGCACCAGTACGACGTAGACACAGAGACCGTATGCGGTTTCCTCCGCGCCCATGGT<br>CTTGACAAGGATTTCAAGGTGAACATTGAGGTGAACCACGCTACCCTCGCCGGCCACACC<br>TTTGAGCATGAACTGGCTTGCGCCGTCGACAACGGCATGCTCGGCAGCATCGATGCCAAC<br>CGCGGCGACGTTCAGAACGGCTGGGACACCGACCAGTTCCCCATCGACAACTACGAGCTG<br>ACTCAGGCCATGCTCGAAATCATCCGCAACGGTGGTCTGGGCAACGGCGGTACCAACTTC<br>GACGCCAAGATCCGTCGTAACTCTACCGACCTCGAGGATCTGTTCATCGCCCACATCAGC<br>GGTATGGACGCCATGGCACGTGCACTGCTCAATGCAGCAGCCATACTGGAGGAGAGCGAG<br>CTGCCTGCCATGAAGAAGGAGCGTTACGCCAGCTTCGACAGCGGCATCGGCAAGGACTTC<br>GAGGACGGCAAGCTCACACTTGAGCAGGCCTATGAGTATGGTAAGAAGGTTGAGGAGCCA<br>AAGCAGACCTCTGGCAAGCAGGAGAAGTATGAGACTATAGTAGCCCTCTACGCTAAGTAG |
| 5586MI182_004 | *Prevotella* | Amino Acid | 98 | MAKEYFPFVGKIPFEGKDSKNVMAFHYYEPEKVVMGKKMKDWLKFAMAWWHTLGQASADP<br>FGGQTRSYEWDKADDAVQRAKDKMDAGFEIMDKLGIEYFCFHDVDLVEEGATVEEYEARM<br>KAITDYALEKMKEYPNIKNLWGTANVFSNKRYMNGASTNPDFDVVARAIVQIKNAIDATI<br>KLGGQNYVFWGGREGYMSLLNTDQKREKEHMATMLTMARDYARKNGFKGTFLIEPKPMEP<br>SKHQYDVDTETVCGFLRAHGLDKDFKVNIEVNHATLAGHTFEHELACAVDNGMLGSIDAN<br>RGDVQNGWDTDQFPIDNYELTQAMLEIIRNGGLGNGGTNFDAKIRRNSTDLEDLFIAHIS<br>GMDAMARALLNAAAILEESELPAMKKERYASFDSGIGKDFEDGKLTLEQAYEYGKKVEEP<br>KQTSGKQEKYETIVALYAK |
| 5586MI193_004 | *Prevotella* | DNA | 99 | ATGACTAAAGAGTATTTCCCTACCATTGGCAAGATTCCCTTTGAGGGACCTGAAAGCAAG<br>AACCCGCTTGCATTCCATTACTATGAGCCCGACCGCCTGGTCATGGGCAAGAAGATGAAA<br>GACTGGCTGCGTTTCGCCATGGCCTGGTGGCACACCCTGGGCCAGGCCTCCGGCGACCAG<br>TTCGGCGGCCAGACCCGCCACTATGCCTGGGATGATCCGGATTGCCCGTATGCACGTGCC<br>AAAGCCAAGGCCGACGCCGGTTTCGAAATCATGCAGAAACTGGGCATTGAATTCTTCTGC<br>TTCCACGACATCGACCTGGTCGAGGATGCCGATGAAATCGCCGAGTACGAGGCCCGGATG<br>AAGGACATCACCGACTATCTGCTCGTCAAGATGAAAGAGACCGGCATCAAGAACCTTTGG<br>GGAACGGCCAACGTATTTGGCCACAAGCGCTACATGAACGGCGCCGCCACCAACCCCGAT<br>TTCGACGTGCTGGCCCGTGCCGCCGTCCAGATCAAGAACGCCATCGACGCCACCATCAAG<br>TTGGGCGGTCAGAACTATGTGTTCTGGGGCGGCCGTGAAGGCTACCAGACCCTGCTCAAT<br>ACCCAGATGCAGCGCGAGAAGGAACACATGGGCCGTATGTTGGCACTGGCCCGCGACTAT<br>GGCCGTGCACACGGTTTCAAGGGCACGTTCCTCATCGAGCCCAAACCGATGGAGCCGACC |

TABLE 2-continued

| Clone No. | Class of organism | Type of Sequence | SEQ ID NO: | Sequence |
|---|---|---|---|---|
| | | | | AAGCACCAGTACGATCAGGATACGGAAACCGTCATCGGCTTCCTGCGCCGCCATGGCCTC<br>GACAAGGACTTCAAGGTCAACATCGAGGTGAACCATGCTACCCTGGCGGGCCACACCTTC<br>GAGCACGAGCTGGCTTGCGCCGTCGACCACGGCATGCTGGGCAGCATCGACGCCAACCGG<br>GGTGATGCCCAGAACGGCTGGGACACCGACCAGTTCCCGATCGATAACTATGAGCTGACG<br>CTGGCCATGCTCCAGATCATCCGCAACGGCGGCCTGGCACCCGGCGGCTCGAACTTCGAT<br>GCGAAGCTGCGTCGCAACTCCACCGATCCGGAAGATATCTTCATCGCGCACATCAGCGCC<br>ATGGATGCCATGGCCCGCGCCCTGGTCAATGCTGTCGCCATTCTCGAGGAATCGCCCATC<br>CCGGCCATGGTCAGGGAACGTTACGCCTCDTTCGACAGCGGAAAGGGCAGGGAATATGAG<br>GAAGGCAGGCTGTCTCTCGAAGACATCGTGGCCTATGCCAAAGCCCACGGCGAACCGAAA<br>CAGATTTCCGGCAAGCAGGAACTCTACGAAACCATCGTGGCTCTCTATTGCAAGTAG |
| 5586MI193_Prevotella 004 | | Amino Acid | 100 | MTKEYFPTIGKIPFEGPESKNPLAFHYYEPDRLVMGKKMKDWLRFAMAWWHTLGQASGDQ<br>FGGQTRHYAWDDPDCPYARAKAKADAGFEIMQKLGIEFFCFHDIDLVEDADEIAEYEARM<br>KDITDYLLVKMKETGIKNLWGTANVFGHKRYMNGAATNPDFDVLARAAVQIKNAIDATIK<br>LGGQNYVFWGGREGYQTLLNTQMQREKEHMGRMLALARDYGRAHGFKGTFLIEPKPMEPT<br>KHQYDQDTETVIGFLRRHGLDKDFKVNIEVNHATLAGHTFEHELACAVDHGMLGSIDANR<br>GDAQNGWDTDQFPIDNYELTLAMLQIIRNGGLAPGGSNFDAKLRRNSTDPEDIFIAHISA<br>MDAMARALVNAVAILEESPIPAMVRERYASFDSGKGREYEEGRLSLEDIVAYAKAHGEPK<br>QISGKQELYETIVALYCK |
| 5586MI195_*Prevotella* 003 | | DNA | 101 | ATGGCAAAAGAGTATTTCCCGCAGATCGGAAAGATCGGCTTTGAGGGTCCTGCAAGCAAG<br>AACCCGCTGGCATTCCATTATTATGACGCCGAGCGCGTGGTGATGGGTAAACCCATGAAA<br>GACTGGTTTAAATTCGCCCTCGCGTGGTGGCACAGCCTCGGCCAGGCCTCCGGCGACCCG<br>TTCGGCGGCCAGACCCGCTCCTACGAGTGGGACAAGGGCGAATGCCCCTACTGCCGCGCC<br>CGCGCCAAGGCGGACGCCGGCTTCGAGATCATGCAAAAGCTCGGCATCGGCTATTTCTGC<br>TTCCACGACGTCGACCTCATCGAAGACACGGACGACATCGCCGAATATGAGGCCCGCCTC<br>AAGGACATCACGGACTACCTGCTCGAAAGGATGCAGGAAACCGGCATCAAGAACCTCTGG<br>GGCACGGCCAATGTCTTCGGTCACAAGCGCTACATGAACGGCGCCGGCACCAATCCGCAG<br>TTCGACATCGTCGCCCGCGCTGCCGTCCAGATCAAGAACGCCCTCGACGCCACCATCAAG<br>CTCGGTGGCTCGAACTACGTCTTCTGGGGCGGCCGCGAAGGTTATTACACGCTGCTCAAC<br>ACCCAGATGCAGCGCGAGAAAGACCACCTCGCCAAGCTCCTCACCGCCGCCCGCGACTAT<br>GCCCGCGCCAAGGGCTTCCAGGGCACCTTCCTGATCGAGCCCAAGCCGATGGAGCCGACC<br>AAGCACCAGTACGATGTCGACACGGAGACTGTAATCGGATTCCTCCGCGCCAACGGACTG<br>GACAAGGACTTCAAGGTCAACATCGAGGTCAACCACGCCACCCTCGCCGGCCATACCTTC<br>GAGCATGAGCTGACCGTCGCCCGCGAGAACGGATTCCTCGGCAGCATCGACGCCAACCGC<br>GGTGACGCCCAGAACGGCTGGGACACCGACCAGTTCCCCGTGGACGCCTACGACCTCACC<br>CAGGCCATGATGCAGGTGCTCCTGAACGGCGGTTTCGGCAACGGCGGCACCAATTTCGAC<br>GCCAAGCTCCGTCGCAGCTCCACCGATCCCGAGGACATCTTCATCGCCCACATCAGCGCG<br>ATGGACGCCATGGCCCACGCCCTGCTGAACGCCGCGGCCATTCTCGAGGAGAGCCCGCTG<br>CCCGCGATGGTCAAGGAGCGTTACGCCTCCTTCGACAGCGGTCTCGGCAAGCAGTTCGAG<br>GAGGGAAAGGCCACGCTGGAGGACCTCTACGACTACGCCAAGGCCCATGGCGAGCCCGTC<br>GCCGCCTCCGGCAAGCAGGAACTGTGTGAAACTTACCTGAATCTGTATGCAAAGTAA |
| 5586MI195_*Prevotella* 003 | | Amino Acid | 102 | MAKEYFPQIGKIGFEGPASKNPLAFHYYDAERVVMGKPMKDWFKFALAWWHSLGQASGDP<br>FGGQTRSYEWDKGECPYCRARAKADAGFEIMQKLGIGYFCFHDVDLIEDTDDIAEYEARL<br>KDITDYLLERMQETGIKNLWGTANVFGHKRYMNGAGTNPQFDIVARAAVQIKNALDATIK<br>LGGSNYVFWGGREGYYTLLNTQMQREKDHLAKLLTAARDYARAKGFQGTFLIEPKPMEPT<br>KHQYDVDTETVIGFLRANGLDKDFKVNIEVNHATLAGHTFEHELTVARENGFLGSIDANR<br>GDAQNGWDTDQFPVDAYDLTQAMMQVLLNGGFGNGGTNFDAKLRRSSTDPEDIFIAHISA<br>MDAMAHALLNAAAILEESPLPAMVKERYASFDSGLGKQFEEGKATLEDLYDYAKAHGEPV<br>AASGKQELCETYLNLYAK |
| 5586MI196_*Prevotella* 003 | | DNA | 103 | ATGACAAAAGAGTATTTCCCTACCATCGGCAAGATCCCCTTTGAGGGACCCGAGAGCAAA<br>AACCCCCTCGCTTTTCATTACTATGAGCCCGACCGCCTGGTCATGGGCAAGAAGATGAAA<br>GACTGGCTGCGTTTCGCCATGGCCTGGTGGCACACCCTGGGCCAGGCCTCCGGCGACCAG<br>TTTGGCGGCCAGACCCGCCACTATGCCTGGGATGATCCGGATTGCCCGTATGCACGTGCC<br>AAAGCCAAGGCCGACGCCGGTTTCGAAATCATGCAGAAACTGGGCATTGAATTCTTCTGC<br>TTCCACGACATCGACCTGATCGAGGATACCGATGACATCGTCGAGTATGAGGCCCGGATG<br>AAGGACATCACCGACTATCTGCTGGTCAAGATGAAAGAGACCGGCATCAAGAATCTCTGG<br>GGAACGGCCAACGTATTCGGGCACAAGCGCTATATGAACGGCGCTGCCACCAACCCCGAT<br>TTCGACGTGCTGGCCCGTGCCGCCGTCCAGATCAAGAACGCCATCGACGCCACCATCAAG<br>CTGGGCGGCCAGAATTATGTGTTCTGGGGCGGGCGTGAAGGCTACCAGAGCCTGCTCAAT<br>ACCCAGATGCAGCGCGAAAAGGAACACATGGGCCGTATGTTGGCACTAGCCCGCGACTAT<br>GGCCGTGCACACGGTTTCAAGGGCACGTTCCTCATCGAGCCCAAACCGATGGAGCCGACC<br>AAGCACCAGTACGATCAGGATACGGAGACCGTCATCGGTTTTCTGCGCCGCCATGGCCTC<br>GACAAGGACTTCAAGGTCAACATCGAGGTGAACCATGCTACCCTGGCGGGCCACACCTTC<br>GAGCACGAGCTGGCCTGCGCCGTCGACCACGGCATGCTGGGCAGTATTGACGCCAACCGC<br>GGTGACGCCCAGAACGGCTGGGACACCGACCAGTTCCCGATCGATAACTATGAGCTGACG<br>CTGGCCATGCTCCAGATCATCCGCAACGGCGGCCTGGCACCCGGCGGCTCGAACTTCGAT<br>GCGAAGCTGCGTCGCAACTCCACCGATCCGGAAGATATCTTCATCGCGCACATCAGCGCC<br>ATGGATGCCATGGCCCGCGCCCTGGTCAACGCTGTCGCCATTCTTGAGGAATCGCCCATT<br>CCGGACATGGTCAAGGAGCGCTACGCTTCGTTCGACAGCGGAAAAGGCAGGGAGTACGAA<br>GAGGGGAAACTTTCCTTCGAGGACCTCGTGGCCTATGCCAAAGCCCACGGCGAACCGAAA<br>CAGATTTCCGGCAAGCAGGAACTCTACGAAACCATCGTGGCTCTCTATTGCAAGTAG |

TABLE 2-continued

| Clone No. | Class of organism | Type of Sequence | SEQ ID NO: | Sequence |
|---|---|---|---|---|
| 5586MI196_003 | *Prevotella* | Amino Acid | 104 | MTKEYFPTIGKIPFEGPESKNPLAFHYYEPDRLVMGKKMKDWLRFAMAWWHTLGQASGDQ<br>FGGQTRHYAWDDPDCDTARAKAKADAGFEIMQKLGIEFFCFHDIDLIEDTDDIVEYEARM<br>KDITDYLLVKMKETGIKNLWGTANVFGHKRYMNGAATNPDFDVLARAAVQIKNAIDATIK<br>LGGQNYVFWGGREGYQSLLNTQMQREKEHMGRMLALARDYGRAHGFKGTFLTEPKPMEPT<br>KHQYDQDTETVIGFLRRHGLDKDFKVNIEVNHATLAGHTFEHELACAVDHGMLGSIDANR<br>GDAQNGWDTDQFPIDNYELTLAMLQIIRNGGLAPGGSNFDAKLRRNSTDPEDTFIAHISA<br>MDAMARALVNAVAILEESPIPDMVKERYASFDSGKGREYEEGKLSFEDLVAYAKAHGEPK<br>QISGKQELYETIVALYCK |
| 5586MI197_003 | *Prevotella* | DNA | 105 | ATGACAAAAGAGTATTTCCCTACCATCGGCAAGATCCCCTTTGAGGGACCCGAGAGCAAA<br>AACCCCCTCGCTTTTCATTACTATGAGCCCGACCGCCTGGTCATGGGCAAGAAGATGAAA<br>GACTGGCTGCGTTTCGCCATGGCCTGGTGGCACACCCTGGGCCAGGCCTCCGGCGACCAG<br>TTTGGCGGCCAGACCCGCCACTATGCCTGGGATGATCCGGATTGCCCGTATGCACGTGCC<br>AAAGCCAAGGCCGACGCCGGTTTCGAAATCATGCAGAAACTGGGCATTGAATTCTTCTGC<br>TTCCACGACATCGACCTGATCGAGGATACCGATGACATCGTCGAGTATGAGGCCCGGATG<br>AAGGACATCACCGACTATCTGCTGGTCAAGATGAAAGAGACCGGCATCAAGAATCTCTGG<br>GGAACGGCCAACGTATTCGGGCACAAGCGCTATATGAACGGCGCTGCCACCAACCCCGAT<br>TTCGACGTGCTGGCCCGTGCCGCCGCCCAGATCAAGAACGCCATCGACGCCACCATCAAG<br>CTGGGCGGCCAGAATTATGTGTTCTGGGGCGGGCGTGAAGGCTACCAGAGCCTGCTCAAT<br>ACCCAGATGCAGCGCGAAAAGGAACACATGGGCCGTATGTTGGCACTAGCCCGCGACTAT<br>GGCCGTGCACACGGTTTCAAGGGCACGCTCCTCATCGAGCCCAAACCGATGGAGCCGACC<br>AAGCACCAGTACGATCAGGATACGGAGACCGTCATCGGTTTTCTGCGCCGCCATGGCCTC<br>GACAAGGACTTCAAGGTCAACATCGAGGTGAACCATGCTACCCTGGCGGGCCACACCTTC<br>GAGCACGAGCTGGCCTGCGCCGTCGACCACGGCATGCTGGGCAGTATTGACGCCAACCGC<br>GGTGACGCCCAGGACGGCTGGGACACCGACCAGTTCCCGATCGATAACTATGAGCTGACG<br>CTGGCCATGCTCCAGATCATCCGCAACGGCGGCCTGGCACCCGGCGGCTCGAACTTCGAT<br>GCGAAGCTGCGTCGCAACTCCACCGATCCGGAAGATATCTTCATCGCGCACATCAGCGCC<br>ATGGATGCCATGGCCCGCGCCCTGGTCAACGCTGTCGCCATTCTTGAGGAATCGCCCATT<br>CCGGACATGGTCAAGGAGCGCTACGCTTCGTTCGACAGCGGAAAAGGCAGGGAGTACGAA<br>GAGGGGAAACTTTCCTTCGAGGACCTCGTGGCCTATGCCAAAGCCCACGGCGAACCGAAA<br>CAGATTTCCGGCAAGCAGGAACTCTACGAAACCATCGTGGCTCTCTATTGCAAGTAG |
| 5586MI197_003 | *Prevotella* | Amino Acid | 106 | MTKEYFPTIGKIPFEGPESKNPLAFHYYEPDRLVMGKKMKDWLRFAMAWWHTLGQASGDQ<br>FGGQTRHYAWDDPDCPYARAKAKADAGFEIMQKLGIEFFCFHDIDLIEDTDDIVEYEARM<br>KDITDYLLVKMKETGIKNLWGTANVFGHKRYMNGAATNPDFDVLARAAAQIKNAIDATIK<br>LGGQNYVFWGGREGYQSLLNTQMQREKEHMGRMLALARDYGRAHGFKGTLLIEPKPMEPT<br>KHQYDQDTETVIGFLRRHGLDKDFKVNIEVNHATLAGHTFEHELACAVDHGMLGSIDANR<br>GDAQDGWDTDQFPIDNYELTLAMLQIIRNGGLADGGSNFDAKLRRNSTDPEDIFIAHISA<br>MDAMARALVNAVAILEESPIPDMVKERYASFDSGKGREYEEGKLSFEDLVAYAKAHGEPK<br>QISGKQELYETIVALYCK |
| 5586MI199_003 | *Prevotella* | DNA | 107 | ATGACAAAAGAGTATTTCCCTACCATCGGCAAGATCCCCTTTGAGGGACCCGAGAGCAAA<br>AACCCCCTCGCTTTTCATTACTATGAGCCCGACCGCCTGGTCATGGGCAAGAAGATGAAA<br>GACTGGCTGCGTTTCGCCATGGCCTGGTGGCACACCCTGGGCCAGGCCTCCGGCGACCAG<br>TTTGGCGGCCAGACCCGCCACTATGCCTGGGATGATCCGGATTGCCCGTATGCACGTGCC<br>AAAGCCAAGGCCGACGCCGGTTTCGAAATCATGCAGAAACTGGGCATTGAATTCTTCTGC<br>TTCCACGACATCGACCTGATCGAGGATACCGATGACATCGTCGAGTATGAGGCCCGGATG<br>AAGGACATCACCGACTATCTGCTGGTCAAGATGAAAGAGACCGGCATCAAGAATCTCTGG<br>GGAACGGCCAACGTATTCGGGCACAAGCGCTATATGAACGGCGCTGCCACCAACCCCGAT<br>TTCGACGTGCTGGCCCGTGCCGCCGTCCAGATCAAGAACGCCATCGACGCCACCATCAAG<br>CTGGGCGGCCAGAATTATGTGTTCTGGGGCGGGCGTGAAGGCTACCAGAGCCTGCTCAAT<br>ACCCAGATGCAGCGCGAAAAGGAACACATGGGCCGTATGTTGGCACTAGCCCGCGACTAT<br>GGCCGTGCACACGGTTTCAAGGGCACGTTCCTCATCGAGCCCAAACCGATGGAGCCGACC<br>AAGCACCAGTACGATCAGGATACGGAGACCGTCATCGGTTTTCTGCGCCGCCATGGCCTC<br>GACAAGGACTTCAAGGTCAACATCGAGGTGAACCATGCTACCCTGGCGGGCCACACCTTC<br>GAGCACGAGCTGGCCTGCGCCGTCGACCACGGCATGCTGGGCAGTATTGACGCCAACCGC<br>GGTGACGCCCAGAACGGCTGGGACACCGACCAGTTCCCGATCGATAACTATGAGCTGACG<br>CTGGCCATGCTCCAGATCATCCGCAACGGCGGCCTGGCACCCGGCGGCTCGAACTTCGAT<br>GCGAAGCTGCGTCGCAACTCCACCGATCCGGAAGATGTCTTCATCGCGCACATCAGCGCC<br>ATGGATGCCATGGCCCGCGCCCTGGTCAACGCTGTCGCCATTCTTGAGGAATCGCCCATT<br>CCGGACATGGTCAAGGAGCGCTACGCTTCGTTCGACAGCGGAAAAGGCAGGGAGTACGAA<br>GAGGGGAAACTTTCCTTCGAGGACCTCGTGGCCTATGCCAAAGCCCACGGCGAACCGAAA<br>CAGATTTCCGGCAAGCAGGAACTCTACGAAACCATCGTGGCTCTCTATTGCAAGTAG |
| 5586MI199_003 | *Prevotella* | Amino Acid | 108 | MTKEYFPTIGKIPFEGPESKNPLAFHYYEPDRLVMGKKMKDWLRFAMAWWHTLGQASGDQ<br>FGGQTRHYAWDDPDCPYARAKAKADAGFEIMQKLGIEFFCFHDIDLIEDTDDIVEYEARM<br>KDITDYLLVKMKETGIKNLWGTANVFGHKRYMNGAATNPDFDVLARAAVQIKNAIDATIK<br>LGGQNYVFWGGREGYQSLLNTQMQREKEHMGRMLALARDYGRAHGFKGTFLIEPKPMEPT<br>KHQYDQDTETVIGFLRRHGLDKDFKVNIEVNHATLAGHTFEHELACAVDHGMLGSIDANR<br>GDAQNGWDTDQFPIDNYELTLAMLQIIRNGGLAPGGSNFDAKLRRNSTDPEDVFIAHISA<br>MDAMARALVNAVAILEESPIPDMVKERYASFDSGKGREYEEGKLSFEDLVAYAKAHGEPK<br>QISGKQELYETIVALYCK |
| 5586MI200_003 | *Prevotella* | DNA | 109 | ATGGCAAAAGAGTATTTCCCGACAATCGGAAAGATCCCCTTCGAGGGCGTTGAGAGCAAG<br>AATCCCCTTGCTTTCCATTATTATGACGCCGAGCGCGTGGTCATGGGCAAGCCCATGAAG |

TABLE 2-continued

| Clone No. | Class of organism | Type of Sequence | SEQ ID NO: | Sequence |
|---|---|---|---|---|
| | | | | GACTGGTTCAAGTTCGCGATGGCCTGGTGGCACACCCTGGGCCAGGCTTCCGCGGACCCG<br>TTCGGCGGCCAGACCCGCTCCTACGAGTGGGACAAGGGCGAGTGCCCCTACTGCCGCGCC<br>CGCGCCAAGGCTGACGCCGGCTTCGAGATCATGCAGAAGCTCGGAATCGGCTACTATTGC<br>TTCCACGACATCGACCTGGTGGAGGACACCGAGGACATCGCCGAATACGAGGCCCGCATG<br>AAGGACATCACCGACTACCTCGTCGAGAAGCAGAAGGAGACCGGCATCAAGAACCTCTGG<br>GGCACCGCGAACGTGTTCGGCAACAAGCGCTACATGAACGGCGCCGCCACGAACCCGCAG<br>TTCGACATCGTCGCCCGCGCGGCCCTGCAGATCAAGAACGCGATCGATGCCACCATCAAG<br>CTCGGCGGCACCGGCTACGTGTTCTGGGGCGGCCGGGAAGGCTACTACACCCTGCTGAAC<br>ACCCAGATGCAGCGCGAGAAGGACCACCTCGCCAAGATGCTCACCGCCGCCCGCGACTAC<br>GCCCGCGCCAACGGCTTCAAGGGCACCTTCCTCATCGAGCCCAAGCCGATGGAGCCCACC<br>AAGCACCAATACGACGTGGACACGGAGACCGTGATCGGCTTCCTCCGCGCCAATGGCCTG<br>GACAAGGACTTCAAGGTGAACATCGAGGTGAACCACGCCACCCTCGCCGGCCACACCTTC<br>GAGCACGAGCTCACCGTGGCCGTTGACAACGGCTTCCTCGGCAGCATCGACGCCAACCGC<br>GGCGACGCCCAGAACGGCTGGGATACCGACCAGTTCCCGGTGGATCCGTACGATCTCACC<br>CAGGCGATGATCCAGATCATCCGCAACGGCGGCTTCAAGGACGGCGGCACCAACTTCGAC<br>GCCAGGCTCCGCCGCTCTTCCACCGACCCGGAGGACATCTTCATCGCCCACATCAGCGCG<br>ATGGACGCCATGGCCCACGCCCTGCTGAACGCCGCCGCCGTCATCGAGGAGAGCCCGCTC<br>TGCGAGATGGTCGCCAAGCGTTACGCTTCCTTCGACAGCGGCCTCGGCAAAAAGTTCGAG<br>GAAGGCAAGGCCACCCTCGAGGAACTCTACGAGTATGCCAAGGCGAACGGTGAGGTCAAG<br>GCCGAATCCGGCAAGCAGGAGCTCTACGAGACCCTTCTGAACCTCTACGCGAAATAG |
| 5586MI200_*Prevotella* 003 | | Amino Acid | 110 | MAKEYFPTIGKIPFEGVESKNPLAFHYYDAERVVMGKPMKDWFKFAMAWWHTLGQASADP<br>FGGQTRSYEWDKGECPYCRARAKADAGFEIMQKLGIGYYCFHDIDLVEDTEDIAEYEARM<br>KDITDYLVEKQKETGIKNLWGTANVFGNKRYMNGAATNPQFDIVARAALQIKNAIDATIK<br>LGGTGYVFWGGREGYYTLLNTQMQREKDHLAKMLTAARDYARANGFKGTFLIEPKPMEPT<br>KHQYDVDTETVIGFLRANGLDKDFKVNIEVNHATLAGHTFEHELTVAVDNGFLGSIDANR<br>GDAQNGWDTDQFPVDPYDLTQAMIQIIRNGGFKDGGTNFDARLRRSSTDPEDIFIAHISA<br>MDAMAHALLNAAAVIEESPLCEMVAKRYASFDSGLGKKFEEGKATLEELYEYAKANGEVK<br>AESGKQELYETLLNLYAK |
| 5586MI203_*Prevotella* 003 | | DNA | 111 | ATGGCACAAGCGTATTTTCCTACCATCGGGAAAATCCCCTTCGAGGGACCCGAAAGCAAG<br>AATCCCCTGGCATTCCATTATTATGAGCCCGACCGCCTGGTCCTGGGCAAGAAGATGAAG<br>GACTGGCTGCGTTTCGCCATGGCCTGGTGGCACACGCTGGGCCAGGCTTCCGGCGACCAG<br>TTCGGCGGCCAGACCCGCCACTACGCCTGGGACGAGCCCGCCACGCCCCTGGAACGGGCC<br>AAGGCCAAGGCGGATGCCGGTTTCGAGATCATGCAGAAACTGGGCATCGAATTCTTCTGC<br>TTCCACGATGTGGACCTCATCGAAGAGGGCGCCACGATCGAGGAATACGAGCAGCGGATG<br>CAGCAGATCACGGATTATCTGCTGGTCAAGATGAAAGAGACCGGCATCCGCAACCTCTGG<br>GGTACGGCCAACGTGTTCGGACACGAGCGCTACATGAACGGCGCGGCCACGAACCCCGAT<br>TTCGATGTCGTGGCCCGCGCGGCCGTGCAGATCAAGACGGCCATCGACGCCACCATCAAG<br>TTGGGCGGCGAGAACTATGTGTTCTGGGGCGGCCGGGAAGGCTATATGAGCCTGCTCAAT<br>ACGCAGATGCACCGCGAGAAGCTGCATCTGGGCAAGATGCTCGCCGCGGCCCGCGACTAC<br>GGACGCGCCCACGGCTTCAAGGGGACCTTCCTCATCGAACCCAAGCCGATGGAACCCACC<br>AAGCATCAGTATGACCAGGATACGGAGACGGTCATCGGTTTCCTGCGCCGCTACGGCCTG<br>GACGAAGACTTCAAGGTGAACATCGAGGTCAACCACGCTACGCTGGCCGGCCATACCTTC<br>GAACACGAACTGGCCACGGCGGTCGATGCCGGCCTGCTGGGCAGCATCGACGCCAACCGC<br>GGCGACGCCCAGAACGGCTGGGATACCGACCAGTTCCCGATCGACAACTACGAACTGACC<br>CTGGCGATGCTGCAGGTCATCCGCAACGGCGGTCTGGCCCCGGGCGGCTCGAATTTCGAT<br>GCCAAGCTCCGCCGGAACTCCACCGATCCGGAAGACATCTTCATTGCCCACATCAGCGCG<br>ATGGATGCGATGGCGCGGGCCCTGCTCAATGCGGCCGCCCTCTGCGAGACGTCCCCGATT<br>CCGGCGATGGTCAAGGCGCGTTACGCTTCGTTCGACAGCGGCGCCGGCAAGGATTTCGAA<br>GAGGGAAGGATGACGCTGGAAGACCTCGTGGCCTATGCCAGGACCCACGGCGAGCCGAAG<br>CGGACCTCGGGCAAGCAGGAACTCTATGAGACCCTCGTGGCGCTTTATTGCAAATAG |
| 5586MI203_*Prevotella* 003 | | Amino Acid | 112 | MAQAYFPTIGKIPFEGPESKNPLAFHYYEPDRLVLGKKMKDWLRFAMAWWHTLGQASGDQ<br>FGGQTRHYAWDEPATPLERAKAKADAGFEIMQKLGIEFFCFHDVDLIEEGATIEEYEQRM<br>QQITDYLLVKMKETGIRNLWGTANVFGHERYMNGAATNPDFDVVARAAVQIKTAIDATIK<br>LGGENYVFWGGREGYMSLLNTQMHREKLHLGKMLAAARDYGRAHGFKGTFLIEPKPMEPT<br>KHQYDQDTETVIGFLRRYGLDEDFKVNIEVNHATLAGHTFEHELATAVDAGLLGSIDANR<br>GDAQNGWDTDQFPIDNYELTLAMLQVIRNGGLAPGGSNFDAKLRRNSTDPEDIFIAHISA<br>MDAMARALLNAAALCETSPIPAMVKARYASFDSGAGKDFEEGRMTLEDLVAYARTHGEPK<br>RTSGKQELYETLVALYCK |
| 5586MI205_*Prevotella* 004 | | DNA | 113 | ATGACCAACGAGTATTTTCCCGGAATCGGTGTGATTCCGTTTGAAGGACAGGAAAGCAAG<br>AATCCCCTGGCTTTCCATTATTATGACGCCAACCGCGTAGTGATGGGCAAACCCATGAAG<br>GAATGGTTCAAATTTGCCATGGCCTGGTGGCATACGCTGGGGCAGGCATCGGCCGATCCC<br>TTCGGCGGACAGACCCGCTCCTACGCATGGGACAAGGGCGAGTGCCCTTACTGCCGTGCC<br>CGCCAGAAGGCCGACGCCGGCTTTGAACTGATGCAGAAGCTGGGAATCGGCTATTTCTGC<br>TTCCACGATGTGAATATCATCGAGGACTGCGAGGACATTGCCGAGTATGAGGCCCGTATG<br>AAGGACATCACGGACTATCTGCTGGTGAAGATGAAGGAAACGGGCATCAAGAATCTGTGG<br>GGCACGGCCAACGTCTTCGGCCACAAGCGCTATATGAACGGCGCCGCCACCAACCCGCAA<br>TTCGACGTGGTAGCCCGCGCTGCGGTCCAGATCAAGAACGCCCTGGACGCCACCATCAAG<br>CTGGGCGGCAGCAATTATGTGTTCTGGGGCGGCCGGGAAGGCTACTACACCCTTTTGAAC<br>ACGCAGATGCAGCGGGAGAAGGACCACCTGGCCCAGATGCTCAAGGCGGCCCGCGACTAT<br>GCCCGCGGCAAGGGATTCAAGGGCACGTTCCTCATTGAGCCCAAGCCCATGGAGCCCACC<br>AAGCACCAGTACGACGTAGATACGGAGACCGTGATTGGTTTCCTGCGCGCCAACGGGCTG<br>GACAAGGACTTCAAGGTGAATATCGAAGTGAACCACGCCACCCTGGCCGGCCATACCTTC |

TABLE 2-continued

| Clone No. | Class of organism | Type of Sequence | SEQ ID NO: | Sequence |
|---|---|---|---|---|
| | | | | GAGCACGAGCTCACCGTGGCCCGCGAAAACGGCTTCCTGGGCAGCATCGACGCCAACCGC<br>GGAGACGCCCAGAACGGCTGGGATACAGACCAGTTCCCCGTGGACGCCTTTGACCTCACC<br>CAGGCCATGATGCAGGTCCTGCTCAACGGCGGATTCGGCAACGGCGGCACCAACTTCGAC<br>GCCAAACTGCGCCGTTCCTCCACGGATCCCGAGGACATCTTCATCGCCCACATCAGCGCC<br>ATGGACGCCATGGCCCACGCCCTCCTGAACGCCGCCGCCATCCTGGAAGAGAGCCCCATG<br>CCGGGCATGGTGAAGGAGCGCTACGCTTCCTTCGACAATGGCCTTGGCAAGAAGTTCGAG<br>GAAGGAAAGGCCACGCTGGAAGAGCTGTACGACTATGCCAAGAAGAACGGCGAGCCTGTG<br>GCCGCTTCCGGAAAGCAGGAACTGTACGAAACGCTGCTGAACCTGTACGCCAAGTAA |
| 5586MI205_*Prevotella* 004 | | Amino Acid | 114 | MTNEYFPGIGVIPFEGQESKNPLAFHYYDANRVVMGKPMKEWFKFAMAWWHTLGQASADP<br>EGGQTRSYAWDKGECPYCRARQKADAGFELMQKLGIGYFCFHDVNIIEDCEDIAEYEARM<br>KDITDYLLVKMKETGIKNLWGTANVFGHKRYMNGAATNPQFDVVARAAVQIKNALDATIK<br>LGGSNYVFWGGREGYYTLLNTQMQREKDHLAQMLKAARDYARGKGFKGTFLIEPKPMEPT<br>KHQYDVDTETVIGFLRANGLDKDFKVNIEVNHATLAGHTFEHELTVARENGFLGSIDANR<br>GDAQNGWDTDQFPVDAFDLTQAMMQVLLNGGFGNGGTNFDAKLRRSSTDPEDIFIAHISA<br>MDAMAHALLNAAAILEESPMPGMVKERYASFDNGLGKKFEEGKATLEELYDYAKKNGEPV<br>AASGKQELYETLLNLYAK |
| 5586MI206_*Prevotella* 004 | | DNA | 115 | ATGGCAAAAGAGTATTTCCCGACTATCGGCAAGATTCCCTTCGAGGGCGTCGAATCCAAG<br>AACCCGATGGCATTCCACTATTATGACGCGAAACGCGTCGTGATGGGCAAGCCCATGAAG<br>GACTGGCTCAAGTTCGCGATGGCCTGGTGGCACACCCTGGGACAGGCTTCCGGCGACCCG<br>TTCGGCGGCCAGACCCGTTCCTACGAGTGGGACAAGGGCGAGTGCCCCTACTGCCGCGCC<br>AAGGCCAAGGCCGACGCCGGTTTCGAGATCATGCAGAAACTGGGCATCGAGTACTACTGC<br>TTCCATGACATCGACCTGGTGGAGGACACCGAGGACATCGCCGAGTACGAGGCCCGCATG<br>AAGGACATCACCGACTACCTCGTCGAGAAGCAGAAGGAGACCGGTATCAAGAACCTCTGG<br>GGCACGGCCAACGTGTTCGGCAACAAGCGCTACATGAACGGCGCCGCCACGAACCCGCAG<br>TTCGACGTCGTCGCCCGCGCCGCCGTCCAGATCAAGAACGCCATCGACGCCACCATCAAA<br>CTCGGCGGCACCTCTTACGTGTTCTGGGGCGGCCGTGAAGGCTACTACACCCTCCTGAAC<br>ACCCAGATGCAGCGCGAGAAGGACCACCTCGCCAAGATGCTCACCGCCGCCCGCGACTAC<br>GCCCGCGCCCACGGCTTCAAGGGCACCTTCCTCATCGAGCCCAAGCCCATGGAGCCCACC<br>AAGCACCAGTACGACGTGGACACGGAGACCGTGATCGGCTTCCTCCGCGCCAACGGCCTG<br>GACAAGGACTTCAAGGTCAATATCGAAGTGAACCACGCCACCCTCGCCGGCCACACCTIC<br>GAGCATGAGCTCACCGTGGCGGTCGATAACGGCTTCCTCGGCTCCATCGACGCCAACCGT<br>GGCGACGCCCAGAACGGCTGGGATACCGACCAGTTCCCGGTGGATCCGTACGACCTCACC<br>CAGGCCATGATGCAGATCATCCGCAACGGCGGCTTCAAGGACGGCGGCACCAACTTCGAC<br>GCCAAACTCCGCCGCTCCTCCACCGACCCGGAGGACATCTTCATCGCCCACATCAGCGCG<br>ATGGACGCCATGGCCCACGCGCTCCTGAACGCCGCCGCCGTCATCGAGGAGAGCCCGCTC<br>TGCAAGATGGTCGAGGAGCGCTACGCTTCCTTCGACAGCGGTCTCGGCAAGCAGTTCGAG<br>GAAGGCAAGGCCACCCTTGAGGACCTCTACGAGTATGCCAAGAAGAACGGCGAGCCCGTC<br>GTCGCTTCCGGCAAGCAGGAGCTCTACGAGACCCTTCTGAACCTCTACGCGAAGTAG |
| 5586MI206_*Prevotella* 004 | | Amino Acid | 116 | MAKEYFPTIGKIPFEGVESKNPMAFHYYDAKRVVMGKPMKDWLKFAMAWWHTLGQASGDP<br>FGGQTRSYEWDKGECPYCRAKAKADAGFEIMQKLGIEYYCFHDIDLVEDTEDIAEYEARM<br>KDITDYLVEKQKETGIKNLWGTANVFGNKRYMNGAATNPQFDVVARAAVQIKNAIDATIK<br>LGGTSYVFWGGREGYYTLLNTQMQREKDHLAKMLTAARDYARAHGFKGTFLTEPKPMEPT<br>KHQYDVDTETVIGFLRANGLDKDFKVNIEVNHATLAGHTFEHELTVAVDNGFLGSIDANR<br>GDAQNGWDTDQFPVDPYDLTQAMMQIIRNGGFKDGGTNFDAKLRRSSTDPEDIFIAHISA<br>MDAMAHALLNAAAVIEESPLCKMVEERYASFDSGLGKQFEEGKATLEDLYEYAKKNGEPV<br>VASGKQELYETLLNLYAK |
| 5586MI208_*Prevotella* 003 | | DNA | 117 | ATGTCAACTGAGTATTTCCCTACAATCGGCAAGATTCCCTTCGAGGGACCCGAGAGCAAG<br>AACCCCATGGCCTTCCACTACTATGAACCCGAAAAGTTGGTGATGGGCAAGAAGATGAAG<br>GACTGGCTGCGITTCGCAATGGCCTGGTGGCACACCCTIGGAGCCGCATCCGGCGACCAG<br>TTCGGCGGACAGACCCGCAGTTACGCCTGGGACAAGGGCGACTGCCCTTACAGCCGCGCC<br>CGCGCCAAGGTCGACGCCGGCTTCGAGATCATGCAGAAGCTCGGCATAGAGTTCTTCTGC<br>TTCCATGACATCGACCTGGTCGAGGATACCGACGACATCGCCGAGTATGAAGCCCGGATG<br>AAAGACATCACGGACTATCTGCTGGAAAAGATGGAGGCTACCGGCATCAAGAACCTCTGG<br>GGCACGGCCAATGTCTTCGGTCACAAGCGTTATATGAACGGTGCAGCCACAAACCCCGAT<br>TTCGCAGTGGTCGCAAGGGCGGCCGTGCAGATCAAGAACGCCATCGACGCCACCATCAAG<br>CTGGGTGGTGAGAACTATGTGTTCTGGGGTGGACGCGAGGGTTATATGAGCCTGCTCAAC<br>ACCCAGATGCAGAGGGAGAAGGAACACCTTGCCAAGATGCTCACCGCCGCACGTGACTAT<br>GCACGCGCCAAAGGTTTCAAGGGCACGTTCCTCATCGAACCCAAGCCGATGGAACCCACC<br>AAGCACCAGTATGACCAGGATACCGAGACCGTTATCGGATTCCTCCGCAGCCACGGCCTG<br>GACAAGGACTTCAAGGTCAACATCGAGGTGAACCACGCCACCCTGGCGGGCCATACCTTC<br>GAGCACGAACTGGCCACCGCCGTCGACAACGGCATGCTCGGCAGCATCGACGCCAACCGC<br>GGAGACGCCCAGAACGGCTGGGACACCGACCAGTTCCCGATCGACAACTTCGAGCTCACG<br>CTTGCCATGATGCAGATAATCCGCAACGGCGGCCTGGCACCGGGCGGTTCGAACTTCGAC<br>GCAAAGCTGCGCCGCAATTCCACCGATCCCGAGGACATCTTCATCGCCCACATCAGCGCG<br>ATGGACGCCATGGCCCGCGCCCTCGTCAACGCCGCCGCCATCCTCGGCGAGTCGCCCGTT<br>CCGGCTATGGTCAAGGACCGCTATGCTTCGTTCGACTGCGGCAAGGGCAAGGACTTCGAA<br>GACGGCAAACTGACTCTCGAAGACATCGTCGCCTACGCCAGGGAGAATGGCGAGCCGAAA<br>CAGATTTCCGGCAAGCAGGAACTCTACGAAACTATCGTCGCTCTTTACTGCAAGTAA |
| 5586MI208_*Prevotella* 003 | | Amino Acid | 118 | MSTEYFPTIGKIPFEGPESKNPMAFHYYEPEKLVMGKKMKDWLRFAMAWWHTLGAASGDQ<br>FGGQTRSYAWDKGDCPYSRARAKVDAGFEIMQKLGIEFFCFHDIDLVEDTDDIAEYEARM<br>KDITDYLLEKMEATGIKNLWGTANVFGHKRYMNGAATNPDFAVVARAAVQIKNAIDATIK |

TABLE 2-continued

| Clone No. | Class of organism | Type of Sequence | SEQ ID NO: | Sequence |
|---|---|---|---|---|
| | | | | LGGENYVFWGGREGYMSLLNTQMQREKEHLAKMLTAARDYARAKGFKGTFLIEPKPMEPT<br>KHQYDQDTETVIGFLRSHGLDKDFKVNIEVNHATLAGHTFEHELATAVDNGMLGSIDANR<br>GDAQNGWDTDQFPIDNFELTLAMMQIIRNGGLAPGGSNFDAKLRRNSTDPEDIFIAHISA<br>MDAMARALVNAAAILGESPVPAMVKDRYASFDCGKGKDFEDGKLTLEDIVAYARENGEPK<br>QISGKQELYETIVALYCK |
| 5586MI210_002 | *Prevotella* | DNA | 119 | ATGTCATATTTTCCTACTATCGGTAACATCCCCTTTGAGGGTGTAGAGAGCAAGAATCCC<br>CTTGCCTTCCATTATTATGACGCTTCCCGCGTAGTTATGGGCAAGCCCATGAAGGAGTGG<br>CTCAAGTTTGCCATGGCCTGGTGGCACACGCTGGGTCAGGCATCGGCCGACCCTTTCGGC<br>GGACAAACCCGCAGCTATGCCTGGGACAAAGGCGAGTGCCCCTACTGCCGTGCCCGTGCC<br>AAGGCCGACGCCGGCTTCGAGCTCATGCAGAAACTGGGCATCGAGTATTTCTGCTCCCAC<br>GACATTGACCTCATCGAGGACTGCGACGACATTGCAGAGTACGAGGCCCGTCTGAAGGAC<br>ATTACGGACTACCTCCTGGAGAAGATGAAGAAGACCGGTATCAAGAACCTGTGGGGTACG<br>GCCAATGTGTTCGGTAACAAGCGTTACATGAACGGTGCTGCTACCAACCCTCAGTTTGAC<br>GTTGTGGCCCGCGCTGCCGTCCAGATCAAGAACGCCATTGACGCTACCATCAAGCTGGGC<br>GGTTCCAACTATGTGTTCTGGGGTGGCCGTGAGGGTTACTACACGCTTCTGAACACCCAG<br>ATGCAGCGTGAGAAGAATCACCTGGCTGCCATGCTCAAGGCTGCCCGCGACTATGCCCGC<br>GCCAACGGTTTCAAGGGCACCTTCCTCATTGAGCCCAAGCCCATGGAGCCCACCAAGCAC<br>CAGTACGACGTAGACACGGAGACCGTGATTGGATTCCTCCGCGCCAACGGTCTGGAGAAG<br>GACTTCAAGGTGAACATTGAGGTGAACCACGCTACTCTTGCCGGTCACACCTTCGAGCAC<br>GAGCTCACCGTGGCCCGTGAGAACGGCTTCCTGGGTTCCATTGACGCCAACCGCGGAGAT<br>GCCCAGAACGGCTGGGACACCGACCAGTTCCCGGTAGATGCCTTTGACCTCACCCAGGCC<br>ATGATGCAGATTCTCCTCAACGGAGGCTCCGGCAATGGCGGTACCAACTTTGACGCCAAG<br>CTGCGCCGTTCCTCCACCGACCCCGAGGACATCTTCATCGCGCACATCAGCGCCATGGAT<br>GCCATGGCTCACGCCCTGCTCAATGCAGCTGCCGTGCTGGAGGAGAGCCCGCTTTGCAAG<br>ATGGTCAAGGAGCGTTACGCTTCCTTCGACAGCGGTCTTGGCAAGCAGTTCGAGGAAGGA<br>AAGGCTACGCTGGAAGATCTGTATGCCTATGCCGTCAAGAACGGTGAGCCCGTGGTGGCT<br>TCCGGCAAGCAGGAACTGTACGAAACCTTCCTGAACCTCTATGCAAAATGGTAA |
| 5586MI210_002 | *Prevotella* | Amino Acid | 120 | MSYFPTIGNIPFEGVESKNPLAFHYYDASRVVMGKPMKEWLKFAMAWWHTLGQASADPFG<br>GQTRSYAWDKGECPYCRARAKADAGFELMQKLGIEYFCSHDIDLIEDCDDIAEYEARLKD<br>ITDYLLEKMKKTGIKNLWGTANVFGNKRYMNGAATNPQFDVVARAAVQIKNAIDATIKLG<br>GSNYVFWGGREGYYTLLNTQMQREKNHLAAMLKAARDYARANGFKGTFLIEPKPMEPTKH<br>QYDVDTETVIGFLRANGLEKDFKVNIEVNHATLAGHTFEHELTVARENGFLGSIDANRGD<br>AQNGWDTDQFPVDAFDLTQAMMQILLNGGSGNGGTNFDAKLRRSSTDPEDIFIAHISAMD<br>AMAHALLNAAAVLEESPLCKMVKERYASFDSGLGKQFEEGKATLEDLYAYAVKNGEPVVA<br>SGKQELYETFLNLYAKW |
| 5586MI212_002 | *Prevotella* | DNA | 121 | ATGTCAACTGAGTATTTCCCTACAATCGGCAAGATTCCCTTCGAGGGACCCGAGAGCAAG<br>AACCCCATGGCCTTCCACTACTATGAACCCGAAAAGTTGGTGATGGGCAAGAAGATGAAG<br>GACTGGCTGCGTTTCGCAATGGCCTGGTGGCACACCCTTGGAGCCGCATCCGGCGACCAG<br>TTCGGCGGACAGACCCGCAGTTACGCCTGGGACAAGGGCGACTGCCCTTACAGCCGCGCC<br>CGCGCCAAGGTCGACGCCGGCTTCGAGATCATGCAGAAGCTCGGCATAGAGTTCTTCTGC<br>TTCCATGACATCGACCTGGTCGAGGATACCGACGACATCGCCGAGTATGAAGCCCGGATG<br>AAAGACATCACGGACTATCTGCTGGAAAAGATGGAGGTTACCGGCATCAAGAACCTCTGG<br>GGCACGGCCAATGTCTTCGGTCACAAGCGTTATATGAACGATGCAGCCACAAACCCCGAT<br>TTCGCAGTGGTCGCAAGGGCGGCCGTGCAGATCAAGAACGCCATCGACGCCACCATCAAG<br>CTGGGTGGTGAGAACTATGTGTTCTGGGGTGGACGCGAGGGTTATATGAGCCTGCTCAAC<br>ACCCAGATGCAGAGGGAGAAGGAACACCTTGCCAAGATGCTCACCGCCGCACGTGACTAT<br>GCACGCGCCAAAGGTTTCAAGGGCACGTTCCTCATCGAACCCGAGCCGATGGAACCCACC<br>AAGCACCAGTATGACCAGGATACCGAGACCGTTATCGGATTCCTCCGCAGCCACGGCCTG<br>GACAAGGACTTCAAGGTCAACATCGAGGTGAACCACGCCACCCTGGCGGGCCATACCTTC<br>GAGCACGAACTGGCCACCGCCGTCGACAACGGCATGCTCGGCAGCATCGACGCCAACCGC<br>GGAGACGCCCAGAACGGCTGGGACACCGACCAGTTCCCGATCGACAACTTCGAGCTCACG<br>CTTGCCATGATGCAGATAATCCGCAACGGCGGCCTGGCACCGGGCGGTTCGAACTTCGAC<br>GCAAAGCTGCGCCGCAATTCCACCGATCCCGAGGACATCATCATCGCCCACATCAGCGCG<br>ATGGACGCCATGGCCCGCGCCCTCGTCAACGCCGCCGCCATCCTCGGCGAGTCGCCCGTT<br>CCGGCTATGGTCAAGGACCGCTATGCTTCGTTCGACTGCGGCAAGGGCAAGGACTTCGAA<br>GACGGCAAACTGACTCTCGAAGACATCGTCGCCTACGCCAGGGAGAATGGCGAGCCGAAA<br>CAGATTTCCGGCAAGCAGGAACTCTACGAAACTATCGTCGCTCTTTACTGCAAGTAA |
| 5586MI212_002 | *Prevotella* | Amino Acid | 122 | MSTEYFPTIGKIPFEGPESKNPMAFHYYEPEKLVMGKKMKDWLRFAMAWWHTLGAASGDQ<br>FGGQTRSYAWDKGDCPYSRARAKVDAGFEIMQKLGIEFFCFHDIDLVEDTDDIAEYEARM<br>KDITDYLLEKMEVTGIKNLWGTANVFGHKRYMNDAATNPDFAVVARAAVQIKNAIDATIK<br>LGGENYVFWGGREGYMSLLNTQMQREKEHLAKMLTAARDYARAKGFKGTFLIEPEPMEPT<br>KHQYDQDTETVIGFLRSHGLDKDFKVNIEVNHATLAGHTFEHELATAVDNGMLGSIDANR<br>GDAQNGWDTDQFPIDNFELTLAMMQIIRNGGLAPGGSNFDAKLRRNSTDPEDIIIAHISA<br>MDAMARALVNAAAILGESPVPAMVKDRYASFDCGKGKDFEDGKLTLEDIVAYARENGEPK<br>QISGKQELYETIVALYCK |
| 5586MI213_003 | *Prevotella* | DNA | 123 | ATGACCAACGAGTATTTTCCCGGAATCGGTGTGATTCCGTTTGAAGGACAGGAAAGCAAG<br>AATCCCCTGGCCTTTCCATTATTATGACGCCAACCGCGTAGTGATGGGCAAACCCATGAAG<br>GAATGGTTCAAATTTGCCATGGCCTGGTGGCATACGCTGGGGCAGGCATCGGCCGATCCC<br>TTCGGCGGACAGACCCGCTCCTACGCATGGGACAAGGGCGAGTGCCCTTACTGCCGTGCC<br>CGCCAGAAGGCCGACGCCGGCTTTGAACTGATGCAGAAGCTGGGAATCGGCTATTTCTGC<br>TTCCACGATGTGGATATCATCGAGGACTGCGAGGACATTGCCGAGTATGAGGCCCGTATG |

TABLE 2-continued

| Clone No. | Class of organism | Type of Sequence | SEQ ID NO: | Sequence |
|---|---|---|---|---|
| | | | | AAGGACATCACGGACTATCTGCTGGTGAAGATGAAGGAAACGGGCATCAAGAATCTGTGG<br>GGCACGGCCAACGTCTTCGGCCACAAGCGCTATATGAACGGCGCCGCCACCAACCCGCAA<br>TTCGACGTGGTAGCCCGCGCTGCGGTCCAGATCAAGAACGCCCTGGACGCCACCATCAAG<br>CTGGGCGGCAGCAATTATGTGTTCTGGGGCGGCCGGGAAGGCTACTACACCCTTTTGAAC<br>ACGCAGATGCAGCGGGAGAAGGACCACCTGGCCCAGATGCTCAAGGCGGCCCGCGACTAT<br>GCCCGCGGCAAGGGATTCAAGGGCACGTTCCTCATTGAGCCCAAGCCCATGGAGCCCACC<br>AAGCACCAGTACGACGTAGATACGGAGACCGTGATTGGTTTCCTGCGCGCCAACGGGCTG<br>GACAAGGACTTCAAGGTGAATATCGAAGTGAACCACGCCACCCTGGCCGGCCATACCTTC<br>GAGCACGAGCTCACCGTGGCCCGCGAAAACGGCTTCCTGGGCAGCATCGACGCCAACCGC<br>GGAGACGCCCAGAACGGCTGGGATACAGACCAGTTCCCCGTGGACGCCTTTGACCTCACC<br>CAGGCCATGATGCAGGTCCTGCTCAACGGCGGATTCGGCAACGGCGGCACCAACTTCGAC<br>GCCAAACTGCGCCGTTCCTCCACGGATCCCGAGGACATCTTCATCGCCCACATCAGCGCC<br>ATGGACGCCATGGCCCACGCCCTCCTGAACGCCGCCGCCATCCTGGAAGAGAGCCCCATG<br>CCGGGCATGGTGAAGGAGCGCTACGCTTCCTTCGACAATGGCCTTGGCAAGAAGTTCGAG<br>GAAGGAAAGGCCACGCTGGAAGAGCTGTACGACTATGCCAAGAAGAACGGCGAGCCTGTG<br>GCCGCTTCCGGAAAGCAGGAACTGTACGAAACGCTGCTGAACCTGTACGCCAAGTAA |
| 5586MI213_003 | *Prevotella* | Amino Acid | 124 | MTNEYFPGIGVIPFEGQESKNPLAFHYYDANRVVMGKPMKEWFKFAMAWWHTLGQASADP<br>FGGQTRSYAWDKGECPYCRARQKADAGFELMQKLGIGYFCFHDVDIIEDCEDIAEYEARM<br>KDITDYLLVKMKETGIKNLWGTANVFGHKRYMNGAATNPQFDVVARAAVQIKNALDATIK<br>LGGSNYVFWGGREGYYTLLNTQMQREKDHLAQMLKAARDYARGKGFKGTFLIEPKPMEPT<br>KHQYDVDTETVIGFLRANGLDKDFKVNIEVNHATLAGHTFEHELTVARENGFLGSIDANR<br>GDAQNGWDTDQFPVDAFDLTQAMMQVLLNGGEGNGGTNEDAKLRRSSTDPEDIFIAHISA<br>MDAMAHALLNAAAILEESPMPGMVKERYASFDNGLGKKFEEGKATLEELYDYAKKNGEPV<br>AASGKQELYETLLNLYAK |
| 5586MI215_003 | *Prevotella* | DNA | 125 | ATGGCAAAAGAGTATTTCCCGCAGATCGGAAAGATCGGCTTTGAGGGTCTTGAGAGCAAG<br>AACCCGATGGCATTCCATTATTATGACGCCGAGCGTGTCGTGCTCGGAAAGAAGATGAAG<br>GACTGGCTGAAGTTCGCGATGGCCTGGTGGCATACGCTCGGACAGGCTTCCGGCGACCCA<br>TTCGGCGGCCAGACTCGCAGCTATGAGTGGGACAAGGGCGAGTGCCCCTACTGCCGTGCC<br>CGCGCCAAGGCCGACGCCGGCTTCGAGCTCATGCAGAAGCTCGGCATCGAGTACTTCTGC<br>TTCCACGACATCGACCTCATCGAGGACTGCGACGACATCGACGAGTACGAGGCCCGGATG<br>AAGGACATCACCGACTACCTGCTGGAGAAGATGAAGGAGACCGGAATCAAGAATCTCTGG<br>GGAACGGCCAACGTCTTCGGTCACAAGCGCTACATGAACGGCGCCGCTACCAATCCGCAG<br>TTTGAAATCGTCGCCCGCGCTGCCGTCCAGATCAAGAACGCGCTCGACGCCACCATCAAG<br>CTCGGCGGCTCCAACTACGTCTTCTGGGGCGGCCGCGAGGGCTATTACACGCTGCTGAAT<br>ACCCAGATGCAGCGCGAGAAGGACCATCTCGCCAGGCTCCTTACCGCCGCCCGCGACTAT<br>GCGCGCGCCAAGGGGTTCAAGGGGACCTTCCCCATCGAGCCGAAGCCGATGGAGCCGACC<br>AAGCACCAGTATGACGTCGACACGGAGACCGTCATCGGTTTCCTCCGCCAGAATGGCCTC<br>GACAAGGACTTCAAGGTCAATATCGAGGTGAACCACGCCACCCTCGCCGGCCATACCTTC<br>GAGCACGAGCTGACCGCGGCCCGGGAGAACGGCTTCCTCGGCAGCATCGACGCCAACCGC<br>GGCGACGCCCAGAACGGCTGGGACACCGACCAGTTCCCGGTGGACGCCTTCGATCTCACG<br>CGGGCCATGATGCAGATCCTGCTCAATGGCGGTTTCGGCAACGGCGGCACCAACTTCGAC<br>GCCAAGCTGCGCCGCAGCTCCACCGATCCCGAGGACATCTTCATCGCCCACATCAGCGCG<br>ATGGACGCCATGGCCCACGCCCTGCTGAATGCGGCCGCCATCCTCGAGGAAAGCCCGCTG<br>CCGGCCCTGGTCAAGCAGCGCTATGCGTCCTTCGACAGCGGTCTCGGCAAGCAGTTCGAG<br>GAGGGTAAGGCCACGCTCGAGGACCTGTACGCATACGCGAAGGAGCACGGCGAGCCCGTC<br>GCGGCCTCCGGCAAGCAGGAGCTCTGCGAGACCTATCTCAACCTCTACGCGAAATAA |
| 5586MI215_003 | *Prevotella* | Amino Acid | 126 | MAKEYFPQIGKIGFEGLESKNPMAFHYYDAERVVLGKKMKDWLKFAMAWWHTLGQASGDP<br>FGGQTRSYEWDKGECPYCRARAKADAGFELMQKLGIEYFCFHDIDLIEDCDDIDEYEARM<br>KDITDYLLEKMKETGIKNLWGTANVEGHKRYMNGAATNPQFEIVARAAVQIKNALDATIK<br>LGGSNYVFWGGREGYYTLLNTQMQREKDHLARLLTAARDYARAKGFKGTFPIEPKPMEPT<br>KHQYDVDTETVIGFLRQNGLDKDFKVNIEVNHATLAGHTFEHELTAARENGFLGSIDANR<br>GDAQNGWDTDQFPVDAFDLTRAMMQILLNGGFGNGGTNFDAKLRRSSTDPEDIFIAHISA<br>MDAMAHALLNAAAILEESPLPALVKQRYASFDSGLGKQFEEGKATLEDLYAYAKEHGEPV<br>AASGKQELCETYLNLYAK |
| 5607MI1_003 | *Prevotella* | DNA | 127 | ATGAGTAAAGAGTATTTTCCTGGGATTGGCAAAATCCCGTATGAGGGAGCCGAGAGCAAG<br>AATGTGATGGCATTCCACTATTATGATCCCGAACGCGTGGTCATGGGCAAGAAAATGAAA<br>GACTGGTTCAAGTTCGCTATTGCCTGGTGGCATACCCTGGGGCAGGCCAGTGCTGACCAG<br>TTTGGCGGACAGACCCGTTTCTATGAATGGGACAAAGCCGAGGACCCCTTGCAGCGTGCC<br>AAGGACAAGATGGATGCCGGTTTTGAAATCATGCAGAAGCTGGGCATCGAGTATTTCTGT<br>TTCCATGATGTGGACCTCATCGAGGAGGCCGATACCATCGAGGAATATGAAGCCCGCATG<br>CAGGCGATTACCGACTACGCGCTGGAGAAGATGAAGGCAACGGGTATCAAGTTGCTGTGG<br>GGCACTGCCAACGTGTTCGGCCACAAGCGTTACATGAACGGCGCCGCCACCAATCCCGAC<br>TTCAATGTCGTGGCACGTGCAGCCGTGCAGATCAAGAACGCCCTCGATGCTACCATCAAG<br>TTGGGCGGAACGAGCTACGTCTTCTGGGGCGGTCGTGAAGGCTATCAGAGCCTGCTCAAC<br>ACCCAGATGCAGCGCGAGAAGAACCACCTGGCCAAGATGCTCACGGCAGCCCGTGACTAT<br>GCCCGTGCTAAGGGCTTCAAGGGCACCTTCCTGATTGAGCCCAAGCCGATGGAACCCACC<br>AAGCACCAGTATGACCAGGACACCGAGACCGTTATCGGCTTCTTGCGTGCCAATGGCCTT<br>GACAAGGACTTTAAGGTCAACATTGAGGTCAACCATGCCACGCTGGCTGGCCACACCTTT<br>GCACATGAGTTGGCAGTGGCTGTGGATAACGGTATGCTGGGCAGCATCGATGCTAACCGT<br>GGTGACCACCAGAACGGCTGGGATACAGACCAGTTCCCCATCAACAGTTATGAACTCACC<br>AATGCTATGCTGCAGATCATGCACGGCGGCGGTTTCAAGGACGGCGGTACCAACTTTGAC<br>GCCAAGCTGCGCCGCAACAGTACCGACCCCGAGGACATCTTTACCGCTCACATCAGTGGT |

TABLE 2-continued

| Clone No. | Class of organism | Type of Sequence | SEQ ID NO: | Sequence |
|---|---|---|---|---|
| | | | | ATGGACGCTCTGGCCCGTGCCCTGTTGAGTGCTGCCGATATCCTTGAGAAGAGCGAGTTG<br>CCTGAAATGCTCAAGGAACGCTATGCCAGCTTTGACGCGGGTGAAGGCAAGCGCTTTGAG<br>GATGGCCAGATGACTCTTGAGGAACTGGTTGCCTATGCCAAGTCCCATGGCGAGCCTGCT<br>ACCATCAGTGGCAAGCAGGAAAAATATGAAGCCATCGTGGCTTTGCACGTCAAGTAA |
| 5607MI1_ 003 | *Prevotella* | Amino Acid | 128 | MSKEYFPGIGKIPYEGAESKNVMAFHYYDPERVVMGKKMKDWFKFAIAWWHTLGQASADQ<br>FGGQTREYEWDKAEDPLQRAKDKMDAGFEIMQKLGIEYFCFHDVDLIEEADTIEEYEARM<br>QAITDYALEKMKATGIKLLWGTANVFGHKRYMNGAATNPDFNVVARAAVQIKNALDATIK<br>LGGTSYVFWGGREGYQSLLNTQMQREKNHLAKMLTAARDYARAKGFKGTFLIEPKPMEPT<br>KHQYDQDTETVIGFLRANGLDKDFKVNIEVNHATLAGHTFAHELAVAVDNGMLGSIDANR<br>GDHQNGWDTDQFPINSYELTNAMLQIMHGGGFKDGGTNFDAKLRRNSTDPEDIFTAHISG<br>MDALARALLSAADILEKSELPEMLKERYASFDAGEGKRFEDGQMTLEELVAYAKSHGEPA<br>TISGKQEKYEAIVALHVK |
| 5607MI2_ 003 | *Prevotella* | DNA | 129 | ATGAGTAAAGAGTATTATCCTGAGATTGGCAAAATCCCGTTTGAGGGTCCCGAGAGCAAG<br>AATGTGATGGCGTTCCATTACTATGAACCCGAACGCGTCGTCATGGGTAAGAAGATGAAA<br>GACTGGCTCAAGTTTGCCATGTGCTGGTGGCACAGCCTGGGTCAGGCCAGTGCCGACCAG<br>TTCGGCGGACAGACACGTTTCTACGAGTGGGACAAGGCCGATACCCCCCTGCAGCGTGCC<br>AAGGACAAAATGGATGCCGGATTTGAAATCATGCAGAAGTTGGGCATCGAGTACTTCTGC<br>TTCCACGATGTGGACCTCATCGAGGAGGCCGATACCATCGAGGAATACGAGGCCCGCATG<br>AAGGCCATTACCGACTATGCGCTGGAGAAGATGCAGGCCACCGGCATCAAGTTGCTGTGG<br>GGCACTGCCAATGTGTTCGGCCACAAGCGCTACATGAACGGCGCCGCCACCAATCCCGAT<br>TTCAATGTCGTGGCACGTGCCGCCGTCCAAATCAAGAATGCCATCGATGCCACCATCAAG<br>CTGGGCGGCACGAGTTACGTCTTCTGGGGTGGTCGTGAGGGCTATCAGAGTCTGCTCAAC<br>ACGCAGATGCAGCGCGAGAAGGACCATCTGGCCCGCATGCTGGCGGCAGCCCGCGACTAT<br>GGCCGTGCCCATGGCTTCAAGGGCACTTTCCTGATCGAGCCCAAACCCATGGAGCCCACC<br>AAGCACCAGTATGATGTGGACACCGAGACCGTGCTCGGCTTCCTGCGTGCCCACGGCCTG<br>GACAAGGACTTCAAGGTTAACATCGAGGICAATCATGCTACGCTGGCGGGACACACTTIC<br>AGCCACGAACTGGCTGTGGCCGTGGACAACGGTATGCTGGGCAGCATCGACGCCAACCGC<br>GGCGATTATCAGAATGGCTGGGACACCGACCAGTTCCCCATCGACAGCTTCGAGCTCACC<br>CAGGCCATGCTGCAGATCATGCGCGGCGGCGGCTTCAAGGACGGAGGTACCAACTTCGAT<br>GCCAAGCTGCGTCGCAACAGTACCGACCCTGAGGACATCTTCATCGCCCACATCAGCGGT<br>ATGGATGCCATGGCACGCGGCCTGTTGAGCGCTGCCGCTATCCTCGAGGATGGCGAGTTG<br>CCCGCGATGCTCAAGGCACGTTATGCCAGCTTTGACCAGGGCGAGGGTAAGCGCTTTGAG<br>GACGGCGAGATGACGCTCGAGCAGCTGGTGGATTATGCAAAGGATTATGCCAAATCGCAC<br>GGCGAGCCTGATGTCATCAGCGGCAAGCAGGAGAAGTTTGAAACCATCGTGGCCCTTTAC<br>GCCAAGTAA |
| 5607MI2_ 003 | *Prevotella* | Amino Acid | 130 | MSKEYYPEIGKIPFEGPESKNVMAFHYYEPERVVMGKKMKDWLKFAMCWWHSLGQASADQ<br>FGGQTRFYEWDKADTPLQRAKDKMDAGFEIMQKLGIEYFCFHDVDLIEEADTIEEYEARM<br>KAITDYALEKMQATGIKLLWGTANVFGHKRYMNGAATNPDFNVVARAAVQIKNAIDATIK<br>LGGTSYVFWGGREGYQSLLNTQMQREKDHLARMLAAARDYGRAHGFKGTFLIEPKPMEPT<br>KHQYDVDTETVLGFLRAHGLDKDFKVNIEVNHATLAGHTFSHELAVAVDNGMLGSIDANR<br>GDYQNGWDTDQFPIDSFELTQAMLQIMRGGGFKDGGTNFDAKLRRNSTDPEDIFIAHISG<br>MDAMARGLLSAAAILEDGELPAMLKARYASFDQGEGKRFEDGEMTLEQLVDYAKDYAKSH<br>GEPDVISGKQEKFETIVALYAK |
| 5607MI3_ 003 | *Prevotella* | DNA | 131 | ATGACCAACGAGTATTTTCCCGGAATCGGTGTGATTCCGTTTGAAGGACAGGAAAGCAAG<br>AATCCCCTGGCTTTCCATTATTATGACGCCAACCGCGTAGTGATGGGCAAACCCATGAAG<br>GAATGGTTCAAATTTGCCATGGCCTGGTGGCATACGCTGGGGCAGGCATCGGCCGATCCC<br>TTCGGCGGACAGACCCGCTCCTACGCATGGGACAAGGGCGAGTGCCCTTACTGCCGTGCC<br>CGCCAGAAGGCCGACGCCGGCTTTGAACTGATGCAGAAGCTGGGAATCGGCTATTTCTGC<br>TTCCACGATGTGGATATCATCGAGGACTGCGAGGACATTGCCGAGTATGAGGCCCGTATG<br>AAGGACATCACGGACTATCTGCTGGTGAAGATGAAGGAAACGGGCATCAAGAATCTGTGG<br>GGCACGGCCAACGTCTTCGGCCACAAGCGCTATATGAACGGCGCCGCCACCAACCCGCAA<br>TTCGACGTGGTAGCCCGCGCTGCGGTCCAGATCAAGAACGCCCTGGACGCCACCATCAAG<br>CTGGGCGGCAGCAATTATGTGTTCTGGGGCGGCCGGGAAGGCTACTACACCCTTTTGAAC<br>ACGCAGATGCAGCGGGAGAAGGACCACCTGGCCCAGATGCTCAAGGCGGCCCGCGACTAT<br>GCCCGCGGCAAGGGATTCAAGGGCACGTTCCTCATTGAGCCCAAGCCCATGGAGCCCACC<br>AAGCACCAGTACGACGTAGATACGGAGACCGTGATTGGTTTCCTGCGCGCCAACGGGCCG<br>GACAAGGACTTCAAGGTGAATATCGAAGTGAACCACGCCACCCTGGCCGGCCATACCTTC<br>GAGCACGAGCTCACCGTGGCCCGCGAAAACGGCTTCCTGGGCAGCATCGACGCCAACCGC<br>GGAGACGCCCAGAACGGCTGGGATACAGACCAGTTCCCCGTGGACGCCTTTGACCTCACC<br>CAGGCCATGATGCAGGTCCTGCTCAACGGCGGATTCGGCAACGGCGGCACCAACTTCGAC<br>GCCAAACTGCGCCGTTCCTCCACGGATCCCGAGGACATCTTCATCGCCCACATCAGCGCC<br>ATGGACGCCATGGCCCACGCCCTCCTGAACGCCGCCGCCATCCTGGAAGAGAGCCCCATG<br>CCGGGCATGGTGAAGGAGCGCTACGCTTCCTTCGACAATGGCCTTGGCAAGAAGTTCGAG<br>GAAGGAAAGGCCACGCTGGAAGAGCTGTACGACTATGCCAAGAAGAACGGCGAGCCTGIG<br>GCCGCTTCCGGAAAGCAGGAACTGTACGAAACGCTGCTGAACCTGTACGCCAAGTAA |
| 5607MI3_ 003 | *Prevotella* | Amino Acid | 132 | MTNEYFPGIGVIPFEGQESKNPLAFHYYDANRVVMGKPMKEWFKFAMAWWHTLGQASADP<br>FGGQTRSYAWDKGECPYCRARQKADAGFELMQKLGIGYFCFHDVDIIEDCEDIAEYEARM<br>KDITDYLLVKMKETGIKNLWGTANVFGHKRYMNGAATNPQFDVVARAAVQIKNALDATIK<br>LGGSNYVFWGGREGYYTLLNTQMQREKDHLAQMLKAARDYARGKGFKGTFLIEPKPMEPT<br>KHQYDVDTETVIGFLRANGPDKDFKVNIEVNHATLAGHTFEHELTVARENGFLGSIDANR<br>GDAQNGWDTDQFPVDAFDLTQAMMQVLLNGGFGNGGTNFDAKLRRSSTDPEDIFIAHISA |

TABLE 2-continued

| Clone No. | Class of organism | Type of Sequence | SEQ ID NO: | Sequence |
|---|---|---|---|---|
| | | | | MDAMAHALLNAAAILEESPMPGMVKERYASFDNGLGKKFEEGKATLEELYDYAKKNGEPV<br>AASGKQELYETLLNLYAK |
| 5607MI4_005 | *Prevotella* | DNA | 133 | ATGACTAAAGAGTATTTCCCTTCCGTCGGCAAGATTGCCTTTGAAGGACCCGAAAGCAAG<br>AACCCTATGGCCTTCCATTATTATGACGCCAATCGCGTGGTAATGGGAAAGCCGATGAAA<br>GAATGGCTTAAATTTGCCATGGCCTGGTGGCACACCCTGGGCCAGGCCTCTGCAGACCCC<br>TTCGGCGGTCAGACCCGCTCCTACGAGTGGGACAAGGGCGAGTGCCCCTACTGCCGCGCC<br>AAGGCCAAGGCCGATGCCGGCTTTGAACTGATGCAGAAACTGGGCATCGAGTATTTCTGC<br>TTCCACGATATAGACCTGGTGGAAGACTGCGATGATATCGCCGAATACGAGGCCCGCATG<br>AAGGACATCACGGACTATCTCCTGGAGAAGATGAAGGAAACCGGCATCAAGAACCTCTGG<br>GGAACCGCCAACGTGTTCGGCCACAAGCGCTATATGAACGGCGCCGCCACCAACCCTCAG<br>TTCGACATCGTGGCCCGTGCCGCTGTCCAGATCAAGAACGCCCTGGATGCCACCATCAAG<br>CTGGGCGGCTCCAACTATGTGTTCTGGGGCGGCCGTGAGGGCTACTATACCCTCCTGAAC<br>ACCCAGATGCAGAGAGAGAAGGACCACCTGGCCAAGATGCTCACCGCCGCCCGCGACTAT<br>GCCCGTGCCAAGGGCTTCAAGGGCACCTTCCTCATCGAACCCAAGCCGATGGAGCCCACC<br>AAGCACCAGTACGACGTAGATACGGAGACCGTGATCGGCTTCCTCCGCGCCAACGGCCTG<br>GACAAGGACTTCAAGGTGAATATTGAGGTGAACCACGCCACCCTGGCCGGCCACACCTTC<br>GAGCACGAGCTCACCGTGGCCCGCGAGAACGGCTTCCTGGGCAGCATCGACGCCAACCGC<br>GGAGACGCCCAGAACGGCTGGGATACGGACCAGTTCCCGGTGGATGCCTTCGACCTCACC<br>CAGGCTATGATGCAGATCCTTCTGAACGGAGGCTTCGGCAACGGCGGTACCAACTTCGAC<br>GCCAAACTGCGCCGCTCCTCCACGGACCCCGAGGACATCTTCATCGCCCACATCAGCGCT<br>ATGGATGCCATGGCCCACGCCCTGCTGAATGCAGCCGCCATCCTGGAGGAAAGCCCGCTT<br>CCGAAGATGCTGAAAGAGCGTTATGCCAGCTTTGACGGCGGTCTGGGCAAGAAGTTCGAA<br>GAAGGCAAGGCCTCTCTGGAAGAACTCTACGAGTATGCCAAGAGCAACGGAGAGCCCGTG<br>GCCGCTTCCGGCAAGCAGGAGCTCTGCGAAACGTACCTGAACCTCTACGCTAAGTAA |
| 5607MI4_005 | *Prevotella* | Amino Acid | 134 | MTKEYFPSVGKIAFEGPESKNPMAFHYYDANRVVMGKPMKEWLKFAMAWWHTLGQASADP<br>FGGQTRSYEWDKGECPYCRAKAKADAGFELMQKLGIEYFCFHDIDLVEDCDDIAEYEARM<br>KDITDYLLEKMKETGIKNLWGTANVFGHKRYMNGAATNPQFDIVARAAVQIKNALDATIK<br>LGGSNYVFWGGREGYYTLLNTQMQREKDHLAKMLTAARDYARAKGFKGTFLIEPKPMEPT<br>KHQYDVDTETVIGFLRANGLDKDFKVNIEVNHATLAGHTFEHELTVARENGFLGSIDANR<br>GDAQNGWDTDQFPVDAFDLTQAMMQILLNGGFGNGGTNFDAKLRRSSTDPEDIFIAHISA<br>MDAMAHALLNAAAILEESPLPKMLKERYASFDGGLGKKFEEGKASLEELYEYAKSNGEPV<br>AASGKQELCETYLNLYAK |
| 5607MI5_002 | *Prevotella* | DNA | 135 | ATGGCTAAAGAATACTTCCCCTCCATCGGCAAAATCCCTTTTGAAGGAGCCGACAGCAAA<br>AATCCCCTCGCTTTCCATTATTATGACGCCGGACGCGTGGTTATGGGCAAGCCCATGAAG<br>GAATGGCTTAAATTCGCCATGGCCTGGTGGCACACGCTGGGCCAGGCCTCCGGAGACCCC<br>TTCGGCGGCCAGACCCGCAGCTACGAATGGGACAAGGGCGAATGCCCCTACTGCCGCGCC<br>AAGGCCAAGGCCGACGCCGGTTTTGAAATCATGCAAAAGCTGGGCATCGAATACTTCTGC<br>TTCCACGATGTGGACCTTATCGAGGATTGCGATGACATTGCCGAATACGAAGCCCGCATG<br>AAGGACATCACGGACTACCTGCTGGAAAAGATGAAGGAGACCGGCATCAAGAACCTCTGG<br>GGCACCGCCAATGTCTTCGGCCACAAGCGCTACATGAACGGCGCCGGCACCAATCCGCAG<br>TTCGATGTGGTGGCCCGTGCCGCCGTCCAGATCAAGAACGCCCTGGACGCCACCATCAAG<br>CTGGGCGGCTCCAACTATGTGTTCTGGGGCGGCCGCGAAGGCTATTACACCCTCCTCAAC<br>ACACAGATGCAGCGGGAAAAAGACCACCTGGCCAAGTTGCTGACGGCCGCCCGCGACTAT<br>GCCCGCGCCAAGGGCTTCAAGGGCACCTTCCTCATTGAGCCCAAACCCATGGAACCCACC<br>AAGCACCAGTACGACGTGGATACGGAGACGGTCATCGGCTTCCTCCGTGCCAACGGCCTG<br>GACAAGGACTTCAAGGTGAACATCGAGGTGAACCACGCCACCCTGGCCGGCCACACCTTC<br>GAGCATGAGCTCACCGTGGCCCGCGAGAACGGTTTCCTGGGCTCCATCGATGCCAACCGC<br>GGCGACGCCCAGAACGGCTGGGACACGGACCAGTTCCCTGTGGACCCGTACGATCTTACC<br>CAGGCCATGATGCAGGTGCTGCTGAACGGCGGCTTCGGCAACGGCGGCACCAACTTCGAC<br>GCCAAACTCCGCCGCTCCTCCACCGACCCTGAGGACATCTTCATCGCCCATATTTCCGCC<br>ATGGATGCCATGGCCCACGCTTTGCTTAACGCAGCTGCCGTGCTGGAAGAGAGCCCCCTG<br>TGCCAGATGGTCAAGGAGCGTTATGCCAGCTTCGACGATGGCCTCGGCAAACAGTTCGAG<br>GAAGGCAAGGCTACCCTGGAAGACCTGTACGAATACGCCAAGGCCCAGGGTGAACCCGTT<br>GTCGCCTCCGGCAAGCAGGAGCTTTACGAGACTCTCCTGAACCTGTATGCCGTCAAGTAA |
| 5607MI5_002 | *Prevotella* | Amino Acid | 136 | MAKEYFPSIGKIPFEGADSKNPLAFHYYDAGRVVMGKPMKEWLKFAMAWWHTLGQASGDP<br>FGGQTRSYEWDKGECPYCRAKAKADAGFEIMQKLGIEYFCFHDVDLIEDCDDIAEYEARM<br>KDITDYLLEKMKETGIKNLWGTANVFGHKRYMNGAGTNPQFDVVARAAVQIKNALDATIK<br>LGGSNYVFWGGREGYYTLLNTQMQREKDHLAKLLTAARDYARAKGFKGTFLIEPKPMEPT<br>KHQYDVDTETVIGFLRANGLDKDFKVNIEVNHATLAGHTFEHELTVARENGFLGSIDANR<br>GDAQNGWDTDQFPVDRYDLTQAMMQVLLNGGFGNGGTNFDAKLRRSSTDPEDIFIAHISA<br>MDAMAHALLNAAAVLEESPLCQMVKERYASFDDGLGKQFEEGKATLEDLYEYAKAQGEPV<br>VASGKQELYETLLNLYAVK |
| 5607MI6_002 | *Prevotella* | DNA | 137 | ATGACCAAAGAATATTTCCCTACCGTCGGGAAGATCCCCTTCGAGGGCCCCGAAAGCAAG<br>AACCCTATGGCGTTCCATTACTATGACCCCAACCGTCTGGTGATGGGCAAGAAGATGAAA<br>GACTGGCTGCGTTTCGCCATGGCCTGGTGGCACACCCTCGGCCAGGCGTCGGGCGACCAG<br>TTCGGCGGCCAGACCCGCAGTTATGCGTGGGACGAGGGAGAATGCCCGTACGAGCGCGCC<br>CGTGCCAAGGCTGACGCCGGCTTCGAGATCATGCAGAAACTCGGTATCGAGTTCTTCTGC<br>TTCCACGACATCGACCTGATCGAGGATACCGACGACATCGCCGAGTATGAGGCCCGCCTG<br>AAAGACATCACGGACTATCTGCTCGAGAAGATGAAAGCCACTGGCATCAAAAATCTCTGG<br>GGAACGGCCAACGTGTTCGGCCACAAGCGTTGCATGAACGGCGCCGCCACCAACCCGGAC<br>TTCGCCGTGCTGGCCCGCGCTGCCGTCCAGATCAAGAACGCCATCGACGCCACCATCAAG |

TABLE 2-continued

| Clone No. | Class of organism | Type of Sequence | SEQ ID NO: | Sequence |
|---|---|---|---|---|
| | | | | CTGGGCGGCGAGAACTATGTGTTCTGGGGTGGCCGCGAAGGCTACACGAGCCTGCTCAAC<br>ACCCAGATGCAGCGTGAGAAAGAGCACCTGGGCCGCCTGCTGTCCCTGGCCCGCGACTAT<br>GGCCGCGCCCACGGCTTCAAGGGTACCTTCCTGATCGAGCCCAAGCCGATGGGACCGACG<br>AAACACCAGTACGACCAGGATACGGAAACTGTCATCGGTTTCCTGCGCCGCCACGGTCTA<br>GACAAGGACTTCAAGGTCAATATCGAGGTGAACCATGCCACGCTGGCGGGCCACACCTTC<br>GAACACGAACTGGCCTGCGCCGTGGATCACGGTATGCTGGGCAGCATCGACGCCAACCGC<br>GGTGACGCACAGAACGGCTGGGATACCGACCAGTTCCCGATCGACAACTTCGAGCTGACC<br>CTTTCCATGCTCCAGATCATCCGCAACGGTGGCCTGGCACCCGGCGGCTCGAATTTCGAT<br>GCCAAGCTGCGCCGCAACTCCACCGATCCCGAAGACATTTTCATCGCGCACATCAGCGCC<br>ATGGACGCCATGGCCCGCGCATTGGTCAATGCGGCCGCCATCCTGGAGGAGAGCGCTATT<br>CCGAAGATGGTCAAGGAGCGTTACGCTTCGTTCGACAGCGGCAAAGGCAAGGAATACGAG<br>GAAGGCAAGCTGACGCTCGAAGACATCGTGGCCTATGCCAAGGCGAACGGAGAACCGAAG<br>CAGATTTCCGGCAAACAGGAACTCTACGAGACGCTTGTCGCACTCTATAGCAAATAA |
| 5607MI6_ 002 | *Prevotella* | Amino Acid | 138 | MTKEYFPTVGKIPFEGPESKNPMAFHYYDPNRLVMGKKMKDWLRFAMAWWHTLGQASGDQ<br>FGGQTRSYAWDEGECRYERARAKADAGFEIMQKLGIEFFCFHDIDLIEDTDDIAEYEARL<br>KDITDYLLEKMKATGIKNLWGTANVFGHKRCMNGAATNPDFAVLARAAVQIKNAIDATIK<br>LGGENYVFWGGREGYTSLLNTQMQREKEHLGRLLSLARDYGRAHGFKGTFLIEPKPMGPT<br>KHQYDQDTETVIGFLRRHGLDKDFKVNIEVNHATLAGHTFEHELACAVDHGMLGSIDANR<br>GDAQNGWDTDQFPIDNFELTLSMLQIIRNGGLAPGGSNFDAKLRRNSTDPEDIFIAHISA<br>MDAMARALVNAAAILEESAIPKMVKERYASFDSGKGKEYEEGKLTLEDIVAYAKANGEPK<br>QISGKQELYETLVALYSK |
| 5607MI7_ 002 | *Prevotella* | DNA | 139 | ATGACCAAAGGGTATTTCCCTACCATCGGCAGGATTCCCTTCGAGGGAACTGAAAGCAAG<br>AATCCCCTCGCATTCCATTACTATGAGCCCGACCGGCTCGTACTGGGCAAGAAAATGAAA<br>GACTGGCTGCGTTTCGCGATGGCCTGGTGGCACACCCTGGGCCAGGCGTCCGGCGACCAG<br>TTCGGCGGCCAGACCCGCAGCTATGCCTGGGACAAGGCCGAGTGCCCCTATGAGCGCGCC<br>AAGGCCAAAGCCGACGCCGGCTTCGAGATCATGCAGAAACTCGGCATCGAGTTCTTCTGT<br>TTCCACGACATTGACCTCGTTGAGGATACCGACGACATCGCCGAGTATGAGGCCCGGATG<br>AAGGACATTACCGACTATCTCCTGGTCAAGATGAAGGAGACCGGAATCAAGAACCTCTGG<br>GGTACGGCCAATGTCTTCGGCCACAAGCGCTATATGAACGGCGCCGCCACCAATCCCGAC<br>TTCGACGTGGIGGCCCGCGCCGCCGTCCAGATCAAGAACGCCCTCGATGCCACCATCAAG<br>CTGGGCGGTGAAAACTATGTGTTCTGGGGCGGCCGCGAAGGCTATATGAGCCTGCTCAAC<br>ACGCAGATGCAGCGTGAGAAGGAGCACCTGGGCCGGATGCTGGTCGCCGCCCGCGACTAC<br>GCCCGCGCCCACGGCTTCAAGGGTACCTTCCTCATCGAGCCCAAACCGATGGAACCGACC<br>AAGCACCAGTACGACCAGGATACGGAAACCGTGATCGGCTTCCTTCGCCGCCACGGCCTG<br>GACAAGGATTTCAAGGTGAACATCGAAGTGAACCACGCCACGCTGGCCGGCCACACCTTC<br>GAGCACGAACTGGCCACCGCCGTCGACTGCGGCCTGCTGGGCAGCATCGACGCCAATCGC<br>GGCGACGCTCAGAACGGCTGGGATACCGACCAGTTCCCGATCGACAACTTCGAACTCACG<br>CTGGCCATGCTGCAGATTATCCGCAACGGCGGTCTGGCACCCGGCGGCTCGAACTTCGAC<br>GCCAAACTGCGCCGTAACTCCACCGATCCGGAAGATATCTTCATCGCCCACATCAGTGCG<br>ATGGACGCGATGGCCCGTGCGCTGGTCAACGCCGCCGCAATCTGGGAAGAGTCTCCCATC<br>CCGCAGATGAAGAAAGAACGCTACGCGTCGTTCGACAGCGGCAAGGGCAAGGAATTCGAA<br>GAGGGCAAGCTCTGCCTCGAAGACCTCGTGGCCTATGCCAAGGCGAACGGAGAACCGAAA<br>CAGATCTCCGGCAGGCAGGAACTATATGAGACCATCGTCGCCCTTTATTGCAAATAG |
| 5607MI7_ 002 | *Prevotella* | Amino Acid | 140 | MTKGYFPTIGRIPFEGTESKNPLAFHYYEPDRLVLGKKMKDWLRFAMAWWHTLGQASGDQ<br>FGGQTRSYAWDKAECPYERAKAKADAGFEIMQKLGIEFFCFHDIDLVEDTDDIAEYEARM<br>KDITDYLLVKMKETGIKNLWGTANVFGHKRYMNGAATNPDFDVVARAAVQIKNALDATIK<br>LGGENYVFWGGREGYMSLLNTQMQREKEHLGRMLVAARDYARAHGFKGTFLTEPKPMEPT<br>KHQYDQDTETVIGFLRRHGLDKDFKVNIEVNHATLAGHTFEHELATAVDCGLLGSIDANR<br>GDAQNGWDTDQFPIDNFELTLAMLQIIRNGGLAPGGSNFDAKLRRNSTDPEDIFIAHISA<br>MDAMARALVNAAAIWEESPTPQMKKERYASFDSGKGKEFEEGKLCLEDLVAYAKANGEPK<br>QISGRQELYETIVALYCK |
| 5608MI1_ 004 | *Prevotella* | DNA | 141 | ATGACCAACGAGTATTTTCCCGGAATCGGTGTGATTCCGTTTGAAGGACAGGAAAGCAAG<br>AATCCCATGGCTTTCCATTATTATGACGCCAACCGCGTAGTGATGGGCAAACCCATGAAG<br>GAATGGTTCAAATTTGCCATGGCCTGGTGGCATACGCTGGGGCAGGCATCGGCCGATCCC<br>TTCGGCGGACAGACCCGCTCCTACGCATGGGACAAGGGCGAGTGCCCTTACTGCCGTGCC<br>CGCCAGAAGGCCGACGCCGGCTTTGAACTGATGCAGAAGCTGGGTATCGGCTATTTCTGC<br>TTCCACGATGTGGATATCATCGAGGACTGCGAAGACATTGCCGAGTATGAGGCCCGTATG<br>AAGGACATCACGGACTATCTGCTGGTGAAGATGAAGGAAACGGGCATCAAGAACCTGTGG<br>GGCACGGCCAACGTCTTCGGCCACAAGCGCTATATGAACGGCGCTGCCACCAACCCGCAG<br>TTCGACGTGGTGGCCCGCGCTGCGGTCCAGATCAAGAACGCCCTGGACGCCACCATCAAG<br>CTGGGCGGCAGCAATTACGTGTTCTGGGGCGGCCGCGAAGGCTATTATACCCTTTGGAAC<br>ACGCAGATGCGGCGGGAGAAGGACCACCTGGCCCAGATGCTCAAGGCAGCCCGTGACTAT<br>GCCCGCGGCAAGGGATTCAAGGGCACGTTCCTCATTGAGCCCAAGCCCATGGAGCCCACC<br>AAGCACCAGTACGACGTAGATACGGAGACCGTGATTGGCTTCCTGCGCGCAAACGGACTG<br>GACAAGGACTTCAAGGTGAATATCGAAGTGAACCACGCCACCCTGGCCGGCCACACCTTC<br>GAGCACGAACTCACCGTGGCCCGCGAAAACGGCTTCCTGGGCAGCATCGACGCCAACCGC<br>GGAGACGCCCAGAACGGTTGGGATACAGACCAGTTCCCCATAGATGCCTTTGACCTCACC<br>CAGGCCATGATGCAGGTCCTGCTCAACGGCGGATTCGGCAACGGCGGCACCAACTTCGAC<br>GCCAAACTGCGCCGTTCCTCCACGGATCCCGAGGACATCTTCATCGCCCACATCGGCGCC<br>ATGGACGCCATGGCCCACGCCCTCCTGAACGCCGCCGCCATCCTGGAAGAGAGCCCCATG<br>CCGGGCATGGTGAAGGAGCGCTACGCTTCCTTCGACAATGGCCTTGGCAAGAAGTTCGAG |

TABLE 2-continued

| Clone No. | Class of organism | Type of Sequence | SEQ ID NO: | Sequence |
|---|---|---|---|---|
| | | | | GAAGGAAAGGCCACGCTGGAAGAGCTGTACGACTATGCCAAGAAGAACGGCGAGCCTGTG<br>GCCGCTTCCGGCAAGCAGGAACTGTACGAAACGCTGCTGAACCTGTACGCCAAGTAA |
| 5608MI1_004 | *Prevotella* | Amino Acid | 142 | MTNEYFPGIGVIPFEGQESKNPMAFHYYDANRVVMGKRMKEWFKFAMAWWHTLGQASADP<br>FGGQTRSYAWDKGECPYCRARCKADAGFELMQKLGIGYFCFHDVDIIEDCEDIAEYEARM<br>KDITDYLLVKMKETGIKNLWGTANVFGHKRYMNGAATNPQEDVVARAAVQIKNALDATIK<br>LGGSNYVFWGGREGYYTLWNTQMRREKDHLAQMLKAARDYARGKGFKGTFLIEPKPMEPT<br>KHQYDVDTETVIGFLRANGLDKDFKVNIEVNHATLAGHTFEHELTVARENGFLGSIDANR<br>GDAQNGWDTDQFPIDAFDLTQAMMQVLLNGGFGNGGTNFDAKLRRSSTDPEDIFIAHIGA<br>MDAMAHALLNAAAILEESPMPGMVKERYASFDNGLGKKFEEGKATLEELYDYAKKNGEPV<br>AASGKQELYETLLNLYAK |
| 5608MI2_002 | *Prevotella* | DNA | 143 | ATGAAAGAATACTTCCCTACCATCGGAAAAATCCCTTTCGAGGGCCCTCAGAGCAAGAAT<br>CCGCTCGCATTCCATTACTATGACGCCAACCGCGTTGTCGCCGGCAAACCCATGAAGGAC<br>TGGCTCAAGTTCGCCATGGCTTGGTGGCACACCCTGGGCGCAGCATCGGCAGACCCCTTC<br>GGCGGCCAGACCCGCAGCTACGAGTGGGACAAAGCCGAGTGCCCTTACTGCCGTGCCCGT<br>GAAAAGGCCGACGCCGGCTTCGAGATCATGCAGAAACTTGGAATCGAGTACTTCTGCTTC<br>CATGACATCGACCTTGTGGAAGACTGCGAGGACATTGCCGAGTACGAGGCCCGCATGAAG<br>GACATCACGGACTACCTCCTGGAGAAGATGAAGGCCACCGGCATCAAGAACCTGTGGGGC<br>ACCGCCAACGTCTTTGGCAACAAGCGCTACATGAACGGCGCAGCCACCAACCCTCAGTTC<br>GACATCGTTGCCCGTGCAGCTGTCCAGATCAAGAACGCCATCGACGCAACAATCAAGCTG<br>GGCGGTACCGGTTACGTATTCTGGGGCGGCCGCGAGGGCTACTACACCCTCCTGAACACC<br>CAGATGCAGCGCGAGAAGGACCACCTTGCCAAGATGCTCACCGCAGCCCGCGACTACGCC<br>CGCGCCAAGGGATTCAAGGGCACATTCCTCATCGAGCCCAAGCCCATGGAGCCCACCAAG<br>CACCAGTACGATGTTGACACGGAAACCGTCATCGGCTTCCTCCGCGCCAACGGCCTGGAC<br>AAGGACTTCAAGGTGAACATCGAGGTGAACCACGCCACCCTGGCCGGCCACACCTTCGAG<br>CACGAGCTCACCGTGGCCGTGGACAACGGCTTCCTGGGCAGCATCGACGCAAACCGCGGC<br>GACGCCCAGAACGGCTGGGACACTGACCAGTTCCCTGTGGATCCTTACGACCTCACCCAG<br>GCAATGATGCAGATTATCCGCAACGGCGGCTTCAAGGACGGCGGCACCAACTTCGACGCC<br>AAACTCCGCCGCAGCTCCACGGACCCCGAGGACATCTTCATCGCCCACATCAGCGCAATG<br>GATGCAATGGCACACGCCCICATCAACGCTGCTGCAGTGCTTGAGGAAAGCCCTCTGTGC<br>GAGATGGTTGCAAAGCGCTACGCCAGCTTTGACAGCGGTCTTGGCAAGAAGTTCGAGGAA<br>GGCAAAGCCACTCTCGAGGAGATCTACGAGTATGCCAAGAAGGCCCCGGCACCCGTCGCC<br>GCCTCCGGCAAGCAGGAGCTCTACGAGACACTGCTCAATCTGTACGCTAAATAA |
| 5608MI2_002 | *Prevotella* | Amino Acid | 144 | MKEYFPTIGKIPFEGPQSKNPLAFHYYDANRVVAGKPMKDWLKFAMAWWHTLGAASADPF<br>GGQTRSYEWDKAECPYCRAREKADAGFEIMQKLGIEYFCFHDIDLVEDCEDIAEYEARMK<br>DITDYLLEKMKATGIKNLWGTANVFGNKRYMNGAATNRQFDIVARAAVQIKNAIDATIKL<br>GGTGYVFWGGREGYYTLLNTQMQREKDHLAKMLTAARDYARAKGFKGTFLIEPKPMEPTK<br>HQYDVDTETVIGFLRANGLDKDFKVNIEVNHATLAGHTFEHELTVAVDNGFLGSIDANRG<br>DAQNGWDTDQFPVDRYDLTQAMMQIIRNGGFKDGGTNFDAKLRRSSTDPEDIFIAHISAM<br>DAMAHALINAAAVLEESPLCEMVAKRYASFDSGLGKKFEEGKATLEEIYEYAKKAPAPVA<br>ASGKQELYEILLNLYAK |
| 5608MI3_004 | *Prevotella* | DNA | 145 | ATGACCAAAGAGTATTTCCCTACAATCGGAAAGATTCCCTTCGAAGGCCCGGAGAGCAAG<br>AATCCGCTGGCATTCCATTACTATGAACCCGACAGAATCATCCTCGGCAGGAAGATGAAG<br>GACTGGCTGCGCTTCGCCGTGGCCTGGTGGCACACCCTCGGCCAGGCGTCCGGCGACCAG<br>TTCGGAGGCCAGACCCGCAACTATGCGTGGGACGAGCCCGAATGCCCGGTAGAGCGCGCG<br>AAAGCCAAGGCCGACGCCGGCTTCGAGCTGATGCAGAAGCTGGGCATCGAGTATTTCTGC<br>TTCCACGACGTAGACCTCATAGAGGAGGCCGCAACCATCGAAGAATATGAGGAGCGCATG<br>GGCATCATAACCGACTACCTGCTCGGGAAGATGAAGGAGACAGGTATCAAGAACCTCTGG<br>GGCACCGCCAACGTGTTCGGCCACAAGCGTTACATGAACGGAGCCGCCACCAACCCCGAC<br>TTCGACGTGGIGGCCCGTGCGGCCGTGCAGATCAAGAACGCCATCGACGCCACCATCAAG<br>CTGGGCGGCGAGAATTACGTATTCTGGGGCGGACGCGAGGGCTATGCAAGCCTGCTCAAC<br>ACTCAGATGCAGCGCGAGAAAGACCACCTGGGACGCATGCTGGCTGCAGCCCGCGACTAT<br>GGCCGCGCCCACGGATTCAAGGGCACTTTCCTCATCGAGCCCAAACCCATGGAGCCTACC<br>AAGCACCAGTACGACCAGGATACCGAGACCGTTATCGCCTTCCTGCGCAGGAACGGCCTC<br>GACAAGGATTTCAAGGTAAACATCGAGGTGAACCACGCCACCCTGGCGGGCCACACCTTC<br>GAGCACGAACTGGCGGTGGCAGTGGACAACGGCCTGCTTGGCAGCATCGACGCCAACCGC<br>GGCGACGCGCAGAACGGATGGGACACCGACCAGTTCCCCATCGACAACTTCGAGCTCACC<br>CAGGCCATGCTGCAGATAATCCGCAACGGCGGACTGGGAACCGGCGGATCGAACTTCGAC<br>GCCAAGCTGCGCCGCAATTCCACCGACCCTGAGGATATCTTCATCGCCCACATCAGTGCG<br>ATGGACGCCATGGCACGCGCGCTGGCAAACGCCGCCGCAATCATCGAAGAGAGCCCCATC<br>CCCGCAATGCTGAAGGAGCGCTACGCATCGTTCGACAGCGGCAAGGGCAAGGAGTTCGAG<br>GACGGCAAACTGAGCCTCGAAGAACTGGTAGCCTACGCCAAGGCGAACGGCGAGCCGAAG<br>CAGATTTCCGGCAAGCAGGAACTCTACGAAACCATAGTGGCCCTCTATTGCAAGTAA |
| 5608MI3_004 | *Prevotella* | Amino Acid | 146 | MTKEYFPTIGKIPFEGPESKNPLAFHYYEPDRIILGRKMKDWLRFAVAWWHTLGQASGDQ<br>FGGQTRNYAWDEPECPVERAKAKADAGFELMQKLGIEYFCFHDVDLIEEAATIEEYEERM<br>GIITDYLLGKMKETGIKNLWGTANVFGHKRYMNGAATNPDFDVVARAAVQIKNAIDATIK<br>LGGENYVFWGGREGYASLLNTQMQREKDHLGRMLAAARDYGRAHGFKGTFLTEPKPMEPT<br>KHQYDQDTETVIAFLRRNGLDKDFKVNIEVNHATLAGHTFEHELAVAVDNGLLGSIDANR<br>GDAQNGWDTDQFPIDNFELTQAMLQIIRNGGLGTGGSNFDAKLRRNSTDPEDIFIAHISA<br>MDAMARALANAAAIIEESPTPAMLKERYASFDSGKGKEFEDGKLSLEELVAYAKANGEPK<br>QISGKQELYETIVALYCK |

TABLE 2-continued

| Clone No. | Class of organism | Type of Sequence | SEQ ID NO: | Sequence |
|---|---|---|---|---|
| 5609MI1_ 005 | *Prevotella* | DNA | 147 | ATGGCACAAGAATACTTCCCTACCATTGGGAAAATCCCCTTCGAGGGCACTGAGAGCAAG AATCCCCTTGCTTTCCATTACTATGAGCCGGAGCGCATTGTCTGCGGCAAACCCATGAAA GAATGGCTCAAGTTTGCCATGGCCTGGTGGCACACGCTGGGGCAGGCATCGGCCGATCCC TTCGGCGGCCAAACCCGCAGCTATGCCTGGGATAAGGGCGAATGCCCCTACTGCCGTGCC CGCGCCAAGGCGGACGCCGGCTTCGAGATTATGCAAAAGCTGGGCATCGAGTACTTCTGC TTCCACGATATCGACCTGGTAGAAGACTGTGACGATATTGCGGAATACGAAGCCCGCATG AAGGACATCACGGACTACCTCCTGGAGAAGATGAAGGAAACCGGTATCAAGAACCTCTGG GGCACCGCCAATGTGTTTGGTCACAAGCGCTACATGAACGGCGCCGCCACCAACCCGCAG TTTGACGTAGTGGCCCGTGCCGCTGTTCAGATTAAGAACGCCATTGACGCCACCATCAAG TTGGGCGGTGCCAATTACGTGTTCTGGGGCGGCCGCGAGGGCTATTACAGCCTCCTGAAC ACCCAGATGCAGCGGGAGAAGGACCACCTGGCCAAGCTGCTCACGGCAGCCCGCGACTAT GCCCGCGCCAACGGCTTCAAGGGAACCTTCCTGATTGAGCCCAAGCCCATGGAGCCCACC AAGCACCAGTACGACGTGGATACGGAGACGGTCATTGGCTTCCTCCGCGCCAACGGCCTG GACAAGGACTTCAAGGTGAATATCGAGGTGAACCACGCCACGTTGGCCGGCCACACCTTT GAGCACGAGCTCACCGTGGCCCGCGAGAACGGCTTCCTGGGCAGCATCGACGCCAACCGC GGCGATGCCCAGAACGGCTGGGATACGGACCAGTTCCCGGTAGACGCTTATGAGCTCACC CAGGCCATGATGCAGGTGCTCCTGAACGGAGGCTTCGGCAACGGCGGCACCAACTTCGAC GCCAAGCTGCGCCGCTCCTCCACGGACCCGGAGGACATCTTCATCGCCCATATCAGTGCG ATGGATGCCATGGCCCACGCCCTGCTCAACGCCGCCGCCGTGCTGGAGGAAAGCCCCCTG TGCCAGATGGTGAAGGAGCGCTACGCCAGCTTTGACAGCGGTCCGGGCAAGCAGTTCGAG GAAGGAAAGGCCACCCTGGAGGACCTGTACAACTACGCCAAAGCCACCGGTGAACCCGTG GTTGCCTCCGGCAAGCAGGAACTTTACGAGACCCTCCTGAACCTCTATGCAAAGTAG |
| 5609MI1_ 005 | *Prevotella* | Amino Acid | 148 | MAQEYFPTIGKIPFEGTESKNPLAFHYYEPERIVCGKPMKEWLKFAMAWWHTLGQASADP FGGQTRSYAWDKGECPYCRARAKADAGFEIMQKLGIEYFCFHDIDLVEDCDDIAEYEARM KDITDYLLEKMKETGIKNLWGTANVFGHKRYMNGAATNPQFDVVARAAVQIKNAIDATIK LGGANYVFWGGREGYYSLLNTQMQREKDHLAKLLTAARDYARANGFKGTFLIEPKPMEPT KHQYDVDTETVIGFLRANGLDKDFKVNIEVNHATLAGHTFEHELTVARENGFLGSIDANR GDAQNGWDTDQFPVDAYELTQAMMQVLLNGGFGNGGTNFDAKLRRSSTDPEDIFIAHISA MDAMAHALLNAAAVLEESPLCQMVKERYASFDSGPGKQFEEGKATLEDLYNYAKATGEPV VASGKQELYETLLNLYAK |
| 5610MI1_ 003 | *Prevotella* | DNA | 149 | ATGGCACAAGAATACTTCCCTACCATTGGAAAATCCCCTTCGAGGGCACTGAGAGCAAG AATCCCCTTGCTTTCCATTACTATGAGCCGGAGCGCATTGTCTGCGGCAAACCCATGAAA GAATGGCTCAAGTTTGCCATGGCCTGGTGGCACACGCTGGGGCAGGCATCGGCCGATCCC TTCGGCGGCCAAACCCGCAGCTATGCCTGGGATAAGGGCGAATGCCCCTACTGCCGTGCC CGTGCCAAGGCGGACGCCGGTTTTGAGATTATGCAAAAGCTGGGCATCGAGTACTTCTGC TTCCACGATATCGACCTGGTAGAAGACTGTGACGATATTGCGGAATACGAAGCCCGCATG AAGGACATCACGGACTACCTCCTGGAGAAGATGAAGGAAACCGGCATCAAGAACCTCTGG GGCACCGCCAATGTGTTTGGTCACAAGCGCTACATGAACGGCGCCGGCACCAATCCGCAG TTTGACGTGGTGGCCCGTGCTGCCGTGCAAATCAAGAACGCCATTGACGCCACCATCAAG TTGGGCGGTGCCAATTACGTGTTCTGGGGCGGCCGCGAGGGCTATTACAGCCTCCTGAAC ACCCAGATGCAGCGGGAGAAGGACCACCTGGCCAAGCTGCTCACGGCAGCCCGCGACTAT GCCCGCGCCAACGGCTTCAAGGGAACCTTCCTGATTGAGCCCAAGCCCATGGAGCCCACC AAGCACCAGTACGACGTGGATACGGAGACGGTCATTGGCTTCCTCCGCGCCAACGGCCTG GACAAGGACTTCAAGGTGAATATCGAGGTGAACCACGCCACGCTGGCCGGCCACACCTTT GAGCACGAACTCACCGTGGCCCGCGAGAACGGCTTCCTGGGCAGCATCGACGCCAACCGC GGCGATGCCCAGAACGGCTGGGATACGGACCAGTTCCCGGTAGACGCTTATGAGCTCACC CAGGCCATGATGCAGGTGCTCCTGAACGGAGGCTTCGGCAACGGCGGCACCAACTTCGAC GCCAAGCTGCGCCGCTCCTCCACGGACCTGGAGGACATCTTCATCGCCCATATCAGTGCG ATGGATGCCATGGCCCACGCCCTGCTCAACGCCGCCGCCGTGCTGGAGGAAAGCCCCCTG TGCCAGATGGTGAAGGAGCGCTACGCCAGCTTTGACAGCGGTCCGGGCAAGCAGTTCGAG GAAGGAAAGGCCACCCTGGAGGACCTGTACAACTACGCCAAAGCCAACGGTGAACCCGTG GTTGCCTCCGGCAAGCAGGAACTTTACGAGACCCTCCTGAACCTCTATGCAAAGTAG |
| 5610MI1_ 003 | *Prevotella* | Amino Acid | 150 | MAQEYFPTIGKIPFEGTESKNPLAFHYYEPERIVCGKPMKEWLKFAMAWWHTLGQASADP FGGQTRSYAWDKGECPYCRARAKADAGFEIMQKLGIEYFCFHDIDLVEDCDDIAEYEARM KDITDYLLEKMKETGIKNLWGTANVFGHKRYMNGAGTNPQFDVVARAAVQIKNAIDATIK LGGANYVFWGGREGYYSLLNTQMQREKDHLAKLLTAARDYARANGFKGTFLIEPKPMEPT KHQYDVDTETVIGFLRANGLDKDFKVNIEVNHATLAGHTFEHELTVARENGFLGSIDANR GDAQNGWDTDQFPVDAYELTQAMMQVLLNGGFGNGGTNFDAKLRRSSTDLEDIFIAHISA MDAMAHALLNAAAVLEESPLCQMVKERYASFDSGPGKQFEEGKATLEDLYNYAKANGEPV VASGKQELYETLLNLYAK |
| 5610MI2_ 004 | *Prevotella* | DNA | 151 | ATGGCAAAAGAATATTTCCCTACCATCGGCAAGATTCCTTTTGAAGGAACCGACAGCAAG AGTCCCCTCGCCTTCCATTACTATGACGCCCAGCGCGTTGTGATGGGCAAACCCATGAAG GAATGGCTCAAGTTCGCCATGGCCTGGTGGCACACCCTGGGCCAGGCATCGGCCGACCCC TTCGGCGGTCAGACCCGCCACTATGCCTGGGATGAAGGCGAATGCCCCTACTGCCGCGCC AAAGCCAAGGCCGACGCCGGCTTCGAGATCATGCAGAAACTGGGCATCGAGTACTTCTGC TTCCACGATGTGGACCTGGTGGAAGACTGCGACGACATCGCCGAGTACGAAGCCCGCATG AAGGACATCACGGACTACCTGCTGGAGAAGATGAAGGAAACCGGCATCAAGAACCTCTGG GGCACGGCCAATGTGTTCGGCCACAAGCGTTACATGAACGGCGCCGGGACCAACCCGCAG TTTGACATTGTGGCCCGCGCTGCCGTCCAGATCAAAAACGCCCTGGACGCCACCATCAAG CTGGGCGGTTCCAACTACGTGTTCTGGGGCAGCCGCGAAGGCTACTACACCCTCCTGAAC ACCCAGATGCAGCGGGAGAAAGACCACCTGGCCAAGCTCCTGACCGCCGCCCGCGACTAC |

TABLE 2-continued

| Clone No. | Class of organism | Type of Sequence | SEQ ID NO: | Sequence |
| --- | --- | --- | --- | --- |
| | | | | GCCCGCGCCAAAGGCTTCAAGGGAACCTTCCTCATCGAGCCCAAACCCATGGAGCCCACC<br>AAGCACCAGTACGACGTGGACACCGAGACCGTAATCGGCTTCCTGCGTGCCAACGGCCTG<br>GACAAGGACTTCAAGGTGAACATCGAGGTGAACCACGCCACCCTGGCTGGCCACACCTIC<br>GAGCACGAACTCACCGTCGCCCGTGAAAACGGCTTCCTCGGATCGATCGACGCCAACCGC<br>GGCGACGCCCAGAACGGCTGGGACACCGACCAGTTCCCCGTAGACGCCTATGACCTCACC<br>CAGGCCATGATGCAGGTGCTGCTGAACGGCGGTTTCGGCAATGGCGGTACCAACTTCGAC<br>GCCAAGCTCCGCCGCTCCTCCACGGATCCGGAAGACATCTTCATCGCCCACATCAGCGCC<br>ATGGACGCCATGGCCCACGCCCTGCTGAACGCCGCCGCCGTGCTGGAAGAAAGCCCGCTT<br>CCCGCCATGGCGAAAGAGCGCTACGCCTCCTTTGACAGCGGACTTGGCAAGAAGTTCGAA<br>GAGGGAAAGGCCACCCTCGAAGAGCTGTACGACTATGCCAAGGCTAACGACGCCCCTGTC<br>GCCGCCTCCGGCAAGCAGGAACTTTACGAAACCTTCTTGAACCTCTATGCAAAATAG |
| 5610MI2_004 | *Prevotella* | Amino Acid | 152 | MAKEYFPTIGKIPFEGTDSKSPLAFHYYDAQRVVMGKPMKEWLKFAMAWWHTLGQASADP<br>EGGQTRHYAWDEGECPYCRAKAKADAGFEIMQKLGIEYFCFHDVELVEDCDDIAEYEARM<br>KDITDYLLEKMKETGIKNLWGTANVFGHKRYMNGAGTNPQFDIVARAAVQIKNALDATIK<br>LGGSNYVFWGSREGYYTLLNTQMQREKDHLAKLLTAARDYARAKGFKGTFLIEPKPMEPT<br>KHQYDVDTETVIGFLRANGLDKDFKVNIEVNHATLAGHTFEHELTVARENGFLGSIDANR<br>GDAQNGWDTDQFPVDAYDLTQAMMQVLLNGGFGNGGTNFDAKLRRSSTDPEDIFIAHISA<br>MDAMAHALLNAAAVLEESPLPAMAKERYASFDSGLGKKFEEGKATLEELYDYAKANDAPV<br>AASGKQELYETFLNLYAK |
| 5751MI1_003 | *Prevotella* | DNA | 153 | ATGGCAAAACAGTATTTTCCGCAAATCGGAAAGATTAAATTCGAAGGAACAGAGAGCAAG<br>AATCCGCTTGCGTTCCATTATTATGACGCAAACAGGGTAGTCCTCGGAAAGGCAATGGAG<br>GAGTGGCTCAAGTTCGCAATGGCTTGGTGGCATACTCTCGGACAGGCTTCCGGAGACCAG<br>TTCGGCGGCCAGACCCGCAGCTACGAGTGGGATCTTGCAGCCACCCCCGAGCAGCGCGCA<br>AAGGACAAGCTCGACGCCGGCTTCGAAATAATGGAGAAACTTGGAATCAAGTATTTCTGT<br>TTCCACGATGTTGACCTTATCGAAGACAGCGACGATATTGCGACATATGAGGCTCGTCTC<br>AAGGACCTTACAGACTACGCTGCAGAGCAGATGAAGCTCCACGACATCAAGCTCCTCTGG<br>GGTACAGCGAATGTATTCGGCAACAAGCGCTACATGAACGGTGCGGCTACAAACCCTGAT<br>TTCGATGTAGTTGCCCGCGCAGCCGTTCAGATTAAGAACGCTATCGACGCGACCATCAAG<br>CTCGGTGGTACCAGCTATGTATTCTGGGGCGGTCGTGAGGGATATCAGAGCCTGCTCAAC<br>ACTCAGATGCAGCGTGAGAAGGACCACCTCGCAACCATGCTTACAATCGCTCGCGACTAT<br>GCTCGCAGCAAGGGCTTTACCGGAACCTTCCTTATCGAGCCTAAGCCGATGGAGCCTACA<br>AAACACCAGTACGACGTAGATACAGAGACTGTTGTCGGCTTCCTCAAGGCACACGGCCTG<br>GACAAGGACTTCAAGGTAAATATCGAGGTTAACCACGCAACTCTCGCAGGCCACACCTTC<br>GAGCACGAACTCACCGTTGCTGTGGATAACGGAATGCTCGGTTCTATCGACGCTAACCGC<br>GGTGATGCACAGAACGGCTGGGATACAGACCAGTTCCCTGTAAGCGCTGAGGAGCTTACC<br>CTCGCTATGATGCAGATTATCCGTAATGGTGGCCTTGGCAACGGAGGATCCAACTTCGAC<br>GCAAAGCTTCGCCGCAACTCTACCGATCCTGAAGACATCTTCATCGCACACATCTGCGGT<br>ATGGATGCAATGGCACACGCTCTCCTCAATGCAGCTGCAATTATCGAGGAGTCTCCTATC<br>CCTACAATGGTTAAGGAGCGTTACGCTTCCTTCGACAGCGGTATGGGTAAGGACTTCGAG<br>GATGGAAAGCTTACCCTCGAGGATCTCTACAGCTACGGCGTGAAGAACGGAGAGCCAAAG<br>CAGACCAGCGCAAAGCAGGAGCTCTATGAGACTCTCATGAATATCTATTGCAAGTAA |
| 5751MI1_003 | *Prevotella* | Amino Acid | 154 | MAKQYFPQIGKIKFEGTESKNPLAFHYYDANRVVLGKAMEEWLKFAMAWWHTLGQASGDQ<br>FGGQTRSYEWDLAATPEQRAKDKLDAGFEIMEKLGIKYFCPHDVDLIEDSDDIATYEARL<br>KDLTDYAAEQMKLEDIKLLWGTANVFGNKRYMNGAATNPDFDVVARAAVQIKNAIDATIK<br>LGGTSYVFWGGREGYQSLLNIQMQREKDHLATMLTIARDYARSKGFTGTFLIEPKPMEPT<br>KHQYDVDTETVVGFLKAHGLDKDFKVNIEVNHATLAGHTFEHELTVAVDNGMLGSIDANR<br>GDAQNGWDTDQFPVSAEELTLAMMQIIRNGGLGNGGSNFDAKLRRNSTDPEDIFTAMICG<br>MDAMAHALLNAAAIIEESPIPTMVKERYASFDSGMGKDFEDGKLTLEDLYSYGVKNGEPK<br>QTSAKQELYETLMNIYCK |
| 5751MI2_003 | *Prevotella* | DNA | 155 | ATGGCAAAAGAATTTTTTCCACAAGTAGGCAAGATTCCATTTGAGGGTCCTGAAAGTACT<br>AACGTACTCGCATTCCACTACTATGATCCAGAACGCGAAGTTCTTGGTAAGAAAATGAAA<br>GATTGGCTGAAGTATGCTATGGCTTGGTGGCACACACTCGGTCAGGCAAGTGGCGACCAA<br>TTCGGTCTTCAAACTCGTTCGTATGAATGGGATGAAGCCGACGATGTTCTTCAACGCGCA<br>AAGGATAAAATGGATGCTGGTTTTGAATTGATGACCAAACTTGGCATTGAATACTACTGC<br>TTCCATGATGTCGACCTTATTGAAGAAGGTGCAACAATTGAAGAATATGAAGCTCGTATG<br>CAAGCTATCACCGACTACGCATTAGAAAAACAAAAAGAAACCGGCATTAAGCTCCTTTGG<br>GGTACTGCTAATGTGTTTGGTCATAAGCGTTATATGAATGGTGCGGCAACAAACCCTGAC<br>TTTGATGTAGTGGCTCGCGCTGCTGTACAAATCAAGAACGCTATCGATGCAACTATCAAG<br>CTTGGTGGTCAAAACTATGTATTCTGGGGTGGCCGCGAAGGTTATATGAGTTTGCTCAAC<br>ACTCAAATGCAACGCGAAAAAGACCACTTGGCAAAGATGCTTACCGCAGCTCGCGACTAT<br>GCTCGTGCTAAGGGCTTCAAGGGTACATTCCTCGTTGAACCTAAGCCTATGGAACCAACT<br>AAGCATCAATATGATACCGATACAGAAACTGTGATTGGTTTCCTCCGTGCAAATGGTCTT<br>GAAAAAGACTTCAAGGTGAACATTGAAGTGAACCATGCTACTCTCGCTCAGCACACTTTC<br>GAACACGAACTCGCTGTGGCTGTCGACAATGGCATGCTCGGTTCTATCGACGCTAACCGT<br>GGCGATGCTCAAAATGGCTGGGATACCGACCAATTCCCAATCGACAACTACGAACTCACC<br>CTCGCTATGCTCCAAATCATTCGCAATGGTGGTCTTGGCAATGGCGGTAGCAACCTCGAC<br>GCTAAGATTCGTCGTAATAGCACCGACCTTGAAGACCTCTTTATCGCTCACATCAGTGGT<br>ATGGATGCTATGGCTCGTGCACTTCTCAATGCTGCTGCAATCGTTGAAAAGAGCGAAATT<br>CCTGCTATGTTGAAGCAGCGTTATGCAAGCTCTGATGCAGGTATGGGTAAGGACTTCGAA<br>GAAGGAAAACTCACTCTCGAACAACTCGTAGACTATGCTAAGGCTAACGGCGAACCTGCT<br>ACAGTAAGCGGCAAGCAAGAAAAGTATGAAACTCTCGTTGCTCTCTACGCTAAGTAA |

TABLE 2-continued

| Clone No. | Class of organism | Type of Sequence | SEQ ID NO: | Sequence |
|---|---|---|---|---|
| 5751MI2_003 | *Prevotella* | Amino Acid | 156 | MAKEFFPQVGKIPFEGPESTNVLAFHYYDPEREVLGKKMKDWLKYAMAWWHTLGQASGDQ<br>FGGQTRSYEWDEADDVLQRAKDKMDAGFELMTKLGIEYYCFHDVDLIEEGATIEEYEARM<br>QAITDYALEKQKETGIKLLWGTANVEGHKRYMNGAATNPDFDVVARAAVQIKNAIDATIK<br>LGGQNYVFWGGREGYMSLLNTQMQREKDHLAKMLTAARDYARAKGFKGTFLVEPKPMEPT<br>KHQYDTDTETVIGFLRANGLEKDFKVNIEVNHATLAQHTFEHELAVAVDNGMLGSIDANR<br>GDAQNGWDTDQFPIDNYELTLAMLQIIRNGGLGNGGSNLDAKIRRNSTDLEDLFIAHISG<br>MDAMARALLNAAAIVEKSEIPAMLKQRYASSDAGMGKDFEEGKLTLEQLVDYAKANGEPA<br>TVSGKQEKYETLVALYAK |
| 5752MI1_003 | *Prevotella* | DNA | 157 | ATGACTAAAGAGTATTTCCCGGGAATCGGAAAGATTCCGTTTGAAGGAACCAAGAGCAAG<br>AACCCCCTGGCCTTCCATTATTATAACGCCTCCCAGGTAGCGATGGGCAAGCCCATGAAG<br>GACTGGCTCAAGTATGCCATGGCCTGGTGGCACACCCTGGGCCAGGCCTCTGCAGACCCC<br>TTTGGCGGCCAGACCCGCTCCTACGAATGGGACAAGGGCGAGTGCCCTTATTGCCGCGCC<br>AAGCAGAAGGCCGATGCCGGCTTTGAGCTCATGCAGAAGCTGGGCATCGAGTACTACTGC<br>TTCCACGACGTGGACATCATCGAGGACTGCGAGGACATTGCCGAGTACGAGGCCCGCATG<br>AAGGACATCACGGACTACCTGCTGGAGAAGCAGAAAGAGACCGGCATCAAGAACCTCTGG<br>GGCACCGCCAACGTGTTTGGCCACAAGCGCTACATGAACGGCGCCGCCACCAACCCTCAG<br>TTTGACATTGTGGCCCGTGCCGCCGTCCAGATCAAGAACGCCCTGGATGCCACCATCAAG<br>CTGGGTGGTACCAACTACGTGTTCTGGGGTGGCCGCGAAGGCTACTACACGCTGCTCAAC<br>ACCCAGATGCAGCGGGAGAAGAACCACCTGGCCAAGATGCTCACCGCCGCCCGCGACTAC<br>GCCCGCGCCAAGGGCTTCAAGGGCACCTTCCTCATTGAGCCCAAACCCATGGAGCCCACC<br>AAGCACCAGTACGACGTGGACACCGAGACCGTGATTGGTTTCATCCGCGCCAACGGCCTG<br>GACAAGGACTTCAAGGTAAACATTGAGGTAAACCACGCCACCCTGGCCGGCCACACCTTT<br>GAGCACGAGCTCACCGTGGCCCGCGAGAACGGCTTCCTGGGCTCCATCGACGCCAACCGC<br>GGAGATGCCCAGAACGGCTGGGATACGGACCAGTTCCCCATCGACGCCCTGGATCTCACC<br>CAGGCTATGATGCAGGTCATCCTCAACGGTGGCTTCGGCAATGGCGGCACCAACTTTGAC<br>GCCAAGCTCCGCCGCTCCTCCACCGATCCCGAGGACATCTTCATCGCCCACATCAGCGCC<br>ATGGATGCCATGGCACACGCCCTCCTGAACGCAGCCGCCATCCTGGAAGAGAGCCCCCTG<br>CCCGCCATGGTCAAGGAGCGTTACGCTTCCTTCGACAGCGGTCTGGGCAAGAAGTTCGAA<br>GAAGGCAAGGCCTCCCTGGAAGAACTTTACGAATATGCCAAGAAGAATGGAGAGCCCGTG<br>GCCGCTTCCGGCAAACAGGAGCTCTGCGAAACTTACTTGAACCTCTATGCAAAGTAG |
| 5752MI1_003 | *Prevotella* | Amino Acid | 158 | MTKEYFPGIGKIPFEGTKSKNPLAFHYYNASQVAMGKPMKDWLKYAMAWWHTLGQASADP<br>FGGQTRSYEWDKGECPYCRAKQKADAGFELMQKLGIEYYCFHDVDIIEDCEDIAEYEARM<br>KDITDYLLEKQKETGIKNLWGTANVFGHKRYMNGAATNPQFDIVARAAVQIKNALDATIK<br>LGGTNYVFWGGREGYYTLLNIQMQREKNHLAKMLTAARDYARAKGFKGTFLIEPKPMEPT<br>KHQYDVDTETVIGFIRANGLDKDFKVNIEVNHATLAGHTFEHELTVARENGFLGSIDANR<br>GDAQNGWDTDQFPIDALDLTQAMMQVILNGGFGNGGTNFDAKLRRSSTDPEDIFIAHISA<br>MDAMAHALLNAAAILEESPLPAMVKERYASFDSGLGKKFEEGKASLEELYEYAKKNGEPV<br>AASGKQELCETYLNLYAK |
| 5752MI2_003 | *Prevotella* | DNA | 159 | ATGACTAAAGAGTATTTCCCGGGAATCGGAAAGATTCCGTTTGAAGGAACCAAGAGCAAG<br>AACCCCCTGGCCTTCCATTATTATAACGCCTCCCAGGTAGTGATGGGCAAGCCCATGAAG<br>GACTGGCTCAAGTATGCCATGGCCTGGTGGCACACCCTGGGCCAGGCCTCTGCAGACCCC<br>TTTGGCGGCCAGACCCGCTCCTACGAATGGGACAAGGGCGAGTGCCCGTACTGCCGCGCC<br>AAGCAGAAGGCCGATGCCGGCTTTGAGCTCATGCAGAAGCTGGGCATCGAGTACTACTGC<br>TTCCACGACGTGGACATCATCGAGGACTGCGAGGACATTGCCGAGTACGAGGCCCGCATG<br>AAGGACATCACGGACTACCTGCTGGAGAAGCAGAAAGAGACCGGCATCAAGAACCTCTGG<br>GGCACCGCCAACGTGTTTGGCCACAAGCGCTACATGAACGGCGCCGCCACCAACCCTCAG<br>TTTGACATTGTGGCCCGTGCCGCCGTCCAGATCAAGAACGCCCTGGATGCCACCATCAAA<br>CTGGGTGGTACCAACTACGTGTTCTGGGGTGGCCGCGAAGGCTACTACACGCTGCTCAAC<br>ACCCAGATGCAGCGGGAGAAGAACCACCTGGCCAAGATGCTCACCGCCGCCCGCGACTAC<br>GCCCGCGCCAAGGGCTTCAAGGGCACCTTCCTCATTGAGCCCAAACCCATGGAGCCCACC<br>AAGCACCAGTACGACGTGGACACCGAGACCGTGATTGGTTTCATCCGCGCCAACGGCCTG<br>GACAAGGACTTCAAGGTAAACATTGAGGTAAACCACGCCACCCTGGCCGGCCACACCTTT<br>GAGCACGAGCTCACCGTGGCCCGCGAGAACGGCTTCCTGGGCTCCATCGACGCCAACCGC<br>GGAGATGCCCAGAACGGCTGGGATACGGACCAGTTCCCCATCGACGCCCTGGATCTCACC<br>CAGGCTATGATGCAGGTCATCCTCAACGGTGGCTTCGGCAATGGCGGCACCAACTTTGAC<br>GCCAAGCTCCGCCGCTCCTCCACCGATCCCGAGGACATCTTCATCGCCCACATCAGCGCC<br>ATGGATGCCATGGCACACGCCCTCCTGAACGCAGCCGCCATCCTGGAAGAGAGCCCCCTG<br>CCCGCCATGGTCAAGGAGCGTTACGCTTCCTTCGACAGCGGTCTGGGCAAGAAGTTCGAA<br>GAAGGCAAGGCCTCCCTGGAAGAACTTTACGAATATGCCAAGAAGAATGGAGAGCCCGTG<br>GCCGCTTCCGGCAAACAGGAGCTCTGCGAAACTTACTTGAACCTCTATGCAAAGTAG |
| 5752MI2_003 | *Prevotella* | Amino Acid | 160 | MTKEYFPGIGKIPFEGTKSKNPLAFHTYNASQVVNGKPMKDWLKYANAWWHTLGQASADP<br>EGGQTRSYEWDKGECPYCRAKQKADAGFELMQKLGIEYYCPHDVDIIEDCEDIAEYEARM<br>KDITDYLLEKQKETGIKNLWGTANVFGHKRYMNGAATNPQFDIVARAAVQIKNALDATIK<br>LGGTNYVFWGGREGYYTLLNIQMQREKNHLAKMLTAARDYARAKGFKGTFLIEPKPMEPT<br>KHQYDVDTETVIGFIRANGLDKDFKVNIEVNHATLAGHTFEHELTVARENGFLGSIDANR<br>GDAQNGWDTDQFPIDALDLTQAMMQVILNGGFGNGGTNFDAKLRRSSTDPEDIFTAHISA<br>MDAMAHALLNAAAILEESPLPAMVKERYASFDSGLGKKFEEGKASLEELYETAKKNGEPV<br>AASGKQELCETYLNLYAK |
| 5752MI3_002 | *Prevotella* | DNA | 161 | ATGGCAAAAGAGTATTTCCCGACTATCGGCAAGATTCCCTTCGAGGGCGTCGAATCCAAG<br>AACCCGATGGCATTCCACTACTATGACGCGAACCGCGTCGTGATGGGCAAGCCCATGAAG<br>GACTGGCTCAAGTTCGCGATGGCCTGGTGGCACACCCTGGGACAGGCTTCCGGCGACCCG |

TABLE 2-continued

| Clone No. | Class of organism | Type of Sequence | SEQ ID NO: | Sequence |
|---|---|---|---|---|
| | | | | TTCGGCGGCCAGACCCGTTCCTACGAGTGGGACAAGGGCGAGTGCCCCTACTGCCGCGCC<br>AAGGCCAAGGCCGACGCCGGCTTCGAGATCATGCAGAAGCTCGGTATCGAGTACTACTGC<br>TTCCATGACATCGACCTCGTGGAGGACACCGAGGACATCGCCGAGTACGAGGCCCGCATG<br>AAGGACATCACCGACTACCTCGTCGAGAAGCAGAAGGAAACCGGCATCAAGAACCTCTGG<br>GGCACGGCCAACGTGTTCGGCAACAAGCGCTACATGAACGGCGCCGCCACGAACCCGCAG<br>TTCGACGTCGTCGCCCGCGCCGCCGTCCAGATCAAGAACGCCATCGACGCCACCATCAAG<br>CTCGGCGGTACCGGTTACGTGTTCTGGGGCGGCCGTGAAGGCTACTACACCCTCCTGAAC<br>ACCCAGATGCAGCGCGAGAAGGACCACCTCGCCAAGATGCTCACCGCCGCCCGCGACTAC<br>GCCCGCGCCCACGGCTTCCAGGGCACCTTCCTCATCGAGCCCAAGCCCATGGAGCCCACC<br>AAGCACCAGTACGACGTGGACACGGAGACCGTGATCGGCTTCCTGCGCGCCAACGGTCTG<br>GACAAGGACTTCAAGGTCAATATCGAGGTGAACCACGCCACCCTCGCCGGCCACACCTTC<br>GAGCACGAGCTCACCGTGGCTGTCGATAACGGCTTCCTCGGCTCCATCGACGCCAACCGC<br>GGCGACGCCCAGAACGGCTGGGACACCGACCAGTTCCCCGTGGACCCGTACGACCTCACC<br>CAGGCCATGATGCAGATCATCCGCAACGGCGGTTTCAAGGACGGCGGCACCAACTTCGAC<br>GCCAAGCTCCGCCGCTCTTCCACCGACCCGGAGGACATCTTCATCGCCCACATCAGCGCG<br>ATGGACGCCATGGCCCACGCCCTGCTGAACGCCGCCGCCGTCATCGAGGAGAGCCCGCTC<br>TGCAAGATGGTCGAGGAGCGCTACGCTTCCTTCGACAGCGGCCTCGGCAAGCAGTTCGAG<br>GAAGGCAAGGCCACCCTCGAGGACCTCTACGAGTATGCCAAGAAGAATGGCGAGCCCGTC<br>GTCGCCTCCGGCAAGCAGGAGCTCTACGAGACGCTGCTGAACCTTTACGCGAAGTAG |
| 5752MI3_ 002 | *Prevotella* | Amino Acid | 162 | MAKEYFPTIGKIPFEGVESKNPMAFHYYDANRVVMGKPMKDWLKFAMAWWHTLGQASGDP<br>FGGQTRSYEWDKGECPYCRAKAKADAGFEIMQKLGIEYYCFHDIDLVEDTEDIAEYEARM<br>KDITDYLVEKQKETGIKNLWGTANVFGNKRYMNGAATNPQFDVVARAAVQIKNAIDATIK<br>LGGTGYVFWGGREGYYTLLNIQMQREKEHLAKMLTAARDYARAHGFQGTFLIEPKPMEPT<br>KHQYEVETETVIGFLRANGLDKDEKVNIEVNHATLAGHTFEHELTVAVDNGFLGSIDANR<br>GDAQNGWDTDQFPVDPYDLTQAMMQIIRNGGFKDGGTNFDAKLRRSSTDPEDIFIAHISA<br>MDAMAHALLNAAAVIEESPLCKMVEERYASFDSGLGKQFEEGKATLEELYETAKKNGEPV<br>VASGKQELYETLLNLYAK |
| 5752MI5_ 003 | *Prevotella* | DNA | 163 | ATGGCAAAAGAGTATTTCCCGACAATCGGTAAGATCCCCTTCGAGGGACCCGAGTCCAAG<br>AACCCGATGGCATTCCACTACTATGACGCGGAGCGCGTGGTGATGGGCAAGAAGATGAAG<br>GACTGGTTCAAGTTCGCGATGGCCTGGTGGCACACCCTGGGCCAGGCTTCCGCCGACCCG<br>TTCGGCGGCCAGACCCGCTCCTACGAGTGGGACAAGGGCGAAGGCCCCTGCTCCCGCGCC<br>CGCGCCAAGGCTGACGCCGGTTTCGAGATCATGCAGAAACTGGGCATCGGCTACTACTGC<br>TTCCACGACATCGACCTGGTGGAGGACACCGAGGACATCGCCGAGTATGAAGCCCGCATG<br>AAGGACATCACCGACTACCTCGTGGAGAAGCAGAAGGAGACCGGCATCAAGAACCTCTGG<br>GGCACGGCCAACGTATTCGGCAACAAGCCCTACATGAACGGCGCCGCCACGAACCCGCAG<br>TTCGACATCGCCGCCCGCGCGGCCCTGCAGACCAAGAACGCCATCGATGCCACCATCAAG<br>CTGGGCGGCACCGGTTACGTGTTCTGGGGCGGCCGTGAAGGCTACTACACCCTCCTGAAC<br>ACCCAGATGCAGCGCGAGAAGGACCACCTTGCCAAGATGCTCACCGCGGCTCGCGACTAT<br>GCCCGCGCCCACGGCTTCAAGGGCACCTTCTTCATCGAGCCGAAACCGATGGAGCCCACC<br>AAGCACCAGTACGACGTGGACACGGAGACCGTGATCGGCTTCCTCCGCGCCAACGGCCTG<br>GACAAGGACTTCAAGGTGAACATCGAAGTGAACCACGCCACCCTCGCCGGCCACACCTTC<br>GAGCACGGGCTCACCGTGGCCGTTGACAACGGCTTCCTCGGCAGCATCGACGCCAACCGC<br>GGAGACGCCCAGAACGGCTGGGATACCGACCAGTTCCCGGTGGATCCGTACGACCTCACC<br>CAGGCGATGATCCAGATCATCCGCAATGGCGGCTTCAAGGACGGCGGTACCAACTTCGAC<br>GCCAAGCTCCGCCGCTCTTCCACCGACCCGGAGGACATCTTCATCGCCCACATCAGCGCG<br>ATGGACGCCATGGCCCACGCCCTGCTGAACGCCGCCGCCGTGCTCGAGGAGAGCCCGCTC<br>TGCGAGATGGTTGCAAAGCGTTACGCTTCCTTCGACAGCGGTCTCGGCAAGAAGTTCGAG<br>GAAGGCAACGCCACCCTCGAGGAACTCTACGAGTACGCCAAGGCGAAGGGCGAGGTCGTT<br>GCCGAATCCGGCAAGCAGGAACTCTACGAGACCCTGCTGAACCTCTACGCGAAGTAG |
| 5752MI5_ 003 | *Prevotella* | Amino Acid | 164 | MAKEYFPTIGKIPFEGPESKNPMAFHYYDAERVVMGKKMKDWFKFAMAWWHTLGQASADP<br>FGGQTRSYEWDKGEGPCSRARAKADAGFEIMQKLGIGYYCFHDIDLVEDTEDIAEYEARM<br>KDITDYLVEKQKETGIKNLWGTANVFGNKPYMNGAATNPQFDIAARAALQTKNAIDATIK<br>LGGTGYVFWGGREGYYTLLNIQMQREKDHLAKMLTAARDYARAHGFKGTFFIEPKPMEPT<br>KHQYDVDTETVIGFLRANGLDKDFKVNIEVNHATLAGHTFEHGLTVAVDNGFLGSIDANR<br>GDAQNGWDTDQFPVDPYDLTQAMIQIIRNGGFKDGGTNFDAKLRRSSTDPEDIFIAHISA<br>MDAMAHALLNAAAVLEESPLCEMVAKRYASFDSGLGKKFEEGNATLEELYEYAKAKGEVV<br>AESGKQELYETLLNLYAK |
| 5752MI6_ 004 | *Prevotella* | DNA | 165 | ATGGCAAAAGAGTATTTCCCGACAATCGGAAAGATCCCCTTCGAGGGCGCTGAGAGCAAG<br>AATCCCCTTGCTTTCCACTATTATGACGCCGAGCGTGTGGTCATGGGCAAGCCCATGAAG<br>GACTGGTTCAAGTTCGCGATGGCCTGGTGGCACACCCTGGGCCAGGCTTCCGCCGACCCG<br>TTCGGCGGCCAGACCCGCTCCTACGAGTGGGACAAGGGCGAGTGCCCCTACTGCCGCGCC<br>CGCCAGAAGGCTGACGCCGGTTTCGAGATCATGCAGAAGCTCGGCATCGGCTACTACTGC<br>TTCCACGACATCGACCTGGTCGAGGACACCGAGGACATCGCCGAGTACGAGGCCCGCATG<br>AAGGACATCACCGACTACCTCGTCGAGAAGCAGAAGGAGACCGGCATCAAGAACCTCTGG<br>GGCACGGCCAACGTGTTCGGCAACAAGCGCTACATGAACGGCGCCGCCACGAACCCGCAG<br>TTCGACATCGTCGCCCACGCGGCCCTGCAGATCAAGAACGCGATCGGCGCCACCATCAAG<br>CTCGGCGGCACCGGTTACGTGTTCTGGGGCGGCCGTGAAGGTTACTACACCCTCCTGAAC<br>ACCCAGATGCAGCGCGAGAAGGACCACCTCGCCAAGATGCTCACCGCCGCCCGCGACTAC<br>GCCCGCGCCAACGGCTTCAAGGGCACCTTCCTCATCGAGCCGAAGCCGATGGAGCCCACC<br>AAGCACCAGTATGACGTGGACACGGAGACCGTGATCGGCTTCCTCCGCGCCAACGGCCTG<br>GACAAGGACTTCAAGGTGAACATCGAGGTGAACCACGCCACCCTCGCCGGCCACACCTTC<br>GAGCACGAGCTCACCGTGGCGGTCGACAACGGCTTCCTCGGCAGCATCGACGCCAACCGC |

TABLE 2-continued

| Clone No. | Class of organism | Type of Sequence | SEQ ID NO: | Sequence |
|---|---|---|---|---|
| | | | | GGTGACGCCCAGAACGGCTGGGATACCGACCAGTTCCCGGTGGATCCGTACGATCTCACC<br>CAGGCGATGATCCAGATCATCCGCAACGGCGGCTTCAAGGATGGCGGCACCAACTTCGAC<br>GCCAAGCTCCGCCGCTCTTCCACCGACCCGGAGGACATCTTCATCGCCCACATCAGCGCG<br>ATGGACGCCATGGCCCACGCCCTGCTGAACGCCGCCGCCGTCATCGAGGAGAGCCCGCTC<br>TGCGAGATGGTCGCCAAGCGCTACGCTTCCTTCGACAGCGGTCTCGGCAAGAAGTTCGAG<br>GAAGGCAACGCCACCCTCGAGGAACTCTACGAGTACGCCAAGGCGAACGGTGAGGTCAAG<br>GCCGAATCCGGCAAGCAGGAGCTCTACGAGACCCTTCTGAACCTCTACGCGAAATAG |
| 5752MI6_<br>004 | *Prevotella* | Amino<br>Acid | 166 | MAKEYFPTIGKIPFEGAESKNPLAFHYYDAERVVMGKPMKDWFKFAMAWWHTLGQASADP<br>FGGQTRSYEWDKGECPYCRARQKADAGFEIMQKLGIGYYCFHDIDLVEDTEDIAEYEARM<br>KDITDYLVEKQKETGIKNLWGTANVFGNKRYMNGAATNPQFDIVAHAALQIKNAIGATIK<br>LGGTGYVFWGGREGYYTLLNTQMQREKDHLAKMLTAARDYARANGFKGTFLIEPKPMEPT<br>KHQYDVDTETVIGFLRANGLDKDFKVNIEVNHATLAGHTFEHELTVAVDNGFLGSIDANR<br>GDAQNGWDTDQFPVDPYDLTQAMIQIIRNGGFKDGGTNFDAKLRRSSTDPEDIFIAHISA<br>MDAMAHALLNAAAVIEESPLCEMVAKRYASFDSGLGKKFEEGNATLEELYEYAKANGEVK<br>AESGKQELYETLLNLYAK |
| 5753MI1_<br>002 | *Prevotella* | DNA | 167 | ATGGCAAAAGAGTATTTCCCCACTATCGGGAAGATTCCTTTCGAAGGAGTCGAGAGCAAG<br>AACCCCCTTGCATTCCATTATTATGACGCAAACCGCATGGTCATGGGCAAGCCCATGAAG<br>GACTGGTTCAAGTTCGCCATGGCATGGTGGCACACCCTGGGACAGGCCTCCGCAGACCCG<br>TTCGGCGGCCAGACCCGCTCCTACGAATGGGACAAGGGCGAATGCCCCTACTGCCGCGCC<br>AGGGCAAAGGCCGATGCCGGCTTCGAGATCATGCAGAAACTGGGTATCGAGTATTTCTGC<br>TTCCATGACATCGACCTGGTAGAGGACTGCGACGACATCGCCGAGTACGAGGCCCGCATG<br>AAGGACATCACGGACTATCTCCTGGAGAAGATGAAGGAAACCGGCATCAAGAACCTCTGG<br>GGCACCGCCAACGTGTTCGGCAACAAGCGTTACATGAACGGCGCCGGCACCAATCCGCAG<br>TTCGACGTAGTGGCCCGCGCTGCCGTCCAGATCAAGAACGCCATCGACGCCACCATCAAG<br>CTCGGCGGTTCCAACTATGTGTTCTGGGGCGGCCGTGAAGGATACTACACCCTGCTGAAC<br>ACCCAGATGCAGCGCGAGAAGGACCACCTCGGCAAACTGCTCACCGCCGCCCGCGACTAT<br>GCCCGCAAGAACGGCTTCAAGGGCACCTTCCTCATCGAGCCCAAGCCGATGGAGCCCACC<br>AAGCACCAGTACGACGTAGACACGGAGACCGTGATCGGCTTCCTCCGCGCCAACGGCCTG<br>GAGAAAGACTTCAAGGTGAACATCGAGGTGAACCACGCCACCCTGGCCGGCCATACCTTC<br>GAGCATGAACTCACCGTGGCCTTGGACAACGGCTTCCTGGGATCCATCGACGCCAACCGC<br>GGCGACGCCCAGAACGGCTGGGATACGGACCAGTTCCCGGTAGACCCGTACGACCTCACC<br>CAGGCCATGATGCAGATCATCCGCAACGGCGGCCTCGGCAACGGCGGTACCAACTTCGAC<br>GCCAAACTGCGCCGTTCCTCCACCGATCCTGAGGACATCTTCATCGCCCACATCAGCGCC<br>ATGGACGCCATGGCCCACGCCCTGCTCAACGCAGCCGCCGTGCTGGAAGAAAGTCCGCTC<br>TGTGAGATGGTCAAGGAGCGCTACGCTTCCTTCGACAGCGGTCTCGGCAAGAAGTTCGAA<br>GAGGGCAAGGCTACCCTGGAAGAAATCTACGAGTATGCCAAGAAGAGCGGCGAACCCGTG<br>GTCGCTTCCGGCAAGCAGGAGCTCTACGAAACCCTGCTGAACCTCTACGCCAAGTAG |
| 5753MI1_<br>002 | *Prevotella* | Amino<br>Acid | 168 | MAKEYFPTIGKIPFEGVESKNPLAFHYYDANRMVMGKPMKDWFKFAMAWWHTLGQASADP<br>FGGQTRSYEWDKGECPYCRARAKADAGFEIMQKLGIEYFCPHDIDLVEDCDDIAEYEARM<br>KDITDYLLEKMKETGIKNLWGTANVFGNKRYMNGAGTNPQFDVVARAAVQIKNATDATIK<br>LGGSNYVFWGGREGYYTLLNTQMQREKDHLGKLLTAARDYARKNGFKGTFLIEPKPMEPT<br>KHQYEVETETVIGFLRANGLEKDEKVNIEVNHATLAGHTFEHELTVAVDNGFLGSIDANR<br>GDAQNGWDTDQFPVDPYDLTQAMMQIIRNGGLGNGGTNFDAKLRRSSTDPEDIFTAHISA<br>MDAMAHALLNAAAVLEESPLCEMVKERYASFDSGLGKKFEEGKATLEEIYEYAKKSGEPV<br>VASGKQELYETLLNLYAK |
| 5753MI2_<br>002 | *Prevotella* | DNA | 169 | ATGGCTAAAGAATACTTCCCCTCCATCGGCAAAATCCCTTTTGAAGGAGGCGACAGCAAA<br>AATCCCCTCGCTTTCCATTATTATGACGCCGGACGCGTGGTTATGGGCAAGCCCATGAAG<br>GAATGGCTTAAATTCGCCATGGCCTGGTGGCACACGCTGGGCCAGGCCTCCGGAGACCCC<br>TTCGGCGGCCAGACCCGCAGCTACGAATGGGACAAGGGCGAATGCCCCTACTGCCGCGCC<br>AAAGCCAAGGCCGACGCCGGTTTTGAAATCATGCAAAAGCTGGGTATCGAATACTTCTGC<br>TTCCACGATGTGGACCTTATCGAGGATTGCGATGACATTGCCGAATACGAAGCCCGCATG<br>AAGGACATCACGGACTACCTGCTGGAAAAGATGAAGGAGACCGGCATCAAGAACCTCTGG<br>GGCACCGCCAATGTCTTCGGCCACAAGCGCTACATGAACGGCGCCGCCACGAACCCGCAG<br>TTCGACGTGGTCGCCCGCGCCGCCGTCCAGATCAAGAACGCGATTGACGCCACCATCAAG<br>CTCGGCGGTACCAGTTATGTATTCTGGGGCGGCCGCGAGGGCTACTACACCCTCCTGAAC<br>ACCCAGATGCAGCGTGAGAAAGACCACCTGGCCAAGATGCTCACCGCAGCCCGCGACTAC<br>GCCCGCGCCAAGGGCTTCAAGGGCACCTTCCTCATCGAGCCCAAGCCGATGGAGCCCACC<br>AAGCACCAGTACGACGTTGACACGGAGACCGTGATCGGCTCCCTGCGCGCCAACGGCCTG<br>GACAAGGACTTCAAGGTGAACATCGAGGTGAACCACGCCACCCTGGCCGGCCACACCTTC<br>GAGCACGAACTCACCGTGGCTGTTGACAACGGCTTCCTGGGCTCCATCGACGCCAACCGC<br>GGCGACGCCCAGAACGGCTGGGATACGGACCAGTTCCCGGTAGACCCGTACGACCTCACC<br>CAGGCCATGATGCAGATTATCCGCAACGGCGGCTTCAAGGACGGCGGCACCAACTTCGAT<br>GCCAAACTGCGCCGCTCTTCCACCGATCCGGAAGACATCTTCATCGCCCACATCAGCGCT<br>ATGGATGCCATGGCACACGCCCTGCTCAACGCCGCCGCCGTGCTGGAAGAGAGCCCGCTG<br>TGCAACATGGTCAAGGAGCGTTACGCCGGCTTCGACAGCGGCCTTGGCAAGAAGTTCGAG<br>GAAGGGAAGGCAACGCTGGAGGAAATCTATGACTATGCCAAGAAGAGCGGCGAACCCGTC<br>GTGGCTTCCGGCAAGCAGGAACTCTACGAAACCATCCTGAACCTCTATGCCAAGTAG |
| 5753MI2_<br>002 | *Prevotella* | Amino<br>Acid | 170 | MAKEYFPSIGKIPFEGGDSKNPLAFHYYDAGRVVMGKPMKEWLKFAMAWWHTLGQASGDP<br>FGGQTRSYEWDKGECPYCRAKAKADAGFEIMQKLGIEYFCFHDVDLIEDCDDIAEYEARM<br>KDITDYLLEKMKETGIKNLWGTANVFGHKRYMNGAATNPQFDVVARAAVQIKNAIDATIK<br>LGGTSYVFWGGREGYYTLLNIQMQREKDHLAKMLTAARDYARAKGFKGTFLIEPKPMEPT |

TABLE 2-continued

| Clone No. | Class of organism | Type of Sequence | SEQ ID NO: | Sequence |
|---|---|---|---|---|
| | | | | KHQYDVDTETVIGSLRANGLDKDFKVNIEVNHATLAGHTFEHELTVAVDNGFLGSIDANR<br>GDAQNGWDTDQFPVDPYDLTQAMMQIIRNGGFKDGGTNFDAKLRRSSTDPEDIFIAHISA<br>MDAMAHALLNAAAVLEESPLCNMVKERYAGFDSGLGKKFEEGKATLEEIYDYAKKSGEPV<br>VASGKQELYETILNLYAK |
| 5753MI4_<br>002 | *Prevotella* | DNA | 171 | ATGTCAAAAGAGTATTTCCCTACAATCGGCAGGGTCCCCTTCGAGGGACCTGAGAGCAAG<br>AATCCGCTGGCGTTCCACTATTACGAGCCGGACCGGCTCGTCCTGGGCAGGAAAATGAAG<br>GACTGGCTGCGCTTCGCAATGGCCTGGTGGCATACGCTCGGGCAGGCTTCCGGCGACCAG<br>TTCGGCGGACAGACCTGCACATACGCCTGGGATGAAGGCGAGTGTCCCGTCTGCCGGGCA<br>AAGGCCAAGGCTGACGCCGGCTTTGAACTGATGCAGAAACTGGGCATCGGGTATTTCTGC<br>TTCCACGACGTGGACCTGGTCGAGGAGGCCGACACCATTGAAGAATACGAGGAGCGGATG<br>CGGATCATCACCGACTACCTGCTCGAGAAGATGGAAGAGACCGGCATCCGCAATCTCTGG<br>GGAACCGCCAATGTCTTCGGACACAAGCGCTATATGAACGGCGCCGCCACCAATCCCGAC<br>TTCGACGTCGTGGCCCGTGCCGCGGTCCAGATCAAGAATGCCATCGATGCCACCATCAAA<br>CTGGGTGGTGAGAACTATGTGTTCTGGGGTGGCCGCGAGGGCTATACGAGCCTGCTCAAC<br>ACGCAGATGCACCGGGAAAAACACCACCTCGGAAATATGCTCAGGGCAGCCCGCGACTAT<br>GGCCGTGCCCACGGTTTCAAGGGAACGTTCCTGATCGAGCCCAAGCCGATGGAGCCGACC<br>AAGCATCAGTACGACCAGGATACGGAGACGGTCATCGGTTTCCTGCGCTGTCACGGCCTG<br>GACAAGGATTTCAAGGTGAACATCGAGGTGAACCACGCCACGCTCGCCGGACACACCTTC<br>GAGCACGAACTGGCCACTGCGGTCGATGCCGGCCTGCTGGGCAGCATCGATGCCAACCGC<br>GGCGACGCCCAGAACGGCTGGGATACCGACCAGTTCCCGATCGACAACTACGAACTCACG<br>CTGGCGATGCTGCAGATCATCCGCAATGGCGGACTCGCACCCGGCGGATCGAACTTCGAT<br>GCCAAGTTGCGCCGCAATTCCACCGATCCGGAAGACATCTTCATCGCCCACATCAGCGCG<br>ATGGACGCGATGGCCCGTGCCCTGCTCAATGCGGCGGCCATCTGGACCGAATCGCCGATT<br>CAGGATATGGTCAGGGACCGCTATGCTTCCTTCGACAGCGGAAAGGGCAGGGAGTTCGAG<br>GAAGGCAGACTCAGTCTGGAAGACCTCGTGGCCTATGCGAAGGAGCACGGTGAGCCGCGC<br>CAGATCTCCGGCAGGCAGGAACTTTATGAAACCATCGTAGCGCTTTACTGCAGGTAA |
| 5753MI4_<br>002 | *Prevotella* | Amino Acid | 172 | MSKEYFPTIGRVPFEGPESKNPLAFHYYEPDRLVLGRKMKEWLRFAMAWWHTLGQASGDQ<br>FGGQTCTYAWDEGECPVCRAKAKADAGFELMQKLGIGYFCFHDVDLVEEADTIEEYEERM<br>RIITDYLLEKMEETGIRNLWGTANVEGHKRYMNGAATNPDFDVVARAAVQIKNAIDATIK<br>LGGENYVFWGGREGYTSLLNTQMHREKHHLGNMLRAARDYGRAHGFKGTFLIEPKPMEPT<br>KHQYDQDTETVIGFLRCHGLDKDFKVNIEVNHATLAGHTFEHELATAVDAGLLGSIDANR<br>GDAQNGWDTDQFPIDNYELTLAMLQIIRNGGLAPGGSNEDAKLRRNSTDPEDTFIANISA<br>MDAMARALLNAAAIWTESPIQDMVRDRYASFDSGKGREFEEGRLSLEDLVAYAKEHGEPR<br>QISGRQELYETIVALYCR |
| 5752MI4_<br>004 | *Prevotella* | DNA | 173 | ATGACTAAAGAGTATTTCCCGGGAATCGGAACGATTCCGTTTGAAGGAACCAAGAGCAAG<br>AACCCCCTGGCCTTCCATTATTATAACGCCTCCCAGGTAGTGATGGGCAAGCCCATGAAG<br>GACTGGCTCAAGTATGCCATGGCCTGGTGGCACACCCTGGGCCAGGCCTCTGCAGACCCC<br>TTTGGCGGCCAGACCCGCTCCTACGAATGGGACAAGGGCGAGTGCCCGTACTGCCGCGCC<br>AAGCAGAAGGCCGATGCCGGCTTTGAGCTCATGCAGAAGCTGGGCATCGAGTACTACTGC<br>TTCCACGACGTGGACATCATCGAGGACTGCGAGGACATTGCCGAGTACGAGGCCCGCATG<br>AAGGACATCACGGACTACCTGCTGGAGAAGCAGAAAGAGACCGGCATCAAGAACCTCTGG<br>GGCACCGCCAACGTGTTTGGCCACAAGCGCTACATGAACGGCGCCGCCACCAACCCTCAG<br>TTTGACATTGTGGCCCGTGCCGCCGTCCAGATCAAGAACGCCCTGGATGCCGCCATCAAA<br>CTGGGTGGTACCAACTACGTGTTCTGGGGTGGCCGCGAAGGCTACTACACGCTGCTCAAC<br>ACCCAGATGCAGCGGGAGAAGAACCACCTGGCCAAGATGCTCACCGCCGCCCGCGACTAC<br>GCCCGCGCCAAGGGCTTCAAGGGCACCTTCCTCATTGAGCCCAAACCCATGGAGCCCACC<br>AAGCACCAGTACGACGTGGACACCGAGACCGTGATTGGTTTCATCCGCGCCAACGGCCTG<br>GACAAGGACTTCAAGGTAAACATTGAGGTAAACCACGCCACCCTGGCCGGCCACACCTTT<br>GAGCACGAGCTCACCGTGGCCCGCGAGAACGGCTTCCTGGGCTCCATCGACGCCAACCGC<br>GGAGATGCCCAGAACGGCTGGGATACGGACCAGTTCCCCATCGACGCCCTGGATCTCACC<br>CAGGCTATGATGCAGGTCATCCTCAACGGTGGCTTCGGCAATGGCGGCACCAACTTTGAC<br>GCCAAGCTCCGCCGCTCCTCCACCGATCCCGAGGACATCTTCATCGCCCACATCAGCGCC<br>ATGGATGCCATGGCACACGCCCTCCTGAACGCAGCCGCCATCCTGGAAGAGAGCCCCCTG<br>CCCGCCATGGTCAAGGAGCGTTACGCTTCCTTCGACAGCGGTCTGGGCAAGAAGTTCGAA<br>GAAGGCAAGGCCTCCCTGGAAGAACTTTACGAATATGCCAAGAAGAATGGAGAGCCCGTG<br>GCCGCTTCCGGCAAACAGGAGCTCTGCGAAACTTACTTGAACCTCTATGCAAAGTAG |
| 5752MI4_<br>004 | *Prevotella* | Amino Acid | 174 | MTKEYFPGIGTIPFEGTKSKNPLAFHYYNASQVVMGKPMKDWLKYAMAWWHTLGQASADP<br>FGGQTRSYEWDKGECPYCRAKQKADAGFELMQKLGIEYYCFHDVDIIEDCEDIAEYEARM<br>KDITDYLLEKQKETGIKNLWGTANVEGHKRYMNGAATNPQFDIVARAAVQIKNALDAAIK<br>LGGTNYVFWGGREGYYTLLNTQMQREKNHLAKMLTAARDYARAKGFKGTFLIEPKPMEPT<br>KHQYDVDTETVIGFIRANGLEKDEKVNIEVNHATLAGHTFEHELTVARENGFLGSIDANR<br>GDAQNGWDTDQFPIDALDLTQAMMQVILNGGEGNGGTNEDAKLRRSSTDPEDIFIAHISA<br>MDAMAHALLNAAATLEESPLPAMVKERYASFDSGLGKKFEEGKASLEELYEYAKKNGEPV<br>AASGKQELCETYLNLYAK |
| 727MI4_<br>006 | *Rhizobiales* | DNA | 175 | GTGACTGATTTCTTCAAGGGCATCGCGCCCGTCAAGTTTGAGGGGCCGCAGAGCTCCAAT<br>CCGCTGGCCTATCGCCACTATAACAAGGACGAAATCGTCCTCGGCAAGCGGATGGAAGAC<br>CATATCCGTCCCGGCGTTGCCTATTGGCACACCTTCGCCTATGAGGGCGGCGATCCGTTT<br>GGCGGCCGCACCTTCGATCGCCCCTGGTTCGACAAGGGTATGGACGGCGCCCGCCTCAAG<br>GCCGACGTGGCCTTCGAACTGTTCGACCTGCTCGACGTTCCTTTCTTCTGTTTCCACGAT<br>GCTGATATCGCTCCCGAAGGCGCAACGCTGGCCGAGAGCAACCGCAATGTGCGCGAGATT<br>GGCGAGATCTTCGCTCGCAAGATGGAAACCAGCCGCACCAAGCTGCTCTGGGGTACGGCA |

TABLE 2-continued

| Clone No. | Class of organism | Type of Sequence | SEQ ID NO: | Sequence |
|---|---|---|---|---|
| | | | | AACCTGTTCTCCAATCGCCGCTACATGGCCGGCGCCGCCACCAACCCGGACCCGGAAATC TTCGCCTATGCCGCTGGGCAGGTGAAGAACGTGCTGGAACTGACCCACGAACTGGGCGGC GCCAACTATGTGCTGTGGGGCGGTCGCGAGGGTTATGAAACCCTGCTCAACACCAAGATC GGCCAGGAAATGGACCAGATGGGCCGTTTTCTGTCGATGGTCGTCGAGCATGCCGAAAAG ATCGGCTTCAAGGGCCAGATCCTGATCGAGCCCAAGCCGCAGGAGCCGAGCAAGCACCAG TATGACTTCGACGTTGCAACCGTTTACGGCTTCCTCAAGAAGTATGGTCTCGAAACCAAG GTGAAGTGCAATATCGAGGTCGGCCATGCCTTCCTCGCCAATCACTCCTTCGAGCATGAA CTGGCTTTGGCCGCATCGCTGGGCATTCTCGGCTCGGTCGACGCCAATCGCAACGATCTA CAGTCCGGCTGGGATACCGACCAGTTCCCCAATAATGTCCCCGAAACCGCACTCGCCTTC TATCAGATTCTCAAGGCGGGCGGACTGGGCAATGGCGGCTGGAACTTCGACGCCCGCGTG CGCCGCCAGTCACTTGATCCGGCCGACCTGCTGCACGGCCATATCGGCGGCCTCGACGTG CTGGCGCGCGGCCTCAAGGCCGCCGCGGCGCTGATCGAGGACGGCACCTATGACAAGGTC GTCGACGCCCGCTATGCCGGCTGGAACCAGGGCCTGGGCAAGGATATCCTTGGTGGCAAG CTGAACCTTGCCGACCTGGCTGCCAAGGTCGACGCCGAAAACCTCAACCCGCAGCCTAGG TCCGGCCAGCAGGAATATCTCGAAAACCTGATCAACCGGTTCGTTTAG |
| 727MI4_ 006 | *Rhizobiales* | Amino Acid | 176 | MTDFFKGIAPVKFEGPQSSNPLAYRHYNKDEIVLGKRMEDHIRPGVAYWHTFAYEGGDPF GGRTFDRPWFDKGMDGARLKADVAFELFDLLDVPFFCFHDADIAPEGATLAESNRNVREI GEIFARKMETSRTKLLWGTANLFSNRRYMAGAATNPDPEIFAYAAGQVKNVLELTHELGG ANYVLWGGREGYETLLNTKIGQEMPQMGRFLSMVVEHAEKIGFKGQILIEPKPQEPSKHQ YDFDVATVYGFLKKYGLETKVKCNIEVGHAFLANHSFEHELALAASLGILGSVDANRNDL QSGWDTDQFPNNVPETALAFYQILKAGGLGNGGWNFDARVRRQSLDPADLLHGHIGGLDV LARGLKAAAALIEDGTYDKVVDARYAGWNQGLGKDILGGKLNLADLAAKVDAENLNPQPR SGQQEYLENLINRFV |

5.5 Example 4: Quantification of XI Enzyme Activity

Figure 3:
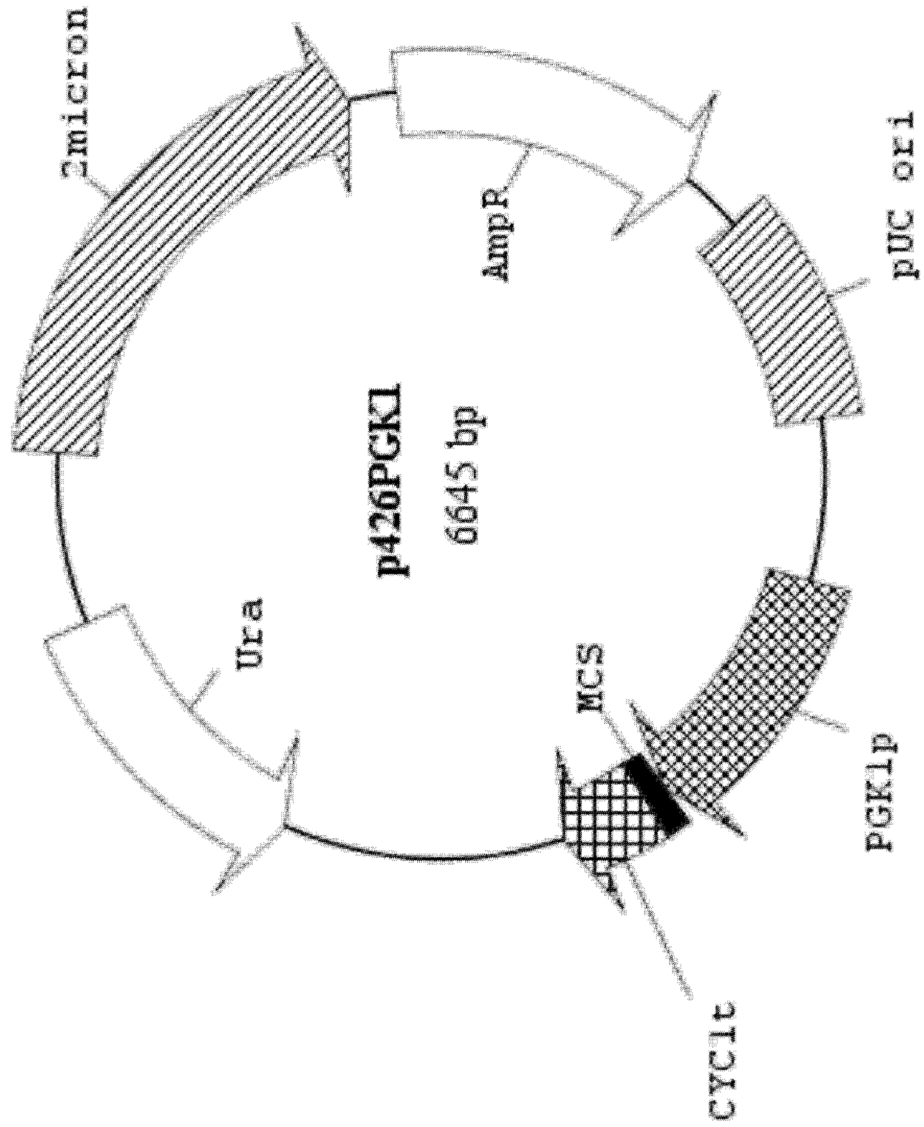
FIG. 3 is a map of the vector p426PGK1 for expressing XI in yeast strain, *Saccharomyces cerevisiae* CEN.PK2-1Ca (ATCC: MYA1108).

The clones identified in the ABD and SBD screens (see Table 2) were subcloned into vector p426PGK1 (FIG. 3), a modified version of p426GPD (ATCC accession number 87361) in which the GPD promoter was replaced with the PGK1 promoter from *Saccharomyces cerevisiae* (ATCC accession number 204501) gDNA. The clones were then transformed into yeast strain MYA11008.

Cells were grown as described in the materials and methods. Cell pellets were resuspended in about 300 μl of lysis buffer: approximate concentrations (50 mM $NaH_2PO_4$ (pH 8.0), 300 mM NaCl, 10 mM imidazole (Sigma, #I5513), to which was added about 2 μl/ml beta-mercaptoethanol (BME)), and protease inhibitor cocktail tablet (Roche, 11836170001) (1 tablet for about 10 ml cell extract). The cell suspension was added to a 2 ml screw-cap microcentrifuge tube that had been pre-aliquotted with about 0.5 ml of acid washed glass beads (425-600 μm). Cells were lysed using a FastPrep-24 (MP Biomedicals, Solon, Ohio) at amplitude setting of about 6 for about 3 repetitions of about 1 minute. Cells were chilled on ice for about 5 minutes between repetitions. Samples were centrifuged at about 10,000×g for about 10 minutes at 4° C. Recovered supernatants were used in the XI enzyme activity assay. XI enzyme activity was performed as described in the materials and methods. Results are shown in Table 3.

TABLE 3

| XI activity at pH 7.5 | | |
|---|---|---|
| SEQ ID NO: | Volumetric Activity | FIOPC |
| 2 | −60.73 | 2.58 |
| 4 | −21.84 | 0.93 |
| 6 | 0.86 | −0.05 |
| 8 | −2.14 | 0.12 |
| 10 | −2.38 | 0.13 |
| 12 | −12.82 | 0.54 |
| 14 | −26.97 | 1.45 |
| 16 | −76.50 | 4.12 |
| 18 | −15.32 | 0.83 |

TABLE 3-continued

| XI activity at pH 7.5 | | |
|---|---|---|
| SEQ ID NO: | Volumetric Activity | FIOPC |
| 20 | −5.33 | 0.29 |
| 22 | 0.48 | −0.03 |
| 24 | 0.36 | −0.02 |
| 26 | 0.81 | −0.04 |
| 28 | −6.65 | 0.36 |
| 30 | −9.10 | 0.49 |
| 32 | −38.10 | 2.05 |
| 34 | −21.76 | 1.17 |
| 36 | −13.82 | 0.59 |
| 38 | −17.58 | 0.75 |
| 40 | −12.34 | 0.52 |
| 42 | −74.88 | 3.18 |
| 44 | −37.10 | 1.57 |
| 46 | −35.57 | 1.51 |
| 48 | −24.69 | 1.05 |
| 50 | −32.23 | 1.37 |
| 52 | −26.72 | 1.13 |
| 54 | −90.79 | 3.85 |
| 56 | −39.89 | 1.69 |
| 58 | −74.26 | 3.15 |
| 60 | −11.91 | 0.64 |
| 62 | −15.43 | 0.83 |
| 64 | −12.98 | 0.70 |
| 66 | −27.45 | 1.48 |
| 68 | −29.43 | 1.59 |
| 70 | −4.54 | 0.24 |
| 72 | −8.93 | 0.48 |
| 74 | −0.20 | 0.01 |
| 76 | −0.33 | 0.02 |
| 78 | −50.55 | 2.15 |
| 80 | −57.13 | 2.42 |
| 82 | −58.09 | 2.47 |
| 84 | −46.42 | 1.97 |
| 86 | −35.95 | 1.53 |
| 88 | −2.16 | 0.09 |
| 90 | −32.77 | 1.39 |
| 92 | −30.82 | 1.31 |
| 94 | −8.16 | 0.35 |
| 96 | −46.18 | 1.96 |
| 98 | −30.05 | 1.28 |
| 100 | −8.40 | 0.45 |
| 102 | −8.34 | 0.45 |

TABLE 3-continued

| XI activity at pH 7.5 | | |
|---|---|---|
| SEQ ID NO: | Volumetric Activity | FIOPC |
| 104 | −3.80 | 0.20 |
| 106 | −4.81 | 0.26 |
| 108 | −12.06 | 0.65 |
| 110 | −6.10 | 0.33 |
| 112 | −7.71 | 0.42 |
| 114 | −4.17 | 0.22 |
| 116 | −7.07 | 0.38 |
| 118 | −13.50 | 0.73 |
| 120 | −1.15 | 0.06 |
| 122 | 0.03 | 0.00 |
| 124 | −4.41 | 0.24 |
| 126 | −0.85 | 0.05 |
| 128 | −14.60 | 0.79 |
| 130 | −17.26 | 0.93 |
| 132 | −0.75 | 0.04 |
| 134 | −11.55 | 0.62 |
| 136 | −7.20 | 0.39 |
| 138 | 0.16 | −0.01 |
| 140 | −3.63 | 0.20 |
| 142 | −3.63 | 0.20 |
| 144 | −1.20 | 0.06 |
| 146 | −16.77 | 0.90 |
| 148 | −2.00 | 0.11 |
| 150 | −1.40 | 0.08 |
| 152 | −3.63 | 0.20 |
| 154 | −7.09 | 0.38 |
| 156 | −0.96 | 0.05 |
| 158 | −2.79 | 0.15 |
| 160 | −3.23 | 0.17 |
| 162 | −10.17 | 0.55 |
| 164 | −0.51 | 0.03 |
| 166 | −3.43 | 0.19 |
| 168 | −5.65 | 0.30 |
| 170 | −2.35 | 0.13 |
| 172 | −1.20 | 0.06 |
| 174 | −2.29 | 0.12 |
| 176 | −1.92 | 0.08 |
| Op-XI (ABD) | −23.56 | NA |
| Op-XI (SBD) | −18.55 | NA |
| Vo—ctrl | −1.74 | NA |

5.6 Example 5: Growth of Yeast Containing XI Clones on Xylose

Figure 4:
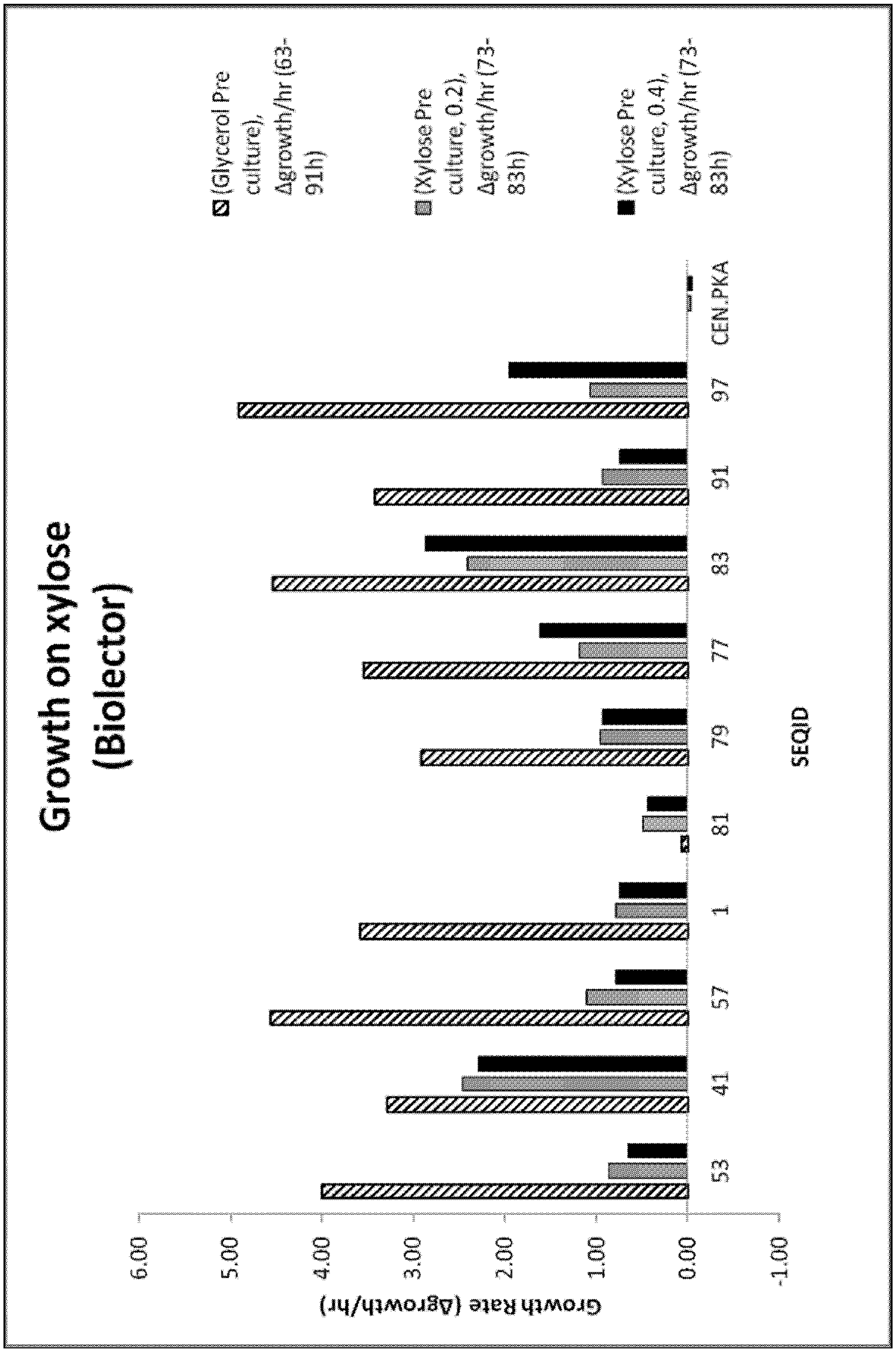
FIG. 4 shows the growth rates on xylose containing media of selected clones expressed in yeast strain, *Saccharomyces cerevisiae* CEN.PK2-1Ca (ATCC: MYA1108).

A subset of the XI genes from Example 3 were expressed in *Saccharomyces cerevisiae* CEN.PK2-1Ca (ATCC: MYA1108) and assayed for ability to confer the ability to grow on xylose. This assay was carried out as follows: colonies were isolated on SC-ura+2% glucose agar plates and inoculated into about 3 ml "pre-cultures" of both SC-ura 2% glycerol and SC-ura 2% xylose media, incubated at about 30° C., about 220 rpm, overnight. Cells were harvested by centrifugation (about 100×g, 5 minutes), supernatant discarded and washed twice and resuspended in about 1 ml of SC-ura 2% xylose. Cells were inoculated into Biolector plates, containing SC-ura, 2% xylose, and inoculums were normalized to two different starting optical densities of about $OD_{600}$ 0.2 and 0.4. Plates were covered using gas permeable seals and incubated in a BioLector microfermentation device (m2p-labs, Model G-BL100) at about 30° C. for about 4 days at 800 rpm and 90% humidity. Growth readings from the Biolector were acquired for 60-100 hours according to manufacturer's recommendations. Results are shown in FIG. 4.

5.7 Example 6: Ethanol Production Under Anaerobic Conditions

A subset of the XI expressing yeast clones in strain *Saccharomyces cerevisiae* CEN.PK2-1Ca (ATCC: MYA1108) were assayed for ability to ferment xylose to ethanol (EtOH). In brief, single colonies were inoculated into about 25 ml of SC-ura medium supplemented with about 0.1% glucose and about 3% xylose. Cultures were incubated under microaerobic conditions at about 30° C. and about 200 rpm. Samples were harvested at about 0, 24, 48, 72 h, and ethanol concentration determined via HPLC standard assays. Ethanol productivity was calculated, and listed in units of grams of EtOH per liter per hour, and FIOPC was generated comparing productivity of the control Op-XI. Results are shown in Table 4.

TABLE 4

| | Anaerobic EtOH Production Time (h) | | | | | |
|---|---|---|---|---|---|---|
| SEQ ID NO: | 0 | 24 | 48 | 72 | EtOH (g/L/h) | FIOPC |
| 6 | 0.28 | 0 | 0 | 0 | −0.004 | −0.5 |
| 8 | 0 | 0 | 0 | 0 | 0.000 | 0.0 |
| 10 | 0 | 0 | 0 | 0 | 0.000 | 0.0 |
| 14 | 0.37 | 0.28 | 0.71 | 1.24 | 0.013 | 1.7 |
| 16 | 0.33 | 0.275 | 0.72 | 1.06 | 0.011 | 1.4 |
| 18 | 0.29 | 0.135 | 0.31 | 0.595 | 0.005 | 0.6 |
| 20 | 0.33 | 0 | 0 | 0 | −0.004 | −0.5 |
| 22 | 0.32 | 0 | 0 | 0 | −0.004 | −0.5 |
| 24 | 0.28 | 0 | 0 | 0 | −0.004 | −0.5 |
| 26 | 0.26 | 0 | 0 | 0 | −0.003 | −0.4 |
| 28 | 0.23 | 0.385 | 1.015 | 1.54 | 0.019 | 2.5 |
| 30 | 0.27 | 0 | 0 | 0.07 | −0.003 | −0.3 |
| 32 | 0 | 0.165 | 0.48 | 0.815 | 0.012 | 1.5 |
| 34 | 0 | 0.125 | 0.33 | 0.615 | 0.009 | 1.1 |
| 36 | 0 | 0 | 0 | 0 | 0.000 | 0.0 |
| 46 | 0 | 0.285 | 0.905 | 1.625 | 0.023 | 3.0 |
| 60 | 0.45 | 0.35 | 0.87 | 1.39 | 0.014 | 1.8 |
| 62 | 0 | 0 | 0 | 0.065 | 0.001 | 0.1 |
| 64 | 0.38 | 0.275 | 0.735 | 1.18 | 0.012 | 1.6 |
| 66 | 0 | 0 | 0.12 | 0.22 | 0.003 | 0.4 |
| 68 | 0 | 0.05 | 0.275 | 0.5 | 0.007 | 0.9 |
| 70 | 0 | 0 | 0 | 0 | 0.000 | 0.0 |
| 72 | 0.119 | 0 | 0.054 | 0.1685 | 0.001 | 0.1 |
| 74 | 0.21 | 0.11 | 0.275 | 0.57 | 0.005 | 0.7 |
| 76 | 0.28 | 0 | 0 | 0 | −0.004 | −0.5 |

TABLE 4-continued

| Anaerobic EtOH Production Time (h) | | | | | | |
|---|---|---|---|---|---|---|
| SEQ ID NO: | 0 | 24 | 48 | 72 | EtOH (g/L/h) | FIOPC |
| 90 | 0 | 0.24 | 0.69 | 1.09 | 0.016 | 2.0 |
| 100 | 0.104 | 0.642 | 0.141 | 0.366 | 0.001 | 0.2 |
| 102 | 0.185 | 0 | 0 | 0.054 | −0.002 | −0.2 |
| 104 | 0.235 | 0.536 | 0 | 0 | −0.005 | −0.7 |
| 106 | 0.188 | 0.4835 | 0 | 0 | −0.004 | −0.6 |
| 108 | 0.19 | 0.5855 | 0.1455 | 0.313 | 0.000 | 0.0 |
| 110 | 0.3 | 0 | 0 | 0.05 | −0.003 | −0.4 |
| 112 | 0.19 | 0.5535 | 0.106 | 0.1135 | −0.003 | −0.4 |
| 114 | 0.174 | 0 | 0 | 0 | −0.002 | −0.3 |
| 116 | 0.15 | 0 | 0.0515 | 0.211 | 0.001 | 0.1 |
| 118 | 0.177 | 0.7075 | 0.5065 | 0.941 | 0.009 | 1.1 |
| 120 | 0.153 | 0 | 0 | 0 | −0.002 | −0.2 |
| 122 | 0.169 | 0.553 | 0 | 0.074 | −0.003 | −0.5 |
| 124 | 0.125 | 0 | 0 | 0 | −0.002 | −0.2 |
| 126 | 0.32 | 0 | 0 | 0 | −0.004 | −0.5 |
| 128 | 0 | 0 | 0 | 0 | 0.000 | 0.0 |
| 130 | 0 | 0 | 0 | 0 | 0.000 | 0.0 |
| 132 | 0.121 | 0 | 0 | 0 | −0.002 | −0.2 |
| 134 | 0.118 | 0 | 0 | 0.1105 | 0.000 | 0.0 |
| 136 | 0.108 | 0 | 0 | 0 | −0.001 | −0.2 |
| 138 | 0.172 | 0.513 | 0 | 0 | −0.004 | −0.6 |
| 140 | 0.17 | 0.542 | 0 | 0.3135 | 0.000 | −0.1 |
| 142 | 0.102 | 0 | 0 | 0 | −0.001 | −0.2 |
| 144 | 0.28 | 0 | 0 | 0 | −0.004 | −0.5 |
| 146 | 0.103 | 0.635 | 0.263 | 0.563 | 0.004 | 0.5 |
| 150 | 0.27 | 0 | 0 | 0 | −0.003 | −0.4 |
| 149 | 0.27 | 0 | 0 | 0 | −0.003 | −0.4 |
| 152 | 0.17 | 0 | 0 | 0 | −0.002 | −0.3 |
| 154 | 0.23 | 0 | 0 | 0 | −0.003 | −0.4 |
| 156 | 0.23 | 0 | 0 | 0 | −0.003 | −0.4 |
| 158 | 0.4 | 0 | 0.105 | 0.23 | −0.002 | −0.2 |
| 160 | 0.38 | 0 | 0 | 0 | −0.005 | −0.6 |
| 162 | 0.36 | 0.055 | 0.23 | 0.41 | 0.001 | 0.2 |
| 164 | 0.32 | 0 | 0 | 0 | −0.004 | −0.5 |
| 166 | 0.31 | 0 | 0 | 0 | −0.004 | −0.5 |
| 168 | 0.32 | 0 | 0.295 | 0.6 | 0.005 | 0.6 |
| 170 | 0.164 | 0.4995 | 0 | 0 | −0.004 | −0.5 |
| 172 | 0.27 | 0 | 0 | 0 | −0.003 | −0.4 |
| 174 | 0.3 | 0 | 0.17 | 0.345 | 0.001 | 0.2 |
| OP-XI (pos) | 0.2385 | 0.5875 | 0.6965 | 0.81508 | 0.008 | NA |
| Host-(neg) | 0.23625 | 0.088125 | 0 | 0 | −0.003 | NA |

5.8 Example 7: Impact of pH on XI Activity

Extracts from strain *Saccharomyces cerevisiae* CEN.PK2-1Ca (ATCC: MYA1108, expressing XI gene candidates in vector p426PGK1, were prepared as described in the Materials and Methods and assayed for XI activity at pH 7.5 and pH 6.0. Percent activity listed was calculated by dividing the VA at pH 6 by the VA at pH 7.5 and multiplying by 100. Results are listed in Table 5.

TABLE 5

| XI activity at pH 6 and pH 7.5 | | | | |
|---|---|---|---|---|
| SEQ ID NO: | Organism Classification | VA, pH 6 (U/ml) | VA, pH 7.5 (U/ml) | Percent activity (pH 6) |
| 2 | *Bacteroidales* | 1.92 | 2.59 | 74% |
| 14 | *Bacteroides* | 0.32 | 0.98 | 32% |
| 16 | *Bacteroides* | 1.16 | 2.40 | 48% |
| 32 | *Bacteroides* | 1.17 | 2.21 | 53% |
| 38 | *Firmicutes* | 2.46 | 2.77 | 89% |
| 42 | *Firmicutes* | 1.71 | 2.18 | 79% |
| 44 | *Firmicutes* | 0.19 | 0.25 | 76% |
| 46 | *Firmicutes* | 1.49 | 1.95 | 76% |
| 50 | *Firmicutes* | 0.81 | 0.95 | 86% |
| 52 | *Firmicutes* | 0.02 | 0.08 | 26% |
| 54 | *Neocallimastigales* | 1.46 | 2.90 | 51% |
| 58 | *Neocallimastigales* | 1.89 | 3.05 | 62% |

TABLE 5-continued

| XI activity at pH 6 and pH 7.5 | | | | |
|---|---|---|---|---|
| SEQ ID NO: | Organism Classification | VA, pH 6 (U/ml) | VA, pH 7.5 (U/ml) | Percent activity (pH 6) |
| 68 | *Neocallimastigales* | 1.50 | 1.97 | 76% |
| 72 | *Neocallimastigales* | 0.57 | 1.04 | 55% |
| 78 | *Prevotella* | 2.40 | 3.61 | 67% |
| 80 | *Prevotella* | 1.52 | 2.29 | 66% |
| 82 | *Prevotella* | 1.48 | 1.65 | 89% |
| 84 | *Prevotella* | 1.79 | 2.96 | 61% |
| 96 | *Prevotella* | 2.13 | 3.56 | 60% |
| 116 | *Prevotella* | 0.06 | 0.13 | 47% |
| Host-neg | | 0.04 | 0.02 | NA |
| Op-XI | | 0.61 | 1.25 | 49% |

5.9 Example 8: $K_m$ for Selected XI Clones

The $K_m$ and $V_{max}$ at pH 6 were determined for a subset of the XI clones, expressed on p426PGK1 vector in *Saccharomyces cerevisiae* CEN.PK2-1Ca (ATCC: MYA1108), using the XI activity assay described in the Materials and Methods and varying the concentrations of xylose from about 40-600 mM. Results shown are calculated using the Hanes Plot, which rearranges the Michaelis-Menten equation ($v=V_{max}[S]/(K_m+[S])$) as: ($[S]/v=K_m/V_{max}+[S]/V_{max}$), where plotting [S]/v against [S], resulting in a straight line and where the y intercept=$K_m/V_{max}$, the slope=$1/V_{max}$, and the x intercept=$-K_m$. Results are listed in Table 6.

TABLE 6

| $K_m$ determination for 3 XIs | | |
|---|---|---|
| SEQ ID NO: | $K_m$ | $V_{max}$ |
| 78 | 35.2 | 27.6 |
| 96 | 33.7 | 28.0 |
| 38 | 28.8 | 28.6 |

Figure 5A:
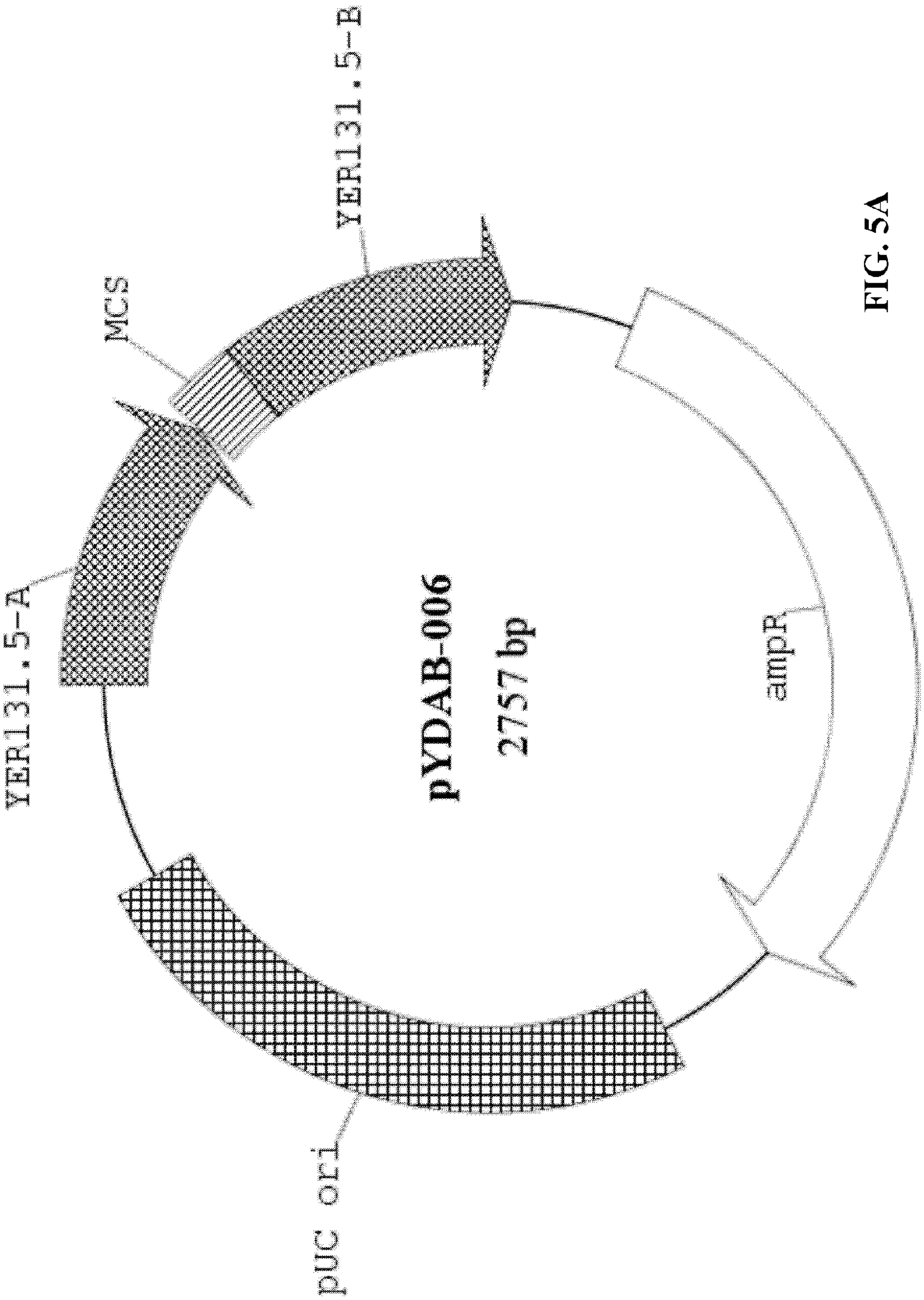
FIGS. 5A-5D are maps for the vectors pYDAB-006, pYDURA01, pYDPt-005 and pYDAB-0006, respectively, all used in creating strains of industrial *S. cerevisiae* strain yBPA130 with a single genomic copy of select XI clones.

5.10 Example 9: Quantification of XI Activity Expressed from Single Genomic Integration Locus A vector named pYDAB006 (FIG. 5A) for integration into locus YER131.5 (between YER131W and YER132C) in the *S. cerevisiae* genome was constructed using conventional cloning methods. The vector backbone with a Pad site at each end was derived from pBluescript II SK (+) (Agilent Technologies, Inc. Santa Clara, Calif.) by standard PCR techniques, which contained only the pUC origin of replication and bla gene encoding ampicillin resistance protein as a selectable marker. Two 300-base pair segments named YER131.5-A and YER 131.5-B were amplified from yeast genomic DNA by standard PCR techniques and connected with a multiple cloning site (MCS 1: 5'-GGCGCGCCTCTAGAAAGCTTACGCGTGAGCTCCCTGCAGGGATATCGGTACCGCGGCCGC-3' (SEQ ID NO:181)) using the overlapping PCR technique. The PCR primers used in the overlapping PCR are shown in Table 7 below:

TABLE 7

| Primers Used in pYDAB006 Construction | | |
|---|---|---|
| Primer | SEQ ID NO: | Sequence (PacI site is underlined) |
| 131.5AF | 182 | caccattaattaaAGCTTTGTAAATATGATGAGAGAATAATATAAATCAAACG |
| 131.5AR | 183 | GGCGCGCCTCTAGAAAGCTTAATCGACAAGAACACTTCTATTTATATAGGTATGAAA |
| 131.5BF | 184 | GCAGGGATATCGGTACCCACCAGCGGCCGCTGAAGAAGGTTTATTTCGTTTCGCTGT |
| 131.5BR | 185 | caccattaattaaCCCAGGTGAGACTGGATGCTCCATA |
| ABMCSF | 186 | GCCTCTAGAAAGCTTACGCGTGAGCTCCCTGCAGGGATATCGGTACCCACCAGCGGCCGC |
| ABMCSR | 187 | CGCTGGTGGGTACCGATATCCCTGCAGGGAGCTCACGCGTAAGCTTTCTAGAGGCGCGCC |

The overlapping PCR product was then ligated with the vector backbone resulting in plasmid pYDAB006.

Figure 5B:
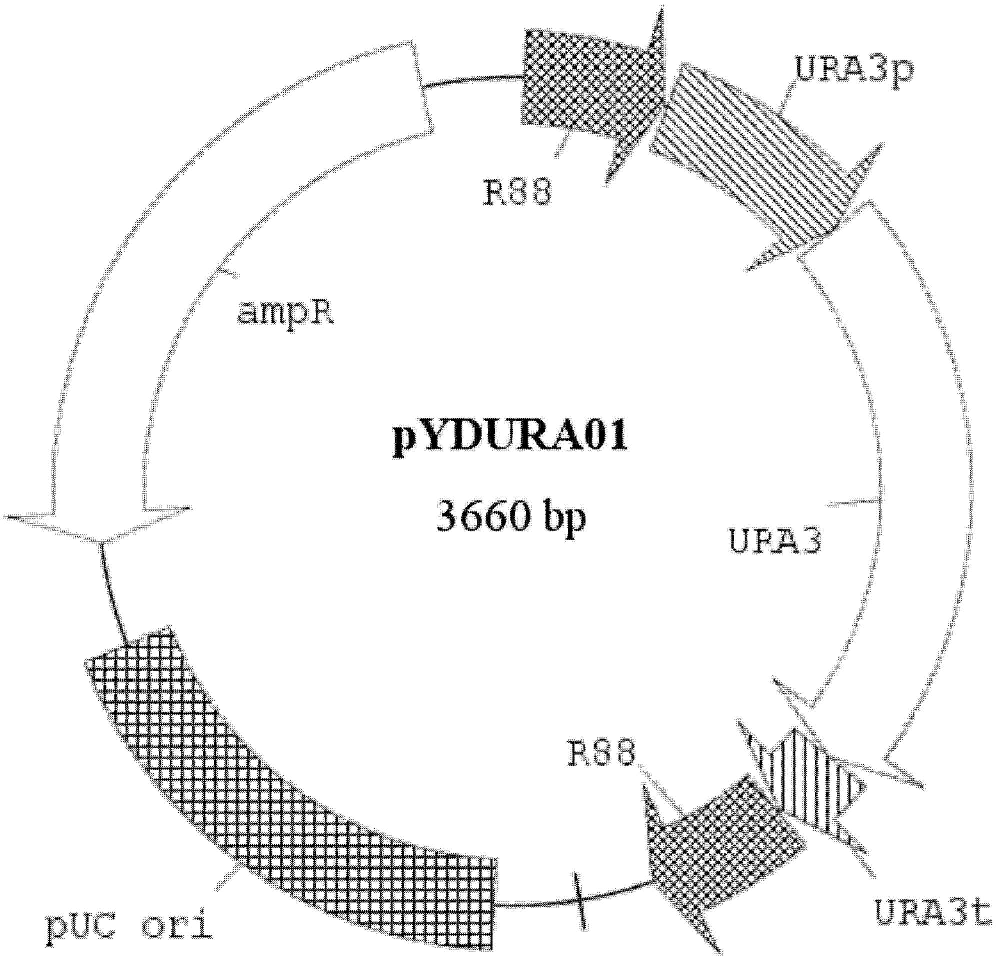

A vector named pYDURA01 (FIG. 5B) for generating yeast selectable and recyclable marker was constructed using similar method as pYDAB006. The URA3 expression cassette was amplified from yeast genomic DNA by standard PCR techniques. The 200 base pair fingerprint sequence (named R88: TGCGTGTGCCGCGAGTCCACGTCTACTCGCGAACCGAGTGCAGGCGGGTCTTCGGCCAGGAC GGCCGTGCGTGACCCCGGCCGCCAGACGAAACGGACCGCGCTCGCCAGACGCTACCCAGCC CGTTCATGCCGGCCGCGAGCCGACCTGTCTCGGTCGCTTCGACGCACGCGCGGTCCTTTCGG GTACTCGCCTAAGAC (SEQ ID NO:188)) at both sides of URA3 cassette was amplified by standard PCR techniques from the genomic DNA of yBPA317, which was a diploid strain having genotypes MATa/MATalpha; URA3/ura3; YDL074.5::P(TDH3)-CBT1-T(CYC1)-R88 YLR388.5::P(TDH3)-StBGL-T(CYC1)-R88/YLR388.5::P(TDH3)-StBGL-T(CYC1)-R88. The primers used in the amplification are described in Table 8 below:

TABLE 8

| Primers Used in pYDURA01 Construction | | |
|---|---|---|
| Primer | SEQ ID NO: | Sequence (KpnI and NotI sites are underlined) |
| NotI-KpnI-R88-F | 189 | caatagcggccgcggtaccTGCGTGTGCCGCGAGTCCAC |
| R88-BamHI-R | 190 | TGTTAGGATCCGTCTTAGGCGAGTACCCGAAAGG |
| BamHI-ura-F | 191 | caataggatccAGGCATATTTATGGTGAAGAATAAGT |
| ura-Xho-R | 192 | TGTTACTCGAGAAATCATTACGACCGAGATTCCCG |

TABLE 8-continued

Primers Used in pYDURA01 Construction

| Primer | SEQ ID NO: | Sequence (KpnI and NotI sites are underlined) |
|---|---|---|
| XhoI-R88-F | 193 | caatactcgagTGCGTGTGCCGCGAGTCCAC |
| R88-NotI-R | 194 | TGTTAGCGGCCGCGTCTTAGGCGAGTACCCGAAAGG |

Figure 5C:
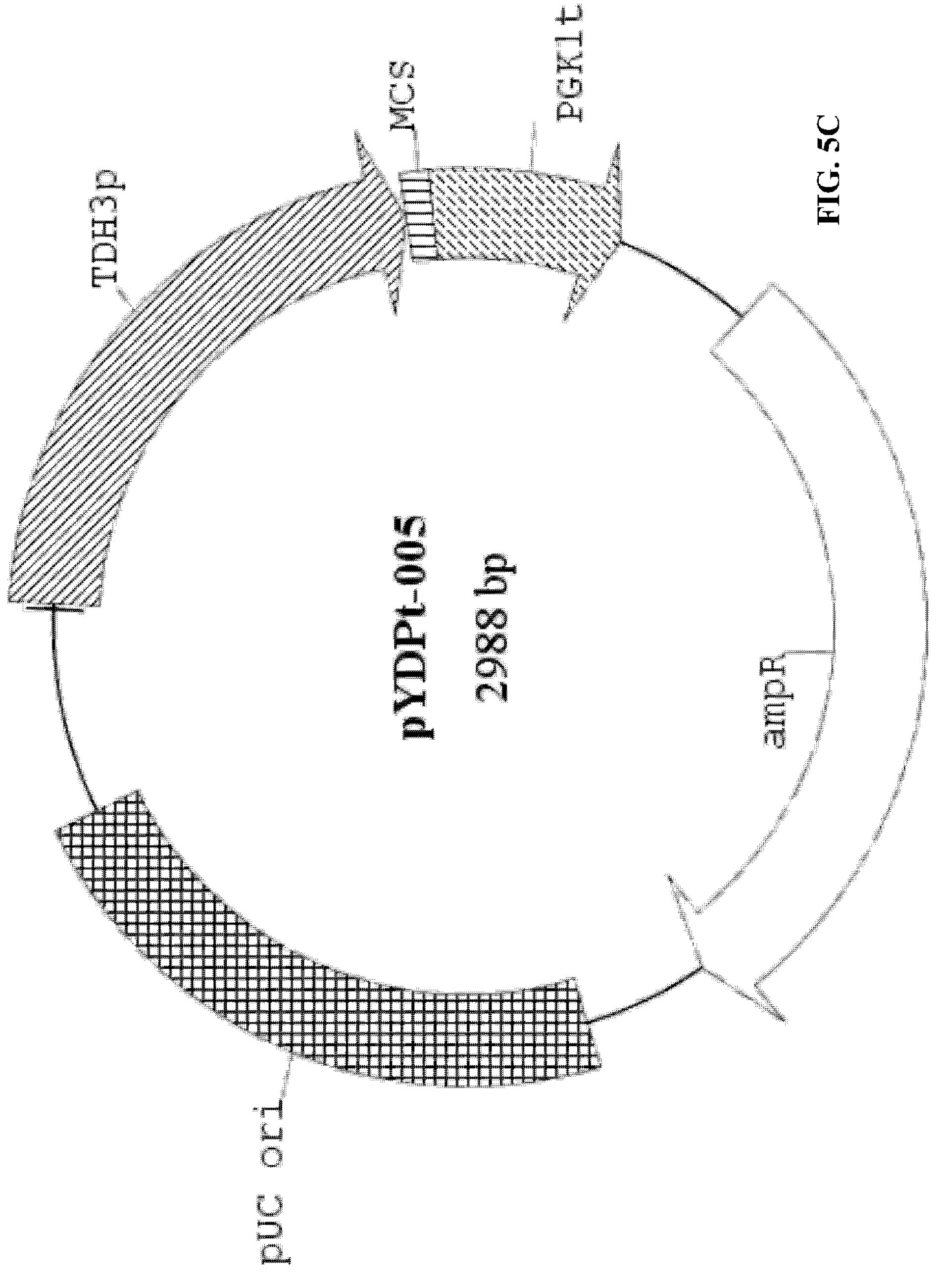

An expression cassette was generated for the XI genes by cloning into a vector named pYDPt005 (FIG. 5C). pYDPt005 was generated using similar method as pYDAB006. It contained a TDH3 promoter and a PGK1 terminator flanking a multiple cloning site (SEQ ID NO: 195)
(MCS 2: 5'-
ACTAGTGGATCCCTCGAGGTCGACGTTTAAAC-3', where single underline is SpeI site, double underline is XhoI site, and jagged underline is PmeI site). The promoter and the terminator were amplified from *S. cerevisiae* genomic DNA; an AscI site was added to the 5' end of the TDH3 promoter while a KpnI site was added to the 3' end of the PGK1 terminator during amplification. Primers used in the amplification are described in Table 9.

TABLE 9

Primers Used in pYDPt005 Construction

| Primer | SEQ ID NO: | Sequence (AscI and KpnI sites are underlined) |
|---|---|---|
| TDH-F | 196 | CACCAGGCGCGCCTCTAGAAAGCTTACGCGTAGTTTATC ATTATCAATACTGCCATTTCAAAGA |
| overlap-TDH-R | 197 | AACGTCGACCTCGAGGGATCCACTAGTTCGAAACTAAGT TCTTGGTGTTTTAAAACT |
| overlap-PGK-F | 198 | GTGGATCCCTCGAGGTCGACGTTTAAACATTGAATTGAA TTGAAATCGATAGATCAAT |
| PGK-R | 199 | CACCAGCGGCCGCGGTACCGATATCCCTGCAGGGAGCTC GAAATATCGAATGGGAAAAAAAAACTGGAT |

Figure 5D:
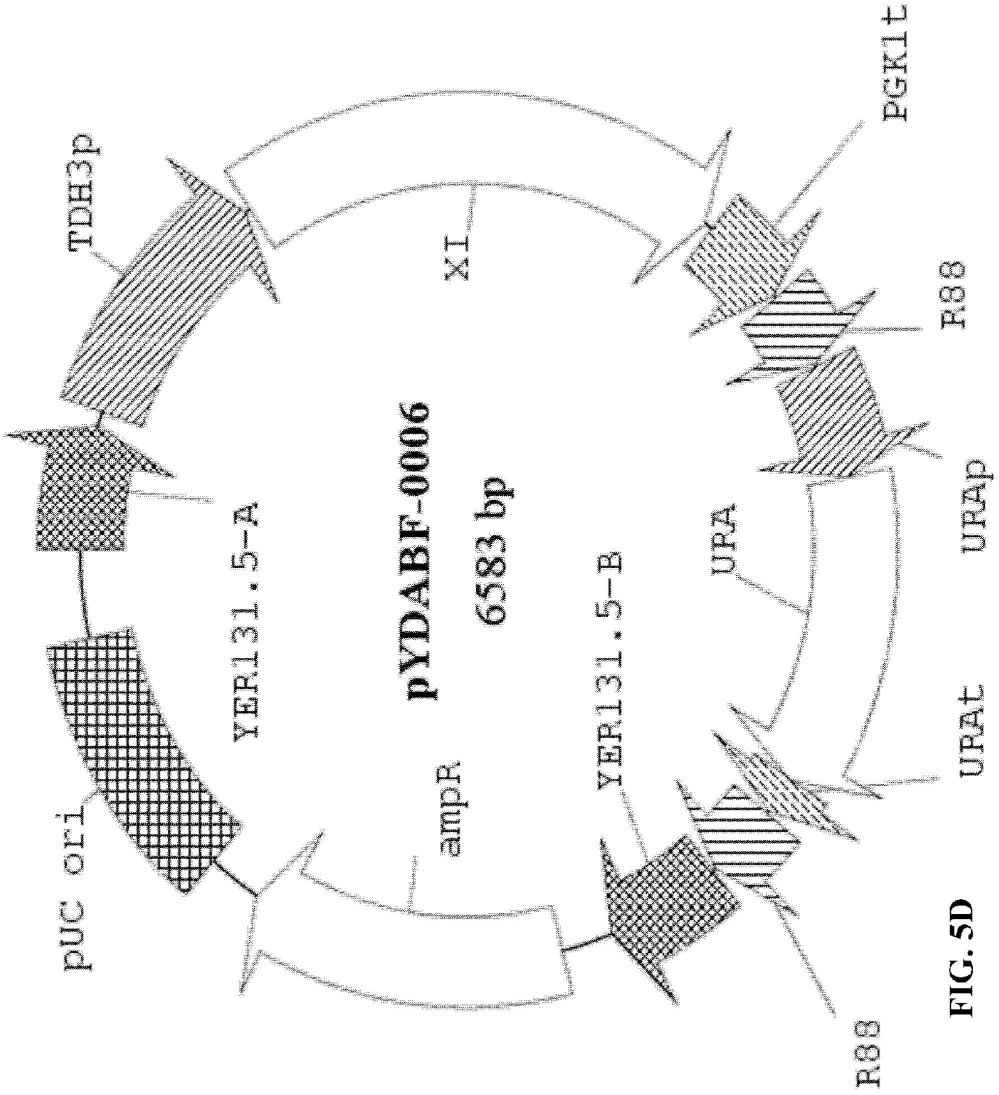

An *Orpinomyces* sp. XI gene (NCBI:169733248) was cloned in this vector between the SpeI and XhoI sites. The *Orpinomyces* sp. XI expression cassette and R88-Ura-R88 fragment were then cloned into vector pYDAB006 using AscI, KpnI and NotI sites; the resulting plasmid was named pYDABF006 (FIG. 5D). Subsequently, the *Orpinomyces* sp. XI gene in pYDABF0006 was replaced with a subset of the XI genes of Table 2 by digestion of pYDABF0006 with SpeI and PmeI and ligation to a DNA fragment encoding the appropriate XI sequence which had been amplified from p426PGK1-XI constructs. A SpeI site followed by a Kozak-like sequence (6 consecutive adenines) was added immediately in front of the start codon of the XI genes while a PmeI site was added to the 3' end of the XI genes during amplification.

XI gene integration cassettes were extracted by PacI digestion and used to transform yeast strain yBPA130 using standard techniques. Transformants were selected for growth on SC-Ura (Synthetic Complete, Ura dropout) agar plates. Integration position and existence of XI cassette in transformants was confirmed by PCR using the primers shown in Table 10.

TABLE 10

Primers Used in Integration Verification

| Primer | SEQ ID NO: | Sequence |
|---|---|---|
| 5' of integration | 200 | ACAGGGATAACAAAGTTTCTCCAGC |
| 3' of integration | 201 | CATACCAAGTCATGCGTTACCAGAG |
| 5' of R88-ura-R88 | 202 | TTTCCCATTCGATATTTCGAGCTCC |
| 3' of integration | 203 | CATACCAAGTCATGCGTTACCAGAG |

Confirmed clones were then grown about 18 hours in liquid YPD to allow looping out of the URA3 marker and were selected for growth on SC+5-FOA agar plate. The absence of the URA3 marker was confirmed by PCR.

Strains containing the confirmed XI expression cassettes were inoculated into about 3 ml of modified YP Media (YP+0.1% Glucose+3.0% Xylose) and incubated overnight at about 30° C. and about 220 rpm. These overnight cultures were subcultured into about 25 ml of the same media to about $OD_{600}$=0.2. Samples were incubated overnight at about 30° C. and about 220 rpm. Cultures were harvested when $OD_{600}$ was between about 3 and 4. Pellets were collected by centrifugation for about 5 minutes at about 4000 rpm. The supernatant was discarded and pellets washed with about 25 ml of distilled-deionized water and centrifuged again using the same conditions. Supernatant was discarded and the pellet frozen at about −20° C. until lysis and characterization.

Cell pellets were thawed and about 200 mg of each pellet sample was weighed out into 2 ml microcentrifuge tubes. About 50 μl of Complete®, EDTA-free Protease Inhibitor cocktail (Roche Part#11873 580 001) at 5 times the concentration stated in the manufacturer's protocol was added to each sample. To this was added about 0.5 ml of Y-PER Plus® Dialyzable Yeast Protein Extraction Reagent (Thermo Scientific Part#78999) (YP+) to each sample. Samples were incubated at about 25° C. for about 4 hours on rotating mixer. Sample supernatants were collected after centrifugation at about 10,000×g for about 10 minutes for characterization.

Total protein concentrations of the XI sample extracts prepared above were carried out using Bio-Rad Protein Assay Dye Reagent Concentrate (Bio-Rad, cat#500-0006, Hercules Calif.) which is a modified version of the Bradford method (Bradford).

Yeast physiological pH ranges are known to range from about pH 6 to about pH 7.5 (Pena, Ramirez et al., 1995, J. Bacteriology 4:1017-1022). Ranking of XI activity at yeast physiological pH was accomplished using the assay conditions at pH 7.5 and modified for pH 6.0 as described in the materials and methods. The specific activities of 20 XIs when expressed from a single copy integrated into the yeast YER131.5 locus were evaluated. The results are listed in Table 11.

TABLE 11

SA of XI Expressed in an Industrial *S. cerevisiae*

| SEQ ID NO: | Organism Classification | SA, pH6 (U/mg) | SA, pH 7.5 (U/mg) |
|---|---|---|---|
| 2 | *Bacteroidales* | 0.86 | 1.08 |
| 14 | *Bacteroides* | 0.33 | 1.07 |
| 16 | *Bacteroides* | 0.57 | 1.05 |
| 32 | *Bacteroides* | 0.53 | 1.00 |
| 38 | *Firmicutes* | 1.00 | 0.94 |
| 42 | *Firmicutes* | 0.79 | 0.82 |
| 44 | *Firmicutes* | 0.08 | 0.10 |
| 46 | *Firmicutes* | 0.62 | 0.69 |
| 50 | *Firmicutes* | 0.35 | 0.41 |
| 52 | *Firmicutes* | 0.01 | 0.03 |
| 54 | *Neocallimastigales* | 0.64 | 1.17 |
| 58 | *Neocallimastigales* | 0.79 | 1.10 |
| 68 | *Neocallimastigales* | 0.01 | 0.02 |
| 72 | *Neocallimastigales* | 0.22 | 0.40 |
| 78 | *Prevotella* | 1.10 | 1.45 |

TABLE 11-continued

SA of XI Expressed in an Industrial *S. cerevisiae*

| SEQ ID NO: | Organism Classification | SA, pH6 (U/mg) | SA, pH 7.5 (U/mg) |
|---|---|---|---|
| 80 | *Prevotella* | 0.74 | 1.11 |
| 82 | *Prevotella* | 0.54 | 0.60 |
| 84 | *Prevotella* | 0.76 | 1.06 |
| 96 | *Prevotella* | 1.10 | 1.62 |
| 116 | *Prevotella* | 0.03 | 0.06 |
| Host neg ctrl | | 0.00 | 0.02 |

5.11 Example 10: Identification of Sequence Motifs in Acid Tolerant XIs

The proposed mechanism of xylose isomerases can be summarized as follows: (i) binding of xylose to xylose isomerase, so that O3 and O4 are coordinated by metal ion I; (ii) enzyme-catalyzed ring opening (the identity of the ring-opening group remains a subject for further investigation; ring opening may be the rate limiting step in the overall isomerization process); (iii) chain extension (sugar binds in a linear extended form) in which O2 and O4 now coordinate metal ion I; (iv) O2 becomes deprotonated causing a shift of metal ion II from position 1 to an adjacent position 2 in which it coordinates O1 and O2 of the sugar together with metal ion I; (v) isomerization via an anionic transition state arises by a hydride shift promoted by electrophilic catalysis provided by both metal ions; (vi) collapse of transition state by return of metal ion II to position 1; (vii) chain contraction to a pseudo-cyclic position with ligands to metal ion I changing from O2/O4 back to O3/O4; (viii) enzyme-catalyzed ring closure; (ix) dissociation of xylulose from xylose isomerase (Lavie et al., 1994, Biochemistry 33(18), 5469-5480).

Many XIs identified contained one or both of two signature sequences characteristic of XIs, [LI]EPKP.{2}P (SEQ ID NO:204) and [FL]HD[^K]D[LIV].[PD].[GDE] (SEQ ID NO:205). Additional sequence motifs present in the top performing *Firmicutes* and *Prevotella* XIs were identified. The motifs are located near the active site including residues in direct contact with the D-xylose and/or the metal ions. The motifs are shown in Table 12 below:

TABLE 12

XI Sequence Motifs

| XI Source Motif | Sequence | SEQ ID NO: |
|---|---|---|
| *Firmicutes*1A | P[FY][AST][MLVI][AS][WYFL]W[HT]N[LFMG]GA | 206 |
| *Firmicutes*1B | P[FY][AS].{2}[WYFL]W[HT][^TV].GA | 207 |
| *Firmicutes*2 | [GSN][IVA]R[YFHG][FYLIV]C[FW]HD.D | 208 |
| *Firmicutes*3 | T[ASTC][NK][^L]F.[NDH][PRKAG][RVA][FY]C | 209 |
| *Firmicutes*4 | [WFY]D[TQVI]D.[FY][PF][^T].{2, 4}[YFH]S[ATL]T | 210 |
| *Firmicutes*5 | GF[NH]FD[SA]KTR | 211 |
| *Prevotella*1A | FG.QT[RK].{2}E[WYF][DNG].{2, 3}[DNEGT][AT] | 212 |
| *Prevotella*1B | FG.QT[RK].{2}E[WYF][DNG].{3}[^C][^P] | 213 |
| *Prevotella*2 | [FW]HD.D[LVI].[DE]EG[^P][TSD][IV][EA]E | 214 |

5.12 Example 11: In Vivo Evaluation of Xylose Isomerase

Haploid *S. cerevisiae* strain yBPA130 (MATa::ura3) and yBPA136 (MATalpha::ura3) were genetically modified to enhance C5 xylose utilization during fermentation. The modification includes the following: the native glucose repressible alcohol dehydrogenase II gene ADH2 was disrupted by inserting an expression cassette of the endogenous transaldolase gene TAL1 (SEQ ID NO:215) and xylulokinase gene XKS1 (SEQ ID NO:216). PHO13 encoding the native alkaline phosphatase specific for p-nitrophenyl phosphate gene was disrupted by inserting the native transketolase-1 gene TKL1 (SEQ ID NO:217). Native aldose reductase gene GRE3 was disrupted by inserting native D-ribulose-5-phosphate 3-epimerase gene RPE1 (SEQ ID NO:218) and Ribose-5-phosphate ketol-isomerase gene RKI1 (SEQ ID NO:219). Also one expression cassette of native galactose permease gene GAL2 (SEQ ID NO:220) was integrated into the *S. cerevisiae* strain, resulting in haploid strains pBPB007 (MATa::ura3) and pBPB008 (MATalpha::ura3). The genotype of pBPB007 and pBPB008 is adh2::TA1-XKS1, pho13::TKL1-XKS1, gre3::RPE1-RKI1 and YLR388.5::GAL2. The sequences are shown in Table 13, below:

TABLE 13

| Sequence Name | Type of sequence | SEQ ID NO: | Sequence |
|---|---|---|---|
| TAL1 (*S. cerevisiae*) | DNA | 215 | ATGTCTGAACCAGCTCAAAAGAAACAAAAGGTTGCTAACAACTCT<br>CTAGAACAATTGAAAGCCTCCGGCACTGTCGTTGTTGCCGACACT<br>GGTGATTTCGGCTCTATTGCCAAGTTTCAACCTCAAGACTCCACA<br>ACTAACCCATCATTGATCTTGGCTGCTGCCAAGCAACCAACTTAC<br>GCCAAGTTGATCGATGTTGCCGTGGAATACGGTAAGAAGCATGGT<br>AAGACCACCGAAGAACAAGTCGAAAATGCTGTGGACAGATTGTTA<br>GTCGAATTCGGTAAGGAGATCTTAAAGATTGTTCCAGGCAGAGTC<br>TCCACCGAAGTTGATGCTAGATTGTCTTTTGACACTCAAGCTACC<br>ATTGAAAAGGCTAGACATATCATTAAATTGTTTGAACAAGAAGGT<br>GTCTCCAAGGAAAGAGTCCTTATTAAAATTGCTTCCACTTGGGAA<br>GGTATTCAAGCTGCCAAAGAATTGGAAGAAAAGGACGGTATCCAC<br>TGTAATTTGACTCTATTATTCTCCTTCGTTCAAGCAGTTGCCTGT<br>GCCGAGGCCCAAGTTACTTTGATTTCCCCATTTGTTGGTAGAATT<br>CTAGACTGGTACAAATCCAGCACTGGTAAAGATTACAAGGGTGAA<br>GCCGACCCAGGTGTTATTTCCGTCAAGAAAATCTACAACTACTAC<br>AAGAAGTACGGTTACAAGACTATTGTTATGGGTGCTTCTTTCAGA<br>AGCACTGACGAAATCAAAAACTTGGCTGGTGTTGACTATCTAACA<br>ATTTCTCCAGCTTTATTGGACAAGTTGATGAACAGTACTGAACCT<br>TTCCCAAGAGTTTTGGACCCTGTCTCCGCTAAGAAGGAAGCCGGC<br>GACAAGATTTCTTACATCAGCGACGAATCTAAATTCAGATTCGAC<br>TTGAATGAAGACGCTATGGCCACTGAAAAATTGTCCGAAGGTATC<br>AGAAAATTCTCTGCCGATATTGTTACTCTATTCGACTTGATTGAA<br>AAGAAAGTTACCGCTTAA |
| XKS1 (*S. cerevisiae*) | DNA | 216 | ATGTTGTGTTCAGTAATTCAGAGACAGACAAGAGAGGTTTCCAAC<br>ACAATGTCTTTAGACTCATACTATCTTGGGTTTGATCTTTCGACC<br>CAACAACTGAAATGTCTCGCCATTAACCAGGACCTAAAAATTGTC<br>CATTCAGAAACAGTGGAATTTGAAAAGGATCTTCCGCATTATCAC<br>ACAAAGAAGGGTGTCTATATACACGGCGACACTATCGAATGTCCC<br>GTAGCCATGTGGTTAGAGGCTCTAGATCTGGTTCTCTCGAAATAT<br>CGCGAGGCTAAATTTCCATTGAACAAAGTTATGGCCGTCTCAGGG<br>TCCTGCCAGCAGCACGGGTCTGTCTACTGGTCCTCCCAAGCCGAA<br>TCTCTGTTAGAGCAATTGAATAAGAAACCGGAAAAAGATTTATTG<br>CACTACGTGAGCTCTGTAGCATTTGCAAGGCAAACCGCCCCCAAT<br>TGGCAAGACCACAGTACTGCAAAGCAATGTCAAGAGTTTGAAGAG<br>TGCATAGGTGGGCCTGAAAAAATGGCTCAATTAACAGGGTCCAGA<br>GCCCATTTTAGATTTACTGGTCCTCAAATTCTGAAAATTGCACAA<br>TTAGAACCAGAAGCTTACGAAAAAACAAAGACCATTTCTTTAGTG<br>TCTAATTTTTTGACTTCTATCTTAGTGGGCCATCTTGTTGAATTA<br>GAGGAGGCAGATGCCTGTGGTATGAACCTTTATGATATACGTGAA<br>AGAAAATTCAGTGATGAGCTACTACATCTAATTGATAGTTCTTCT<br>AAGGATAAAACTATCAGACAAAAATTAATGAGAGCACCCATGAAA<br>AATTTGATAGCGGGTACCATCTGTAAATATTTTATTGAGAAGTAC<br>GGTTTCAATACAAACTGCAAGGTCTCTCCCATGACTGGGGATAAT<br>TTAGCCACTATATGTTCTTTACCCCTGCGGAAGAATGACGTTCTC<br>GTTTCCCTAGGAACAAGTACTACAGTTCTTCTGGTCACCGATAAG<br>TATCACCCCTCTCCGAACTATCATCTTTTC<br>ATTCATCCAACTCTGCCAAACCATTATATGGGTATGATTTGTTAT<br>TGTAATGGTTCTTTGGCAAGGGAGAGGATAAGAGACGAGTTAAAC<br>AAAGAACGGGAAAATAATTATGAGAAGACTAACGATTGGACTCTT<br>TTTAATCAAGCTGTGCTAGATGACTCAGAAAGTAGTGAAAATGAA<br>TTAGGTGTATATTTTCCTCTGGGGGAGATCGTTCCTAGCGTAAAA<br>GCCATAAACAAAAGGGTTATCTTCAATCCAAAAACGGGTATGATT<br>GAAAGAGAGGTGGCCAAGTTCAAAGACAAGAGGCACGATGCCAAA<br>AATATTGTAGAATCACAGGCTTTAAGTTGCAGGGTAAGAATATCT<br>CCCCTGCTTTCGGATTCAAACGCAAGCTCACAACAGAGACTGAAC<br>GAAGATACAATCGTGAAGTTTGATTACGATGAATCTCCGCTGCGG<br>GACTACCTAAATAAAAGGCCAGAAAGGACTTTTTTTGTAGGTGGG<br>GCTTCTAAAAACGATGCTATTGTGAAGAAGTTTGCTCAAGTCATT |

TABLE 13-continued

| Sequence Name | Type of sequence | SEQ ID NO: | Sequence |
|---|---|---|---|
| | | | GGTGCTACAAAGGGTAATTTTAGGCTAGAAACACCAAACTCATGT<br>GCCCTTGGTGGTTGTTATAAGGCCATGTGGTCATTGTTATATGAC<br>TCTAATAAAATTGCAGTTCCTTTTGATAAATTTCTGAATGACAAT<br>TTTCCATGGCATGTAATGGAAAGCATATCCGATGTGGATAATGAA<br>AATTGGGATCGCTATAATTCCAAGATTGTCCCCTTAAGCGAACTG<br>GAAAAGACTCTCATCTAA |
| TKL1 (*S. cerevisiae*) | DNA | 217 | ATGACTCAATTCACTGACATTGATAAGCTAGCCGTCTCCACCATA<br>AGAATTTTGGCTGTGGACACCGTATCCAAGGCCAACTCAGGTCAC<br>CCAGGTGCTCCATTGGGTATGGCACCAGCTGCACACGTTCTATGG<br>AGTCAAATGCGCATGAACCCAACCAACCCAGACTGGATCAACAGA<br>GATAGATTTGTCTTGTCTAACGGTCACGCGGTCGCTTTGTTGTAT<br>TCTATGCTACATTTGACTGGTTACGATCTGTCTATTGAAGACTTG<br>AAACAGTTCAGACAGTTGGGTTCCAGAACACCAGGTCATCCTGAA<br>TTTGAGTTGCCAGGTGTTGAAGTTACTACCGGTCCATTAGGTCAA<br>GGTATCTCCAACGCTGTTGGTATGGCCATGGCTCAAGCTAACCTG<br>GCTGCCACTTACAACAAGCCGGGCTTTACCTTGTCTGACAACTAC<br>ACCTATGTTTTCTTGGGTGACGGTTGTTTGCAAGAAGGTATTTCT<br>TCAGAAGCTTCCTCCTTGGCTGGTCATTTGAAATTGGGTAACTTG<br>ATTGCCATCTACGATGACAACAAGATCACTATCGATGGTGCTACC<br>AGTATCTCATTCGATGAAGATGTTGCTAAGAGATACGAAGCCTAC<br>GGTTGGGAAGTTTTGTACGTAGAAAATGGTAACGAAGATCTAGCC<br>GGTATTGCCAAGGCTATTGCTCAAGCTAAGTTATCCAAGGACAAA<br>CCAACTTTGATCAAAATGACCACAACCATTGGTTACGGTTCCTTG<br>CATGCCGGCTCTCACTCTGTGCACGGTGCCCCATTGAAAGCAGAT<br>GATGTTAAACAACTAAAGAGCAAATTCGGTTTCAACCCAGACAAG<br>TCCTTTGTTGTTCCACAAGAAGTTTACGACCACTACCAAAAGACA<br>ATTTTAAAGCCAGGTGTCGAAGCCAACAACAAGTGGAACAAGTTG<br>TTCAGCGAATACCAAAAGAAATTCCCAGAATTAGGTGCTGAATTG<br>GCTAGAAGATTGAGCGGCCAACTACCCGCA<br>AATTGGGAATCTAAGTTGCCAACTTACACCGCCAAGGACTCTGCC<br>GTGGCCACTAGAAAATTATCAGAAACTGTTCTTGAGGATGTTTAC<br>AATCAATTGCCAGAGTTGATTGGTGGTTCTGCCGATTTAACACCT<br>TCTAACTTGACCAGATGGAAGGAAGCCCTTGACTTCCAACCTCCT<br>TCTTCCGGTTCAGGTAACTACTCTGGTAGATACATTAGGTACGGT<br>ATTAGAGAACACGCTATGGGTGCCATAATGAACGGTATTTCAGCT<br>TTCGGTGCCAACTACAAACCATACGGTGGTACTTTCTTGAACTtC<br>GTTTCTTATGCTGCTGGTGCCGTTAGATTGTCCGCTTTGTCTGGC<br>CACCCAGTTATTTGGGTTGCTACACATGACTCTATCGGTGTCGGT<br>GAAGATGGTCCAACACATCAACCTATTGAAACTTTAGCACACTTC<br>AGATCCCTACCAAACATTCAAGTTTGGAGACCAGCTGATGGTAAC<br>GAAGTTTCTGCCGCCTACAAGAACTCTTTAGAATCCAAGCATACT<br>CCAAGTATCATTGCTTTGTCCAGACAAAACTTGCCACAATTGGAA<br>GGTAGCTCTATTGAAAGCGCTTCTAAGGGTGGTTACGTACTACAA<br>GATGTTGCTAACCCAGATATTATTTTAGTGGCTACTGGTTCCGAA<br>GTGTCTTTGAGTGTTGAAGCTGCTAAGACTTTGGCCGCAAAGAAC<br>ATCAAGGCTCGTGTTGTTTCTCTACCAGATTTCTTCACTTTTGAC<br>AAACAACCCCTAGAATACAGACTATCAGTCTTACCAGACAACGTT<br>CCAATCATGTCTGTTGAAGTTTTGGCTACCACATGTTGGGGCAAA<br>TACGCTCATCAATCCTTCGGTATTGACAGATTTGGTGCCTCCGGT<br>AAGGCACCAGAAGTCTTCAAGTTCTTCGGTTTCACCCCAGAAGGT<br>GTTGCTGAAAGAGCTCAAAAGACCATTGCATTCTATAAGGGTGAC<br>AAGCTAATTTCTCCTTTGAAAAAAGCTTTCTAA |
| RPE1 (*S. cerevisiae*) | DNA | 218 | ATGGTCAAACCAATTATAGCTCCCAGTATCCTTGCTTCTGACTTC<br>GCCAACTTGGGTTGCGAATGTCATAAGGTCATCAACGCCGGCGCA<br>GATTGGTTACATATCGATGTCATGGACGGCCATTTTGTTCCAAAC<br>ATTACTCTGGGCCAACCAATTGTTACCTCCCTACGTCGTTCTGTG<br>CCACGCCCTGGCGATGCTAGCAACACAGAAAAGAAGCCCACTGCG<br>TTCTTCGATTGTCACATGATGGTTGAAAATCCTGAAAAATGGGTC<br>GACGATTTTGCTAAATGTGGTGCTGACCAATTTACGTTCCACTAC<br>GAGGCCACACAAGACCCTTTGCATTTAGTTAAGTTGATTAAGTCT<br>AAGGGCATCAAAGCTGCATGCGCCATCAAACCTGGTACTTCTGTT<br>GACGTTTTATTTGAACTAGCTCCTCATTTGGATATGGCTCTTGTT<br>ATGACTGTGGAACCTGGGTTTGGAGGCCAAAAATTCATGGAAGAC<br>ATGATGCCAAAAGTGGAAACTTTGAGAGCCAAGTTCCCCCATTTG<br>AATATCCAAGTCGATGGTGGTTTGGGCAAGGAGACCATCCCGAAA<br>GCCGCCAAAGCCGGTGCCAACGTTATTGTCGCTGGTACCAGTGTT<br>TTCACTGCAGCTGACCCGCACGATGTTATCTCCTTCATGAAAGAA<br>GAAGTCTCGAAGGAATTGCGTTCTAGAGATTTGCTAGATTAG |
| RKI1 (*S. cerevisiae*) | DNA | 219 | ATGGCTGCCGGTGTCCCAAAAATTGATGCGTTAGAATCTTTGGGC<br>AATCCTTTGGAGGATGCCAAGAGAGCTGCAGCATACAGAGCAGTT<br>GATGAAAATTTAAAATTTGATGATCACAAAATTATTGGAATTGGT<br>AGTGGTAGCACAGTGGTTTATGTTGCCGAAAGAATTGGACAATAT<br>TTGCATGACCCTAAATTTTATGAAGTAGCGTCTAAATTCATTTGC |

TABLE 13-continued

| Sequence Name | Type of sequence | SEQ ID NO: | Sequence |
|---|---|---|---|
| | | | ATTCCAACAGGATTCCAATCAAGAAACTTGATTTTGGATAACAAG<br>TTGCAATTAGGCTCCATTGAACAGTATCCTCGCATTGATATAGCG<br>TTTGACGGTGCTGATGAAGTGGATGAGAATTTACAATTAATTAAA<br>GGTGGTGGTGCTTGTCTATTTCAAGAAAAATTGGTTAGTACTAGT<br>GCTAAAACCTTCATTGTCGTTGCTGATTCAAGAAAAAAGTCACCA<br>AAACATTTAGGTAAGAACTGGAGGCAAGGTGTTCCCATTGAAATT<br>GTACCTTCCTCATACGTGAGGGTCAAGAATGATCTATTAGAACAA<br>TTGCATGCTGAAAAAGTTGACATCAGACAAGGAGGTTCTGCTAAA<br>GCAGGTCCTGTTGTAACTGACAATAATAACTTCATTATCGATGCG<br>GATTTCGGTGAAATTTCCGATCCAAGAAAATTGCATAGAGAAATC<br>AAACTGTTAGTGGGCGTGGTGGAAACAGGTTTATTCATCGACAAC<br>GCTTCAAAAGCCTACTTCGGTAATTCTGACGGTAGTGTTGAAGTT<br>ACCGAAAAGTGA |
| GAL2 (*S. cerevisiae*) | DNA | 220 | ATGGCAGTTGAGGAGAACAATATGCCTGTTGTTTCACAGCAACCC<br>CAAGCTGGTGAAGACGTGATCTCTTCACTCAGTAAAGATTCCCAT<br>TTAAGCGCACAATCTCAAAAGTATTCTAATGATGAATTGAAAGCC<br>GGTGAGTCAGGGTCTGAAGGCTCCCAAAGTGTTCCTATAGAGATA<br>CCCAAGAAGCCCATGTCTGAATATGTTACCGTTTCCTTGCTTTGT<br>TTGTGTGTTGCCTTCGGCGGCTTCATGTTTGGCTGGGATACCGGT<br>ACTATTTCTGGGTTTGTTGTCCAAACAGACTTTTTGAGAAGGTTT<br>GGTATGAAACATAAGGATGGTACCCACTATTTGTCAAACGTCAGA<br>ACAGGTTTAATCGTCGCCATTTTCAATATTGGCTGTGCCTTTGGT<br>GGTATTATACTTTCCAAAGGTGGAGATATGTATGGCCGTAAAAAG<br>GGTCTTTCGATTGTCGTCTCGGTTTATATAGTTGGTATTATCATT<br>CAAATTGCCTCTATCAACAAGTGGTACCAATATTTCATTGGTAGA<br>ATCATATCTGGTTTGGGTGTCGGCGGCATCGCCGTCTTATGTCCT<br>ATGTTGATCTCTGAAATTGCTCCAAAGCACTTGAGAGGCACACTA<br>GTTTCTTGTTATCAGCTGATGATTACTGCAGGTATCTTTTTGGGC<br>TACTGTACTAATTACGGTACAAAGAGCTATTCGAACTCAGTTCAA<br>TGGAGAGTTCCATTAGGGCTATGTTTCGCTTGGTCATTATTTATG<br>ATTGGCGCTTTGACGTTAGTTCCTGAATCCCCACGTTATTTATGT<br>GAGGTGAATAAGGTAGAAGACGCCAAGCGTTCCATTGCTAAGTCT<br>AACAAGGTGTCACCAGAGGATCCTGCCGTCCAGGCAGAGTTAGAT<br>CTGATCATGGCCGGTATAGAAGCTGAAAAACTGGCTGGCAATGCG<br>TCCTGGGGGGAATTATTTTCCACCAAGACCAAAGTATTTCAACGT<br>TTGTTGATGGGTGTGTTTGTTCAAATGTTC<br>CAACAATTAACCGGTAACAATTATTTTTTCTACTACGGTACCGTT<br>ATTTTCAAGTCAGTTGGCCTGGATGATTCCTTTGAAACATCCATT<br>GTCATTGGTGTAGTCAACTTTGCCTCCACTTTCTTTAGTTTGTGG<br>ACTGTCGAAAACTTGGGACATCGTAAATGTTTACTTTTGGGCGCT<br>GCCACTATGATGGCTTGTATGGTCATCTACGCCTCTGTTGGTGTT<br>ACTAGATTATATCCTCACGGTAAAAGCCAGCCATCTTCTAAAGGT<br>GCCGGTAACTGTATGATTGTCTTTACCTGTTTTTATATTTTCTGT<br>TATGCCACAACCTGGGCGCCAGTTGCCTGGGTCATCACAGCAGAA<br>TCATTCCCACTGAGAGTCAAGTCGAAATGTATGGCGTTGGCCTCT<br>GCTTCCAATTGGGTATGGGGGTTCTTGATTGCATTTTTCACCCCA<br>TTCATCACATCTGCCATTAACTTCTACTACGGTTATGTCTTCATG<br>GGCTGTTTGGTTGCCATGTTTTTTTATGTCTTTTTCTTTGTTCCA<br>GAAACTAAAGGCCTATCGTTAGAAGAAATTCAAGAATTATGGGAA<br>GAAGGTGTTTTACCTTGGAAATCTGAAGGCTGGATTCCTTCATCC<br>AGAAGAGGTAATAATTACGATTTAGAGGATTTACAACATGACGAC<br>AAACCGTGGTACAAGGCCATGCTAGAATAA |

Figure 6:
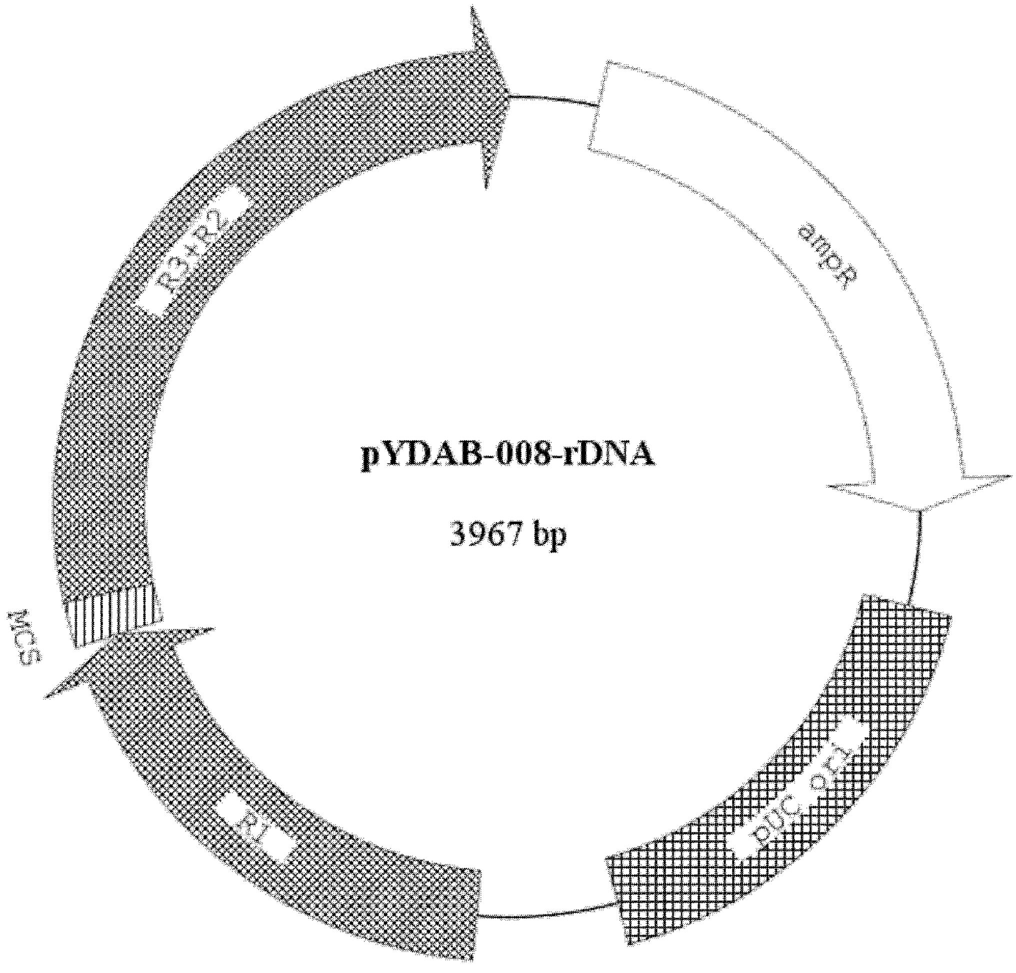
FIG. 6 is a map of vector YDAB008-rDNA for multiple XI integration into *S. cerevisiae* strain yBPB007 and yBPB008.

A vector named pYDAB008 rDNA (FIG. 6) for integration xylose isomerase into ribosomal DNA loci in *S. cerevisiae* genome was constructed using conventional cloning methods. This vector can confer high copy number integration of genes and resulting in high-level expression of proteins. The vector was derived from pBluescript II SK (+) (Agilent Technologies, Inc., Santa Clara, Calif.). The pUC origin of replication and bla gene encoding ampicillin resistance was amplified with specific primer sequences as a selectable marker for cloning. A 741 base-pair segment R1 region, 253 base-pair R3 region and a 874 base-pair R2 region were amplified from yeast genomic DNA by PCR amplifications. A multiple cloning site of SEQ ID NO:181 (: 5'-GGCGCGCCTCTAGAAAGCTTACGCGTGAGCTC-CCTGCAGGGATATCGGTACCGCGGCCGC-3') was inserted between the R1 and R3/R2 regions by assembly using overlapping PCR. All primers used in above reactions are shown in Table 14. Overlapping PCR products were then ligated in one reaction and result in rDNA integration plasmid named pYDAB008 rDNA (FIG. 6).

TABLE 14

| Primer | SEQ ID NO: | Sequence (PacI restriction site is underlined) |
| --- | --- | --- |
| Primers Used in pYDAB008 rDNA vector construction | | |
| PacI-rDNA(R1)-R | 221 | CACCATTAATTAACCCGGGGCACCTGTCACTTTGGAA |
| rDNA (R1)-over-R | 222 | CGCGTAAGCTTTCTAGAGGCGCGCCAAGCTTTTACACTCTTGACCAGCGCA |
| AB vector-MCS-R | 223 | CCGCTGGTGGGTACCGATATCCCTGCAGGGAGCTCACGCGTAAGCTTTCTAGAGGCG |
| rDNA(R3)-over-R | 224 | CTGCAGGGATATCGGTACCCACCAGCGGCCGCAGGCCTTGGGTGCTTGCTGGCGAA |
| rDNA(R3)-over-R | 225 | ACCTCTGCATGCGAATTCTTAAGACAAATAAAATTTATAGAGACTTGT |
| rDNA(R2)-over-R | 226 | GTCTTAAGAATTCGCATGCAGAGGTAGTTTCAAGGT |
| PacI-rDNA(R2)-R | 227 | CACCATTAATTAATACGTATTTCTCGCCGAGAAAAACTT |

pYDABF 0015 (a plasmid comprising a Boles codon optimized nucleic acid of SEQ ID NO:244, encoding a xylose isomerase of SEQ ID NO:78) and pYDABF-0026 (a plasmid comprising a Boles codon optimized nucleic acid of SEQ ID NO:245, encoding a xylose isomerase of SEQ ID NO: SEQ ID NO:96) (both described in Example 10) were digested with Asc I and Kpn I restriction enzymes (New England Biolabs Inc., MA, USA) and the XI-coding insert ligated to pYDAB008 rDNA integration vector described above (FIG. 6). The resulting plasmids were named pYDABF-0033 (SEQ ID NO:78) and pYDABF-0036 (SEQ ID NO:96). Additionally, Boles codon optimized nucleic acids encoding xylose isomerase of SEQ ID NO:54 and SEQ ID NO:58 (SEQ ID NO:238 and SEQ ID NO:239, respectively) were ordered from Genewiz (Genewiz Inc., NJ, USA) were digested with Asc I and Kpn I restriction enzymes (New England Biolabs Inc., MA, USA) and ligated to pYDAB008 rDNA integration vector (FIG. 6). The codon-optimized sequences are set forth in Table 15, below:

TABLE 15

| Sequence Description | SEQ ID NO: | Sequence |
| --- | --- | --- |
| Codon optimized DNA encoding XI of SEQ ID NO: 54 | 238 | ATGGCTAAGGAATACTTCCCAGAAATTGGTAAGATTAAGTTCGAAGGTAAGGACTCTAAGAACCCAATGGCTTTCCACTACTACGACCCAGAAAAGGTTATTATGGGTAAGCCAATGAAGGACTGGTTGAGATTCGCTATGGCTTGGTGGCACACCTTGTGTGCTGAAGGTGGTGACCAATTCGGTGGTGGTACTAAGAAGTTCCCATGGAACAACGGTGCTGACGCTGTTGAAATTGCTAAGCAAAAGGCTGACGCTGGTTTCGAAATTATGCAAAAGTTGGGTATTCCATACTTCTGTTTCCACGACGTTGACTTGGTTTCTGAAGGTGCTTCTGTTGAAGAATACGAAGCTAACTTGAAGGCTATTACCGACTACTTGGCTGTTAAGATGAAGGAAACCGGAATTAAGTTGTTGTGGTCTACCGCTAACGTTTTCGGTAACGGTAGATACATGAACGGTGCTTCTACCAACCCAGACTTCGACGTTGTTGCTAGAGCTATTGTTCAAATTAAGAACGCTATTGACGCTGGTATTAAGTTGGGTGCTGAAAACTACGTTTTCTGGGGTGGTAGAGAAGGTTACATGTCTTTGTTGAACACCGACCAAAAGAGAGAAAAGGAACACATGGCTACCATGTTGACCATGGCTAGAGACTACGCTAGAGCTAAGGGTTTCAAGGGTACTTTCTTGATTGAACCAAAGCCAATGGAACCATCTAAGCACCAATACGACGTTGACACCGAAACCGTTATTGGTTTCTTGAAGGCTCACAACTTGGACAAGGACTTCAAGGTTAACATTGAAGTTAACCACGCTACCTTGGCTGGTCACACCTTCGAACACGAATTGGCTGTTGCTGTTGACAACAACATGTTGGGTTCTATTGACGCTAACAGAGGTGACTACCAAAACGGTTGGGACACCGACCAATTCCCAATTGACCAATACGAATTGGTTCAAGCTTGGATGGAAATTATTAGAGGTGGTGGTTTGGGTACAGGTGGTACTAACTTCGACGCTAAGACCAGAAGAAACTCTACCGACTTGGAAGACATTTTCATTGCTCACATTGCTGGTATGGACGCTATGGCTAGAGCTTTGGAATCTGCTGCTAAGTTGTTGGAAGAATCTCCATACAAGGCTATGAAGGCTGCTAGATACGCTTCTTTCGACAACGGTATTGGTAAGGACTTCGAAGACGGTAAGTTGACCTTGGAACAAGCTTACGAATACGGTAAGAAGGTTGGTGAACCAAAGCAAACCTCTGGTAAGCAAGAATTGTACGAAGCTATTGTTGCTATGTACGCTTAA |
| Codon optimized DNA encoding XI of SEQ ID NO: 58 | 239 | ATGGCTAAGGAATACTTCCCAGAAATTGGTAAGATTAAGTTCGAAGGTAAGGACTCTAAGAACCCAATGGCTTTCCACTACTACGACGCTGAAAAGGTTATTATGGGTAAGCCAATGAAGGAATGGTTGAGATTCGCTATGGCTTGGTGGCACACCTTGTGTGCTGAAGGTGGTGACCAA |

TABLE 15-continued

| Sequence Description | SEQ ID NO: | Sequence |
|---|---|---|
| | | TTCGGTGGTGGTACTAAGAAGTTCCCATGGAACGAAGGTACTGAC GCTGTTACCATTGCTAAGCAAAAGGCTGACGCTGGTTTCGAAATT ATGCAAAAGTTGGGTTTCCCATACTTCTGTTTCCACGACATTGAC TTGGTTTCTGAAGGTAACTCTATTGAAGAATACGAAGCTAACTTG CAAGCTATTACCGACTACTTGAAGGTTAAGATGGAAGAAACCGGA ATTAAGTTGTTGTGGTCTACCGCTAACGTTTTCGGTAACGGTAGA TACATGAACGGTGCTTCTACCAACCCAGACTTCGACGTTGTTGCT AGAGCTATTGTTCAAATTAAGAACGCTATTGACGCTGGTATTAAG TTGGGTGCTGAAAACTACGTTTTCTGGGGTGGTAGAGAAGGTTAC ATGTCTTTGTTGAACACCGACCAAAAGAGAGAAAAGGAACACATG GCTACCATGTTGACCATGGCTAGAGACTACGCTAGATCTAAGGGT TTCAAGGGTACTTTCTTGATTGAACCAAAGCCAATGGAACCATCT AAGCACCAATACGACGTTGACACCGAAACCGTTATTGGTTTCTTG AAGGCTCACAACTTGGACAAGGACTTCAAGGTTAACATTGAAGTT AACCACGCTACCTTGGCTGGTCACACCTTCGAACACGAATTGGCT GTTGCTGTTGACAACGGTATGTTGGGTTCTATTGACGCTAACAGA GGTGACTACCAAAACGGTTGGGACACCGACCAATTCCCAATTGAC CAATACGAATTGGTTCAAGCTTGGATGGAAATTATTAGAGGTGGT GGTTTGGGTACTGGTGGTACAAACTTCGACGCTAAGACCAGAAGA AACTCTACCGACTTGGAAGACATTTTCATTGCTCACATTTCTGGT ATGGACGCTATGGCTAGAGCTTTGGAATCTGCTGCTAAGTTGTTG GAAGAATCTCCATACTGTGCTATGAAGAAGGCTAGATACGCTTCT TTCGACTCTGGTATTGGTAAGGACTTCGAAGACGGTAAGTTGACC TTGGAACAAGCTTACGAATACGGTAAGAAGGTTGGTGAACCAAAG CAAACCTCTGGTAAGCAAGAATTGTACGAAGCTATTGTTGCTATG TACGCTTAA |
| Codon optimized DNA encoding XI of SEQ ID NO: 78 | 244 | ATGGCTAAGGAATATTTCCCATTCACCGGTAAGATTCCATTCGAA GGTAAGGACTCTAAGAACGTTATGGCTTTCCACTATTATGAACCA GAAAAGGTTGTTATGGGTAAGAAGATGAAGGACTGGTTGAAGTTC GCTATGGCTTGGTGGCACACCTTGGGTGGTGCTTCTGCTGACCAA TTCGGTGGTCAAACCAGATCTTATGAATGGGACAAGGCTGGTGAC GCTGTTCAAAGAGCTAAGGACAAGATGGACGCTGGTTTCGAAATT ATGGACAAGTTGGGTATTGAATATTTCTGTTTCCACGACGTTGAC TTGGTTGAAGAAGGTGACACCATTGAAGAATATGAAGCTAGAATG AAGGCTATTACCGACTATGCTCAAGAAAAGATGAAGCAATTCCCA AACATTAAGTTGTTGTGGGGTACTGCTAACGTTTTCGGTAACAAG AGATATGCTAACGGTGCTTCTACCAACCCAGACTTCGACGTTGTT GCTAGAGCTATTGTTCAAATTAAGAACGCTATTGATGCTACCATT AAGTTGGGTGGTACTAACTATGTTTTCTGGGGTGGTAGAGAAGGT TATATGTCTTTGTTGAACACCGACCAAAAGAGAGAAAAGGAACAC ATGGCTACCATGTTGACCATGGCTAGAGACTATGCTAGAGCTAAG GGTTTCAAGGGTACTTTCTTGATTGAACCAAAGCCAATGGAACCA TCTAAGCACCAATATGACGTTGACACCGAAACCGTTATTGGTTTC TTGAAGGCTCACAACTTGGACAAGGACTTCAAGGTTAACATTGAA GTTAACCACGCTACCTTGGCTGGTCACACCTTCGAACACGAATTG GCTTGTGCTGTTGACGCTGGTATGTTGGGTTCTATTGACGCTAAC AGAGGTGACGCTCAAAACGGTTGGGACACCGACCAATTCCCAATT GACAACTATGAATTGACCCAAGCTATGTTGGAAATTATTAGAAAC GGTGGTTTGGGTAACGGTGGAACCAACTTCGACGCTAAGATTAGA AGAAACTCTACCGACTTGGAAGACTTGTTCATTGCTCACATTTCT GGTATGGACGCTATGGCTAGAGCTTTGATGAACGCTGCTGACATT TTGGAAAACTCTGAATTGCCAGCTATGAAGAAGGCTAGATATGCT TCTTTCGACCAAGGTGTTGGTAAGGACTTCGAAGACGGTAAGTTG ACCTTGGAACAAGTTTATGAATATGGTAAGAAGGTTGGTGAACCA AAGCAAACCTCTGGTAAGCAAGAAAAGTATGAAACCATTGTTGCT TTGTATGCTAAGTAA |
| Codon optimized DNA encoding XI of SEQ ID NO: 96 | 245 | ATGGCTAAGGAATATTTCCCATTCATTGGTAAGGTTCCATTCGAA GGTACTGAATCTAAGAACGTTATGGCTTTCCACTATTATGAACCA GAAAAGGTTGTTATGGGTAAGAAGATGAAGGACTGGTTGAAGTTC GCTATGGCTTGGTGGCACACCTTGGGTGGTGCTTCTGCTGACCAA TTCGGTGGTCAAACCAGATCTTATGAATGGGACAAGGCTGCTGAC GCTGTTCAAAGAGCTAAGGACAAGATGGACGCTGGTTTCGAAATT ATGGACAAGTTGGGTATTGAATATTTCTGTTTCCACGACGTTGAC TTGGTTGAAGAAGGTGAAACCGTTGCTGAATATGAAGCTAGAATG AAGGTTATTACCGACTATGCTTTGGAAAAGATGCAACAATTCCCA AACATTAAGTTGTTGTGGGGTACTGCTAACGTTTTCGGTCACAAG AGATATGCTAACGGTGCTTCTACCAACCCAGACTTCGACGTTGTT GCTAGAGCTATTGTTCAAATTAAGAACGCTATTGATGCTACCATT AAGTTGGGTGGTACTAACTATGTTTTCTGGGGTGGTAGAGAAGGT TATATGTCTTTGTTGAACACCGACCAAAAGAGAGAAAAGGAACAC ATGGCTACCATGTTGACCATGGCTAGAGACTATGCTAGAGCTAAG GGTTTCAAGGGTACTTTCTTGATTGAACCAAAGCCAATGGAACCA TCTAAGCACCAATATGACGTTGACACCGAAACCGTTATTGGTTTC TTGAGGGCTCACGGTTTGGACAAGGACTTCAAGGTTAACATTGAA |

TABLE 15-continued

| Sequence Description | SEQ ID NO: | Sequence |
|---|---|---|
| | | GTTAACCACGCTACCTTGGCTGGTCACACCTTCGAACACGAATTG<br>GCTTGTGCTGTTGACGCTGGTATGTTGGGTTCTATTGACGCTAAC<br>AGAGGTGACGCTCAAAACGGTTGGGACACCGACCAATTCCCAATT<br>GACAACTATGAATTGACCCAAGCTATGATGGAAATTATTAGAAAC<br>GGTGGTTTGGGTAACGGTGGAACCAACTTCGACGCTAAGATTAGA<br>AGAAACTCTACCGACTTGGAAGACTTGTTCATTGCTCACATTTCT<br>GGTATGGACGCTATGGCTAGAGCTTTGATGAACGCTGCTGCTATT<br>TTGGAAGAATCTGAATTGCCAGCTATGAAGAAGGCTAGATATGCT<br>TCTTTCGACGAAGGTATTGGTAAGGACTTCGAAGACGGTAAGTTG<br>TCTTTGGAACAAGTTTATGAATATGGTAAGAAGGTTGAAGAACCA<br>AAGCAAACCTCTGGTAAGCAAGAAAAGTATGAAACCATTGTTGCT<br>TTGTATGCTAAGTAA |

The resulting plasmids were named pYDABF-0033 (SEQ ID NO:78) and pYDABF-0036 (SEQ ID NO:96), pYDABF-0231 (SEQ ID NO:54) and pYDABF-0232 (SEQ ID NO:58).

The rDNA integration cassette was linearized by Pac I restriction enzyme digestion (New England Biolabs Inc., MA, USA) and purified with DNA column purification kit (Zymo Research, Irvine, Calif., USA). The integration cassette was transformed into modified haploid *S. cerevisiae* strain pBPB007 (MATa::ura3) and pBPB008 (MAT alpha::ura3) using the standard protocol described in previous examples. Transformants were plated on SC-xylose (SC complete+2% xylose) agar plates, about 2-3 days at about 30° C. Colonies that grew on SC-xylose agar plates were then checked by colony PCR analysis with primer sets shown in Table 16 (SEQ ID NOs:228, 229, 230, 231) to confirm the presence of xylose isomerase in the genome.

TABLE 16

Primers Used in Integration Verification

| Primer | SEQ ID NO: | Sequence |
|---|---|---|
| N16PCR_F | 228 | CCCCATCGACAACTACGAGCTCACT |
| N16PCR_R | 229 | CAACTTGCCGTCCTCGAAGTCCTTG |
| N05PCR_F | 230 | CGAGCCTGAGAAGGTCGTGATGGGA |
| N05PCR_R | 231 | TACGTCGAAGTCGGGGTTGGTAGAA |
| N08PCR_F | 240 | TACTTGGCTGTTAAGATGAAG |
| N08PCR_R | 241 | ATCTAGCAGCCTTCATAGCCTT |
| N17PCR_F | 242 | CGAAGGTACTGACGCTGTTACC |
| N17PCR_R | 243 | CGAAAGAAGCGTATCTAGCCTT |

Confirmed haploid strains were BD31328 (MATa), BD31336 (MATalpha), BD31526 (MATa) and BD31527 (MATalpha), BD34364 (MATa) and BD34365 (MATalpha), BD34366 (MATa) and BD34367 (MATalpha). Diploid strains BD31378 (expressing a xylose isomerase of SEQ ID NO:96), BD31365 (expressing a xylose isomerase of SEQ ID NO:78), BD34369 (expressing a xylose isomerase of SEQ ID NO:54) and BD34377 (expressing a xylose isomerase of SEQ ID NO:58) were generated by conventional plate mating on YPXylose (YP+2% xylose) agar plates, about 2 days at about 30° C. Colony PCR with specific primers checking mating types were performed (shown in Table 17) and single colonies having MATa and MATalpha were picked as diploid strains BD 31378 (SEQ ID NO:96), BD31365 (SEQ ID NO:78), BD34369 (SEQ ID NO:54) and BD34377 (SEQ ID NO:58).

A linear fragment encoding the URA3 sequence (SEQ ID NO:237; TTAATTAAGTTAATTACCTTTTTTGCGAG-GCATATTTATGGTGAAGAATAAGTTTTGACCATC AAAGAAGGTTAATGTGGCTGTGGTTTCAGGGTC-CATAAAGCTTTTCAATTCATCATTTTTTTT TTAT-TCTTTTTTTTGATTCCGGTTTCCTTGAAATTTTTTT-GATTCGGTAATCTCCGAACAGAAG GAAGAACGAAGGAAGGAGCACAGACTTAGATTG-GTATATATACGCATATGTAGTGTTGAAG AAACAT-GAAATTGCCCAGTATTCTTAACCCAACTGCACA-GAACAAAAACCTGCAGGAAACG AAGATAAATCATGTCGAAAGCTA-CATATAAGGAACGTGCTGCTACTCATCCTAGTCCT-GTTG CTGCCAAGCTATTTAATATCATGCAC-GAAAAGCAAACAAACTTGTGTGCTTCATTGGATGTT CGTACCACCAAGGAATTACTGGAGTTAGTT-GAAGCATTAGGTCCCAAAATTTGTTTACTAAA AACACATGTGGATATCTTGACTGATTTTTCCATG-GAGGGCACAGTTAAGCCGCTAAAGGCAT TATC-CGCCAAGTACAATTTTTTACTCTTCGAAGACA-GAAAATTTGCTGACATTGGTAATACA GTCAAATTGCAGTACTCTGCGGGTGTATACA-GAATAGCAGAATGGGCAGACATTACGAATG CACACGGTGTGGTGGGCCCAGGTATTGTTAGCG-GTTTGAAGCAGGCGGCAGAAGAAGTAAC AAAGGAACCTAGAGGCCTTTTGATGTTAGCAGAAT-TGTCATGCAAGGGCTCCCTAGCTACTG GAGAATATACTAAGGGTACTGTTGACATTGC-GAAGAGCGACAAAGATTTTGTTATCGGCTTT ATT-GCTCAAAGAGACATGGGTGGAAGAGATGAAGGT-TACGATTGGTTGATTATGACACCCG GTGTGGGTTTAGATGACAAGGGAGACGCAT-TGGGTCAACAGTATAGAACCGTGGATGATGT GGTCTCTACAGGATCTGACATTATTATTGTTG-GAAGAGGACTATTTGCAAAGGGAAGGGATG CTAAGGTAGAGGGTGAACGTTACAGAAAAGCAG-GCTGGGAAGCATATTTGAGAAGATGCGG CCAG-CAAAACTAAAAAACTGTATTATAAGTAAATGCATG-TATACTAAACTCACAAATTAGA GCTTCAATTTAATTATATCAGTTATTAC-CCGGGAATCTCGGTCGTAATGATTTTTATAATGAC GAAAAAAAAAAAAATTGGAAAGAAAAAGCTTCATG-GCCTTTATAAAAAGGAACCATCCAATA CCTCGCCA-GAACCAAGTAACAGTATTTTACGGTTAATTAA) was transformed into BD 31378 (SEQ ID NO:96), BD31365 (SEQ ID NO:78), BD34369 (SEQ ID NO:54) and BD34377

(SEQ ID NO:58) by a conventional transformation protocol, and transformants were plated on SCXylose-URA (Synthetic Complete, Uracil dropout) for selection. Colonies were checked by PCR with primers shown in Table 17, SEQ ID NO:235, SEQ ID NO:236). Confirmed strains are BD31446 (SEQ ID NO:78), BD31448 (SEQ ID NO:96), BD34373 (SEQ ID NO:54) and BD34378 (SEQ ID NO:58).

TABLE 17

Primers Used in Mating Type Verification

| Primer | SEQ ID NO: | Sequence |
|---|---|---|
| 1-mating type-R | 232 | AGTCACATCAAGATCGTTTAT |
| 2-mating type alpha-F | 233 | GCACGGAATATGGGACTACTT |
| 3-mating type a-F | 234 | ACTCCACTTCAAGTAAGAGTT |
| Ura fix-F | 235 | GAACAAAAACCTGCAGGAAACGAAGAT |
| Ura fix-R | 236 | GCTCTAATTTGTGAGTTTAGTATACATGCAT |

Table 18 below shows the genotypes of the resulting yeast strains:

TABLE 18

Strain Construction

| Name | Parent Strain | Description |
|---|---|---|
| pBPB007 | yBPA130 | MATa, ura3, adh2 :: TAL1-XKS1, pho13:: TKL1-XKS1, gre3:: RPE1-RKI1 and YLR388.5:: GAL2 |
| pBPB008 | yBPA136 | MATalpha, ura3, adh2 :: TAL1-XKS1, pho13:: TKL1-XKS1, gre3:: RPE1-RKI1 and YLR388.5:: GAL2 |
| BD31328 | pBPB007 | MATa, ura3, adh2 :: TAL1-XKS1, pho13:: TKL1-XKS1, gre3:: RPE1-RKI1 and YLR388.5:: GAL2, rDNA::XI (SEQ ID NO: 96) |
| BD31336 | pBPB008 | MATalpha, ura3, adh2 :: TAL1-XKS1, pho13:: TKL1-XKS1, gre3:: RPE1-RKI1 and YLR388.5:: GAL2, rDNA::XI (SEQ ID NO: 96) |
| BD31526 | pBPB007 | MATa, ura3, adh2 :: TAL1-XKS1, pho13:: TKL1-XKS1, gre3:: RPE1-RKI1 and YLR388.5:: GAL2, rDNA::XI (SEQ ID NO: 78) |
| BD31527 | pBPB008 | MATalpha, ura3, adh2 :: TAL1-XKS1, pho13:: TKL1-XKS1, gre3:: RPE1-RKI1 and YLR388.5:: GAL2, rDNA::XI (SEQ ID NO: 78) |
| BD34364 | pBPB007 | MATa, ura3, adh2 :: TAL1-XKS1, pho13:: TKL1-XKS1, gre3:: RPE1-RKI1 and YLR388.5:: GAL2, rDNA::XI (SEQ ID NO: 238) |
| BD34365 | pBPB008 | MATalpha, ura3, adh2 :: TAL1-XKS1, pho13:: TKL1-XKS1, gre3:: RPE1-RKI1 and YLR388.5:: GAL2, rDNA::XI (SEQ ID NO: 238) |
| BD34366 | pBPB007 | MATa, ura3, adh2 :: TAL1-XKS1, pho13:: TKL1-XKS1, gre3:: RPE1-RKI1 and YLR388.5:: GAL2, rDNA::XI (SEQ ID NO: 239) |
| BD34367 | pBPB008 | MATalpha, ura3, adh2 :: TAL1-XKS1, pho13:: TKL1-XKS1, gre3:: RPE1-RKI1 and YLR388.5:: GAL2, rDNA::XI (SEQ ID NO: 239) |
| BD31378 | BD31328 BD31336 | MATa/alpha, ura3, adh2 :: TAL1-XKS1, pho13:: TKL1-XKS1, gre3:: RPE1-RKI1 and YLR388.5:: GAL2, rDNA::XI (SEQ ID NO: 96) |

TABLE 18-continued

Strain Construction

| Name | Parent Strain | Description |
|---|---|---|
| BD31365 | BD31526 BD31527 | MATa/alpha, ura3, adh2 :: TAL1-XKS1, pho13:: TKL1-XKS1, gre3:: RPE1-RKI1 and YLR388.5:: GAL2, rDNA::XI (SEQ ID NO: 78) |
| BD34369 | BD34364 BD34365 | MATa/alpha, ura3, adh2 :: TAL1-XKS1, pho13:: TKL1-XKS1, gre3:: RPE1-RKI1 and YLR388.5:: GAL2, rDNA::XI (SEQ ID NO: 238) |
| BD34377 | BD34366 BD34367 | MATa/alpha, ura3, adh2 :: TAL1-XKS1, pho13:: TKL1-XKS1, gre3:: RPE1-RKI1 and YLR388.5:: GAL2, rDNA::XI (SEQ ID NO: 239) |
| BD31448 | BD31378 | MATa/alpha, adh2 :: TAL1-XKS1, pho13:: TKL1-XKS1, gre3:: RPE1-RKI1 and YLR388.5:: GAL2, rDNA::XI (SEQ ID NO: 96) |
| BD31446 | BD31365 | MATa/alpha. adh2 :: TAL1-XKS1, pho13:: TKL1-XKS1, gre3:: RPE1-RKI1 and YLR388.5:: GAL2, rDNA::XI (SEQ ID NO: 78) |

5.13 Example 12: Fermentation Performance of Yeast Strain Expressing Different Xylose Isomerases Fermentation performances of two different XI-expressing yeast strains were evaluated using the DasGip fermentation systems (Eppendorf, Inc.). DasGip fermenters allowed close control over agitation, pH, and temperature ensuring consistency of the environment during fermentation. DasGip fermenters were used to test performance of the yeast strains expressing the XI genes on hydrolysate (Hz) (neutralized with magnesium bases) as a primary carbon source. Prior to the start of fermentation strains were subjected to propagation testing consisting of two steps as described below.

Seed 1:

About 1 ml of strain glycerol stock was inoculated into about 100 ml of YP (Yeast extract, Peptone) medium containing about 2% glucose and about 1% xylose in the 250 ml bellco baffled flask (Bellco, Inc.). Strains were cultivated at about 30° C. with about 200 rpm agitation for at least 18 hours until at full saturation. Optical density was assessed by measuring light absorbance at wavelength of 600 nm.

Seed 2:

About 20 ml of saturated SEED 1 (see preceding paragraph) was inoculated into 3 L Bioflo unit (New Brunswick, Inc.) containing about 2.1 L of basal medium at pH 6.0 (1% v/v inoculation). Cultivation was conducted at about 30° C. in a fed batch mode with constant air flow of about 2 L/min. Agitation ramp (rpm) was about 200-626 rpm over about 15 hours starting at about 5 hours of elapsed fermentation time (EFT). Feeding profile was about 0-4.8 ml/min over 20 hours. The basal medium contained (per 1 L): about 20% of neutralized hydrolysate (Hz); about 20 g/L sucrose (from cane juice); about 35 ml of nutrients mixture (Table 19), about 1 ml of vitamin mixture (Table 20); about 0.4 ml of antifoam 1410 (Dow Corning, Inc.) and water. Feed medium contained (per 1 L): about 20% neutralized hydrolysate (Hz), about 110 g/L sucrose (from cane juice), about 35 ml of nutrient mixture; about 1 ml of vitamin mixture, about 0.4 ml of antifoam 1410 (Dow Corning, Inc.) and water.

TABLE 19

| Nutrients mixture | | |
|---|---|---|
| Component | FW g/mol | Conc. |
| $KH_2PO_4$ $H_2O$ | 154.1 | 99.1 g/L |
| Urea | 60.06 | 65.6 g/L |
| $MgSO_4$—$7H_2O$ | 192.4 | 14.6 g/L |
| DI Water | NA | To 1.0 L |

TABLE 20

| Vitamin mixture (1000x) | |
|---|---|
| Components | mM |
| $ZnSO_4$ | 100 |
| $H_3BO_3$ | 24 |
| KI | 1.8 |
| $MnSO_4$ | 20 |
| $CuSO_4$ | 10 |
| $Na_2MoO_4$ | 1.5 |
| $CoCl_2$ | 1.5 |
| $FeCl_3$ | 1.23 |

Figure 7A:
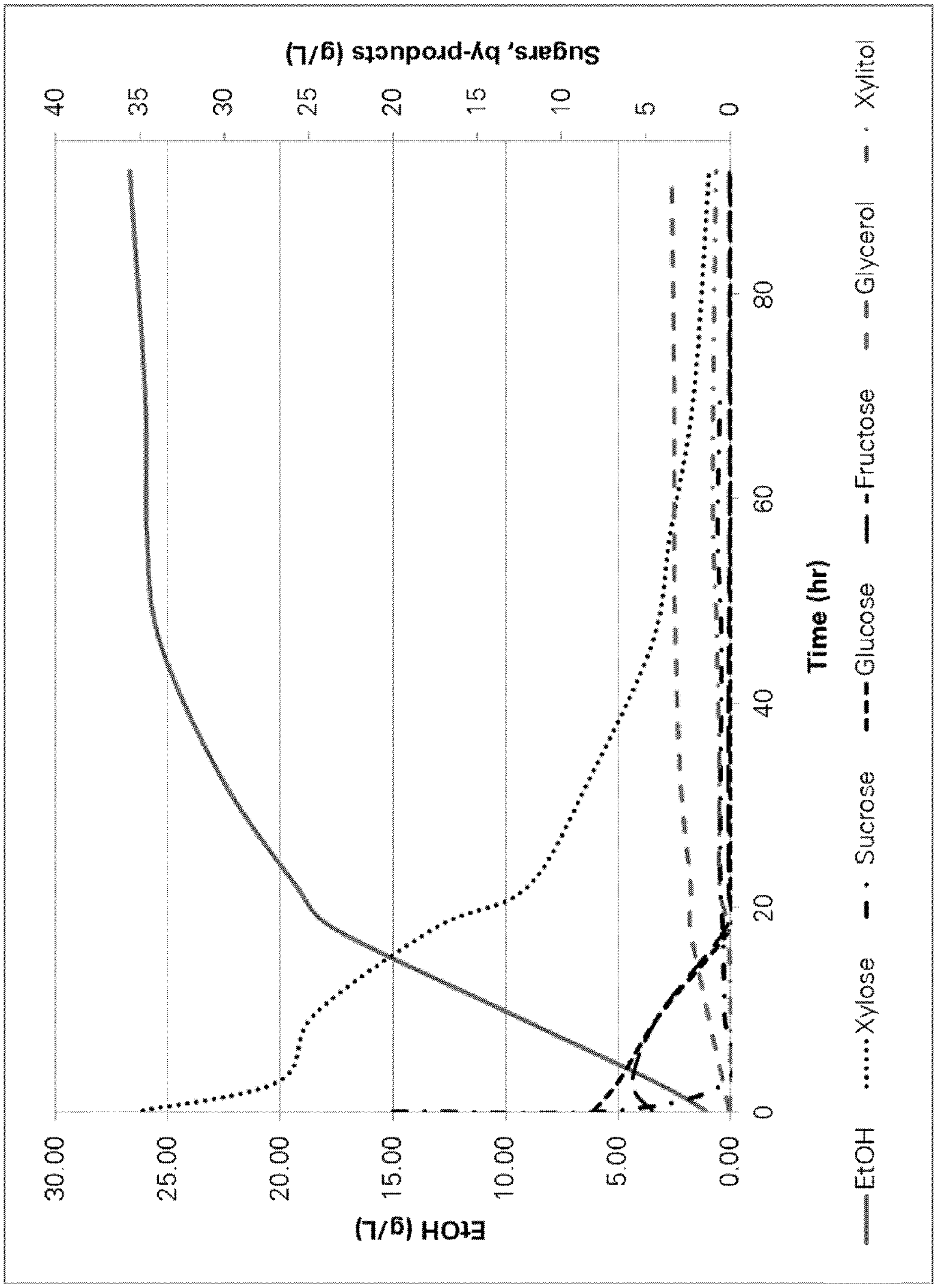
FIGS. 7A-7D show monosaccharide (including xylose) utilization and ethanol production by strains of industrial *S. cerevisiae* with multiple copies of XI clones integrated into ribosomal DNA loci.
Figure 7B:
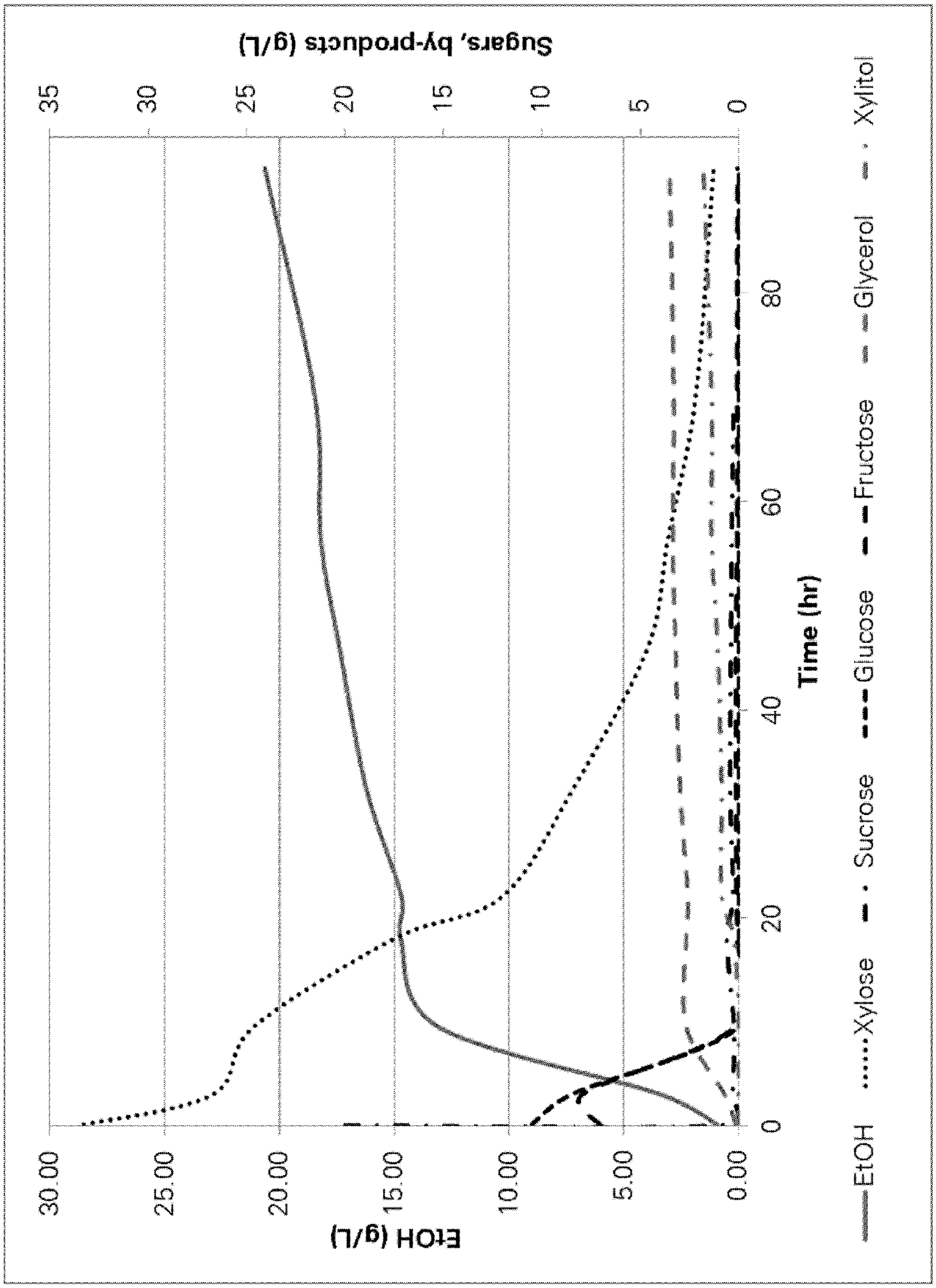

DasGip Fermentation:

Strains were tested in small scale fermentation using the DasGip system in the industrially relevant medium containing detoxified hydrolysate and sucrose. Strains were propagated as described above; DasGip inoculation was performed using the following protocol:

Cell dry weight of SEED 2 was assessed based on the final optical density. Cell dry weight and optical density (600 nm) correlation was used to estimate the volume of the SEED 2 culture needed for fermentation. Targeted inoculation level was about 7% v/v; about 1.5 g/L cell dry weight. Appropriate volume of SEED 2 culture was harvested by centrifugation (about 5000 rpm for 10 min) to pellet the cells and resuspended in about 17.5 ml of PBS. Resuspended cell solution was used to inoculate a 500 ml DasGip unit containing about 250 ml of detoxified hydrolysate and nutrient solution (about 3.5 ml/100 ml of medium). Fermentation was performed at about 32° C. at pH 6.3 with about 200 rpm. The duration of fermentation was about 92 hours with regular sampling. Sampling was conducted by a 25 ml steriological pipette through the port in the head plate of the DasGip unit. About 3 ml of culture were taken out, harvested by centrifugation (about 5000 rpm for 10 min) to pellet the cells and the supernatant was submitted for analysis. Standard analytical techniques such as high-pressure liquid chromatography (HPLC) were used to determine concentration of sugars and ethanol in the medium. Fermentation performances for yeast strains BD31378 (expressing a xylose isomerase of SEQ ID NO:96) and BD31365 (expressing a xylose isomerase of SEQ ID NO:78) are presented in FIG. 7A and FIG. 7B, respectively.

Serum Bottle Fermentation:

Fermentation performances of BD34373 (SEQ ID NO:54) and BD34378 (SEQ ID NO:58) were evaluated using the serum bottle fermentation system. New Wheaton Thin-Flng Lyp Stopper (VWR Inc., PA, USA) wrap individual 125 mL Anaerobic Media bottles (VWR Inc., PA, USA) allowed close control over agitation, pH, and temperature ensuring consistency of the environment during fermentation. Serum bottle fermentations were used to test performance of the yeast strains expressing XI genes on clean sugar media (see Table 21 (below), supplemented with nutrients (Table 19, above) and vitamins (Table 20, above)).

TABLE 21

| Clean sugar | |
|---|---|
| Component | Conc. |
| Glucose | 80 g/L |
| Xylose | 80 g/L |
| Arabinose | 5.0 g/L |
| Acetic acid | 8.0 g/L |

Figure 7C:
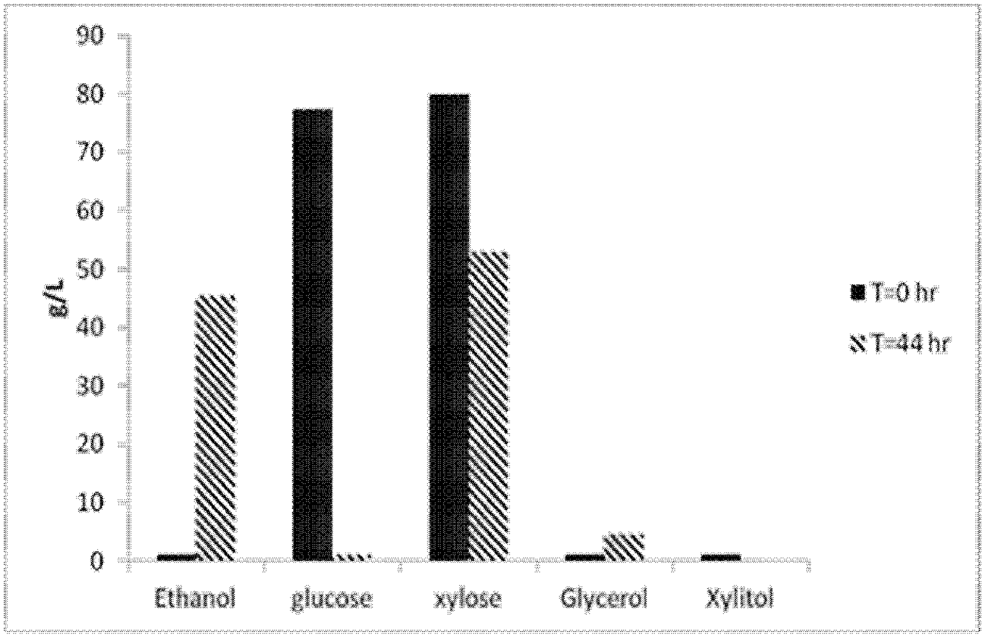
Figure 7D:
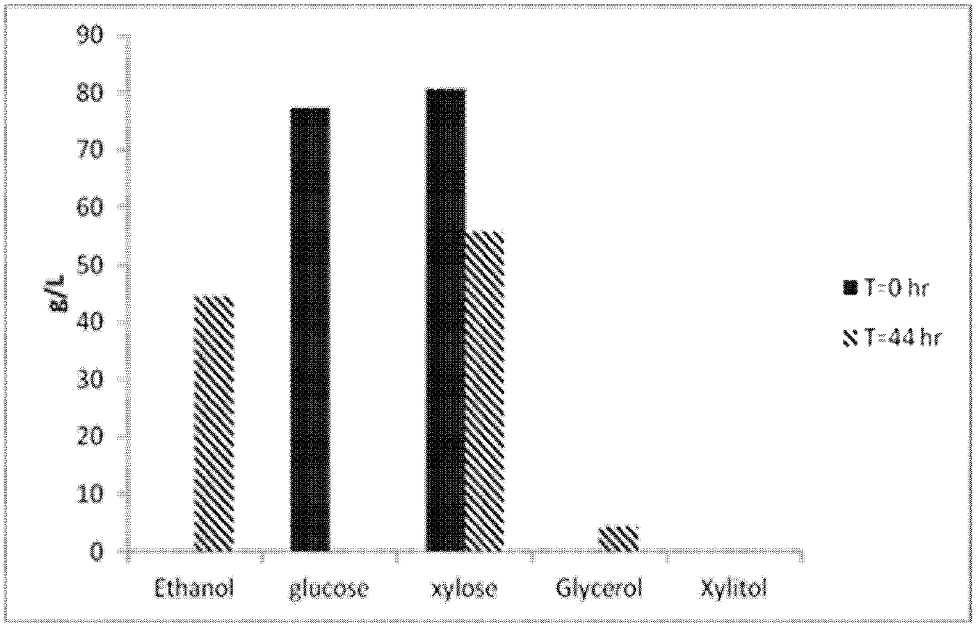

Yeast cells were inoculated into about 200 ml of YP (Yeast extract, Peptone) medium containing about 0.5% glucose and about 3% xylose in the 500 ml bellco baffled flask (Bellco, Inc.). Strains were cultivated at about 30° C. with about 200 rpm agitation for at least 18 hours until at full saturation. Optical density was assessed by measuring light absorbance at wavelength of 600 nm. Targeted inoculation level was about 1.5 g/L cell dry weight. Appropriate volume of SEED culture was harvested by centrifugation (about 3500 rpm for 10 min) to pellet the cells and resuspended in about 20 ml of media. Resuspended cell solution was used to inoculate a 150 ml serum bottle containing about 90 ml of fermentation media. The autoclaved stopper was placed into serum bottles and then the serum bottles were clamped with aluminium seals (Bellco Inc., USA) by using a seal crimper (Bellco Inc., USA). The aluminium seal cap was peeled off and then the needle (Fisher, USA) inserted. Fermentation was performed at about 35° C., pH 5.5 with about 200 rpm. The duration of fermentation was about 44 hours. Fermentation performances for yeast strains BD34373 (SEQ ID NO:54) is presented in FIG. 7C and BD34378 (SEQ ID NO:58) are presented in FIG. 7D.

5.14 Example 13: Comparative Activity of XI's Encoded by Codon Optimized vs. Non-Optimized Open Reading Frames The coding sequences for the XIs of SEQ ID NOs:38, 78 and 96 were subject to codon optimization using two approaches: the Boles codon optimization method and the DNA 2.0 Gene Designer software. The codon optimized sequences are set forth in Table 22 below:

TABLE 22

| Sequence Description | SEQ ID NO: | Sequence |
|---|---|---|
| Boles codon optimized DNA encoding XI of SEQ ID NO: 78 | 244 | ATGGCTAAGGAATATTTCCCATTCACCGGTAAGATTCCATTCGAA<br>GGTAAGGACTCTAAGAACGTTATGGCTTTCCACTATTATGAACCA<br>GAAAAGGTTGTTATGGGTAAGAAGATGAAGGACTGGTTGAAGTTC<br>GCTATGGCTTGGTGGCACACCTTGGGTGGTGCTTCTGCTGACCAA<br>TTCGGTGGTCAAACCAGATCTTATGAATGGGACAAGGCTGGTGAC<br>GCTGTTCAAAGAGCTAAGGACAAGATGGACGCTGGTTTCGAAATT<br>ATGGACAAGTTGGGTATTGAATATTTCTGTTTCCACGACGTTGAC |

TABLE 22-continued

| Sequence Description | SEQ ID NO: | Sequence |
|---|---|---|
| | | TTGGTTGAAGAAGGTGACACCATTGAAGAATATGAAGCTAGAATG<br>AAGGCTATTACCGACTATGCTCAAGAAAAGATGAAGCAATTCCCA<br>AACATTAAGTTGTTGTGGGGTACTGCTAACGTTTTCGGTAACAAG<br>AGATATGCTAACGGTGCTTCTACCAACCCAGACTTCGACGTTGTT<br>GCTAGAGCTATTGTTCAAATTAAGAACGCTATTGATGCTACCATT<br>AAGTTGGGTGGTACTAACTATGTTTTCTGGGGTGGTAGAGAAGGT<br>TATATGTCTTTGTTGAACACCGACCAAAAGAGAGAAAAGGAACAC<br>ATGGCTACCATGTTGACCATGGCTAGAGACTATGCTAGAGCTAAG<br>GGTTTCAAGGGTACTTTCTTGATTGAACCAAAGCCAATGGAACCA<br>TCTAAGCACCAATATGACGTTGACACCGAAACCGTTATTGGTTTC<br>TTGAAGGCTCACAACTTGGACAAGGACTTCAAGGTTAACATTGAA<br>GTTAACCACGCTACCTTGGCTGGTCACACCTTCGAACACGAATTG<br>GCTTGTGCTGTTGACGCTGGTATGTTGGGTTCTATTGACGCTAAC<br>AGAGGTGACGCTCAAAACGGTTGGGACACCGACCAATTCCCAATT<br>GACAACTATGAATTGACCCAAGCTATGTTGGAAATTATTAGAAAC<br>GGTGGTTTGGGTAACGGTGGAACCAACTTCGACGCTAAGATTAGA<br>AGAAACTCTACCGACTTGGAAGACTTGTTCATTGCTCACATTTCT<br>GGTATGGACGCTATGGCTAGAGCTTTGATGAACGCTGCTGACATT<br>TTGGAAAACTCTGAATTGCCAGCTATGAAGAAGGCTAGATATGCT<br>TCTTTCGACCAAGGTGTTGGTAAGGACTTCGAAGACGGTAAGTTG<br>ACCTTGGAACAAGTTTATGAATATGGTAAGAAGGTTGGTGAACCA<br>AAGCAAACCTCTGGTAAGCAAGAAAAGTATGAAACCATTGTTGCT<br>TTGTATGCTAAGTAA |
| Boles codon optimized DNA encoding XI of SEQ ID NO: 96 | 245 | ATGGCTAAGGAATATTTCCCATTCATTGGTAAGGTTCCATTCGAA<br>GGTACTGAATCTAAGAACGTTATGGCTTTCCACTATTATGAACCA<br>GAAAAGGTTGTTATGGGTAAGAAGATGAAGGACTGGTTGAAGTTC<br>GCTATGGCTTGGTGGCACACCTTGGGTGGTGCTTCTGCTGACCAA<br>TTCGGTGGTCAAACCAGATCTTATGAATGGGACAAGGCTGCTGAC<br>GCTGTTCAAAGAGCTAAGGACAAGATGGACGCTGGTTTCGAAATT<br>ATGGACAAGTTGGGTATTGAATATTTCTGTTTCCACGACGTTGAC<br>TTGGTTGAAGAAGGTGAAACCGTTGCTGAATATGAAGCTAGAATG<br>AAGGTTATTACCGACTATGCTTTGGAAAAGATGCAACAATTCCCA<br>AACATTAAGTTGTTGTGGGGTACTGCTAACGTTTTCGGTCACAAG<br>AGATATGCTAACGGTGCTTCTACCAACCCAGACTTCGACGTTGTT<br>GCTAGAGCTATTGTTCAAATTAAGAACGCTATTGATGCTACCATT<br>AAGTTGGGTGGTACTAACTATGTTTTCTGGGGTGGTAGAGAAGGT<br>TATATGTCTTTGTTGAACACCGACCAAAAGAGAGAAAAGGAACAC<br>ATGGCTACCATGTTGACCATGGCTAGAGACTATGCTAGAGCTAAG<br>GGTTTCAAGGGTACTTTCTTGATTGAACCAAAGCCAATGGAACCA<br>TCTAAGCACCAATATGACGTTGACACCGAAACCGTTATTGGTTTC<br>TTGAGGGCTCACGGTTTGGACAAGGACTTCAAGGTTAACATTGAA<br>GTTAACCACGCTACCTTGGCTGGTCACACCTTCGAACACGAATTG<br>GCTTGTGCTGTTGACGCTGGTATGTTGGGTTCTATTGACGCTAAC<br>AGAGGTGACGCTCAAAACGGTTGGGACACCGACCAATTCCCAATT<br>GACAACTATGAATTGACCCAAGCTATGATGGAAATTATTAGAAAC<br>GGTGGTTTGGGTAACGGTGGAACCAACTTCGACGCTAAGATTAGA<br>AGAAACTCTACCGACTTGGAAGACTTGTTCATTGCTCACATTTCT<br>GGTATGGACGCTATGGCTAGAGCTTTGATGAACGCTGCTGCTATT<br>TTGGAAGAATCTGAATTGCCAGCTATGAAGAAGGCTAGATATGCT<br>TCTTTCGACGAAGGTATTGGTAAGGACTTCGAAGACGGTAAGTTG<br>TCTTTGGAACAAGTTTATGAATATGGTAAGAAGGTTGAAGAACCA<br>AAGCAAACCTCTGGTAAGCAAGAAAAGTATGAAACCATTGTTGCT<br>TTGTATGCTAAGTAA |
| Boles codon optimized DNA encoding XI of SEQ ID NO: 38 | 246 | ATGAAGGAAATTTTCCCAAACATTCCAGAAATTAAGTTCGAAGGT<br>AAGGACTCTAAGAACCCATTCGCTTTCCACTATTATAACCCAGAC<br>CAAATTATTTTGGGTAAGCCAATGAAGGAACACTTGCCATTCGCT<br>ATGGCTTGGTGGCACAACTTGGGTGCTACCGGTGTTGACATGTTC<br>GGTGCTGGTCCAGCTGACAAGTCTTTCGGTGCTAAGGTTGGTACT<br>ATGGAACACGCTAAGGCTAAGGTTGACGCTGGTTTCGAATTCATG<br>AAGAAGTTGGGTATTAGATATTTCTGTTTCCACGACGTTGACTTG<br>GTTCCAGAATGTGCTGACATTAAGGACACCAACAAGGAATTGGAC<br>GAAATTTCTGACTATATTTTGGAAAAGATGAAGGGTACTGACATT<br>AAGTGTTTGTGGGGTACTGCTAACATGTTCTCTAACCCAAGATTC<br>TGTAACGGTGCTGGTTCTACCAACTCTGCTGACGTTTTCGCTTTC<br>GCTGCTGCTCAAGTTAAGAAGGCTTTGGACATTACCGTTAAGTTG<br>GGTGGTAGAGGTTATGTTTTCTGGGGTGGTAGAGAAGGTTATGAA<br>ACCTTGTTGAACACCGACGTTAAGTTCGAACAAGAAAACATTGCT<br>AGATTGATGAAGATGGCTGTTGAATATGGTAGATCTATTGGTTTC<br>AAGGGTGACTTCTATATTGAACCAAAGCCAAAGGAACCAATGAAG<br>CACCAATATGACTTCGACGCTGCTACCGCTATTGGTTTCTTGAGG<br>GCTCACGGTTTGGACAAGGACTTCAAGTTGAACATTGAAGCTAAC<br>CACGCTACCTTGGCTGGTCACACCTTCCAACACGACTTGAGAATT<br>TCTGCTATTAACGGTATGTTGGGTTCTATTGACGCTAACCAAGGT<br>GACATGTTGTTGGGTTGGGACACCGACGAATTCCCATTCGACGTT |

TABLE 22-continued

| Sequence Description | SEQ ID NO: | Sequence |
|---|---|---|
| | | TATTCTGCTACCCAATGTATGTATGAAGTTTTGAAGAACGGTGGT TTGACCGGTGGTTTCAACTTCGACTCTAAGACCAGAAGACCATCT TATACCATGGAAGACATGTTCTTGGCTTATATTTTGGGTATGGAC ACCTTCGCTTTGGGTTTGATTAAGGCTGCTCAAATTATTGAAGAC GGTAGAATTGACCAATTCATTGAAAAGAAGTATTCTTCTTTCAGA GAAACCGAAATTGGTCAAAAGATTTTGAACAACAAGACCTCTTTG AAGGAATTGTCTGACTATGCTTGTAAGATGGGTGCTCCAGAATTG CCAGGTTCTGGTAGACAAGAAATGTTGGAAGCTATTGTTAACGAC GTTTTGTTCGGTAAGTAA |
| DNA 2.0 codon optimized DNA encoding XI of SEQ ID NO: 78 | 247 | ATGGCTAAGGAATACTTTCCATTCACCGGAAAGATACCATTTGAA GGTAAAGATTCTAAAAACGTAATGGCTTTTCATTATTACGAACCA GAAAAAGTTGTTATGGGCAAAAAGATGAAAGATTGGTTGAAATTT GCGATGGCTTGGTGGCATACACTCGGGGGAGCTTCCGCTGATCAA TTTGGCGGACAAACCAGATCATACGAATGGGATAAAGCAGGCGAT GCCGTGCAGAGAGCAAAGGATAAAATGGATGCTGGTTTCGAAATT ATGGATAAGCTAGGTATCGAATACTTCTGCTTCCATGACGTCGAT TTGGTTGAAGAGGGCGATACTATCGAGGAATACGAGGCGAGAATG AAGGCTATAACAGACTACGCCCAGGAGAAAATGAAACAATTTCCT AACATCAAATTACTCTGGGGTACTGCCAATGTGTTTGGTAACAAA AGATACGCAAACGGGGCTTCAACTAATCCTGACTTCGATGTTGTT GCAAGAGCCATTGTTCAAATCAAAAACGCGATAGACGCTACTATT AAACTAGGTGGCACGAATTACGTCTTTTGGGGTGGAAGGGAAGGT TACATGTCTCTGCTTAATACAGATCAGAAGAGAGAGAAGGAACAC ATGGCAACAATGCTCACTATGGCCCGTGACTACGCAAGAGCAAAA GGTTTTAAGGGCACTTTCCTTATCGAACCAAAGCCTATGGAACCA TCAAAACACCAATATGATGTTGACACAGAAACTGTGATCGGCTTT TTGAAAGCTCATAACTTGGACAAGGATTTCAAAGTAAACATTGAA GTTAATCATGCTACACTAGCAGGACACACATTTGAACACGAACTG GCCTGTGCGGTAGATGCAGGGATGCTGGGTTCTATCGACGCTAAT AGAGGGGATGCTCAAAATGGTTGGGATACCGATCAATTTCCAATC GACAATTACGAATTAACACAAGCTATGTTGGAGATTATTAGAAAT GGAGGTTTGGGTAATGGGGGTACAAACTTCGATGCTAAGATTCGT CGAAATTCCACAGACTTAGAAGATTTGTTCATTGCGCATATATCT GGTATGGATGCTATGGCCAGAGCATTAATGAATGCCGCTGACATC TTAGAAAACAGTGAACTTCCAGCAATGAAAAAGGCCAGATATGCC TCTTTCGATCAAGGTGTAGGAAAAGATTTTGAGGACGGCAAGTTG ACTTTAGAACAAGTCTATGAATACGGTAAAAAGGTCGGCGAACCT AAGCAAACCAGCGGAAAGCAAGAGAAATACGAGACTATCGTGGCT CTTTATGCAAAATAA |
| DNA 2.0 codon optimized DNA encoding XI of SEQ ID NO: 96 | 248 | ATGGCCAAGGAGTACTTCCCTTTTATCGGCAAGGTCCCATTTGAA GGGACAGAATCCAAAAACGTCATGGCTTTTCACTACTATGAACCT GAGAAGGTAGTTATGGGTAAAAAGATGAAAGATTGGTTGAAGTTT GCAATGGCATGGTGGCATACCTTGGGTGGGGCCTCTGCTGATCAA TTTGGAGGACAAACTAGATCATACGAATGGGATAAAGCAGCTGAT GCCGTTCAAAGAGCCAAAGATAAAATGGATGCCGGGTTCGAAATC ATGGACAAATTGGGTATCGAATATTTCTGCTTCCATGATGTAGAC CTTGTTGAGGAGGGTGAAACCGTCGCTGAATATGAGGCGAGAATG AAGGTTATTACGGATTACGCACTAGAAAAGATGCAGCAGTTTCCA AACATAAAACTATTGTGGGGTACTGCTAATGTTTTCGGACATAAA CGTTACGCTAACGGAGCTTCCACTAATCCAGACTTTGATGTTGTC GCGAGAGCTATCGTTCAAATCAAAAATGCAATCGATGCTACAATT AAGTTAGGAGGGACAAATTACGTGTTCTGGGGTGGTAGAGAAGGT TACATGAGCCTGCTTAATACAGATCAAAAGAGAGAAAAGGAGCAC ATGGCAACAATGCTAACAATGGCTAGAGATTATGCCCGAGCTAAG GGCTTCAAAGGCACTTTTCTGATAGAACCTAAACCAATGGAACCA TCTAAACACCAATACGATGTAGACACCGAAACTGTAATAGGCTTC CTTCGTGCACATGGTTTGGATAAAGATTTTAAGGTGAACATTGAA GTGAATCATGCTACTTTAGCCGGTCACACTTTTGAACATGAATTA GCATGTGCTGTTGATGCGGGAATGTTGGGTTCTATCGATGCCAAC AGAGGCGACGCCCAAAATGGTTGGGACACAGACCAGTTTCCTATT GACAATTACGAACTCACCCAAGCTATGATGGAAATTATCAGGAAT GGGGGACTGGGAAATGGTGGTACGAACTTTGATGCGAAGATAAGG AGAAACTCTACTGACTTAGAAGATTTGTTTATAGCACATATTTCA GGTATGGACGCTATGGCAAGAGCTTTAATGAATGCCGCAGCAATC TTGGAGGAAAGTGAACTCCCAGCTATGAAAAAGGCAAGATACGCA AGTTTTGATGAGGGTATTGGCAAAGACTTCGAAGATGGTAAACTA TCTTTAGAACAAGTGTACGAGTATGGCAAAAAGGTAGAGGAACCA AAACAAACATCAGGCAAACAAGAGAAATATGAAACAATTGTCGCT CTTTACGCGAAGTAA |
| DNA 2.0 codon optimized DNA encoding XI of SEQ ID NO: 38 | 249 | ATGAAGGAAATCTTCCCTAACATCCCAGAGATCAAATTCGAAGGC AAAGACTCTAAAAATCCATTTGCCTTCCACTATTACAACCCAGAC CAGATCATTTTAGGTAAACCAATGAAGGAGCACTTGCCATTTGCT ATGGCTTGGTGGCATAATCTAGGCGCCACTGGTGTTGATATGTTT |

TABLE 22-continued

| Sequence Description | SEQ ID NO: | Sequence |
|---|---|---|
| | | GGTGCAGGCCCTGCGGACAAATCTTTCGGAGCTAAAGTAGGAACT ATGGAACATGCAAAAGCGAAAGTTGATGCTGGGTTTGAGTTCATG AAGAAATTAGGAATCAGATATTTCTGCTTTCATGATGTTGACTTG GTTCCTGAGTGTGCTGACATTAAGGATACAAACAAGGAACTTGAT GAAATCTCTGACTACATTTTGGAAAAGATGAAAGGTACTGACATA AAGTGTTTGTGGGGCACGGCTAATATGTTTTCCAATCCAAGATTT TGTAACGGCGCTGGCTCAACTAATTCAGCAGATGTCTTTGCATTC GCTGCTGCACAAGTCAAGAAAGCACTTGACATTACAGTCAAACTG GGTGGGAGAGGATACGTTTTCTGGGGTGGTAGAGAAGGCTACGAA ACATTGTTGAATACAGACGTTAAGTTTGAACAAGAGAATATTGCA AGGTTAATGAAAATGGCAGTGGAATATGGGCGTTCTATAGGTTTT AAAGGTGATTTCTACATTGAGCCAAAACCAAAGGAACCTATGAAA CATCAATACGATTTCGATGCCGCAACAGCAATAGGTTTCCTTAGA GCCCACGGGTTGGATAAAGACTTTAAGCTCAATATCGAAGCCAAC CACGCAACACTTGCAGGCCATACATTTCAACATGATCTTAGAATA TCTGCTATTAACGGAATGCTCGGCTCAATTGATGCCAATCAGGGT GATATGCTACTAGGTTGGGATACTGATGAGTTTCCATTTGATGTA TACTCCGCTACACAATGCATGTATGAGGTGTTGAAAAATGGTGGT CTGACCGGTGGCTTCAACTTCGATAGTAAGACCAGACGTCCTTCA TACACTATGGAAGATATGTTTCTGGCGTATATCTTAGGTATGGAC ACATTTGCTTTAGGTCTAATCAAAGCCGCTCAAATCATTGAAGAT GGCAGAATTGACCAGTTTATAGAAAAGAAATACTCCAGTTTTCGA GAAACCGAAATCGGACAAAAGATTCTCAATAACAAAACTTCATTG AAGGAATTATCTGATTACGCCTGTAAGATGGGTGCGCCAGAATTA CCTGGAAGCGGTAGACAAGAGATGCTTGAAGCTATCGTGAATGAT GTATTGTTTGGAAAATAA |

The codon optimized DNA sequences were synthesized and incorporated into expression cassettes substantially as described in Example 12. Yeast strains were generated that included single copies of individual XI open reading frames integrated into the yeast YER131.5 locus. Strains confirmed to contain the XI expression cassettes were inoculated into about 3 ml of modified YP Media (YP+0.1% Glucose+3.0% Xylose) and incubated overnight at about 30° C. and about 220 rpm. These overnight cultures were subcultured into about 25 ml of the same media to about $OD_{600}$=0.2. Samples were incubated overnight at about 30° C. and about 220 rpm. Cultures were harvested when $OD_{600}$ was between about 3 and 4. Pellets were collected by centrifugation for about 5 minutes at about 4000 rpm. The supernatants were discarded and pellets washed with about 25 ml of distilled-deionized water and centrifuged again using the same conditions. Supernatants were discarded and the pellet frozen at about −20° C. until lysis and characterization.

Cell pellets were thawed and about 200 mg of each pellet sample was weighed out into 2 ml microcentrifuge tubes. About 50 μl of Complete®, EDTA-free Protease Inhibitor cocktail (Roche Part#11873 580 001) at 5 times the concentration stated in the manufacturer's protocol was added to each sample. To this was added about 0.5 ml of Y-PER Plus® Dialyzable Yeast Protein Extraction Reagent (Thermo Scientific Part#78999) (YP+) to each sample. Samples were incubated at about 25° C. for about 4 hours on rotating mixer. Sample supernatants were collected after centrifugation at about 10,000×g for about 10 minutes for characterization.

Total protein concentrations of the XI sample extracts prepared above were carried out using Bio-Rad Protein Assay Dye Reagent Concentrate (Bio-Rad, cat#500-0006, Hercules Calif.) which is a modified version of the Bradford method (Bradford). In this assay, optical density readings were taken on a spectrophotometer set to 595 nm, and the standard curve was plotted as a linear regression line.

XI activity was determined using assay conditions at pH 7.5 as described in the Section 5.1.2. The specific activities of the codon optimized XIs are shown in Table 23.

TABLE 23

| Protein SEQ ID NO. | Nucleic Acid SEQ ID NO: | Codon optimization method | SA, pH 7.5 (U/mg) |
|---|---|---|---|
| 78 | 77 | Native | 0.43 |
| 78 | 247 | DNA2.0—Codon Optimization | 0.14 |
| 78 | 244 | Boles Codon Optimization | 0.53 |
| 96 | 95 | Native | 0.42 |
| 96 | 248 | DNA2.0—Codon Optimization | 0.14 |
| 96 | 245 | Boles Codon Optimization | 0.40 |
| 38 | 37 | Native | 0.25 |
| 38 | 249 | DNA2.0—Codon Optimization | 0.27 |
| 38 | 246 | Boles Codon Optimization | 0.40 |

Because these specific activity data are determined on the basis of the total cellular protein mass, any variations in specific activity for any given XI are due to expression levels. These data demonstrate that the Boles codon optimization approach improves the expressibility of bacterial XIs in *S. cerevisiae.*

5.15 Example 14: Comparative Activity of XI's of the Disclosure vs. *Orpinomyces* sp. XI The specific activities of exemplary XIs of the disclosure were compared to the specific activity of a known XI, *Orpinomyces* sp. XI assigned Genbank Accession No. 169733248. The XIs were incorporated into expression cassettes substantially as described in Example 12. Yeast strains were generated that included single copies of individual XI open reading frames integrated into the yeast YER131.5 locus. Activity of the individual clones was measured at pH 7.5 using a similar approach to that used in Example 12, except that the total protein concentrations were based on optical density readings at 450 nm and 595 nm, with the standard curve was plotted as a parametric fit. Results are shown in Table 24, below.

TABLE 24

| Protein SEQ ID NO. | Nucleic Acid SEQ ID NO: | Codon optimization method | SA, pH 7.5 (U/mg) | % activity as compared to *Orpinomyces* XI |
|---|---|---|---|---|
| NA | NA | Host negative control (no recombinant XI) | 0.005 | 7% |
| Genbank Accession No. 169733248 | | *Orpinomyces sp.* XI (Native) | 0.071 | 100% |
| 96 | 95 | Native | 0.137 | 193% |

TABLE 24-continued

| Protein SEQ ID NO. | Nucleic Acid SEQ ID NO: | Codon optimization method | SA, pH 7.5 (U/mg) | % activity as compared to *Orpinomyces* XI |
|---|---|---|---|---|
| 54 | 238 | Boles codon optimization | 0.193 | 272% |
| 58 | 239 | Boles codon optimization | 0.205 | 288% |

While various specific embodiments have been illustrated and described, it will be appreciated that various changes can be made without departing from the spirit and scope of the invention(s).

What is claimed is:

1. An isolated nucleic acid sequence comprising a nucleotide sequence having at least 90%, at least 93%, at least 95%, at least 96%, at least 98%, or at least 99% sequence identity, or having 100% sequence identity, to the nucleotide sequence of SEQ ID NO: 245 or to a portion thereof encoding a xylose isomerase catalytic or dimerization domain, wherein the nucleic acid encodes a polypeptide with at least one substitution relative to the polypeptide having the sequence of SEQ ID NO: 96 or at least one heterologous amino acid flanking the N-terminal or the C-terminal.

2. The nucleic acid sequence of claim 1, which is codon optimized for expression in a eukaryotic cell.

3. The nucleic acid sequence of claim 1, which is codon optimized for expression in yeast.

4. A vector comprising the nucleic acid sequence of claim 1.

5. The vector of claim 4, which further comprises an origin of replication.

6. The vector of claim 4, which further comprises a promoter sequence operably linked to said nucleic acid sequence.

7. The vector of claim 6, wherein the promoter sequence is operable in yeast.

8. The vector of claim 6, wherein the promoter sequence is operable in filamentous fungi.

9. A recombinant cell engineered to express a polypeptide encoded by the nucleic acid sequence of claim 1.

10. The recombinant cell of claim 9, wherein the cell is a eukaryotic cell.

11. The recombinant cell of claim 9, wherein the cell is a yeast cell.

12. The recombinant cell of claim 11, wherein the yeast cell is a yeast cell of the genus *Saccharomyces*, *Kluyveromyces*, *Candida*, *Pichia*, *Schizosaccharomyces*, *Hansenula*, *Klockera*, *Schwanniomyces*, *Issatchenkia* or *Yarrowia*.

13. The recombinant cell of claim 11, wherein the yeast cell is of the species *S. cerevisiae*, *S. bulderi*, *S. barnetti*, *S. exiguus*, *S. uvarum*, *S. diastaticus*, *K lactis*, *K. marxiames* or *K. fragili*, or *Issatchenkia orientalis*.

14. The recombinant cell of claim 13, wherein the cell is a *S. cerevisiae* cell.

15. The recombinant cell of claim 14, comprising one or more genetic modifications resulting in at least one, any two, any three, any four or all of the following phenotypes:
  (a) an increase in transport of xylose into the cell;
  (b) an increase in xylulose kinase activity;
  (c) an increase in aerobic growth rate on xylose;

(d) an increase in flux through the pentose phosphate pathway into glycolysis;

(e) a decrease in aldose reductase activity;

(f) a decrease in sensitivity to catabolite repression;

(g) an increase in tolerance to ethanol, intermediates, osmolality or organic acids; and (h) a reduced production of byproducts.

16. The recombinant cell of claim 15, wherein one or more genetic modifications result in increased expression levels of one or more of a hexose or pentose transporter, a xylulose kinase, an enzyme from the pentose phosphate pathway, a glycolytic enzyme and an ethanologenic enzyme.

17. A host cell transformed with the vector of claim 4.

18. The host cell of claim 17 which is a prokaryotic cell.

19. The host cell of claim 18 which is a bacterial cell.

20. The host cell of claim 17 which is a eukaryotic cell.

* * * * *

UNITED STATES PATENT AND TRADEMARK OFFICE
CERTIFICATE OF CORRECTION

PATENT NO. : 9,982,249 B2
APPLICATION NO. : 14/417080
DATED : May 29, 2018
INVENTOR(S) : Nunn, Jr. et al.

It is certified that error appears in the above-identified patent and that said Letters Patent is hereby corrected as shown below:

On the Title Page

Please amend the inventors as follows:
Item (72) Inventors: David Neal Nunn, Jr., Carlsbad, CA (US); Peter Luginbuhl, San Diego, CA (US); Ling Li, San Diego, CA (US); Adam Martin Burja, San Diego, CA (US); Jon Peter Flash Bartnek, San Diego, CA (US)

Signed and Sealed this
Twenty-fifth Day of September, 2018

Andrei Iancu
*Director of the United States Patent and Trademark Office*